(12) United States Patent
Folkes et al.

(10) Patent No.: US 7,846,929 B2
(45) Date of Patent: Dec. 7, 2010

(54) PHOSPHOINOSITIDE 3-KINASE INHIBITOR COMPOUNDS AND METHODS OF USE

(75) Inventors: Adrian Folkes, Slough (GB); Stephen Shuttleworth, Slough (GB); Sally Oxenford, Slough (GB); Tim Hancox, Slough (GB); Tracy Bayliss, Slough (GB); Georgette Castanedo, Redwood City, CA (US); Richard Goldsmith, Belmont, CA (US); Janet Gunzner, Berkeley, CA (US); Tim Heffron, San Francisco, CA (US); Kimberly Malesky, San Francisco, CA (US); Simon Mathieu, Burlingame, CA (US); Alan Olivero, Half Moon Bay, CA (US); Daniel P. Sutherlin, South San Francisco, CA (US); Vickie Tsui, San Francisco, CA (US); Shumei Wang, Foster City, CA (US); Christian Wiesmann, Brisbane, CA (US); Bing-Yan Zhu, Palo Alto, CA (US); Jennafer Dotson, Belmont, CA (US)

(73) Assignees: Genentech, Inc., South San Francisco, CA (US); Piramed Limited, Slough (GB)

( * ) Notice: Subject to any disclaimer, the term of this patent is extended or adjusted under 35 U.S.C. 154(b) by 688 days.

(21) Appl. No.: 11/789,427

(22) Filed: Apr. 24, 2007

(65) Prior Publication Data

US 2008/0039459 A1    Feb. 14, 2008

Related U.S. Application Data

(60) Provisional application No. 60/795,047, filed on Apr. 26, 2006.

(51) Int. Cl.
*A61K 31/5377*  (2006.01)
*C07D 413/14*  (2006.01)

(52) U.S. Cl. .................................... 514/234.5; 544/116
(58) Field of Classification Search ................. 544/116; 514/234.5
See application file for complete search history.

(56) References Cited

U.S. PATENT DOCUMENTS

| | | | |
|---|---|---|---|
| 3,475,429 | A | 10/1969 | Woitun et al. |
| 3,661,908 | A | 5/1972 | Woitun et al. |
| 3,763,156 | A | 10/1973 | Woitun et al. |
| 3,838,121 | A | 9/1974 | Woitun et al. |
| 4,007,187 | A | 2/1977 | Fauran et al. |
| 4,146,716 | A | 3/1979 | Cox et al. |
| 4,196,207 | A | 4/1980 | Webber et al. |
| 6,608,053 | B2 | 8/2003 | Hayakawa et al. |
| 6,838,457 | B2 | 1/2005 | Hayakawa et al. |
| 7,037,915 | B2 | 5/2006 | Hayakawa et al. |
| 7,173,029 | B2 | 2/2007 | Hayakawa et al. |

FOREIGN PATENT DOCUMENTS

| | | |
|---|---|---|
| EP | 1277738 A1 | 1/2003 |
| GB | 1393161 | 5/1975 |
| WO | WO 2004/065391 A1 | 8/2004 |
| WO | WO 2006/046031 A1 | 5/2006 |
| WO | WO 2006/046035 A1 | 5/2006 |
| WO | WO 2006/046040 A1 | 5/2006 |

OTHER PUBLICATIONS

Cancer and Metastasis Reviews (1998), 17(1), 91-106.*
Science (1999), vol. 286, 531-537.*
Byrn et al., Solid-State Chemistry of Drugs, Second Edition, 1999, pp. 233-247.*
Briel et al. "Selective Nucleophilic Replacement of the Benzylsulfanyl Group in 2, 4-Disulfanyl-substituted Thieno[2,3-d]pyrimidin-6-carboxylic Acid Derivatives by Secondary Amines", *Journal Heterocyclic Chem.*, 42(5), 841-846, Jul.-Aug. 2005.
Bachman et al., "The *PIK3CA* gene is mutated with high frequency in human breast cancers", *Cancer Biology & Therapy*, 3(8), 772-775, Aug. 2004.
Berge et al., "Pharmaceutical Salts", *Journal of Pharmaceutical Sciences*, 66(1), Jan. 1-19, 1977.

(Continued)

*Primary Examiner*—Rebecca L Anderson
(74) *Attorney, Agent, or Firm*—Viksnins Harris & Padys PLLP

(57) ABSTRACT

Compounds of Formulas Ia and Ib, and including stereoisomers, geometric isomers, tautomers, solvates, metabolites and pharmaceutically acceptable salts thereof, are useful for inhibiting lipid kinases including PI3K, and for treating disorders such as cancer mediated by lipid kinases. Methods of using compounds of Formula Ia and Ib for in vitro, in situ, and in vivo diagnosis, prevention or treatment of such disorders in mammalian cells, or associated pathological conditions, are disclosed.

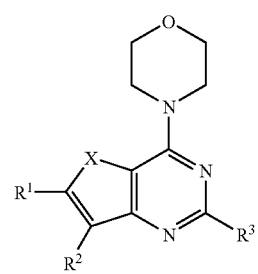

Ia

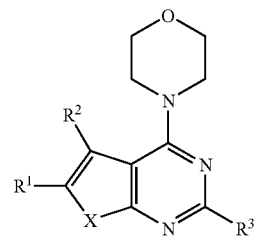

Ib

57 Claims, No Drawings

OTHER PUBLICATIONS

C. Garcia-Echeverria et al., "Drug discovery approaches targeting the PI3/Akt pathway in cancer", *Oncogene*, 27, 5511-5526, 2008.

Kang et al., "Phosphatidylinositol 3-kinase mutations identified in human cancer are oncogenic", *PNAS*, 102(3), 802-807, Jan. 18, 2005.

Raynaud et al., "Biological properties of potent inhibitors of class I phophatidylinositide 3-kinases: from PI-103 through PI-540, PI-620 to the oral agent GDC-0941", *Mol. Cancer Ther.*, 8(7), 1725-1738, Jul. 2009.

Samuels et al., "High frequency of mutations of the *PIK3CA* gene in human cancers", *Science*, 304, 554, Apr. 23, 2004.

Shayesteh et al., "*PIK3CA* is implicated as an oncogene in ovarian cancer", *Nature Genetics*, 21, 99-102, Jan. 1999.

Workman et al., "Drugging the PI3 kinome", *Nature Biotechnology*, 24(7), 794-796, Jul. 2006.

Yap et al., "Targeting the PI3K-AKT-mTOR pathway: progress, pitfalls, and promises", *Current Opinion in Pharmacology*, 8, 393-412, 2008.

\* cited by examiner

PHOSPHOINOSITIDE 3-KINASE INHIBITOR COMPOUNDS AND METHODS OF USE

PRIORITY OF INVENTION

This application claims priority to U.S. Provisional Application No. 60/795,047 that was filed on 26 Apr. 2006. The entire content of this provisional application is hereby incorporated herein by reference.

FIELD OF THE INVENTION

The invention relates generally to compounds with anti-cancer activity and more specifically to compounds which inhibit PI3 kinase activity. The invention also relates to methods of using the compounds for in vitro, in situ, and in vivo diagnosis or treatment of mammalian cells, or associated pathological conditions.

BACKGROUND OF THE INVENTION

Phosphatidylinositol (hereinafter abbreviated as "PI") is one of a number of phospholipids found in cell membranes. In recent years it has become clear that PI plays an important role in intracellular signal transduction. Cell signaling via 3'-phosphorylated phosphoinositides has been implicated in a variety of cellular processes, e.g., malignant transformation, growth factor signaling, inflammation, and immunity (Rameh et al (1999) J. Biol Chem, 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60).

Phosphoinositide 3-kinases (PI3K) are lipid kinases that phosphorylate lipids at the 3-hydroxyl residue of an inositol ring (Whitman et al (1988) Nature, 332:664). The 3-phosphorylated phospholipids (PIP3s) generated by PI3-kinases act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

The PI3 kinase family comprises at least 15 different enzymes sub-classified by structural homology and are divided into 3 classes based on sequence homology and the product formed by enzyme catalysis. The class I PI3 kinases are composed of 2 subunits: a 110 kd catalytic subunit and an 85 kd regulatory subunit. The regulatory subunits contain SH2 domains and bind to tyrosine residues phosphorylated by growth factor receptors with a tyrosine kinase activity or oncogene products, thereby inducing the PI3K activity of the p110 catalytic subunit which phosphorylates its lipid substrate. Class I PI3 kinases are involved in important signal transduction events downstream of cytokines, integrins, growth factors and immunoreceptors, which suggests that control of this pathway may lead to important therapeutic effects such as modulating cell proliferation and carcinogenesis. Class I PI3Ks can phosphorylate phosphatidylinositol (PI), phosphatidylinositol-4-phosphate, and phosphatidylinositol-4,5-biphosphate (PIP2) to produce phosphatidylinositol-3-phosphate (PIP), phosphatidylinositol-3,4-biphosphate, and phosphatidylinositol-3,4,5-triphosphate, respectively. Class II PI3Ks phosphorylate PI and phosphatidylinositol-4-phosphate. Class III PI3Ks can only phosphorylate PI.

The main PI3-kinase isoform in cancer is the Class I PI3-kinase, p110α. (U.S. Pat. Nos. 5,824,492; 5,846,824; 6,274,327). Other isoforms are implicated in cardiovascular and immune-inflammatory disease (Workman P (2004) "Inhibiting the phosphoinositide 3-kinase pathway for cancer treatment" Biochem Soc Trans 32:393-396; Patel et al (2004) "Identification of potent selective inhibitors of PI3K as candidate anticancer drugs" Proceedings of the American Association of Cancer Research (Abstract LB-247) 95th Annual Meeting, March 27-31, Orlando, Fla., USA; Ahmadi K and Waterfield M D (2004) "Phosphoinositide 3-Kinase: Function and Mechanisms" Encyclopedia of Biological Chemistry (Lennarz W J, Lane M D eds) Elsevier/Academic Press).

Several components of the PI3-kinase/Akt/PTEN pathway are implicated in oncogenesis. In addition to growth factor receptor tyrosine kinases, integrin-dependent cell adhesion and G-protein coupled receptors activate PI3-kinase both directly and indirectly through adaptor molecules. Functional loss of PTEN (the most commonly mutated tumor-suppressor gene in cancer after p53), oncogene mutations in PI3 kinase (Samuels et al (2004) Science 304:554), amplification of PI3-kinase and overexpression of Akt have been established in many malignancies. In addition, persistent signaling through the PI3-kinase/Akt pathway by stimulation of the insulin-like growth factor receptor is a mechanism of resistance to epidermal growth factor receptor inhibitors such as AG1478 and trastuzumab. Oncogenic mutations of p110alpha have been found at a significant frequency in colon, breast, brain, liver, ovarian, gastric, lung, and head and neck solid tumors. PTEN abnormalities are found in glioblastoma, melanoma, prostate, endometrial, ovarian, breast, lung, head and neck, hepatocellular, and thyroid cancers.

The levels of phosphatidylinositol-3,4,5-triphosphate (PIP3), the primary product of PI3-kinase activation, increase upon treatment of cells with a variety of agonists. PI3-kinase activation, therefore, is believed to be involved in a range of cellular responses including cell growth, differentiation, and apoptosis (Parker et al (1995) Current Biology, 5:577-99; Yao et al (1995) Science, 267:2003-05). Though the downstream targets of phosphorylated lipids generated following PI3 kinase activation have not been well characterized, emerging evidence suggests that pleckstrin-homology domain- and FYVE-finger domain-containing proteins are activated when binding to various phosphatidylinositol lipids (Sternmark et al (1999) J Cell Sci, 112:4175-83; Lemmon et al (1997) Trends Cell Biol, 7:237-42). In vitro, some isoforms of protein kinase C (PKC) are directly activated by PIP3, and the PKC-related protein kinase, PKB, has been shown to be activated by PI3 kinase (Burgering et al (1995) Nature, 376:599-602).

The initial purification and molecular cloning of PI3 kinase revealed that it was a heterodimer consisting of p85 and p110 subunits (Otsu et al (1991) Cell 65:91-104; Hiles et al (1992) Cell 70:419-29). Since then, four distinct Class I PI3Ks have been identified, designated PI3K α (alpha), β (beta), δ (delta), and ω (gamma), each consisting of a distinct 110 kDa catalytic subunit and a regulatory subunit. More specifically, three of the catalytic subunits, i.e., p110.alpha., p110.beta. and p110.delta., each interact with the same regulatory subunit, p85; whereas p110.gamma. interacts with a distinct regulatory subunit, p101. As described below, the patterns of expression of each of these PI3Ks in human cells and tissues are also distinct.

The cellular functions of the individual isoforms of PI3 kinases are not completely elucidated. Bovine p110 alpha was described after cloning as related to the *Saccharomyces cerevisiae* protein: Vps34p, a protein involved in vacuolar protein processing. The recombinant p110 alpha product was also shown to associate with p85 alpha, to yield a PI3K activity in transfected COS-1 cells (Hiles et al. (1992), Cell, 70:419-29). A second human p110 isoform was cloned and designated p110 beta (Hu et al (1993) Mol Cell Biol 13:7677-88). This isoform is said to associate with p85 in cells, and to be ubiquitously expressed, as p110 beta mRNA has been found in numerous human and mouse tissues as well as in human umbilical vein endothelial cells, Jurkat human leukemic T cells, 293 human embryonic kidney cells, mouse 3T3 fibroblasts, HeLa cells, and NBT2 rat bladder carcinoma cells. Identification of the p110 delta isoform of PI3 kinase is described in Chantry et al., J Biol Chem, 272:19236-41 (1997). It was observed that the human p110 delta isoform is expressed in a tissue-restricted fashion. It is expressed at high levels in lymphocytes and lymphoid tissues, suggesting that the protein might play a role in PI3 kinase-mediated signaling in the immune system (U.S. Pat. Nos. 5,858,753; 5,822,910; 5,985,589; WO 97/46688; and Vanhaesebroeck et al (1997) Proc Natl Acad Sci USA, 94:4330-5).

In each of the PI3K alpha, beta, and delta subtypes, the p85 subunit acts to localize PI3 kinase to the plasma membrane by the interaction of its SH2 domain with phosphorylated tyrosine residues (present in an appropriate sequence context) in target proteins (Rameh et al (1995) Cell, 83:821-30). Two isoforms of p85 have been identified, p85alpha, which is ubiquitously expressed, and p85 beta, which is primarily found in the brain and lymphoid tissues (Volinia et al (1992) Oncogene, 7:789-93). Association of the p85 subunit to the PI3 kinase p110 alpha, beta, or delta catalytic subunits appears to be required for the catalytic activity and stability of these enzymes. In addition, the binding of Ras proteins also upregulates PI3 kinase activity. Cloning of p110 gamma revealed further complexity within the PI3K family of enzymes (Stoyanov et al (1995) Science, 269:690-93). The p110 gamma isoform is closely related to p110 alpha and p110 beta (45-48% identity in the catalytic domain), but does not make use of p85 as a targeting subunit. Instead, PI3K contains an additional domain termed a "pleckstrin homology domain" near its amino terminus. This domain allows interaction of p110 gamma with the beta, gamma subunits of heterotrimeric G proteins and this interaction appears to regulate its activity. The p101 regulatory subunit for PI3Kgamma was originally cloned in swine, and the human ortholog identified subsequently (Krugmann et al (1999) J Biol Chem, 274:17152-8).

Thus, PI3 kinases can be defined by their amino acid identity or by their activity. Additional members of this growing gene family include more distantly related lipid and protein kinases including Vps34 TOR1, and TOR2 of *Saccharomyces cerevisiae* (and their mammalian homologs such as FRAP and mTOR), the ataxia telangiectasia gene product (ATR) and the catalytic subunit of DNA-dependent protein kinase (DNA-PK). See generally, Hunter (1995) Cell, 83:1-4.

PI3 kinase also appears involved in leukocyte activation. A p85-associated PI3 kinase activity has been shown to physically associate with the cytoplasmic domain of CD28, which is an important costimulatory molecule for the activation of T-cells in response to antigen (Pages et al (1994) Nature, 369:327-29; Rudd, (1996) Immunity 4:527-34). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al (1991) Science, 251:313-16). Mutation of CD28 such that it can no longer interact with PI3 kinase leads to a failure to initiate IL2 production, suggesting a critical role for PI3 kinase in T cell activation.

Inhibition of class I PI3 kinase induces apoptosis, blocks tumor induced angiogenesis in vivo, and increases the radiosensitivity of certain tumors. At least two compounds, LY294002 and wortmannin, have been widely used as PI3 kinase inhibitors. These compounds, however, are nonspecific PI3K inhibitors, as they do not distinguish among the four members of Class I PI3 kinases. For example, the IC50 values of wortmannin (U.S. Pat. No. 6,703,414) against each of the various Class I PI3 kinases are in the range of 1-10 nanomolar (nM). LY294002 (2-(4-morpholinyl)-8-phenyl-4H-1-benzopyran-4-one) is a well known specific inhibitor of class I PI3 kinases and has anti-cancer properties (Chiosis et al (2001) Bioorganic & Med. Chem. Lett. 11:909-913; Vlahos et al (1994) J. Biol. Chem. 269(7):5241-5248; Walker et al (2000) Mol. Cell 6:909-919; Fruman et al (1998) Ann Rev Biochem, 67:481-507). However, the anti-cancer applications of LY294002 are severely limited by its lack of aqueous solubility and its poor pharmacokinetics. Moreover, LY294002 has no tissue specific properties and has been demonstrated to be rapidly metabolized in animals. Because of these factors, LY294002 would need to be administered at frequent intervals and thus has the potential to also inhibit PI3 kinases in normal cells thereby leading to undesirable side effects.

There continues to be a need for class I PI3 kinase inhibitors with improved pharmacokinetic and pharmacodynamic properties. The PI3 kinase/Akt/PTEN pathway is thus an attractive target for cancer drug development since such agents would be expected to inhibit proliferation, reverse the repression of apoptosis and surmount resistance to cytotoxic agents in cancer cells. PI3 kinase inhibitors have been reported (Yaguchi et al (2006) Jour. of the Nat. Cancer Inst. 98(8):545-556; U.S. Pat. Nos. 6,608,056;. 6,608,053; 6,838, 457; 6,770,641; 6,653,320; 6,403,588; WO 2004017950; US 2004092561; WO 2004007491; WO 2004006916; WO 2003037886; US 2003149074; WO 2003035618; WO 2003034997; US 2003158212; EP 1417976; US 2004053946; JP 2001247477; JP 08175990; JP 08176070). Wortmannin analogs have PI3 kinase activity in mammals (U.S. Pat. No. 6,703,414; WO 97/15658).

SUMMARY OF THE INVENTION

The invention relates generally to fused bicyclic thienopyrimidine and furanopyrimidine compounds with anti-cancer activity, and more specifically with PI3 kinase inhibitory activity. Certain hyperproliferative disorders are characterized by the modulation of PI3 kinase function, for example by mutations or overexpression of the proteins. Accordingly, the compounds of the invention may be useful in the treatment of hyperproliferative disorders such as cancer. The compounds may inhibit tumor growth in mammals and may be useful for treating human cancer patients.

The invention also relates to methods of using the compounds for in vitro, in situ, and in vivo diagnosis or treatment of mammalian cells, organisms, or associated pathological conditions.

More specifically, one aspect of the invention provides 4-morpholino thienopyrimidine and furanopyrimidine compounds of Formulas Ia and Ib:

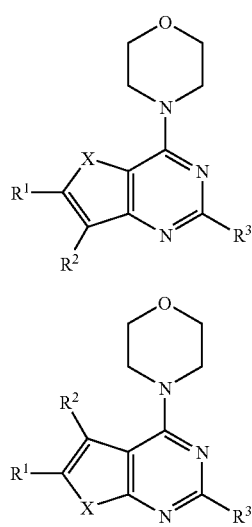

and stereoisomers, geometric isomers, tautomers, solvates, metabolites, and pharmaceutically acceptable salts thereof, wherein X is O or S. Groups $R^1$, $R^2$ and $R^3$ are as defined herein.

Another aspect of the invention provides a pharmaceutical composition comprising a thienopyrimidine or furanopyrimidine compound of Formulas Ia or Ib and a pharmaceutically acceptable carrier. The pharmaceutical composition may further comprise one or more additional therapeutic agents selected from anti-proliferative agents, anti-inflammatory agents, immunomodulatory agents, neurotropic factors, agents for treating cardiovascular disease, agents for treating liver disease, anti-viral agents, agents for treating blood disorders, agents for treating diabetes, and agents for treating immunodeficiency disorders.

Another aspect of the invention provides methods of inhibiting PI3 kinase activity, comprising contacting a PI3 kinase with an effective inhibitory amount of a compound of Formula Ia or Ib, or a stereoisomer, geometric isomer, tautomer, solvate, metabolite, or pharmaceutically acceptable salt or prodrug thereof.

Another aspect of the invention provides methods of preventing or treating a disease or disorder modulated by PI3 kinases, comprising administering to a mammal in need of such treatment an effective amount of a compound of Formula Ia or Ib, or a stereoisomer, geometric isomer, tautomer, solvate, metabolite, or pharmaceutically acceptable salt or prodrug thereof. Examples of such diseases, conditions and disorders include, but are not limited to, hyperproliferative disorders (e.g., cancer, including melanoma and other cancers of the skin), neurodegeneration, cardiac hypertrophy, pain, migraine, neurotraumatic diseases, stroke, diabetes, hepatomegaly, cardiovascular disease, Alzheimer's disease, cystic fibrosis, viral diseases, autoimmune diseases, atherosclerosis, restenosis, psoriasis, allergic disorders, inflammation, neurological disorders, hormone-related diseases, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, and CNS disorders.

Another aspect of the invention provides methods of preventing or treating a hyperproliferative disorder, comprising administering to a mammal in need of such treatment an effective amount of a compound of Formula Ia or Ib, or a stereoisomer, geometric isomer, tautomer, solvate, metabolite, or pharmaceutically acceptable salt or prodrug thereof, alone or in combination with one or more additional compounds having anti-hyperproliferative properties.

In a further aspect the present invention provides a method of using a compound of this invention to treat a disease or condition modulated by PI3 kinase in a mammal.

An additional aspect of the invention is the use of a compound of this invention in the preparation of a medicament for the treatment or prevention of a disease or condition modulated by PI3 kinase in a mammal.

Another aspect of the invention includes kits comprising a compound of Formula Ia or Ib, or a stereoisomer, geometric isomer, tautomer, solvate, metabolite, or pharmaceutically acceptable salt or prodrug thereof, a container, and optionally a package insert or label indicating a treatment.

Another aspect of the invention includes methods of preparing, methods of separating, and methods of purifying compounds of Formula Ia and Ib.

Additional advantages and novel features of this invention shall be set forth in part in the description that follows, and in part will become apparent to those skilled in the art upon examination of the following specification or may be learned by the practice of the invention. The advantages of the invention may be realized and attained by means of the instrumentalities, combinations, compositions, and methods particularly pointed out in the appended claims.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls.

Definitions

The term "alkyl" as used herein refers to a saturated linear or branched-chain monovalent hydrocarbon radical of one to twelve carbon atoms, wherein the alkyl radical may be optionally substituted independently with one or more substituents described below. Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (1-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkenyl" refers to linear or branched-chain monovalent hydrocarbon radical of two to twelve carbon atoms with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkynyl" refers to a linear or branched monovalent hydrocarbon radical of two to twelve carbon atoms with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The terms "carbocycle", "carbocyclyl", "carbocyclic ring" and "cycloalkyl" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-20 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, biphenyl, indenyl, indanyl, 1,2-dihydronapthalene, 1,2,3,4-tetrahydronapthyl, and the like. Aryl groups are optionally substituted independently with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to 20 ring atoms in which at least one ring atom is a heteroatom selected from nitrogen, oxygen and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. The heterocyclyl may be a carbon radical or heteroatom radical. The term "heterocycle" includes heterocycloalkoxy. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring carbon atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), nitrogen (nitrogen-linked) or oxygen (oxygen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

"Fused bicyclic $C_4$-$C_{20}$ heterocyclyl" and "Fused bicyclic $C_1$-$C_{20}$ heteroaryl" containing one or more heteroatoms independently selected from nitrogen, oxygen, and sulfur, differ only by their aromatic character, and have two rings fused together, i.e. share a common bond. Fused bicyclic heterocyclyl and heteroaryl radicals may be attached to the C-2 position of the pyrimidine ring according to Formulas Ia and Ib at any carbon (carbon-linked), or nitrogen (nitrogen-linked) atom of the fused bicyclic $C_4$-$C_{20}$ heterocyclyl or fused bicyclic $C_1$-$C_{20}$ heteroaryl group $R^3$ group. Fused bicyclic heterocyclyl and heteroaryl radicals include, but are not limited to: 1H-indazole, 1H-indole, indolin-2-one, 1-(indolin-1-yl)ethanone, 1H-benzo[d][1,2,3]triazole, 1H-pyrazolo[3,4-b]pyridine, 1H-pyrazolo[3,4-d]pyrimidine, 1H-benzo[d]imidazole, 1H-benzo[d]imidazol-2(3H)-one, 1H-pyrazolo[3,4-c]pyridine, 1H-pyrrolo[2,3-c]pyridine, 3H-imidazo[4,5-c]pyridine, 7H-pyrrolo[2,3-d]pyrimidine, 7H-purine, 1H-pyrazolo[4,3-d]pyrimidine, 5H-pyrrolo[3,2-d]pyrimidine, 2-amino-1H-purin-6(9H)-one, quinoline, quinazoline, quinoxaline, isoquinoline, isoquinolin-1(2H)-one, 3,4-dihydroisoquinolin-1(2H)-one, 3,4-dihydroquinolin-2(1H)-one, quinazolin-2(1H)-one, quinoxalin-2(1H)-one, 1,8-naphthyridine, pyrido[3,4-d]pyrimidine, and pyrido[3,2-b]pyrazine. Fused bicyclic heterocycles and fused bicyclic heteroaryls are optionally substituted independently with one or more substituents described herein.

The substituent groups that alkyl, alkenyl, alkynyl, carbocyclyl, heterocyclyl, aryl, heteroaryl, fused bicyclic $C_4$-$C_{20}$ heterocyclyl, and fused bicyclic $C_1$-$C_{20}$ heteroaryl are optionally substituted with include F, Cl, Br, I, CN, $CF_3$, $-NO_2$, oxo, $R^{10}$, $-C(=Y)R^{10}$, $-C(=Y)OR^{10}$, $-C(=Y)NR^{10}R^{11}$, $-(CR^{14}R^{15})_nNR^{10}R^{11}$, $-(CR^{14}R^{15})_nOR^{10}$, $-NR^{10}R^{11}$, $-NR^{12}C(=Y)R^{10}$, $-NR^{12}C(=Y)OR^{11}$, $-NR^{12}C(=Y)NR^{10}R^{11}$, $-NR^{12}SO_2R^{10}$, $=NR^{12}$, $OR^{10}$, $-OC(=Y)R^{10}$, $-OC(=Y)OR^{10}$, $-OC(=Y)NR^{10}R^{11}$, $-OS(O)_2(OR^{10})$, $-OP(=Y)(OR^{10})(OR^{11})$, $-OP(OR^{10})(OR^{11})$, $SR^{10}$, $-S(O)R^{10}$, $-S(O)_2R^{10}$, $-S(O)_2NR^{10}R^{11}$, $-S(O)(OR^{10})$, $-S(O)_2(OR^{10})$, $-SC(=Y)R^{10}$, $-SC(=Y)OR^{10}$, $-SC(=Y)NR^{10}R^{11}$, $C_1$-$C_{12}$ optionally substituted alkyl, $C_2$-$C_8$ optionally substituted alkenyl, $C_2$-$C_8$ optionally substituted alkynyl, $C_3$-$C_{12}$ optionally substituted carbocyclyl, $C_2$-$C_{20}$ optionally substituted heterocyclyl, $C_6$-$C_{20}$ optionally substituted aryl, $C_1$-$C_{20}$ optionally substituted heteroaryl, $-(CR^{14}R^{15})_t-NR^{12}C(=O)(CR^{14}R^{15})NR^{10}R^{11}$, and $(CR^{14}R^{15})_t-NR^{10}R^{11}$ The terms "treat" and "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

A "chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (TYKBRB®, GSK572016, Glaxo Smith Kline), Lonafamib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlomaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofemine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE™ (Cremophor-free), albumin-engineered nanoparticle formulations of paclitaxel (American Pharmaceutical Partners, Schaumberg, Ill.), and TAXOTERE® (doxetaxel; Rhône-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINE® (vinorelbine); novantrone; teniposide; edatrexate; daunomycin; aminopterin; capecitabine (XELODA®); ibandronate; CPT-11; topoisomerase inhibitor RFS 2000; difluoromethylomithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; a topoisomerase 1 inhibitor such as LURTOTECAN®; ABARELIX® rmRH; (ix) anti-angiogenic agents such as bevacizumab (AVASTIN®, Genentech); and (x) pharmaceutically acceptable salts, acids and derivatives of any of the above.

The term "prodrug" as used in this application refers to a precursor or derivative form of a compound of the invention that is less cytotoxic to cells compared to the parent compound or drug and is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound.

Accordingly, the invention includes metabolites of compounds of the invention, including compounds produced by a process comprising contacting a compound of this invention with a mammal for a period of time sufficient to yield a metabolic product thereof.

A "liposome" is a small vesicle composed of various types of lipids, phospholipids and/or surfactant which is useful for delivery of a drug (such as the PI3 kinase inhibitors disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, DMSO, ethyl acetate, acetic acid, and ethanolamine. The term "hydrate" refers to the complex where the solvent molecule is water.

The term "protecting group" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, Protective Groups in Organic Synthesis, John Wiley & Sons, New York, 1991.

The terms "compound of this invention," and "compounds of the present invention" and "compounds of Formula Ia and Ib" include compounds of Formulas Ia and Ib and stereoisomers, geometric isomers, tautomers, solvates, metabolites, and pharmaceutically acceptable salts and prodrugs thereof.

The term "mammal" includes, but is not limited to, humans, mice, rats, guinea pigs, monkeys, dogs, cats, horses, cows, pigs, and sheep, and poultry.

PI3 Kinase Inhibitor Compounds

The present invention provides 4-morpholino thienopyrimidine and furanopyrimidine compounds, and pharmaceutical formulations thereof, that are potentially useful in the treatment of diseases, conditions and/or disorders modulated by PI3 kinases. The compounds may inhibit p110 isoforms including alpha, beta, gamma, and delta as pan inhibitors. The compounds may be p110 isoform selective inhibitors by selective inhibition of one of the p110 isoforms.

More specifically, the present invention provides compounds of Formulas Ia and Ib.

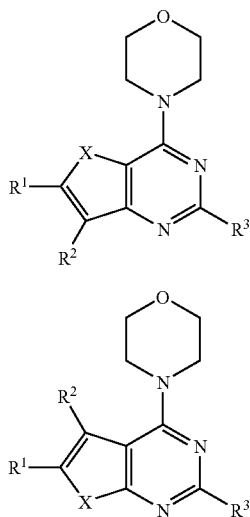

and stereoisomers, geometric isomers, tautomers, solvates, metabolites, and pharmaceutically acceptable salts thereof, wherein:

X is O or S;

$R^1$ is selected from H, F, Cl, Br, I, CN, —$CR^{14}R^{15}$—$NR^{16}R^{17}$, —$CR^{14}R^{15}$—$NHR^{10}$, —$(CR^{14}R^{15})_nNR^{10}R^{11}$, —$C(CR^{14}R^{15})_nNR^{12}C(=Y)R^{10}$, —$(CR^{14}R^{15})_nNR^{12}S(O)_2$ $R^{10}$, —$(CR^{14}R^{15})_mOR^{10}$, —$(CR^{14}R^{15})_nS(O)_2R^{10}$, —$(CR^{14}R^{15})_nS(O)_2NR^{10}R^{11}$, —$C(OR^{10})R^{11}R^{14}$, —$C(R^{14})$ =$CR^{18}R^{19}$, —$C(=Y)R^{10}$, —$C(=Y)OR^{10}$, —$C(=Y)NR^{10}R^{11}$, —$C(=Y)NR^{12}OR^{10}$, —$C(=O)NR^{12}S(O)_2$, —$C(=O)NR^{12}(CR^{14}R^{15})_mNR^{10}R^{11}$, —$NO_2$, —$NHR^{12}$, —$NR^{12}C(=Y)R^{11}$, —$NR^{12}C(=Y)OR^{11}$, —$NR^{12}C(=Y)NR^{10}R^{11}$, —$NR^{12}S(O)_2R^{10}$, —$NR^{12}SO_2NR^{10}R^{11}$, —$S(O)_2R^{10}$, —$S(O)_2NR^{10}R^{11}$, —$SC(=Y)R^{10}$, —$SC(=Y)OR^{10}$, $C_2$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl;

$R^2$ is selected from H, F, Cl, Br, I, CN, $CF_3$, —$NO_2$, —$C(=Y)R^{10}$, —$C(=Y)OR^{10}$, —$C(=Y)NR^{10}R^{11}$, —$(CR^{14}R^{15})_mNR^{10}R^{11}$, —$(CR^{14}R^{15})_nOR^{10}$, —$(CR^{14}R^{15})_t$—$NR^{12}C(=O)(CR^{14}R^{15})NR^{10}R^{11}$, —$NR^{12}C(=Y)R^{10}$, —$NR^{12}C(=Y)OR^{10}$, —$NR^{12}C(=Y)NR^{10}R^{11}$, —$NR^{12}SO_2R^{10}$, $OR^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})$ $(OR^{11})$, —$OP(OR^{10})(OR^{11})$, $SR^{10}$, —$S(O)R^{10}$, —$S(O)_2R^{10}$, —$S(O)_2NR^{10}R^{11}$, —$S(O)(OR^{10})$, —$S(O)_2(OR^{10})$, —$SC(=Y)R^{10}$, —$SC(=Y)OR^{10}$, —$SC(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

$R^3$ is fused bicyclic $C_4$-$C_{20}$ heterocyclyl or fused bicyclic $C_1$-$C_{20}$ heteroaryl;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, $(CH_2)_mOR^{10}NR^{10}R^{11}$, $CF_3$, F, Cl, Br, I, $SO_2R^{10}$, $C(=O)R^{10}$, $NR^{12}C(=Y)R^{11}$, $NR^{12}S(O)_2R^{11}$, $C(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or —$(CH_2)_n$-aryl, or $R^{14}$ and $R^{15}$ together with the atoms to which they are attached form a saturated or partially unsaturated $C_3$-$C_{12}$ carbocyclic ring, $R^{16}$ and $R^{17}$ are independently H, $C_1$-$C_{12}$ alkyl, $C_2$-$C_8$ alkenyl, $C_2$-$C_8$ alkynyl, $C_3$-$C_{12}$ carbocyclyl, or $C_6$-$C_{20}$ aryl, $R^{18}$ and $R^{19}$ together with the carbon to which they are attached form a $C_3$-$C_{20}$ heterocyclic ring, where said alkyl, alkenyl, alkynyl, carbocyclyl, heterocyclyl, aryl and heteroaryl are optionally substituted with one or more groups independently selected from F, Cl, Br, I, CN, $CF_3$, —$NO_2$, oxo, $R^{10}$, —$C(=Y)R^{10}$, —$C(=Y)OR^{10}$, —$C(=Y)NR^{10}R^{11}$, —$(CR^{14}R^{15})_nNR^{10}R^{11}$, —$(CR^{14}R^{15})_n$ $OR^{10}$, —$NR^{10}R^{11}$, —$NR^{12}C(=Y)R^{10}$, —$NR^{12}C(=Y)$ $OR^{11}$, —$NR^{12}C(=Y)NR^{10}R^{11}$, —$NR^{12}SO_2R^{10}$, =$NR^{12}$, $OR^{10}$, —$OC(=Y)R^{10}$, —$OC(=Y)OR^{10}$, —$OC(=Y)$ $NR^{10}R^{11}$, —$OS(O)_2(OR^{10})$, —$OP(=Y)(OR^{10})(OR^{11})$, —$OP(OR^{10})(OR^{11})$, $SR^{10}$, —$S(O)R^{10}$, —$S(O)_2R^{10}$, —$S(O)_2NR^{10}R^{11}$, —$S(O)(OR^{10})$, —$S(O)_2(OR^{10})$, —$SC(=Y)R^{10}$, —$SC(=Y)OR^{10}$, —$SC(=Y)NR^{10}R^{11}$, $C_1$-$C_{12}$ optionally substituted alkyl, $C_2$-$C_8$ optionally substituted alkenyl, $C_2$-$C_8$ optionally substituted alkynyl, $C_3$-$C_{12}$ optionally substituted carbocyclyl, $C_2$-$C_{20}$ optionally substituted heterocyclyl, $C_6$-$C_{20}$ optionally substituted aryl, $C_1$-$C_{20}$ optionally substituted heteroaryl, —$(CR^{14}R^{15})_t$—$NR^{12}C(=O)$ $(CR^{14}R^{15})NR^{10}R^{11}$, and $(CR^{14}R^{15})_t$—$NR^{10}R^{11}$;

Y is O, S, or $NR^{12}$;

m is 0, 1, 2, 3, 4, 5 or 6;

n is 1, 2, 3, 4, 5 or 6; and t is 2, 3, 4, 5 or 6.

In another embodiment, the present invention provides compounds of Formulas Ia and Ib wherein:

X is O or S;

$R^1$ is selected from H, $-CR^{14}R^{15}-NR^{10}R^{11}$, $-(CR^{14}R^{15})_n NR^{10}R^{11}$, $-C(R^{14}R^{15})_n NR^{12}C(=Y)R^{10}$, $-(CR^{14}R^{15})_n NR^{12}S(O)_2 R^{10}$, $-(CR^{14}R^{15})_n OR^{10}$, $-(CR^{14}R^{15})_n S(O)_2 R^{10}$, $-(CR^{14}R^{15})_n S(O)_2 NR^{10}R^{11}$, $-C(=Y)R^{10}$, $-C(=Y)OR^{10}$, $-C(=Y)NR^{10}R^{11}$, $-C(=Y)NR^{12}OR^{10}$, $-C(=O)NR^{12}S(O)_2 R^{10}$, $-C(=O)NR^{12}(CR^{14}R^{15})_m NR^{10}R^{11}$, $-NO_2$, $-NHR^{12}$, $-NR^{12}C(=Y)R^{11}$, $-NR^{12}C(=Y)OR^{11}$, $-NR^{12}C(=Y)NR^{10}R^{11}$, $-NR^{12}S(O)_2 R^{10}$, $-NR^{12}SO_2 NR^{10}R^{11}$, $-S(O)_2 R^{10}$, $-S(O)_2 NR^{10}R^{11}$, $-SC(=Y)R^{10}$, $-SC(=Y)OR^{10}$, $C_2$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl;

$R^2$ is selected from H, F, Cl, Br, I, CN, $CF_3$, $-NO_2$, $-C(=Y)R^{10}$, $-C(=Y)OR^{10}$, $-C(=Y)NR^{10}R^{11}$, $-(CR^{14}R^{15})_m NR^{10}R^{11}$, $-(CR^{14}R^{15})_n OR^{10}$, $-(CR^{14}R^{15})_t NR^{12}C(=O)(CR^{14}R^{15})NR^{10}R^{11}$, $-NR^{12}C(=Y)R^{10}$, $-NR^{12}C(=Y)OR^{10}$, $-NR^{12}C(=Y)NR^{10}R^{11}$, $-NR^{12}SO_2 R^{10}$, $OR^{10}$, $-OC(=Y)R^{10}$, $-OC(=Y)OR^{10}$, $-OC(=Y)NR^{10}R^{11}$, $-OS(O)_2(OR^{10})$, $-OP(=Y)(OR^{10})(OR^{11})$, $-OP(OR^{10})(OR^{11})$, $SR^{10}$, $-S(O)R^{10}$, $-S(O)_2 R^{10}$, $-S(O)_2 NR^{10}R^{11}$, $-S(O)(OR^{10})$, $-S(O)_2(OR^{10})$, $-SC(=Y)R^{10}$, $-SC(=Y)OR^{10}$, $-SC(=Y)NR^{10}R^{11}$, $C_2$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl $C_6$-$C_{20}$ aryl, and $C_1$-$C_{20}$ heteroaryl;

$R^3$ is fused bicyclic $C_2$-$C_{20}$ heterocyclyl or fused bicyclic $C_1$-$C_{20}$ heteroaryl;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, $(CH_2)_n OR^{10}$, $NR^{10}R^{11}$, $CF_3$, F, Cl, Br, I, $SO_2 R^{10}$, $C(=O)R^{10}$, $NR^{12}C(=Y)R^{11}$, $C(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or $-(CH_2)_n$-aryl, or $R^{14}$ and $R^{15}$ together with the atoms to which they are attached form a saturated or partially unsaturated $C_3$-$C_{12}$ carbocyclic ring, where said alkyl, alkenyl, alkynyl, carbocyclyl, heterocyclyl, aryl and heteroaryl are optionally substituted with one or more groups independently selected from F, Cl, Br, I, CN, $CF_3$, $-NO_2$, oxo, $-C(=Y)R^{10}$, $-C(=Y)OR^{10}$, $-C(=Y)NR^{10}R^{11}$, $-(CR^{14}R^{15})_n NR^{10}R^{11}$, $-(CR^{14}R^{15})_n OR^{10}$, $-NR^{10}R^{11}$, $-NR^{12}C(=Y)R^{10}$, $-NR^{12}C(=Y)OR^{11}$, $-NR^{12}C(=Y)NR^{10}R^{11}$, $-NR^{12}SO_2 R^{10}$, $=NR^{12}$, $OR^{10}$, $-OC(=Y)R^{10}$, $-OC(=Y)OR^{10}$, $-OC(=Y)NR^{10}R^{11}$, $-OS(O)_2(OR^{10})$, $-OP(=Y)(OR^{10})(OR^{11})$, $-OP(OR^{10})(OR^{11})$, $SR^{10}$, $-S(O)R^{10}$, $-S(O)_2 R^{10}$, $-S(O)_2 NR^{10}R^{11}$, $-S(O)(OR^{10})$, $-S(O)_2(OR^{10})$, $-SC(=Y)R^{10}$, $-SC(=Y)OR^{10}$, $-SC(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, $C_1$-$C_{20}$ heteroaryl, $-(CR^{14}R^{15})_t NR^{12}C(=O)(CR^{14}R^{15})NR^{10}R^{11}$, and $(CR^{14}R^{15})_t NR^{10}R^{11}$;

Y is O, S, or $NR^{12}$;

m is 0, 1, 2, 3, 4, 5 or 6;

n is 1, 2, 3, 4, 5 or 6; and t is 2, 3, 4, 5 or 6.

Formula Ia and Ib compounds are regioisomers, i.e. differ by the placement of atom X in the thienopyrimidine (X=sulfur) or furanopyrimidine (X=oxygen) ring system. Parent molecules of Formula Ia and Ib compounds are:

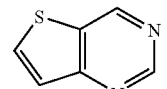  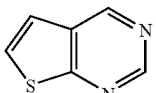

thieno[3,2-d]pyrimidine    thieno[2,3-d]pyrimidine

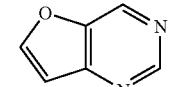  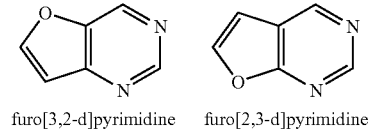

furo[3,2-d]pyrimidine    furo[2,3-d]pyrimidine

Compounds of the invention thus include both regioisomers of each of the 4-morpholino thienopyrimidine and 4-morpholino furanopyrimidine compounds, and the substituted forms as described by $R^1$, $R^2$, and $R^3$ herein:

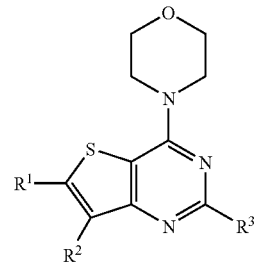

Ia-S

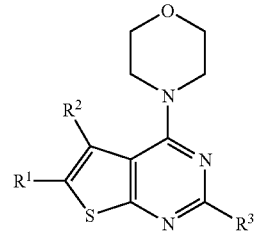

Ib-S

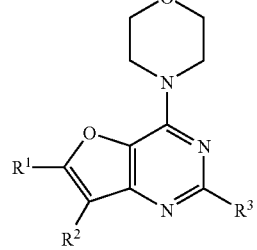

Ia-O

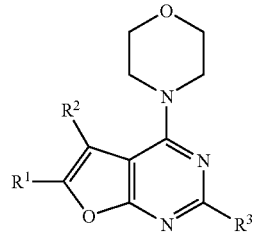

Ib-O

In certain embodiments, $R^1$ is $-(CR^{14}R^{15})_t NR^{10}R^{11}$ where t is 2 or 3, and $R^{10}$ and $R^{11}$ together with the nitrogen to which they are attached form the $C_3$-$C_{20}$ heterocyclic ring.

In certain embodiments, $R^1$ is $-(CR^{14}R^{15})_n NR^{12}S(O)_2 R^{10}$ where n is 1 or 2; $R^{12}$, $R^{14}$, and $R^{15}$ are independently selected from H and $C_1$-$C_{12}$ alkyl; and $R^{10}$ is $C_1$-$C_{12}$ alkyl or $C_6$-$C_{20}$ aryl.

In certain embodiments, $R^1$ is $-(CR^{14}R^{15})_n OR^{10}$ where n is 1 or 2, and $R^{10}$, $R^{14}$, and $R^{15}$ are independently selected from H and $C_1$-$C_{12}$ alkyl.

In certain embodiments, $R^1$ is $-(CR^{14}R^{15})_n S(O)_2 R^{10}$ where n is 1 or 2, and $R^{14}$ and $R^{15}$ are H. $R^{10}$ may be $C_1$-$C_{12}$ alkyl or $C_6$-$C_{20}$ aryl.

In certain embodiments, $R^1$ is $-(CR^{14}R^{15})_n S(O)_2 NR^{10}R^{11}$ where n is 1 or 2, and $R^{14}$ and $R^{15}$ are H.

In certain embodiments, $R^1$ is $-C(=Y)NR^{10}R^{11}$ where Y is O, and $R^{10}$ and $R^{11}$ together with the nitrogen to which they are attached form the $C_2$-$C_{20}$ heterocyclic ring. $R^{10}$ and $R^{11}$ together with the nitrogen to which they are attached may form a $C_2$-$C_{20}$ heterocyclic ring selected from morpholinyl, piperidinyl, piperazinyl, and pyrrolidinyl.

In certain embodiments, $R^1$ is $-C(=Y)NR^{10}R^{11}$ where Y is O, and $R^{10}$ and $R^{11}$ are independently selected from H and $C_1$-$C_{12}$ alkyl.

In certain embodiments, $R^1$ is $-C(=Y)NR^{10}R^{11}$ where Y is O, and $R^{10}$ and $R^{11}$ are independently selected from H, $C_3$-$C_{12}$ carbocyclyl, $C_2$-$C_{20}$ heterocyclyl, $C_6$-$C_{20}$ aryl, and $C_1$-$C_{20}$ heteroaryl.

In certain embodiments, $R^1$ is $-NHR^{12}$ where $R^{12}$ is $C_3$-$C_{12}$ carbocyclyl, $C_2$-$C_{20}$ heterocyclyl, $C_6$-$C_{20}$ aryl, or $C_1$-$C_{20}$ heteroaryl. $R^{12}$ may be phenyl or 4-pyridyl.

In certain embodiments, $R^1$ is $-NR^{12}C(=Y)R^{11}$ where Y is O, $R^{12}$ is H or $C_1$-$C_{12}$ alkyl, and $R^{11}$ is $C_1$-$C_{12}$ alkyl, $C_3$-$C_{12}$ carbocyclyl, $C_2$-$C_{20}$ heterocyclyl, $C_6$-$C_{20}$ aryl, or $C_1$-$C_{20}$ heteroaryl. $R^{11}$ includes, but is not limited to, methyl, ethyl, propyl, isopropyl, isobutyl, 2,2-dimethylpropyl, and tert-butyl. $R^{11}$ also includes, but is not limited to, cyclopropyl, cyclobutyl, cyclopentyl, and cyclohexyl.

In certain embodiments, $R^1$ is $-NR^{12}S(O)_2R^{10}$ where $R^{12}$ is H or $C_1$-$C_{12}$ alkyl, and $R^{10}$ is $C_1$-$C_{12}$ alkyl, $C_3$-$C_{12}$ carbocyclyl, $C_2$-$C_{20}$ heterocyclyl, $C_6$-$C_{20}$ aryl, or $C_1$-$C_{20}$ heteroaryl.

In certain embodiments, $R^1$ is $S(O)_2NR^{10}R^{11}$ where $R^{10}$ and $R^{11}$ together with the nitrogen to which they are attached form a $C_2$-$C_{20}$ heterocyclic ring selected from morpholinyl, piperidinyl, piperazinyl, and pyrrolidinyl.

In certain embodiments, $R^1$ is $S(O)_2NR^{10}R^{11}$ where $R^{10}$ and $R^{11}$ are independently selected from H and $C_1$-$C_{12}$ alkyl. $R^{10}$ and $R^{11}$ may be independently selected from H, substituted ethyl, and substituted propyl.

In certain embodiments, $R^1$ is $C_2$-$C_{12}$ alkyl.

In certain embodiments, $R^1$ is $C_2$-$C_8$ alkenyl.

In certain embodiments, $R^1$ is $C_2$-$C_8$ alkynyl. The $C_2$-$C_8$ alkynyl may be substituted with $C_2$-$C_{20}$ heterocyclyl, which includes, but is not limited to, morpholinyl, piperidinyl, piperazinyl, and pyrrolidinyl.

In certain embodiments, $R^1$ is selected from the groups:

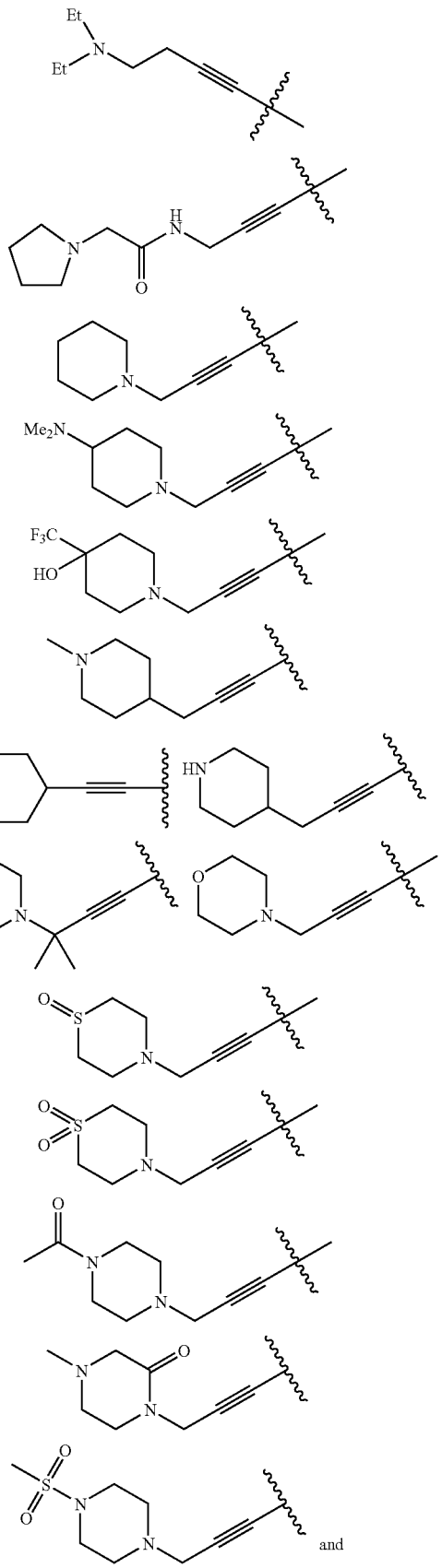

and

-continued

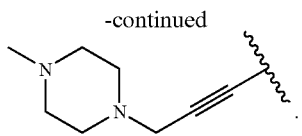

In certain embodiments, $R^1$ is $C_6$-$C_{20}$ aryl, such as phenyl.

In certain embodiments, $R^1$ is $C_3$-$C_{12}$ carbocyclyl.

In certain embodiments, $R^1$ is $C_2$-$C_{20}$ heterocyclyl.

In certain embodiments, $R^1$ is $C_1$-$C_{20}$ heteroaryl, such as 2-pyridyl, 3-pyridyl, 4-pyridyl, or 5-pyrimidinyl.

In certain embodiments, $R^2$ is H.

In certain embodiments, $R^2$ is methyl ($CH_3$).

Exemplary embodiments of $R^3$ include, but are not limited to: 1H-indazole, 1H-indole, indolin-2-one, 1-(indolin-1-yl)ethanone, 1H-benzo[d][1,2,3]triazole, 1H-pyrazolo[3,4-b]pyridine, 1H-pyrazolo[3,4-d]pyrimidine, 1H-benzo[d]imidazole, 1H-benzo[d]imidazol-2(3H)-one, 1H-pyrazolo[3,4-c]pyridine, 1H-pyrrolo[2,3-c]pyridine, 3H-imidazo[4,5-c]pyridine, 7H-pyrrolo[2,3-d]pyrimidine, 7H-purine, 1H-pyrazolo[4,3-d]pyrimidine, 5H-pyrrolo[3,2-d]pyrimidine, 2-amino-1H-purin-6(9H)-one, quinoline, quinazoline, quinoxaline, isoquinoline, isoquinolin-1(2H)-one, 3,4-dihydroisoquinolin-1(2H)-one, 3,4-dihydroquinolin-2(1H)-one, quinazolin-2(1H)-one, quinoxalin-2(1H)-one, 1,8-naphthyridine, pyrido[3,4-d]pyrimidine, and pyrido[3,2-b]pyrazine.

The attachment site of the $R^3$ group to the C-2 position of the pyrimidine ring according to Formulas Ia and Ib may be at any carbon (carbon-linked), nitrogen (nitrogen-linked) or oxygen (oxygen-linked) atom of the fused bicyclic $C_4$-$C_{20}$ heterocyclyl or fused bicyclic $C_1$-$C_{20}$ heteroaryl group $R^3$ group.

Exemplary embodiments of $R^3$ include the following groups, where the wavy line indicates the site of attachment to the pyrimidine ring:

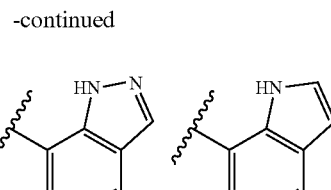

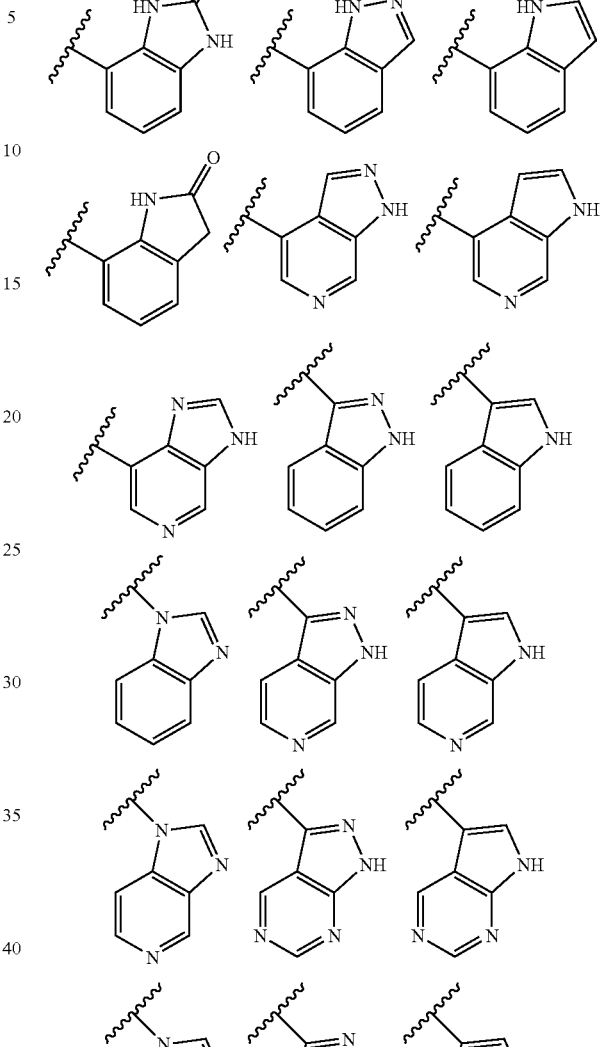

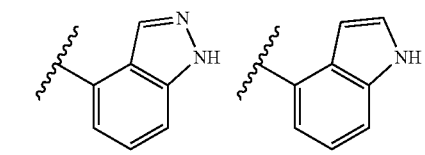

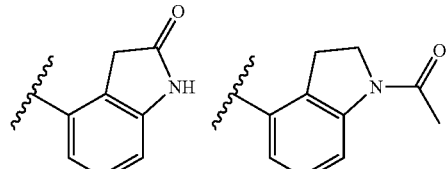

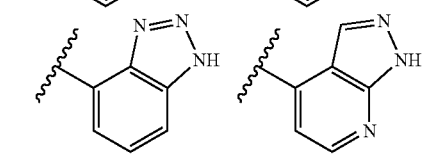

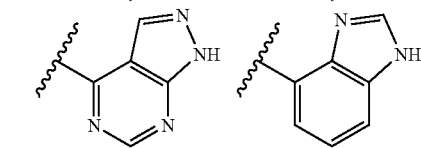

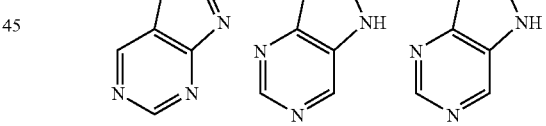

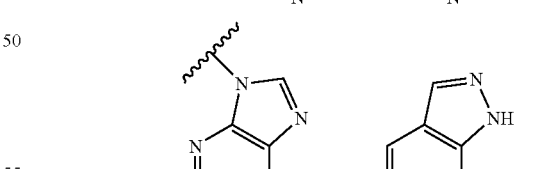

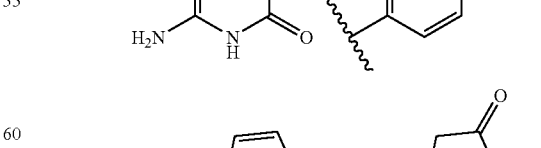

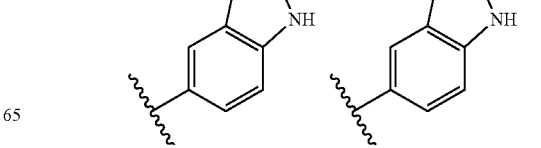

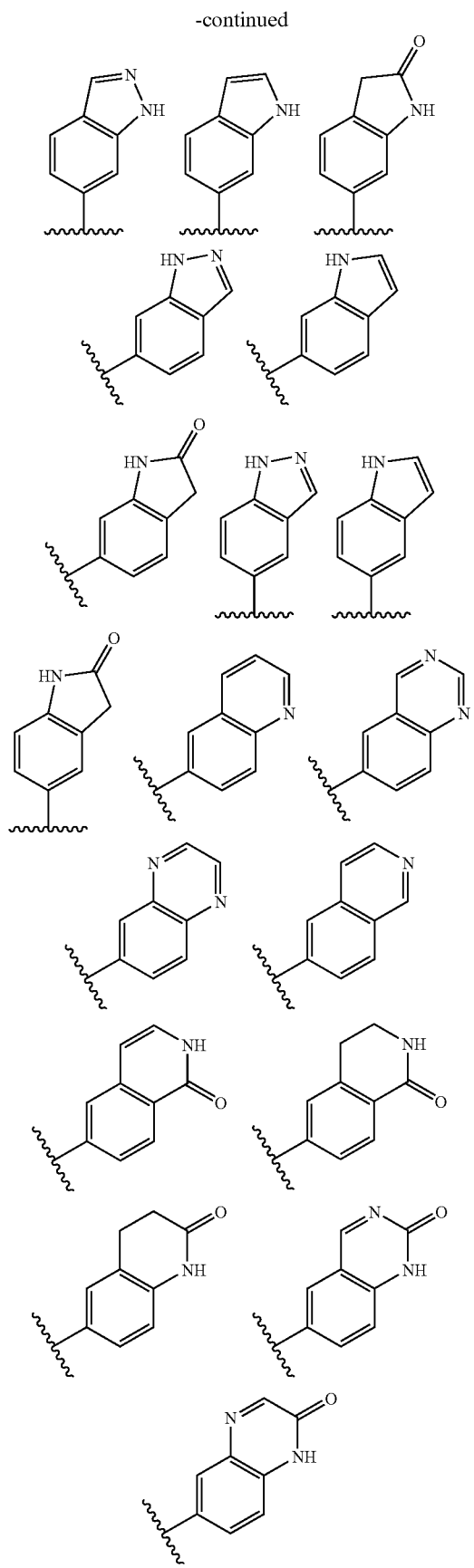
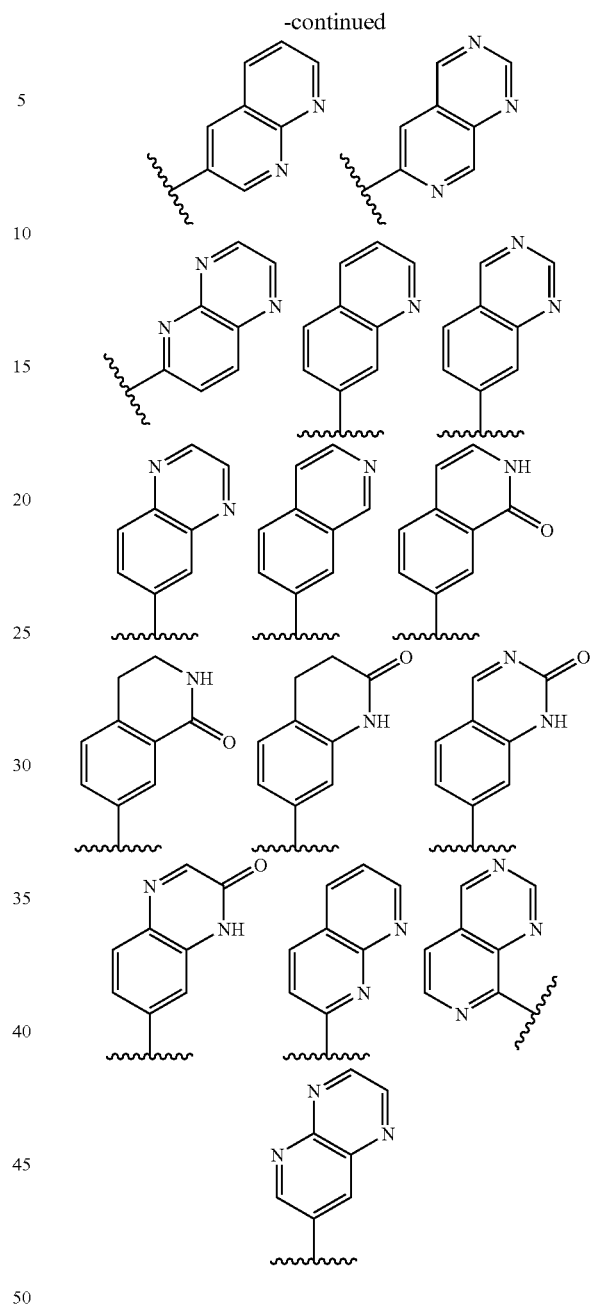

where the wavy line indicates the site of attachment.

Exemplary embodiments of $R^3$ include fused bicyclic $C_4$-$C_{20}$ heterocyclyl and fused bicyclic $C_1$-$C_{20}$ heteroaryl, including those exemplified above, substituted with one or more groups independently selected from F, Cl, Br, I, CN, $CF_3$, —$NO_2$, oxo, —C(=Y)$R^{10}$, —C(=Y)O$R^{10}$, —C(=Y)N$R^{10}R^{11}$, —(C$R^{14}R^{15}$)$_n$N$R^{10}R^{11}$, —(C$R^{14}R^{15}$)$_n$O$R^{10}$, —N$R^{10}R^{11}$, —N$R^{12}$C(=Y)$R^{10}$, —N$R^{12}$C(=Y)O$R^{11}$, —N$R^{12}$C(=Y)N$R^{10}R^{11}$, —N$R^{12}SO_2R^{10}$, =N$R^{12}$, O$R^{10}$, —OC(=Y)$R^{10}$, —OC(=Y)O$R^{10}$, —OC(=Y)N$R^{10}R^{11}$, —OS(O)$_2$(O$R^{10}$), —OP(=Y)(O$R^{10}$)(O$R^{11}$), —OP(O$R^{10}$)(O$R^{11}$), S$R^{10}$, —S(O)$R^{10}$, —S(O)$_2R^{10}$, —S(O)$_2$N$R^{10}R^{11}$, —S(O)(O$R^{10}$), —S(O)$_2$(O$R^{10}$), —SC(=Y)$R^{10}$, —SC(=Y)O$R^{10}$, —SC(=Y)N$R^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, $C_1$-$C_{20}$ heteroaryl, —(C$R^{14}R^{15}$)$_t$—N$R^{12}$C(=O)(C$R^{14}R^{15}$)N$R^{10}R^{11}$, and (C$R^{14}R^{15}$)$_t$—N$R^{10}R^{11}$.

The Formula Ia and Ib compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all geometric and positional isomers. For example, if a Formula Ia and Ib compound incorporates a double bond or a fused ring, the cis- and trans-forms, as well as mixtures thereof, are embraced within the scope of the invention. Both the single positional isomers and mixture of positional isomers are also within the scope of the present invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I and $^{125}$I. Certain isotopically-labeled compounds of the present invention (e.g., those labeled with $^3$H and $^{14}$C) are useful in compound and/or substrate tissue distribution assays. Tritiated ($^3$H) and carbon-14 ($^{14}$C) isotopes are useful for their ease of preparation and detectability. Further, substitution with heavier isotopes such as deuterium (i.e., 2H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Preparation of Formula Ia and Ib Compounds

Thienopyrimidine and furanopyrimidine compounds of Formula Ia and Ib may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-19, Wiley, N.Y. (1967-1999 ed.), or *Beilsteins Handbuch der organischen Chemie*, 4, Aufl. ed. Springer-Verlag, Berlin, including supplements (also available via the Beilstein online database).

In certain embodiments, compounds of Formula Ia or Ib may be readily prepared using procedures well-known to prepare thiophenes, furans, pyrimidines (U.S. Pat. Nos. 6,608,053; 6,492,383; 6,232,320; 6,187,777; 3,763,156 3,661,908; 3,475,429; 5,075,305; US 2003/220365; GB 1393161; WO 93/13664;); and other heterocycles, which are described in: Comprehensive Heterocyclic Chemistry, Editors Katritzky and Rees, Pergamon Press, 1984.

Compounds of Formula Ia and Ib may be prepared singly or as compound libraries comprising at least 2, for example 5 to 1,000 compounds, or 10 to 100 compounds. Libraries of compounds of Formula Ia or Ib may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

For illustrative purposes, Schemes 1-7 show general methods for preparing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In preparing compounds of Formulas Ia and Ib, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethylenoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Scheme 1

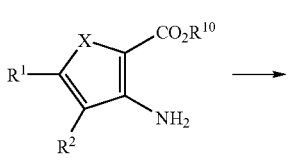

51

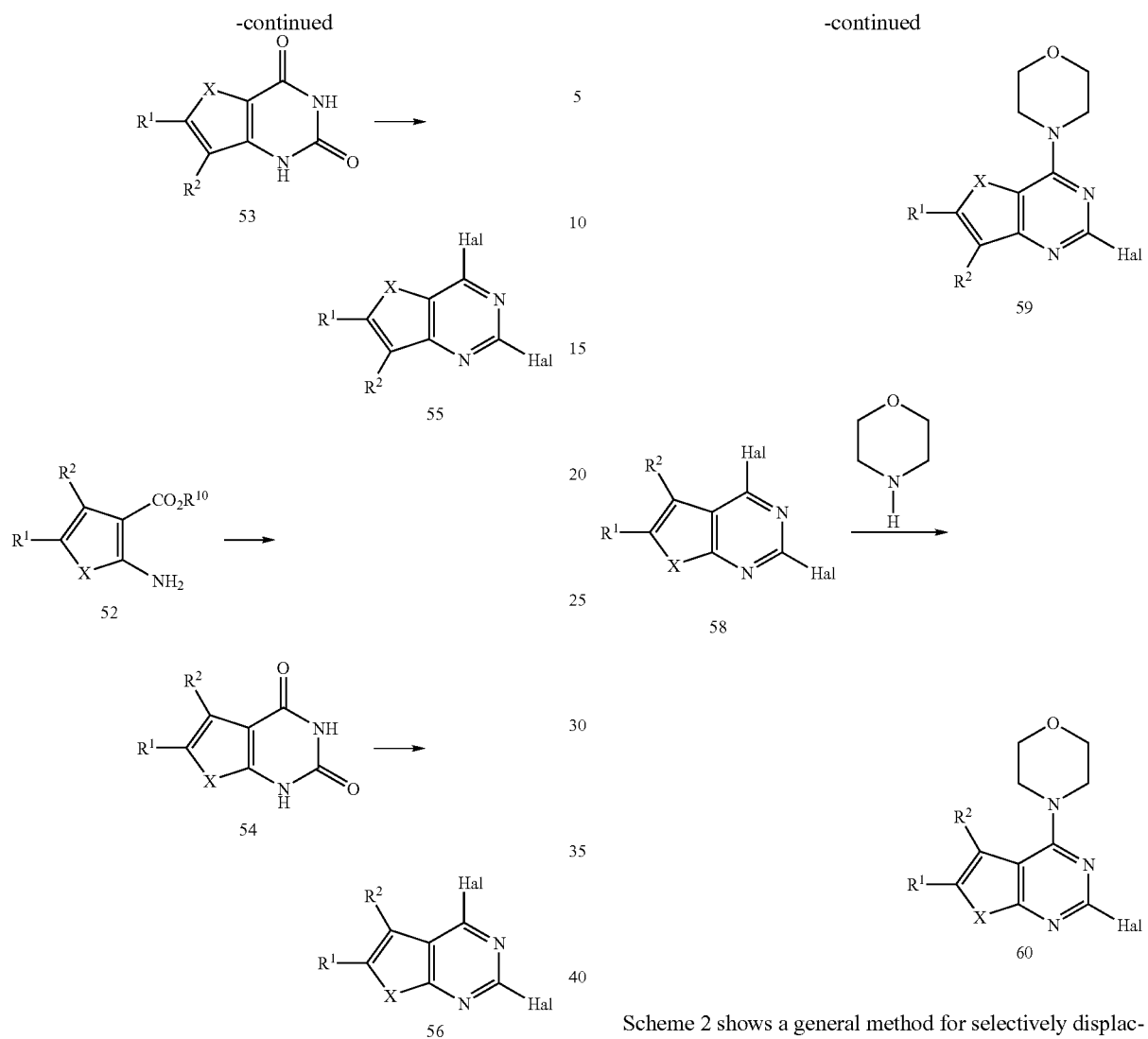

Scheme 1 shows a general method for preparation of the thienopyrimidine and furanopyrimidine intermediates 55 and 56 from 2-carboxyester, 3-amino thiophene (X=S) and furan (X=O), and 2-amino, 3-carboxy ester thiophene (X=S) and furan (X=O) reagents, respectively 51 and 52, wherein X is O or S; Hal is Cl, Br, or I; and $R^1$, $R^2$, and $R^{10}$ are as defined for Formula Ia and Ib compounds, or precursors or prodrugs thereto.

Scheme 2 shows a general method for selectively displacing a 4-halide from bis-halo thienopyrimidine and 4-morpholino furanopyrimidine intermediates 57 and 58 with morpholine under basic conditions in an organic solvent to prepare 2-halo, 4-morpholino thienopyrimidine and 4-morpholino furanopyrimidine compounds 59 and 60 respectively, wherein X is O or S; Hal is Cl, Br, or I; and $R^1$ and $R^2$ are as defined for Formula Ia and Ib compounds, or precursors or prodrugs thereto.

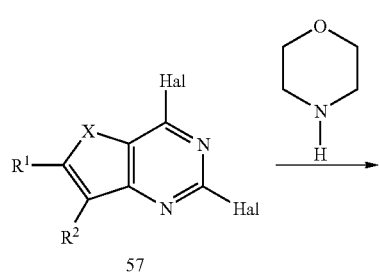

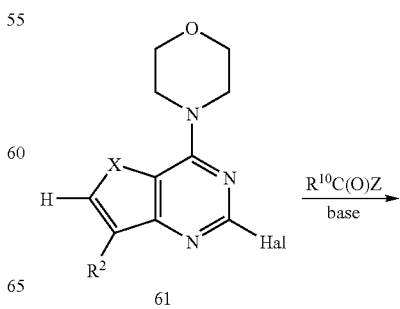

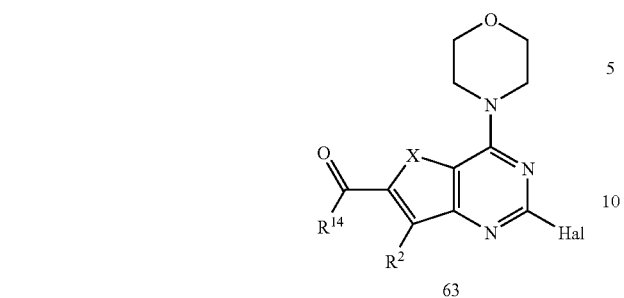

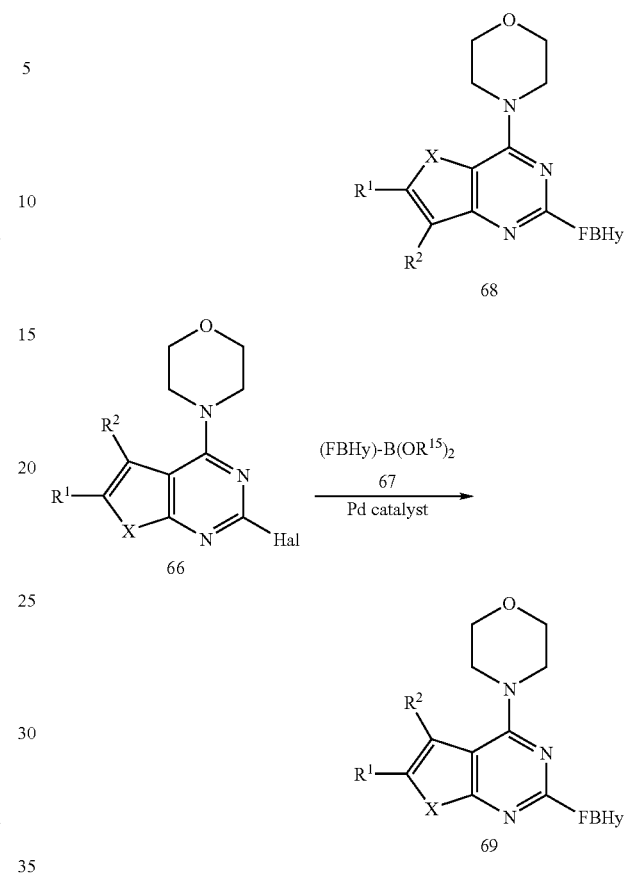

Scheme 3 shows a general method for derivatizing the 6-position of 2-halo, 4-morpholino, 6-hydrogen thienopyrimidine and 4-morpholino furanopyrimidine compounds 61 and 62 where $R^{11}$ is H. Treating 61 or 62 with a lithiating reagent to remove the 6 position proton, followed by adding an acylating reagent $R^{10}C(O)Z$ where Z is a leaving group, such as halide, NHS ester, carboxylate, or dialkylamino, gives 2-halo, 4-morpholino, 6-acyl thienopyrimidine and 4-morpholino furanopyrimidine compounds 63 and 64, wherein X is O or S; Hal is Cl, Br, or I; and $R^2$ and $R^{10}$ are as defined for Formula Ia and Ib compounds, or precursors or prodrugs thereto. An example of $R^{10}C(O)Z$ to prepare 6-formyl compounds ($R^{10}$=H) is N,N'-dimethylformamide (DMF).

Scheme 4

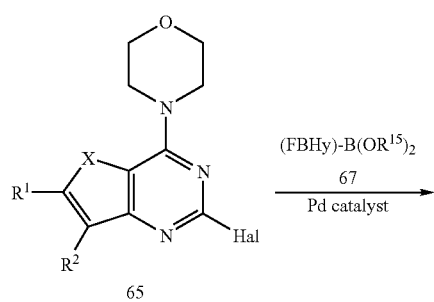

Scheme 4 shows a general method for Suzuki-type coupling of a 2-halo pyrimidine intermediate (65 and 66) with a fused bicyclic heterocycle or heteroaryl boronate acid ($R^{15}$=H) or ester ($R^{15}$=alkyl) reagent 67 to prepare the 2-fused bicyclic heterocycle or heteroaryl (FBHy), 4-morpholino thienopyrimidine and 4-morpholino fliranopyrimidine compounds (68 and 69) of Formulas Ia and Ib wherein X is O or S; Hal is Cl, Br, or I; and $R^1$ and $R^2$ are as defined for Formula Ia and Ib compounds, or precursors or prodrugs thereto. For reviews of the Suzuki reaction, see: Miyaura et al. (1995) Chem. Rev. 95:2457-2483; Suzuki, A. (1999) J. Organomet. Chem. 576:147-168; Suzuki, A. in Metal-Catalyzed Cross-Coupling Reactions, Diederich, F., Stang, P. J., Eds., VCH, Weinheim, DE (1998), pp 49-97. The palladium catalyst may be any that is typically used for Suzuki-type cross-couplings, such as $PdCl_2(PPh_3)_2$, $Pd(PPh_3)_4$, $Pd(OAc)_2$, $PdCl_2$(dppf)-DCM, $Pd_2(dba)_3$/Pt—$Bu)_3$ (Owens et al (2003) Bioorganic & Med. Chem. Letters 13:4143-4145; Molander et al (2002) Organic Letters 4(11):1867-1870; U.S. Pat. No. 6,448,433).

Scheme 5

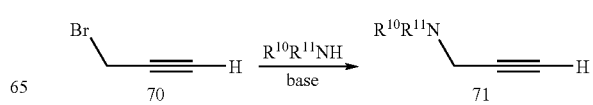

-continued

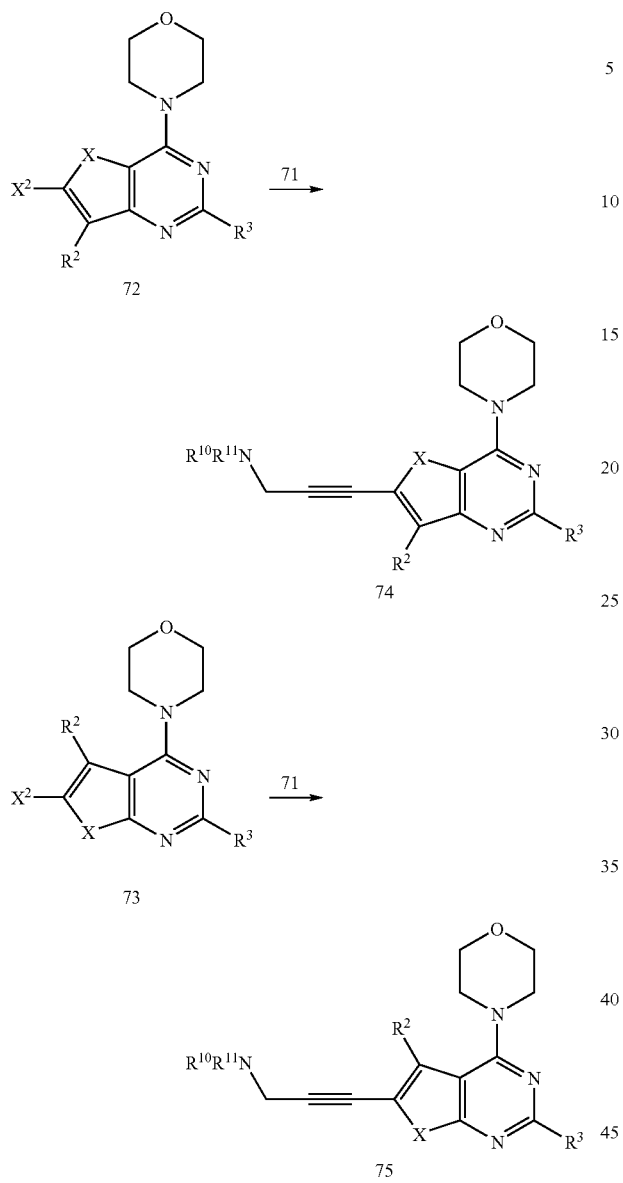

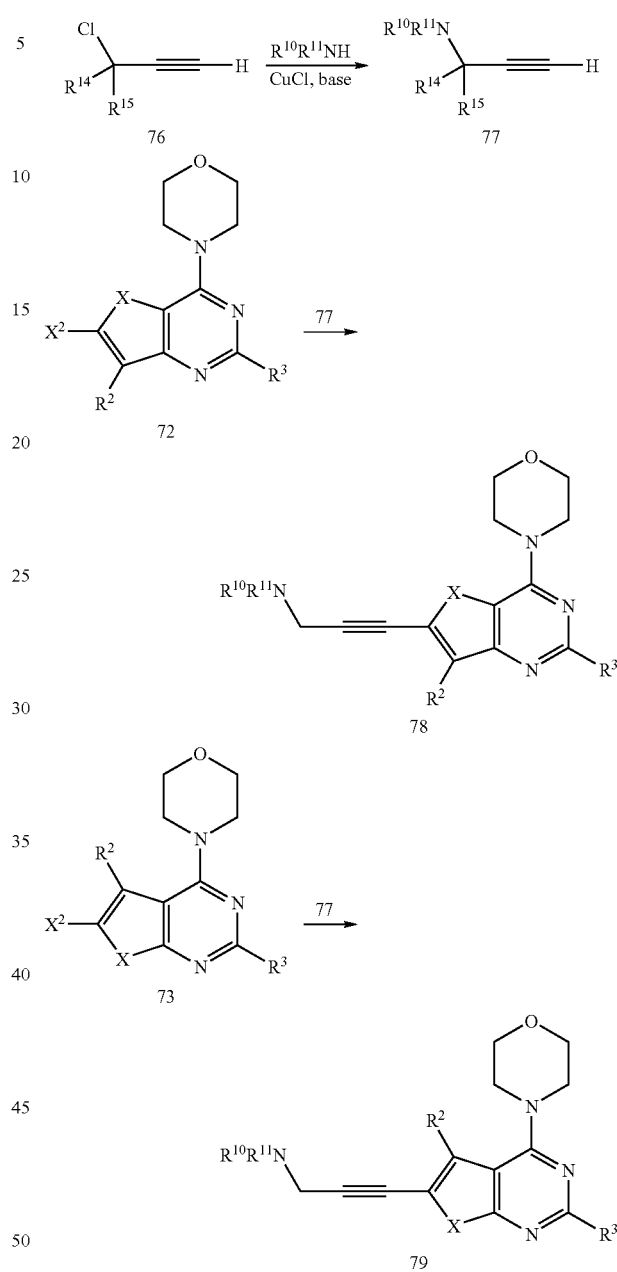

Scheme 5 shows a general method for the synthesis of alkynes 71, which can be used to prepare alkynylated derivatives of compounds 72 and 73. Propargylic amines 71 may be prepared by reaction of propargyl bromide 70 with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) in the presence of an appropriate base ($Cs_2CO_3$ or the like). For reviews of alkynyl amines and related syntheses see Booker-Milburn, K. I., *Comprehensive Organic Functional Group Transformations* (1995), 2:1039-1074; and Viehe, H. G., (1967) Angew. Chem., Int. Ed. Eng., 6(9):767-778. Alkynes 71 may subsequently be reacted with intermediates 72 ($X^2$=bromo or iodo) or 73 (via Sonogashira coupling), to provide compounds 74 and 75, respectively, wherein X is O or S, and $R^2$ and $R^3$ are as defined for Formula Ia and Ib compounds, or precursors or prodrugs thereto.

Scheme 6 shows a general method for the synthesis of alkynes 77, which can be used to prepare alkynylated derivatives of compounds 72 and 73. Gem-dialkyl propargylic amines 77 may be prepared using methods described by Zaragoza, F., et al. (2004) J. Med. Chem., 47:2833. According to Scheme 10, gem-dialkyl chloride 76 ($R^{14}$ and $R^{15}$ are independently methyl, ethyl or other alkyl group) can be reacted with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) in the presence of CuCl and an appropriate base (e.g. TEA or the like) to provide the alkyne 77. Alkyne 77 can be reacted with intermediates 72 or 73 (via Sonogashira coupling) to provide compounds 78 and 79, respectively, wherein X is O or S, and $R^2$ and $R^3$ are as defined for Formula Ia and Ib compounds, or precursors or prodrugs thereto.

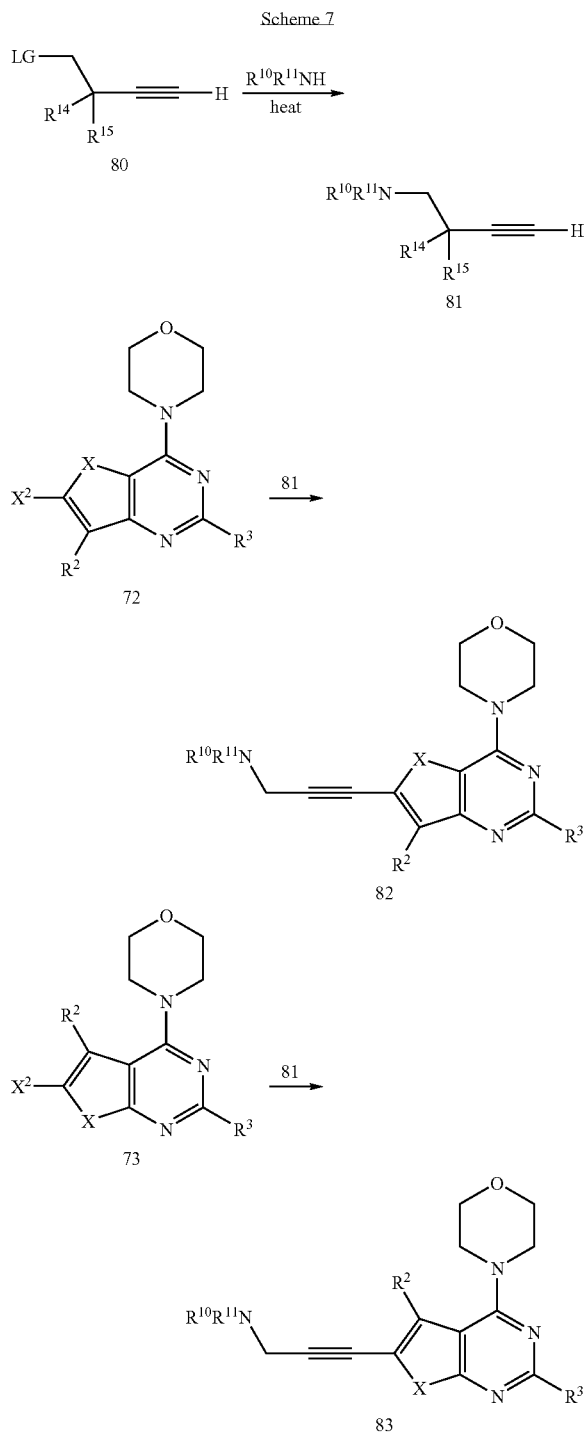

Scheme 7 shows a general scheme for the synthesis of alkynes 81, which can be used to prepare alkynylated derivatives of compounds 72 and 73. But-3-yn-1-amines 81 (wherein $R^{14}$ and $R^{15}$ are independently H, alkyl, aryl, heteroaryl, or $R^{14}$ and $R^{15}$ together with the carbon atom to which they are attached form a carbocyclic or heterocyclic ring) can be prepared from reaction of alkynes 80 (LG=tosylate or other leaving group) with an amine of the formula $R^{10}R^{11}NH$ (wherein $R^{10}$ and $R^{11}$ are independently selected from H, alkyl, aryl and heteroaryl, or $R^{10}$ and $R^{11}$ together with the nitrogen to which they are attached form a heterocyclic ring) using the protocol described by Olomucki M. et al (1960) Ann. Chim. 5:845. Alkynes 81 can subsequently be reacted with intermediates 72 or 73 (via Sonogashira coupling), according to the descriptions provided for Schemes 5 and 7 to provide compounds 82 and 83, respectively, wherein X is O or S, and $R^2$ and $R^3$ are as defined for Formula Ia and Ib compounds, or precursors or prodrugs thereto.

Methods of Separation

In the methods of preparing the compounds of this invention, it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point and molecular weight in distillation and sublimation, presence or absence of polar functional groups in chromatography, stability of materials in acidic and basic media in multiphase extraction, and the like. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem., (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

Biological Evaluation

Determination of the activity of PI3 kinase activity of a compound of Formula Ia or Ib is possible by a number of direct and indirect detection methods. Certain exemplary compounds described herein were prepared, characterized, and assayed for their PI3K binding activity (Examples 364 and 365) and in vitro activity against tumor cells (Example 366). The range of PI3K binding activities was less than 1 nM (nanomolar) to about 10 μM (micromolar). Certain exemplary compounds of the invention had PI3K binding activity $IC_{50}$ values less than 10 nM. Certain compounds of the invention had tumor cell-based activity $IC_{50}$ values less than 100 nM.

The Formula Ia and Ib compounds may inhibit p110 catalytic subunit isoforms including alpha, beta, gamma, and delta as pan inhibitors. Certain Formula Ia and Ib compounds may be p110 isoform selective inhibitors by selectively inhibiting one of one of the p110 isoforms; alpha, beta, gamma, or delta. One embodiment of the invention is a Formula Ia or Ib compound which is a p110 alpha selective inhibitor. A p110 selective inhibitor may mitigate the risk of toxicity due to potential toxicities associated with inhibiting the other p110 isoforms. Certain Formula Ia and Ib compounds may be p110 isoform pan inhibitors by possessing significant binding to two or more of the p110 isoforms. One embodiment of the invention is a Formula Ia or Ib compound which is a pan inhibitor of PI3K.

Binding of Formula Ia and Ib compounds from Tables 1a and 1b to purified preparations of p110 isoforms alpha, beta, delta, and gamma was measured by a Scintillation Proximity Assay (SPA) to determine binding activity ($IC_{50}$ μMol) and selectivity of binding of beta, delta, and gamma isoforms relative to alpha (Example 365). These values are expressed in Table 2.

The cytotoxic or cytostatic activity of Formula Ia and Ib exemplary compounds was measured by: establishing a proliferating mammalian tumor cell line in a cell culture medium, adding a Formula Ia or Ib compound, culturing the cells for a period from about 6 hours to about 5 days; and measuring cell viability (Example 366). Cell-based in vitro assays were used to measure viability, i.e. proliferation ($IC_{50}$), cytotoxicity ($EC_{50}$), and induction of apoptosis (caspase activation).

The in vitro potency of Formula Ia and Ib exemplary compounds was measured by the cell proliferation assay, CellTiter-Glo® Luminescent Cell Viability Assay, commercially available from Promega Corp., Madison, Wis. (Example 366). This homogeneous assay method is based on the recombinant expression of Coleoptera luciferase (U.S. Pat. Nos. 5,583,024; 5,674,713; 5,700,670) and determines the number of viable cells in culture based on quantitation of the ATP present, an indicator of metabolically active cells (Crouch et al (1993) J. Immunol. Meth. 160:81-88; U.S. Pat. No. 6,602,677). The CellTiter-Glo Assay was conducted in 96 or 384 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system can detect as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time.

The anti-proliferative effects of Formula Ia and Ib exemplary compounds were measured by the CellTiter-Glob Assay (Example 366) against several tumor cell lines, including PC3, Detroit 562, and MDAMB361.1. $EC_{50}$ values were established for the tested compounds. The range of in vitro cell potency activities was about 100 nM to about 10 μM.

Certain ADME properties were measured for certain exemplary compounds by assays including: Caco-2 Permeability (Example 367), Hepatocyte Clearance (Example 368), Cytochrome P450 Inhibition (Example 369), Cytochrome P450 Induction (Example 370), Plasma Protein Binding (Example 371), and HERG channel blockage (Example 372).

Exemplary Formula Ia and Ib compounds No. 101-446 which were made according to the methods of this invention include the following structures and their corresponding names (ChemDraw Ultra, CambridgeSoft Corp., Cambridge Mass.) in Tables 1a and 1b.

TABLE 1a

| No. | Structure | Name |
|---|---|---|
| 101. | 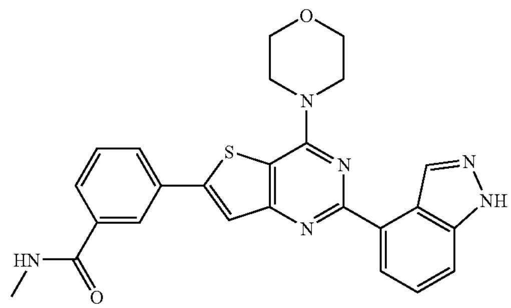 | 3-(2-(1H-indazol-4-yl)-4-morpholinothieno[3,2-d]pyrimidin-6-yl)-N-methylbenzamide |
| 102. | 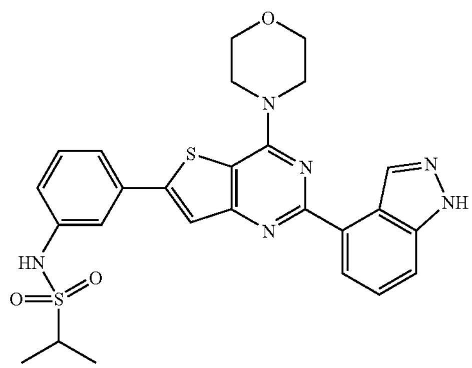 | 2-(1H-indazol-4-yl)-4-morpholino-6-(3-isopropylsulfonylaminophenyl)thieno[3,2-d]pyrimidine |
| 103. | 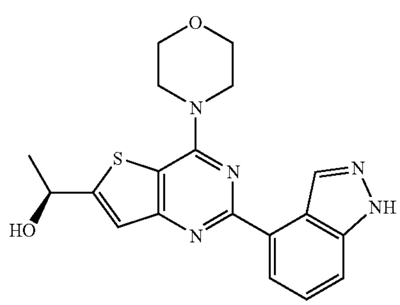 | (S)-1-(2-(1H-indazol-4-yl)-4-morpholinothieno[3,2-d]pyrimidin-6-yl)ethanol |
| 104. | 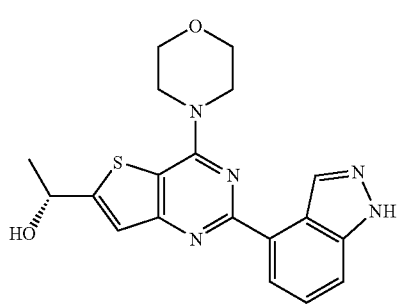 | (R)-1-(2-(1H-indazol-4-yl)-4-morpholinothieno[3,2-d]pyrimidin-6-yl)ethanol |

TABLE 1a-continued

| No. | Structure | Name |
|---|---|---|
| 105. | 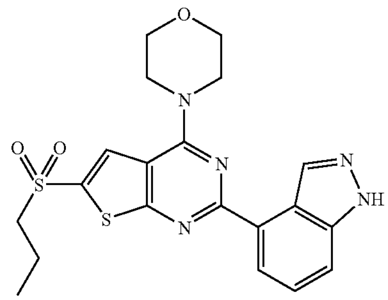 | 2-(1H-indazol-4-yl)-4-morpholino-6-(propylsulfonyl)thieno[2,3-d]pyrimidin |
| 106. | 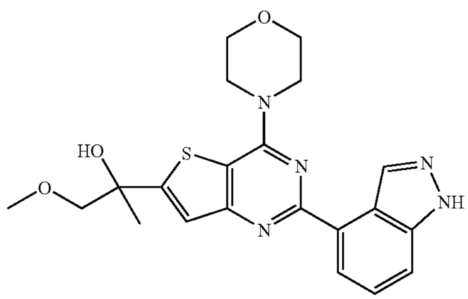 | 2-(2-(1H-indazol-4-yl)-4-morpholinothieno[3,2-d]pyrimidin-6-yl)-1-methoxypropan-2-ol |
| 107. | 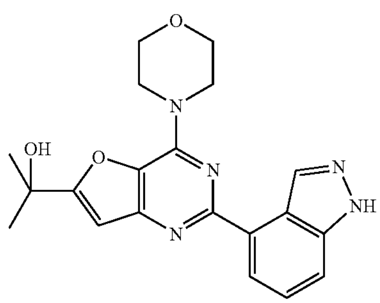 | 2-(2-(1H-indazol-4-yl)-4-morpholinofuro[3,2-d]pyrimidin-6-yl)propan-2-ol |
| 108. | 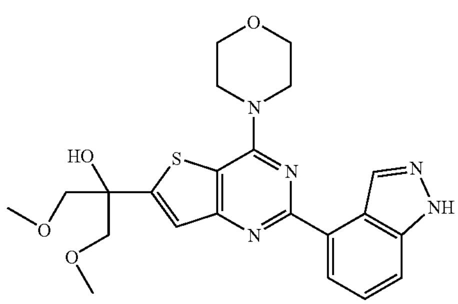 | 2-(2-(1H-indazol-4-yl)-4-morpholinothieno[3,2-d]pyrimidin-6-yl)-1,3-dimethoxypropan-2-ol |
| 109. | 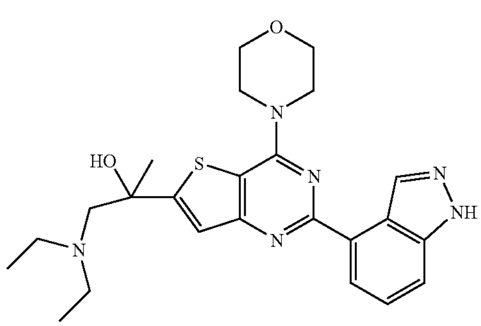 | 2-(2-(1H-indazol-4-yl)-4-morpholinothieno[3,2-d]pyrimidin-6-yl)-1-(diethylamino)propan-2-ol |

TABLE 1a-continued

| No. | Structure | Name |
|---|---|---|
| 110. | 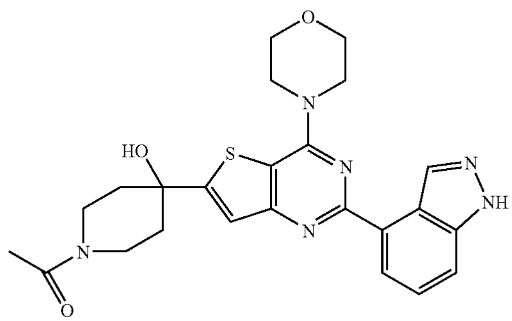 | 1-(4-(2-(1H-indazol-4-yl)-4-morpholinothieno[3,2-d]pyrimidin-6-yl)-4-hydroxypiperidin-1-yl)ethanone |
| 111. | 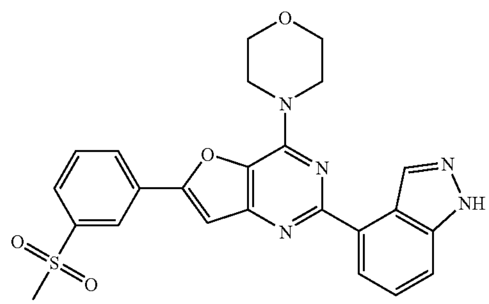 | 2-(1H-indazol-4-yl)-6-(3-(methylsulfonyl)phenyl)-4-morpholinofuro[3,2-d]pyrimidine |
| 112. | 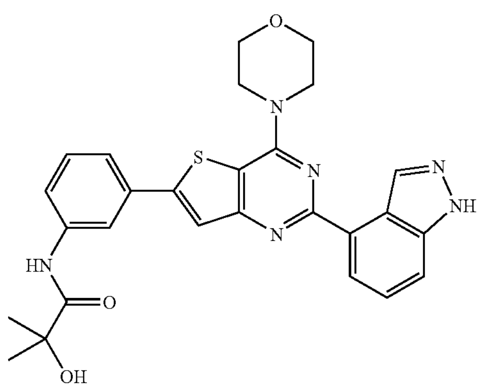 | N-(3-(2-(1H-indazol-4-yl)-4-morpholinothieno[3,2-d]pyrimidin-6-yl)phenyl)-2-hydroxy-2-methylpropanamide |
| 113. | 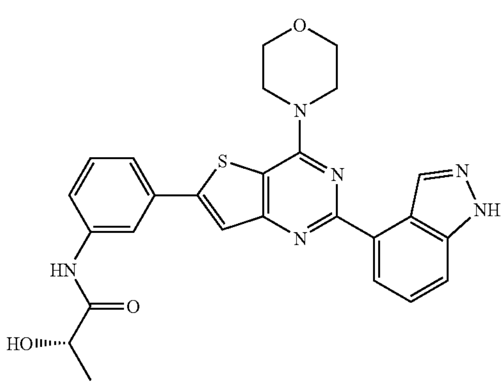 | (2S)-N-(3-(2-(1H-indazol-4-yl)-4-morpholinothieno[3,2-d]pyrimidin-6-yl)phenyl)-2-hydroxypropanamide |

TABLE 1a-continued

| No. | Structure | Name |
|---|---|---|
| 114. | 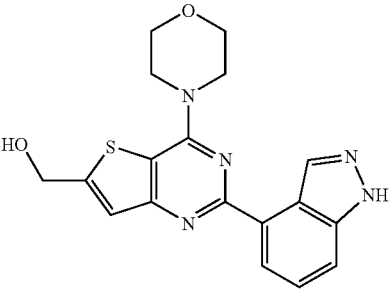 | (2-(1H-indazol-4-yl)-4-morpholinothieno[3,2-d]pyrimidin-6-yl)methanol |
| 115. | 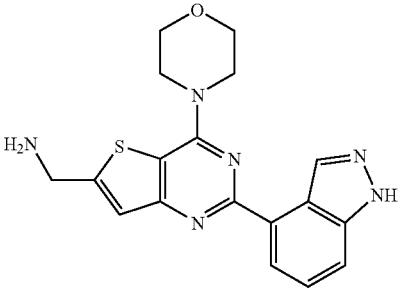 | (2-(1H-indazol-4-yl)-4-morpholinothieno[3,2-d]pyrimidin-6-yl)methanamine |
| 116. | 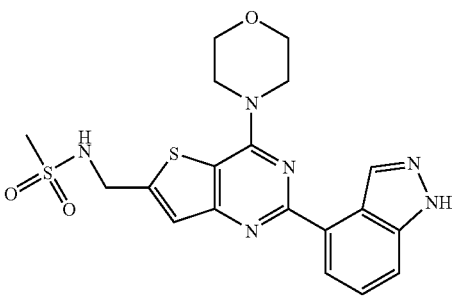 | (2-(1H-indazol-4-yl)-4-morpholinothieno[3,2-d]pyrimidin-6-yl)methan(methylsulfonyl)amine |
| 117. | 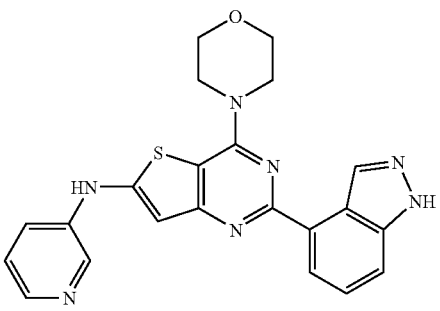 | 2-(1H-indazol-4-yl)-4-morpholino-N-(pyridin-3-yl)thieno[3,2-d]pyrimidin-6-amine |
| 118. | 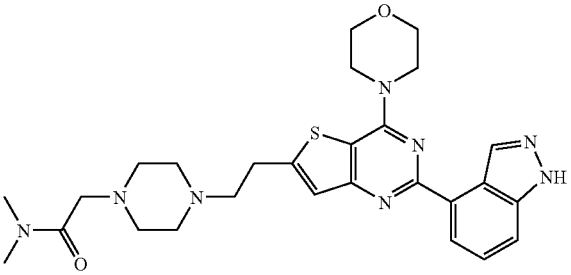 | 2-(4-(2-(2-(1H-indazol-4-yl)-4-morpholinothieno[3,2-d]pyrimidin-6-yl)ethyl)piperazin-1-yl)-N,N-dimethylacetamide |

TABLE 1a-continued

| No. | Structure | Name |
|---|---|---|
| 119. | 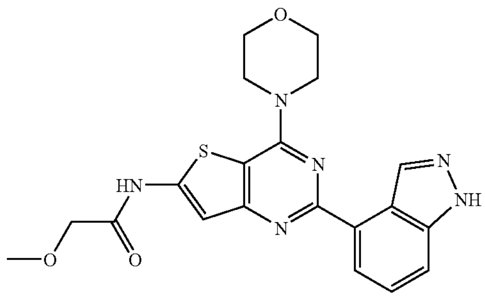 | N-(2-(1H-indazol-4-yl)-4-morpholinothieno[3,2-d]pyrimidin-6-yl)-2-methoxyacetamide |
| 120. | 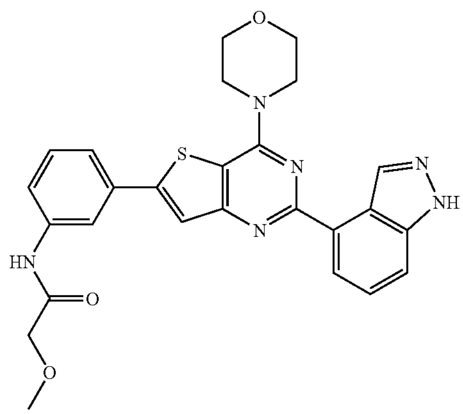 | N-(3-(2-(1H-indazol-4-yl)-4-morpholinothieno[3,2-d]pyrimidin-6-yl)phenyl)-2-methoxyacetamide |
| 121. | 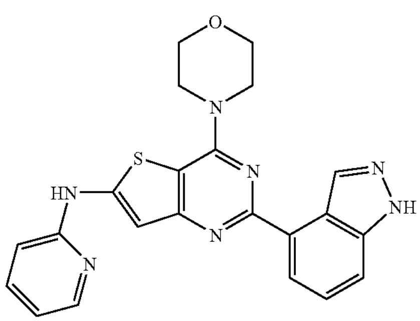 | 2-(1H-indazol-4-yl)-4-morpholino-N-(pyridin-2-yl)thieno[3,2-d]pyrimidin-6-amine |
| 122. | 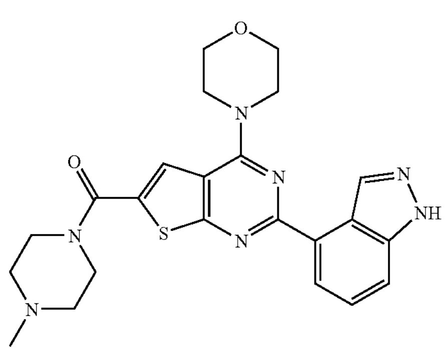 | (2-(1H-indazol-4-yl)-4-morpholinothieno[2,3-d]pyrimidin-6-yl)(4-methylpiperazin-1-yl)methanone |

TABLE 1a-continued

| No. | Structure | Name |
|-----|-----------|------|
| 123. | 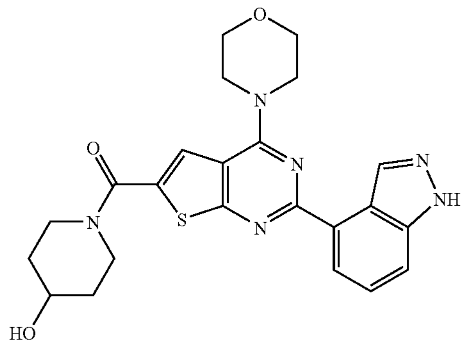 | (2-(1H-indazol-4-yl)-4-morpholinothieno[2,3-d]pyrimidin-6-yl)(4-hydroxypiperidin-1-yl)methanone |
| 124. | 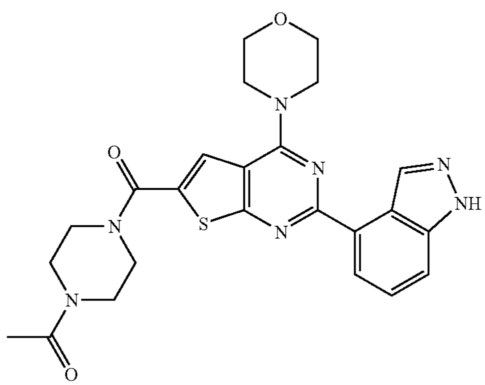 | (2-(1H-indazol-4-yl)-4-morpholinothieno[2,3-d]pyrimidin-6-yl)(4-acetylpiperazin-1-yl)methanone |
| 125. | 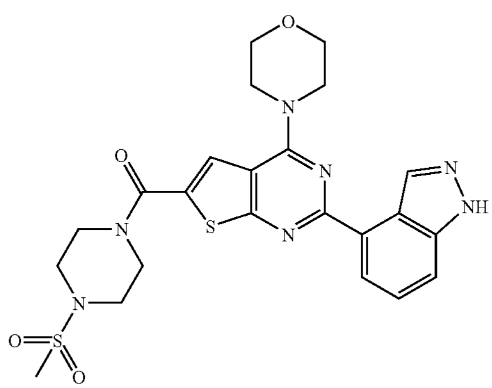 | (2-(1H-indazol-4-yl)-4-morpholinothieno[2,3-d]pyrimidin-6-yl)(4-methylsulfonylpiperazin-1-yl)methanone |
| 126. | 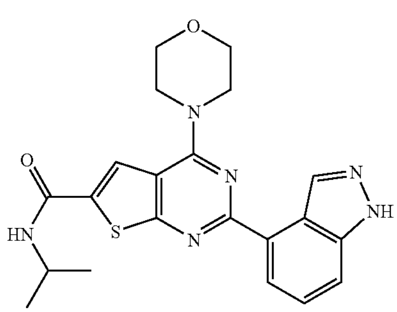 | 2-(1H-indazol-4-yl)-N-isopropyl-4-morpholinothieno[2,3-d]pyrimidine-6-carboxamide |

TABLE 1a-continued

| No. | Structure | Name |
|---|---|---|
| 127. | 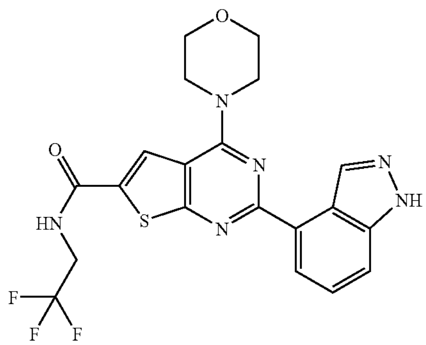 | N-(2,2,2-trifluoroethyl)-2-(1H-indazol-4-yl)-4-morpholinothieno[2,3-d]pyrimidine-6-carboxamide |
| 128. | 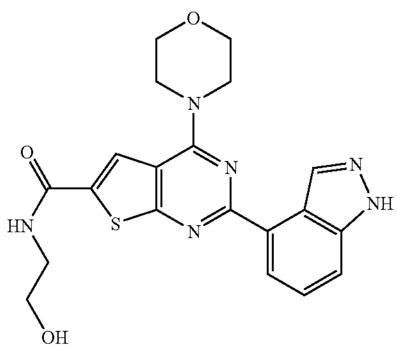 | N-(2-hydroxyethyl)-2-(1H-indazol-4-yl)-4-morpholinothieno[2,3-d]pyrimidine-6-carboxamide |
| 129. | 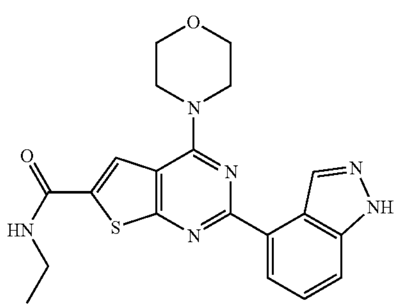 | N-ethyl-2-(1H-indazol-4-yl)-4-morpholinothieno[2,3-d]pyrimidine-6-carboxamide |
| 130. | 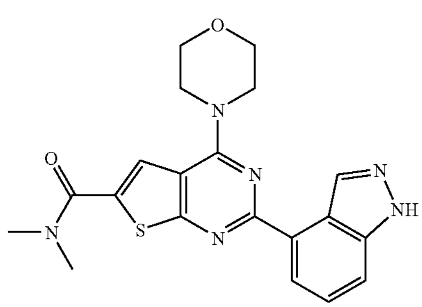 | 2-(1H-indazol-4-yl)-N,N-dimethyl-4-morpholinothieno[2,3-d]pyrimidine-6-carboxamide |

TABLE 1a-continued

| No. | Structure | Name |
|---|---|---|
| 131. | 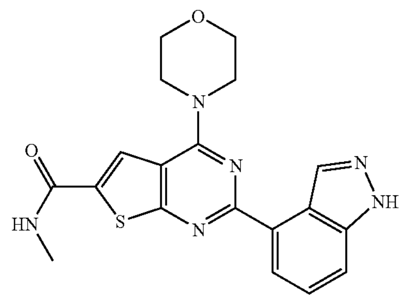 | 2-(1H-indazol-4-yl)-N-methyl-4-morpholinothieno[2,3-d]pyrimidine-6-carboxamide |
| 132. | 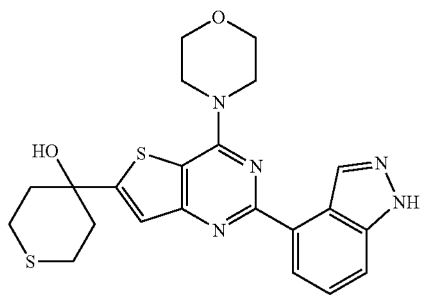 | 4-(2-(1H-indazol-4-yl)-4-morpholinothieno[3,2-d]pyrimidin-6-yl)-tetrahydro-2H-thiopyran-4-ol |
| 133. | 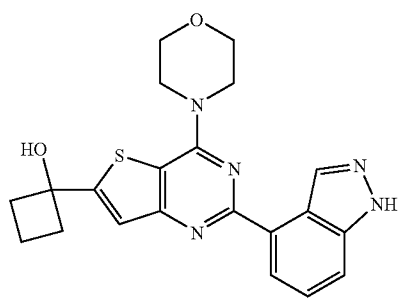 | 1-(2-(1H-indazol-4-yl)-4-morpholinothieno[3,2-d]pyrimidin-6-yl)cyclobutanol |
| 134. | 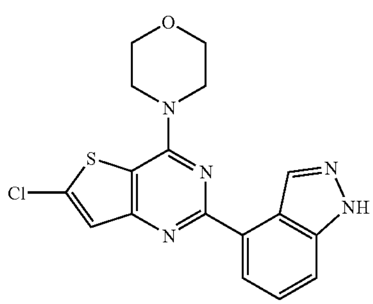 | 6-chloro-2-(1H-indazol-4-yl)-4-morpholinothieno[3,2-d]pyrimidine |
| 135. | 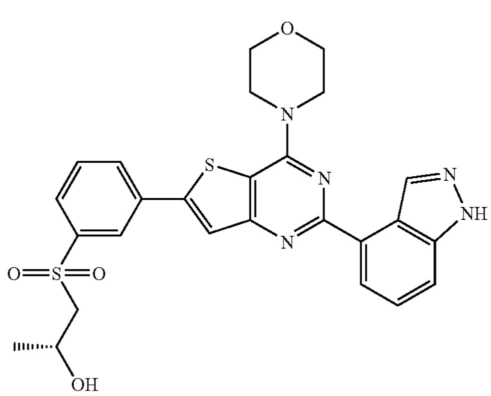 | (R)-1-(3-(2-(1H-indazol-4-yl)-4-morpholinothieno[3,2-d]pyrimidin-6-yl)phenylsulfonyl)propan-2-ol |

TABLE 1a-continued

| No. | Structure | Name |
|---|---|---|
| 136. | 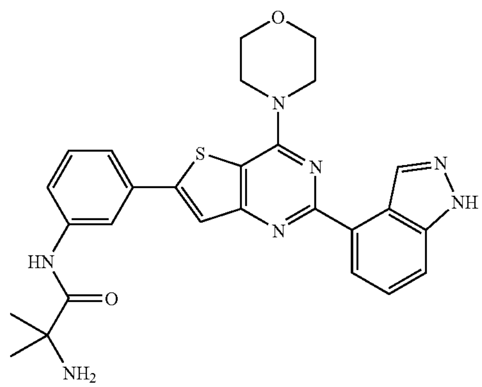 | N-(3-(2-(1H-indazol-4-yl)-4-morpholinothieno[3,2-d]pyrimidin-6-yl)phenyl)-2-amino-2-methylpropanamide |
| 137. | 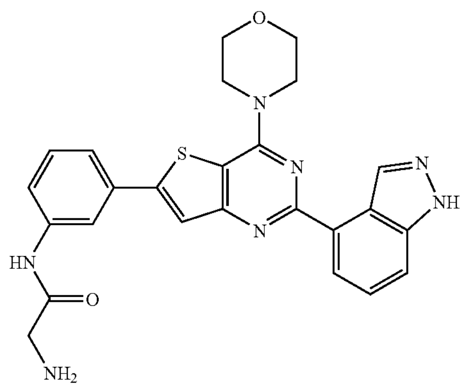 | N-(3-(2-(1H-indazol-4-yl)-4-morpholinothieno[3,2-d]pyrimidin-6-yl)phenyl)-2-aminoacetamide |
| 138. | 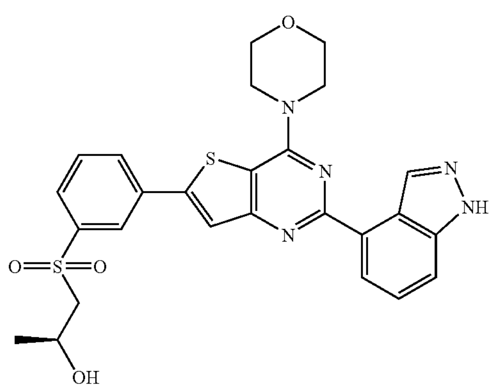 | (S)-1-(3-(2-(1H-indazol-4-yl)-4-morpholinothieno[3,2-d]pyrimidin-6-yl)phenylsulfonyl)propan-2-ol |
| 139. | 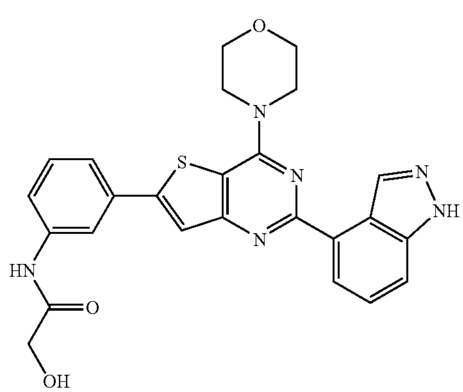 | N-(3-(2-(1H-indazol-4-yl)-4-morpholinothieno[3,2-d]pyrimidin-6-yl)phenyl)-2-hydroxyacetamide |

TABLE 1a-continued

| No. | Structure | Name |
|---|---|---|
| 140. | 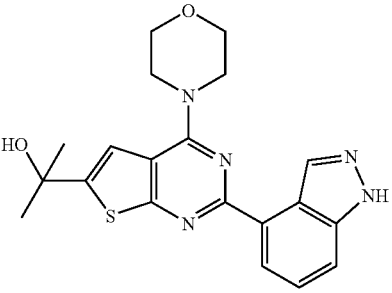 | 2-(2-(1H-indazol-4-yl)-4-morpholinothieno[2,3-d]pyrimidin-6-yl)propan-2-ol |
| 141. | 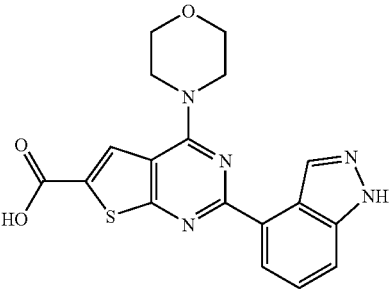 | 2-(1H-indazol-4-yl)-4-morpholinothieno[2,3-d]pyrimidine-6-carboxylic acid |
| 142. | 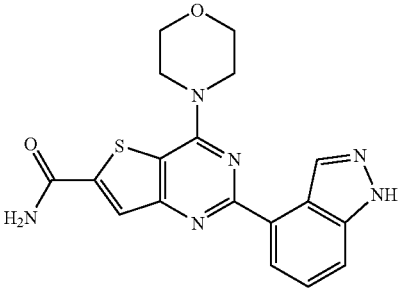 | 2-(1H-indazol-4-yl)-4-morpholinothieno[3,2-d]pyrimidine-6-carboxamide |
| 143. | 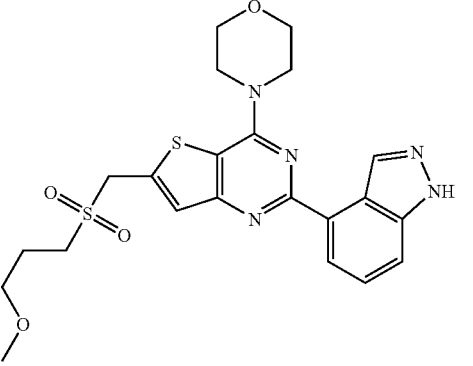 | 6-((3-methoxypropylsulfonyl)methyl)-2-(1H-indazol-4-yl)-4-morpholinothieno[3,2-d]pyrimidine |
| 144. | 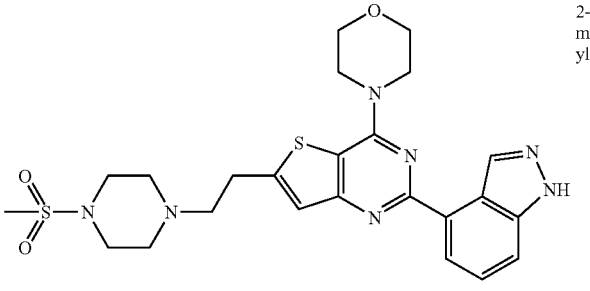 | 2-(1H-indazol-4-yl)-4-morpholino-6-(2-(4-methylsulfonylpiperazin-1-yl)ethyl)thieno[3,2-d]pyrimidine |

TABLE 1a-continued

| No. | Structure | Name |
| --- | --- | --- |
| 145. | 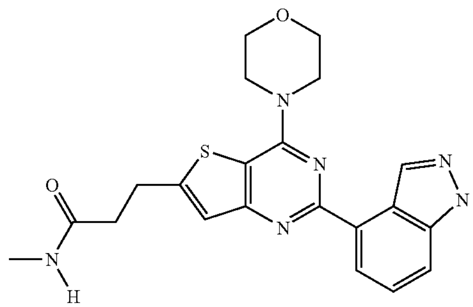 | 3-(2-(1H-indazol-4-yl)-4-morpholinothieno[3,2-d]pyrimidin-6-yl)-N-methylpropanamide |
| 146. | 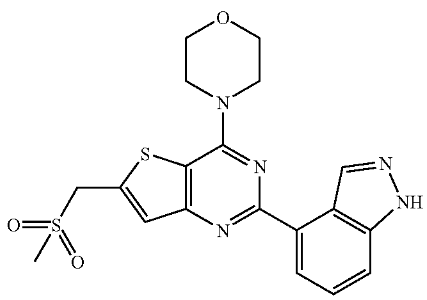 | 2-(1H-indazol-4-yl)-6-((methylsulfonyl)methyl)-4-morpholinothieno[3,2-d]pyrimidine |
| 147. | 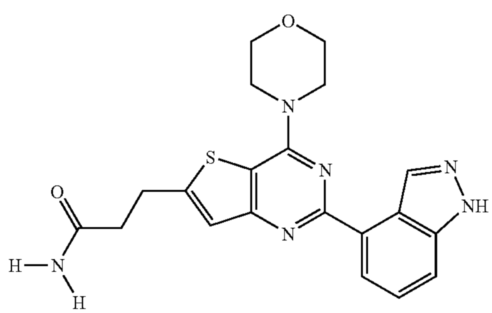 | 3-(2-(1H-indazol-4-yl)-4-morpholinothieno[3,2-d]pyrimidin-6-yl)propanamide |
| 148. | 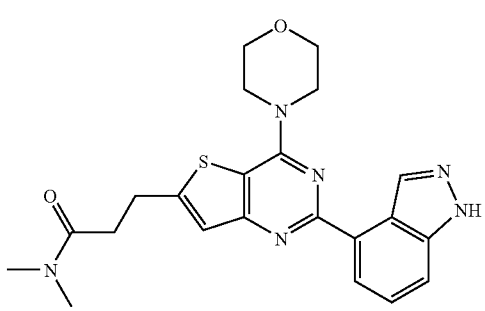 | 3-(2-(1H-indazol-4-yl)-4-morpholinothieno[3,2-d]pyrimidin-6-yl)-N,N-dimethylpropanamide |

TABLE 1a-continued

| No. | Structure | Name |
|---|---|---|
| 149. | 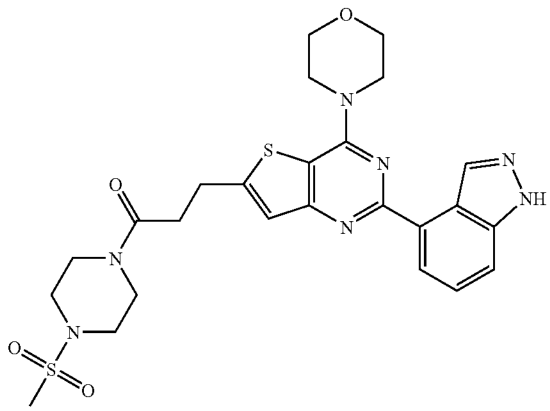 | 3-(2-(1H-indazol-4-yl)-4-morpholinothieno[2,3-d]pyrimidin-6-yl)-1-(4-methylsulfonylpiperazin-1-yl)propanone |
| 150. | 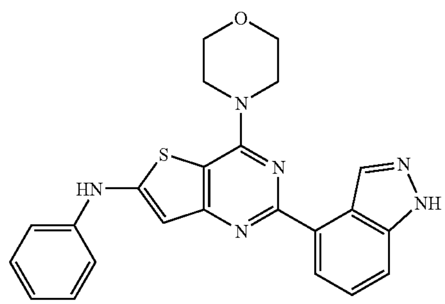 | 2-(1H-indazol-4-yl)-4-morpholino-N-phenylthieno[3,2-d]pyrimidin-6-amine |
| 151. | 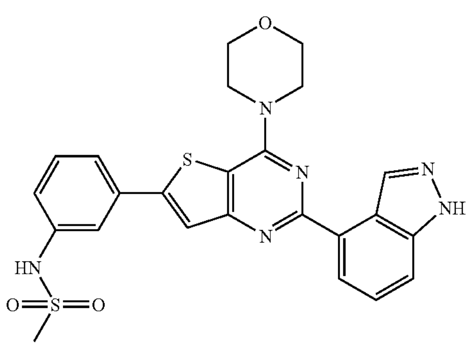 | 3-(2-(1H-indazol-4-yl)-4-morpholinothieno[3,2-d]pyrimidin-6-yl)benzenemethylsulfonamide |
| 152. | 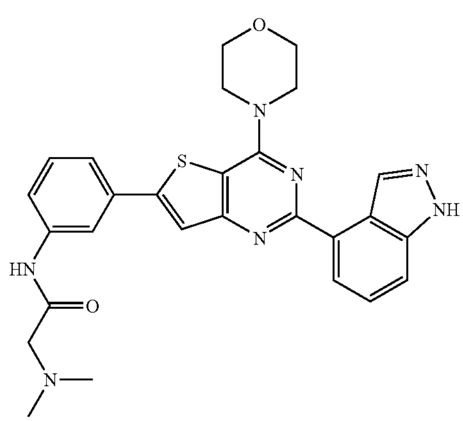 | N-(3-(2-(1H-indazol-4-yl)-4-morpholinothieno[3,2-d]pyrimidin-6-yl)phenyl)-2-(dimethylamino)acetamide |

TABLE 1a-continued

| No. | Structure | Name |
|---|---|---|
| 153. | 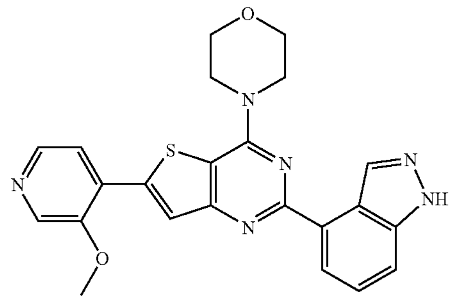 | 2-(1H-indazol-4-yl)-6-(3-methoxypyridin-4-yl)-4-morpholinothieno[3,2-d]pyrimidine |
| 154. | 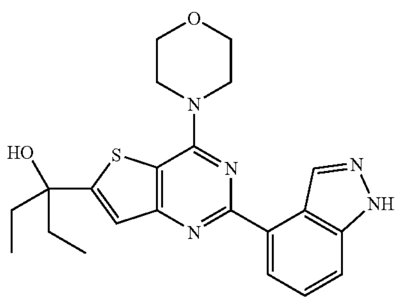 | 3-(2-(1H-indazol-4-yl)-4-morpholinothieno[3,2-d]pyrimidin-6-yl)pentan-3-ol |
| 155. | 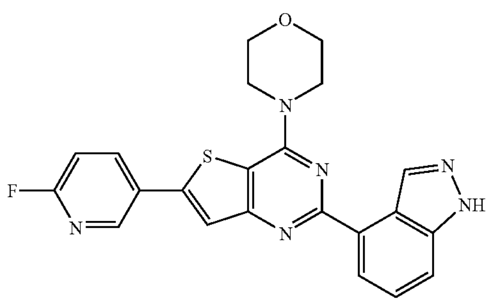 | 6-(6-fluoropyridin-3-yl)-2-(1H-indazol-4-yl)-4-morpholinothieno[3,2-d]pyrimidine |
| 156. | 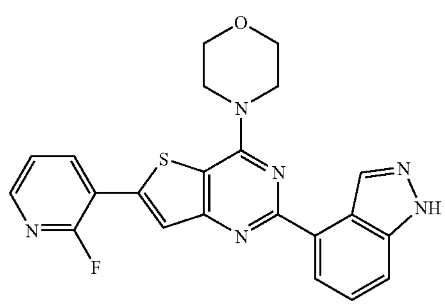 | 6-(2-fluoropyridin-3-yl)-2-(1H-indazol-4-yl)-4-morpholinothieno[3,2-d]pyrimidine |
| 157. | 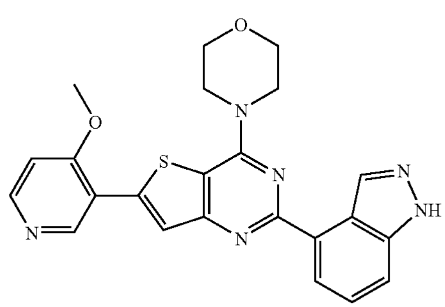 | 2-(1H-indazol-4-yl)-6-(4-methoxypyridin-3-yl)-4-morpholinothieno[3,2-d]pyrimidine |

TABLE 1a-continued

| No. | Structure | Name |
|---|---|---|
| 158. | 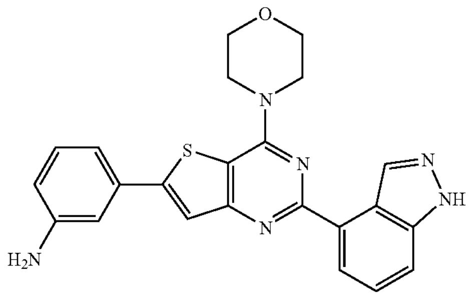 | 3-(2-(1H-indazol-4-yl)-4-morpholinothieno[3,2-d]pyrimidin-6-yl)benzenamine |
| 159. | 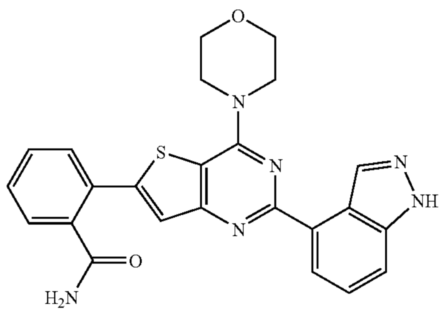 | 2-(2-(1H-indazol-4-yl)-4-morpholinothieno[3,2-d]pyrimidin-6-yl)benzamide |
| 160. | 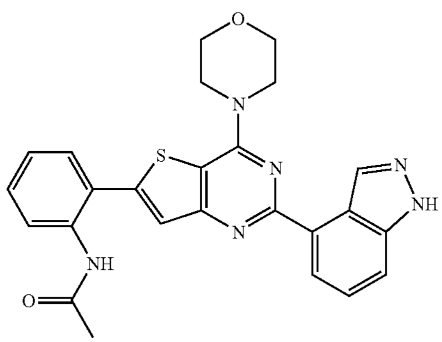 | N-(2-(2-(1H-indazol-4-yl)-4-morpholinothieno[3,2-d]pyrimidin-6-yl)phenyl)acetamide |
| 161. | 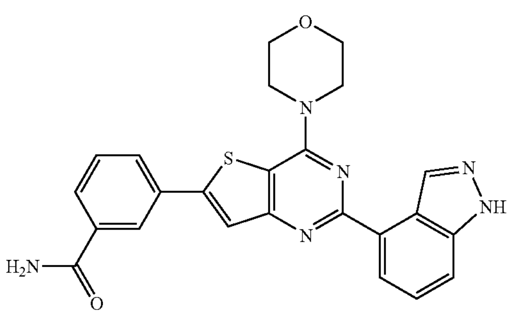 | 3-(2-(1H-indazol-4-yl)-4-morpholinothieno[3,2-d]pyrimidin-6-yl)benzamide |
| 162. | 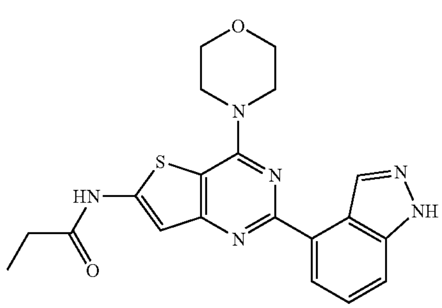 | N-(2-(1H-indazol-4-yl)-4-morpholinothieno[3,2-d]pyrimidin-6-yl)propionamide |

TABLE 1a-continued
| No. | Structure | Name |
|---|---|---|
| 163. | 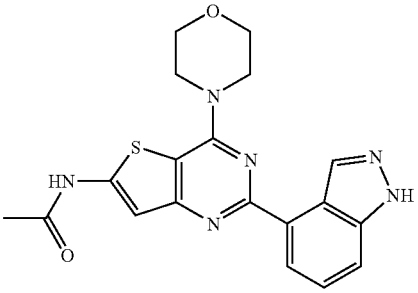 | N-(2-(1H-indazol-4-yl)-4-morpholinothieno[3,2-d]pyrimidin-6-yl)acetamide |
| 164. | 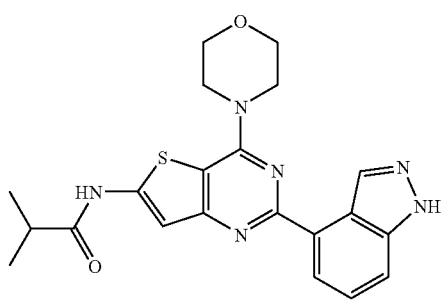 | N-(2-(1H-indazol-4-yl)-4-morpholinothieno[3,2-d]pyrimidin-6-yl)isobutyramide |
| 165. | 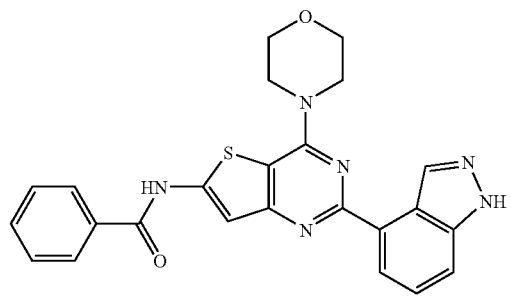 | N-(2-(1H-indazol-4-yl)-4-morpholinothieno[3,2-d]pyrimidin-6-yl)benzamide |
| 166. | 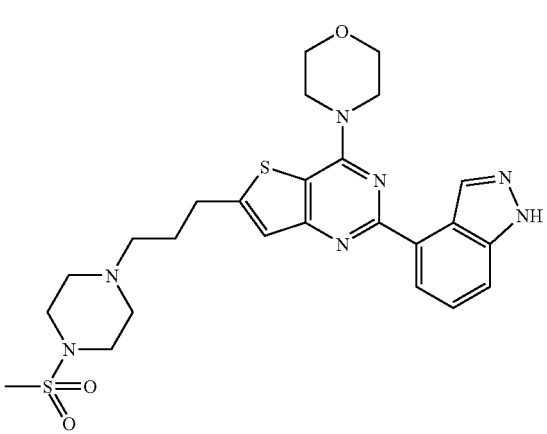 | 3-(1H-indazol-4-yl)-4-morpholino-6-(2-(4-methylsulfonylpiperazin-1-yl)propyl)thieno[3,2-d]pyrimidine |

TABLE 1a-continued

| No. | Structure | Name |
|---|---|---|
| 167. | 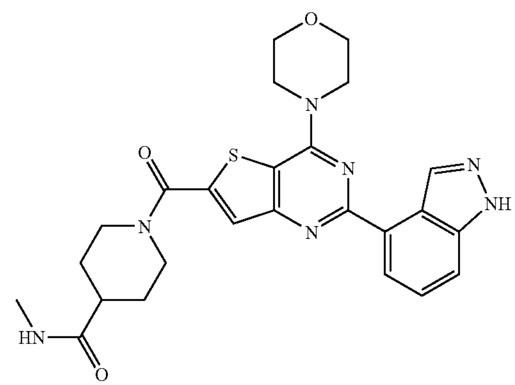 | (2-(1H-indazol-4-yl)-4-morpholinothieno[3,2-d]pyrimidin-6-yl)(4-(methylacetamido)piperidin-1-yl)methanone |
| 168. | 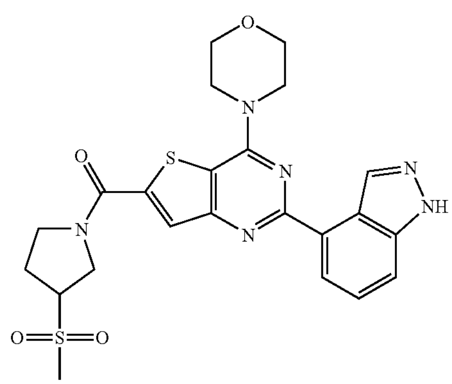 | (2-(1H-indazol-4-yl)-4-morpholinothieno[3,2-d]pyrimidin-6-yl)(3-(methylsulfonyl)pyrrolidin-1-yl)methanone |
| 169. | 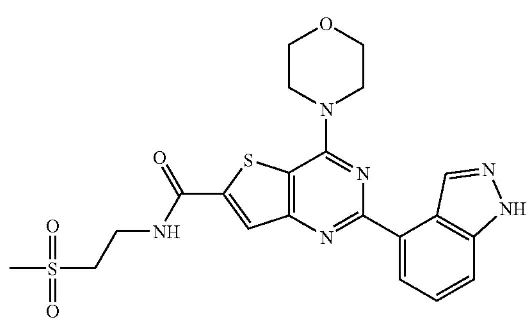 | 2-(1H-indazol-4-yl)-N-(2-(methylsulfonyl)ethyl)-4-morpholinothieno[3,2-d]pyrimidine-6-carboxamide |
| 170. | 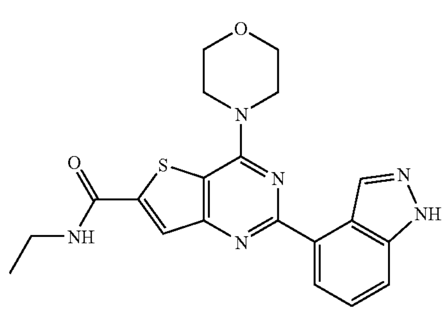 | N-ethyl-2-(1H-indazol-4-yl)-4-morpholinothieno[3,2-d]pyrimidine-6-carboxamide |

TABLE 1a-continued

| No. | Structure | Name |
|-----|-----------|------|
| 171. | 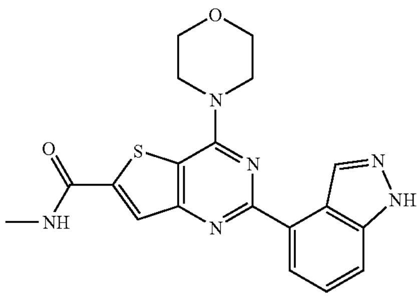 | 2-(1H-indazol-4-yl)-N-methyl-4-morpholinothieno[3,2-d]pyrimidine-6-carboxamide |
| 172. | 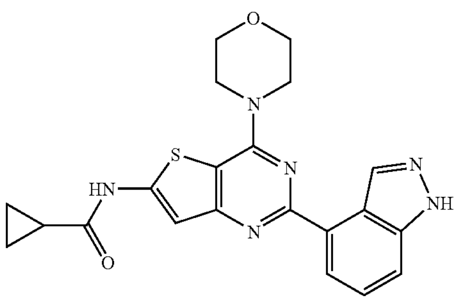 | N-(2-(1H-indazol-4-yl)-4-morpholinothieno[3,2-d]pyrimidin-6-yl)cyclopropanecarboxamide |
| 173. | 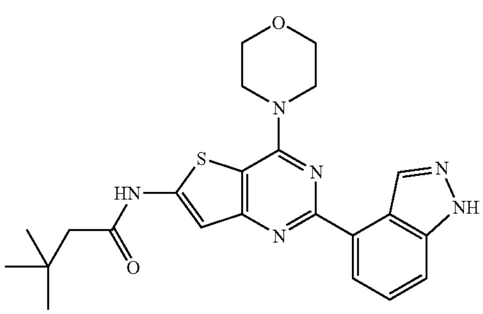 | N-(2-(1H-indazol-4-yl)-4-morpholinothieno[3,2-d]pyrimidin-6-yl)-3,3-dimethylbutanamide |
| 174. | 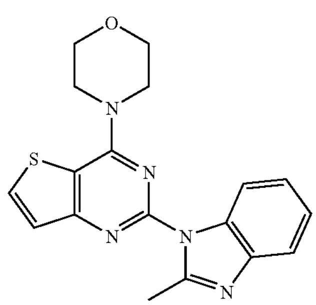 | 2-(2-methyl-1H-benzo[d]imidazol-1-yl)-4-morpholinothieno[3,2-d]pyrimidine |
| 175. | 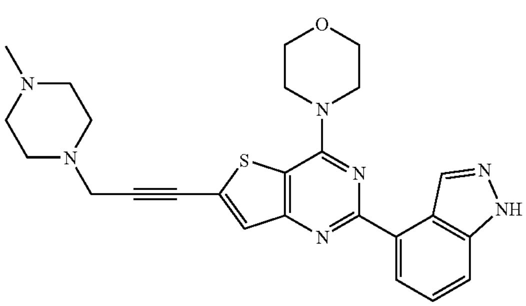 | 2-(1H-indazol-4-yl)-6-(3-(4-methylpiperazin-1-yl)prop-1-ynyl)-4-morpholinothieno[3,2-d]pyrimidine |

TABLE 1a-continued

| No. | Structure | Name |
|---|---|---|
| 176. | 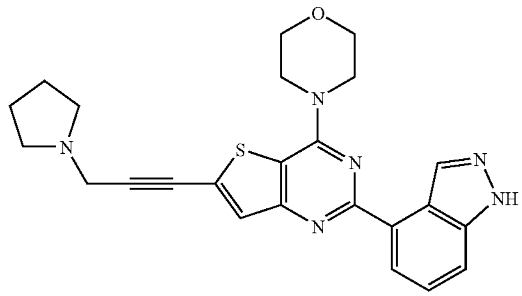 | 2-(1H-indazol-4-yl)-4-morpholino-6-(3-(pyrrolidin-1-yl)prop-1-ynyl)thieno[3,2-d]pyrimidine |
| 177. | 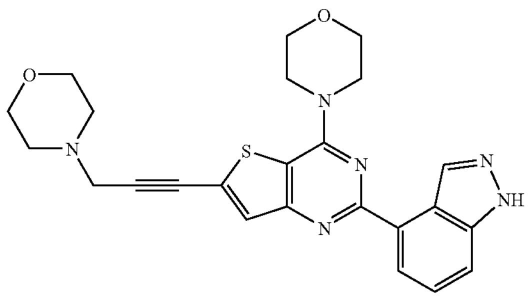 | 2-(1H-indazol-4-yl)-4-morpholino-6-(3-morpholinoprop-1-ynyl)thieno[3,2-d]pyrimidine |
| 178. | 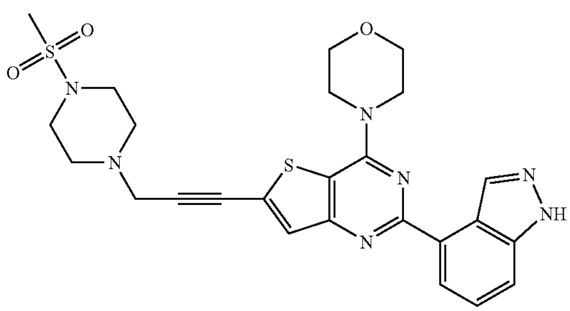 | 2-(1H-indazol-4-yl)-4-morpholino-6-(3-(4-methylsulfonylpiperazin-1-yl)thieno[3,2-d]pyrimidine |
| 179. | 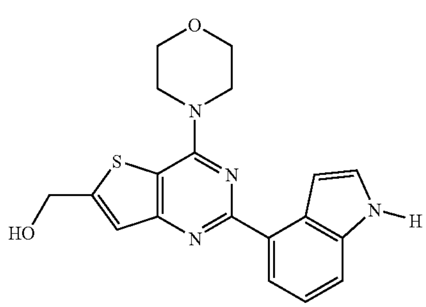 | (2-(1H-indol-4-yl)-4-morpholinothieno[3,2-d]pyrimidin-6-yl)methanol |
| 180. | 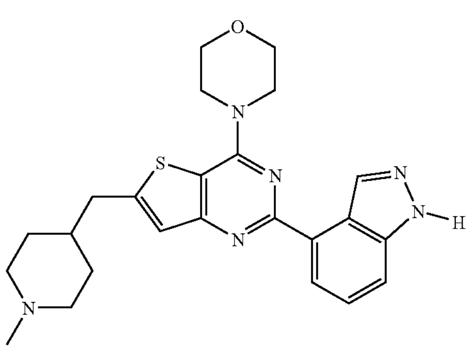 | 2-(1H-indazol-4-yl)-6-((1-methylpiperidin-4-yl)methyl)-4-morpholinothieno[3,2-d]pyrimidine |

TABLE 1a-continued

| No. | Structure | Name |
|---|---|---|
| 181. | 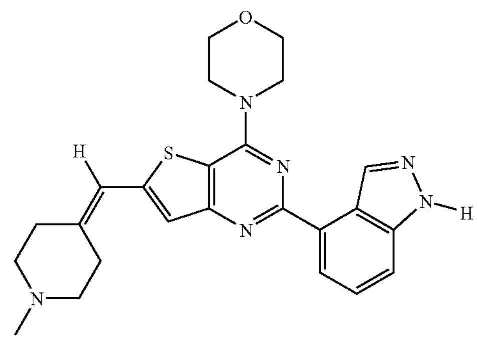 | 2-(1H-indazol-4-yl)-6-((1-methylpiperidin-4-ylidene)methyl)-4-morpholinothieno[3,2-d]pyrimidine |
| 182. | 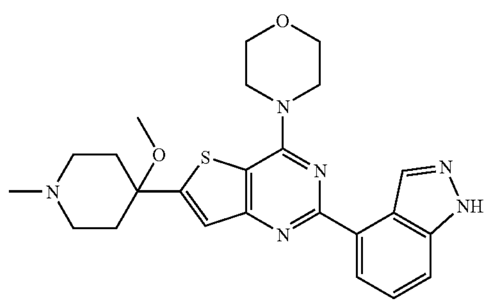 | 2-(1H-indazol-4-yl)-6-(4-methoxy-1-methylpiperidin-4-yl)-4-morpholinothieno[3,2-d]pyrimidine |
| 183. | 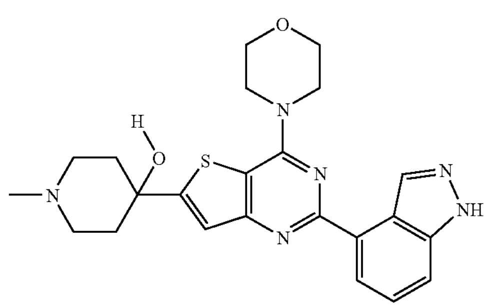 | 4-(2-(1H-indazol-4-yl)-4-morpholinothieno[3,2-d]pyrimidin-6-yl)-1-methylpiperidin-4-ol |
| 184. | 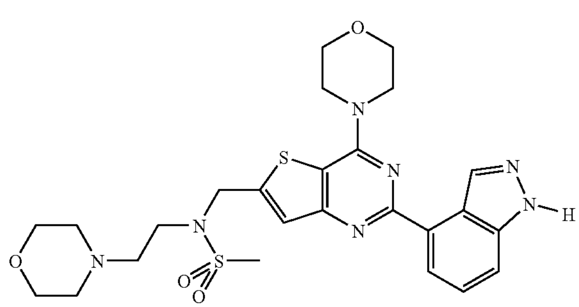 | (2-(1H-indazol-4-yl)-4-morpholinothieno[3,2-d]pyrimidin-6-yl)-N-sulfonylmethyl-N-(2-morpholinoethyl)methanamine |

TABLE 1a-continued

| No. | Structure | Name |
|---|---|---|
| 185. | 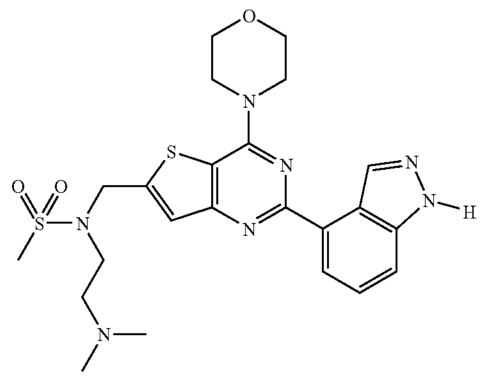 | (2-(1H-indazol-4-yl)-4-morpholinothieno[3,2-d]pyrimidin-6-yl)-N-methylsulfonyl-N-(2-N,N-dimethylaminoethyl)methanamine |
| 186. | 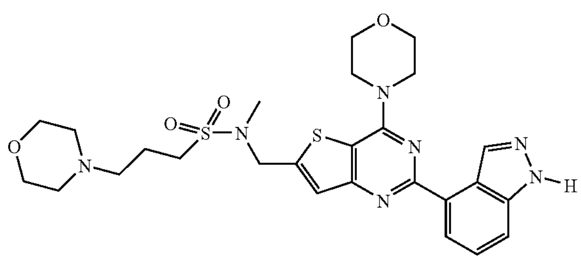 | (2-(1H-indazol-4-yl)-4-morpholinothieno[3,2-d]pyrimidin-6-yl)-N-methyl,N-(3-morpholinopropylsulfonyl)methanamine |
| 187. | 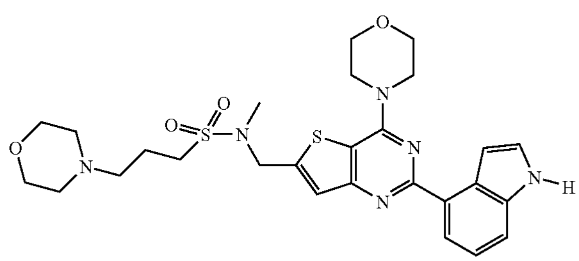 | (2-(1H-indol-4-yl)-4-morpholinothieno[3,2-d]pyrimidin-6-yl)-N-methyl,N-(3-morpholinopropylsulfonyl)methanamine |
| 188. | 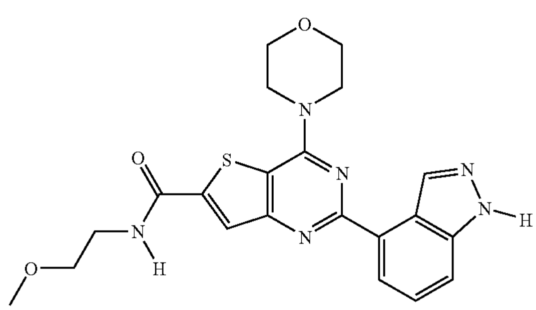 | 2-(1H-indazol-4-yl)-N-(2-methoxyethyl)-4-morpholinothieno[3,2-d]pyrimidine-6-carboxamide |
| 189. | 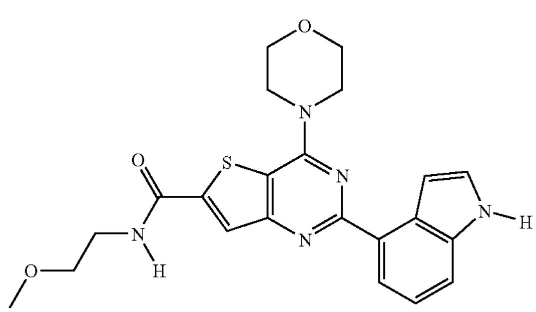 | 2-(1H-indol-4-yl)-N-(2-methoxyethyl)-4-morpholinothieno[3,2-d]pyrimidine-6-carboxamide |

TABLE 1a-continued

| No. | Structure | Name |
|---|---|---|
| 190. | 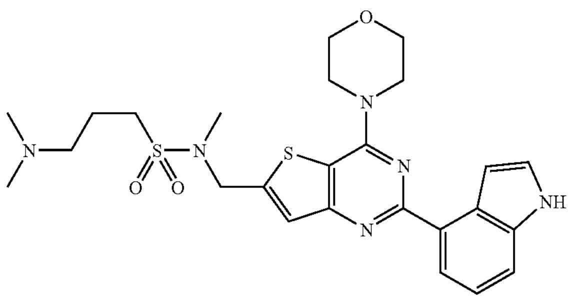 | (2-(1H-indol-4-yl)-4-morpholinothieno[3,2-d]pyrimidin-6-yl)-N-methyl-N-(2-N,N-dimethylaminosulfonyl)methanamine |
| 191. | 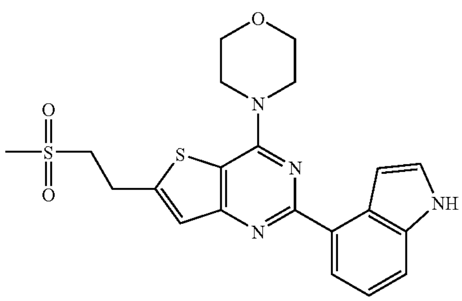 | 2-(1H-indol-4-yl)-6-(2-(methylsulfonyl)ethyl)-4-morpholinothieno[3,2-d]pyrimidine |
| 192. | 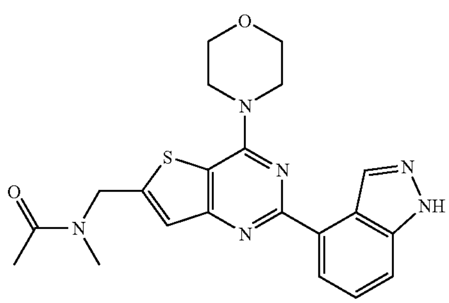 | N-((2-(1H-indazol-4-yl)-4-morpholinothieno[3,2-d]pyrimidin-6-yl)methyl)-N-methylacetamide |
| 193. | 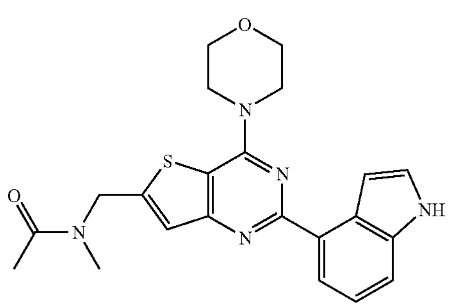 | N-((2-(1H-indol-4-yl)-4-morpholinothieno[3,2-d]pyrimidin-6-yl)methyl)-N-methylacetamide |
| 194. | 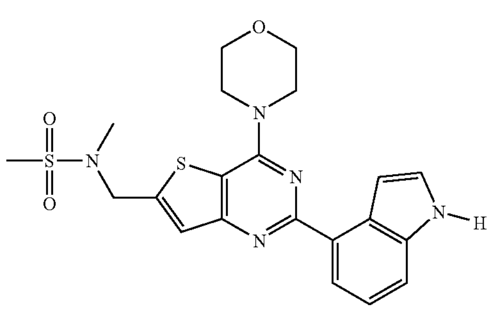 | N-((2-(1H-indol-4-yl)-4-morpholinothieno[3,2-d]pyrimidin-6-yl)methyl)-N-(methyl)methylsulfonamide |

TABLE 1a-continued

| No. | Structure | Name |
|-----|-----------|------|
| 195. | 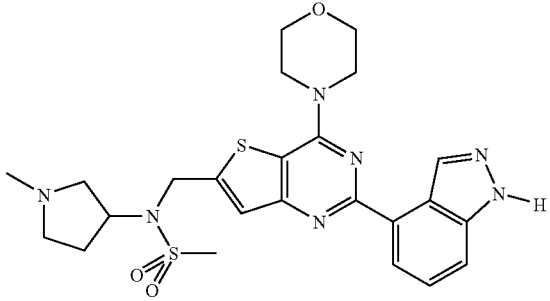 | N-((2-(1H-indazol-4-yl)-4-morpholinothieno[3,2-d]pyrimidin-6-yl)methyl)-N-methylsulfonyl-1-methylpyrrolidin-3-amine |
| 196. | 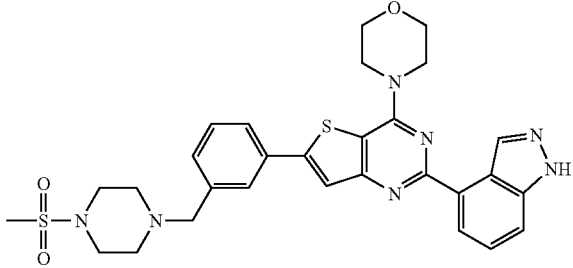 | 2-(1H-indazol-4-yl)-6-(3-((4-methylsulfonylpiperazin-1-yl)methyl)phenyl)-4-morpholinothieno[3,2-d]pyrimidine |
| 197. | 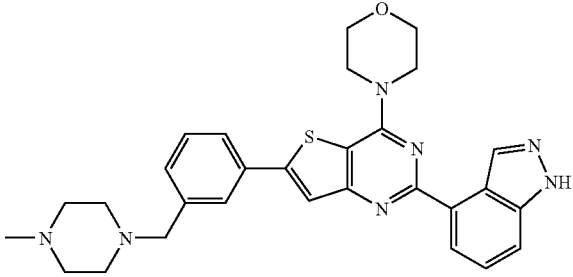 | 2-(1H-indazol-4-yl)-6-(3-((4-methylpiperazin-1-yl)methyl)phenyl)-4-morpholinothieno[3,2-d]pyrimidine |
| 198. | 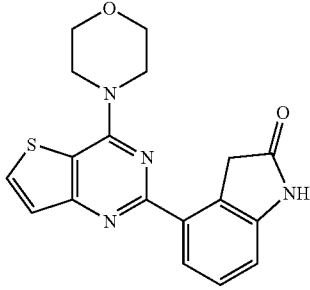 | 4-(4-morpholinothieno[3,2-d]pyrimidin-2-yl)indolin-2-one |
| 199. | 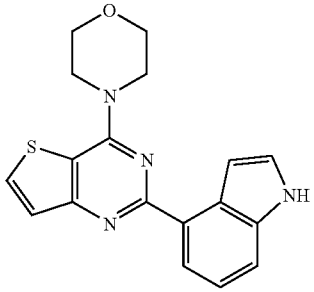 | 2-(1H-indol-4-yl)-4-morpholinothieno[3,2-d]pyrimidine |

TABLE 1a-continued

| No. | Structure | Name |
|---|---|---|
| 200. | 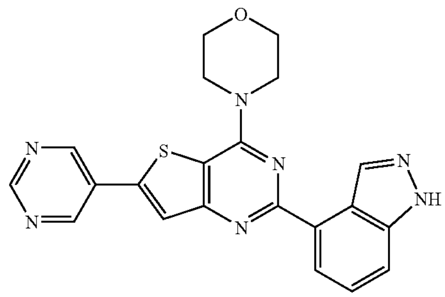 | 2-(1H-indazol-4-yl)-4-morpholino-6-(pyrimidin-5-yl)thieno[3,2-d]pyrimidine |
| 201. | 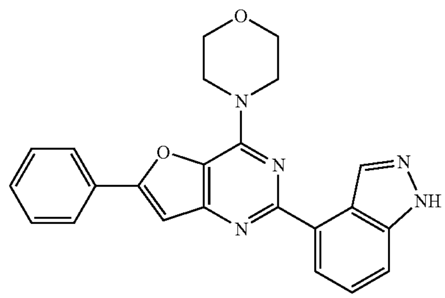 | 2-(1H-indazol-4-yl)-4-morpholino-6-phenylfuro[3,2-d]pyrimidine |
| 202. | 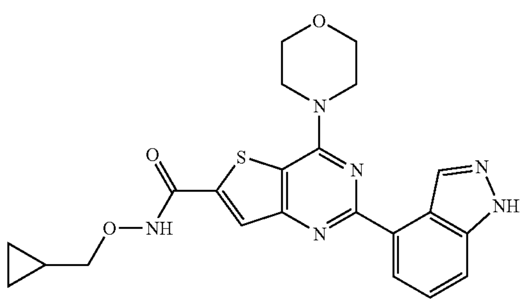 | N-(cyclopropylmethoxy)-2-(1H-indazol-4-yl)-4-morpholinothieno[3,2-d]pyrimidine-6-carboxamide |
| 203. | 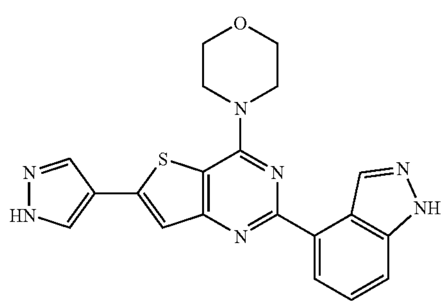 | 2-(1H-indazol-4-yl)-4-morpholino-6-(1H-pyrazol-4-yl)thieno[3,2-d]pyrimidine |
| 204. | 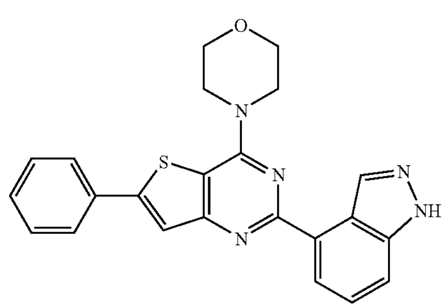 | 2-(1H-indazol-4-yl)-4-morpholino-6-phenylthieno[3,2-d]pyrimidine |

TABLE 1a-continued

| No. | Structure | Name |
|---|---|---|
| 205. | 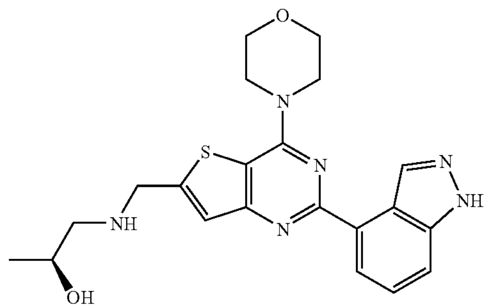 | (S)-1-((2-(1H-indazol-4-yl)-4-morpholinothieno[3,2-d]pyrimidin-6-yl)methylamino)propan-2-ol |
| 206. | 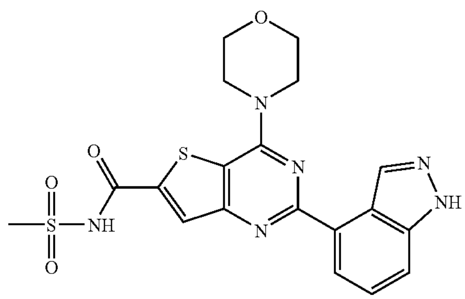 | 2-(1H-indazol-4-yl)-N-(methylsulfonyl)-4-morpholinothieno[3,2-d]pyrimidine-6-carboxamide |
| 207. | 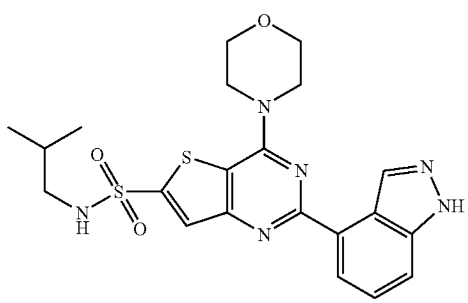 | 6-(isobutylaminosulfonyl)-2-(1H-indazol-4-yl)-4-morpholinothieno[3,2-d]pyrimidine |
| 208. | 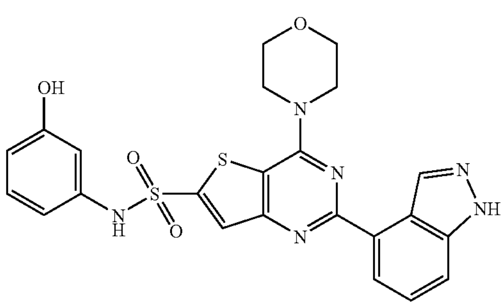 | 6-(3-hydroxyphenylaminosulfonyl)-2-(1H-indazol-4-yl)-4-morpholinothieno[3,2-d]pyrimidine |
| 209. | 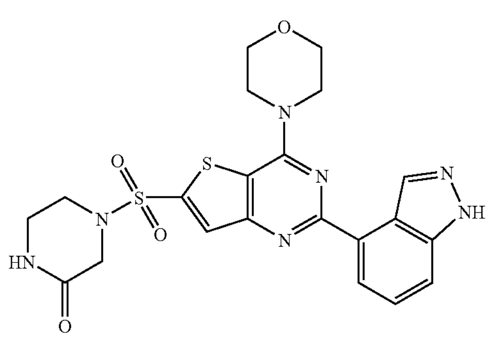 | 6-((4-piperazin-2-one)sulfonyl)-2-(1H-indazol-4-yl)-4-morpholinothieno[3,2-d]pyrimidine |

TABLE 1a-continued

| No. | Structure | Name |
|---|---|---|
| 210. | 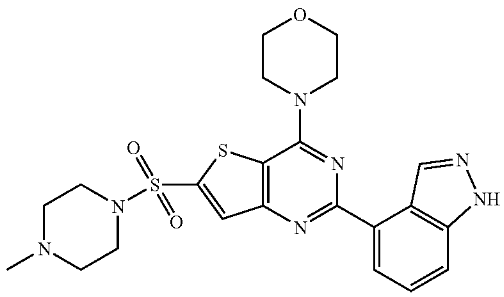 | 6-(4-methylpiperazinesulfonyl)-2-(1H-indazol-4-yl)-4-morpholinothieno[3,2-d]pyrimidine |
| 211. | 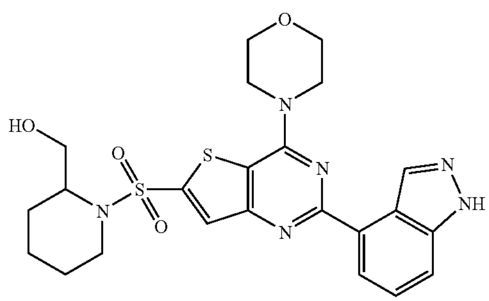 | 6-(2-hydroxymethylpiperidinesulfonyl)-2-(1H-indazol-4-yl)-4-morpholinothieno[3,2-d]pyrimidine |
| 212. | 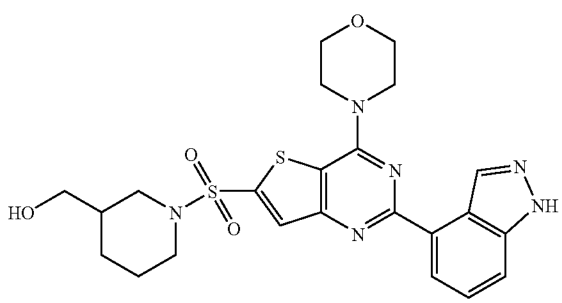 | 6-(3-hydroxymethylpiperidinesulfonyl)-2-(1H-indazol-4-yl)-4-morpholinothieno[3,2-d]pyrimidine |
| 213. | 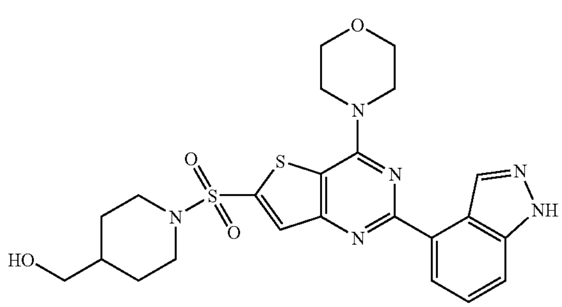 | 6-(4-hydroxymethylpiperidinesulfonyl)-2-(1H-indazol-4-yl)-4-morpholinothieno[3,2-d]pyrimidine |
| 214. | 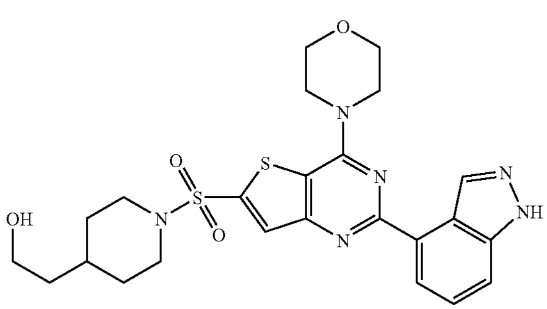 | 6-(4-(2-hydroxyethyl)piperidinesulfonyl)-2-(1H-indazol-4-yl)-4-morpholinothieno[3,2-d]pyrimidine |

TABLE 1a-continued

| No. | Structure | Name |
| --- | --- | --- |
| 215. | 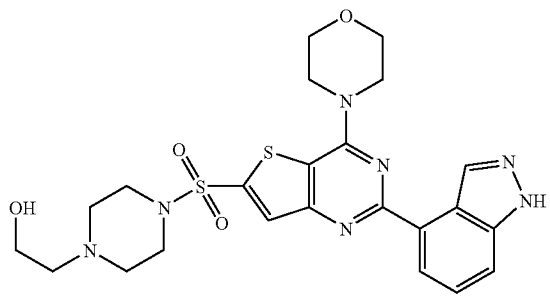 | 6-(4-(2-hydroxyethyl)piperazinesulfonyl)-2-(1H-indazol-4-yl)-4-morpholinothieno[3,2-d]pyrimidine |
| 216. | 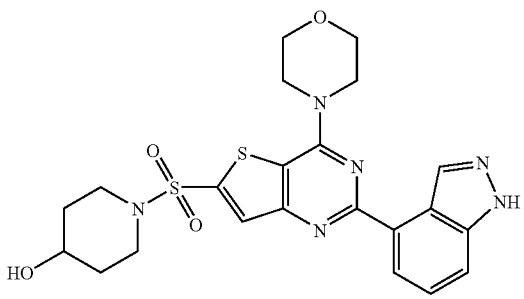 | 6-(4-hydroxypiperidinesulfonyl)-2-(1H-indazol-4-yl)-4-morpholinothieno[3,2-d]pyrimidine |
| 217. | 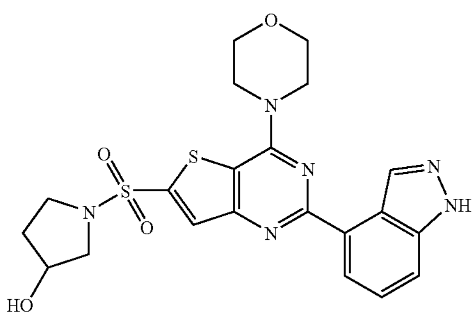 | 6-(3-hydroxypyrrolidinesulfonyl)-2-(1H-indazol-4-yl)-4-morpholinothieno[3,2-d]pyrimidine |
| 218. | 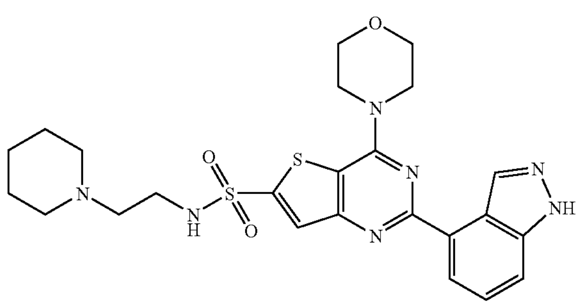 | 6-(2-piperidinylethylaminosulfonyl)-2-(1H-indazol-4-yl)-4-morpholinothieno[3,2-d]pyrimidine |
| 219. | 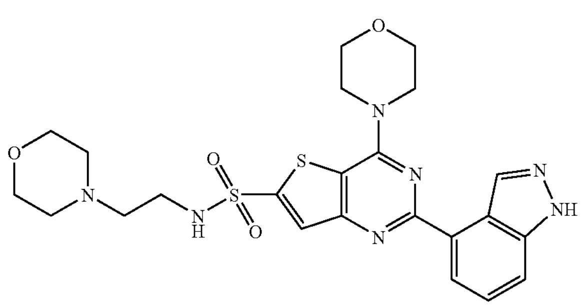 | 6-(2-N-morpholinoethylaminosulfonyl)-2-(1H-indazol-4-yl)-4-morpholinothieno[3,2-d]pyrimidine |

TABLE 1a-continued

| No. | Structure | Name |
| --- | --- | --- |
| 220. | 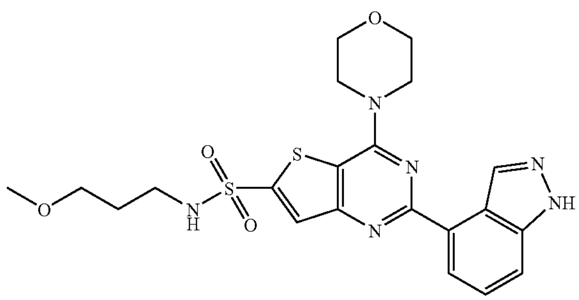 | 6-(3-methoxypropylaminosulfonyl)-2-(1H-indazol-4-yl)-4-morpholinothieno[3,2-d]pyrimidine |
| 221. | 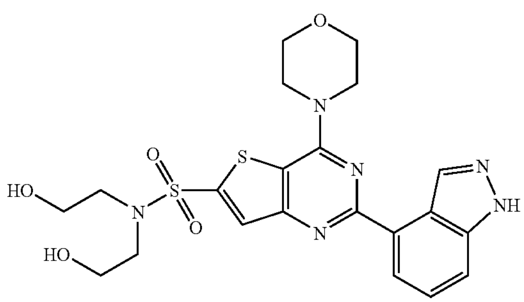 | 6-(N,N-bis-2-hydroxyethylaminosulfonyl)-2-(1H-indazol-4-yl)-4-morpholinothieno[3,2-d]pyrimidine |
| 222. | 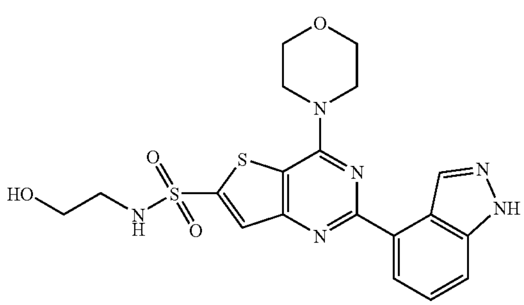 | 6-(2-hydroxyethylaminosulfonyl)-2-(1H-indazol-4-yl)-4-morpholinothieno[3,2-d]pyrimidine |
| 223. | 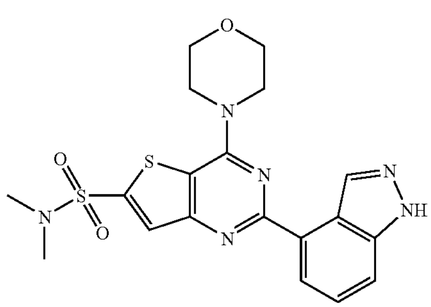 | 6-(dimethylaminosulfonyl)-2-(1H-indazol-4-yl)-4-morpholinothieno[3,2-d]pyrimidine |
| 224. | 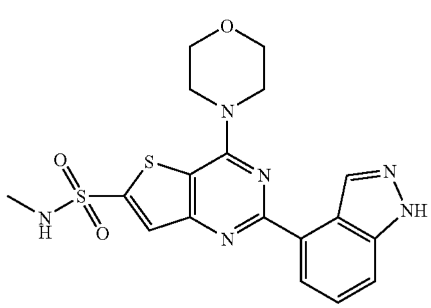 | 6-(methylaminosulfonyl)-2-(1H-indazol-4-yl)-4-morpholinothieno[3,2-d]pyrimidine |

TABLE 1a-continued

| No. | Structure | Name |
|---|---|---|
| 225. | 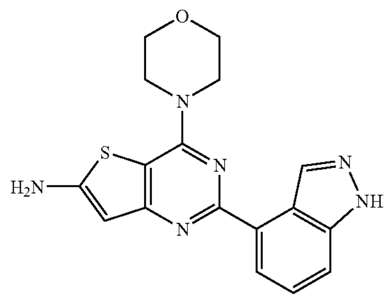 | 2-(1H-indazol-4-yl)-4-morpholinothieno[3,2-d]pyrimidin-6-amine |
| 226. | 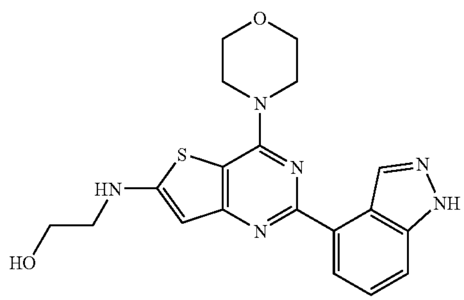 | 2-(2-(1H-indazol-4-yl)-4-morpholinothieno[3,2-d]pyrimidin-6-ylamino)ethanol |
| 227. | 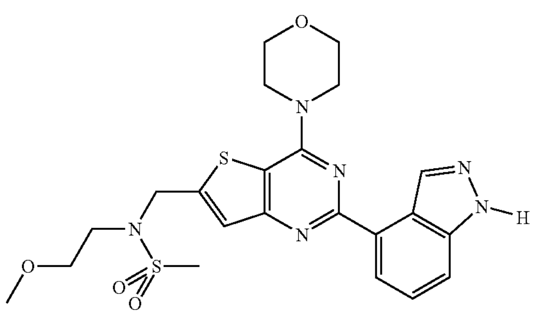 | (2-(1H-indazol-4-yl)-4-morpholinothieno[3,2-d]pyrimidin-6-yl)-N-sulfonylmethyl-N-(2-methoxyethyl)methanamine |
| 228. | 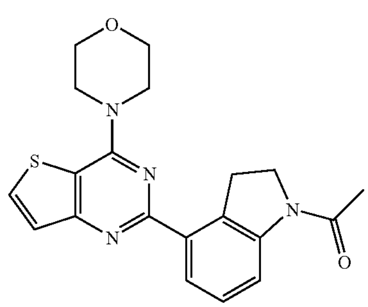 | 1-(4-(4-morpholinothieno[3,2-d]pyrimidin-2-yl)indolin-1-yl)ethanone |
| 229. | 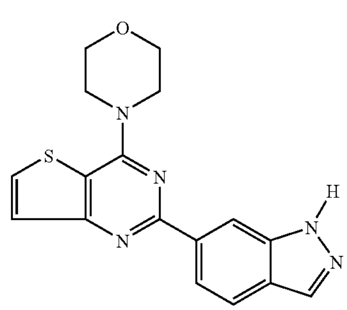 | 2-(1H-indazol-6-yl)-4-morpholinothieno[3,2-d]pyrimidine |

TABLE 1a-continued

| No. | Structure | Name |
|---|---|---|
| 230. | 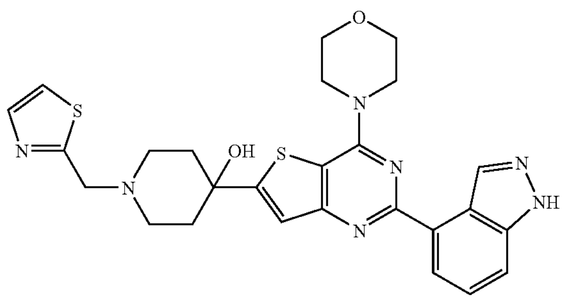 | 4-(2-(1H-indazol-4-yl)-4-morpholinothieno[3,2-d]pyrimidin-6-yl)-1-((thiazol-2-yl)methyl)piperidin-4-ol |
| 231. | 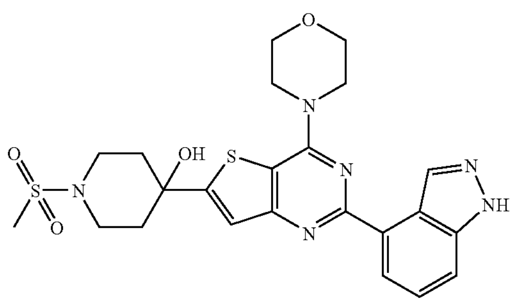 | 4-(2-(1H-indazol-4-yl)-4-morpholinothieno[3,2-d]pyrimidin-6-yl)-1-(methylsulfonyl)piperidin-4-ol |
| 232. | 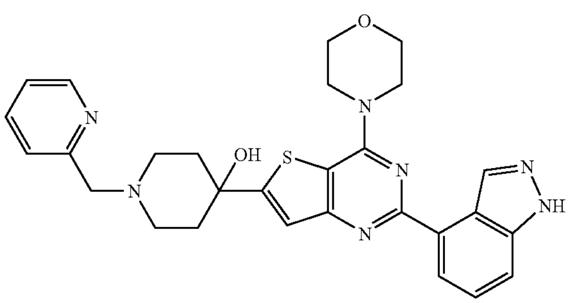 | 4-(2-(1H-indazol-4-yl)-4-morpholinothieno[3,2-d]pyrimidin-6-yl)-1-((pyridin-2-yl)methyl)piperidin-4-ol |
| 233. | 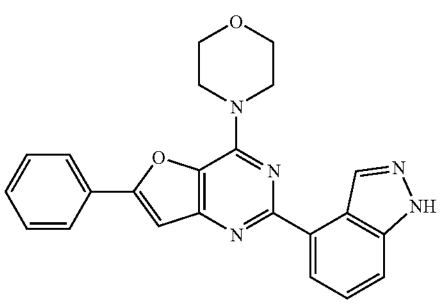 | 2-(1H-indazol-4-yl)-4-morpholino-6-phenylfuro[3,2-d]pyrimidine |
| 234. | 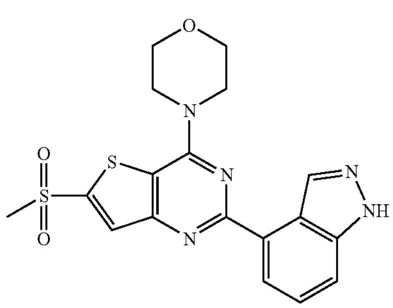 | 2-(1H-indazol-4-yl)-6-(methylsulfonyl)-4-morpholinothieno[3,2-d]pyrimidine |

TABLE 1a-continued

| No. | Structure | Name |
|---|---|---|
| 235. | 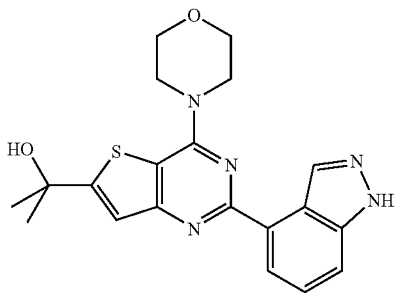 | 2-(2-(1H-indazol-4-yl)-4-morpholinothieno[3,2-d]pyrimidin-6-yl)propan-2-ol |
| 236. | 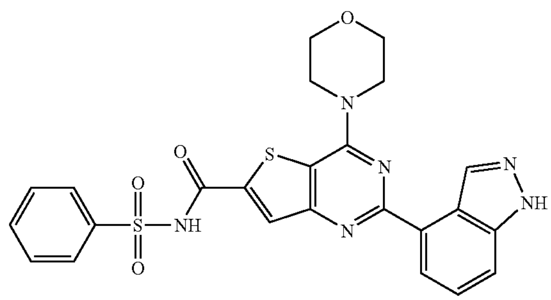 | 2-(1H-indazol-4-yl)-4-morpholinothieno[3,2-d]pyrimidine-6-(N-phenylsulfonyl)carboxamide |
| 237. | 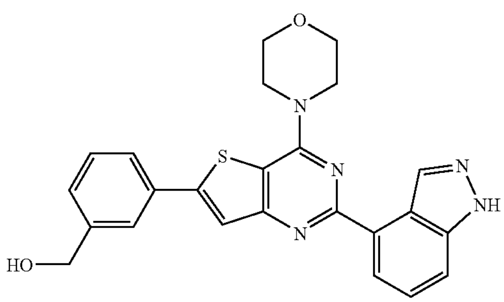 | (3-(2-(1H-indazol-4-yl)-4-morpholinothieno[3,2-d]pyrimidin-6-yl)phenyl)methanol |
| 238. | 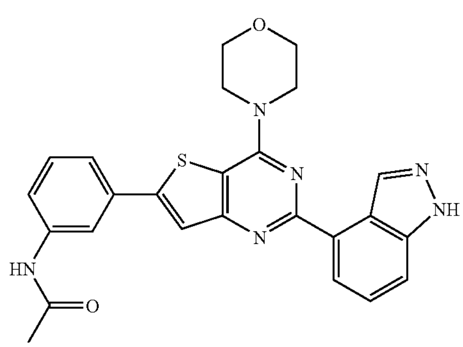 | N-(3-(2-(1H-indazol-4-yl)-4-morpholinothieno[3,2-d]pyrimidin-6-yl)phenyl)acetamide |
| 239. | 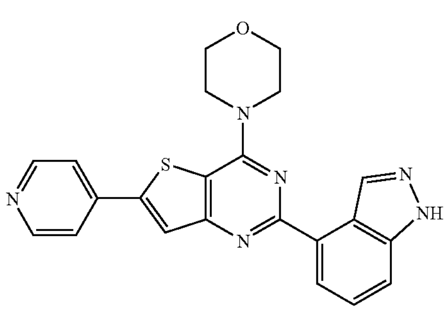 | 2-(1H-indazol-4-yl)-4-morpholino-6-(pyridin-4-yl)thieno[3,2-d]pyrimidine |

TABLE 1a-continued

| No. | Structure | Name |
|---|---|---|
| 240. | 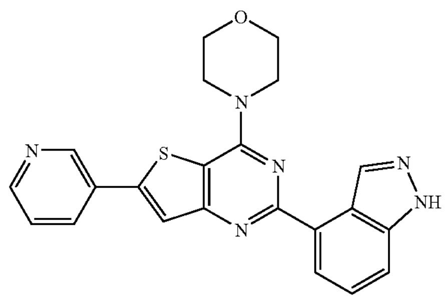 | 2-(1H-indazol-4-yl)-4-morpholino-6-(pyridin-3-yl)thieno[3,2-d]pyrimidine |
| 241. | 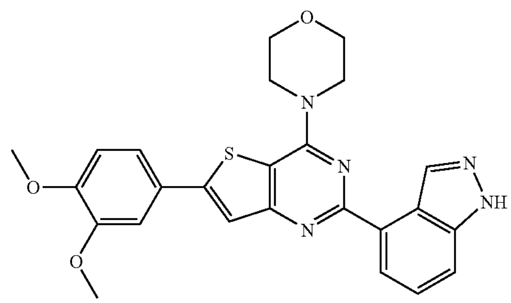 | 2-(1H-indazol-4-yl)-6-(3,4-dimethoxyphenyl)-4-morpholinothieno[3,2-d]pyrimidine |
| 242. | 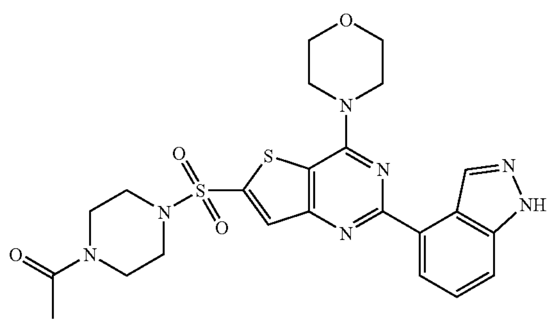 | 2-(1H-indazol-4-yl)-4-morpholino-6-(4-acetyl-piperazinosulfonyl)thieno[3,2-d]pyrimidine |
| 243. | 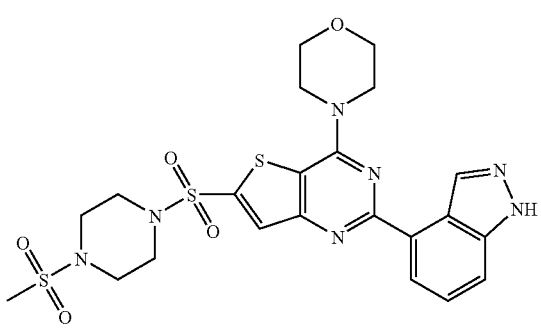 | 2-(1H-indazol-4-yl)-4-morpholino-6-(4-methylsulfonyl-piperazinosulfonyl)thieno[3,2-d]pyrimidine |
| 244. | 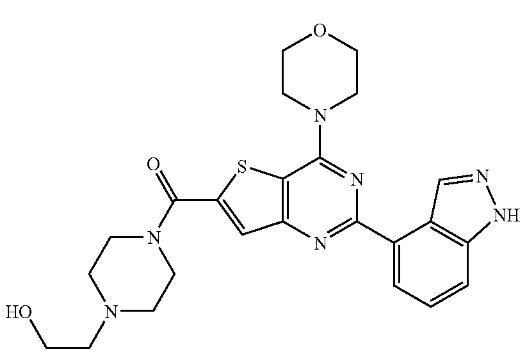 | (2-(1H-indazol-4-yl)-4-morpholinothieno[3,2-d]pyrimidin-6-yl)(4-(2-hydroxyethyl)piperazin-1-yl)methanone |

TABLE 1a-continued

| No. | Structure | Name |
|---|---|---|
| 245. | 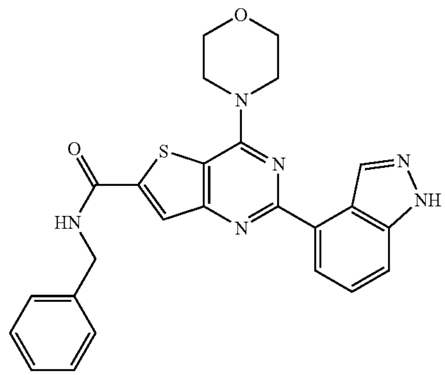 | N-benzyl-2-(1H-indazol-4-yl)-4-morpholinothieno[3,2-d]pyrimidine-6-carboxamide |
| 246. | 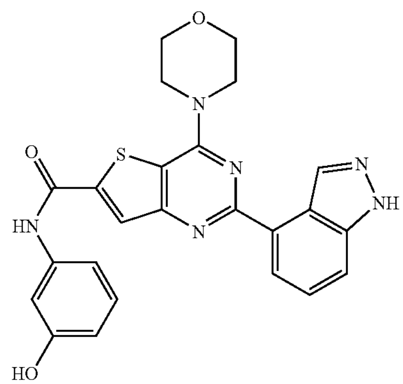 | N-(3-hydroxyphenyl)-2-(1H-indazol-4-yl)-4-morpholinothieno[3,2-d]pyrimidine-6-carboxamide |
| 247. | 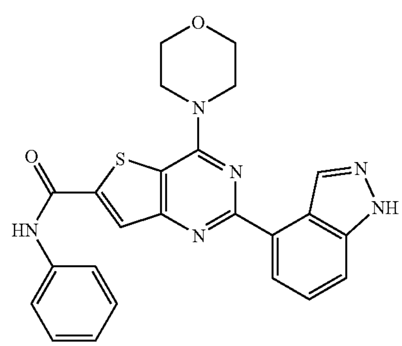 | 2-(1H-indazol-4-yl)-4-morpholino-N-phenylthieno[3,2-d]pyrimidine-6-carboxamide |
| 248. | 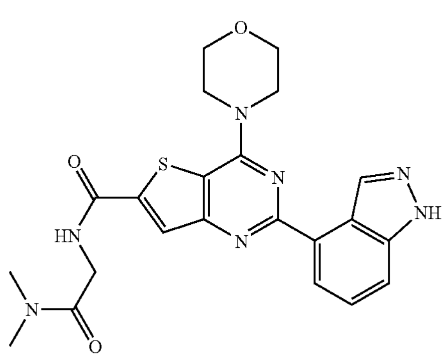 | N-((dimethylcarbamoyl)methyl)-2-(1H-indazol-4-yl)-4-morpholinothieno[3,2-d]pyrimidine-6-carboxamide |

TABLE 1a-continued

| No. | Structure | Name |
|---|---|---|
| 249. | 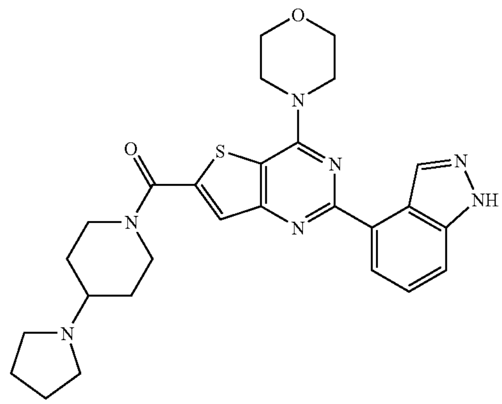 | (2-(1H-indazol-4-yl)-4-morpholinothieno[3,2-d]pyrimidin-6-yl)(4-(pyrrolidin-1-yl)piperidin-1-yl)methanone |
| 250. | 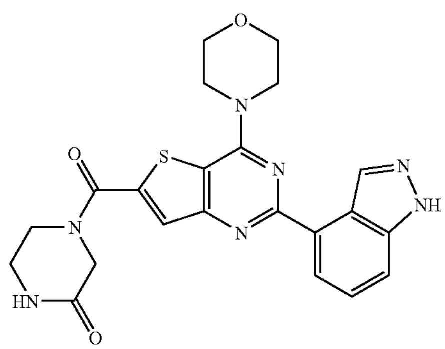 | (2-(1H-indazol-4-yl)-4-morpholinothieno[3,2-d]pyrimidin-6-yl)(piperazin-2-one)methanone |
| 251. | 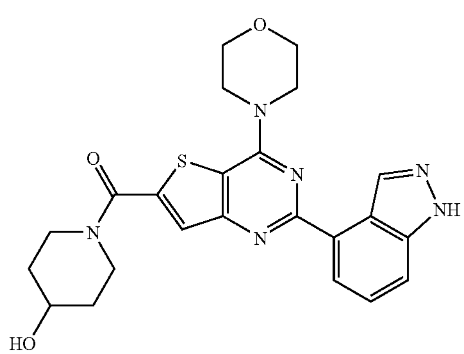 | (2-(1H-indazol-4-yl)-4-morpholinothieno[3,2-d]pyrimidin-6-yl)(4-hydroxypiperidin-1-yl)methanone |
| 252. | 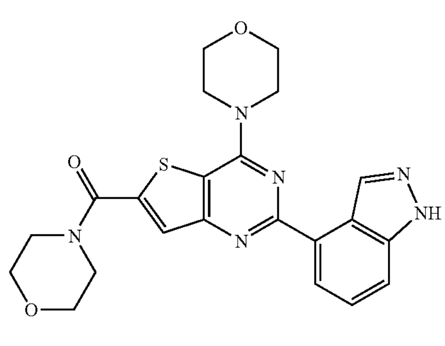 | (2-(1H-indazol-4-yl)-4-morpholinothieno[3,2-d]pyrimidin-6-yl)(morpholino)methanone |

TABLE 1a-continued

| No. | Structure | Name |
|---|---|---|
| 253. | 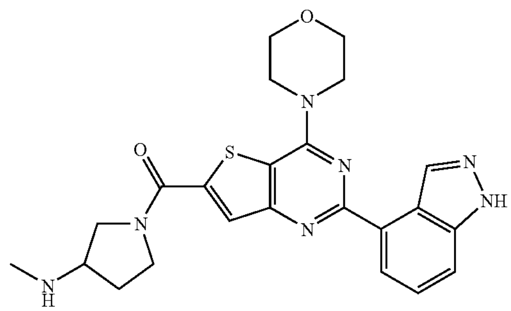 | (2-(1H-indazol-4-yl)-4-morpholinothieno[3,2-d]pyrimidin-6-yl)(3-(methylamino)pyrrolidin-1-yl)methanone |
| 254. | 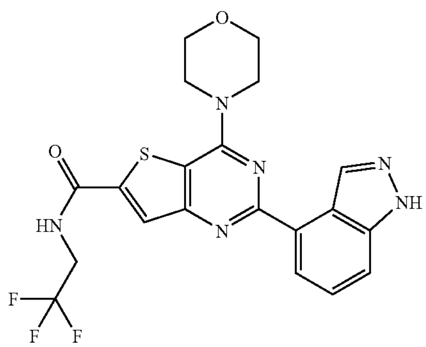 | N-(2,2,2-trifluoroethyl)-2-(1H-indazol-4-yl)-4-morpholinothieno[3,2-d]pyrimidine-6-carboxamide |
| 255. | 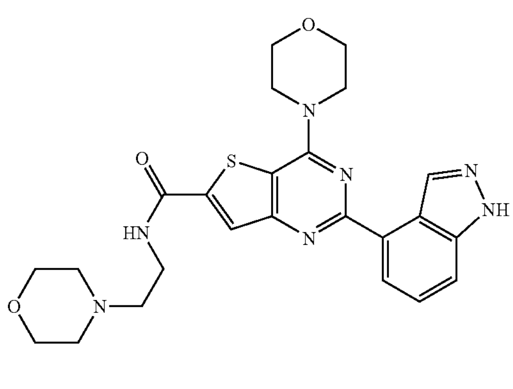 | 2-(1H-indazol-4-yl)-4-morpholino-N-(2-morpholinoethyl)thieno[3,2-d]pyrimidine-6-carboxamide |
| 256. | 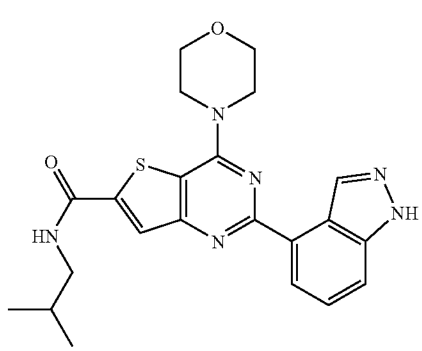 | 2-(1H-indazol-4-yl)-N-isobutyl-4-morpholinothieno[3,2-d]pyrimidine-6-carboxamide |

TABLE 1a-continued

| No. | Structure | Name |
|---|---|---|
| 257. | 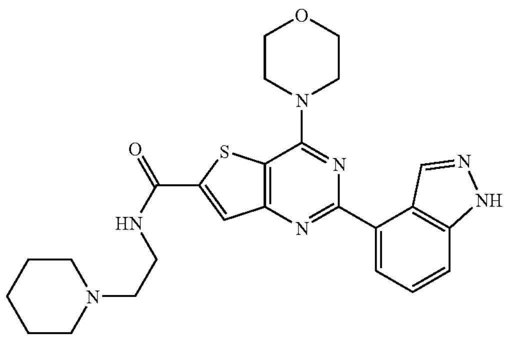 | 2-(1H-indazol-4-yl)-4-morpholino-N-(2-(piperidin-1-yl)ethyl)thieno[3,2-d]pyrimidine-6-carboxamide |
| 258. | 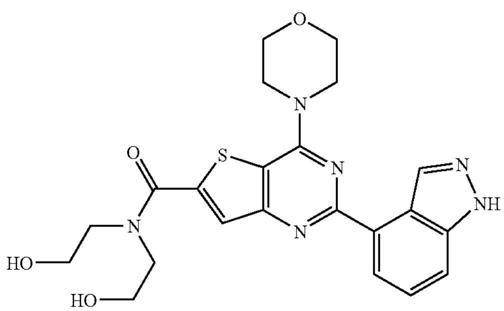 | N,N-bis(2-hydroxyethyl)-2-(1H-indazol-4-yl)-4-morpholinothieno[3,2-d]pyrimidine-6-carboxamide |
| 259. | 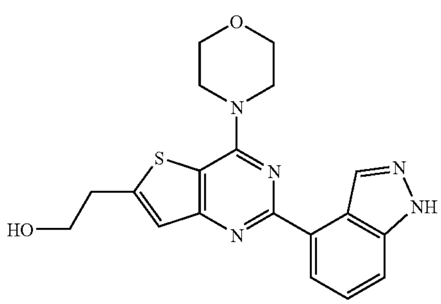 | 2-(2-(1H-indazol-4-yl)-4-morpholinothieno[3,2-d]pyrimidin-6-yl)ethanol |
| 260. | 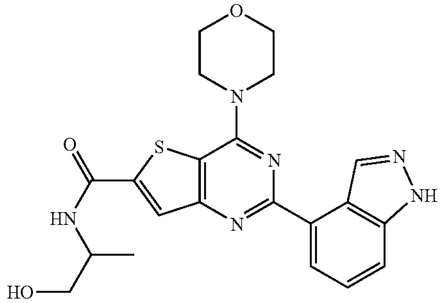 | N-(1-hydroxypropan-2-yl)-2-(1H-indazol-4-yl)-4-morpholinothieno[3,2-d]pyrimidine-6-carboxamide |

TABLE 1a-continued
| No. | Structure | Name |
|---|---|---|
| 261. | 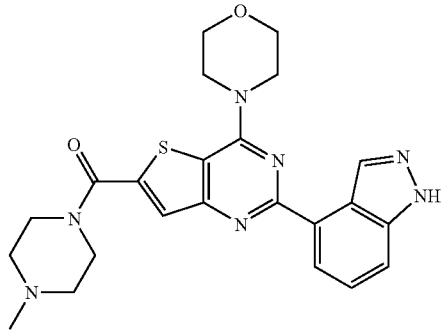 | (2-(1H-indazol-4-yl)-4-morpholinothieno[3,2-d]pyrimidin-6-yl)(4-methylpiperazin-1-yl)methanone |
| 262. | 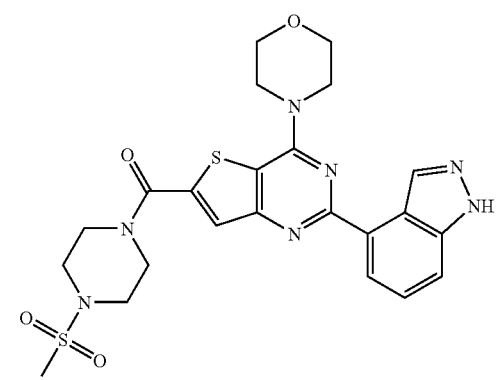 | (2-(1H-indazol-4-yl)-4-morpholinothieno[3,2-d]pyrimidin-6-yl)(4-methylsulfonylpiperazin-1-yl)methanone |
| 263. | 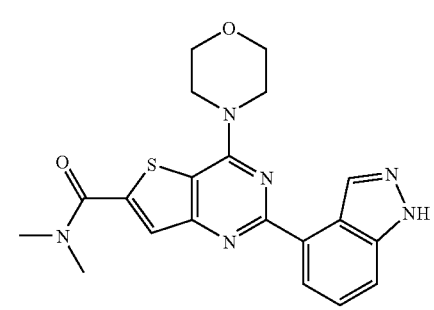 | 2-(1H-indazol-4-yl)-N,N-dimethyl-4-morpholinothieno[3,2-d]pyrimidine-6-carboxamide |
| 264. | 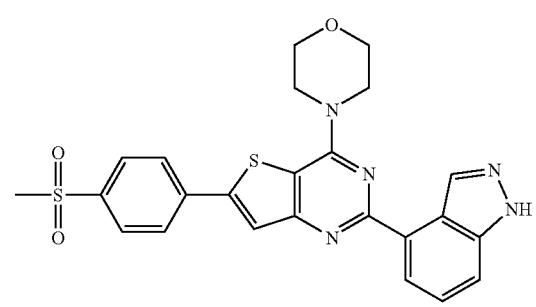 | 2-(1H-indazol-4-yl)-6-(4-(methylsulfonyl)phenyl)-4-morpholinothieno[3,2-d]pyrimidine |

TABLE 1a-continued
| No. | Structure | Name |
|---|---|---|
| 265. | 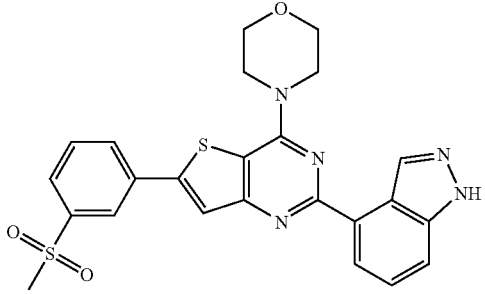 | 2-(1H-indazol-4-yl)-6-(3-(methylsulfonyl)phenyl)-4-morpholinothieno[3,2-d]pyrimidine |
| 266. | 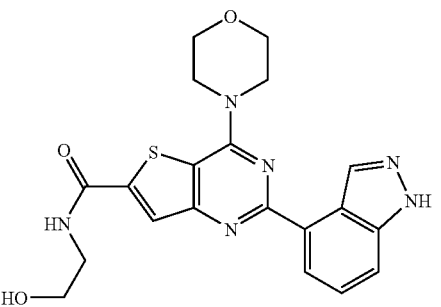 | N-(2-hydroxyethyl)-2-(1H-indazol-4-yl)-4-morpholinothieno[3,2-d]pyrimidine-6-carboxamide |
| 267. | 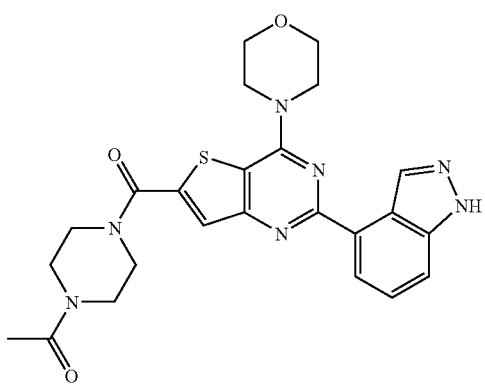 | (2-(1H-indazol-4-yl)-4-morpholinothieno[3,2-d]pyrimidin-6-yl)(4-acetylpiperazin-1-yl)methanone |
| 268. | 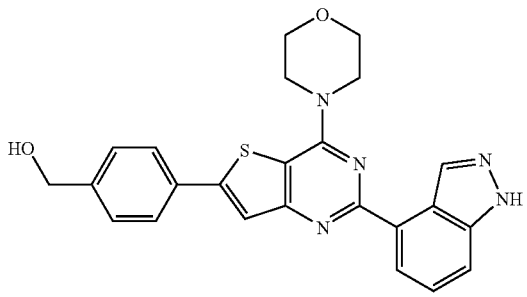 | (4-(2-(1H-indazol-4-yl)-4-morpholinothieno[3,2-d]pyrimidin-6-yl)phenyl)methanol |

TABLE 1a-continued

| No. | Structure | Name |
|---|---|---|
| 269. | 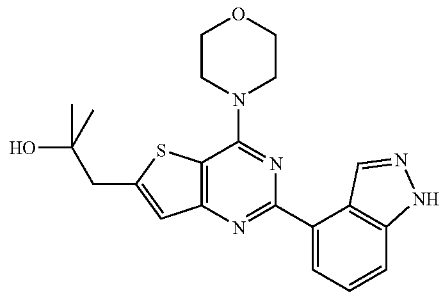 | 1-(2-(1H-indazol-4-yl)-4-morpholinothieno[3,2-d]pyrimidin-6-yl)-2-methylpropan-2-ol |
| 270. | 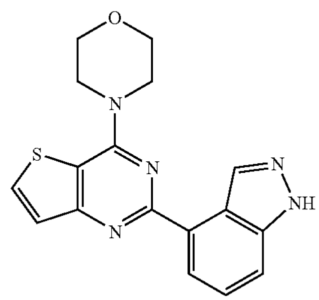 | 2-(1H-indazol-4-yl)-4-morpholinothieno[3,2-d]pyrimidine |
| 271. | 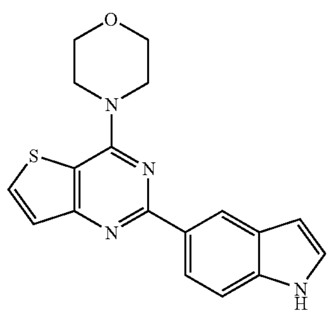 | 2-(1H-indol-5-yl)-4-morpholinothieno[3,2-d]pyrimidine |
| 272. | 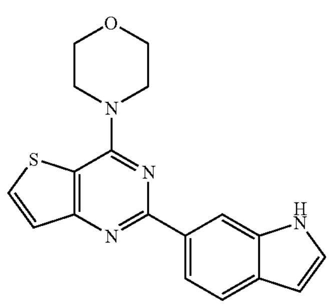 | 2-(1H-indol-6-yl)-4-morpholinothieno[3,2-d]pyrimidine |
| 273. | 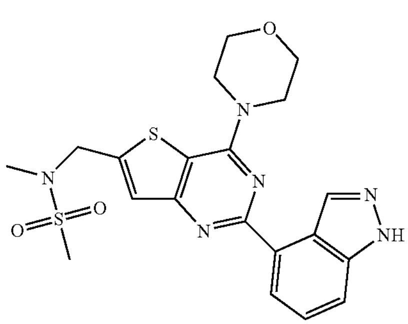 | N-((2-(1H-indazol-4-yl)-4-morpholinothieno[3,2-d]pyrimidin-6-yl)methyl)-N-(methyl)methylsulfonamide |

TABLE 1a-continued

| No. | Structure | Name |
|---|---|---|
| 274. | 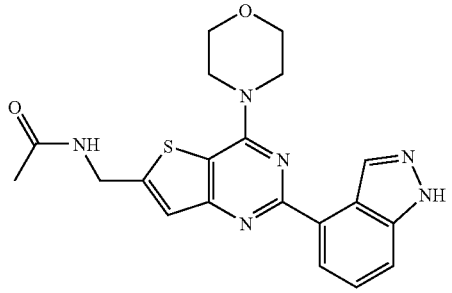 | N-((2-(1H-indazol-4-yl)-4-morpholinothieno[3,2-d]pyrimidin-6-yl)methyl)acetamide |
| 275. | 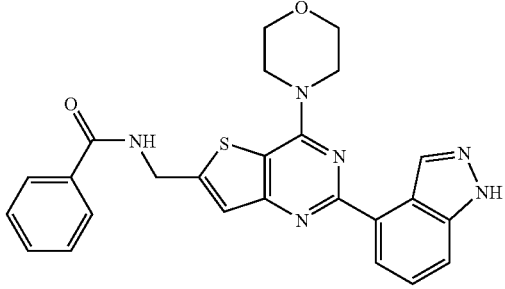 | N-((2-(1H-indazol-4-yl)-4-morpholinothieno[3,2-d]pyrimidin-6-yl)methyl)benzamide |
| 276. | 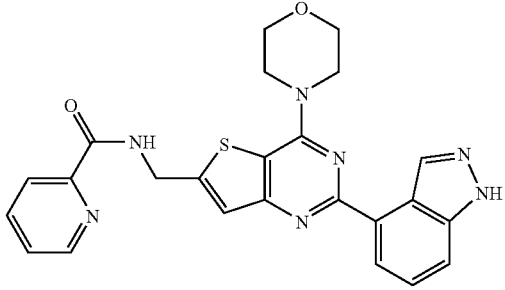 | N-((2-(1H-indazol-4-yl)-4-morpholinothieno[3,2-d]pyrimidin-6-yl)methyl)picolinamide |
| 277. | 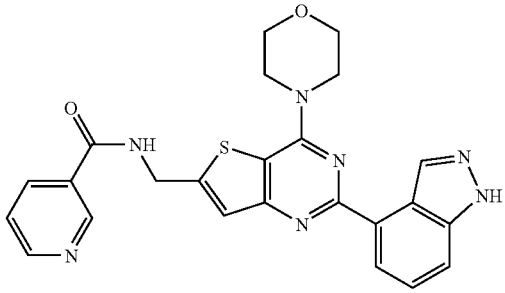 | N-((2-(1H-indazol-4-yl)-4-morpholinothieno[3,2-d]pyrimidin-6-yl)methyl)nicotinamide |
| 278. | 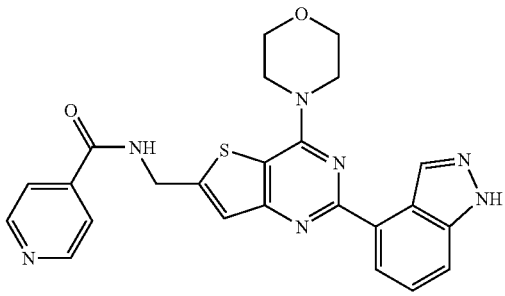 | N-((2-(1H-indazol-4-yl)-4-morpholinothieno[3,2-d]pyrimidin-6-yl)methyl)isonicotinamide |

TABLE 1a-continued

| No. | Structure | Name |
|---|---|---|
| 279. | 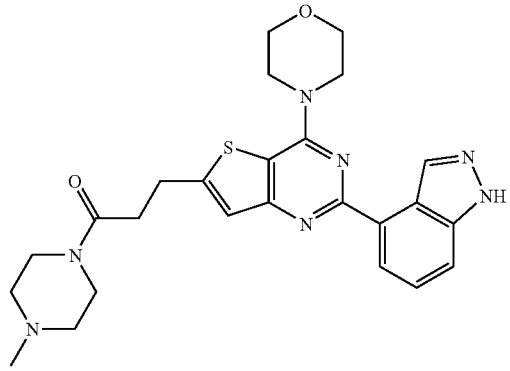 | 3-(2-(1H-indazol-4-yl)-4-morpholinothieno[3,2-d]pyrimidin-6-yl)-1-(4-methylpiperazin-1-yl)propan-1-one |
| 280. | 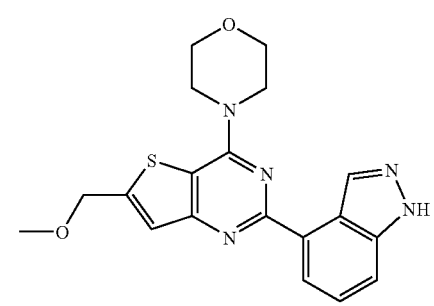 | 2-(1H-indazol-4-yl)-6-(methoxymethyl)-4-morpholinothieno[3,2-d]pyrimidine |
| 281. | 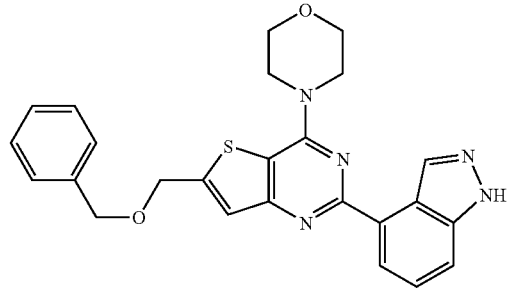 | 6-((benzyloxy)methyl)-2-(1H-indazol-4-yl)-4-morpholinothieno[3,2-d]pyrimidine |
| 282. | 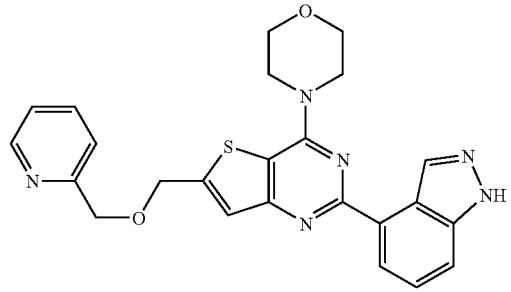 | 6-(((pyridin-2-yl)methoxy)methyl)-2-(1H-indazol-4-yl)-4-morpholinothieno[3,2-d]pyrimidine |
| 283. | 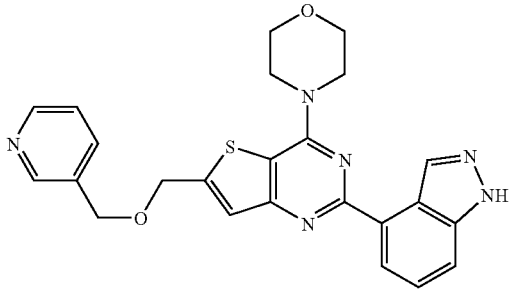 | 6-(((pyridin-3-yl)methoxy)methyl)-2-(1H-indazol-4-yl)-4-morpholinothieno[3,2-d]pyrimidine |

TABLE 1a-continued

| No. | Structure | Name |
| --- | --- | --- |
| 284. | 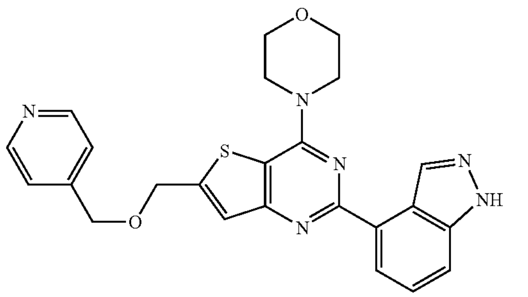 | 6-(((pyridin-4-yl)methoxy)methyl)-2-(1H-indazol-4-yl)-4-morpholinothieno[3,2-d]pyrimidine |
| 285. | 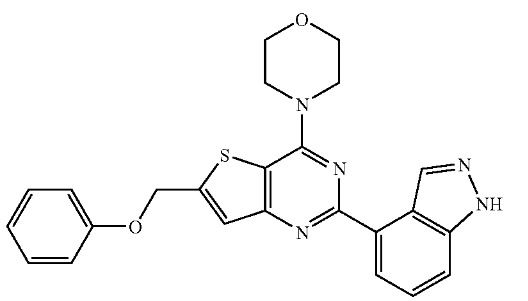 | 2-(1H-indazol-4-yl)-4-morpholino-6-(phenoxymethyl)thieno[3,2-d]pyrimidine |

TABLE 1b

| Example | Structure | Name |
| --- | --- | --- |
| 286. | 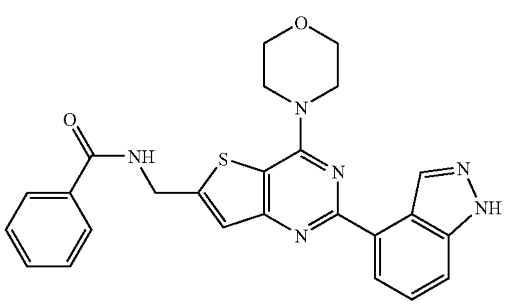 | N-((2-(1H-indazol-4-yl)-4-morpholinothieno[3,2-d]pyrimidin-6-yl)methyl)benzamide |
| 287. | 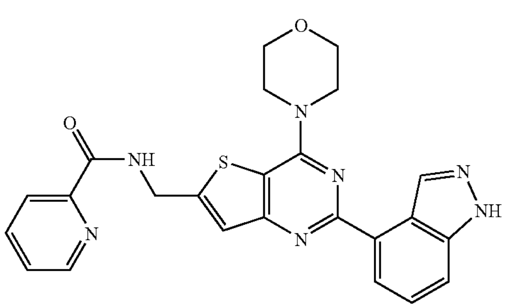 | N-((2-(1H-indazol-4-yl)-4-morpholinothieno[3,2-d]pyrimidin-6-yl)methyl)picolinamide |

TABLE 1b-continued

| Example | Structure | Name |
|---|---|---|
| 288. | 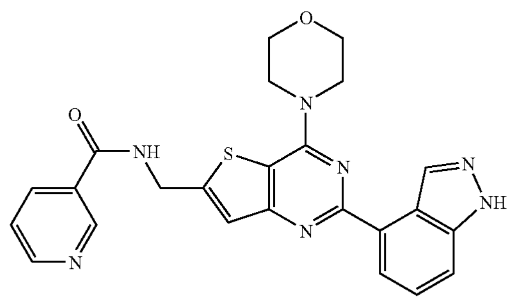 | N-((2-(1H-indazol-4-yl)-4-morpholinothieno[3,2-d]pyrimidin-6-yl)methyl)nicotinamide |
| 289. | 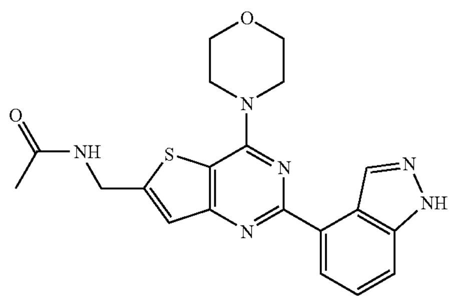 | N-((2-(1H-indazol-4-yl)-4-morpholinothieno[3,2-d]pyrimidin-6-yl)methyl)acetamide |
| 290. | 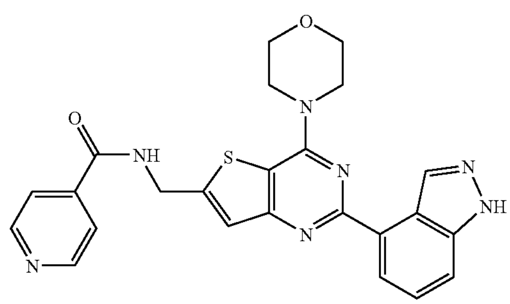 | N-((2-(1H-indazol-4-yl)-4-morpholinothieno[3,2-d]pyrimidin-6-yl)methyl)isonicotinamide |
| 291. | 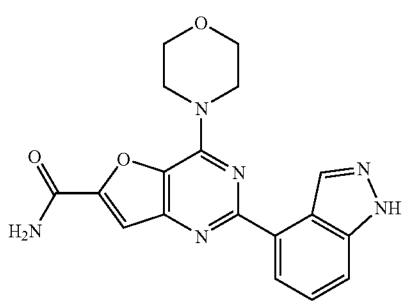 | 2-(1H-indazol-4-yl)-4-morpholinofuro[3,2-d]pyrimidine-6-carboxamide |
| 292. | 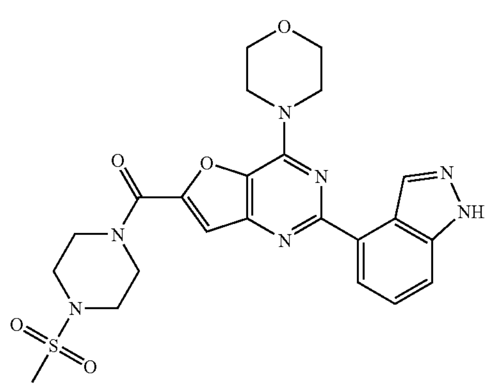 | (2-(1H-indazol-4-yl)-4-morpholinofuro[3,2-d]pyrimidin-6-yl)(4-N-methylsulfonylpiperazin-1-yl)methanone |

TABLE 1b-continued

| Example | Structure | Name |
|---|---|---|
| 293. | 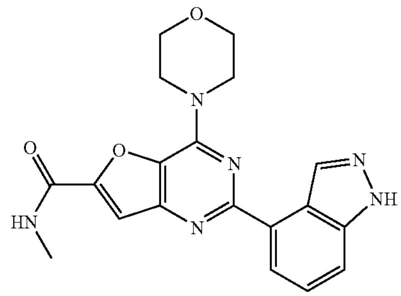 | 2-(1H-indazol-4-yl)-N-methyl-4-morpholinofuro[3,2-d]pyrimidine-6-carboxamide |
| 294. | 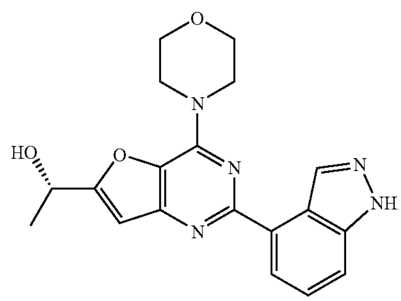 | (S)-1-(2-(1H-indazol-4-yl)-4-morpholinofuro[3,2-d]pyrimidin-6-yl)ethanol |
| 295. | 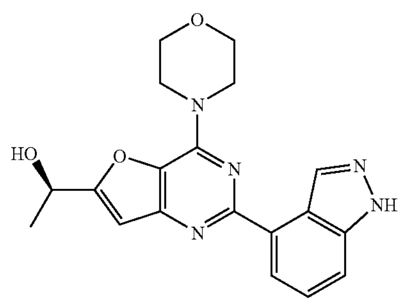 | (R)-1-(2-(1H-indazol-4-yl)-4-morpholinofuro[3,2-d]pyrimidin-6-yl)ethanol |
| 296. | 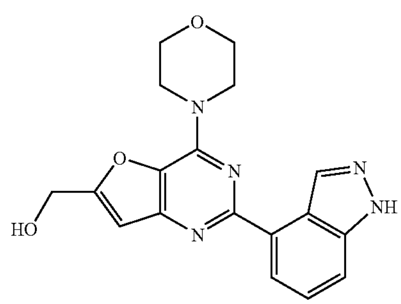 | (2-(1H-indazol-4-yl)-4-morpholinofuro[3,2-d]pyrimidin-6-yl)methanol |
| 297. | 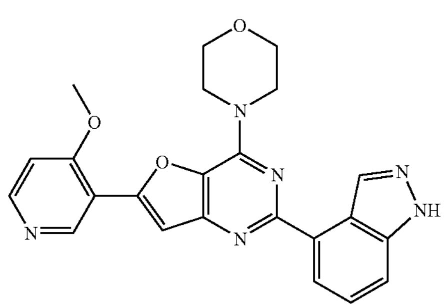 | 2-(1H-indazol-4-yl)-6-(4-methoxypyridin-3-yl)-4-morpholinofuro[3,2-d]pyrimidine |

TABLE 1b-continued

| Example | Structure | Name |
|---|---|---|
| 298. | 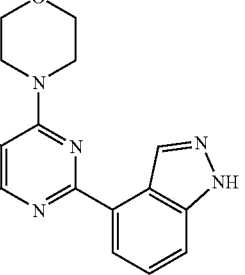 | 2-(1H-indazol-4-yl)-4-morpholinothieno[2,3-d]pyrimidine-6-carboxamide |
| 299. | 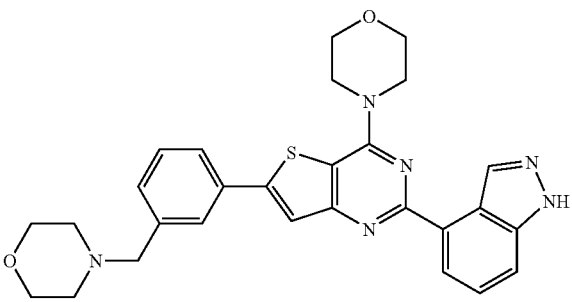 | 2-(1H-indazol-4-yl)-4-morpholino-6-(3-(morpholinomethyl)phenyl)thieno[3,2-d]pyrimidine |
| 300. | 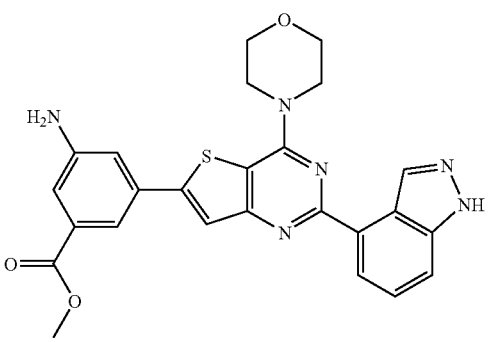 | methyl 3-(2-(1H-indazol-4-yl)-4-morpholinothieno[3,2-d]pyrimidin-6-yl)-5-aminobenzoate |
| 301. | 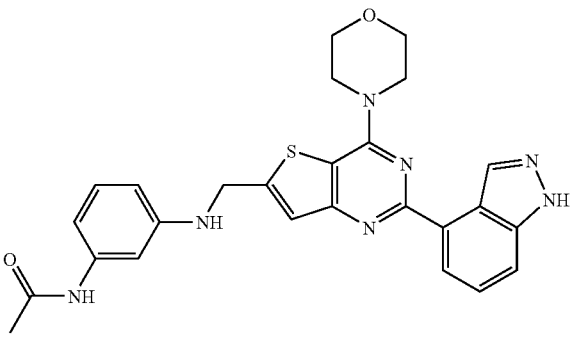 | N-(3-((2-(1H-indazol-4-yl)-4-morpholinothieno[3,2-d]pyrimidin-6-yl)methylamino)phenyl)acetamide |
| 302. | 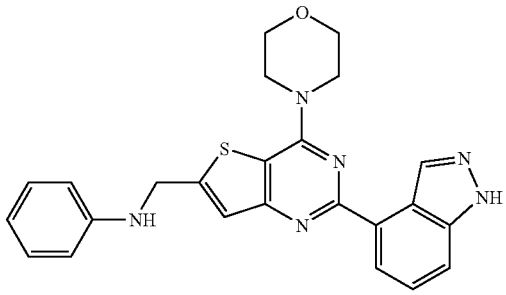 | N-((2-(1H-indazol-4-yl)-4-morpholinothieno[3,2-d]pyrimidin-6-yl)methyl)benzenamine |

TABLE 1b-continued

| Example | Structure | Name |
|---|---|---|
| 303. | 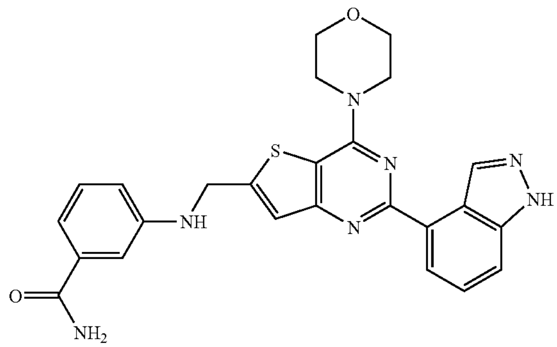 | 3-((2-(1H-indazol-4-yl)-4-morpholinothieno[3,2-d]pyrimidin-6-yl)methylamino)benzamide |
| 304. | 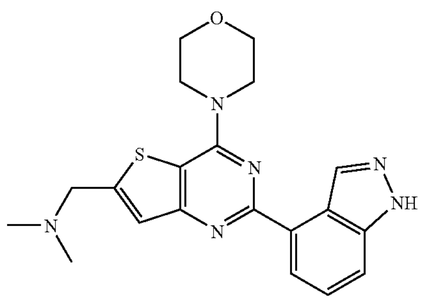 | (2-(1H-indazol-4-yl)-4-morpholinothieno[3,2-d]pyrimidin-6-yl)-N,N-dimethylmethanamine |
| 305. | 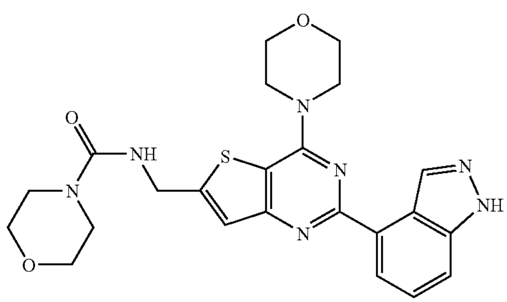 | N-((2-(1H-indazol-4-yl)-4-morpholinothieno[3,2-d]pyrimidin-6-yl)methyl)morpholine-4-carboxamide |
| 306. | 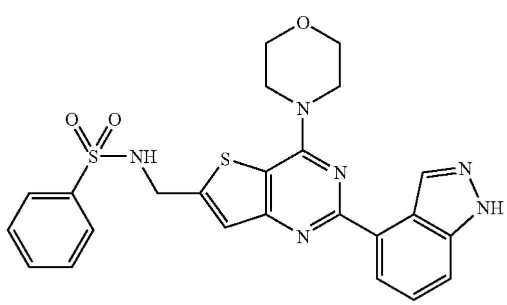 | (2-(1H-indazol-4-yl)-4-morpholinothieno[3,2-d]pyrimidin-6-yl)N-phenylsulfonylmethanamine |
| 307. | 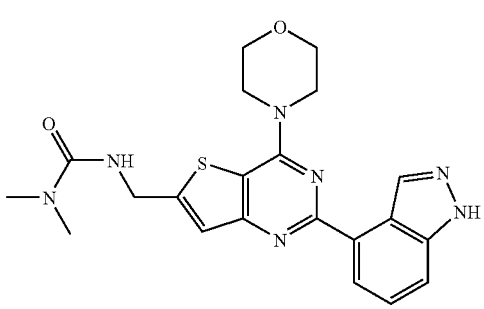 | 3-((2-(1H-indazol-4-yl)-4-morpholinothieno[3,2-d]pyrimidin-6-yl)methyl)-1,1-dimethylurea |

TABLE 1b-continued

| Example | Structure | Name |
|---|---|---|
| 308. | 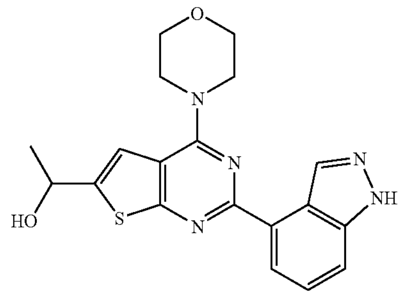 | 1-(2-(1H-indazol-4-yl)-4-morpholinothieno[2,3-d]pyrimidin-6-yl)ethanol |
| 309. | 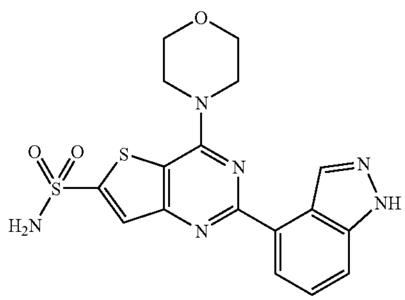 | 2-(1H-indazol-4-yl)-4-morpholinothieno[3,2-d]pyrimidin-6-yl)sulfonamide |
| 310. | 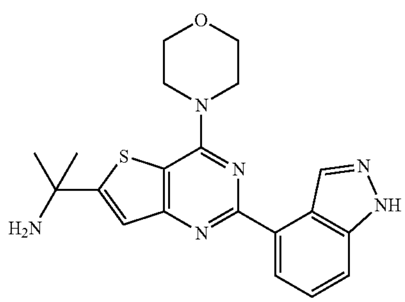 | 2-(2-(1H-indazol-4-yl)-4-morpholinothieno[3,2-d]pyrimidin-6-yl)propan-2-amine |
| 311. | 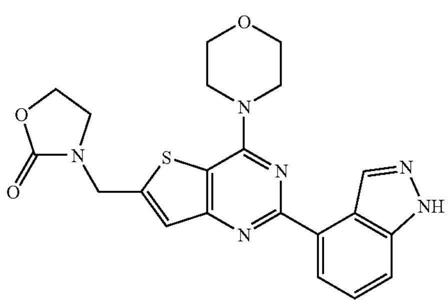 | 3-((2-(1H-indazol-4-yl)-4-morpholinothieno[3,2-d]pyrimidin-6-yl)methyl)oxazolidin-2-one |
| 312. | 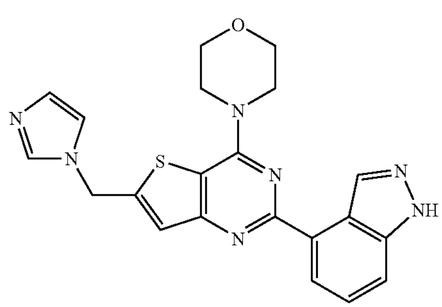 | 6-((1H-imidazol-1-yl)methyl)-2-(1H-indazol-4-yl)-4-morpholinothieno[3,2-d]pyrimidine |

TABLE 1b-continued

| Example | Structure | Name |
| --- | --- | --- |
| 313. | 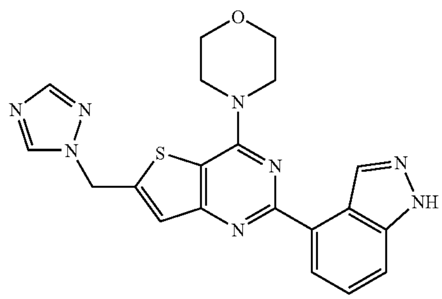 | 6-((1H-1,2,4-triazol-1-yl)methyl)-2-(1H-indazol-4-yl)-4-morpholinothieno[3,2-d]pyrimidine |
| 314. | 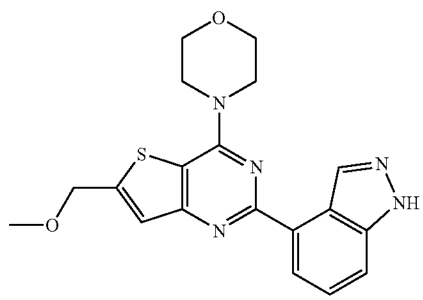 | 2-(1H-indazol-4-yl)-6-(methoxymethyl)-4-morpholinothieno[3,2-d]pyrimidine |
| 315. | 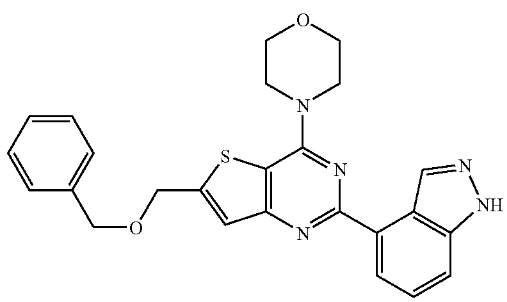 | 6-((benzyloxy)methyl)-2-(1H-indazol-4-yl)-4-morpholinothieno[3,2-d]pyrimidine |
| 316. | 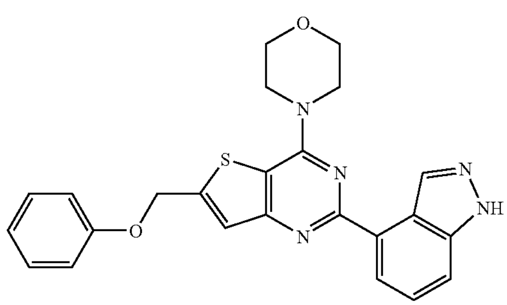 | 2-(1H-indazol-4-yl)-4-morpholino-6-(phenoxymethyl)thieno[3,2-d]pyrimidine |
| 317. | 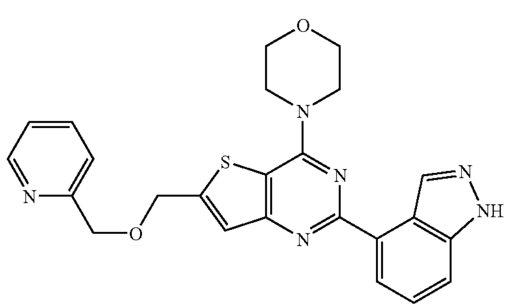 | 6-(((pyridin-2-yl)methoxy)methyl)-2-(1H-indazol-4-yl)-4-morpholinothieno[3,2-d]pyrimidine |

TABLE 1b-continued

| Example | Structure | Name |
| --- | --- | --- |
| 318. | 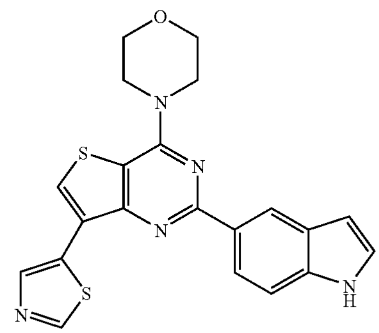 | 4-morpholino-2-(1H-pyrrolo[2,3-b]pyridin-5-yl)-7-(thiazol-5-yl)thieno[3,2-d]pyrimidine |
| 319. | 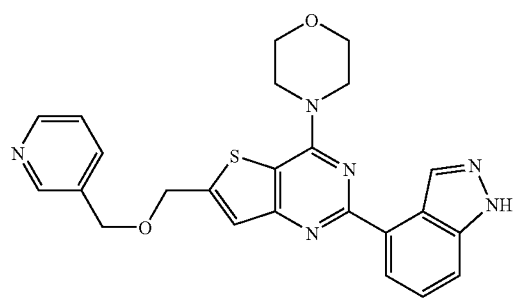 | 6-(((pyridin-3-yl)methoxy)methyl)-2-(1H-indazol-4-yl)-4-morpholinothieno[3,2-d]pyrimidine |
| 320. | 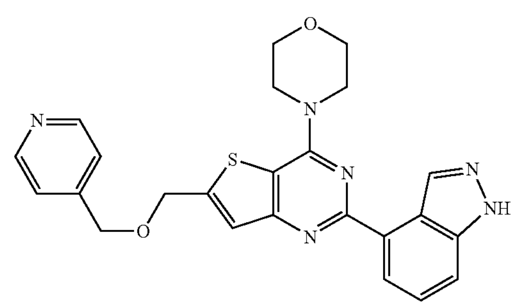 | 6-(((pyridin-4-yl)methoxy)methyl)-2-(1H-indazol-4-yl)-4-morpholinothieno[3,2-d]pyrimidine |
| 321. | 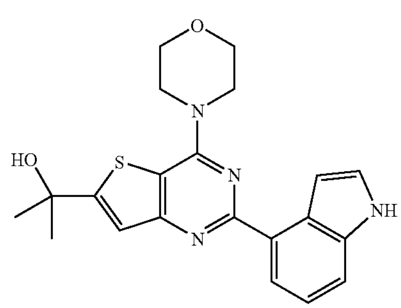 | 2-(2-(1H-indol-4-yl)-4-morpholinothieno[3,2-d]pyrimidin-6-yl)propan-2-ol |
| 322. | 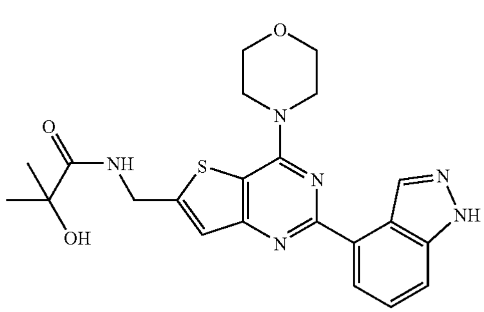 | N-((2-(1H-indazol-4-yl)-4-morpholinothieno[3,2-d]pyrimidin-6-yl)methyl)-2-hydroxy-2-methylpropanamide |

TABLE 1b-continued

| Example | Structure | Name |
| --- | --- | --- |
| 323. | 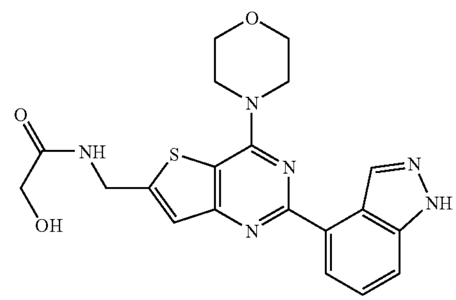 | N-((2-(1H-indazol-4-yl)-4-morpholinothieno[3,2-d]pyrimidin-6-yl)methyl)-2-hydroxyacetamide |
| 324. | 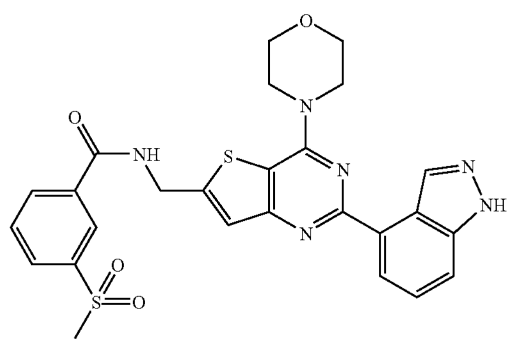 | N-((2-(1H-indazol-4-yl)-4-morpholinothieno[3,2-d]pyrimidin-6-yl)methyl)-3-(methylsulfonyl)benzamide |
| 325. | 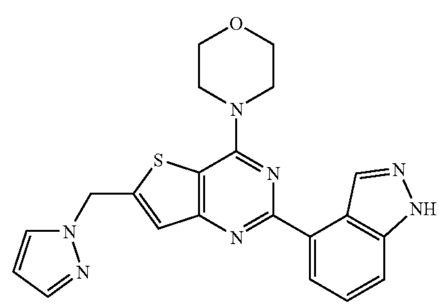 | 6-((1H-pyrazol-1-yl)methyl)-2-(1H-indazol-4-yl)-4-morpholinothieno[3,2-d]pyrimidine |
| 326. | 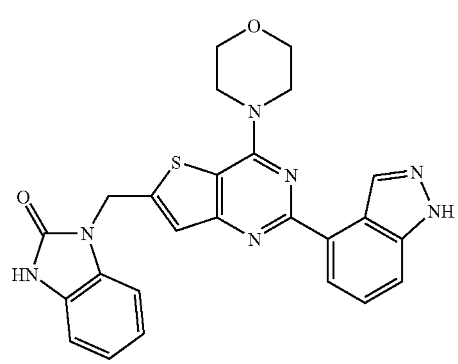 | 1-((2-(1H-indazol-4-yl)-4-morpholinothieno[3,2-d]pyrimidin-6-yl)methyl)-1H-benzo[d]imidazol-2(3H)-one |

TABLE 1b-continued

| Example | Structure | Name |
|---|---|---|
| 327. | 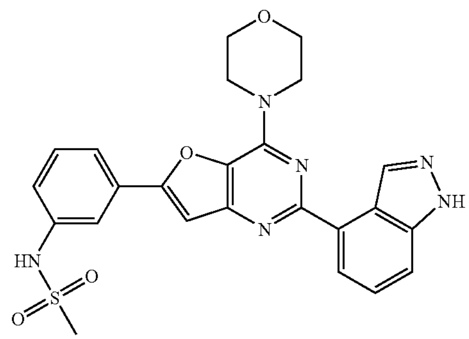 | 3-(2-(1H-indazol-4-yl)-4-morpholinofuro[3,2-d]pyrimidin-6-yl)-N-methylsulfonylbenzenamine |
| 328. | 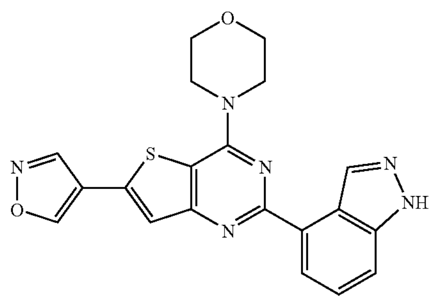 | 2-(1H-indazol-4-yl)-6-(isoxazol-4-yl)-4-morpholinothieno[3,2-d]pyrimidine |
| 329. | 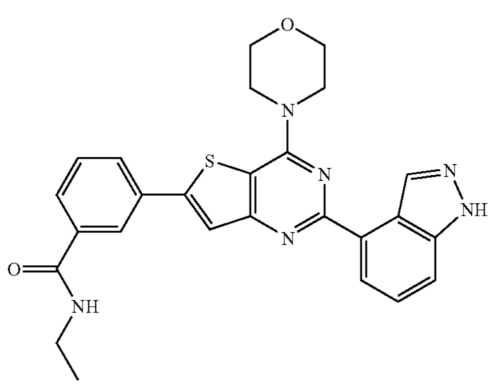 | 3-(2-(1H-indazol-4-yl)-4-morpholinothieno[3,2-d]pyrimidin-6-yl)-N-ethylbenzamide |
| 330. | 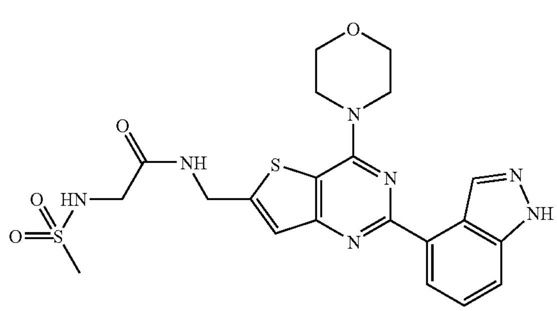 | N-((2-(1H-indazol-4-yl)-4-morpholinothieno[3,2-d]pyrimidin-6-yl)methyl)-2-(N-methylsulfonylamino)acetamide |

TABLE 1b-continued

| Example | Structure | Name |
|---|---|---|
| 331. | 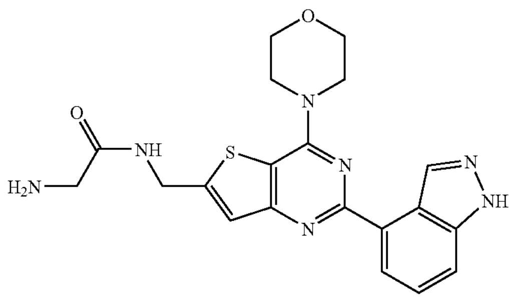 | N-((2-(1H-indazol-4-yl)-4-morpholinothieno[3,2-d]pyrimidin-6-yl)methyl)-2-aminoacetamide |
| 332. | 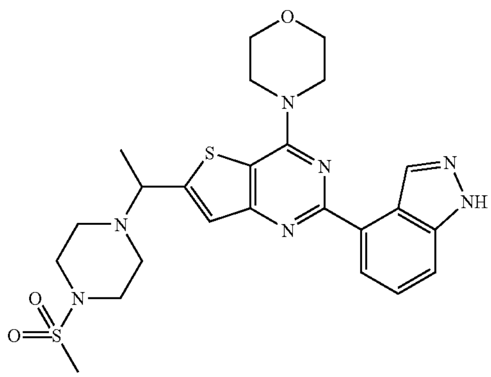 | 2-(1H-indazol-4-yl)-4-morpholino-6-(1-(4-N-methylsulfonylpiperazin-1-yl)ethyl)thieno[3,2-d]pyrimidine |
| 333. | 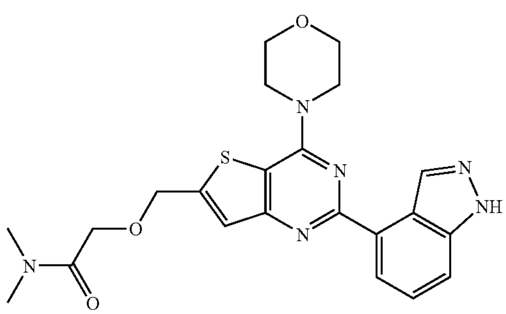 | 2-((2-(1H-indazol-4-yl)-4-morpholinothieno[3,2-d]pyrimidin-6-yl)methoxy)-N,N-dimethylacetamide |
| 334. | 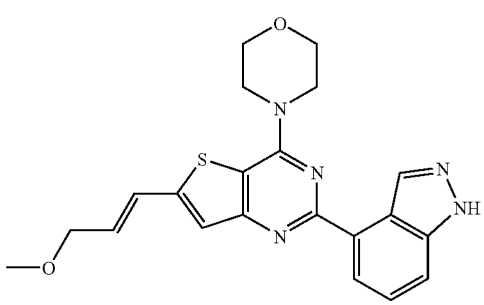 | 2-(1H-indazol-4-yl)-6-((E)-3-methoxyprop-1-enyl)-4-morpholinothieno[3,2-d]pyrimidine |
| 335. | 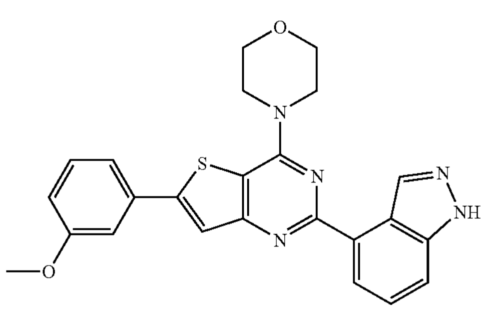 | 2-(1H-indazol-4-yl)-6-(3-methoxyphenyl)-4-morpholinothieno[3,2-d]pyrimidine |

TABLE 1b-continued

| Example | Structure | Name |
|---|---|---|
| 336. | 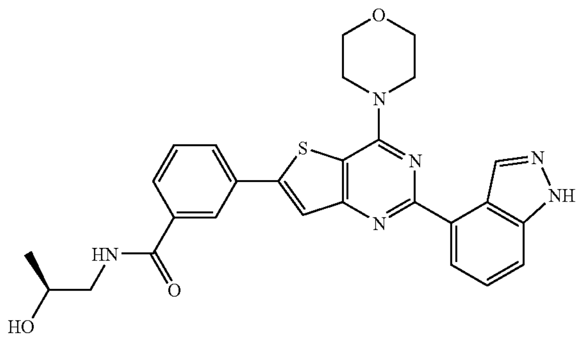 | 3-(2-(1H-indazol-4-yl)-4-morpholinothieno[3,2-d]pyrimidin-6-yl)-N-((S)-2-hydroxypropyl)benzamide |
| 337. | 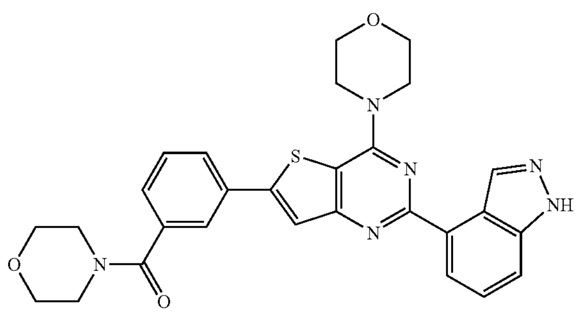 | (3-(2-(1H-indazol-4-yl)-4-morpholinothieno[3,2-d]pyrimidin-6-yl)phenyl)(morpholino)methanone |
| 338. | 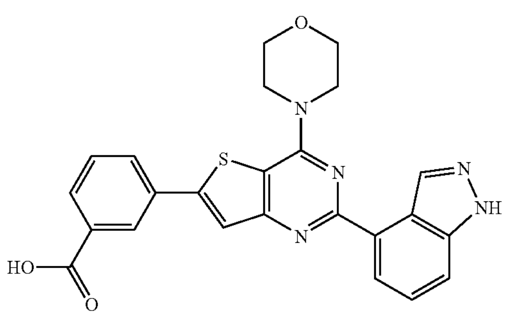 | 3-(2-(1H-indazol-4-yl)-4-morpholinothieno[3,2-d]pyrimidin-6-yl)benzoic acid |
| 339. | 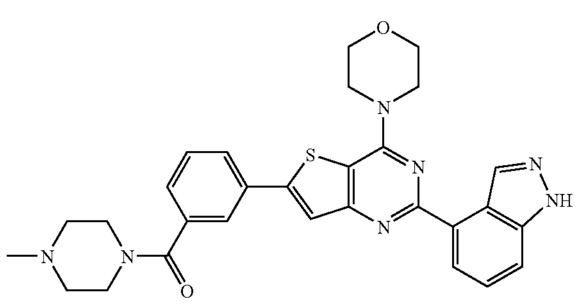 | (3-(2-(1H-indazol-4-yl)-4-morpholinothieno[3,2-d]pyrimidin-6-yl)phenyl)(4-methylpiperazin-1-yl)methanone |

TABLE 1b-continued

| Example | Structure | Name |
|---|---|---|
| 340. | 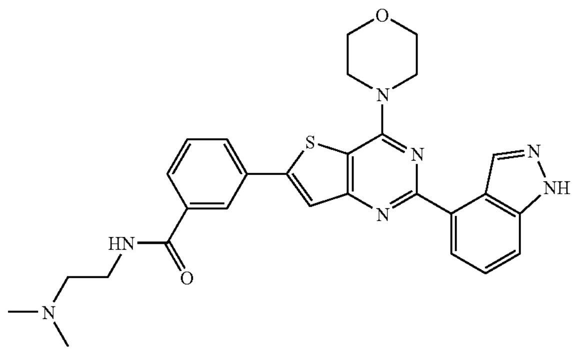 | 3-(2-(1H-indazol-4-yl)-4-morpholinothieno[3,2-d]pyrimidin-6-yl)-N-(2-(dimethylamino)ethyl)benzamide |
| 341. | 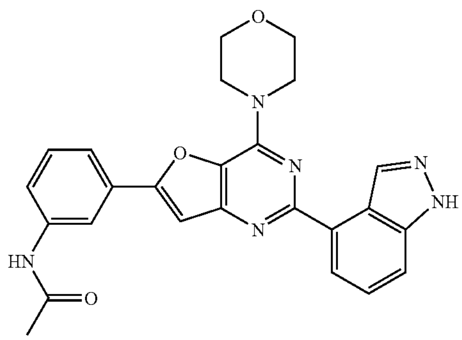 | N-(3-(2-(1H-indazol-4-yl)-4-morpholinofuro[3,2-d]pyrimidin-6-yl)phenyl)acetamide |
| 342. | 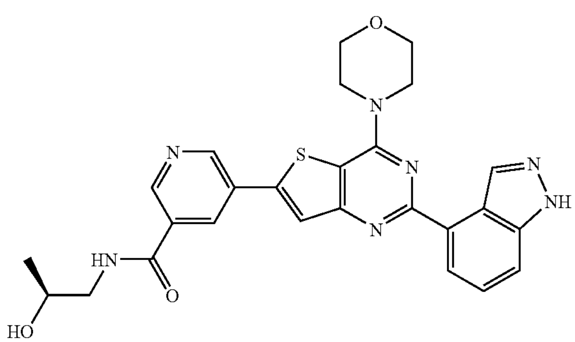 | 5-(2-(1H-indazol-4-yl)-4-morpholinothieno[3,2-d]pyrimidin-6-yl)-N-((S)-2-hydroxypropyl)pyridine-3-carboxamide |
| 343. | 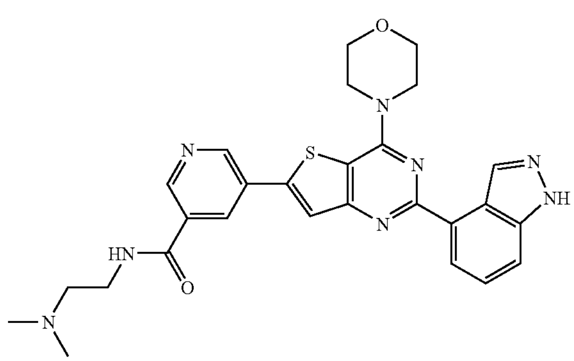 | 5-(2-(1H-indazol-4-yl)-4-morpholinothieno[3,2-d]pyrimidin-6-yl)-N-(2-(dimethylamino)ethyl)pyridine-3-carboxamide |

TABLE 1b-continued

| Example | Structure | Name |
|---|---|---|
| 344. | 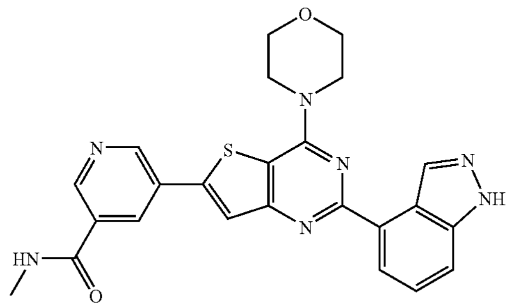 | 5-(2-(1H-indazol-4-yl)-4-morpholinothieno[3,2-d]pyrimidin-6-yl)-N-methylpyridine-3-carboxamide |
| 345. | 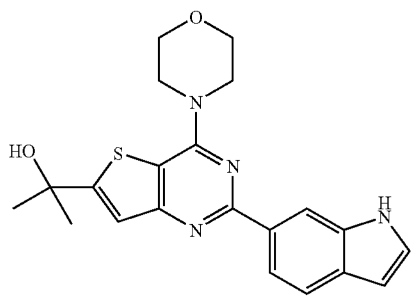 | 2-(2-(1H-indol-6-yl)-4-morpholinothieno[3,2-d]pyrimidin-6-yl)propan-2-ol |
| 346. | 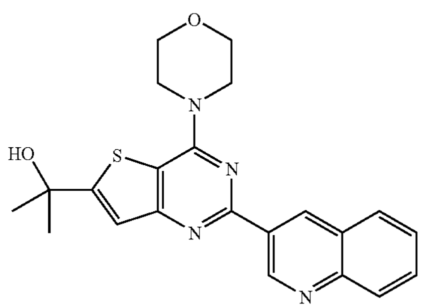 | 2-(4-morpholino-2-(quinolin-3-yl)thieno[3,2-d]pyrimidin-6-yl)propan-2-ol |
| 347. | 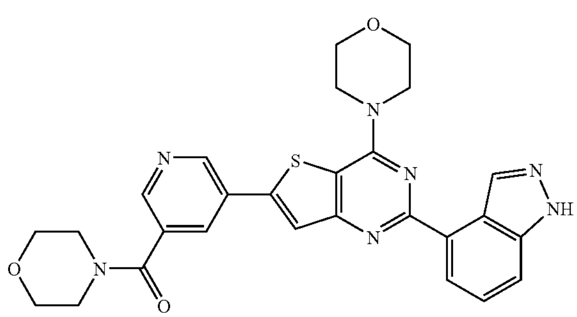 | (5-(2-(1H-indazol-4-yl)-4-morpholinothieno[3,2-d]pyrimidin-6-yl)pyridin-3-yl)(morpholino)methanone |
| 348. | 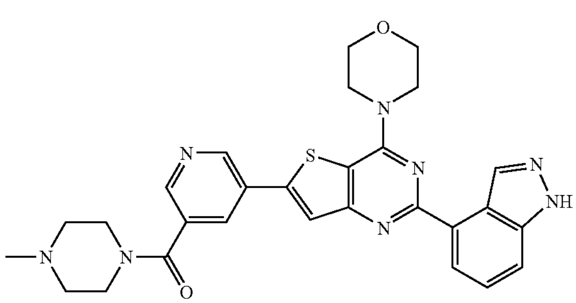 | (5-(2-(1H-indazol-4-yl)-4-morpholinothieno[3,2-d]pyrimidin-6-yl)pyridin-3-yl)(4-methylpiperazin-1-yl)methanone |

TABLE 1b-continued

| Example | Structure | Name |
|---|---|---|
| 349. | 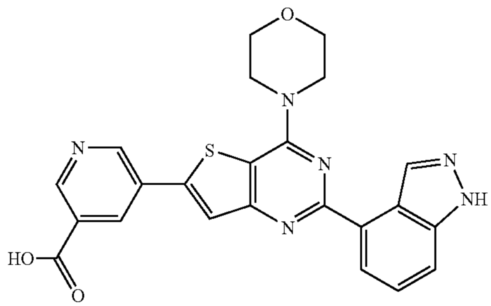 | 5-(2-(1H-indazol-4-yl)-4-morpholinothieno[3,2-d]pyrimidin-6-yl)pyridine-3-carboxylic acid |
| 350. | 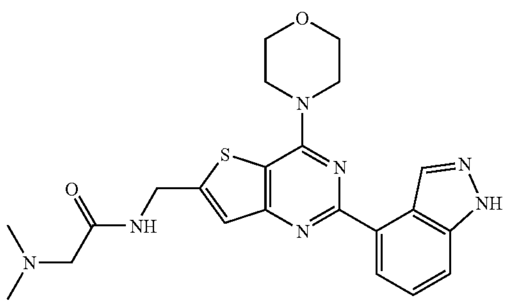 | N-((2-(1H-indazol-4-yl)-4-morpholinothieno[3,2-d]pyrimidin-6-yl)methyl)-2-(dimethylamino)acetamide |
| 351. | 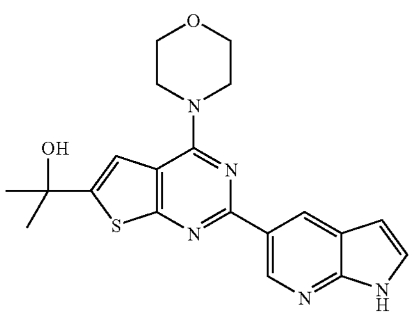 | 2-(4-morpholino-2-(1H-pyrrolo[2,3-b]pyridin-5-yl)thieno[2,3-d]pyrimidin-6-yl)propan-2-ol |
| 352. | 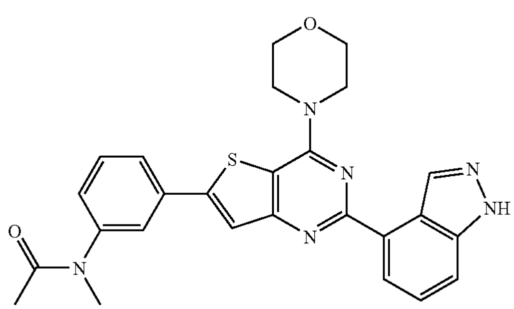 | N-(3-(2-(1H-indazol-4-yl)-4-morpholinothieno[3,2-d]pyrimidin-6-yl)phenyl)-N-methylacetamide |
| 353. | 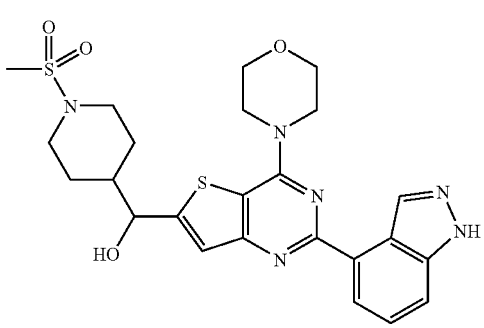 | (2-(1H-indazol-4-yl)-4-morpholinothieno[3,2-d]pyrimidin-6-yl)(4-N-methylsulfonylpiperidin-4-yl)methanol |

TABLE 1b-continued

| Example | Structure | Name |
|---|---|---|
| 354. | 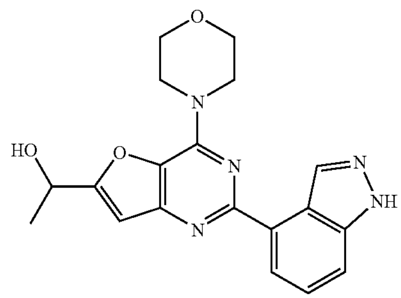 | 1-(2-(1H-indazol-4-yl)-4-morpholinofuro[3,2-d]pyrimidin-6-yl)ethanol |
| 355. | 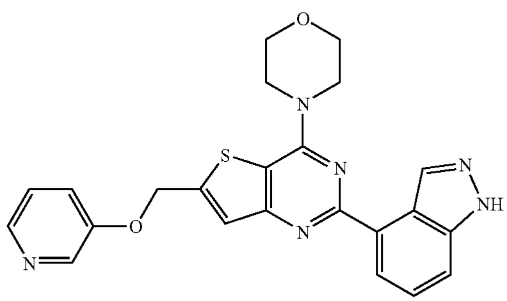 | 2-(1H-indazol-4-yl)-4-morpholino-6-((pyridin-3-yloxy)methyl)thieno[3,2-d]pyrimidine |
| 356. | 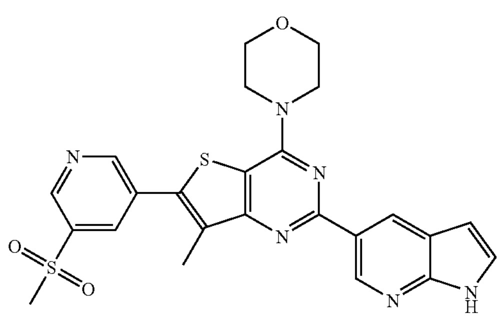 | 7-methyl-6-(5-(methylsulfonyl)pyridin-3-yl)-4-morpholino-2-(1H-pyrrolo[2,3-b]pyridin-5-yl)thieno[3,2-d]pyrimidine |
| 357. | 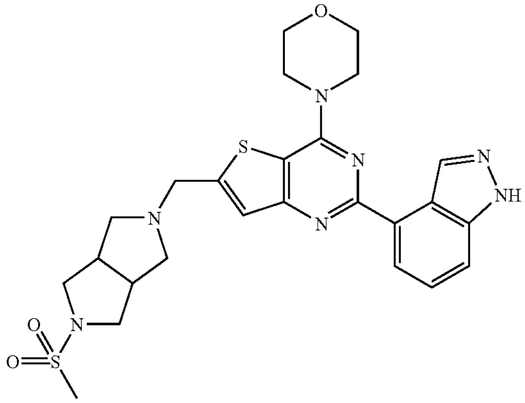 | 6-((hexahydro-2-methylsulfonylpyrrolo[3,4-c]pyrrol-5(1H)-yl)methyl)-2-(1H-indazol-4-yl)-4-morpholinothieno[3,2-d]pyrimidine |

TABLE 1b-continued

| Example | Structure | Name |
|---|---|---|
| 358. | 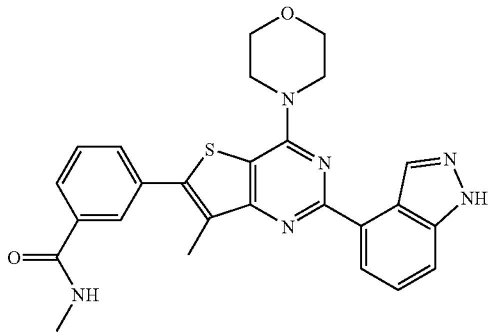 | 3-(2-(1H-indazol-4-yl)-7-methyl-4-morpholinothieno[3,2-d]pyrimidin-6-yl)-N-methylbenzamide |
| 359. | 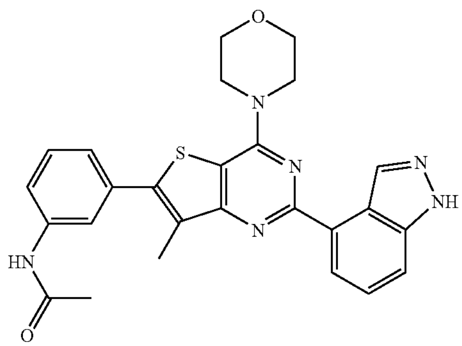 | N-(3-(2-(1H-indazol-4-yl)-7-methyl-4-morpholinothieno[3,2-d]pyrimidin-6-yl)phenyl)acetamide |
| 360. | 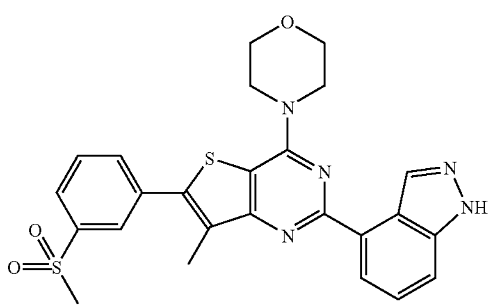 | 2-(1H-indazol-4-yl)-7-methyl-6-(3-(methylsulfonyl)phenyl)-4-morpholinothieno[3,2-d]pyrimidine |
| 361. | 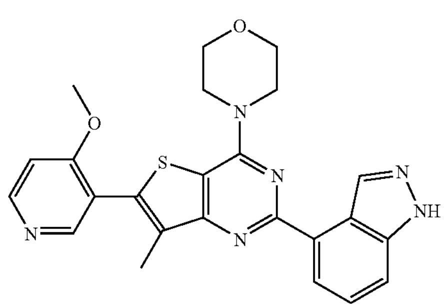 | 2-(1H-indazol-4-yl)-6-(4-methoxypyridin-3-yl)-7-methyl-4-morpholinothieno[3,2-d]pyrimidine |

TABLE 1b-continued

| Example | Structure | Name |
|---|---|---|
| 362. | 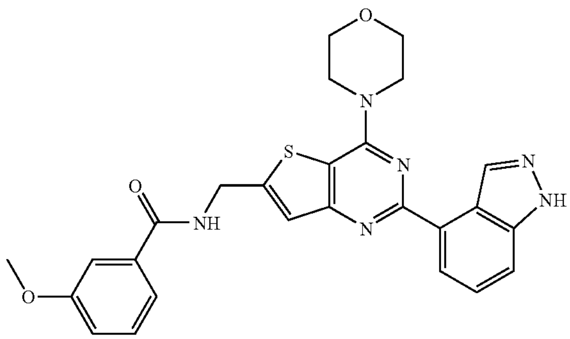 | N-((2-(1H-indazol-4-yl)-4-morpholinothieno[3,2-d]pyrimidin-6-yl)methyl)-3-methoxybenzamide |
| 363. | 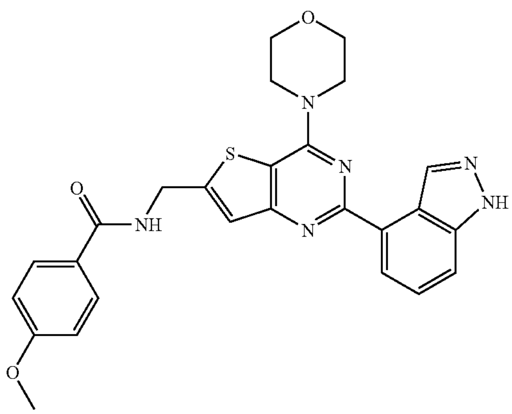 | N-((2-(1H-indazol-4-yl)-4-morpholinothieno[3,2-d]pyrimidin-6-yl)methyl)-4-methoxybenzamide |
| 364. | 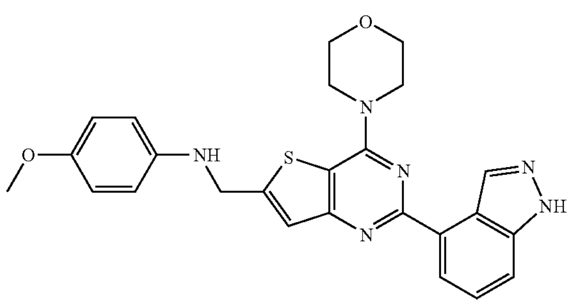 | N-((2-(1H-indazol-4-yl)-4-morpholinothieno[3,2-d]pyrimidin-6-yl)methyl)-4-methoxybenzenamine |
| 365. | 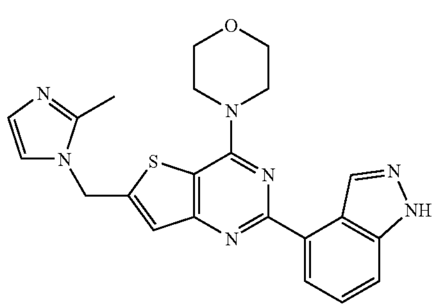 | 2-(1H-indazol-4-yl)-6-((2-methyl-1H-imidazol-1-yl)methyl)-4-morpholinothieno[3,2-d]pyrimidine |

TABLE 1b-continued

| Example | Structure | Name |
|---|---|---|
| 366. | 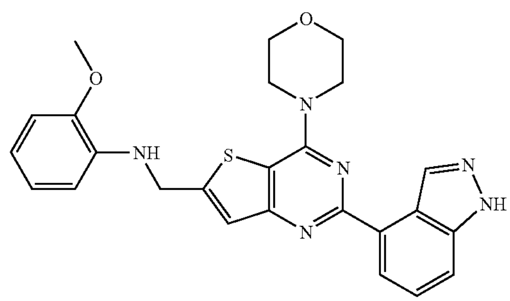 | N-((2-(1H-indazol-4-yl)-4-morpholinothieno[3,2-d]pyrimidin-6-yl)methyl)-2-methoxybenzenamine |
| 367. | 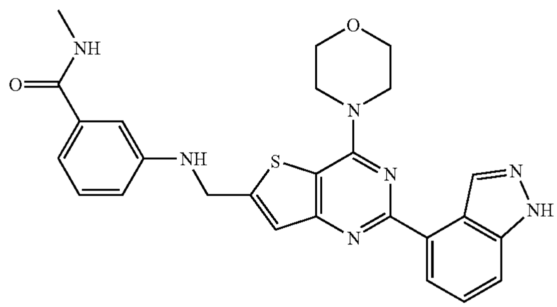 | 3-((2-(1H-indazol-4-yl)-4-morpholinothieno[3,2-d]pyrimidin-6-yl)methylamino)-N-methylbenzamide |
| 368. | 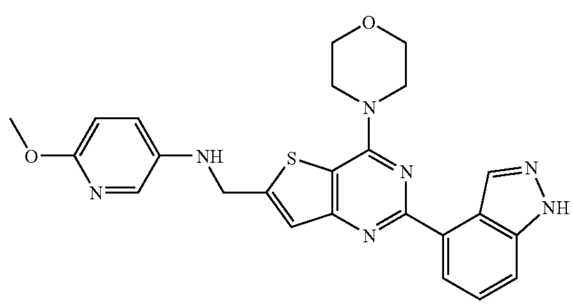 | N-((2-(1H-indazol-4-yl)-4-morpholinothieno[3,2-d]pyrimidin-6-yl)methyl)-6-methoxypyridin-3-amine |
| 369. | 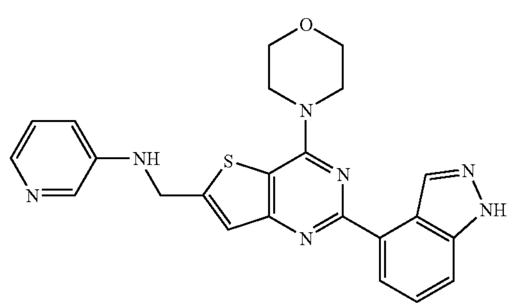 | N-((2-(1H-indazol-4-yl)-4-morpholinothieno[3,2-d]pyrimidin-6-yl)methyl)pyridin-3-amine |
| 370. | 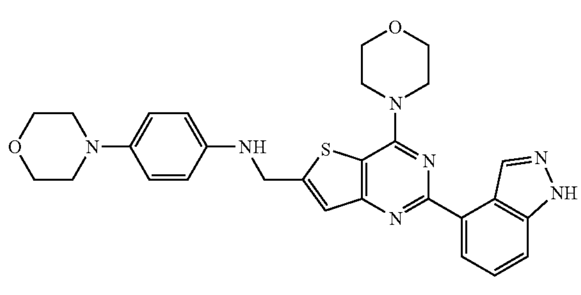 | N-((2-(1H-indazol-4-yl)-4-morpholinothieno[3,2-d]pyrimidin-6-yl)methyl)-4-morpholinobenzenamine |

TABLE 1b-continued

| Example | Structure | Name |
|---|---|---|
| 371. | 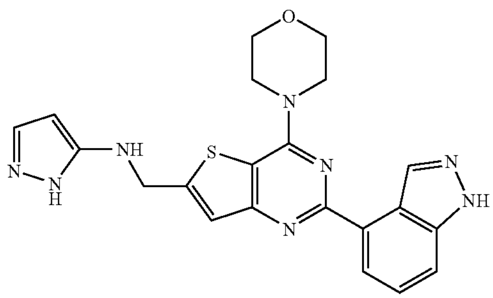 | N-((2-(1H-indazol-4-yl)-4-morpholinothieno[3,2-d]pyrimidin-6-yl)methyl)-1H-pyrazol-5-amine |
| 372. | 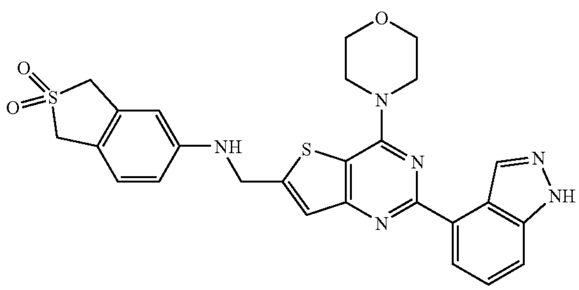 | N-((2-(1H-indazol-4-yl)-4-morpholinothieno[3,2-d]pyrimidin-6-yl)methyl)-1,3-dihydrobenzo[c]thiopen-1,1-dioxide-5-amine |
| 373. | 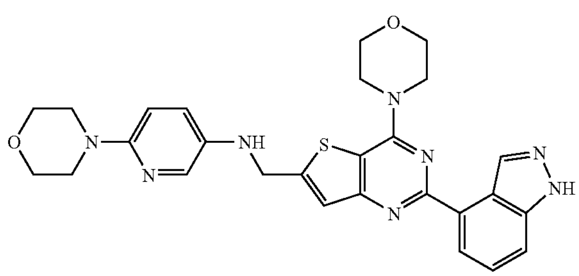 | N-((2-(1H-indazol-4-yl)-4-morpholinothieno[3,2-d]pyrimidin-6-yl)methyl)-6-morpholinopyridin-3-amine |
| 374. | 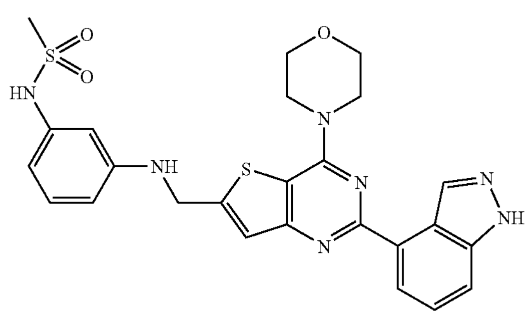 | N1-((2-(1H-indazol-4-yl)-4-morpholinothieno[3,2-d]pyrimidin-6-yl)methyl)-3-methylsulfonylaminobenzene-1-amine |
| 375. | 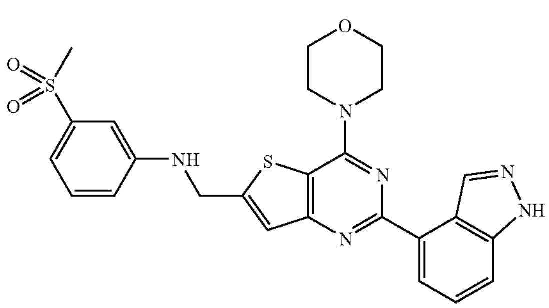 | N-((2-(1H-indazol-4-yl)-4-morpholinothieno[3,2-d]pyrimidin-6-yl)methyl)-3-(methylsulfonyl)benzenamine |

TABLE 1b-continued

| Example | Structure | Name |
|---|---|---|
| 376. | 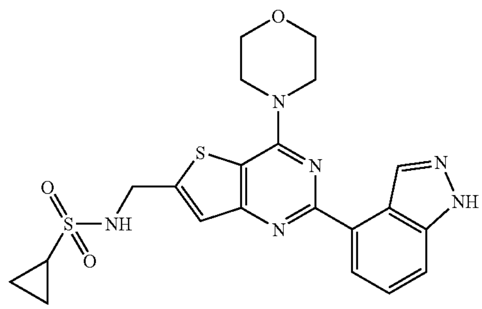 | (2-(1H-indazol-4-yl)-4-morpholinothieno[3,2-d]pyrimidin-6-yl)-N-cyclopropylsulfonylmethanamine |
| 377. | 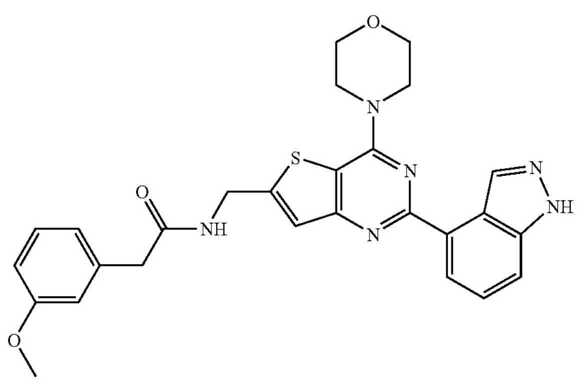 | N-((2-(1H-indazol-4-yl)-4-morpholinothieno[3,2-d]pyrimidin-6-yl)methyl)-2-(3-methoxyphenyl)acetamide |
| 378. | 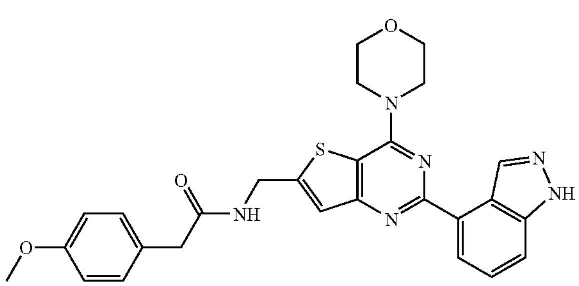 | N-((2-(1H-indazol-4-yl)-4-morpholinothieno[3,2-d]pyrimidin-6-yl)methyl)-2-(4-methoxyphenyl)acetamide |
| 379. | 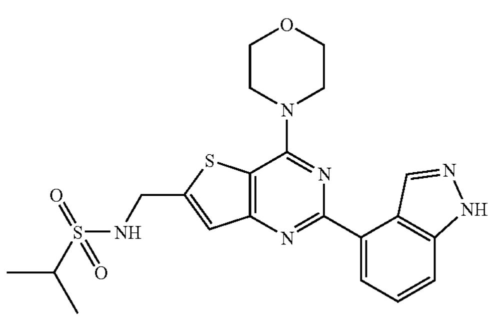 | (2-(1H-indazol-4-yl)-4-morpholinothieno[3,2-d]pyrimidin-6-yl)-N-methylsulfonylmethanamine |

TABLE 1b-continued

| Example | Structure | Name |
|---|---|---|
| 380. | 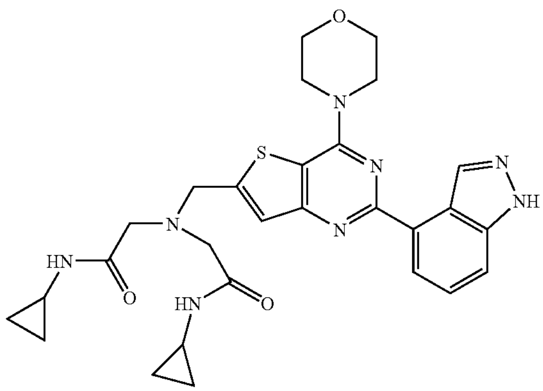 | 2-(N-((2-(1H-indazol-4-yl)-4-morpholinothieno[3,2-d]pyrimidin-6-yl)methyl)-N,N-bis-(N-cyclopropylacetamide)-methanamine |
| 381. | 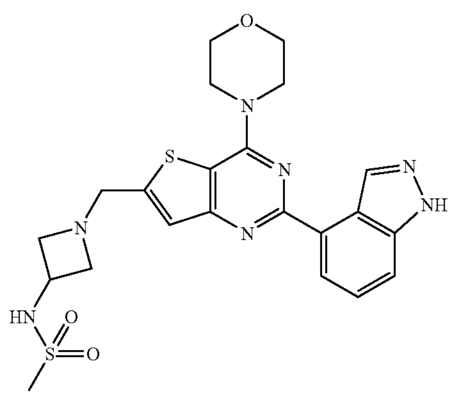 | 1-((2-(1H-indazol-4-yl)-4-morpholinothieno[3,2-d]pyrimidin-6-yl)methyl)-N-methylsulfonylazetidin-3-amine |
| 382. | 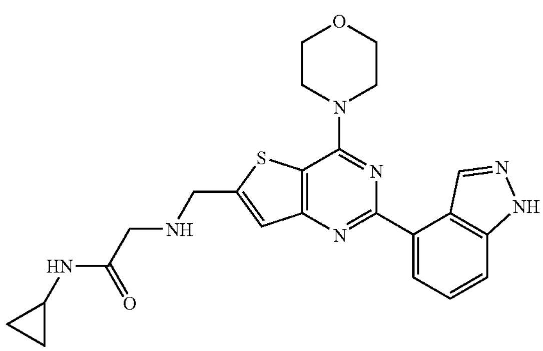 | 2-((2-(1H-indazol-4-yl)-4-morpholinothieno[3,2-d]pyrimidin-6-yl)methylamino)-N-cyclopropylacetamide |
| 383. | 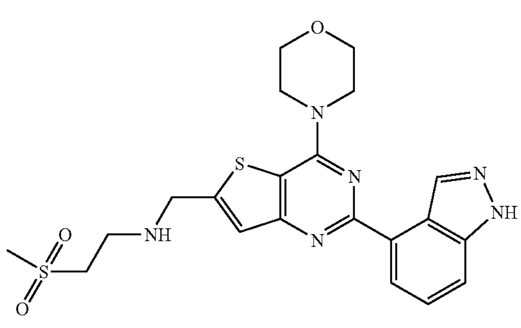 | N-((2-(1H-indazol-4-yl)-4-morpholinothieno[3,2-d]pyrimidin-6-yl)methyl)-2-(methylsulfonyl)ethanamine |

TABLE 1b-continued

| Example | Structure | Name |
|---|---|---|
| 384. | 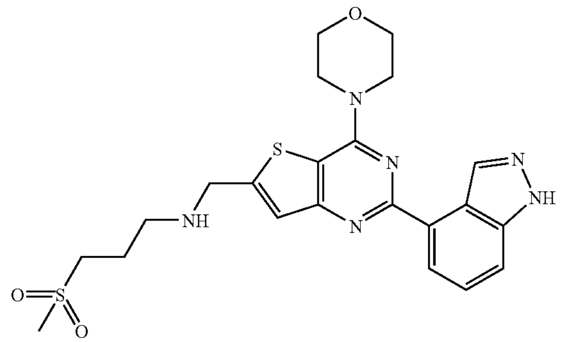 | N-((2-(1H-indazol-4-yl)-4-morpholinothieno[3,2-d]pyrimidin-6-yl)methyl)-3-(methylsulfonyl)propan-1-amine |
| 385. | 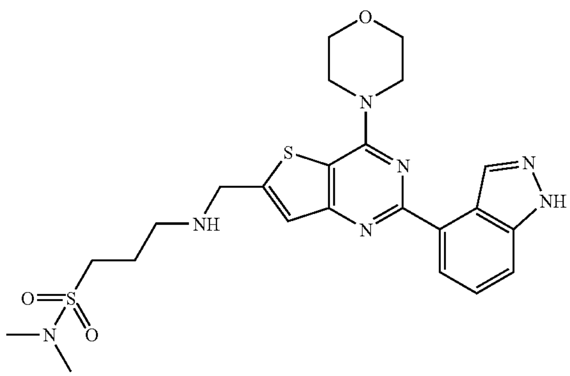 | N-((2-(1H-indazol-4-yl)-4-morpholinothieno[3,2-d]pyrimidin-6-yl)methyl)-3-(dimethylaminosulfonyl)propan-1-amine |
| 386. | 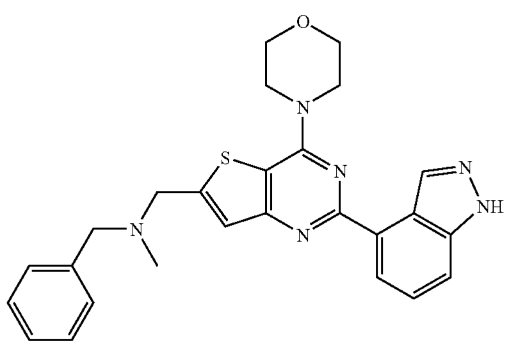 | N-((2-(1H-indazol-4-yl)-4-morpholinothieno[3,2-d]pyrimidin-6-yl)methyl)-N-methyl(phenyl)methanamine |
| 387. | 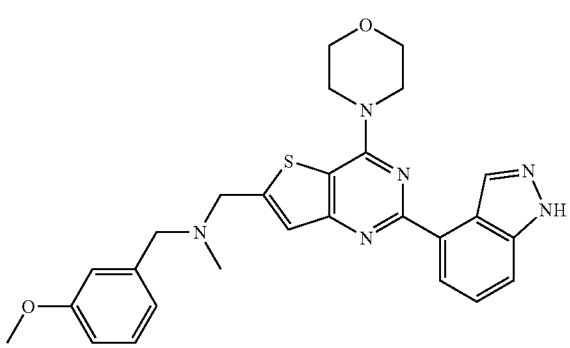 | N-((2-(1H-indazol-4-yl)-4-morpholinothieno[3,2-d]pyrimidin-6-yl)methyl)(3-methoxyphenyl)-N-methylmethanamine |

TABLE 1b-continued

| Example | Structure | Name |
|---|---|---|
| 388. | 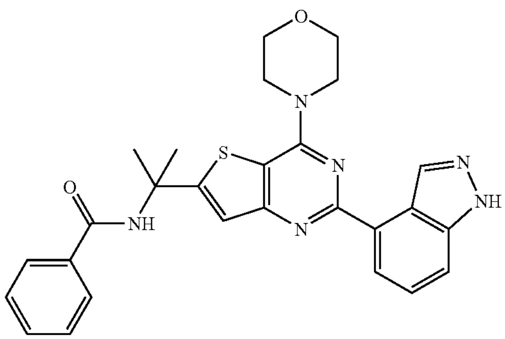 | N-(2-(2-(1H-indazol-4-yl)-4-morpholinothieno[3,2-d]pyrimidin-6-yl)propan-2-yl)benzamide |
| 389. | 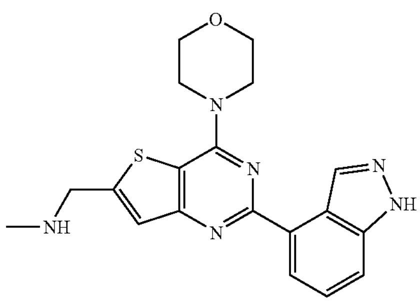 | (2-(1H-indazol-4-yl)-4-morpholinothieno[3,2-d]pyrimidin-6-yl)-N-methylmethanamine |
| 390. | 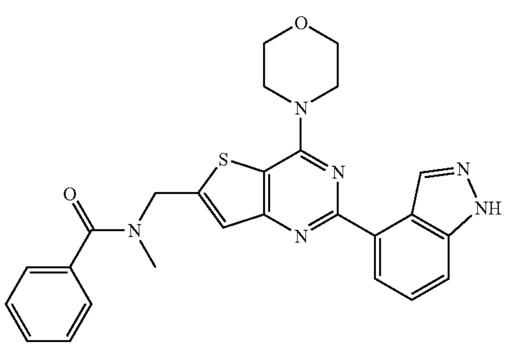 | N-((2-(1H-indazol-4-yl)-4-morpholinothieno[3,2-d]pyrimidin-6-yl)methyl)-N-methylbenzamide |
| 391. | 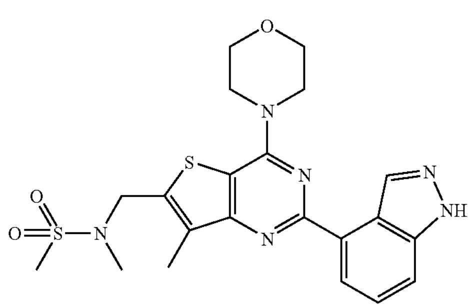 | N-((2-(1H-indazol-4-yl)-7-methyl-4-morpholinothieno[3,2-d]pyrimidin-6-yl)methyl)-N-methylsulfonyl-methanamine |

TABLE 1b-continued

| Example | Structure | Name |
|---|---|---|
| 392. | 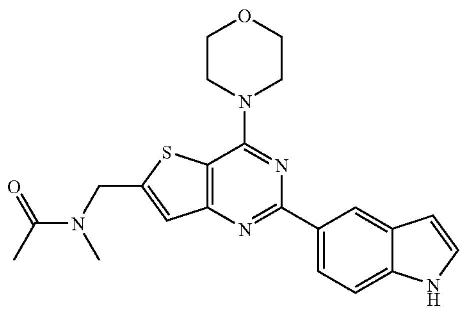 | N-((2-(1H-indol-5-yl)-4-morpholinothieno[3,2-d]pyrimidin-6-yl)methyl)-N-methylacetamide |
| 393. | 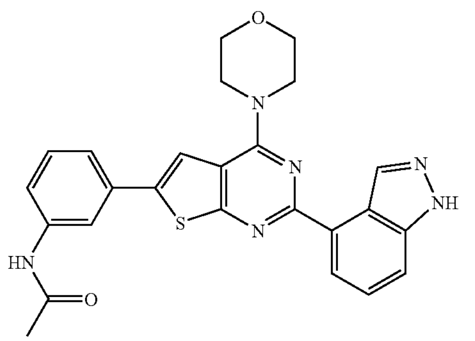 | N-(3-(2-(1H-indazol-4-yl)-4-morpholinothieno[2,3-d]pyrimidin-6-yl)phenyl)acetamide |
| 394. | 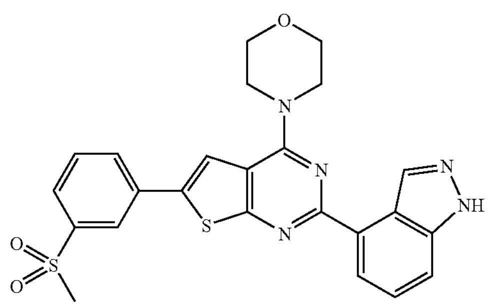 | 2-(1H-indazol-4-yl)-6-(3-(methylsulfonyl)phenyl)-4-morpholinothieno[2,3-d]pyrimidine |
| 395. | 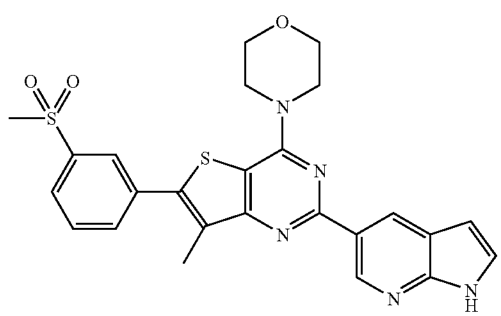 | 7-methyl-6-(3-(methylsulfonyl)phenyl)-4-morpholino-2-(1H-pyrrolo[2,3-b]pyridin-5-yl)thieno[3,2-d]pyrimidine |
| 396. | 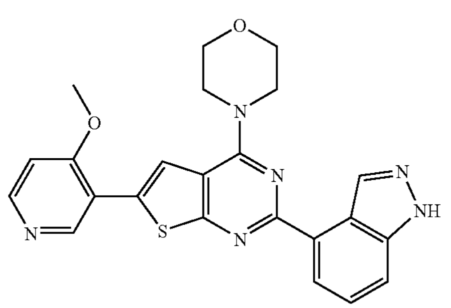 | 2-(1H-indazol-4-yl)-6-(4-methoxypyridin-3-yl)-4-morpholinothieno[2,3-d]pyrimidine |

TABLE 1b-continued

| Example | Structure | Name |
|---|---|---|
| 397. | 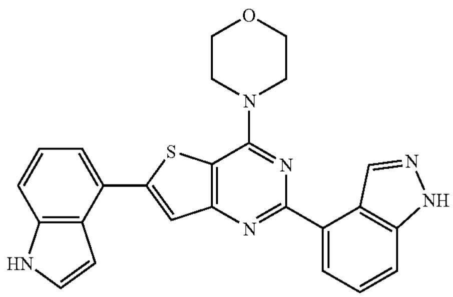 | 2-(1H-indazol-4-yl)-6-(1H-indol-4-yl)-4-morpholinothieno[3,2-d]pyrimidine |
| 398. | 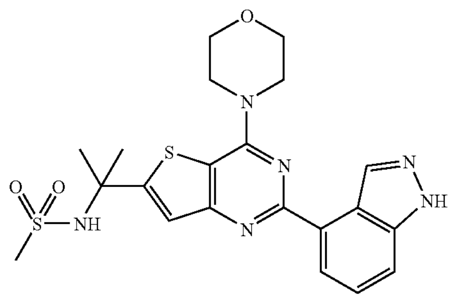 | 2-(2-(1H-indazol-4-yl)-4-morpholinothieno[3,2-d]pyrimidin-6-yl)-N-methylsulfonylpropan-2-amine |
| 399. | 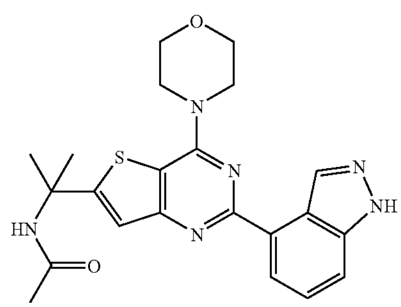 | N-(2-(2-(1H-indazol-4-yl)-4-morpholinothieno[3,2-d]pyrimidin-6-yl)propan-2-yl)acetamide |
| 400. | 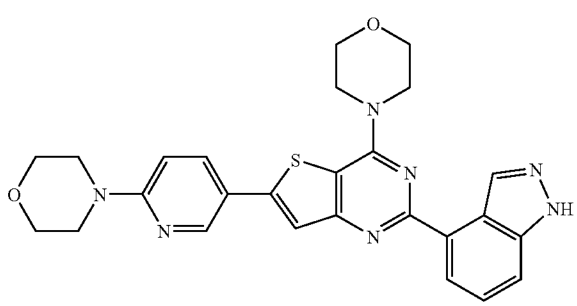 | 2-(1H-indazol-4-yl)-4-morpholino-6-(6-morpholinopyridin-3-yl)thieno[3,2-d]pyrimidine |
| 401. | 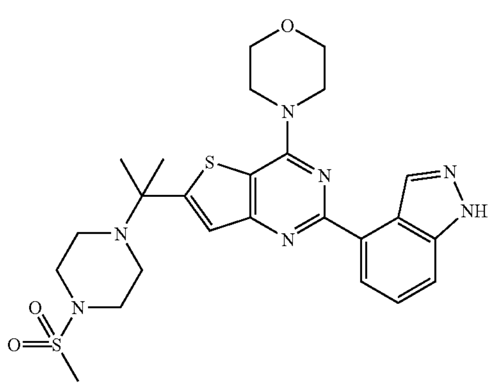 | 2-(1H-indazol-4-yl)-6-(2-(4-N-methylsulfonylpiperazin-1-yl)propan-2-yl)-4-morpholinothieno[3,2-d]pyrimidine |

TABLE 1b-continued

| Example | Structure | Name |
|---|---|---|
| 402. | 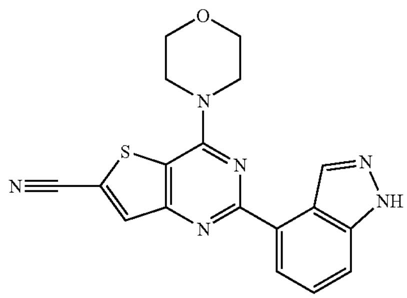 | 2-(1H-indazol-4-yl)-4-morpholinothieno[3,2-d]pyrimidine-6-carbonitrile |
| 403. | 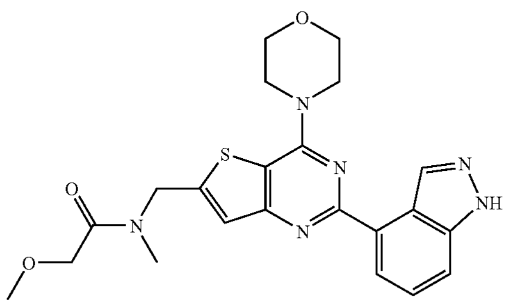 | N-((2-(1H-indazol-4-yl)-4-morpholinothieno[3,2-d]pyrimidin-6-yl)methyl)-2-methoxy-N-methylacetamide |
| 404. | 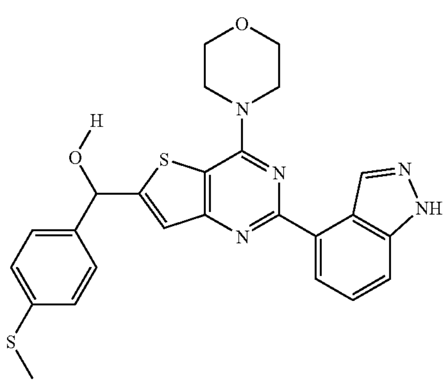 | (2-(1H-indazol-4-yl)-4-morpholinothieno[3,2-d]pyrimidin-6-yl)(4-(methylthio)phenyl)methanol |
| 405. | 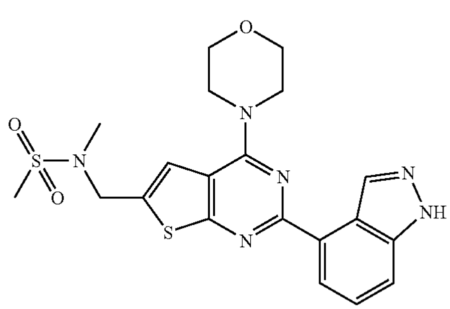 | (2-(1H-indazol-4-yl)-4-morpholinothieno[2,3-d]pyrimidin-6-yl)-N-methylsulfonyl,N-methylmethanamine |

TABLE 1b-continued

| Example | Structure | Name |
|---|---|---|
| 406. | 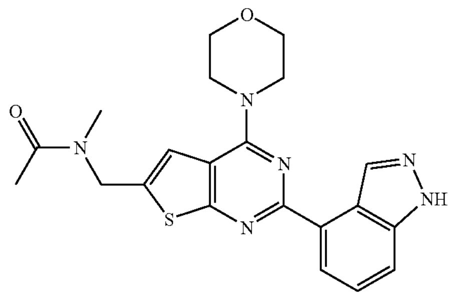 | N-((2-(1H-indazol-4-yl)-4-morpholinothieno[2,3-d]pyrimidin-6-yl)methyl)-N-methylacetamide |
| 407. | 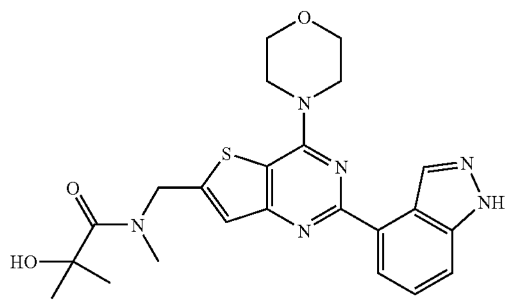 | N-((2-(1H-indazol-4-yl)-4-morpholinothieno[3,2-d]pyrimidin-6-yl)methyl)-2-hydroxy-N,2-dimethylpropanamide |
| 408. | 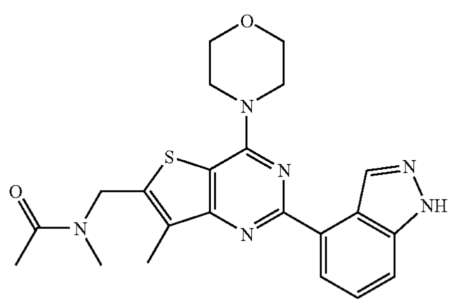 | N-((2-(1H-indazol-4-yl)-7-methyl-4-morpholinothieno[3,2-d]pyrimidin-6-yl)methyl)-N-methylacetamide |
| 409. | 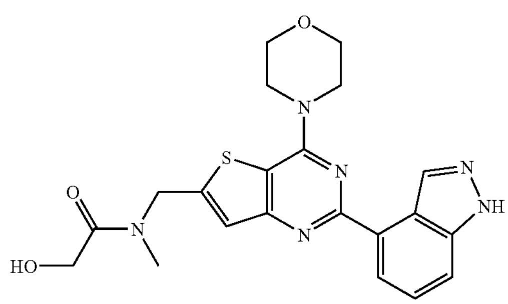 | N-((2-(1H-indazol-4-yl)-4-morpholinothieno[3,2-d]pyrimidin-6-yl)methyl)-2-hydroxy-N-methylacetamide |
| 410. | 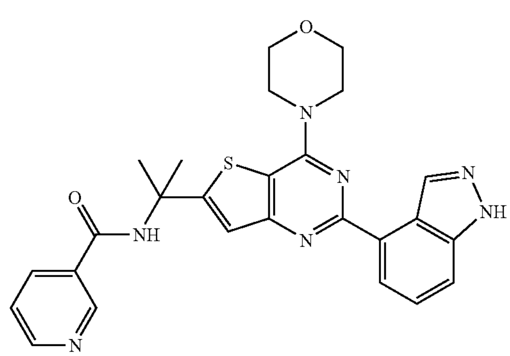 | N-(2-(2-(1H-indazol-4-yl)-4-morpholinothieno[3,2-d]pyrimidin-6-yl)propan-2-yl)nicotinamide |

TABLE 1b-continued

| Example | Structure | Name |
|---|---|---|
| 411. | 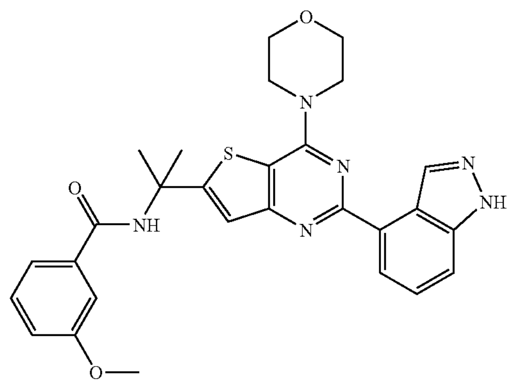 | N-(2-(2-(1H-indazol-4-yl)-4-morpholinothieno[3,2-d]pyrimidin-6-yl)propan-2-yl)-3-methoxybenzamide |
| 412. | 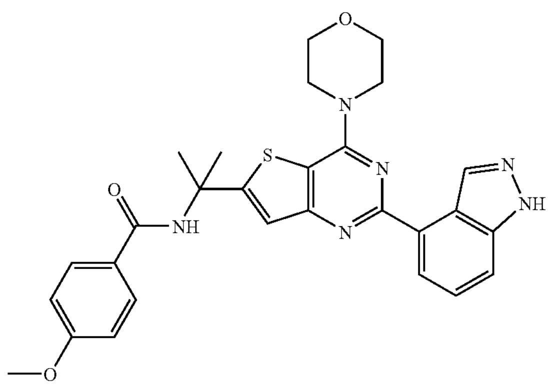 | N-(2-(2-(1H-indazol-4-yl)-4-morpholinothieno[3,2-d]pyrimidin-6-yl)propan-2-yl)-4-methoxybenzamide |
| 413. | 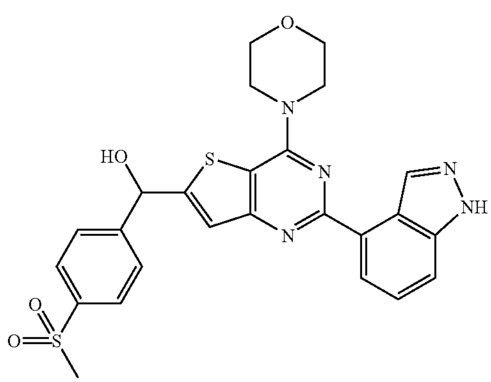 | (2-(1H-indazol-4-yl)-4-morpholinothieno[3,2-d]pyrimidin-6-yl)(4-(methylsulfonyl)phenyl)methanol |
| 414. | 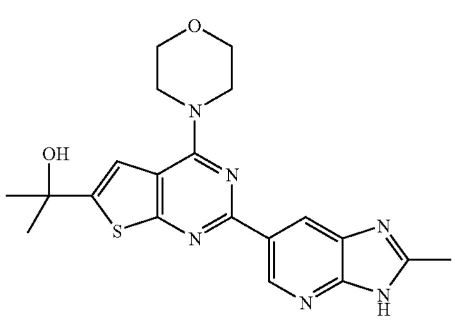 | 2-(2-(2-methyl-3H-imidazo[4,5-b]pyridin-6-yl)-4-morpholinothieno[2,3-d]pyrimidin-6-yl)propan-2-ol |

TABLE 1b-continued

| Example | Structure | Name |
|---|---|---|
| 415. | 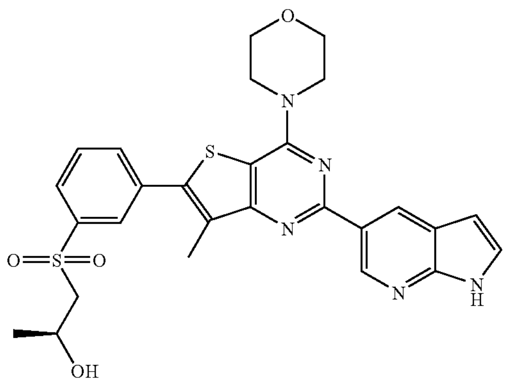 | (S)-1-(3-(7-methyl-4-morpholino-2-(1H-pyrrolo[2,3-b]pyridin-5-yl)thieno[3,2-d]pyrimidin-6-yl)phenylsulfonyl)propan-2-ol |
| 416. | 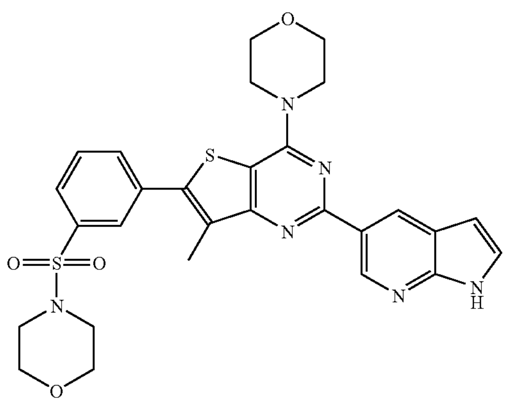 | 7-methyl-6-(3-(N-morpholino)sulfonyl)phenyl)-4-morpholino-2-(1H-pyrrolo [2,3-b]pyridin-5-yl)thieno[3,2-d]pyrimidine |
| 417. | 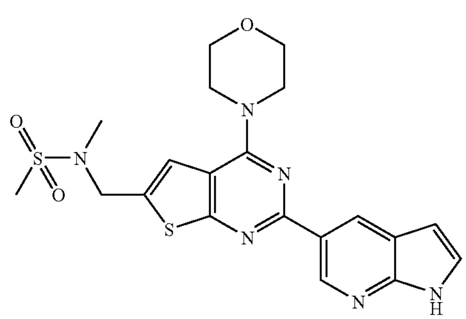 | N-methyl,N-methylsulfonyl(4-morpholino-2-(1H-pyrrolo[2,3-b]pyridin-5-yl)thieno[2,3-d]pyrimidin-6-yl)methanamine |
| 418. | 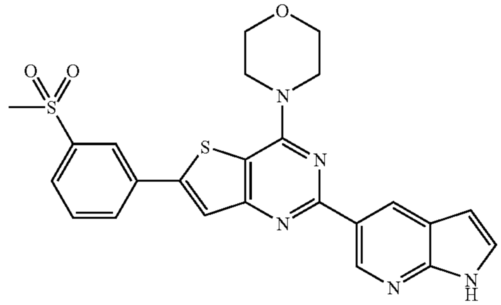 | 6-(3-(methylsulfonyl)phenyl)-4-morpholino-2-(1H-pyrrolo[2,3-b]pyridin-5-yl)thieno[3,2-d]pyrimidine |

TABLE 1b-continued

| Example | Structure | Name |
| --- | --- | --- |
| 419. | 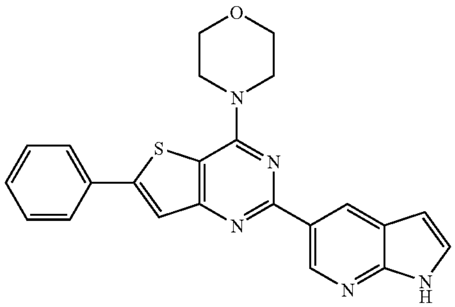 | 4-morpholino-6-phenyl-2-(1H-pyrrolo[2,3-b]pyridin-5-yl)thieno[3,2-d]pyrimidine |
| 420. | 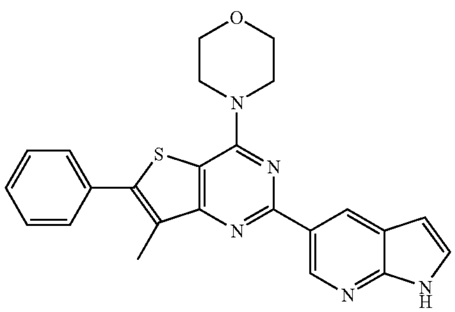 | 7-methyl-4-morpholino-6-phenyl-2-(1H-pyrrolo[2,3-b]pyridin-5-yl)thieno[3,2-d]pyrimidine |
| 421. | 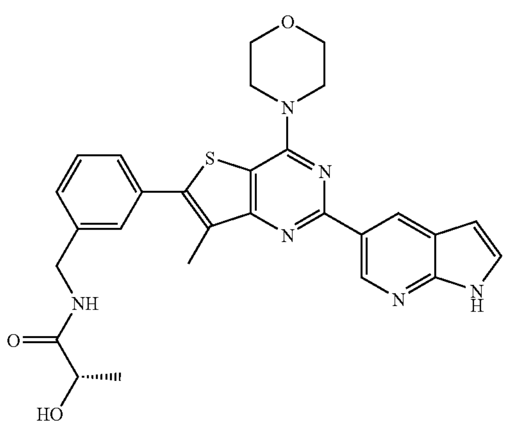 | (2S)-2-hydroxy-N-((3-(7-methyl-4-morpholino-2-(1H-pyrrolo[2,3-b]pyridin-5-yl)thieno[3,2-d]pyrimidin-6-yl)phenyl)methyl)propanamide |
| 422. | 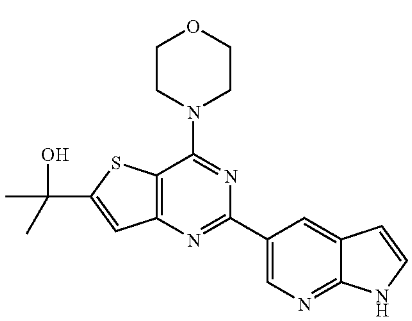 | 2-(4-morpholino-2-(1H-pyrrolo[2,3-b]pyridin-5-yl)thieno[3,2-d]pyrimidin-6-yl)propan-2-ol |

TABLE 1b-continued

| Example | Structure | Name |
|---|---|---|
| 423. | 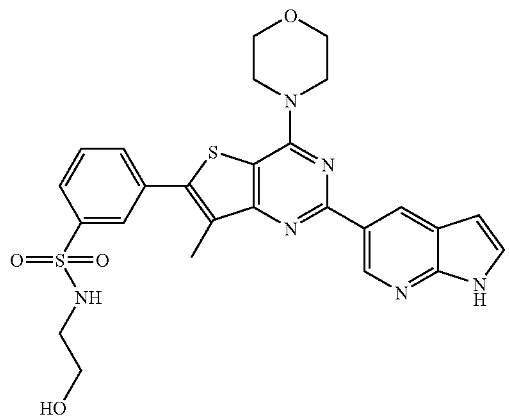 | 7-methyl-6-(3-(2-hydroxyethylaminosulfonyl)phenyl)-4-morpholino-2-(1H-pyrrolo[2,3-b]pyridin-5-yl)thieno[3,2-d]pyrimidine |
| 424. | 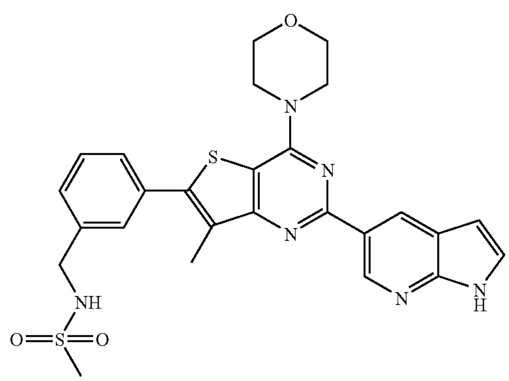 | N-methylsulfonyl(3-(7-methyl-4-morpholino-2-(1H-pyrrolo[2,3-b]pyridin-5-yl)thieno[3,2-d]pyrimidin-6-yl)phenyl)methanamine |
| 425. | 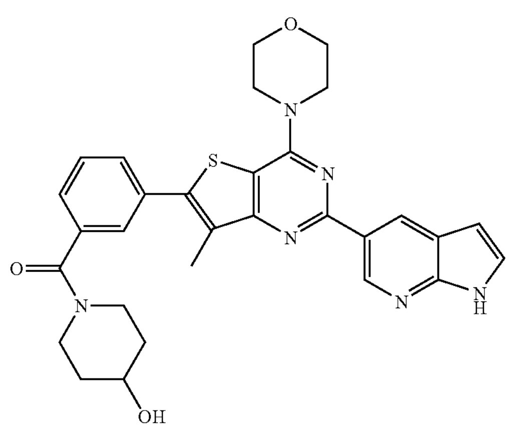 | (4-hydroxypiperidin-1-yl)(3-(7-methyl-4-morpholino-2-(1H-pyrrolo[2,3-b]pyridin-5-yl)thieno[3,2-d]pyrimidin-6-yl)phenyl)methanone |

TABLE 1b-continued

| Example | Structure | Name |
|---|---|---|
| 426. | 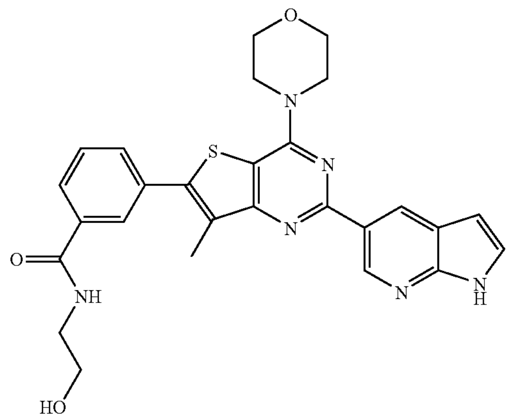 | N-(2-hydroxyethyl)-3-(7-methyl-4-morpholino-2-(1H-pyrrolo[2,3-b]pyridin-5-yl)thieno[3,2-d]pyrimidin-6-yl)benzamide |
| 427. | 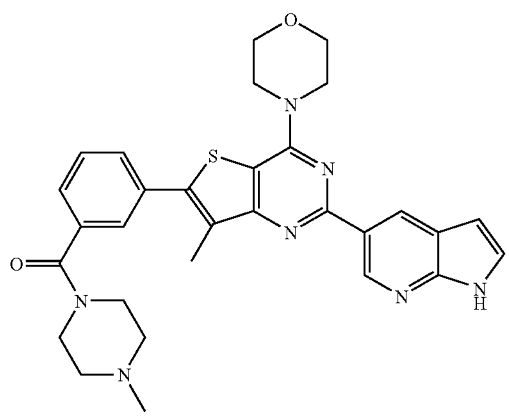 | (3-(7-methyl-4-morpholino-2-(1H-pyrrolo[2,3-b]pyridin-5-yl)thieno[3,2-d]pyrimidin-6-yl)phenyl)(4-methylpiperazin-1-yl)methanone |
| 428. | 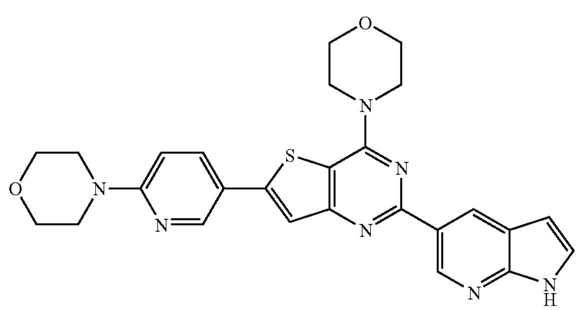 | 4-morpholino-6-(6-morpholinopyridin-3-yl)-2-(1H-pyrrolo[2,3-b]pyridin-5-yl)thieno[3,2-d]pyrimidine |
| 429. | 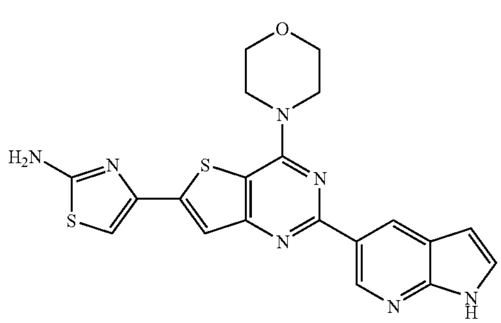 | 4-(4-morpholino-2-(1H-pyrrolo[2,3-b]pyridin-5-yl)thieno[3,2-d]pyrimidin-6-yl)thiazol-2-amine |

TABLE 1b-continued

| Example | Structure | Name |
|---|---|---|
| 430. | 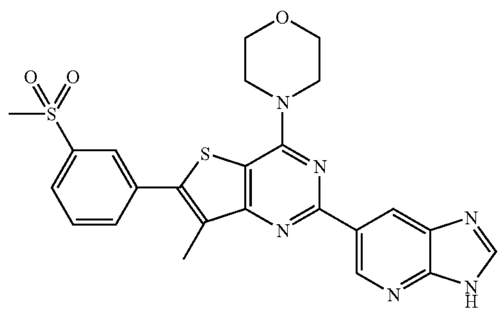 | 6-(7-methyl-6-(3-(methylsulfonyl)phenyl)-4-morpholinothieno[3,2-d]pyrimidin-2-yl)-3H-imidazo[4,5-b]pyridine |
| 431. | 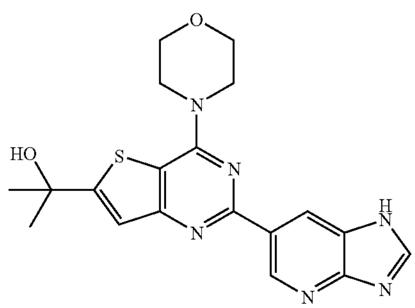 | 2-(2-(1H-imidazo[4,5-b]pyridin-6-yl)-4-morpholinothieno[3,2-d]pyrimidin-6-yl)propan-2-ol |
| 432. | 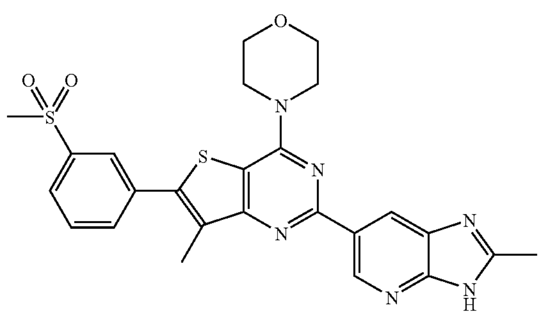 | 2-methyl-6-(7-methyl-6-(3-(methylsulfonyl)phenyl)-4-morpholinothieno[3,2-d]pyrimidin-2-yl)-3H-imidazo[4,5-b]pyridine |
| 433. | 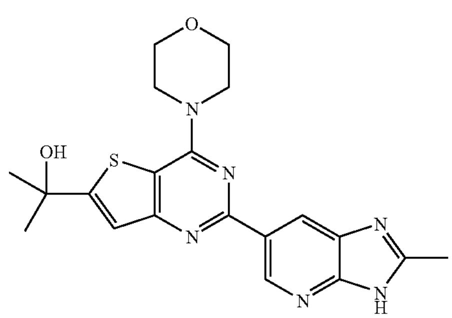 | 2-(2-(2-methyl-3H-imidazo[4,5-b]pyridin-6-yl)-4-morpholinothieno[3,2-d]pyrimidin-6-yl)propan-2-ol |
| 434. | 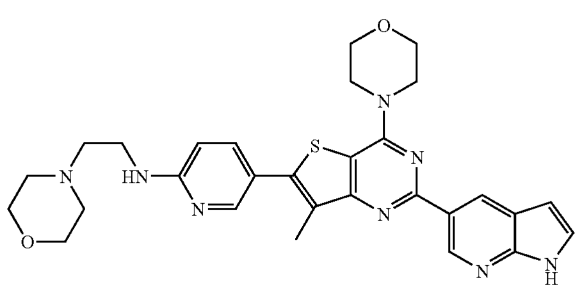 | 5-(7-methyl-4-morpholino-2-(1H-pyrrolo[2,3-b]pyridin-5-yl)thieno[3,2-d]pyrimidin-6-yl)-N-(2-morpholinoethyl)pyridin-2-amine |

TABLE 1b-continued

| Example | Structure | Name |
|---|---|---|
| 435. | 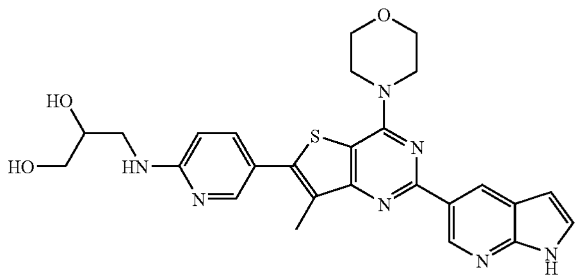 | 3-(5-(7-methyl-4-morpholino-2-(1H-pyrrolo[2,3-b]pyridin-5-yl)thieno[3,2-d]pyrimidin-6-yl)pyridin-2-ylamino)propane-1,2-diol |
| 436. | 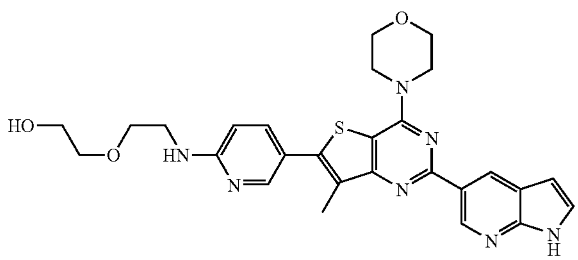 | 2-(2-(5-(7-methyl-4-morpholino-2-(1H-pyrrolo[2,3-b]pyridin-5-yl)thieno[3,2-d]pyrimidin-6-yl)pyridin-2-ylamino)ethoxy)ethanol |
| 437. | 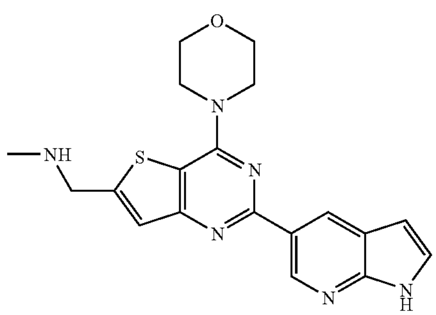 | N-methyl(4-morpholino-2-(1H-pyrrolo[2,3-b]pyridin-5-yl)thieno[3,2-d]pyrimidin-6-yl)methanamine |
| 438. | 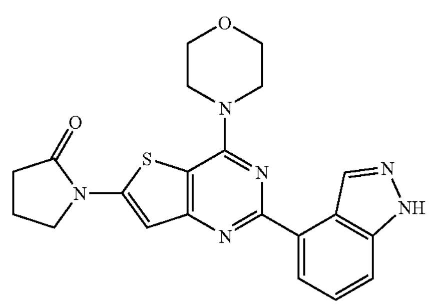 | 1-(2-(1H-indazol-4-yl)-4-morpholinothieno[3,2-d]pyrimidin-6-yl)pyrrolidin-2-one |
| 439. | 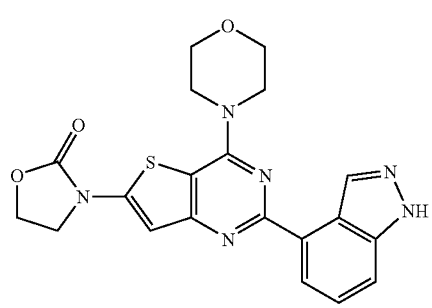 | 3-(2-(1H-indazol-4-yl)-4-morpholinothieno[3,2-d]pyrimidin-6-yl)oxazolidin-2-one |

TABLE 1b-continued
| Example | Structure | Name |
|---------|-----------|------|
| 440. | 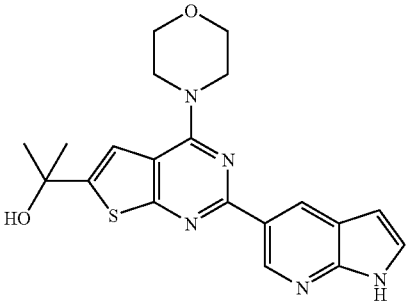 | 2-(4-morpholino-2-(1H-pyrrolo[2,3-b]pyridin-5-yl)thieno[2,3-d]pyrimidin-6-yl)propan-2-ol |
| 441. | 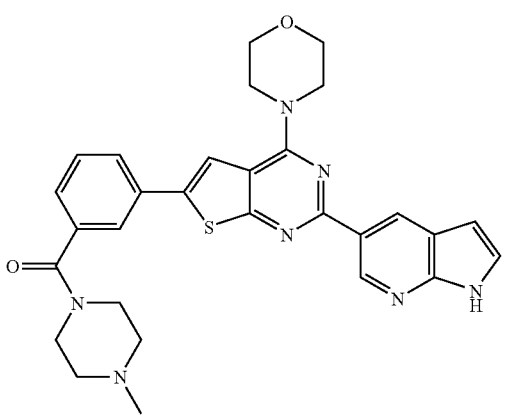 | (4-methylpiperazin-1-yl)(3-(4-morpholino-2-(1H-pyrrolo[2,3-b]pyridin-5-yl)thieno[2,3-d]pyrimidin-6-yl)phenyl)methanone |
| 442. | 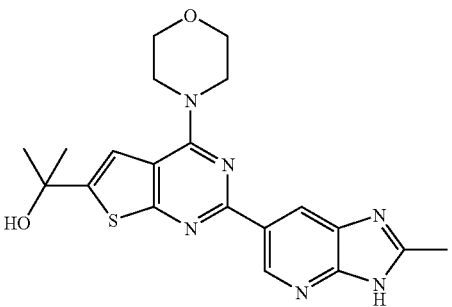 | 2-(2-(2-methyl-3H-imidazo[4,5-b]pyridin-6-yl)-4-morpholinothieno[2,3-d]pyrimidin-6-yl)propan-2-ol |
| 443. | 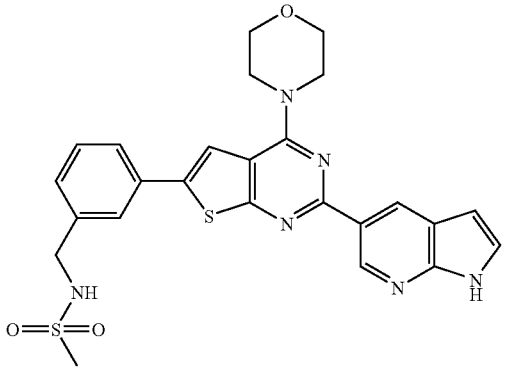 | N-(3-(4-morpholino-2-(1H-pyrrolo[2,3-b]pyridin-5-yl)thieno[2,3-d]pyrimidin-6-yl)benzyl)methanesulfonamide |

TABLE 1b-continued

| Example | Structure | Name |
| --- | --- | --- |
| 444. | 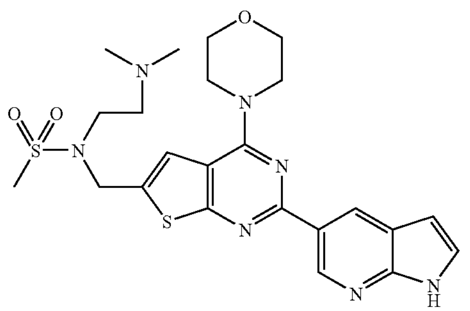 | N-(2-(dimethylamino)ethyl)-N-((4-morpholino-2-(1H-pyrrolo[2,3-b]pyridin-5-yl)thieno[2,3-d]pyrimidin-6-yl)methyl)methanesulfonamide |
| 445. | 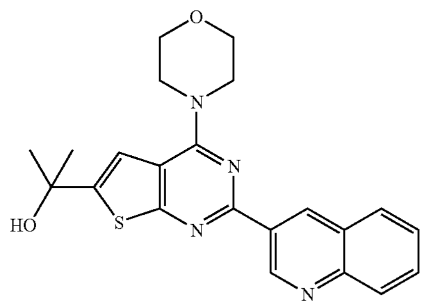 | 2-(4-morpholino-2-(quinolin-3-yl)thieno[2,3-d]pyrimidin-6-yl)propan-2-ol |
| 446. | 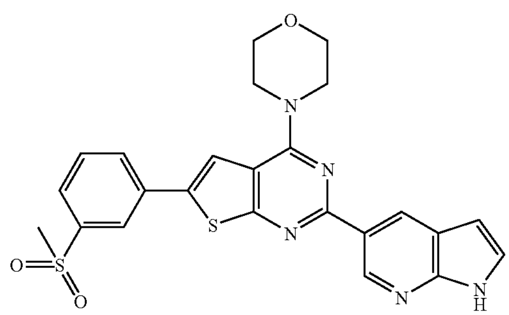 | 4-(6-(3-(methylsulfonyl)phenyl)-2-(1H-pyrrolo[2,3-b]pyridin-5-yl)thieno[2,3-d]pyrimidin-4-yl)morpholine |

Administration of compounds of formula Ia and Ib

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula Ia or Ib compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula Ia and Ib Compounds

Compounds of the present invention are useful for treating diseases, conditions and/or disorders including, but not limited to, those characterized by over expression of lipid kinases, e.g. PI3 kinase. Accordingly, another aspect of this invention includes methods of treating or preventing diseases or conditions that can be treated or prevented by inhibiting lipid kinases, including PI3. In one embodiment, the method comprises administering to a mammal in need thereof a therapeutically effective amount of a compound of Formula Ia or Ib, or a stereoisomer, geometric isomer, tautomer, solvate, metabolite, or pharmaceutically acceptable salt or prodrug thereof.

Diseases and conditions treatable according to the methods of this invention include, but are not limited to, cancer, stroke, diabetes, hepatomegaly, cardiovascular disease, Alzheimer's disease, cystic fibrosis, viral disease, autoimmune diseases, atherosclerosis, restenosis, psoriasis, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, chronic myelogenous leukemia (CML), liver disease, pathologic immune conditions involving T cell activation, and CNS disorders in a patient. In one embodiment, a human patient is treated with a compound of Formula Ia or Ib and a pharmaceutically acceptable carrier, adjuvant, or vehicle, wherein said compound of Formula Ia or Ib is present in an amount to detectably inhibit PI3 kinase activity.

Cancers which can be treated according to the methods of this invention include, but are not limited to, breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, hairy cells, buccal cavity and pharynx (oral), lip, tongue, mouth, pharynx, small intestine, colon-rectum, large intestine, rectum, brain and central nervous system, Hodgkin's and leukemia.

Cardiovascular diseases which can be treated according to the methods of this invention include, but are not limited to, restenosis, cardiomegaly, atherosclerosis, myocardial infarction, and congestive heart failure.

Neurodegenerative disease which can be treated according to the methods of this invention include, but are not limited to, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

Inflammatory diseases which can be treated according to the methods of this invention include, but are not limited to, rheumatoid arthritis, psoriasis, contact dermatitis, and delayed hypersensitivity reactions.

Another aspect of this invention provides a compound of this invention for use in the treatment of the diseases or conditions described herein in a mammal, for example, a human, suffering from such disease or condition. Also provided is the use of a compound of this invention in the preparation of a medicament for the treatment of the diseases and conditions described herein in a warm-blooded animal, such as a mammal, for example a human, suffering from such disorder.

Pharmaceutical Formulations

In order to use a compound of this invention for the therapeutic treatment (including prophylactic treatment) of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula Ia or Ib having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound of this invention for use herein is preferably sterile. In particular, formulations to be used for in vivo administration must be sterile. Such sterilization is readily accomplished by filtration through sterile filtration membranes.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formula Ia and Ib may be prepared. Suitable examples of sustained-release preparations include semipermeable matrices of solid hydrophobic polymers containing a compound of Formula Ia or Ib, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form, and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula Ia or Ib suitable for oral administration may be prepared as discrete units such as pills, capsules, cachets or tablets each containing a predetermined amount of a compound of Formula Ia or Ib.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula Ia or Ib intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula Ia or Ib compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula Ia or Ib may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formulas Ia and Ib may be employed alone or in combination with other therapeutic agents for the treatment of a disease or disorder described herein, such as a hyperproliferative disorder (e.g., cancer). In certain embodiments, a compound of Formula Ia or Ib is combined in a pharmaceutical combination formulation, or dosing regimen as combination therapy, with a second compound that has anti-hyperproliferative properties or that is useful for treating a hyperproliferative disorder (e.g., cancer). The second compound of the pharmaceutical combination formulation or dosing regimen preferably has complementary activities to the compound of Formula Ia or Ib such that they do not adversely affect each other. Such compounds are suitably present in combination in amounts that are effective for the purpose intended. In one embodiment, a composition of this invention comprises a compound of Formula Ia or Ib, or a stereoisomer, geometric isomer, tautomer, solvate, metabolite, or pharmaceutically acceptable salt or prodrug thereof, in combination with a chemotherapeutic agent such as described herein.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In a particular embodiment of anti-cancer therapy, a compound of Formula Ia or Ib, or a stereoisomer, geometric isomer, tautomer, solvate, metabolite, or pharmaceutically acceptable salt or prodrug thereof, may be combined with other chemotherapeutic, hormonal or antibody agents such as those described herein, as well as combined with surgical therapy and radiotherapy. Combination therapies according to the present invention thus comprise the administration of at least one compound of Formula Ia or Ib, or a stereoisomer, geometric isomer, tautomer, solvate, metabolite, or pharmaceutically acceptable salt or prodrug thereof, and the use of at least one other cancer treatment method. The amounts of the compound(s) of Formula Ia or Ib and the other pharmaceutically active chemotherapeutic agent(s) and the relative timings of administration will be selected in order to achieve the desired combined therapeutic effect.

Metabolites of Compounds of Formulas Ia and Ib

Also falling within the scope of this invention are the in vivo metabolic products of Formulas Ia and Ib described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formulas Ia and Ib, including compounds produced by a process comprising contacting a compound of this invention with a mammal for a period of time sufficient to yield a metabolic product thereof.

Metabolite products typically are identified by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Prodrugs of Formula Ia and Ib Compounds

In addition to compounds of Formulas Ia and Ib, the invention also includes pharmaceutically acceptable prodrugs of such compounds. Prodrugs include compounds wherein an amino acid residue, or a polypeptide chain of two or more (e.g., two, three or four) amino acid residues, is covalently joined through an amide or ester bond to a free amino, hydroxy or carboxylic acid group of a compound of the present invention. The amino acid residues include but are not limited to the 20 naturally occurring amino acids commonly designated by three letter symbols and also includes phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutyric acid, citrulline, homocysteine, homoserine, methyl-alanine, para-benzoylphenylalanine, phenylglycine, propargylglycine, sarcosine, methionine sulfone and tert-butylglycine.

Additional types of prodrugs are also encompassed. For instance, a free carboxyl group of a compound of Formula Ia or Ib can be derivatized as an amide or alkyl ester. As another example, compounds of this invention comprising free hydroxy groups may be derivatized as prodrugs by converting the hydroxy group into a group such as, but not limited to, a phosphate ester, hemisuccinate, dimethylaminoacetate, or phosphoryloxymethyloxycarbonyl group, as outlined in Advanced Drug Delivery Reviews, (1996) 19:115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers, wherein the acyl group may be an alkyl ester optionally substituted with groups including, but not limited to, ether, amine and carboxylic acid functionalities, or where the acyl group is an amino acid ester as described above, are also encompassed. Prodrugs of this type are described in J. Med. Chem., (1996), 39:10. More specific examples include replacement of the hydrogen atom of the alcohol group with a group such as $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyloxymethyl, N—$(C_1-C_6)$alkoxycarbonylaminomethyl, succinoyl, $(C_1-C_6)$alkanoyl, α-amino$(C_1-C_4)$alkanoyl, arylacyl and (X-aminoacyl, or α-aminoacyl-α-aminoacyl, where each α-aminoacyl group is independently selected from the naturally occurring L-amino acids, $P(O)(OH)_2$, —P(O)(O $(C_1-C_6)$alkyl$)_2$ or glycosyl (the radical resulting from the removal of a hydroxyl group of the hemiacetal form of a carbohydrate).

Free amine groups of compounds of Formulas Ia and Ib can also be derivatized as amides, sulfonamides or phosphonamides. All of these moieties may incorporate groups including, but not limited to, ether, amine and carboxylic acid functionalities. For example, a prodrug can be formed by the replacement of a hydrogen atom in the amine group with a group such as R-carbonyl, RO-carbonyl, NRR'-carbonyl, wherein R and R' are each independently $(C_1-C_{10})$alkyl, $(C_3-C_7)$cycloalkyl, or benzyl, or R-carbonyl is a natural α-aminoacyl or natural α-aminoacyl-natural α-aminoacyl, —C(OH)C(O)OY wherein Y is H, $(C_1-C_6)$alkyl or benzyl, —C(OY$_0$)Y$_1$ wherein Y$_0$ is $(C_1-C_4)$ alkyl and Y$_1$ is $(C_1-C_6)$ alkyl, carboxy$(C_1-C_6)$alkyl, amino$(C_1-C_4)$alkyl or mono-N— or di-N,N—$(C_1-C_6)$alkylaminoalkyl, or —C(Y$_2$)Y$_3$ wherein Y$_2$ is H or methyl and Y$_3$ is mono-N— or di-N,N—$(C_1-C_6)$alkylamino, morpholino, piperidin-1-yl or pyrrolidin-1-yl.

For additional examples of prodrug derivatives, see, for example, a) *Design of Prodrugs*, edited by H. Bundgaard, (Elsevier, 1985) and *Methods in Enzymology*, Vol. 42, p. 309-396, edited by K. Widder, et al. (Academic Press, 1985); b) *A Textbook of Drug Design and Development*, edited by Krogsgaard-Larsen and H. Bundgaard, Chapter 5 *"Design and Application of Prodrugs,"* by H. Bundgaard p. 113-191 (1991); c) H. Bundgaard, Advanced Drug Delivery Reviews, 8:1-38 (1992); d) H. Bundgaard, et al., Journal of Pharmaceutical Sciences, 77:285 (1988); and e) N. Kakeya, et al., Chem. Pharm. Bull., 32:692 (1984), each of which is specifically incorporated herein by reference.

Articles of Manufacture

In another embodiment of the invention, an article of manufacture, or "kit", containing materials useful for the treatment of the diseases and disorders described above is provided. In one embodiment, the kit comprises a container comprising a compound of Formula Ia or Ib, or a stereoisomer, geometric isomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula Ia or Ib or a formulation thereof which is effective for treating the condition and may have a sterile access port (for example, the container may be an intravenous solution bag or a vial having a stopper pierceable by a hypodermic injection needle). At least one active agent in the composition is a compound of Formula Ia or Ib. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula Ia or Ib can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula Ia or Ib and, if present, the second pharmaceutical formulation. For example, if the kit comprises a first composition comprising a compound of Formula Ia or Ib and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula Ia or Ib, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula Ia or Ib contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula Ia or Ib and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

General Preparative Procedures

General Procedure A

Suzuki Coupling:

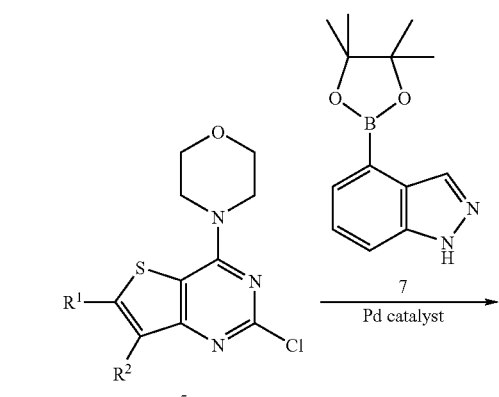

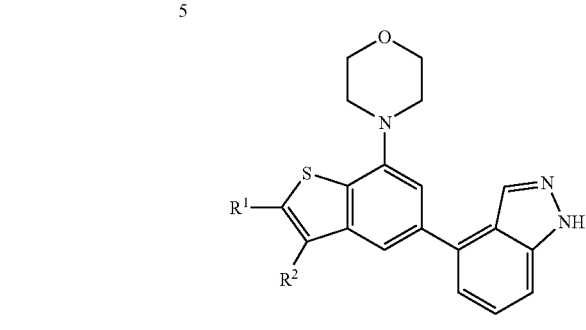

The Suzuki-type coupling reaction is useful to attach a fused bicyclic heterocycle or fused bicyclic heteroaryl at the 2-position of the pyrimidine ring (see Scheme 4). Generally, substituted 2-chloro-4-morpholinothieno[3,2-d]pyrimidine 5 or 2-chloro-4-morpholinothieno[2,3-d]pyrimidine 6 may be combined with 1.5 equivalents of 4-(4,4,5,5-tetramethyl-1,3,2-dioxaborolan-2-yl)1H-indazole 7, and dissolved in 3 equivalents of sodium carbonate as a 1 molar solution in water and an equal volume of acetonitrile. A catalytic amount, or more, of a low valent palladium reagent, such as bis(triphenylphosphine)palladium(II) dichloride, is added. A variety of boronic acids or boronic esters can be used in place of the indazole boronic ester indicated. Also alternatively, the nitrogen of the indazole may be protected, for example with a tetrahydropyranyl group; see compound 40. In some cases potassium acetate was used in place of sodium carbonate to adjust the pH of the aqueous layer. The reaction was then heated to about 140-150° C. under pressure in a Biotage Optimizer microwave reactor (Biotage, Inc.) for 10 to 30 minutes. The contents are extracted with ethyl acetate, or another organic solvent. After evaporation of the organic layer the product, 8 or 9, may be purified on silica or by reverse phase HPLC.

General Procedure B

Amide Coupling:

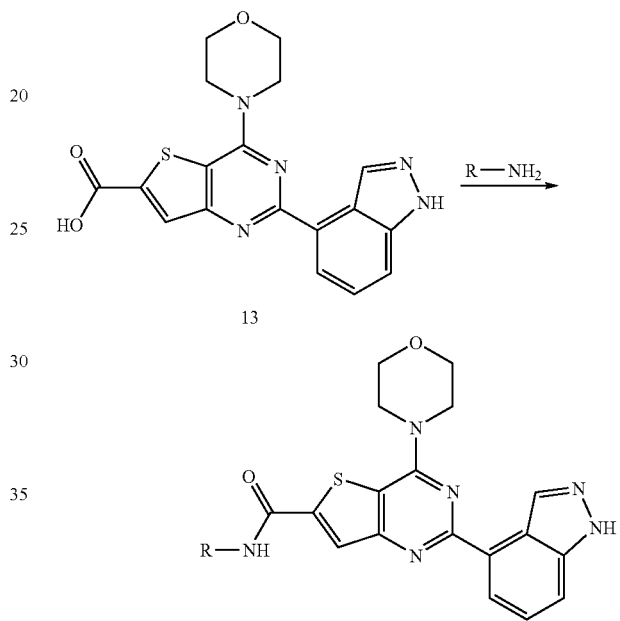

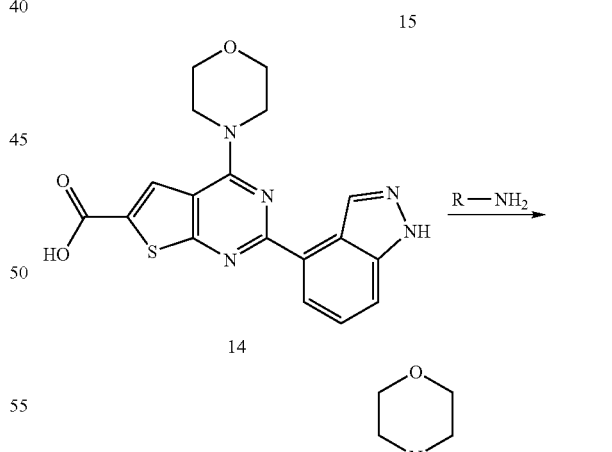

2-(1H-Indazol-4-yl)-4-morpholinothieno[3,2-d]pyrimidine-6-carboxylic acid 13 or 2-(1H-indazol-4-yl)-4-morpholinothieno[2,3-d]pyrimidine-6-carboxylic acid 14 is treated with 1.5 eq HATU, 3 eq of alkylamine and 3 eq of DIPEA in DMF to approximately 0.1 M concentration. The reaction is stirred until complete and extracted in ethylacetate with saturated bicarbonate solution one time. The organic layer is dried, filtered and concentrated to yield the crude intermediate. This intermediate is purified via reverse phase HPLC to yield product 15 or 16.

General Procedure C
Sulfonamide Formation:

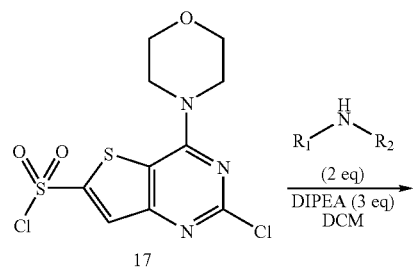

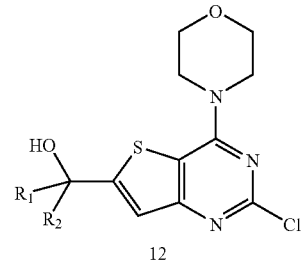

12

2-Chloro-4-morpholinothieno[3,2-d]pyrimidine 4 was suspended to a 0.2 molar concentration in THF and cooled to −50° C. in a dry ice/acetonitrile bath before adding 2 equivalents of 2.5 M nBuLi in hexanes. After 15 min 3.0 molar equivalents of a cyclic or acyclic ketone was added to the solution. The reaction continued to stir at −50° C. for 1 h and then in most cases was allowed to come to 0° C. When the reaction was complete by TLC or mass spec. it was quenched into a saturated ammonium chloride solution and extracted two times with EtOAc. The organic layer was concentrated and either used as a crude mixture, purified on silica, or the product 12 could be dissolved in a minimal amount of acetonitrile and filtered to remove remaining starting material 4.

General Procedure E Suzuki coupling reactions in one pot

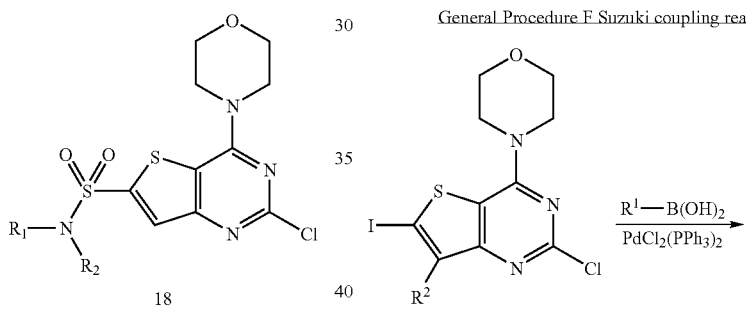

2-Chloro-4-morpholinothieno[3,2-d]pyrimidine-6-sulfonyl chloride 17 was suspended in 1 mL of DCM before addition of 2 eq of amine and 3 eq of DIPEA. The reactions were monitored by LCMS until complete. The crude reaction mixtures were diluted with ethyl acetate, extracted with saturated ammonium chloride and back-extracted once with ethyl acetate. The organic layers were combined and concentrated to dryness. The crude sulfonamide intermediates 18 were used directly in the subsequent Suzuki couplings.

General procedure D Alcohol synthesis

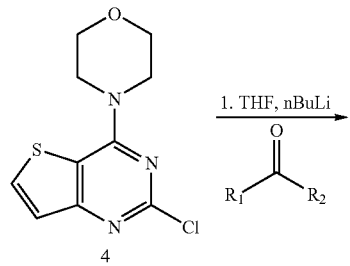

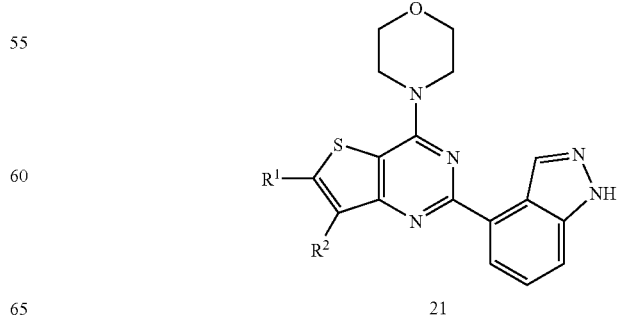

2-Chloro-6-iodo-4-morpholinothieno[3,2-d]pyrimidine 19 (1 eq), phenylboronic acid or heterocycleboronic acid (R¹—B(OH)₂, 1.1 eq) and bis(triphenylphosphine)palladium (II) dichloride (0.1 eq) in 1 M Na₂CO₃ aqueous solution (3 eq) and acetonitrile (3 eq) was heated to 100° C. in a sealed microwave reactor for 10 to 40 min to give 20. Upon completion, 4-(4,4,5,5-tetramethyl-1,3,2-dioxaborolan-2-yl)-1H-indazole 7 (1.3 eq) and bis(triphenylphosphine)palladium(II) dichloride (0.1 eq) were added in the same pot. The reaction mixture was heated to 150° C. in a sealed microwave reactor for 10 to 15 min. The mixture was extracted with ethyl acetate (3×5 mL). The combined organic layers were concentrated to yield crude 21.

General Procedure G Amide coupling reaction

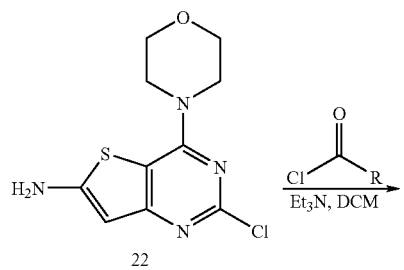

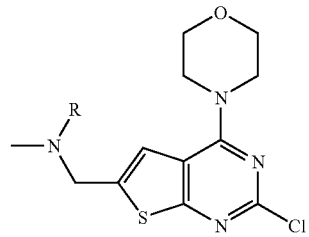

To a 0.25 to 0.40 M solution of 1-(2-chloro-4-morpholinothieno[2,3-d]pyrimidin-6-yl)-N-methylmethanamine in DCM cooled to 0° C. was added 1.5 eq. of TEA, followed by the drop-wise addition of 1.0 to 1.5 eq. of an alkyl or aryl-acid chloride or sulfonylchloride, diluted in DCM. The reaction is stirred at ambient temperature and monitored for completeness by LCMS. After completion, the reaction volume is increased with DCM, and dilute aqueous sodium bicarbonate is added to the solution. The organic and aqueous layers are separated. Finally, the organic layer is washed with brine and dried (MgSO₄). The dried organic solution is concentrated in vacuo and purified by silica chromatography if desired General Procedure I Amide coupling reaction for benzenamine

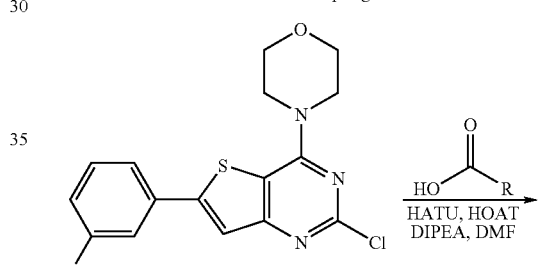

2-Chloro-4-morpholinothieno[3,2-d]pyrimidin-6-amine 22 (1 eq), Acid chloride (1.5~2 eq) and triethylamine (2 eq) in dichloromethane was stirred. The reaction was monitored by LC/MS until complete. The mixture was evaporated to give the crude amide 23, which was directly used for the next step reaction without purification.

General Procedure H Preparation of acetamide, benzamidines, and sulfonamides

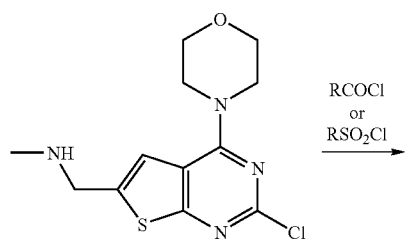

3-(2-Chloro-4-morpholinothieno[3,2-d]pyrimidin-6-yl)benzenamine 24 (1 eq), carboxylic acid (RCO₂H, 1.5 eq), 1-hydroxy-7-azabenzotriazole (0.2 eq), O-(7-azabenzotriazol-1-yl)-(N,N,N',N'-tetramethyluronium hexafluorophosphate (HATU, 1.5 eq), and N,N-diisopropylethylamine (2.5 eq) in DMF was stirred at room temperature. The reaction was monitored by LC/MS until complete. The reaction mixture was diluted with ethyl acetate, washed with saturated sodium bicarbonate and brine. The organic layer was dried over MgSO₄, filtered and evaporated to yield amide product 25.

General Procedure J 6-Iodo displacement and 2-Suzuki coupling

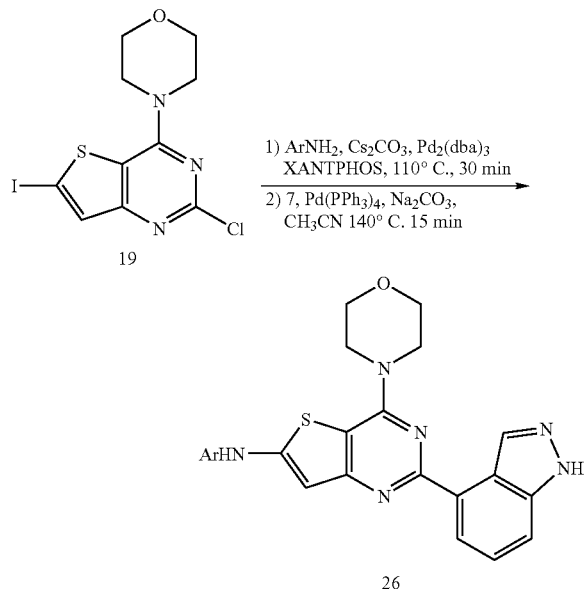

To a solution of 2-chloro-6-iodo-4-morpholinothieno[3,2-d]pyrimidine 19 (0.05 g, 0.13 mmol) in DMF (1.00 ml) was added the appropriate aniline (200 mol %), Cs-$_2$CO$_3$ (50 mol %), Pd$_2$(dba)$_3$ (5 mol %), and XANTPHOS (10 mol %). The reaction was heated to 110° C. under pressure in a Biotage optimizer microwave reactor for 30 min. The resulting solution was concentrated in vacuo to give 26, after following General Procedure A.

General Procedure K 6-Aminoalkyl acylation and 2-Suzuki coupling

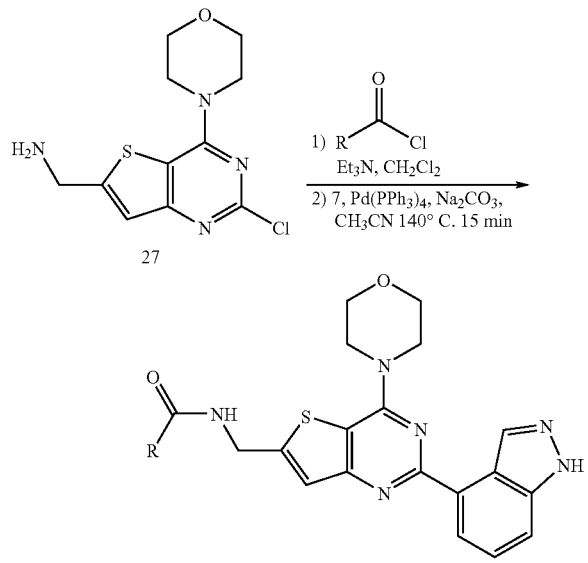

To a solution of (2-chloro-4-morpholinothieno[3,2-d]pyrimidin-6-yl)methanamine 27 (50 mg, 0.2 mmol) in CH$_2$Cl$_2$ (4 mL) was added Et$_3$N (84 µL, 0.6 mmol) and the appropriate acid chloride or HCl salt thereof (0.3 mmol). The reaction stirred 18-48 hr at room temperature before being quenched with water. The aqueous layer was extracted with EtOAc. The combined organics were dried over Na$_2$SO$_4$ and concentrated in vacuo. The 2-chloro crude product was coupled with boronate reagent 7 and palladium catalyst according to General Procedure A to give 28 which was purified by reversed phase HPLC purification.

Alternatively, to a solution of (2-chloro-4-morpholinothieno[3,2-d]pyrimidin-6-yl)methanamine 27 (111 mg, 0.39 mmol) in DMF (5 mL) was added 2,6-lutidine (48.2 µL, 0.41 mmol) and the appropriate acid chloride or HCl salt thereof (0.39 mmol). The reaction stirred 18-72 hr at room temperature before being quenched with water. The aqueous layer was extracted with EtOAc. The combined organics were dried over MgSO$_4$ and concentrated in vacuo. The 2-chloro crude product was coupled with boronate reagent 7 and palladium catalyst according to General Procedure A to give 20 mg of 28 which was purified by reversed phase HPLC purification.

General Procedure L Amine Substitution on Fluoropyridine

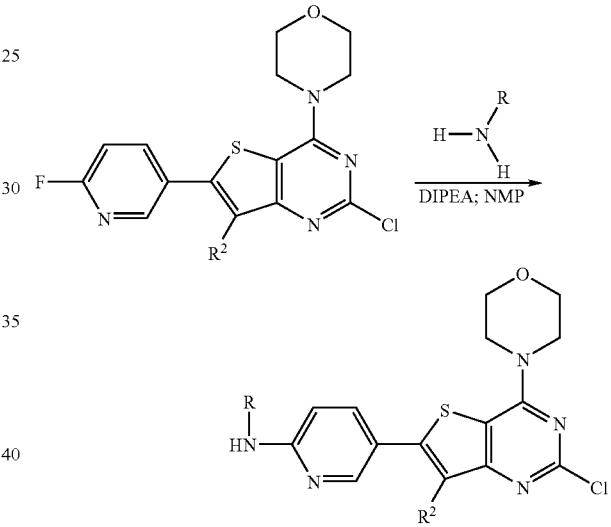

A mixture of 2-chloro-6-(6-fluoropyridin-3-yl)-4-morpholinothieno[3,2-d]pyrimidine or 2-chloro-6-(6-fluoropyridin-3-yl)-4-morpholinothieno[2,3-d]pyrimidine compound, about four equivalents of a primary or secondary amine (R=H, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, or C$_1$-C$_{20}$ heteroaryl), and about two eq. diisopropylethylamine in N-methylpyrrolidine (~0.1M) is heated to about 130-140° C. in a sealed microwave reactor for 10~40 min, followed by removal of volatiles under high vacuum. The crude mixture is purified by flash chromatography to give intermediate 2-chloro-6-(6-aminopyridin-3-yl)-4-morpholinothieno[3,2-d]pyrimidine or 2-chloro-6-(6-aminopyridin-3-yl)-4-morpholinothieno[2,3-d]pyrimidine compound, which may be Suzuki coupled with a fused bicyclic heterocycle or heteroaryl boronate reagent following General Procedure A.

EXAMPLES

In order to illustrate the invention, the following examples are included. However, it is to be understood that these examples do not limit the invention and are only meant to suggest a method of practicing the invention. Persons skilled in the art will recognize that the chemical reactions described may be readily adapted to prepare a number of other PI3K inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

In the examples described below, unless otherwise indicated all temperatures are set forth in degrees Celsius. Reagents were purchased from commercial suppliers such as Aldrich Chemical Company, Lancaster, TCI or Maybridge, and were used without further purification unless otherwise indicated.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried.

Column chromatography was conducted on a Biotage system (Manufacturer: Dyax Corporation) having a silica gel column or on a silica SEP PAK® cartridge (Waters). $^1$H NMR spectra were recorded on a Varian instrument operating at 400 MHz. $^1$H NMR spectra were obtained in deuterated CDCl$_3$, d$_6$-DMSO, CH$_3$OD or d$_6$-acetone solutions (reported in ppm), using chloroform as the reference standard (7.25 ppm). When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Example 1

2,4-Dichloro-thieno[3,2-d]pyrimidine 3

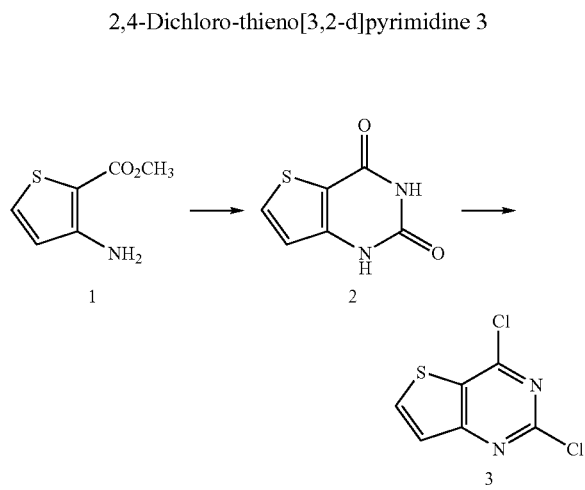

A mixture of methyl 3-amino-2-thiophenecarboxylate 1 (13.48 g, 85.85 mmol) and urea (29.75 g, 5 eq.) was heated at 190° C. for 2 hours. The hot reaction mixture was poured onto sodium hydroxide solution and any insoluble material was removed by filtration. The mixture was then acidified (HCl, 2N) to yield 1H-thieno[3,2-d]pyrimidine-2,4-dione 2 as a white precipitate, which was collected by filtration and air dried (9.49 g, 66%). $^1$H NMR 400 MHz, d$_6$-DMSO) 6.90 (1H, d, J=5.2 Hz), 8.10 (1H, d, J=5.2 Hz), 11.60-11.10 (2H, br s).

A mixture of 1H-thieno[3,2-d]pyrimidine-2,4-dione 2 (9.49 g, 56.49 mmol) and phosphorous oxychloride (150 mL) was heated at reflux for 6 h. The reaction mixture was then cooled and poured onto ice/water with vigorous stirring yielding a precipitate. The mixture was then filtered to yield 2,4-dichloro-thieno[3,2-d]pyrimidine 3 as a white solid (8.68 g, 75%). $^1$H NMR (400 MHz, CDCl$_3$) 7.56 (1H, d, J=5.5 Hz), 8.13 (1H, d, J=5.5 Hz).

Example 2

2-Chloro-4-morpholin-4-yl-thieno[3,2-d]pyrimidine 4

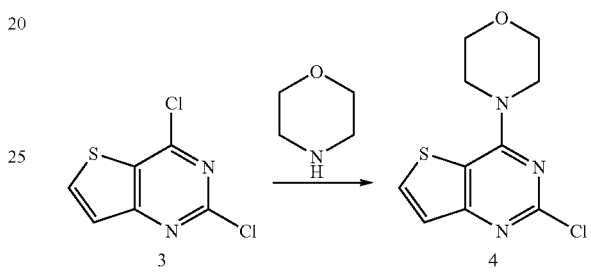

A mixture of 2,4-dichloro-thieno[3,2-d]pyrimidine 3, (8.68 g, 42.34 mmol), morpholine (8.11 mL, 2.2 eq.) and MeOH (150 mL) was stirred at room temperature for 1 h. The reaction mixture was then filtered, washed with water and MeOH, to yield 2-chloro-4-morpholin-4-yl-thieno[3,2-d]pyrimidine 4 as a white solid (11.04 g, 100%). $^1$H NMR (400 MHz, d$_6$-DMSO) 3.74 (4H, t, J=4.9 Hz), 3.90 (4H, t, J=4.9 Hz), 7.40 (1H, d, J=5.6 Hz), 8.30 (1H, d, J=5.6 Hz).

Example 3

2-Chloro-4-morpholin-4-yl-thieno[3,2-d]pyrimidine-6-carbaldehyde 10

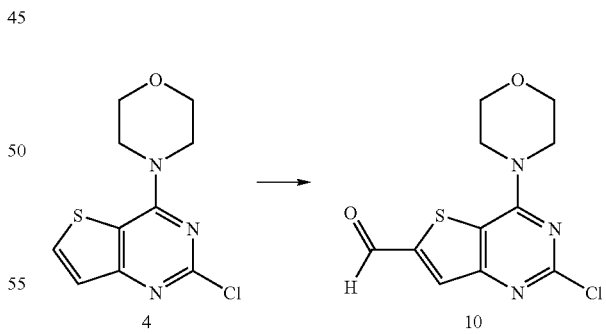

To a suspension of 2-chloro-4-morpholin-4-yl-thieno[3,2-d]pyrimidine 4 (1.75 g, 6.85 mmol) in dry THF (40 mL) at −78° C. was added a 2.5M solution of n-butyllithium (nBuLi) in hexane (3.3 mL, 1.2 eq.). After stirring for 1 h, dry DMF (796 μL, 1.5 eq.) was added. The reaction mixture was stirred for 1 h at −78° C. and then warmed slowly to room temperature. After a further 2 h at room temperature the reaction mixture poured onto ice/water yielding a yellow precipitate. This was collected by filtration and air-dried to yield 2-chloro-4-morpholin-4-yl-thieno[3,2-d]pyrimidine-6-carbaldehyde 10 (1.50 g, 77%). $^1$H NMR (400 MHz, d$_6$-DMSO) 3.76 (4H, t, J=4.9), 3.95 (4H, t, J=4.9), 8.28 (1H, s), 10.20 (1H, s).

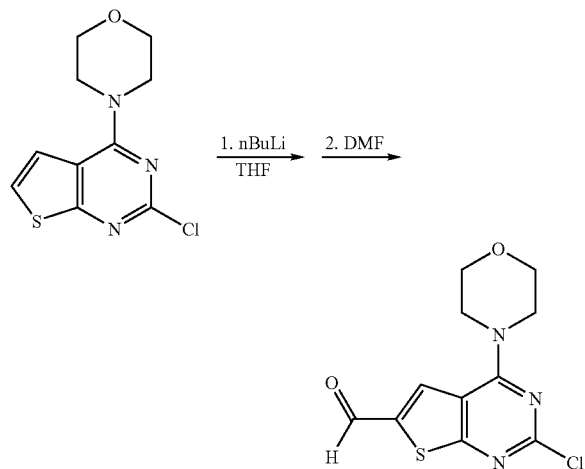

Also, to a suspension of 4-(2-chlorothieno[2,3-d]pyrimidin-4-yl)morpholine (1.75 g, 6.85 mmol) in dry THF at −78° C. was added a 2.5M solution of n-butyllithium (nBuLi) in hexane (3.3 mL, 1.2 eq.). After stirring for 1 h, dry DMF (796 uL, 1.5 eq.) was added. The reaction mixture was stirred for 1 h at −78° C. and then warmed slowly to room temperature. After a further 2 h at room temperature the reaction mixture was poured onto ice/water yielding a yellow precipitate. This was collected by filtration and air-dried to yield 2-chloro-4-morpholinothieno[2,3-d]pyrimidine-6-carbaldehyde (1.5 g, 77% yield) MS (Q1) 284 (M)+

Example 4

4-(4,4,5,5-Tetramethyl-[1,3,2]dioxaborolan-2-yl)-1H-indazole 7-route 1

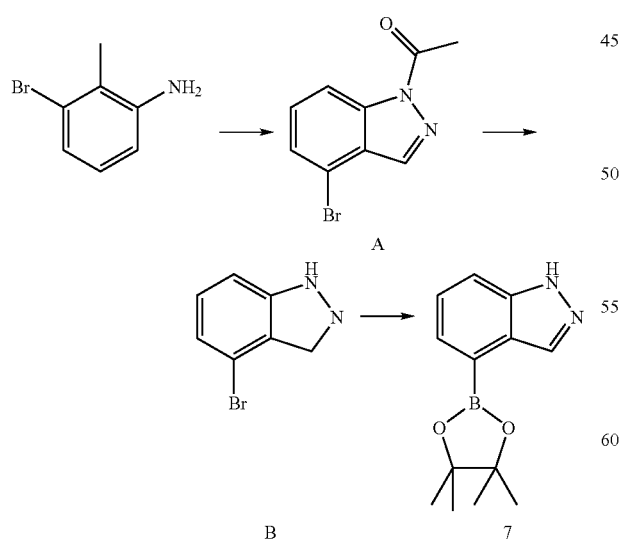

To a solution of 3-bromo-2-methyl aniline (5.0 g, 26.9 mmol) in chloroform (50 mL) was added potassium acetate (1.05 eq., 28.2 mmol, 2.77 g). Acetic anhydride (2.0 eq., 53.7 mmol, 5.07 mL) was added with concurrent cooling in ice-water. The mixture was then stirred at room temperature for 10 minutes after which time a white gelatinous solid formed. 18-Crown-6 (0.2 eq., 5.37 mmol, 1.42 g) was then added followed by iso-amyl nitrite (2.2 eq., 59.1 mmol, 7.94 mL) and the mixture was heated under reflux for 18 h. The reaction mixture was allowed to cool, and was partitioned between chloroform (3×100 mL) and saturated aqueous sodium hydrogen carbonate (100 mL). The combined organic extracts were washed with brine (100 mL), separated and dried (MgSO$_4$).

The crude product was evaporated onto silica and purified by chromatography eluting with 20%→40% EtOAc-petrol to give 1-(4-bromo-indazol-1-yl)-ethanone A (3.14 g, 49%) as an orange solid, and 4-bromo-1H-indazole B (2.13 g, 40%) as a pale orange solid.

A $^1$H NMR (400 MHz, CDCl$_3$) 2.80 (3H, s), 7.41 (1H, t, J=7.8 Hz), 7.50 (1H, d, J=7.8 Hz), 8.15 (1H, s), 8.40 (1H, d, J=7.8 Hz).

B: $^1$H NMR (400 MHz, CDCl$_3$) 7.25 (1H, t, J=7.3 Hz), 7.33 (1H, d, J=7.3 Hz), 7.46 (1H, d, J=7.3 Hz), 8.11 (1H, s), 10.20 (1H, br s).

To a solution of the 1-(4-bromo-indazol-1-yl)-ethanone A (3.09 g, 12.9 mmol) in MeOH (50 mL) was added 6N aqueous HCl (30 mL) and the mixture was stirred at room temperature for 7 h. The MeOH was evaporated and the mixture partitioned between EtOAc (2×50 mL) and water (50 mL). The combined organic layers were washed with brine (50 mL), separated and dried (MgSO$_4$). The solvent was removed by evaporation under reduced pressure to give 4-bromo-1H-indazole B (2.36 g, 93%).

To a solution of the 4-bromo-1H-indazole B (500 mg, 2.54 mmol) and bis(pinacolato)diboron (1.5 eq., 3.81 mmol) in DMSO (20 mL) was added potassium acetate (3.0 eq., 7.61 mmol, 747 mg; dried in drying pistol) and PdCl$_2$(dppf)$_2$ (3 mol %, 0.076 mmol, 62 mg). The mixture was degassed with argon and heated at 80° C. for 40 h. The reaction mixture was allowed to cool and partitioned between water (50 mL) and ether (3×50 mL). The combined organic layers were washed with brine (50 mL), separated and dried (MgSO$_4$). The crude material was purified by chromatography eluting with 30%→40% EtOAc-petrol to give an inseparable 3:1 mixture of the 4-(4,4,5,5-tetramethyl-[1,3,2]dioxaborolan-2-yl)-1H-indazole 7 (369 mg, 60%) and indazole (60 mg, 20%), isolated as a yellow gum which solidified upon standing to furnish as an off-white solid. $^1$H NMR (400 MHz, d$_6$-DMSO) 1.41 (12H, s), 7.40 (1H, dd, J=8.4 Hz, 6.9 Hz), 7.59 (1H, d, J=8.4 Hz), 7.67 (1H, d, J=6.9 Hz), 10.00 (1H, br s), 8.45 (1H, s), and indazole: 7.40 (1H, t), 7.18 (1H, t, J=7.9 Hz), 7.50 (1H, d, J=9.1 Hz), 7.77 (1H, d, J=7.9 Hz), 8.09 (1H, s). Impurity at 1.25.

Example 5

4-(4,4,5,5-Tetramethyl-[1,3,2]dioxaborolan-2-yl)-1H-indazole 7-route 2

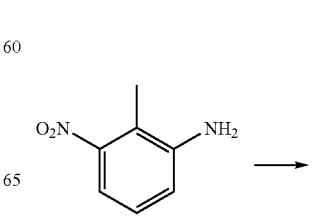

-continued

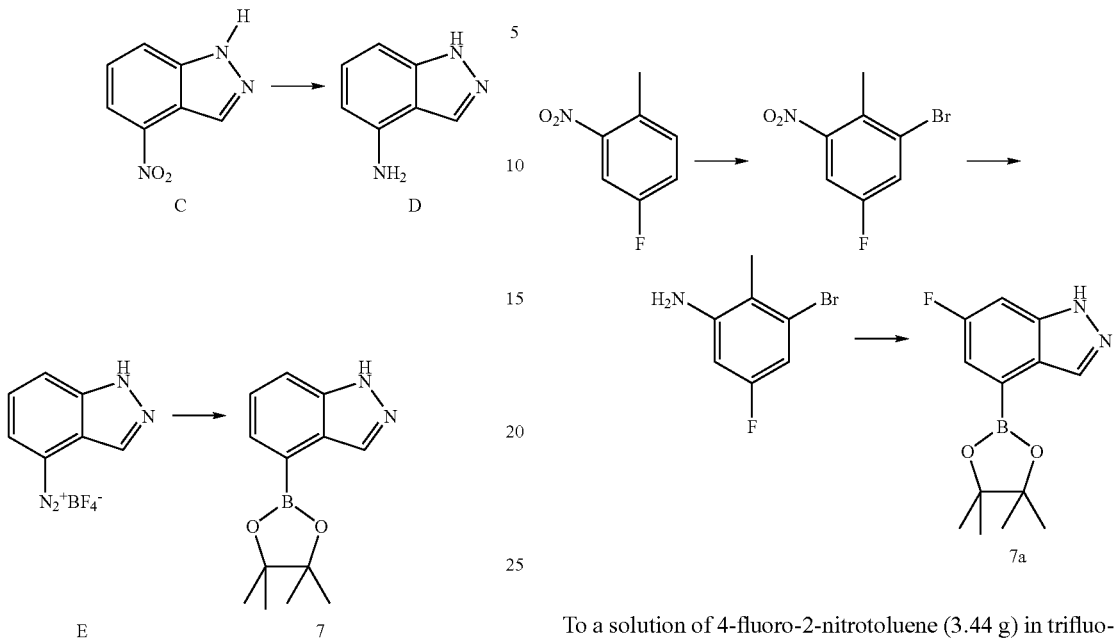

Example 6

6-Fluoroindazole-4-Boronate Ester 7a

To a solution of 2-methyl-3-nitroaniline (2.27 g, 14.91 mmol) in acetic acid (60 mL) was added a solution of sodium nitrite (1.13 g, 1.1 eq.) in water (5 mL). After 2 h, the deep red solution was poured onto ice/water and the resulting precipitate collected by filtration to yield 4-nitro-1H-indazole C (1.98 g, 81%).

A mixture of 4-nitro-1H-indazole C (760 mg, 4.68 mmol), palladium on charcoal (10%, cat.) and ethanol (30 mL) was stirred under a balloon of hydrogen for 4 h. The reaction mixture was then filtered through celite, and the solvent removed in vacuo to yield 1H-indazol-4-ylamine D (631 mg, 100%).

An aqueous solution of sodium nitrite (337 mg, 4.89 mmol) in water (2 mL) was added dropwise to a suspension of 1H-indazol-4-ylamine D (631 mg, 4.74 mmol) in 6M hydrochloric acid (7.2 mL) at below 0° C. After stirring for 30 minutes, sodium tetrafluoroborate (724 mg) was added to the reaction mixture. A viscous solution resulted, which was filtered and washed briefly with water to yield 1H-indazole-4-diazonium tetrafluoroborate salt E (69) (218 mg, 20%) as a deep red solid.

Dry methanol (4 mL) was purged with argon for 5 minutes. To this was added 1H-indazole-4-diazonium tetrafluoroborate salt (218 mg, 0.94 mmol), bis-pinacolato diboron (239 mg, 1.0 eq.) and [1,1'-bis(diphenylphosphino)ferrocene]palladium (II) chloride (20 mg). The reaction mixture was stirred for 5 h and then filtered through celite. The residue was purified using flash chromatography to yield 4-(4,4,5,5-Tetramethyl-[1,3,2]dioxaborolan-2-yl)-1H-indazole 7, (117 mg).

To a solution of 4-fluoro-2-nitrotoluene (3.44 g) in trifluoroacetic acid (13 mL) was added concentrated sulfuric acid (4 mL) followed by N-bromosuccinimide (5.92 g). The reaction mixture was stirred for 16 h and was then quenched with brine, extracted into ethyl acetate, and dried ($MgSO_4$). The solvent was removed in vacuo to furnish crude 1-bromo-5-fluoro-2-methyl-3-nitro-benzene (5.96 g).

To a solution of crude 1-bromo-5-fluoro-2-methyl-3-nitro-benzene (5.96 g) in MeOH (90 mL) was added concentrated hydrochloric acid (11.7 mL) and iron (6.1 g) and the reaction mixture was heated to reflux. After 16 h, the mixture was cooled, diluted with DCM, washed with sodium carbonate solution, dried ($MgSO_4$) and the solvent removed in vacuo. The residue was purified using flash chromatography to yield 3-bromo-5-fluoro-2-methyl-phenylamine (1.46 g).

To a solution of 3-bromo-5-fluoro-2-methyl-phenylamine (470 mg) in dioxane (6 mL) was added triethylamine (1.28 mL), palladium acetate (25 mg), 2-dicyclohexylphosphino biphenyl (161 mg) and pinacol borane (1.001 ml) and the mixture was heated to 80° C. for 4 h. The reaction mixture was cooled, diluted with chloroform, washed with brine, dried ($MgSO_4$) and the solvent removed in vacuo. The residue was purified using flash chromatography to yield 7a (466 mg).

Example 6a

6-(Tributylstannyl)-1-((2-(trimethylsilyl)ethoxy)methyl)-1H-imidazo[4,5-b]pyridine 50

To 3.07 g of 5-bromo-2,3-diaminopyridine was added 20 mL formic acid under $N_2$ and the reaction was heated to reflux for four hours and allowed to cool to room temperature. The reaction was stirred overnight at room temperature and complete reaction was confirmed by LCMS. The solution was concentrated in vacuo and purified by flash chromatography (DCM/MeOH) to give 1.64 g of compound 47 (51% yield). Compound 47 (1.64 g) in 40 mL THF was added to 0.22 g (1.1 eq) NaH in 10 mL THF under $N_2$ at −78° C. The reaction was stirred at −78° C. for 30 minutes followed by the addition of 1.45 g of SEM-Cl (1.05 eq) and allowed to warm up to room temperature. The reaction was stirred at room temperature overnight and complete reaction was confirmed by LCMS. The reaction was quenched with water followed by the addition of NaCl (not saturated) and the two products extracted with EtOAc and concentrated in vacuo. The two regioisomers were separated by flash chromatography (EtOAc/Hexanes) to give 1.68 g 48 and 0.5 g 49 (80% overall yield). Compound 49 (0.5 g) was dissolved in 50 mL dioxane followed by the addition of 1.76 g (2.0 eq) of Bis (tributyltin), 88 mg (0.05 eq) of Pd(PPh$_3$)$_4$, and 0.19 g (3.0 eq) of LiCl. The reaction mixture was heated to reflux under N$_2$ for 1.5 hours and complete reaction confirmed by LCMS. The mixture was cooled to room temperature, filtered through celite (celite washed with EtOAc), rotovapped and purified by flash chromatography (EtOAc/Hexanes) to give 501 mg of 6-(tributylstannyl)-1-((2-(trimethylsilyl)ethoxy)methyl)-1H-imidazo[4,5-b]pyridine 50 (61% yield). MS (Q1) 539.2 (M)+

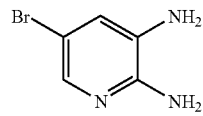

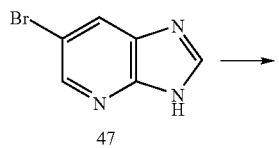

47

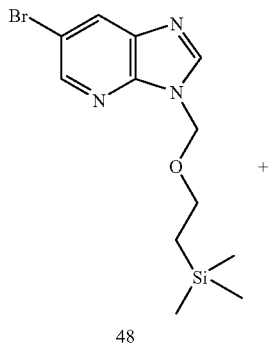

48

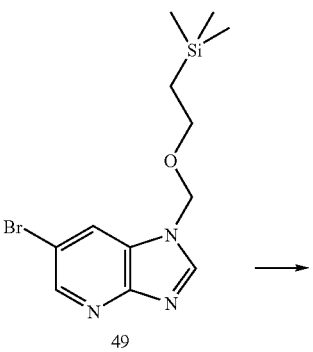

49

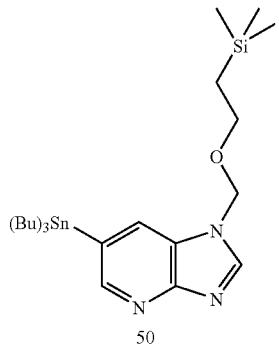

50

Example 6b

2-Methyl-6-(4,4,5,5-tetramethyl-1,3-dioxolan-2-yl)-3-((2-(trimethylsilyl)ethoxy)methyl)-3H-imidazo[4,5-b]pyridine 54

To 5.06 g of 5-bromo-2,3-diaminopyridine was added 50 mL acetic acid under N$_2$ and the reaction was heated to reflux overnight. Complete reaction was confirmed by LCMS. The solution was concentrated in vacuo and purified by flash chromatography (DCM/MeOH) to give 4.68 g of compound 51 (82% yield). Compound 51 (4.68 g) in 150 mL THF was added to 0.63 g (1.1 eq) NaH in 10 mL THF under N$_2$ at −78° C. The reaction was stirred at −78° C. for 30 minutes followed by the addition of 3.86 g of SEM-Cl (1.05 eq) and allowed to warm up to room temperature. The reaction was stirred at room temperature 4.5 hours and complete reaction was confirmed by LCMS. The reaction was quenched with water followed by the addition of NaCl (not saturated) and the two products extracted with EtOAc and concentrated in vacuo. The two regioisomers were separated by flash chromatography (EtOAc/Hexanes) to give 2.84 g 52 and 1.94 g 53 (63% overall yield). Compound 52 (2.08 g) was dissolved in 50 mL toluene followed by the addition of 2.32 g (1.5 eq) of Bis (pinacolato)diboron, 0.24 g (0.05 eq) of PdCl$_2$(dppf), and 1.79 g (3.0 eq) of KOAc. The reaction mixture was heated to 95° C. under N$_2$ and let stir overnight. Complete reaction confirmed by LCMS. The mixture was cooled to room temperature, rotovapped and purified by flash chromatography (EtOAc/Hexanes) to give 1.83 g of 2-methyl-6-(4,4,5,5-tetramethyl-1,3-dioxolan-2-yl)-3-((2-(trimethylsilyl)ethoxy)methyl)-3H-imidazo[4,5-b]pyridine 54 (77% yield). MS (Q1) 390.2 (M)+

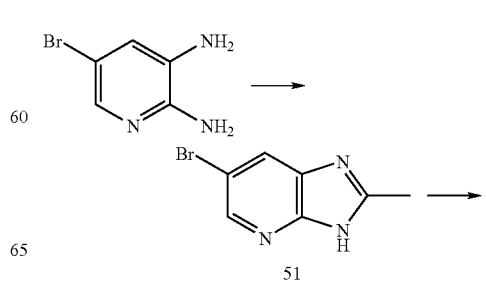

51

-continued

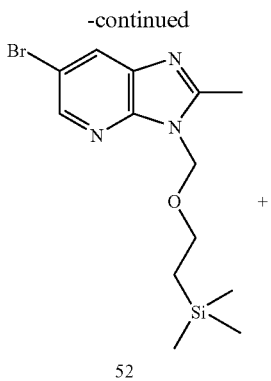

52

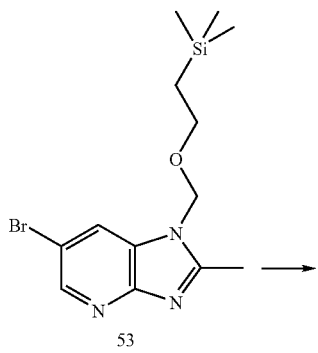

53

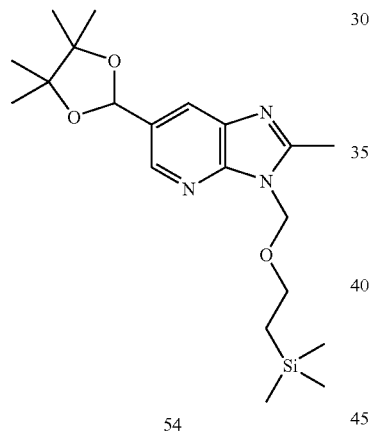

54

Example 7

2-(1H-Indazol-4-yl)-4-morpholin-4-yl-thieno[3,2-d]pyrimidine-6-carbaldehyde 11

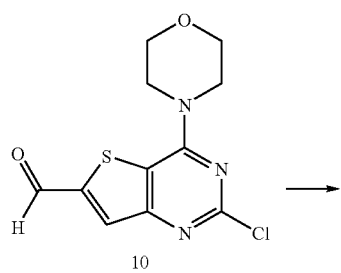

10

-continued

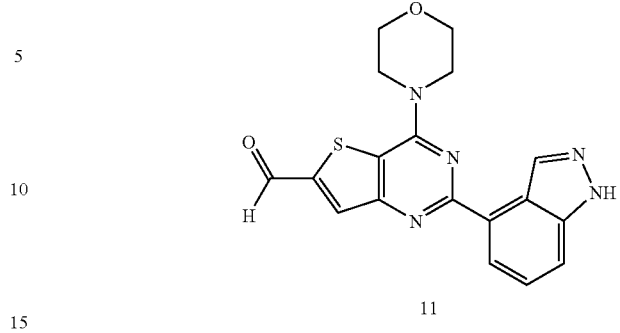

11

A mixture of 2-chloro-4-morpholin-4-yl-thieno[3,2-d]pyrimidine-6-carbaldehyde 10 (100 mg, 0.35 mmol), 4-(4,4,5,5-tetramethyl-[1,3,2]dioxaborolan-2-yl)-1H-indazole (70) (95 mg, 0.39 mmol) and sodium carbonate (112 mg) were suspended in toluene (2.5 mL), ethanol (1.5 mL) and water (0.7 mL). To this was added bis(triphenylphosphine)palladium(II) chloride (13.5 mg) and the reaction vessel was flushed with argon. The reaction mixture was microwaved at 120° C. for 1 h and then partitioned between DCM and water, the organic layer was washed with brine, dried over magnesium sulfate, filtered and evaporated in vacuo. The resulting residue was purified using flash chromatography to yield 2-(1H-indazol-4-yl)-4-morpholin-4-yl-thieno[3,2-d]pyrimidine-6-carbaldehyde 11 (97 mg).

Example 8

(2-Chloro-4-morpholinothieno[3,2-d]pyrimidin-6-yl)methanol 29

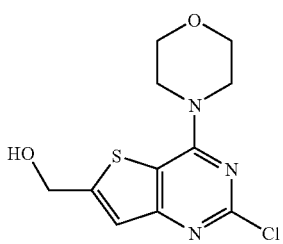

29

A solution of 2-chloro-4-morpholinothieno[3,2-d]pyrimidine-6-carbaldehyde 10 (1.0 g, 3.5 mmol) in MeOH (30 mL) at 0° C. was treated with NaBH$_4$ (0.1 g, 3.5 mmol). The solution was allowed to warm to room temperature and stirred 15 min. The reaction mixture was quenched with a mixture of a saturated solution of sodium bicarbonate and water (1:1, v/v). The aqueous solution was extracted with EtOAc. The combined organic layers were dried over Na$_2$SO$_4$ and concentrated in vacuo. The crude material 29 required no further purification (0.9 g, 90%). MS (Q1) 286 (M)+

Example 9

6-(Bromomethyl)-2-chloro-4-morpholinothieno[3,2-d]pyrimidine 30

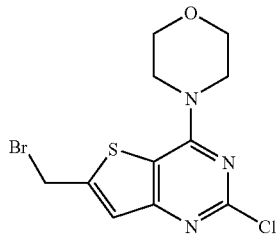

To a solution of (2-chloro-4-morpholinothieno[3,2-d]pyrimidin-6-yl)methanol 29 (100 mg, 0.4 mmol) in benzene (3.0 mL) at 0° C. was added PBr$_3$ (30 µL, 0.4 mmol). The reaction was heated at reflux for 1 hour. After cooling to room temperature the reaction was quenched by the addition of water. The aqueous layer was extracted with EtOAc. The combined organics were dried over Na$_2$SO$_4$ and concentrated in vacuo. The crude product 30 did not require further purification (115 mg, 94%). MS (Q1) 350 (M)+

Example 10

2-((2-Chloro-4-morpholinothieno[3,2-d]pyrimidin-6-yl)methyl)isoindoline-1,3-dione 31

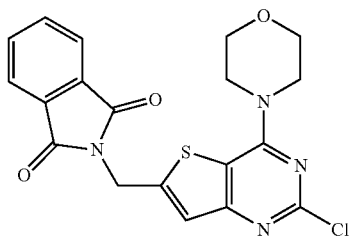

To a solution of 6-(bromomethyl)-2-chloro-4-morpholinothieno[3,2-d]pyrimidine 30 (0.3 g, 0.9 mmol) in DMF (10 mL) was added K$_2$CO$_3$ (0.2 g, 1.3 mmol), and phthalimide (0.1 g, 0.9 mmol). The resulting solution stirred 20 h at room temperature. The reaction was concentrated in vacuo and diluted with water (10 mL). The heterogeneous mixture was filtered to afford 2-((2-chloro-4-morpholinothieno[3,2-d]pyrimidin-6-yl)methyl)isoindoline-1,3-dione 31 (0.3 g, 75%). MS (Q1) 415 (M)+

Example 11

(2-Chloro-4-morpholinothieno[3,2-d]pyrimidin-6-yl)methanamine 27

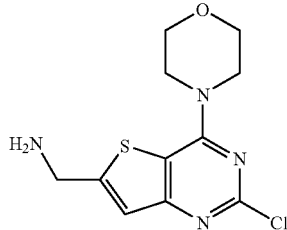

To a solution of 2-((2-chloro-4-morpholinothieno[3,2-d]pyrimidin-6-yl)methyl)isoindoline-1,3-dione 31 (100 mg, 0.24 mmol) in MeOH (7 mL) was added H$_2$NNH$_2$·H$_2$O (24 µL, 0.48 mmol). The reaction was heated at reflux for 1 h. After cooling to room temperature the reaction was quenched with water (10 mL) and extracted with EtOAc. The combined organics were dried over Na$_2$SO$_4$ and concentrated in vacuo to afford (2-chloro-4-morpholinothieno[3,2-d]pyrimidin-6-yl)methanamine 27 (0.05 g, 73%). MS (Q1) 285 (M)+

Example 11a1

(2-Chloro-4-morpholinothieno[3,2-d]pyrimidin-6-yl)-N-methylmethanamine 55

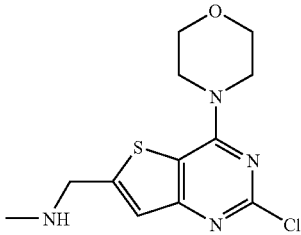

To 3.0 g of 2-chloro-4-morpholin-4-yl-thieno[3,2-d]pyrimidine-6-carbaldehyde 10 in 50 mL Toluene and 50 mL THF was added 30 mL of NH$_2$ME (40% in water) and the mixture stirred under N$_2$ for two days. The mixture was concentrated in vacuo and redissolved in 50 mL THF and 50 mL MeOH followed by the portionwise addition of 1.6 g (4.0 eq) NaBH$_4$ and the reaction mixture stirred overnight at room temperature. Complete reaction was confirmed by LCMS and the mixture was concentrated in vacuo and purified by flash chromatography (95/5% EtOAc/EtOH 20 min followed by a gradient up to 100% EtOH over 30 min more) to give 2.45 g of 1-(2-chloro-4-morpholinothieno[3,2-d]pyrimidin-6-yl)-N-methylmethanamine 55 (77.5% yield). MS (Q1) 300 (M)+

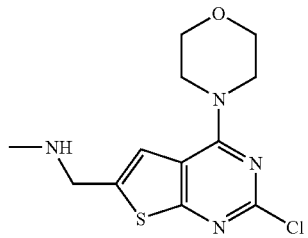

Also, to a solution of 2-chloro-4-morpholin-4-yl-thieno[3,2-d]pyrimidine-6-carbaldehyde (2.0 g) in 50 mL THF was added 20 mL of 40% methylamine in water. The reaction mixture was stirred at room temperature under N₂ for 24 hours. The solvents were removed in vacuo and the residue was dissolved in 50 mL MeOH and 50 mL THF and the NaBH₄ added portion-wise. This reaction mixture was stirred at room temperature under N₂ for 24 hours and complete reaction was confirmed by LCMS. The solvents were removed in vacuo and the crude product purified by flash chromatography (EtOAc/EtOH) to give 1.12 g of 1-(2-chloro-4-morpholinothieno[2,3-d]pyrimidin-6-yl)-N-methylmethanamine (53% yield). MS (Q1) 300 (M)+

Example 11b 1-(2-Chloro-7-methyl-4-morpholinothieno[3,2-d]pyrimidin-6-yl)-N-methylmethanamine 56

To 3.46 g of 2-chloro-7-methyl-4-morpholinothieno[3,2-d]pyrimidine-6-carbaldehyde in 20 mL toluene and 20 mL THF followed by the addition of 15 mL of NH₂ME (40% in water) and the mixture stirred under N₂ overnight. The mixture was concentrated in vacuo and redissolved in 30 mL MeOH and 20 mL THF followed by the portionwise addition of 1.76 g (4.0 eq) NaBH₄ and the reaction mixture stirred four days at room temperature. Complete reaction was confirmed by LCMS and the mixture was concentrated in vacuo and purified by flash chromatography (97/3% EtOAc/EtOH 20 min followed by a gradient up to 100% EtOH over 30 min more) to give 2.53 g of 1-(2-chloro-7-methyl-4-morpholinothieno[3,2-d]pyrimidin-6-yl)-N-methylmethanamine 56 (70% yield). MS (Q1) 313.8 (M)+

Example 12

2-Chloro-6-iodo-4-morpholinothieno[3,2-d]pyrimidine 19

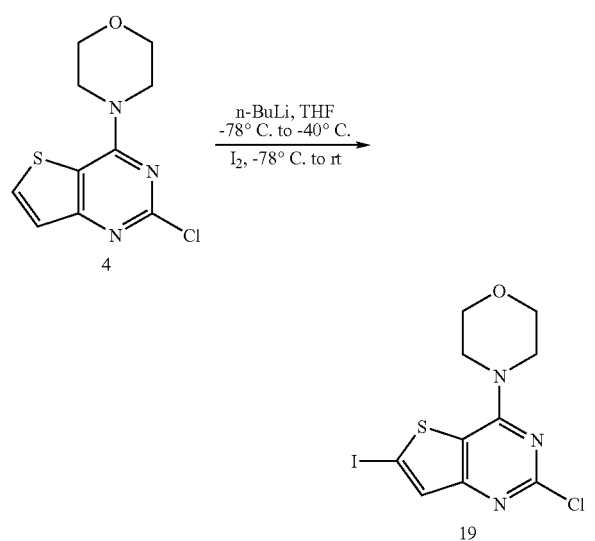

Following the procedures in U.S. Pat. No. 6,492,383, 2.5 M of n-butyllithium (9.4 mL, 22.48 mmol) in hexane solution was added to a mixture of 2-chloro-4-morpholinothieno[3,2-d]pyrimidine 4 (3.0 g, 11.74 mmol) in 60 mL of THF at −78° C. The reaction mixture was allowed to warm to −40° C. and stirred for 30 min. A solution of iodine (6.0 g, 23.48 mmol) in 10 mL of THF was added dropwise. After the addition was completed. The reaction mixture was brought to room temperature and stirred for 2 h. The mixture was quenched by diluting with dichloromethane and extracting with H₂O (2×100 mL). The organic layer was washed with Na₂S₂O₃ (2×100 mL), H₂O (2×100 mL), dried over MgSO₄, filtered and evaporated to afford 2-chloro-6-iodo-4-morpholinothieno[3,2-d]pyrimidine 19 (3.4 g, 75%).

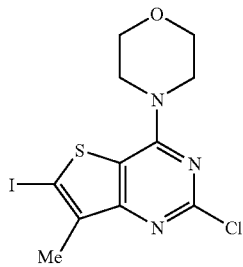

Also, to a solution of 2-chloro-7-methyl-4-morpholinothieno[3,2-d]pyrimidine (3.0 g, 11.1 mmol; prepared according to the procedure for the synthesis of 2-chloro-4-morpholin-4-yl-thieno[3,2-d]pyrimidine but commencing with 3-amino-4-methyl-thiophene-2-carboxylic acid ethyl ester) in THF (60 mL) at −78° C. was added n-BuLi (8.9 mL, 2.5 M in Et₂O). The resulting slurry was warmed to −40° C. and stirred 50 min. The reaction mixture was then cooled to −78° C. and a solution of I₂ (5.6 g, 22.2 mmol) in THF (30 mL) was added. The solution was warmed to room temperature and stirred 5 h. The reaction was quenched by the addition of water. The organic layer was separated and the aqueous layer was extracted with CH₂Cl₂. The combined organics were washed with saturated aqueous Na₂S₂O₃, dried over Na₂SO₄, filtered, and concentrated in vacuo to provide 2-chloro-6-iodo-7-methyl-4-morpholinothieno[3,2-d]pyrimidine (3.8 g, 84% yield).

Example 13

Tert-butyl furan-3-ylcarbamate 32

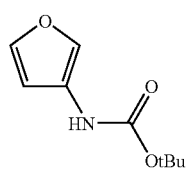

3-Furoic acid (5.60 g, 1.0 eq) was dissolved in tert-butanol (200 ml) and treated with triethylamine (10 ml, 1.4 eq) and diphenyl phosphoryl azide (12 ml, 1.1 eq). Mixture was heated at reflux for 18 h. Reaction mixture was cooled to room temperature, then concentrated to 50 ml and poured into saturated aq. NaHCO₃. Mixture was stirred at 0° C. for 2 h. Solid was collected by filtration and dried under high vacuum. The crude reaction mixture was purified by flash chromatography to yield tert-butyl furan-3-ylcarbamate 32

(6.95 g, 76%): ¹H NMR (CDCl$_3$, 400 MHz) δ 7.71 (bs, 1H), 7.27 (m, 1H), 6.27 (bs, 1H), 6.20 (bs, 1H), 1.50 (s, 9H); MS (Q1) 184 (M)⁺.

Example 14

Tert-butyl 2-(methoxycarbonyl)furan-3-ylcarbamate 33

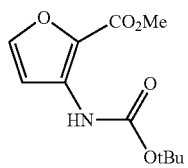

33

To a solution of tert-butyl furan-3-ylcarbamate 32 (1.7 g, 1.0 eq) in THF (50 ml) at −30° C. was added TMEDA (1.75 ml, 1.3 eq) followed by 1.6M solution of n-butyllithium (8.4 ml, 2.25 eq, 1.6M in hexanes). Reaction mixture was allowed to warm up to 0° C. and stirred for 1 h, before being cooled back to −30° C. Dimethyl carbonate (2.4 ml, 3.0 eq) was quickly added, before the reaction mixture was allowed to warm up to room temperature for 1 hr. Reaction mixture was quenched with 2M HCl, followed by addition of saturated aq. NaCl. Mixture was extracted with ethyl acetate. The combined organic extracts were dried with Na$_2$SO$_4$ and concentrated. The crude reaction mixture was purified by flash chromatography to yield tert-butyl 2-(methoxycarbonyl)furan-3-ylcarbamate 33 (1.14 g, 51%): MS (Q1) 242 (M)⁺.

Example 15

Methyl 3-aminofuran-2-carboxylate 34

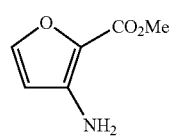

34

Tert-butyl 2-(methoxycarbonyl)furan-3-ylcarbamate 33 (1.14 g, 1.0 eq) was dissolved in dichloromethane (8 ml) and treated with trifluoroacetic acid (5 ml). Reaction mixture was stirred at room temperature for 3 h, and was then concentrated. Residue was dissolved in dichloromethane and washed with saturated aq. NaHCO$_3$. The organic layer was dried (Na$_2$SO$_4$) and concentrated Mixture was extracted with ethyl acetate. The combined organic extracts were dried with Na$_2$SO$_4$ and concentrated. The crude reaction mixture was purified by flash chromatography to yield methyl 3-aminofuran-2-carboxylate 34 (574 mg, 86%): MS (Q1) 142 (M)⁺.

Example 16

Ethyl 3-ureidofuran-2-carboxylate 35

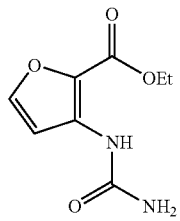

35

To a solution of methyl 3-aminofuran-2-carboxylate 34 (100 mg, 1.0 eq) in dichloromethane (3 ml) at −78° C. was added chlorosulfonyl isocyanate (0.09 ml, 1.4 eq) dropwise. The reaction was slowly warmed to room temperature and stirred for 40 minutes. Reaction was concentrated. To the residue was added 6N HCl (3.5 ml) and mixture was heated to 100° C. for 20 minutes. Reaction mixture was allowed to cool down to room temperature, and was neutralized with saturated aq. NaHCO$_3$. Solid was collected by filtration to yield ethyl 3-ureidofuran-2-carboxylate 35 (120 mg, 92%) as a beige solid which was used in the next reaction without further purification.

Example 17

Furo[3,2-d]pyrimidine-2,4-diol 36

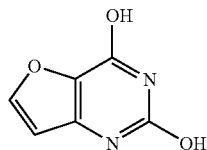

Ethyl 3-ureidofuran-2-carboxylate 35 (120 mg, 1.0 eq) was suspended in methanol (6 ml) and treated with 1.5 M NaOH (1.5 ml). Reaction mixture was heated to reflux for 90 minutes. Reaction mixture was allowed to cool down to room temperature, and was acidified with 6N HCl up to pH 3. Mixture was concentrated. Methanol was added to residue and solid was filtered and dried at 95° C. under high vacuum for 24 h to yield furo[3,2-d]pyrimidine-2,4-diol 36 (90 mg, 91%) which was used in the next reaction without further purification.

Example 18

2,4-Dichlorofuro[3,2-d]pyrimidine 37

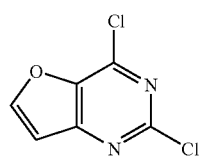

37

Furo[3,2-d]pyrimidine-2,4-diol 36 (39 mg, 1.0 eq) was dissolved in POCl$_3$ (1.8 ml). Mixture was cooled to −40° C. and N,N-diisopropylethylamine (0.45 ml) wad slowly added.

Reaction mixture was then heated to reflux for 48 h, then cooled to room temperature Reaction mixture was poured into ice/water. Mixture was extracted with ethyl acetate. The combined organic layers were washed with saturated aq. NaHCO$_3$, dried (Na$_2$SO$_4$) and concentrated to yield 2,4-dichlorofuro[3,2-d]pyrimidine 37 (23 mg, 48%) which was used in the next reaction without further purification.

Example 19

2-Chloro-4-morpholinofuro[3,2-d]pyrimidine 38

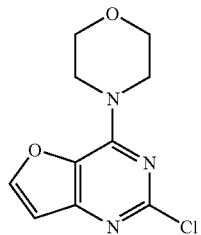

38

2,4-Dichlorofuro[3,2-d]pyrimidine 37 (23 mg, 1.0 eq) was suspended in methanol (1.7 ml) and treated with morpholine (0.09 ml, 4.0 eq). Reaction mixture was stirred at room temperature for 2 h, before being quenched with saturated aq. NaHCO$_3$. Mixture was extracted with dichloromethane. The combined organic layers were dried (Na$_2$SO$_4$) and concentrated to yield 2-chloro-4-morpholinofuro[3,2-d]pyrimidine 38 (14 mg, 48%) which was used in the next reaction without further purification.

Example 20

2-Chloro-4-morpholinofuro[3,2-d]pyrimidine-6-carbaldehyde 39

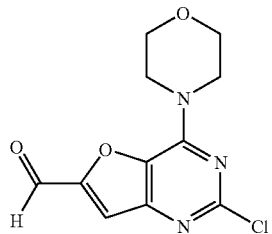

39

To a solution of 2-chloro-4-morpholinofuro[3,2-d]pyrimidine 38 (40 mg, 1.0 eq) dissolved in THF (1.7 ml) at −78° C. was added 1.6M solution of n-butyllithium (0.14 ml, 1.3 eq, 1.6M in hexanes). Reaction mixture was stirred at −78° C. for 30 minutes. DMF (0.05 ml, 4.0 eq) was added and reaction mixture was allowed to slowly warm up to room temperature and stirred for 90 minutes. Reaction mixture was quenched with water, and extracted with dichloromethane. The combined organic layers were dried (Na$_2$SO$_4$) and concentrated. The crude reaction mixture was purified by flash chromatography to yield 2-chloro-4-morpholinofuro[3,2-d]pyrimidine-6-carbaldehyde 39 (22 mg, 50%): $^1$H NMR (CDCl$_3$, 400 MHz) δ 9.92 (s, 1H), 7.48 (s, 1H), 4.12 (m, 4H), 3.86 (dd, 4H); MS (Q1) 268 (M)$^+$.

Example 21

1-(Tetrahydro-2H-pyran-2-yl)-4-(4,4,5,5-tetramethyl-1,3,2-dioxaborolan-2-yl)-1H-indazole 40

Route A

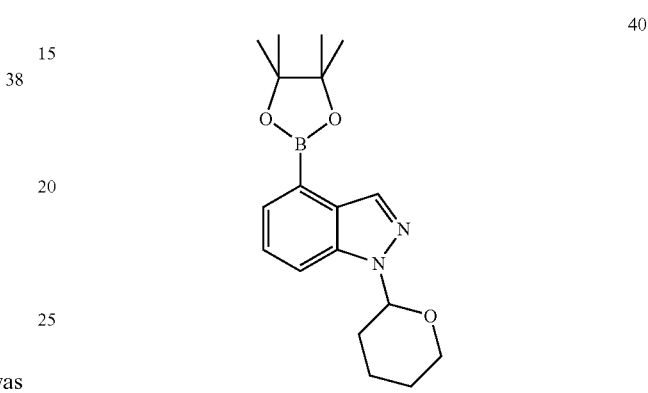

Step A: Preparation of 4-chloro-1H-indazole: To a 250 ml flask with stirbar was added 2-methyl-3-chloroaniline (8.4 ml, 9.95 g, 70.6 mmol), potassium acetate (8.3 g, 84.7 mmol) and chloroform (120 ml). This mixture was cooled to 0° C. with stirring. To the cooled mixture was added acetic anhydride (20.0 ml, 212 mmol) drop wise over 2 minutes. The reaction mixture was warmed to 25° C. and stirred for 1 hour. At this point, the reaction was heated to 60° C. Isoamyl nitrite (18.9 ml, 141 mmol) was added and the reaction was stirred overnight at 60° C. Once complete, water (75 ml) and THF (150 ml) were added and the reaction was cooled to 0° C. LiOH (20.7 g, 494 mmol) was added and the reaction was stirred at 0° C. for 3 hours. Water (200 ml) was added and the product was extracted with EtOAc (300 ml, 100 ml). The organic layers were combined, dried with MgSO$_4$ and concentrated in vacuo to yield 11.07 g (100%) as an orange solid. $^1$H NMR (400 MHz, CDCl$_3$) δ 8.18 (d, J=1 Hz, 1H), 7.33 (d, J=8 Hz 1H), 7.31 (t, J=7 Hz, 1H), 7.17 (dd, J=7 Hz, 1 Hz 1H). LCMS (ESI pos) m/e 153 (M+1).

Step B: Preparation of 4-chloro-1-(tetrahydro-2H-pyran-2-yl)-1H-indazole: To a 1 L flask with mechanical stirrer was added 4-chloro-1H-indazole (75.0 g, 0.492 mol), pyridinium p-toluenesulfonate (1.24 g, 4.92 mmol), CH$_2$Cl$_2$ (500 ml) and 3,4-dihydro-2H-pyran (98.6 ml, 1.08 mol). With stirring, this mixture was heated to 45° C. for 16 hours. Analysis of reaction mixture shows production of both isomers of product. Cooled reaction to 25° C. and added CH$_2$Cl$_2$ (200 ml). Washed the solution with water (300 ml) and saturated NaHCO$_3$ (250 ml). Dried the organics with MgSO$_4$ and concentrated to dryness. Purified the crude product by dissolving in EtOAc/Hexanes (4:6, 1 L) and adding SiO$_2$ (1.2 L). The mixture was filtered and the cake was washed with EtOAc/Hexanes (4:6, 2 L). The organics were concentrated in vacuo to yield 110.2 g (95%) as an orange solid. Isomer 1: $^1$H NMR (400 MHz, CDCl$_3$) δ 8.10 (d, J=1 Hz, 1H), 7.50 (dd, J=9 Hz, 1 Hz 1H), 7.29 (dd, J=9 Hz, 8 Hz 1H), 7.15 (dd, J=8 Hz, 1 Hz 1H) 5.71 (dd, J=9 Hz, 3 Hz 1H) 4.02 (m, 1H) 3.55 (m, 1H) 2.51 (m, 1H) 2.02 (m, 2H) 1.55 (m, 3H). LCMS (ESI pos) m/e 237 (M+1); Isomer 2: ¹H NMR (400 MHz, CDCl₃) δ 8.25 (d, J=1 Hz, 1H), 7.62 (dd, J=9 Hz, 1 Hz 1H), 7.20 (dd, J=9 Hz, 8 Hz 1H), 7.06 (dd, J=8 Hz, 1 Hz 1H) 5.69 (dd, J=9 Hz, 3 Hz 1H) 4.15 (m, 1H) 3.80 (m, 1H) 2.22 (m, 2H) 2.05 (m, 1H) 1.75 (m, 3H). LCMS (ESI pos) m/e 237 (M+1).

Step C: Preparation of 1-(tetrahydro-2H-pyran-2-yl)-4-(4, 4,5,5-tetramethyl-1,3,2-dioxaborolan-2-yl)-1H-indazole: To a 500 ml flask with stirbar was added 4-chloro-1-(tetrahydro-2H-pyran-2-yl)-1H-indazole (10.0 g, 42.2 mmol), DMSO (176 ml), PdCl₂(PPh₃)₂ (6.2 g, 8.86 mmol), tricyclohexylphosphine (0.47 g, 1.69 mmol), bis(pinacolato)diboron (16.1 g, 63.4 mmol) and potassium acetate (12.4 g, 0.127 mol). With stirring, the mixture was heated to 130° C. for 16 hours. The reaction was cooled to 25° C. and EtOAc (600 ml) was added and washed with water (2×250 ml). The organics were dried with MgSO₄ and concentrated in vacuo to dryness. The crude product was purified by SiO₂ plug (120 g), eluting with 10% EtOAc/Hexanes (IL) and 30% EtOAc/Hexanes (1 L). The filtrate was concentrated in vacuo to give 13.9 g (100%) of product 40 as a 20% (wt/wt) solution in ethyl acetate. ¹H NMR shows the presence of ~20% (wt/wt) bis(pinacolato) diboron. ¹H NMR (400 MHz, CDCl₃) δ 8.37 (s, 1H), 7.62 (dd, J=14 Hz, 2 Hz 1H), 7.60 (dd, J=7 Hz, 1 Hz 1H), 7.31 (dd, J=8 Hz, 7 Hz 1H) 5.65 (dd, J=9 Hz, 3 Hz 1H) 4.05 (m, 1H) 3.75 (m, 1H) 2.59 (m, 1H) 2.15 (m, 1H) 2.05 (m, 1H) 1.75 (m, 3H) 1.34 (s, 12H). LCMS (ESI pos) m/e 245 (M+1).

Example 22

1-(Tetrahydro-2H-pyran-2-yl)-4-(4,4,5,5-tetramethyl-1,3,2 dioxaborolan-2-yl)-1H-indazole 40

Route B

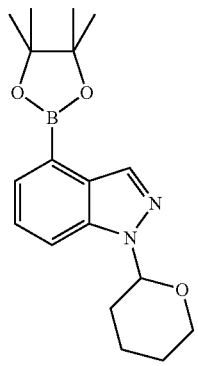

Step A: Preparation of 4-nitro-1H-indazole: A mixture of 2-methyl-3-nitro aniline (200 g, 1.315 moles), acetic acid (8000 ml) was cooled to 15-20° C. and a solution of sodium nitrite (90.6 g, 1.315 moles) in water (200 ml) was slowly added over 30 min. After the addition, the reaction temp. was increased to 25-30° C. and the reaction was stirred at this temp for 2-3 h. Reaction progress was monitored by TLC and after completion of reaction product was filtered and residue was washed with acetic acid (1000 ml). Acetic acid was distilled under vacuum (550 mm of Hg) below 80° C. and water (8000 ml) was added, cooled to 25-30° C. and stirred for 30 min. The slurry was filtered and washed with water (1000 ml). Crude product was dried under heating at 70-80° C. for 2 hours, then was taken in 5% ethyl acetate/n-hexane (100:2000 ml) solution and stirred for 1-1.5 h at ambient temperature. The suspension was filtered and washed with 5% ethyl acetate/n-hexane mixture (25:475 ml). The product obtained was dried under vacuum at below 80° C. for 10-12 h to give a brown solid (150 g, 70%): m.p: 200-203° C.; ¹H NMR (200 MHz, CDCl₃) δ 13.4 (br, 1H), 8.6 (s, 1H), 8.2-7.95 (dd, 2H), 7.4 (m, 1H). ESMS m/z 164 (M+1). Purity: 95% (HPLC)

Step B: Preparation of 4-amino-1H-indazole: A mixture of 4-nitro-1H-indazole (200 g, 1.22 moles) and 10% palladium on carbon (20.0 g,) in EtOH (3000 ml) was hydrogenated at ambient temperature (reaction was exothermic and temperature increased to 50° C.). After completion of reaction, the catalyst was removed by filtration. The solvent was evaporated under vacuum at below 80° C. and cooled to room temperature and n-hexane (1000 ml) was added to the residue and stirred for 30 min. Isolated solid was filtered and washed with n-hexane (200 ml). Product was dried under vacuum at 70-80° C. for 10-12 h to give a brown solid (114 g, 70%), m.p.: 136-143° C. ¹H NMR (200 MHz, CDCl₃) δ 12 (br, 1H), 8.0 (s, 1H), 7.1-7.0 (dd, 2H), 6.5 (d, 1H), 3.9 (m, 2H). ESMS m/z 134 (M+1). Purity: 90-95% (HPLC)

Step C: Preparation of 4-iodo-1H-indazole: A mixture of 4-amino-1H-indazole (50.0 g, 0.375 moles) in water (100 ml) and con. hydrochloric acid (182 ml) was cooled to –10° C. To this a solution of sodium nitrite (51.7 g, 0.75 moles) in water (75 ml) was added drop wise at –10° C. in about 30-60 min. (during addition frothing was observed). In another flask a mixture of potassium iodide (311 g, 1.87 moles) in water (3000 ml) was prepared at room temperature and to this above cooled diazonium salt at 30-40° C. was added in about 30-40 min. The reaction was maintained at 30° C. for 1 h and after completion of reaction, ethyl acetate (500 ml) was added and the reaction mixture was filtered through Celite. The layers were separated and the aq. layer was extracted with ethyl acetate (2×500 ml). The combined organic layers were washed with 5% hypo solution (2×500 ml), brine (500 ml), dried (Na₂SO₄) and concentrated. Crude product was purified by chromatography (silica gel, hexane, 15-20% ethyl acetate/hexane) to furnish product as an orange solid (23.0 g, 25%). m.p: 151-177 C: ¹H NMR (200 MHz, CDCl₃) δ 12.4 (br, 1H), 8.0 (s, 1H), 7.6 (dd, 2H), 7.1 (d, 1H). ESMS m/z 245 (M+1). Purity: 95-98% (HPLC).

Step D: Preparation of 4-iodo-1-(2-tetrahydropyranyl) indazole: A mixture of 4-amino-1H-indazole (250.0 g, 1.024 moles), 3,4-dihydro-2H-pyran (126.0 g, 1.5 moles) and PPTS (2.57 g, 0.01 moles) in CH₂Cl₂ (1250 ml) was heated to 50° C. for 2 h. The reaction was cooled to r.t and poured into water (625 ml), the layers were separated, and aqueous layer was extracted with CH₂Cl₂ (250 ml). The combined organic layers were washed with water (625 ml), dried (Na₂SO₄) and concentrated. Crude residue was purified by chromatography (silica gel, hexane, 5-10% ethyl acetate/hexane) to furnish product as oil (807.0 g, 60%). ¹H NMR (200 MHz, CDCl₃) δ 8.5 (s, 1H), 7.8 (m, 1H), 7.6 (d, 1H), 7.25 (m, 1H), 5.7 (dd, 1H), 4.2-3.8 (dd, 1H), 2.2-2.0 (m, 4H) 2.0-1.8 (m, 4H). ESMS m/z 329 (M+1).

Step E: Preparation of 1-(tetrahydro-2H-pyran-2-yl)-4-(4, 4,5,5-tetramethyl-1,3,2-dioxaborolan-2-yl)-1H-indazole: A mixture of 4-iodo-1-(2-tetrahydropyranyl) indazole (100 g, 0.304 moles), bispinacalotodiborane (96.4 g, 0.381 moles), PdCl₂ (dppf) (8.91 g, 0.012 moles) and potassium acetate (85.97 g, 0.905 moles) in DMSO (500 ml) were heated to 80° C. for 2-3 h. After completion, reaction was cooled to r.t and water (1500 ml) was added. Reaction mass was extracted into ethyl acetate (3×200 ml) and combined organic layers were evaporated, dried (Na₂SO₄) and concentrated. Crude product was purified by column chromatography (silica gel, hexane, 5-10% ethyl acetate/hexane) to obtain product 40 as viscous brown oil (70.0 g, 70%). 5: $^1$H NMR (CDCl$_3$) δ 8.5 (s, 1H), 7.8 (m, 1H), 7.6 (d, 1H), 7.25 (m, 1H), 5.7 (dd, 1H), 4.2-3.8 (dd, 1H), 2.2-2.0 (m, 4H) 2.0-1.8 (m, 4H) 1.4-1.2 (s, 12H). ESMS m/z 329 (M+1).

Example 23

Ethyl 5-phenyl-3-ureidofuran-2-carboxylate 41

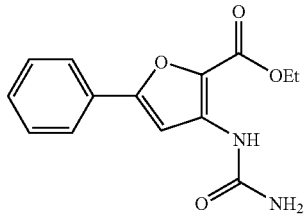

To a solution of 3-amino-5-phenyl-furan-2-carboxylate ester (116 mg, 1.0 eq) in dichloromethane (3 ml) at −78° C. was added chlorosulfonyl isocyanate (0.06 ml, 1.3 eq) dropwise (Redman, A. Me.; Dumas, J.; Scott, W. J. Org. Lett. (2000) 2:2061-2063). The reaction was slowly warmed to room temperature and stirred for 40 minutes. The reaction was concentrated. To the residue was added 6N HCl (2.5 ml) and mixture was heated to 100° C. for 20 minutes. Reaction mixture was allowed to cool down to room temperature, and was neutralized with saturated aq. NaHCO$_3$. Solid was collected by filtration to yield 5-phenyl-3-ureidofuran-2-carboxylate 41 (130 mg, 95%) as a beige solid which was used in the next reaction without further purification.

Example 24

6-Phenylfuro[3,2-d]pyrimidine-2,4-diol 42

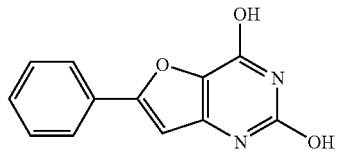

5-Phenyl-3-ureidofuran-2-carboxylate 41 (125 mg, 1.0 eq) was suspended in methanol (5 ml) and treated with 1.5 M NaOH (1 ml). Reaction mixture was heated to reflux for 90 minutes. Reaction mixture was allowed to cool down to room temperature, and was acidified with 6N HCl up to pH 3. Solid was filtered and dried at 95° C. under high vacuum for 24 h to yield 6-phenylfuro[3,2-d]pyrimidine-2,4-diol (79 mg, 76%) as a beige solid which was used in the next reaction without further purification.

Example 25

2,4-Dichloro-6-phenylfuro[3,2-d]pyrimidine 43

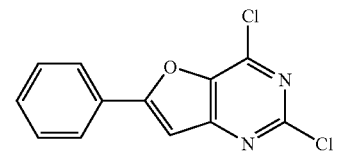

6-phenylfuro[3,2-d]pyrimidine-2,4-diol 42 (80 mg, 1.0 eq) was dissolved in POCl$_3$ (2.4 ml). Mixture was cooled to −40° C. and N,N-diisopropylethylamine (0.6 ml) wad slowly added. Reaction mixture was then heated to reflux for 48 h, then cooled to room temperature. The reaction mixture was poured into ice/water. Mixture was extracted with ethyl acetate. The combined organic layers were washed with saturated aq. NaHCO$_3$, dried (Na$_2$SO$_4$) and concentrated to yield 2,4-dichloro-6-phenylfuro[3,2-d]pyrimidine 43 (76 mg, 82%) which was used in the next reaction without further purification.

Example 26

2-Chloro-4-morpholino-6-phenylfuro[3,2-d]pyrimidine 44

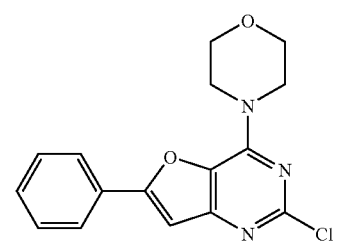

2,4-Dichloro-6-phenylfuro[3,2-d]pyrimidine 43 (165 mg, 1.0 eq) was suspended in methanol (4.2 ml) and treated with morpholine (0.22 ml, 4.0 eq). Reaction mixture was stirred at room temperature for 4 h. Solid was filtered to yield pure 2-chloro-4-morpholino-6-phenylfuro[3,2-d]pyrimidine 44 (163 mg, 83% yield) as a beige solid: $^1$H NMR (CDCl$_3$, 400 MHz) δ 7.80 (m, 2H), 7.51 (m, 3H), 6.99 (m, 1H), 4.10 (m, 4H), 3.89 (m, 1H); MS (Q1) 316 (M)$^+$.

Example 27

2-Chloro-6-iodo-4-morpholinofuro[3,2-d]pyrimidine 45

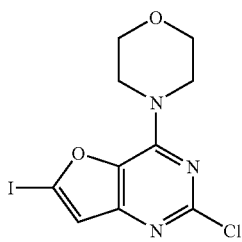

To a solution of 2-chloro-4-morpholinofuro[3,2-d]pyrimidine 38 (50 mg, 1.0 eq) dissolved in THF (2.1 ml) at −78° C. was added 1.6M solution of n-butyllithium (0.17 ml, 1.3 eq, 1.6M in hexanes). Reaction mixture was stirred at −78° C. for 30 minutes. A solution of iodine (159 mg, 3.0 eq) in THF (0.6 ml) was added and reaction mixture was allowed to slowly warm up to room temperature and stirred for 45 minutes. The reaction mixture was quenched with saturated aq. $Na_2S_2O_3$, and extracted with dichloromethane. The combined organic layers were dried ($Na_2SO_4$) and concentrated. The crude reaction mixture was purified by flash chromatography to yield 2-chloro-6-iodo-4-morpholinofuro[3,2-d]pyrimidine 45 (63 mg, 83%): MS (Q1) 366 (M)$^+$.

Example 28

2-(2-Chloro-4-morpholinofuro[3,2-d]pyrimidin-6-yl)propan-2-ol 46

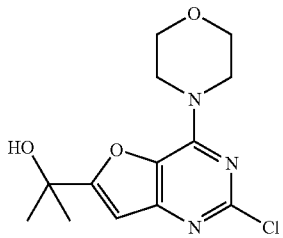

To a solution of 2-chloro-4-morpholinofuro[3,2-d]pyrimidine 38 (60 mg, 1.0 eq) dissolved in THF (2.5 ml) at −78° C. was added 1.6M solution of n-butyllithium (0.20 ml, 1.3 eq, 1.6M in hexanes). Reaction mixture was stirred at −78° C. for 30 minutes. Acetone (0.07 ml, 4.0 eq) was added and reaction mixture was allowed to warm up to −40° C. and stirred for 1 h. The crude reaction mixture was concentrated and purified by reverse phase HPLC to afford 2-(2-chloro-4-morpholinofuro[3,2-d]pyrimidin-6-yl)propan-2-ol 46. MS (Q1) 298 (M)$^+$.

Example 29

3-(2-(1H-indazol-4-yl)-4-morpholinothieno[3,2-d]pyrimidin-6-yl)-N-methylbenzamide 101

120 mg of 2-chloro-6-iodo-4-morpholinothieno[3,2-d]pyrimidine 19, 62 mg of 3-(N-methylaminocarbonylphenyl) boronic acid and 22 mg of bis(triphenylphosphine)palladium (II) dichloride in 0.6 mL of 1M $Na_2CO_3$ aqueous solution and 0.6 mL of acetonitrile was heated to 100° C. in a sealed microwave reactor for 15 min. The mixture was diluted with $H_2O$ and then extracted with ethyl acetate (3×20 mL). The combined organic layers were concentrated. The crude product was purified by reverse phase HPLC to give 75 mg of 3-(2-chloro-4-morpholinothieno[3,2-d]-6-yl)-N-methylbenzamide.

3-(2-Chloro-4-morpholinothieno[3,2-d]-6-yl)-N-methylbenzamide (50 mg) was coupled to 4-(4,4,5,5-tetramethyl-1,3,2-dioxaborolan-2-yl)-1H-indazole 7 via General Procedure A. The product was purified by reverse phase HPLC to yield 13.3 mg of 101. MS (Q1) 471 (M)$^+$.

Example 30

2-(1H-indazol-4-yl)-4-morpholino-6-(3-isopropylsulfonylaminophenyl)thieno[3,2-d]pyrimidine 102

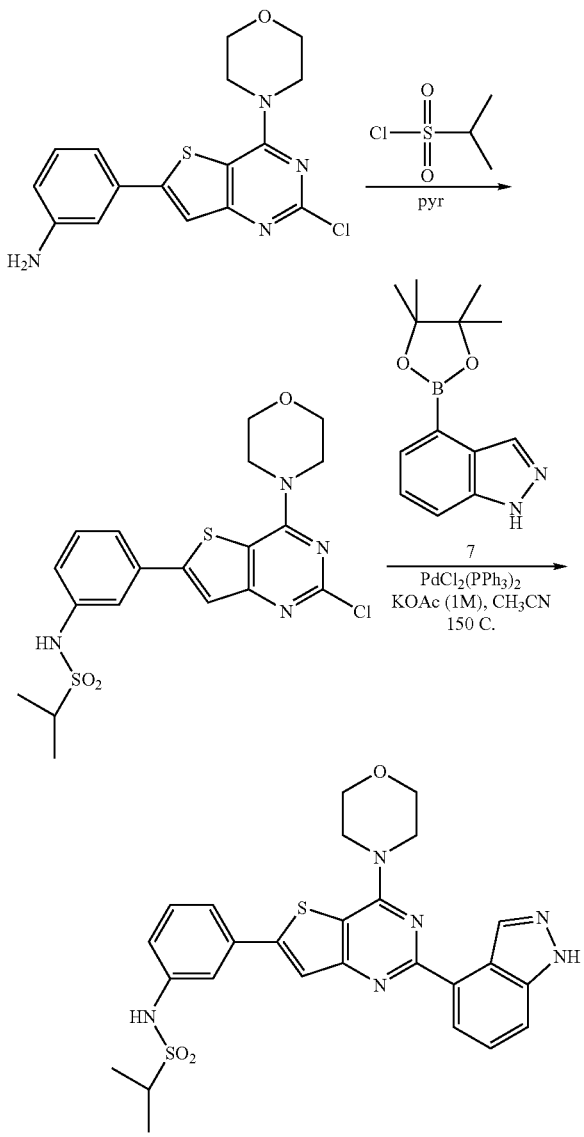

120 mg of 2-chloro-4-morpholinothieno[3,2-d]pyrimidin-6-yl)benzenamine, 43 μL of isopropylsulfonyl chloride in 1 mL of pyridine was stirred overnight at room temperature. The reaction mixture was evaporated. The crude product was purified by reverse phase HPLC to give 47 mg of chloro intermediate.

Chloro intermediate (21 mg) was coupled to 4-(4,4,5,5-tetramethyl-1,3,2-dioxaborolan-2-yl)-1H-indazole 7 via General Procedure A. The product was purified by reverse phase HPLC to yield 10 mg of 102. MS (Q1) 535 (M)+

Example 31

(S)-1-(2-(1-H-indazol-4-yl)-4-morpholinothieno[3,2-d]pyrimidin-6-yl)ethanol 103 and (R)-1-(2-(1H-indazol-4-yl)-4-morpholinothieno[3,2-d]pyrimidin-6-yl)ethanol 104

To 100 mg of 2-chloro-4-morpholinothieno[3,2-d]pyrimidine 4 was added acetaldehyde via General Procedure D. The crude chloride was subjected to Procedure A to give a separable mixture of 103 and 104. MS (Q1) 382.2 (M)+

Example 32

2-(1H-indazol-4-yl)-4-morpholino-6-(propylsulfonyl)thieno[2,3-d]pyrimidine 105

500 mg of 2-chloro-4-morpholinothieno[2,3-d]pyrimidine was cooled to −78° C. in 50 mL of THF before adding 1.3 eq of a 2.5M solution of nBuLi in hexanes. The reaction was stirred at −78° C. for 30 minutes before warming to −40° C. for several minutes to allow for complete formation of the Lithium anion. The reaction was then re-cooled to −78° C. and sulfur dioxide gas was bubbled in via cannula to the reaction solution for 2 minutes. The reaction was cooled to 0° C. and quenched with water. The aqueous was extracted with ethyl acetate to remove any 2-chloro-4-morpholinothieno[2,3-d]pyrimidine. The aqueous layer was then lyophilized and purified via reverse phase HPLC to afford 180 mg of pure 2-chloro-4-morpholinothieno[2,3-d]pyrimidine-6-sulfinic acid.

To 90 mg of 2-chloro-4-morpholinothieno[2,3-d]pyrimidine-6-sulfinic acid in 1.5 mL of DMF was added 1.05 eq of NaH (60% oil dispersion). The reaction was stirred at room temperature for 30 minutes prior to addition of 1.05 eq of iodopropane, whereupon the temperature was raised to 50° C. and the reaction was complete in 30 minutes. The reaction was cooled to room temperature and then extracted into Ethyl Acetate with a saturated bicarbonate solution two times. The organic layer was dried with $MgSO_4$, filtered and concentrated to dryness. The crude chloride was subjected to Procedure A to give 27.6 mg of 105. MS (Q1) 444.1 (M)+.

Example 33

2-(2-(1H-indazol-4-yl)-4-morpholinothieno[3,2-d]pyrimidin-6-yl)-1-methoxypropan-2-ol 106

200 mg of 2-chloro-4-morpholinothieno[3,2-d]pyrimidine 4 was used along with methoxyacetone following General Procedure D to give the corresponding tertiary alcohol. 60 mg of the crude material was used in a palladium catalyzed cross coupling reaction following general procedure A to give 23 mg of 106 after reversed phase HPLC purification. MS (Q1) 426 (M)+

Example 34

2-(2-(1H-Indazol-4-yl)-4-morpholinofuro[3,2-d]pyrimidin-6-yl)propan-2-ol 107

2-(2-chloro-4-morpholinofuro[3,2-d]pyrimidin-6-yl)propan-2-ol (60 mg, 1.0 eq) was dissolved in acetonitrile (2.0 ml) and treated with 4-(4,4,5,5-tetramethyl-1,3,2-dioxaborolan-2-yl)-1H-indazole 7 (123 mg, 2.5 eq), $PdCl_2(PPh_3)_2$ (14.1 mg, 0.10 eq) and 1M potassium acetate (0.6 ml). The vial was sealed and heated with stirring in the microwave to 140° C. for 30 minutes. The crude reaction mixture was concentrated and purified by reverse phase HPLC to afford 2-(2-(1H-indazol-4-yl)-4-morpholinofuro[3,2-d]pyrimidin-6-yl)propan-2-ol 107. MS (Q1) 380 (M)+.

2-(2-(1H-indazol-4-yl)-4-morpholinothieno[3,2-d]pyrimidin-6-yl)-1,3-dimethoxypropan-2-ol 108

200 mg of 2-chloro-4-morpholinothieno[3,2-d]pyrimidine 4 was used along with 1,3-dimethoxyacetone following General Procedure D to give the corresponding tertiary alcohol. 60 mg of the crude material was used in a palladium catalyzed cross coupling reaction following general procedure A to give 15 mg of 108 after reversed phase HPLC purification. MS (Q1) 456 (M)+

Example 35

2-(2-(1H-indazol-4-yl)-4-morpholinothieno[3,2-d]pyrimidin-6-yl)-1-(diethylamino)propan-2-ol 109

200 mg of 2-chloro-4-morpholinothieno[3,2-d]pyrimidine 4 was used along with (N,N-diethylamino)acetone following general procedure D to give the corresponding tertiary alcohol. 60 mg of the crude material was used in a palladium catalyzed cross coupling reaction following general procedure A to give 12 mg of 109 after reversed phase HPLC purification. MS (Q1) 467 (M)+

Example 36

1-(4-(2-(1H-indazol-4-yl)-4-morpholinothieno[3,2-d]pyrimidin-6-yl)-4-hydroxypiperidin-1-yl)ethanone 110

200 mg of 2-chloro-4-morpholinothieno[3,2-d]pyrimidine 4 was used along with 1-acetyl-4-piperidone following general procedure D to give the corresponding tertiary alcohol. The crude reaction mixture was triturated with acetonitrile and 60 mg of tertiary alcohol was used in a palladium catalyzed cross coupling reaction following general procedure A to give 25 mg of 110 after reversed phase HPLC purification. MS (Q1) 479 (M)+

Example 37

2-(1H-Indazol-4-yl)-6-(3-(methylsulfonyl)phenyl)-4-morpholinofuro[3,2-d]pyrimidine 111

2-Chloro-6-iodo-4-morpholinofuro[3,2-d]pyrimidine (40 mg, 1.0 eq) was dissolved in acetonitrile (0.4 ml) and treated with 3-(methylsulfonyl)phenylboronic acid (23 mg, 1.05 eq), $PdCl_2(PPh_3)_2$ (7.7 mg, 0.10 eq) and 1M $Na_2CO_3$ (0.33 ml). The vial was sealed and heated with stirring in the microwave to 100° C. for 30 minutes. Reaction mixture was quenched with saturated aq. $NaHCO_3$ and extracted with dichloromethane. The combined organic layers were dried (Na$_2$SO$_4$) and concentrated. The residue was dissolved in acetonitrile (0.4 ml) and treated with 4-(4,4,5,5-tetramethyl-1,3,2-dioxaborolan-2-yl)-1H-indazole 7 (53 mg, 2.0 eq), PdCl$_2$(PPh$_3$)$_2$ (7.7 mg, 0.10 eq) and 1M Na$_2$CO$_3$ (0.33 ml). The vial was sealed and heated with stirring in the microwave to 150° C. for 15 minutes. The crude reaction mixture was concentrated and purified by reverse phase HPLC to afford 2-(1H-indazol-4-yl)-6-(3-(methylsulfonyl)phenyl)-4-morpholinofuro[3,2-d]pyrimidine 111 MS (Q1) 476 (M)$^+$.

Example 38

N-(3-(2-(1H-indazol-4-yl)-4-morpholinothieno[3,2-d]pyrimidin-6-yl)phenyl)-2-hydroxy-2-methylpropanamide 112

2-Chloro-6-iodo-4-morpholinothieno[3,2-d]pyrimidine 19 (300 mg), 3-aminophenylboronic acid (134 mg), and bis(triphenylphosphine)palladium(II) dichloride (55 mg) in 0.6 mL of 1M Na$_2$CO$_3$ aqueous solution and 0.6 mL of acetonitrile was heated to 100° C. in a sealed microwave reactor for 15 min. The reaction mixture was diluted with ethyl acetate (80 mL), washed with H$_2$O (50 mL). The organic layer was dried over MgSO$_4$, filtered and evaporated to yield 270 mg of 3-(2-chloro-4-morpholinothieno[3,2-d]pyrimidin-6-yl)benzenamine.

3-(2-Chloro-4-morpholinothieno[3,2-d]pyrimidin-6-yl)benzenamine (50 mg) was reacted with 2-hydroxyisobutyric acid via General Procedure I to give N-(3-(2-chloro-4-morpholinothieno[3,2-d]pyrimidin-6-yl)phenyl)-2-hydroxy-2-methylpropanamine. 62 mg of the crude N-(3-(2-chloro-4-morpholinothieno[3,2-d]pyrimidin-6-yl)phenyl)-2-hydroxy-2-methylpropanamine was coupled to 4-(4,4,5,5-tetramethyl-1,3,2-dioxaborolan-2-yl)-1H-indazole 7 via General Procedure A. The product was purified by reverse phase HPLC to yield 16.2 mg of 112. MS (Q1) 515 (M)$^+$.

Example 39

(2S)—N-(3-(2-(1H-indazol-4-yl)-4-morpholinothieno[3,2-d]pyrimidin-6-yl)phenyl)-2-hydroxypropanamide 113

3-(2-Chloro-4-morpholinothieno[3,2-d]pyrimidin-6-yl)benzenamine (50 mg) was reacted with L-lactic acid via General Procedure I to give (2S)—N-3-(2-chloro-4-morpholinothieno[3,2-d]pyrimidin-6-yl)phenyl)-2-hydroxypropanamide. 60 mg of the crude (2S)—N-3-(2-chloro-4-morpholinothieno[3,2-d]pyrimidin-6-yl)phenyl)-2-hydroxypropanamide was coupled to 4-(4,4,5,5-tetramethyl-1,3,2-dioxaborolan-2-yl)-1H-indazole 7 via General Procedure A. The product was purified by reverse phase HPLC to yield 3 mg of 113. MS (Q1) 501 (M)$^+$.

Example 40

(2-(1H-indazol-4-yl)-4-morpholinothieno[3,2-d]pyrimidin-6-yl)methanol 114

This compound was prepared from (2-chloro-4-morpholinothieno[3,2-d]pyrimidin-6-yl)methanol using the General Procedure A to give 114 after reversed phase HPLC purification (54%). MS (Q1) 368 (M)+

Example 41

(2-(1H-indazol-4-yl)-4-morpholinothieno[3,2-d]pyrimidin-6-yl)methanamine 115

This compound was prepared from (2-chloro-4-morpholinothieno[3,2-d]pyrimidin-6-yl)methanamine 27 from Example 11, and using the General Procedure A to give 115 after reversed phase HPLC purification (35%). MS (Q1) 367 (M)+

Example 42

(2-(1H-indazol-4-yl)-4-morpholinothieno[3,2-d]pyrimidin-6-yl)methane(methylsulfonyl)amine 116

To a solution of (2-chloro-4-morpholinothieno[3,2-d]pyrimidin-6-yl)methanamine (50 mg, 0.2 mmol) in CH$_2$Cl$_2$ (4 mL) was added Et$_3$N (84 µL, 0.6 mmol) and MeSO$_2$Cl (26 µL, 0.3 mmol). The reaction stirred 18 h at room temperature before being quenched with water (2 mL). The aqueous layer was extracted with EtOAc. The combined organics were dried over Na$_2$SO$_4$ and concentrated in vacuo. The crude sulfonamide was utilized according to General Procedure A to provide 116 after reversed phase HPLC purification (13% over 2 steps). MS (Q1) 445 (M)+

Example 43

2-(1H-indazol-4-yl)-4-morpholino-N-(pyridin-3-yl)thieno[3,2-d]pyrimidin-6-amine 117

Prepared according to the General Procedure J to give 117 (6% over 2 steps). MS (Q1) 430 (M)+

Example 44

2-(4-(2-(2-(1H-indazol-4-yl)-4-morpholinothieno[3,2-d]pyrimidin-6-yl)ethyl)piperazin-1-yl)-N,N-dimethylacetamide 118

Following the procedures of Example 67 to prepare 144, and using N,N-dimethyl-2-piperazin-1-yl-acetamide, 118 was prepared. NMR: CDCl$_3$: 2.49-2.62 (8H, m, CH$_2$), 2.68-2.84 (2H, m, CH$_2$), 2.91 (3H, s, Me), 3.02 (3H, s, Me), 3.08 (2H, t, J 7.22, CH$_2$), 3.13 (2H, s, CH$_2$), 3.79-3.84 (4H, m, CH$_2$), 3.98-4.02 (4H, m, CH$_2$), 7.20 (1H, s, Ar), 7.44 (1H, t, J 8.0, Ar), 7.52 (1H, d, J 8.15, Ar), 8.22 (1H, d, J 7.35, Ar) and 8.95 (1H, s, Ar). MS: (ESI+): MH+ 535.36

Example 45

N-(2-(1H-indazol-4-yl)-4-morpholinothieno[3,2-d]pyrimidin-6-yl)-2-methoxyacetamide 119

55 mg of 2-chloro-4-morpholinothieno[3,2-d]pyrimidin-6-amine was reacted with 26 mg of methoxyacetyl chloride via General Procedure G to give N-(2-chloro-4-morpholinothieno[3,2-d]pyrimidin-6-yl)-2-methoxyacetamide.

70 mg of crude N-(2-chloro-4-morpholinothieno[3,2-d]pyrimidin-6-yl)-2-methoxyacetamide was coupled to 4-(4,4,5,5-tetramethyl-1,3,2-dioxaborolan-2-yl)-1H-indazole 7 via General Procedure A. The product was purified by reverse phase HPLC to yield 28.1 mg of 119. MS (Q1) 425 (M)$^+$

Example 46

N-(3-(2-(1H-indazol-4-yl)-4-morpholinothieno[3,2-d]pyrimidin-6-yl)phenyl)-2-methoxyacetamide 120

3-(2-Chloro-4-morpholinothieno[3,2-d]pyrimidin-6-yl) benzenamine (60 mg), methoxyacetyl chloride (23 mg), and 36 μL of triethylamine in dichloromethane was stirred for 1 h. The reaction mixture was evaporated to give N-(3-(2-chloro-4-morpholinothieno[3,2-d]pyrimidin-6-yl)phenyl)-2-methoxyacetamide. 70 mg of the crude N-(3-(2-chloro-4-morpholinothieno[3,2-d]pyrimidin-6-yl)phenyl)-2-methoxyacetamide was coupled to 4-(4,4,5,5-tetramethyl-1,3,2-dioxaborolan-2-yl)-1H-indazole 7 via General Procedure A. The product was purified by reverse phase HPLC to yield 17.3 mg of 120. MS (Q1) 501 (M)$^+$.

Example 47

2-(1H-indazol-4-yl)-4-morpholino-N-(pyridin-2-yl)thieno[3,2-d]pyrimidin-6-amine 121

Prepared according to the General Procedure J to give 121 (12% over 2 steps). MS (Q1) 430 (M)+

Example 48

(2-(1H-indazol-4-yl)-4-morpholinothieno[2,3-d]pyrimidin-6-yl)(4-methylpiperazin-1-yl)methanone 122

45 mg of 2-(1H-indazol-4-yl)-4-morpholinothieno[2,3-d]pyrimidine-6-carboxylic acid 14 was coupled to 1-methylpiperazine via General Procedure B. The product was purified via reverse phase HPLC to give 34.5 mg of 122. MS (Q1) 464.2 (M)+.

Example 49

(2-(1H-indazol-4-yl)-4-morpholinothieno[2,3-d]pyrimidin-6-yl)(4-hydroxypiperidin-1-yl)methanone 123

45 mg of 2-(1H-indazol-4-yl)-4-morpholinothieno[2,3-d]pyrimidine-6-carboxylic acid 14 was coupled to piperidin-4-ol via General Procedure B. The product was purified via reverse phase HPLC to give 46.6 mg of 123 MS (Q1) 465.1 (M)+.

Example 50

(2-(1H-indazol-4-yl)-4-morpholinothieno[2,3-d]pyrimidin-6-yl)(4-acetylpiperazin-1-yl)methanone 124

45 mg of 2-(1H-indazol-4-yl)-4-morpholinothieno[2,3-d]pyrimidine-6-carboxylic acid 14 was coupled to 1-acetylpiperazine via General Procedure B. The product was purified via reverse phase HPLC to give 52.5 mg of 124. MS (Q1) 492.2 (M)+.

Example 51

(2-(1H-indazol-4-yl)-4-morpholinothieno[2,3-d]pyrimidin-6-yl)(4-methylsulfonylpiperazin-1-yl)methanone 125

45 mg of 2-(1H-indazol-4-yl)-4-morpholinothieno[2,3-d]pyrimidine-6-carboxylic acid 14 was coupled to 1-methanesulfonylpiperazine via General Procedure B. The product was purified via reverse phase HPLC to give 55 mg of 125. MS (Q1) 528.1 (M)+.

Example 52

2-(1H-indazol-4-yl)-N-isopropyl-4-morpholinothieno[2,3-d]pyrimidine-6-carboxamide 126

45 mg of 2-(1H-indazol-4-yl)-4-morpholinothieno[2,3-d]pyrimidine-6-carboxylic acid. 14 was coupled to propan-2-amine via General Procedure B. The product was purified via reverse phase HPLC to give 28.1 mg of 126. MS (Q1) 423.2 (M)+.

Example 53

N-(2,2,2-trifluoroethyl)-2-(1H-indazol-4-yl)-4-morpholinothieno[2,3-d]pyrimidine-6-carboxamide 127

45 mg of 2-(1H-indazol-4-yl)-4-morpholinothieno[2,3-d]pyrimidine-6-carboxylic acid 14 was coupled to 2,2,2-trifluoroethanamine via General Procedure B. The product was purified via reverse phase HPLC to give 15 mg of 127. MS (Q1) 463.1 (M)+.

Example 54

N-(2-hydroxyethyl)-2-(1H-indazol-4-yl)-4-morpholinothieno[2,3-d]pyrimidine-6-carboxamide 128

45 mg of 2-(1H-indazol-4-yl)-4-morpholinothieno[2,3-d]pyrimidine-6-carboxylic acid 14 was coupled to ethanolamine via General Procedure B. The product was purified via reverse phase HPLC to give 10.2 mg of 128. MS (Q1) 425.1 (M)+.

Example 55

N-ethyl-2-(1H-indazol-4-yl)-4-morpholinothieno[2,3-d]pyrimidine-6-carboxamide 129

45 mg of 2-(1H-indazol-4-yl)-4-morpholinothieno[2,3-d]pyrimidine-6-carboxylic acid 14 was coupled to ethylamine HCl via General Procedure B. The product was purified via reverse phase HPLC to give 31.8 mg of 129. MS (Q1) 409.2 (M)+.

Example 56

2-(1H-indazol-4-yl)-N,N-dimethyl-4-morpholinothieno[2,3-d]pyrimidine-6-carboxamide 130

45 mg of 2-(1H-indazol-4-yl)-4-morpholinothieno[2,3-d]pyrimidine-6-carboxylic acid 14 was coupled to dimethylamine HCl via General Procedure B. The product was purified via reverse phase HPLC to give 33 mg of 130. MS (Q1) 409.2 (M)+.

Example 57

2-(1H-indazol-4-yl)-N-methyl-4-morpholinothieno[2,3-d]pyrimidine-6-carboxamide 131

45 mg of 2-(1H-indazol-4-yl)-4-morpholinothieno[2,3-d]pyrimidine-6-carboxylic acid 14 was coupled to methylamine HCl via General Procedure B. The product was purified via reverse phase HPLC to give 36.4 mg of 131. MS (Q1) 395.2 (M)+.

Example 58

4-(2-(1H-indazol-4-yl)-4-morpholinothieno[3,2-d]pyrimidin-6-yl)-tetrahydro-2H-thiopyran-4-ol 132

250 mg of 2-chloro-4-morpholinothieno[3,2-d]pyrimidine 4 was used along with tetrahydrothiopyran-4-one following general procedure D to give the corresponding tertiary alcohol. The crude reaction mixture was triturated with acetonitrile to isolate 60 mg of tertiary alcohol that was used in a palladium catalyzed cross coupling reaction following general procedure A to give 35 mg of 132 after reversed phase HPLC purification. MS (Q1) 454 (M)+

Example 59

1-(2-(1H-indazol-4-yl)-4-morpholinothieno[3,2-d]pyrimidin-6-yl)cyclobutanol 133

250 mg of 2-chloro-4-morpholinothieno[3,2-d]pyrimidine 4 was used along with cyclobutanone following general procedure D to give the corresponding tertiary alcohol. 100 mg of the crude material was used in a palladium catalyzed cross coupling reaction following general procedure A to give 35 mg of 133 after reversed phase HPLC purification. MS (Q1) 408 (M)+

Example 60

6-chloro-2-(1H-indazol-4-yl)-4-morpholinothieno[3,2-d]pyrimidine 134

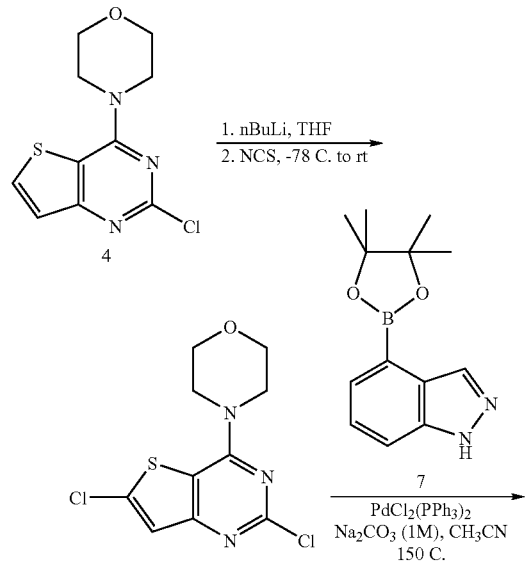

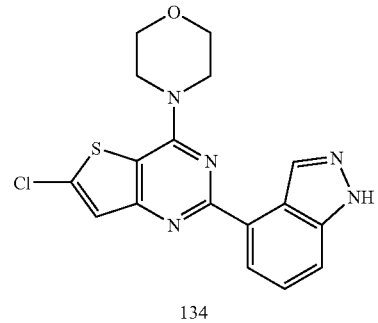

134 n-Butyllithium (1.6 mL, 3.914 mmol) in 2.5 M hexane solution was added to a mixture of 2-chloro-4-morpholinothieno[3,2-d]pyrimidine 4 (500 mg, 1.957 mmol) in 10 mL of THF at −78° C. The reaction mixture was allowed to warm to −40° C. and stirred for 40 min. A solution of N-chlorosuccinimide (523 mg, 3.914 mmol) in 8 mL of THF was added dropwise. After the addition was completed. The reaction mixture was brought to room temperature and stirred for 2 h. The reaction was monitored by LC/MS. The mixture was diluted with ether and extracted with 1N HCl (2×60 mL). The aqueous layer was then basified and extracted with ethyl acetate (2×100 mL). The organic layer was washed with $H_2O$ (60 mL), dried over $MgSO_4$, filtered and evaporated. The crude product was purified by ISCO Combiflash (5-50% ethyl acetate/hexane) to afford 2,6-dichloro-4-morpholinothieno[3,2-d]pyrimidine (284 mg, 50%).

40 mg of 2,6-dichloro-4-morpholinothieno[3,2-d]pyrimidine was coupled to 4-(4,4,5,5-tetramethyl-1,3,2-dioxaborolan-2-yl)-1H-indazole 7 via General Procedure A. The product was purified by reverse phase HPLC to yield 4.4 mg of 134. MS (Q1) 372 (M)+

Example 61

(R)-1-(3-(2-(1H-indazol-4-yl)-4-morpholinothieno[3,2-d]pyrimidin-6-yl)phenylsulfonyl)propan-2-ol 135

607 μL of R-(+) propylene oxide was added to a mixture of 2 g of 3-mercaptophenylboronic acid and aluminum oxide (~30 eq, neutral, activated, ~150 mesh) in diethyl ether at room temperature. The reaction was monitored by LC/MS until complete. The mixture was evaporated, and then added 1N HCl. The resulting mixture was extracted with ethyl acetate (3×150 mL). The combined organic layers were dried over $MgSO_4$, filtered and evaporated to give 3-((R)-2-hydroxypropylthio)phenylboronic acid (1.3, 70%). The crude product was directly used for next step reaction without purification.

100 mg of 2-chloro-6-iodo-4-morpholinothieno[3,2-d]pyrimidine 19 was coupled to 3-((R)-2-hydroxypropylthio)phenylboronic acid via General Procedure I to yield (R)-1-(3-(2-(H-indazol-4-yl)-4-morpholinothieno[3,2-d]pyrimidin-6-yl)phenylthio)propan-2-ol.

A solution of 322 mg of oxone in 4 mL $H_2O$ was added to a mixture of 132 mg of (R)-1-(3-(2-(1H-indazol-4-yl)-4-morpholinothieno[3,2-d]pyrimidin-6-yl)phenylthio)propan-2-ol in 8 mL of methanol. The reaction mixture was stirred for 2 h. The mixture was filtered and the filtrate was evaporated. The product was purified by reverse phase HPLC to yield 3.8 mg of 135. MS (Q1) 536 (M)+

Example 62

N-(3-(2-(1H-indazol-4-yl)-4-morpholinothieno[3,2-d]pyrimidin-6-yl)phenyl)-2-amino-2-methylpropanamide 136

3-(2-Chloro-4-morpholinothieno[3,2-d]pyrimidin-6-yl)benzenamine (50 mg) was reacted with Boc-2-aminoisobutric acid via General Procedure I to give tert-butyl(3-(2-chloro-4-morpholinothieno[3,2-d]pyrimidin-6-yl)phenylcarbamoyl)propan-2-ylcarbamate. 75 mg of the crude tert-butyl(3-(2-chloro-4-morpholinothieno[3,2-d]pyrimidin-6-yl)phenylcarbamoyl)propan-2-ylcarbamate was coupled to 4-(4,4,5,5-tetramethyl-1,3,2-dioxaborolan-2-yl)-1H-indazole 7 via General Procedure A to yield tert-butyl(3-(2-(1H-indazol-4-yl)-4-morpholinothieno[3,2-d]pyrimidin-6-yl)phenylcarbamoyl)propan-2-ylcarbamate.

Tert-butyl(3-(2-(1H-indazol-4-yl)-4-morpholinothieno[3,2-d]pyrimidin-6-yl)phenylcarbamoyl)propan-2-ylcarbamate (86 mg) was treated with 2 mL of trifluoroacetic acid/dichloromethane (1:1). Upon completion, the reaction mixture was evaporated. The product was purified by reverse phase HPLC to yield 18.8 mg of 136. MS (Q1) 514 (M)+

Example 63

N-(3-(2-(1H-indazol-4-yl)-4-morpholinothieno[3,2-d]pyrimidin-6-yl)phenyl)-2-aminoacetamide 137

3-(2-Chloro-4-morpholinothieno[3,2-d]pyrimidin-6-yl)benzenamine (50 mg) was reacted with Boc-glycine via General Procedure I to give tert-butyl(3-(2-chloro-4-morpholinothieno[3,2-d]pyrimidin-6-yl)phenylcarbamoyl)methylcarbamate. 70 mg of the crude tert-butyl (3-(2-chloro-4-morpholinothieno[3,2-d]pyrimidin-6-yl)phenylcarbamoyl)methylcarbamate was coupled to 4-(4,4,5,5-tetramethyl-1,3,2-dioxaborolan-2-yl)-1H-indazole 7 via General Procedure A to yield tert-butyl(3-(2-(1H-indazol-4-yl)-4-morpholinothieno[3,2-d]pyrimidin-6-yl)phenylcarbamoyl)methylcarbamate.

Tert-butyl(3-(2-(1H-indazol-4-yl)-4-morpholinothieno[3,2-d]pyrimidin-6-yl)phenylcarbamoyl)methylcarbamate (82 mg) was treated with 2 mL of trifluoroacetic acid/dichloromethane (1:1). Upon completion, the reaction mixture was evaporated. The product was purified by reverse phase HPLC to yield 13.9 mg of 137. MS (Q1) 486 (M)$^+$.

Example 64

(S)-1-(3-(2-(1H-indazol-4-yl)-4-morpholinothieno[3,2-d]pyrimidin-6-yl)phenylsulfonyl)propan-2-ol 138

S-(−) Propylene oxide (152 µL) was added to a mixture of 500 mg of 3-mercaptophenylboronic acid and aluminum oxide (~30 eq, neutral, activated, ~150 mesh) in diethyl ether at room temperature. The reaction was monitored by LC/MS until complete. The reaction mixture was evaporated, and then added 1N HCl. The resulting mixture was extracted with ethyl acetate (3×50 mL). The combined organic layers were dried over MgSO$_4$, filtered and evaporated to give 3-((S)-2-hydroxypropylthio)phenylboronic acid (414 mg, 90%). The crude product was directly used for next step reaction without purification.

50 mg of 2-chloro-6-iodo-4-morpholinothieno[3,2-d]pyrimidine 19 was coupled to 3-((S)-2-hydroxypropylthio)phenylboronic acid via General Procedure I to yield (S)-1-(3-(2-(1H-indazol-4-yl)-4-morpholinothieno[3,2-g]pyrimidin-6-yl)phenylthio)propan-2-ol.

A solution of 161 mg of oxone in 2 mL H$_2$O was added to a mixture of 66 mg of (S)-1-(3-(2-(1H-indazol-4-yl)-4-morpholinothieno[3,2-d]pyrimidin-6-yl)phenylthio)propan-2-ol in 4 mL of methanol. The reaction mixture was stirred for 1 h. The mixture was filtered and the filtrate was evaporated. The product was purified by reverse phase HPLC to yield 3 mg of 138. MS (Q1) 536 (M)+

Example 65

N-(3-(2-(1H-indazol-4-yl)-4-morpholinothieno[3,2-d]pyrimidin-6-yl)phenyl)-2-hydroxyacetamide 139

3-(2-Chloro-4-morpholinothieno[3,2-d]pyrimidin-6-yl)benzenamine (40 mg) was reacted with glycolic acid via General Procedure I to give N-(3-(2-chloro-4-morpholinothieno[3,2-d]pyrimidin-6-yl)phenyl)-2-hydroxyacetamine. 47 mg of the crude N-(3-(2-chloro-4-morpholinothieno[3,2-d]pyrimidin-6-yl)phenyl)-2-hydroxyacetamine was coupled to 4-(4,4,5,5-tetramethyl-1,3,2-dioxaborolan-2-yl)-1H-indazole 7 via General Procedure A. The product was purified by reverse phase HPLC to yield 3 mg of 139. MS (Q1) 487 (M)$^+$.

Example 66

2-(2-(1H-indazol-4-yl)-4-morpholinothieno[2,3-d]pyrimidin-6-yl)propan-2-ol 140

100 mg of 2-chloro-4-morpholinothieno[2,3-d]pyrimidine in 2 mL of THF was cooled to −78° C. before adding 1.3 eq of 2.5 M nBuLi in hexanes solution. The solution was stirred at −78° C. for 30 minutes before warming to −40° C. and adding 10 eq of acetone. The reaction was stirred at −40° C. for 30 minutes then slowly allowed to warm to 0° C. before quenching with water. The THF was evaporated and the water was extracted with Ethyl Acetate. The organic layer was dried with MgSO$_4$, filtered and evaporated. The crude chloride was subjected to Procedure A to give 76 mg of 140. MS (Q1) 396.2 (M)+.

Example 67

2-(1H-indazol-4-yl)-4-morpholinothieno[2,3-d]pyrimidine-6-carboxylic acid 141 (14)

2-Chloro-4-morpholinothieno[2,3-d]pyrimidine (500 mg) was cooled to −78° C. in 50 mL of THF before adding 1.3 eq of a 2.5M solution of nBuLi in hexanes. The reaction was stirred at −78° C. for 30 minutes before warming to −40° C. for several minutes to allow for complete formation of the lithium anion. The reaction was then re-cooled to −78° C. and carbon dioxide gas evolved from dry ice was bubbled in via cannula to the reaction solution for 1 hour. The reaction was then slowly warmed to 0° C. over 30 minutes and the THF was concentrated by rotovap. The reaction was then quenched with water and extracted with Ethyl Acetate to remove any 2-chloro-4-morpholinothieno[2,3-d]pyrimidine. The aqueous layer was then brought to pH of 2-3 by adding concentrated HCl. The resultant solid that crashed out of the aqueous layer was then collected by Buchner funnel, rinsed with water and dried overnight under vacuum to yield 494 mg of 2-chloro-4-morpholinothieno[2,3-d]pyrimidine-6-carboxylic acid.

2-Chloro-4-morpholinothieno[2,3-d]pyrimidine-6-carboxylic acid (444 mg) was reacted with 7 via General Procedure A. Upon extraction into Ethyl Acetate, the product remained in the aqueous layer and was treated with 20 eq of Amberlite IR-120 ion-exchange resin for 2 hours or until the solution became cloudy. The solution was first filtered thru a coarse filter flask to remove the resin and was then filtered thru a Buchner funnel to collect the 476 mg of 2-(1H-indazol-4-yl)-4-morpholinothieno[2,3-d]pyrimidine-6-carboxylic acid as a light brown solid. 25 mg of this product was then purified via reverse phase HPLC to give 12.8 mg of 141 (14). MS (Q1) 382.1 (M)+.

Example 68

2-(1H-indazol-4-yl)-4-morpholinothieno[3,2-d]pyrimidine-6-carboxamide 142

2-Chloro-4-morpholinothieno[3,2-d]pyrimidine-6-carboxylic acid (100 mg) was coupled to ammonium chloride via General Procedure B. The reaction mixture dissolved in Ethyl acetate and extracted with saturated ammonium chloride solution. The organic layer was concentrated to dryness and subjected to Procedure A to give 16 mg of 142. MS (Q1) 381.1 (M)+.

Example 69

6-((3-methoxypropylsulfonyl)methyl)-2-(1H-indazol-4-yl)-4-morpholinothieno[3,2-d]pyrimidine 143

To a mixture of (2-chloro-4-morpholin-4-yl-thieno[3,2-d]pyrimidin-6-yl)-methanol (500 mg) and triethylamine (0.5 mL) in dichloromethane (20 mL) at 0° C. was added methanesulfonyl chloride (0.27 mL). The reaction mixture was stirred at room temperature for 16 h and then quenched with water (20 mL) and extracted into dichloromethane (2×20 mL). The combined organics were washed with aqueous brine solution (2×20 mL), dried ($MgSO_4$) and concentrated to give methanesulfonic acid 2-methyl-4-morpholin-4-yl-thieno[3,2-d]pyrimidin-6-ylmethyl ester as a yellow solid (523 mg).

To a solution of methanesulfonic acid 2-methyl-4-morpholin-4-yl-thieno[3,2-d]pyrimidin-6-ylmethyl ester (300 mg) in DMF (8 mL) was added potassium thioacetate (113 mg). The reaction was stirred at 60° C. for 16 h and then allowed to cool to room temperature. The reaction mixture was then quenched with water (20 mL) and extracted into ethyl acetate (2×20 mL). The combined organics were washed with aqueous brine solution (3×20 mL), dried ($MgSO_4$), concentrated and purified using column chromatography to give thioacetic acid S-(2-methyl-4-morpholin-4-yl-thieno[3,2-d]pyrimidin-6-ylmethyl) ester as an off-white solid (210 mg).

To a solution of thioacetic acid S-(2-methyl-4-morpholin-4-yl-thieno[3,2-d]pyrimidin-6-ylmethyl) ester (200 mg) in methanol (10 mL) at 0° C. was added a solution of sodium methoxide (35 mg) in methanol (2 mL). The reaction mixture was stirred at 0° C. for 30 min and then a solution of toluene-4-sulfonic acid 3-methoxy-propyl ester (156 mg) in methanol (3 mL) was added dropwise. The reaction mixture was stirred at room temperature for 16 h and then quenched with water (20 mL) and extracted into ethyl acetate (2×20 mL). The combined organics were washed with aqueous brine solution (2×20 mL), dried ($MgSO_4$), concentrated and purified using column chromatography to give 6-(3-methoxy-propylsulfanylmethyl)-2-methyl-4-morpholin-4-yl-thieno[3,2-d]pyrimidine as a white solid (170 mg).

To a solution of 6-(3-methoxy-propylsulfanylmethyl)-2-methyl-4-morpholin-4-yl-thieno[3,2-d]pyrimidine (170 mg) in dichloromethane (10 mL) at 0° C. was added m-chloroperoxybenzoic acid (224 mg) portionwise. The reaction mixture was stirred at room temperature for 16 h and then quenched with aqueous sodium thiosulfate solution (20 mL) and extracted into dichloromethane (2×20 mL). The combined organics were washed with saturated aqueous sodium hydrogencarbonate solution (2×20 mL) and aqueous brine solution (2×20 mL), dried ($MgSO_4$) and concentrated to give 6-(3-methoxy-propane-1-sulfonylmethyl)-2-methyl-4-morpholin-4-yl-thieno[3,2-d]pyrimidine as a white solid (190 mg).

Suzuki coupling with 6-(3-methoxy-propane-1-sulfonylmethyl)-2-methyl-4-morpholin-4-yl-thieno[3,2-d]pyrimidine (190 mg) was carried out using the standard method. Purification using column chromatography gave 143 as a white solid (54 mg). NMR: DMSO: 1.92-2.00 (2 H, m, $CH_2$), 2.18-2.24 (2 H, m, $CH_2$), 3.22 (3 H, s, Me), 3.42 (2 H, t, J 7.22, $CH_2$), 3.79-3.84 (4 H, m, $CH_2$), 3.98-4.02 (4 H, m, $CH_2$), 5.05 (2 H, s, $CH_2$), 7.44 (1 H, t, J 8.0, Ar), 7.60 (1 H, s, Ar), 7.62 (1 H, d, J 8.15, Ar), 8.21 (1 H, d, J 7.35, Ar), 8.85 (1 H, s, Ar) and 13.15 (1 H, s, NH). MS: (ESI+): MH+ 488.14

Example 70

2-(1H-indazol-4-yl)-4-morpholino-6-(2-(4-methylsulfonylpiperazin-1-yl)ethyl)thieno[3,2-d]pyrimidine 144

To a suspension of methoxymethyl triphenylphosphonium chloride (7.24 g) in THF (100 mL) at 0° C. was added n-butyllithium (6.76 mL of a 2.M solution in hexanes). The reaction mixture was stirred at 0° C. for 1 h and then a suspension of 2-chloro-4-morpholin-4-yl-thieno[3,2-d]pyrimidine-6-carbaldehyde 10 (2 g) in THF (30 mL) was added dropwise. The reaction mixture was stirred at room temperature for 16 h and then quenched with water (80 mL) and extracted with ethyl acetate (2×80 mL). The combined organics were washed with aqueous brine solution (2×80 mL), dried ($MgSO_4$), concentrated and purified using column chromatography to give 2-chloro-6-(2-methoxy-vinyl)-4-morpholin-4-yl-thieno[3,2-d]pyrimidine (mixture of cis/trans isomers) as a yellow solid (2.24 g).

To a solution of 2-chloro-6-(2-methoxy-vinyl)-4-morpholin-4-yl-thieno[3,2-d]pyrimidine (1.05 g) in THF (30 mL) was added 4 N aqueous hydrogen chloride solution (15 mL). The reaction mixture was stirred at 50° C. for 16 h and then allowed to cool to room temperature. The reaction mixture was diluted with water (30 mL) and extracted into ethyl acetate (3×30 mL). The combined organics were dried ($MgSO_4$) and concentrated to give a crude mixture containing (2-chloro-4-morpholin-4-yl-thieno[3,2-d]pyrimidin-6-yl) acetaldehyde.

To a solution of crude (2-chloro-4-morpholin-4-yl-thieno[3,2-d]pyrimidin-6-yl)-acetaldehyde (300 mg) and 1-methanesulfonyl-piperazine (243 mg) in 1,2-dichloroethane (10 mL) at room temperature was added trimethylorthoformate (0.33 mL). The reaction mixture was stirred at room temperature for 1 h and then sodium triacetoxyborohydride (534 mg) was added. The reaction mixture was stirred at room temperature for 16 h and then quenched with saturated aqueous sodium carbonate solution (20 mL) and extracted into dichloromethane (2×20 mL). The combined organics were washed with aqueous brine solution (2×20 mL), dried ($MgSO_4$), concentrated and purified using column chromatography to give 2-chloro-6-[2-(4-methanesulfonyl-piperazin-1-yl)-ethyl]-4-morpholin-4-yl-thieno[3,2-d]pyrimidine as a white solid (100 mg).

Suzuki coupling with 2-chloro-6-[2-(4-methanesulfonyl-piperazin-1-yl)-ethyl]-4-morpholin-4-yl-thieno[3,2-d]pyrimidine (100 mg) was carried out using the standard method. Purification using column chromatography gave 144 as a white solid (24 mg). NMR: CDCl$_3$: 2.54-2.62 (4 H, m, CH$_2$), 2.71 (3 H, s, Me), 2.72-2.80 (2 H, m, CH$_2$), 3.02-3.11 (2 H, m, CH$_2$), 3.20-3.28 (4 H, m, CH$_2$), 3.79-3.84 (4 H, m, CH$_2$), 3.98-4.02 (4 H, m, CH$_2$), 7.40 (1 H, s, Ar), 7.44 (1 H, t, J 8.0, Ar), 7.62 (1 H, d, J 8.15, Ar), 8.21 (1 H, d, J 7.35, Ar) and 8.90 (1 H, s, Ar). MS: (ESI+): MH+ 528.24

Example 71

3-(2-(1H-indazol-4-yl)-4-morpholinothieno[3,2-d] pyrimidin-6-yl)-N-methylpropanamide 145

Following the procedures of Example 67b, and using methylamine, 145 was prepared. NMR: DMSO: 2.52-2.60 (2 H, m, CH$_2$), 2.61 (3 H, s, Me), 3.18 (2 H, t, J 7.22, CH$_2$), 3.79-3.84 (4 H, m, CH$_2$), 3.98-4.02 (4 H, m, CH$_2$), 7.30 (1 H, s, Ar), 7.41 (1 H, t, J 8.0, Ar), 7.62 (1 H, d, J 8.15, Ar), 7.81-7.84 (1 H, m, NH), 8.21 (1 H, d, J 7.35, Ar), 8.85 (1 H, s, Ar) and 13.15 (1 H, s, NH). MS: (ESI+): MH+ 423.18

Example 72

2-(1H-indazol-4-yl)-6-((methylsulfonyl)methyl)-4-morpholinothieno[3,2-d]pyrimidine 146

Following the procedures of Example 67aa, and using methyl iodide, 146 was prepared. NMR: DMSO: 3.06 (3 H, s, Me), 3.79-3.84 (4 H, m, CH$_2$), 3.98-4.02 (4 H, m, CH$_2$), 5.02 (2 H, s, Me), 7.40 (1 H, s, Ar), 7.44 (1 H, t, J 8.0, Ar), 7.62 (1 H, d, J 8.15, Ar), 8.21 (1 H, d, J 7.35, Ar), 8.85 (1 H, s, Ar) and 13.15 (1 H, s, NH). MS: (ESI+): MH+ 430.10

Example 73

3-(2-(1H-indazol-4-yl)-4-morpholinothieno[3,2-d] pyrimidin-6-yl)propanamide 147

Following the procedures of Example 67b, and using Ammonium acetate, 147 was prepared. NMR: DMSO: 2.54 (2 H, t, J 7.27, CH$_2$), 3.16 (2 H, t, J 7.22, CH$_2$), 3.79-3.84 (4 H, m, CH$_2$), 3.98-4.02 (4 H, m, CH$_2$), 7.40 (1 H, s, Ar), 7.44 (1 H, t, J 8.0, Ar), 7.62 (1 H, d, J 8.15, Ar), 8.21 (H, d, J 7.35, Ar), 8.85 (1 H, s, Ar) and 13.15 (1 H, s, NH). MS: (ESI+): MH+ 409.15

Example 74

3-(2-(1H-indazol-4-yl)-4-morpholinothieno[3,2-d] pyrimidin-6-yl)-N,N-dimethylpropanamide 148

To solution of triethylphosphonoacetate (2.1 mL) in THF (50 mL) at 0° C. was added sodium hydride (254 mg). The mixture was stirred at 0° C. for 1 h and then 2-chloro-4-morpholin-4-yl-thieno[3,2-d]pyrimidine-6-carbaldehyde 10 (1.5 g) was added. The reaction mixture was stirred at 50° C. for 16 h and then allowed to cool to room temperature. The reaction was quenched by addition of water (50 mL) and then filtered to give 3-(2-chloro-4-morpholin-4-yl-thieno[3,2-d]pyrimidin-6-yl)-acrylic acid ethyl ester as a yellow solid (1.64 g).
To as solution of 3-(2-chloro-4-morpholin-4-yl-thieno[3,2-d]pyrimidin-6-yl)-acrylic acid ethyl ester (2 g) in ethyl acetate (100 mL) was added a suspension of Pd/C (200 mg) in ethanol (10 mL). The flask was flushed with nitrogen and then a hydrogen balloon was fitted. The reaction mixture was stirred at room temperature for 16 h. The mixture was then filtered through Celite and the filtrate concentrated to give 3-(2-chloro-4-morpholin-4-yl-thieno[3,2-d]pyrimidin-6-yl) propionic acid ethyl ester as a yellow solid (1.83 g).
To a mixture of 3-(2-chloro-4-morpholin-4-yl-thieno[3,2-d]pyrimidin-6-yl)propionic acid ethyl ester (1 g) in methanol (30 mL) was added 1 N aqueous sodium hydroxide solution (10 mL). The reaction mixture was stirred at room temperature for 1 h and then acidified to pH 6 using 2 M aqueous hydrochloric acid. The product was then filtered and washed with water to give 3-(2-chloro-4-morpholin-4-yl-thieno[3,2-d]pyrimidin-6-yl)-propionic acid as a greenish-yellow solid (612 mg).
A mixture of 3-(2-chloro-4-morpholin-4-yl-thieno[3,2-d]pyrimidin-6-yl)-propionic acid (200 mg), 4-(4,4,5,5-tetramethyl-[1,3,2]dioxaborolan-2-yl)-1H-indazole (209 mg), 1 M aqueous sodium carbonate solution (1.83 mL) and PdCl$_2$(PPh$_3$)$_2$ (22 mg) in acetonitrile (3 mL) was reacted in the microwave at 140° C. for 15 min. The reaction mixture was then poured into a mixture of ethyl acetate (20 mL) and water (20 mL). The aqueous layer was collected and carefully acidified to pH 6 using 2 M aqueous hydrochloric acid. The product was then filtered and washed with water to give 3-[2-(1H-indazol-4-yl-4-morpholin-4-yl-thieno[3,2-d]pyrimidin-6-yl]-propionic acid as a grey solid (145 mg).
To a solution of 3-[2-(1H-indazol-4-yl-4-morpholin-4-yl-thieno[3,2-d]pyrimidin-6-yl]-propionic acid (145 mg) in DMF (5 mL) at room temperature was added carbonyldiimidazole (115 mg). The reaction mixture was then stirred at room temperature for 1 h. Then, triethylamine (0.15 mL) and dimethylamine hydrochloride (58 mg) were added and the solution was stirred at room temperature for 16 h. The reaction was then quenched with water (20 mL) and extracted into ethyl acetate (2×20 mL). The combined organics were washed with aqueous brine solution (3×20 mL), dried (MgSO$_4$), concentrated and purified using column chromatography to give 148 as a white solid (96 mg). NMR: DMSO: 2.68-2.84 (2 H, m, CH$_2$), 2.86 (3 H, s, Me), 3.02 (3 H, s, Me), 3.18 (2 H, t, J 7.22, CH$_2$), 3.79-3.84 (4 H, m, CH$_2$), 3.98-4.02 (4 H, m, CH$_2$), 7.40 (1 H, s, Ar), 7.44 (1 H, t, J 8.0, Ar), 7.62 (1 H, d, J 8.15, Ar), 8.21 (1 H, d, J 7.35, Ar), 8.85 (1 H, s, Ar) and 13.15 (1 H, s, NH). MS: (ESI+): MH+ 437.22

Example 75

3-(2-(1H-indazol-4-yl)-4-morpholinothieno[2,3-d] pyrimidin-6-yl)-1-(4-methylsulfonylpiperazin-1-yl) propanone 149

Following the procedures of Example 67b, and using 1-methanesulfonyl-piperazine, 149 was prepared. NMR: DMSO: 2.86 (3 H, s, Me), 2.88-2.92 (2 H, m, CH$_2$), 3.05-3.15 (4 H, m, CH$_2$), 3.20 (2 H, t, J 7.22, CH$_2$), 3.58-3.63 (4 H, m, CH$_2$), 3.79-3.84 (4 H, m, CH$_2$), 3.98-4.02 (4 H, m, CH$_2$), 7.40 (1 H, s, Ar), 7.44 (1 H, t, J 8.0, Ar), 7.62 (1 H, d, J 8.15, Ar), 8.21 (1 H, d, J 7.35, Ar), 8.85 (1 H, s, Ar) and 13.15 (1 H, s, NH). MS: (ESI+): MH+ 556.26

Example 76

2-(1H-indazol-4-yl)-4-morpholino-N-phenylthieno [3,2-d]pyrimidin-6-amine 150

Prepared according to the General Procedure J to give 150 (10% over 2 steps). MS (Q1) 429 (M)+

247

Example 77

3-(2-(1H-indazol-4-yl)-4-morpholinothieno[3,2-d]pyrimidin-6-yl)benzenmethylsulfonamide 151

50 mg of 2-chloro-6-iodo-4-morpholinothieno[3,2-d]pyrimidine 19 was coupled to 3-methylsulfonylaminophenylboronic acid via General Procedure I. The product was purified by reverse phase HPLC to yield 37.4 mg of 151. MS (Q1) 507 $(M)^+$.

Example 78

N-(3-(2-(1H-indazol-4-yl)-4-morpholinothieno[3,2-d]pyrimidin-6-yl)phenyl)-2-(dimethylamino)acetamide 152

55 mg of 3-(2-chloro-4-morpholinothieno[3,2-d]pyrimidin-6-yl)benzenamine was reacted with N,N-dimethylglycine via General Procedure I to give N-(3-(2-chloro-4-morpholinothieno[3,2-d]pyrimidin-6-yl)phenyl)-2-(dimethylamino)acetamide. 70 mg of the crude N-(3-(2-chloro-4-morpholinothieno[3,2-d]pyrimidin-6-yl)phenyl)-2-(dimethylamino)acetamide was coupled to 4-(4,4,5,5-tetramethyl-1,3,2-dioxaborolan-2-yl)-1H-indazole 7 via General Procedure A. The product was purified by reverse phase HPLC to yield 3 mg of 152. MS (Q1) 514 $(M)^+$.

Example 79

2-(1H-indazol-4-yl)-6-(3-methoxypyridin-4-yl)-4-morpholinothieno[3,2-d]pyrimidine 153

50 mg of 2-chloro-6-iodo-4-morpholinothieno[3,2-d]pyrimidine 19 was coupled to 2-methoxypyridine-3-boronic acid via General Procedure I. The product was purified by reverse phase HPLC to yield 7.2 mg of 153. MS (Q1) 445 $(M)^+$.

Example 80

3-(2-(1H-indazol-4-yl)-4-morpholinothieno[3,2-d]pyrimidin-6-yl)pentan-3-ol 154

225 mg of 2-chloro-4-morpholinothieno[3,2-d]pyrimidine 4 was used along with 3-propanone following general procedure D to give the corresponding tertiary alcohol. 100 mg of the crude material was used in a palladium catalyzed cross coupling reaction following general procedure A to give 45 mg of 154 after reversed phase HPLC purification. MS (Q1) 424 (M)+

Example 81

6-(6-fluoropyridin-3-yl)-2-(1H-indazol-4-yl)-4-morpholinothieno[3,2-d]pyrimidine 155

50 mg of 2-chloro-6-iodo-4-morpholinothieno[3,2-d]pyrimidine 19 was coupled to 2-fluoropyridine-5-boronic acid via General Procedure I. The product was purified by reverse phase HPLC to yield 4.7 mg of 155. MS (Q1) 433 $(M)^+$.

248

Example 82

6-(2-fluoropyridin-3-yl)-2-(1H-indazol-4-yl)-4-morpholinothieno[3,2-d]pyrimidine 156

50 mg of 2-chloro-6-iodo-4-morpholinothieno[3,2-d]pyrimidine 19 was coupled to 2-fluoropyridine-3-boronic acid via General Procedure I. The product was purified by reverse phase HPLC to yield 7.3 mg of 156. MS (Q1) 433 $(M)^+$.

Example 83

2-(1H-indazol-4-yl)-6-(4-methoxypyridin-3-yl)-4-morpholinothieno[3,2-d]pyrimidine 157

50 mg of 2-chloro-6-iodo-4-morpholinothieno[3,2-d]pyrimidine 19 was coupled to 4-methoxypyridine-3-boronic acid via General Procedure I. The product was purified by reverse phase HPLC to yield 19.1 mg of 157. MS (Q1) 445 $(M)^+$.

Example 84

3-(2-(1H-indazol-4-yl)-4-morpholinothieno[3,2-d]pyrimidin-6-yl)benzenamine 158

2-Chloro-6-iodo-4-morpholinothieno[3,2-d]pyrimidine 19 (50 mg) was coupled to 3-aminophenylboronic acid via General Procedure I. The product was purified by reverse phase HPLC to yield 14.9 mg of 158. MS (Q1) 429 $(M)^+$.

Example 85

2-(2-(1H-indazol-4-yl)-4-morpholinothieno[3,2-d]pyrimidin-6-yl)benzamide 159

2-Chloro-6-iodo-4-morpholinothieno[3,2-d]pyrimidine 19 (50 mg) was coupled to 2-(aminocarbonylphenyl)boronic acid via General Procedure I. The product was purified by reverse phase HPLC to yield 9.2 mg of 159. MS (Q1) 457 $(M)^+$.

Example 86

N-(2-(2-(1H-indazol-4-yl)-4-morpholinothieno[3,2-d]pyrimidin-6-yl)phenyl)acetamide 160

2-Chloro-6-iodo-4-morpholinothieno[3,2-d]pyrimidine 19 (50 mg) was coupled to 2-(acetylaminophenyl)boronic acid via General Procedure I. The product was purified by reverse phase HPLC to yield 22.9 mg of 160. MS (Q1) 471 $(M)^+$.

Example 87

3-(2-(1H-indazol-4-yl)-4-morpholinothieno[3,2-d]pyrimidin-6-yl)benzamide 161

2-Chloro-6-iodo-4-morpholinothieno[3,2-d]pyrimidine 19 (50 mg) was coupled to 3-aminocarbonylphenylboronic acid via General Procedure I. The product was purified by reverse phase HPLC to yield 3.9 mg of 161. MS (Q1) 457 $(M)^+$.

Example 88

N-(2-(1H-indazol-4-yl)-4-morpholinothieno[3,2-d]pyrimidin-6-yl)propionamide 162

Tert-butyl 2-chloro-4-morpholinothieno[3,2-d]pyrimidin-6-ylcarbamate (800 mg) was treated with 5 mL of trifluoroacetic acid/dichloromethane (1:1). The reaction mixture was stirred at room temperature until complete. The reaction mixture was evaporated. The residue was diluted with ethyl acetate (100 mL), washed with saturated sodium bicarbonate (50 mL) and brine (50 mL). The aqueous layer was back-extracted with ethyl acetate (2×60 mL), and then washed with saturated sodium bicarbonate and brine. The combined organic layers were dried over $MgSO_4$, filtered and evaporated to afford 580 mg of 2-chloro-4-morpholinothieno[3,2-d]pyrimidin-6-amine.

2-Chloro-4-morpholinothieno[3,2-d]pyrimidin-6-amine (35 mg) was reacted with 23 μL of propionyl chloride via General Procedure G to give N-(2-chloro-4-morpholinothieno[3,2-d]pyrimidin-6-yl)propionamide.

The crude N-(2-chloro-4-morpholinothieno[3,2-d]pyrimidin-6-yl)propionamide (42 mg) was coupled to 4-(4,4,5,5-tetramethyl-1,3,2-dioxaborolan-2-yl)-1H-indazole 7 via General Procedure A. The product was purified by reverse phase HPLC to yield 19.8 mg of 162. MS (Q1) 409 $(M)^+$

Example 89

N-(2-(1H-indazol-4-yl)-4-morpholinothieno[3,2-d]pyrimidin-6-yl)acetamide 163

2-Chloro-4-morpholinothieno[3,2-d]pyrimidin-6-amine (40 mg) was reacted with 21 μL of acetyl chloride via General Procedure G to give N-(2-chloro-4-morpholinothieno[3,2-d]pyrimidin-6-yl)acetamide.

The crude N-(2-chloro-4-morpholinothieno[3,2-d]pyrimidin-6-yl)acetamide (46 mg) was coupled to 4-(4,4,5,5-tetramethyl-1,3,2-dioxaborolan-2-yl)-1H-indazole 7 via General Procedure A. The product was purified by reverse phase HPLC to yield 24.2 mg of 163. MS (Q1) 395 $(M)^+$

Example 90

N-(2-(1H-indazol-4-yl)-4-morpholinothieno[3,2-d]pyrimidin-6-yl)isobutyramide 164

2-Chloro-4-morpholinothieno[3,2-d]pyrimidin-6-amine (35 mg) was reacted with 27 μL of isobutyryl chloride via General Procedure G to give N-(2-chloro-4-morpholinothieno[3,2-d]pyrimidin-6-yl)isobutyramide.

The crude N-(2-chloro-4-morpholinothieno[3,2-d]pyrimidin-6-yl)isobutyramide (45 mg) was coupled to 4-(4,4,5,5-tetramethyl-1,3,2-dioxaborolan-2-yl)-1H-indazole 7 via General Procedure A. The product was purified by reverse phase HPLC to yield 1.9 mg of 164. MS (Q1) 423 $(M)^+$

Example 91

N-(2-(1H-indazol-4-yl)-4-morpholinothieno[3,2-d]pyrimidin-6-yl)benzamide 165

2-Chloro-4-morpholinothieno[3,2-d]pyrimidin-6-amine (35 mg) was reacted with 30 μL of benzoyl chloride via General Procedure G to give N-(2-chloro-4-morpholinothieno[3,2-d]pyrimidin-6-yl)benzamide.

Crude N-(2-chloro-4-morpholinothieno[3,2-d]pyrimidin-6-yl)benzamide (49 mg) was coupled to 4-(4,4,5,5-tetramethyl-1,3,2-dioxaborolan-2-yl)-1H-indazole 7 via General Procedure A. The product was purified by reverse phase HPLC to yield 8.2 mg of 165. MS (Q1) 457 $(M)^+$

Example 92

3-(1H-indazol-4-yl)-4-morpholino-6-(2-(4-methylsulfonylpiperazin-1-yl)propyl)thieno[3,2-d]pyrimidine 166

A mixture of 2-(1H-indazol-4-yl)-6-[3-(4-methanesulfonyl-piperazin-1-yl)-prop-1-ynyl]-4-morpholin-4-yl-thieno[3,2-d]pyrimidine and 10% Pd/C was stirred overnight under an atmosphere of hydrogen in methanol and dichloromethane. Purification using flash chromatography yielded 166. (CDCl3): 2.78-2.82 (4H, m), 2.82 (3H, s), 3.34-3.39 (4H, m), 3.70 (2H, s), 3.92-3.96 (4H, m), 4.07-4.11 (4H, m), 7.52 (1H, dd), 7.61-7.65 (2H, m), 8.30 (1H, d, J=7.2), 9.02 (1H, s), 10.10 (1H, br). ESI+: MH+ 538

Example 93

(2-(1H-indazol-4-yl)-4-morpholinothieno[3,2-d]pyrimidin-6-yl)(4-(methylacetamido)piperidin-1-yl)methanone 167

2-(1H-Indazol-4-yl)-4-morpholinothieno[3,2-d]pyrimidine-6-carboxylic acid 13 (45 mg) was coupled to N-methylpiperidine-4-carboxamide via General Procedure B. The product was purified via reverse phase HPLC to give 26.3 mg of 167. MS (Q1) 506.2 (M)+.

Example 94

(2-(1H-indazol-4-yl)-4-morpholinothieno[3,2-d]pyrimidin-6-yl)(3-(methylsulfonyl)pyrrolidin-1-yl)methanone 168

2-(1H-Indazol-4-yl)-4-morpholinothieno[3,2-d]pyrimidine-6-carboxylic acid 13 (45 mg) was coupled to 3-(methylsulfonyl)pyrrolidine via General Procedure B. The product was purified via reverse phase HPLC to give 26.1 mg of 168. MS (Q1) 513.1 (M)+.

Example 95

2-(1H-indazol-4-yl)-N-(2-(methylsulfonyl)ethyl)-4-morpholinothieno[3,2-d]pyrimidine-6-carboxamide 169

2-(1H-Indazol-4-yl)-4-morpholinothieno[3,2-d]pyrimidine-6-carboxylic acid 13 (45 mg) was coupled to 2-(methylsulfonyl)ethanamine via General Procedure B. The product was purified via reverse phase HPLC to give 26.8 mg of 169. MS (Q1) 487.1 (M)+.

Example 96

N-ethyl-2-(1H-indazol-4-yl)-4-morpholinothieno[3,2-d]pyrimidine-6-carboxamide 170

2-(1H-Indazol-4-yl)-4-morpholinothieno[3,2-d]pyrimidine-6-carboxylic acid 13 (45 mg) was coupled to ethylamine HCl via General Procedure B. The product was purified via reverse phase HPLC to give 10.6 mg of 170. MS (Q1) 409.2 (M)+.

Example 97

2-(1H-indazol-4-yl)-N-methyl-4-morpholinothieno [3,2-d]pyrimidine-6-carboxamide 171

2-(1H-Indazol-4-yl)-4-morpholinothieno[3,2-d]pyrimidine-6-carboxylic acid 13 (75 mg) was coupled to methylamine HCl via General Procedure B. The product was purified via reverse phase HPLC to give 38.8 mg of 171. MS (Q1) 395.1 (M)+.

Example 98

N-(2-(1H-indazol-4-yl)-4-morpholinothieno[3,2-d] pyrimidin-6-yl)cyclopropanecarboxamide 172

2-Chloro-4-morpholinothieno[3,2-d]pyrimidin-6-amine (40 mg) was reacted with 27 µL of cyclopropanecarbonyl chloride via General Procedure G to give N-(2-chloro-4-morpholinothieno[3,2-d]pyrimidin-6-yl)cyclopropanecarboxamide.

Crude N-(2-chloro-4-morpholinothieno[3,2-d]pyrimidin-6-yl)cyclopropanecarboxamide (50 mg) was coupled to 4-(4,4,5,5-tetramethyl-1,3,2-dioxaborolan-2-yl)-1H-indazole 7 via General Procedure A. The product was purified by reverse phase HPLC to yield 12.1 mg of 172. MS (Q1) 421 (M)+

Example 99

N-(2-(1H-indazol-4-yl)-4-morpholinothieno[3,2-d] pyrimidin-6-yl)-3,3-dimethylbutanamide 173

2-Chloro-4-morpholinothieno[3,2-d]pyrimidin-6-amine (40 mg) was reacted with 41 µL of tert-butylacetyl chloride via General Procedure G to give N-(2-chloro-4-morpholinothieno[3,2-d]pyrimidin-6-yl)-3,3-dimethylbutanamide.

Crude N-(2-chloro-4-morpholinothieno[3,2-d]pyrimidin-6-yl)-3,3-dimethylbutanamide (55 mg) was coupled to 4-(4,4,5,5-tetramethyl-1,3,2-dioxaborolan-2-yl)-1H-indazole 7 via General Procedure A. The product was purified by reverse phase HPLC to yield 16.9 mg of 173. MS (Q1) 451 (M)+

Example 100

2-(2-methyl-1H-benzo[d]imidazol-1-yl)-4-morpholinothieno[3,2-d]pyrimidine 174

A mixture of 2-chloro-4-morpholin-4-yl-thieno[3,2-d]pyrimidine 4 (155 mg) and 2-methylbenzimidazole (161 mg) were heated together at 135° C. overnight. The mixture was then cooled, diluted with water and extracted with ethyl acetate. Combined extracts were dried ($Na_2SO_4$), filtered and concentrated. Flash chromatography followed by trituration gave 174 (28%). NMR: ($CDCl_3$): 2.95 (s, 3H, $CH_3$), 3.89-3.91 (m, 4H, $2×CH_2$), 4.07-4.09 (m, 4H, $2×CH_2$), 7.25-7.28 (m, 2H, 2×ArH), 7.50 (d, H, ArH, J=5.47 Hz), 7.71 (m, H, ArH), 7.85 (d, H, ArH, J=5.48 Hz), 8.09 (m, H, ArH). MS: (ESI+): MH+=352.13

Example 101

2-(1H-indazol-4-yl)-6-(3-(4-methylpiperazin-1-yl) prop-1-ynyl)-4-morpholinothieno[3,2-d]pyrimidine 175

A mixture of 2-chloro-6-iodo-4-morpholin-4-yl-thieno[3,2-d]pyrimidine 19, prepared according to Example 12, (1.57 g), propargyl alcohol (288 µL), copper iodide (39 mg), bis (triphenylphosphine)palladium(II) chloride (146 mg), triethylamine (25 ml), and tetrahydrofuran (30 ml) were stirred under nitrogen for 10 days. The reaction mixture was then partitioned between chloroform and brine, the combined organics were then dried ($MgSO_4$). The solvents were removed in vacuo. The crude product was then purified using flash chromatography to yield 3-(2-chloro-4-morpholin-4-yl-thieno[3,2-d]pyrimidin-6-yl)-prop-2-yn-1-ol (1.2 g).

To 3-(2-chloro-4-morpholin-4-yl-thieno[3,2-d]pyrimidin-6-yl)-prop-2-yn-1-ol (142 mg) in chloroform (10 ml) was added triethylamine (77 µL) and methanesulfonyl chloride (49 µL). Stir at room temperature for 2 hours then partition between chloroform and brine, the combined organics were dried ($MgSO_4$). The solvents were removed in vacuo to yield methanesulfonic acid 3-(2-chloro-4-morpholin-4-yl-thieno [3,2-d]pyrimidin-6-yl)-prop-2-ynyl ester (150 mg).

A mixture of methanesulfonic acid 3-(2-chloro-4-morpholin-4-yl-thieno[3,2-d]pyrimidin-6-yl)-prop-2-ynyl ester (150 mg), potassium carbonate (64 mg), N-methylpiperazine (45 µL) and acetonitrile (5 ml) were stirred at 50° C. for 3 hours. The reaction mixture was then cooled, diluted with dichloromethane, washed with brine, dried ($MgSO_4$) and the solvents reduced in vacuo to yield 2-chloro-6-[3-(4-methyl-piperazin-1-yl)-prop-1-ynyl]-4-morpholin-4-yl-thieno[3,2-d] pyrimidine (101 mg).

Suzuki coupling with 2-chloro-6-[3-(4-methyl-piperazin-1-yl)-prop-1-ynyl]-4-morpholin-4-yl-thieno[3,2-d]pyrimidine and indazole 4-boronate ester was carried out using the standard conditions to yield 175 which was purified using flash chromatography. NMR (DMSO): 2.18 (3H, s), 2.30-2.42 (4H, br), 2.50-2.63 (4H, br), 3.68 (2H, s), 3.83-3.88 (4H, m), 4.00-4.05 (4H, m), 7.46-7.51 (1H, m), 7.70 (1H, d, J=8.3), 7.78 (1H, s), 8.22 (1H, d, J=5.2), 8.88 (1H, s), 13.18 (1H, br). ESI+: MH+ 474 (14%)

Example 102

2-(1H-indazol-4-yl)-4-morpholino-6-(3-(pyrrolidin-1-yl)prop-1-ynyl)thieno[3,2-d]pyrimidine 176

2-(1H-Indazol-4-yl)-4-morpholin-4-yl-6-(3-pyrrolidin-1-yl-prop-1-ynyl)-thieno[3,2-d]pyrimidine 176 was prepared by the procedures of Example 93 using pyrrolidine. NMR: (CDCl): 1.88-1.96 (4H, m), 2.72-2.83 (4H, m), 3.70 (2H, s), 3.92-3.96 (4H, m), 4.07-4.11 (4H, m), 7.52 (1H, dd), 7.61-7.65 (2H, m), 8.30 (1H, d, J=7.2), 9.02 (1H, s), 10.10 (1H, br). ESI+: MH+ 445

Example 103

2-(1H-indazol-4-yl)-4-morpholino-6-(3-morpholinoprop-1-ynyl)thieno[3,2-d]pyrimidine 177

2-(1H-Indazol-4-yl)-4-morpholin-4-yl-6-(3-morpholin-4-yl-prop-1-ynyl)-thieno[3,2-d]pyrimidine 177 was prepared by the procedures of Example 93 using morpholine. NMR: (CDCl3): 2.65-2.72 (4H, m), 3.62 (2H, s), 3.78-3.82 (4H, m), 3.92-3.96 (4H, m), 4.07-4.11 (4H, m), 7.52 (1H, dd), 7.61-7.65 (2H, m), 8.30 (1H, d, J=7.2), 9.02 (1H, s), 10.10 (1H, br). ESI+: MH+ 461

Example 104

2-(1H-indazol-4-yl)-4-morpholino-6-(3-(4-methyl-sulfonylpiperazin-1-yl)thieno[3,2-d]pyrimidine 178

2-(1H-Indazol-4-yl)-6-[3-(4-methanesulfonyl-piperazin-1-yl)-prop-1-ynyl]-4-morpholin-4-yl-thieno[3,2-d]pyrimidine-178 was prepared by the procedures of Example 93 using 1-methanesulfonyl-piperazine. (CDCl3): 2.78-2.82 (4H, m), 2.82 (3H, s), 3.34-3.39 (4H, m), 3.70 (2H, s), 3.92-3.96 (4H, m), 4.07-4.11 (4H, m), 7.52 (1H, dd), 7.61-7.65 (2H, m), 8.30 (1H, d, J=7.2), 9.02 (1H, s), 10.10 (1H, br)

Example 105

(2-(1H-indol-4-yl)-4-morpholinothieno[3,2-d]pyrimidin-6-yl)methanol 179

2-(1H-indol-4-yl)-4-morpholin-4-yl-thieno[3,2-d]pyrimidine-6-carbaldehyde from Experimental 106 was reduced to yield 179. NMR: (400 MHz, CDCl3): 8.26 (1H, b, s), 8.18 (1H, d, J 7.36), 7.54 (1H, m), 7.50 (1H, d, J 5.02), 7.40 (2H, m), 7.30 (1H, d, J 7.82), 4.99 (2H, d, J 4.75), 4.09 (4H, t, J 4.83), 3.91 (4H, t, J 4.82), 2.16 (1H, b, t) MS: (M+H)+ 367.11

Example 106

2-(1H-indazol-4-yl)-6-((1-methylpiperidin-4-yl)methyl)-4-morpholinothieno[3,2-d]pyrimidine 180

Reduction of 181 with Pd/C in methanol-dichloromethane and hydrogen 180. NMR: d4-MeOH: 1.69 (2H, m); 2.2 (3H, m); 2.87 (3H, s); 3.00 (2H, t); 3.12 (2H, d, J=6.7 Hz); 3.50 (2H, br d); 4.00 (4H, t, J=4.8 Hz); 4.20 (4H, t, J=4.8 Hz); 7.42 (1H, s); 7.60 (1H, t, J=7.7 Hz); 7.77 (1H, d, J=7.4 Hz); 8.92 (1H, s). MS: (ESI+): MH+ 449

Example 107

2-(1H-indazol-4-yl)-6-((1-methylpiperidin-4-ylidene)methyl)-4-morpholinothieno[3,2-d]pyrimidine 181

A mixture of 6-bromomethyl-2-chloro-4-morpholin-4-yl-thieno[3,2-d]pyrimidine 30 from Example 9 (1.0 g) and trimethyl phosphate (5 mL) was heated at reflux for 3 h. After cooling to room temperature, water (20 mL) was added and the product filtered, washed with water and dried under vacuum to give (2-chloro-4-morpholin-4-yl-thieno[3,2-d]pyrimidin-6-ylmethyl)-phosphonic acid dimethyl ester as a yellow solid (0.54 g).

To a suspension of (2-chloro-4-morpholin-4-yl-thieno[3,2-d]pyrimidin-6-ylmethyl)-phosphonic acid dimethyl ester (0.80 gm) in THF (10 mL) at −78° C. was added dropwise lithium diisopropylamide (1.17 mL of a 2.0 M solution in THF/heptane/ethylbenzene). The mixture was warmed to room temperature and a solution of 4-oxo-piperidine-1-carboxylic acid tert-butyl ester (0.48 g) in THF (10 mL) was added via cannula. The mixture was then stirred at room temperature for 2 h, quenched with brine (20 mL) and extracted into dichloromethane (2×20 mL). The combined organics were dried (MgSO₄), reduced in vacuo and purified by column chromatography to give 4-(2-chloro-4-morpholin-4-yl-thieno[3,2-d]pyrimidin-6-ylmethylene)-piperidine-1-carboxylic acid tert-butyl ester as a yellow oil (0.862 g).

To a suspension of 4-(2-chloro-4-morpholin-4-yl-thieno[3,2-d]pyrimidin-6-ylmethylene)-piperidine-1-carboxylic acid tert-butyl ester (0.85 g) in dichloromethane (10 mL) at room temperature was added hydrogen chloride (2 mL of a 2.0 M solution in diethyl ether). The reaction mixture was stirred at room temperature for 16 h and then reduced in vacuo. The residue was redissolved in dichloromethane (10 mL) and washed with saturated sodium carbonated solution (2×10 mL) and brine (10 mL), dried (MgSO₄) and reduced in vacuo to give 2-chloro-4-morpholin-4-yl-6-piperidin-4-ylidenemethyl-thieno[3,2-d]pyrimidine (0.53 g).

To a mixture of 2-chloro-4-morpholin-4-yl-6-piperidin-4-ylidenemethyl-thieno[3,2-d]pyrimidine (500 mg) and formic acid (2.5 mL) at room temperature was added formaldehyde (0.5 mL of a 37 wt % solution in water). The reaction mixture was stirred at 60° C. for 16 h. The mixture was then diluted with dichloromethane (2 mL) and washed with 2 M aqueous sodium hydroxide solution (20 mL) and brine (20 mL), dried (MgSO₄), reduced in vacuo and purified by column chromatography to give 2-chloro-6-(1-methyl-piperidin-4-ylidenemethyl)-4-morpholin-4-yl-thieno[3,2-d]pyrimidine as a yellow solid (0.15 g).

2-Chloro-6-(1-methyl-piperidin-4-ylidenemethyl)-4-morpholin-4-yl-thieno[3,2-d]pyrimidine was reacted with 4-(4,4,5,5-tetramethyl-[1,3,2]dioxaborolan-2-yl)-1H-indazole in general procedure A. Purification on silica yielded 181. NMR: (CDCl₃) 2.37 (3H, s); 2.55 (6H, m); 2.82 (2H, t, J=5.5 Hz); 3.93 (4H, t, J=4.8 Hz); 4.10 (4H, t, J=4.8 Hz); 6.44 (1H, s); 7.33 (1H, s); 7.51 (1H, s); 7.60 (1H, d, J=8.2 Hz); 8.28 (1H, d, J=7.1 Hz); 9.03 (1H, s); 10.25 (br s). M+H (447)

Example 108

2-(1H-indazol-4-yl)-6-(4-methoxy-1-methylpiperidin-4-yl)-4-morpholinothieno[3,2-d]pyrimidine 182

To a solution of 4-(2-chloro-4-morpholin-4-yl-thieno[3,2-d]pyrimidin-6-yl)-4-hydroxy-piperidine-1-carboxylic acid tert-butyl ester (335 mg) in DMF (3 ml) was added sodium hydride (60% w/w suspension in mineral oil, 41 mg) at 0° C. After 30 min, iodomethane (56 ul) was added and the reaction mixture was warmed slowly to room temperature overnight. Ethyl acetate/brine extraction and purification on silica afforded. 4-(2-chloro-4-morpholin-4-yl-thieno[3,2-d]pyrimidin-6-yl)-4-methoxy-piperidine-1-carboxylic acid tert-butyl ester (219 mg).

The BOC group was then removed using HCl in ether under standard procedures to yield 2-chloro-6-(4-methoxy-piperidin-4-yl)-4-morpholin-4-yl-thieno[3,2-d]pyrimidine.

To 2-chloro-6-(4-methoxy-piperidin-4-yl)-4-morpholin-4-yl-thieno[3,2-d]pyrimidine (175 mg) in methanol (3 ml) was added formaldehyde (37% solution in water, 0.11 ml) and sodium borohydride (54 mg). The reaction mixture was stirred at room temperature overnight. Chloroform/brine extraction and purification on silica gave 2-chloro-4-yl)-6-(4-methoxy-1-methyl-piperidin-4-yl)-4-morpholin-4-yl-thieno[3,2-d]pyrimidine.

Suzuki coupling with 2-chloro-4-yl)-6-(4-methoxy-1-methyl-piperidin-4-yl)-4-morpholin-4-yl-thieno[3,2-d]pyrimidine and indazole boronate ester was carried out using the standard conditions to give the title compound. NMR: (CDCl3/MeOD): 2.20-2.38 (4H, m), 2.46 (3H, s), 2.55-2.69 (2H, m), 2.80-2.92 (2H, m), 3.22 (3H, s), 3.95-4.02 (4H, m), 4.12-4.20 (4H, m), 7.44 (1H, s), 7.56 (1H, m), 7.68 (1H, d), 8.20 (1H, d), 8.90 (1H, s) MS: (ESI+): MH+ 465 (10%)

Example 109

4-(2-(1H-indazol-4-yl)-4-morpholinothieno[3,2-d]pyrimidin-6-yl)-1-methylpiperidin-4-ol 183

To a solution of 2-chloro-4-morpholin-4-yl-thieno[3,2-d]pyrimidine 4 (288 mg) in anhydrous tetrahydrofuran (10 ml), with stirring at −78° C., was added 2.5M n-butyllithium in hexanes (541 μL). The reaction mixture was warmed gradually to −40° C. over 1 hour and then cooled to −78oC 1-methyl-4-piperidone (138 μL) was then added. The reaction mixture was gradually warmed to room temperature and then left to stir for 3 days. The reaction mixture was then quenched with water the precipitate formed filtered. This crude product was then purified using flash chromatography to yield 1-(2-chloro-4-morpholin-4-yl-thieno[3,2-d]pyrimidin-6-yl)-methyl-piperidin-4-ol (135 mg).

Suzuki coupling with 1-(2-chloro-4-morpholin-4-yl-thieno[3,2-d]pyrimidin-6-yl)-methyl-piperidin-4-ol (135 mg) and indazole boronate ester was carried out using the standard conditions to give 183. NMR (MeOD) 9.00 (1H, s), 8.25 (2H, d), 7.72 (1H, d), 7.60 (1H, t), 7.51 (1H, s), 4.22-4.18 (4H, m), 4.01-3.99 (4H, m), 3.27-3.05 (4H, m), 2.82 (3H, s), 2.55-2.48 (2H, m), 2.28-2.20 (2H, m) MH+ 451

Example 110

(2-(1H-indazol-4-yl)-4-morpholinothieno[3,2-d]pyrimidin-6-yl)-N-sulfonylmethyl-N-(2-morpholinoethyl)methanamine 184

To a solution of 4-(2-aminoethyl)morpholine (0.5 g) in dichloromethane (5 ml) at 0° C. was added methane sulphonyl chloride (0.33 ml) and triethylamine (0.59 ml) The reaction mixture was warmed to room temperature and stirred for 2 hours. The reaction mixture was diluted with dichloromethane, the combined organics washed with brine, dried (MgSO$_4$) and the solvents removed in vacuo to give a crude residue which was purified by flash chromatography to yield N-(2-morpholin-4-yl-ethyl)-methanesulfonamide (596 mg).

To a solution of N-(2-Morpholin-4-yl-ethyl)-methanesulfonamide in tetrahydrofuran under nitrogen was added sodium hydride, 60% dispersion in mineral (16 mg). The mixture was stirred at room temperature for 40 minutes. A solution of 6-Bromomethyl-2-chloro-4-morpholin-4-yl-thieno[3,2-d]pyrimidine (125 mg) in tetrahydrofuran (5 ml) was added. The reaction mixture was stirred at room temperature for 3.5 hours, then 50° C. for 3.5 hours. The solvents were removed in vacuo to give a crude product which was purified by flash chromatography to yield N-(2-Chloro-4-morpholin-4-yl-thieno[3,2-d]pyrimidin-6-ylmethyl)-N-(2-morpholin-4-yl-ethyl)-methanesulfonamide (138 mg).

N-(2-Chloro-4-morpholin-4-yl-thieno[3,2-d]pyrimidin-6-ylmethyl)-N-(2-morpholin-4-yl-ethyl)-methanesulfonamide was reacted with 4-(4,4,5,5-Tetramethyl-[1,3,2]dioxaborolan-2-yl)-1H-indazole in general procedure A. Purification by flash chromatography on silica yielded 184. NMR: 400 MHz; CDCl3: 2.49 (4H, m); 2.60 (2H, t, J=5.9 Hz); 3.09 (3H, s); 3.48 (2H, m); 3.70 (4H, m); 3.92 (4H, m); 4.08 (4H, m); 4.82 (2H, s); 7.47 (1H, s); 7.52 (1H, t, J=7.7 Hz); 7.60 (1H, d, J=8.1 Hz); 8.28 (1H, d, J=7.1 Hz); 9.00 (1H, s); 10.15 (1H, br s). MS: (ESI+): 558

Example 111

(2-(1H-indazol-4-yl)-4-morpholinothieno[3,2-d]pyrimidin-6-yl)-N-methylsulfonyl-N-(2-N,N-dimethylaminoethyl)methanamine 185

To a solution of N,N-dimethylethylenediamine (0.5 g) in dichloromethane (10 ml) at 0° C. was added triethylamine (0.87 ml) and methane sulphonyl chloride. The reaction mixture was warmed to room temperature and stirred for 1 hour. The reaction mixture was partitioned between dichloromethane and saturated sodium bicarbonate solution, the combined organics were dried (MgSO$_4$) and the solvents removed in vacuo to yield a crude product. This was purified by flash chromatography to yield N-(2-dimethylaminoethyl)-methanesulfonamide (0.46 g).

To a solution of N-(2-dimethylamino-ethyl)-methanesulfonamide (50 mg) in tetrahydrofuran under nitrogen was added sodium hydride, 60% dispersion in mineral oil, (13 mg). The reaction mixture was stirred at room temperature for 30 minutes, the 6-Bromomethyl-2-chloro-4-morpholin-4-yl-thieno[3,2-d]pyrimidine in tetrahydrofuran (5 ml) was added dropwise. The reaction mixture was stirred for 5 days. The solvents were removed in vacuo to give a crude product which was purified by flash chromatography to yield N-(2-Chloro-4-morpholin-4-yl-thieno[3,2-d]pyrimidin-6-ylmethyl)-N-(2-dimethylamino-ethyl)-methanesulfonamide (35 mg).

N-(2-Chloro-4-morpholin-4-yl-thieno[3,2-d]pyrimidin-6-ylmethyl)-N-(2-dimethylamino-ethyl)-methanesulfonamide was reacted with 4-(4,4,5,5-Tetramethyl-[1,3,2]dioxaborolan-2-yl)-1H-indazole in general procedure A. Purification by flash chromatography on silica yielded 185. NMR: 400 MHz; CDCl3: 2.30 (6H, s); 2.55 (2H, m); 3.05 (3H, s); 3.45 (2H, m); 3.94 (4H, t, J=4.8 Hz); 4.10 (4H, t, J=4.8 Hz); 4.82 (2H, s); 7.48 (1H, s); 7.52 (1H, t, J=7.8 Hz); 7.60 (1H, d, J=8.3 Hz); 8.28 (1H, d, J=7.3 Hz); 9.02 (1H, s); 10.15 (1H, br s). MS: (ESI+): 516

Example 112

(2-(1H-indazol-4-yl)-4-morpholinothieno[3,2-d]pyrimidin-6-yl)-N-methyl,N-(3-morpholinopropylsulfonyl)methanamine 186

3-Chloro-propane-1-sulfonic acid (2-chloro-4-morpholin-4-yl-thieno[3,2-d]pyrimidin-6-ylmethyl)-methylamide was reacted with 4-(4,4,5,5-tetramethyl-[1,3,2]dioxaborolan-2-yl)-1H-indazole in general procedure A. Purification on silica yielded 3-chloro-propane-1-sulfonic acid [2-(1H-indazol-4-yl)-4-morpholin-4-yl-thieno[3,2-d]pyrimidin-6-ylmethyl]-methyl-amide.

To a solution of 3-chloro-propane-1-sulfonic acid [2-(1H-indazol-4-yl)-4-morpholin-4-yl-thieno[3,2-d]pyrimidin-6-ylmethyl]-methylamide (45 mg) in acetonitrile (2 mL) was added morpholine (38 μL), potassium carbonate (18 mg) and potassium iodide (2 mg). the reaction mixture was heated at 80° C. for 72 h and allowed to cool to room temperature before quenching with water (30 mL) and extracting into dichloromethane (2×30 mL). The combined organics were washed with brine (30 mL), dried (MgSO$_4$), reduced in vacuo and purified by column chromatography to give 186 as an off-white solid (27 mg). NMR: CDCl$_3$: 1.97 (m, 2H), 2.36-2.43 (m, 6H), 2.87 (s, 3H), 3.07 (m, 2H), 3.63 (t, J=4.6, 4H), 3.84 (t, J=4.8, 4H), 4.01 (t, J=4.8, 4H), 4.61 (s, 2H), 7.39 (s, 1H), 7.43 (t, J=8.2, 1H), 7.51 (d, J=8.3, 1H), 8.20 (d, J=6.8, 1H), 8.94 (s, 1H), 10.30 (brs, 1H). MS: ESI+: MH+ 572.09

Example 113

(2-(1H-indol-4-yl)-4-morpholinothieno[3,2-d]pyrimidin-6-yl)-N-methyl,N-(3-morpholinopropylsulfonyl)methanamine 187

3-Chloro-propane-1-sulfonic acid (2-chloro-4-morpholin-4-yl-thieno[3,2-d]pyrimidin-6-ylmethyl)-methyl-amide was reacted with indole boronic acid in general procedure A. Purification on silica yielded 3-chloro-propane-1-sulfonic acid [2-(1H-indol-4-yl)-4-morpholin-4-yl-thieno[3,2-d]pyrimidin-6-ylmethyl]-methyl-amide.

To a solution of 3-chloro-propane-1-sulfonic acid [2-(1H-indol-4-yl)-4-morpholin-4-yl-thieno[3,2-d]pyrimidin-6-ylmethyl]-methyl-amide (18 mg) in acetonitrile (1 mL) at room temperature was added morpholine (15 μL), potassium carbonate (7 mg) and potassium iodide (2 mg). The reaction mixture was stirred at 80° C. for 72 h and allowed to cool to room temperature before quenching with water (30 mL) and extracting into dichloromethane (2×30 mL). The combined organics were washed with brine (30 mL), dried ($MgSO_4$), reduced in vacuo and purified by column chromatography to give the title compound as an off-white solid (7 mg). NMR: $CDCl_3$: 1.96 (m, 2H), 2.43-2.37 (m, 6H), 2.87 (s, 3H), 3.05 (m, 2H), 3.84 (t, J=4.8, 4H), 4.01 (t, J=4.8, 4H), 4.60 (s, 2H), 7.21-7.27 (m, 2H), 7.39 (s, 1H), 7.42-7.47 (m, 2H), 8.11 (d, J=7.2, 1H), 8.25 (s, 1H). MS: (ESI+): MH+ 571

Example 114

2-(1H-indazol-4-yl)-N-(2-methoxyethyl)-4-morpholinothieno[3,2-d]pyrimidine-6-carboxamide 188

45 mg of 2-(1H-indazol-4-yl)-4-morpholinothieno[3,2-d]pyrimidine-6-carboxylic acid 13 was coupled to 2-methoxymethanamine via General Procedure B. The product was purified via reverse phase HPLC to give 18.8 mg of 188. MS (Q1) 439.1 (M)+.

Example 115

2-(1H-indol-4-yl)-N-(2-methoxyethyl)-4-morpholinothieno[3,2-d]pyrimidine-6-carboxamide 189

To 2-Chloro-4-morpholin-4-yl-thieno[3,2-d]pyrimidine-6-carbaldehyde 10 in dichloromethane (2 ml) was added 2M oxalyl chloride solution in dichloromethane (0.75 ml) followed by 2 microdrops of dimethylformamide. The reaction mixture was stirred at room temperature overnight. The solvent was removed in vacuo to give a crude product. This crude product was stirred in dichloromethane (5 ml) and to it was added 2-methoxyethylamine (34.8 μL) and triethylamine (61.5 μL). The reaction mixture was stirred at room temperature overnight. It was then partitioned between dichloromethane and saturated sodium bicarbonate solution, the combined organics were dried ($MgSO_4$) and the solvents removed in vacuo to give a crude residue. This was purified by flash chromatography to yield 2-Methyl-4-morpholin-4-yl-thieno[3,2-d]pyrimidine-6-carboxylic acid (2-methoxyethyl)-amide (30 mg).

2-Methyl-4-morpholin-4-yl-thieno[3,2-d]pyrimidine-6-carboxylic acid (2-methoxyethyl)-amide was reacted with indole boronic acid in general procedure A. Purification on silica yielded 189. NMR: 400 MHz; $CDCl_3$ 3.44 (3H, s); 3.60 (2H, m); 3.70 (2H, m); 3.92 (4H, t, J=4.8 Hz); 4.15 (4H, t, J=4.8 Hz); 6.74 (1H, br t); 7.30 (1H, d, J=7.8 Hz); 7.35 (1H, m); 7.52 (1H, d, J=8.0 Hz); 7.57 (1H, s); 7.82 (1H, s); 8.20 (1H, d, J=7.4 Hz); 8.30 (1H, br s). MS: (ESI+) M+H (438)

Example 116

(2-(1H-indol-4-yl)-4-morpholinothieno[3,2-d]pyrimidin-6-yl)-N-methyl-N-(2-N,N-dimethylaminosulfonyl)methanamine 190

To a solution of (2-chloro-4-morpholin-4-yl-thieno[3,2-d]pyrimidin-6-ylmethyl)-methyl-amine (220 mg) in dichloromethane (7 mL) at room temperature was added triethylamine (0.174 mL) and then 3-chloropropane sulfonyl chloride (0.134 mL). The reaction mixture was stirred at room temperature for 30 min and then quenched with water (25 mL) and extracted into dichloromethane (3×25 mL). The combined organics were washed with brine (30 mL), dried ($MgSO_4$), reduced in vacuo and purified by column chromatography to give 3-chloro-propane-1-sulfonic acid (2-chloro-4-morpholin-4-yl-thieno[3,2-d]pyrimidin-6-ylmethyl)-methyl-amide (301 mg).

3-Chloro-propane-1-sulfonic acid (2-chloro-4-morpholin-4-yl-thieno[3,2-d]pyrimidin-6-ylmethyl)-methyl-amide was reacted with indole boronic acid in general procedure A. Purification on silica yielded 3-chloro-propane-1-sulfonic acid [2-(1H-indol-4-yl)-4-morpholin-4-yl-thieno[3,2-d]pyrimidin-6-ylmethyl]-methyl-amide.

To a solution of 3-chloro-propane-1-sulfonic acid [2-(1H-indol-4-yl)-4-morpholin-4-yl-thieno[3,2-d]pyrimidin-6-ylmethyl]-methyl-amide (59 mg) in acetonitrile (1.0 mL) and DMF (1 mL) was added potassium carbonate (19 mg), potassium iodide (19 mg) and a solution of methyl amine (26 mg) in acetonitrile (0.5 mL). The reaction mixture was heated at 60° C. for 12 h and then allowed to cool to room temperature. The reaction mixture was then purified on silica to give the title compound as an off-white solid (45 mg). NMR: DMSOd6: 11.2 (1H, s); 8.11 (1H, d, J=7.2 Hz); 7.51 (2H, m); 7.43 (2H, m); 7.19 (H, t, J=7.7 Hz); 4.69 (2H, s); 3.99 (4H, m); 3.82 (4H, m); 3.19 (2H, m) 2.85 (3H, s); 2.32 (2H, m); 2.13 (6H, s); 1.86 (2H, m). MS: (ESI+): MH+ 529.2

Example 117

2-(1H-indol-4-yl)-6-(2-(methylsulfonyl)ethyl)-4-morpholinothieno[3,2-d]pyrimidine 191

2-Chloro-4-morpholin-4-yl-thieno[3,2-d]pyrimidine-6-carbaldehyde 10 (200 mg), 4-indole-boronic acid (125 mg), sodium hydrogen carbonate (178 mg) and $PdCl_2(PPh_3)_2$ (4 mg) in toluene (1.5 ml), ethanol (0.75 ml) and water (0.4 ml) were heated in a microwave at 120° C. for 45 min. Chloroform/water extraction and purification on silica gave 2-(1H-indol-4-yl)-4-morpholin-4-yl-thieno[3,2-d]pyrimidine-6-carbaldehyde (257 mg).

To a suspension of 2-(1H-indol-4-yl)-4-morpholin-4-yl-thieno[3,2-d]pyrimidine-6-carbaldehyde (54 mg) in anhydrous methanol (8 ml) was added phosphorus sulphone (34 mg), followed by sodium methoxide (148 ul). The reaction mixture was stirred at room temperature for 4.5 hours, then evaporated onto silica and purified by flash chromatography to give 2-(1H-indol-4-yl)-6-((E)-2-methanesulfonyl-vinyl))-4-morpholin-4-yl-thieno[3,2-d]pyrimidine (30 mg).

2-(1H-Indol-4-yl)-6-((E)-2-methanesulfonyl-vinyl))-4-morpholin-4-yl-thieno[3,2-d]pyrimidine (25 mg) was hydrogenated under atmospheric pressure using 10% palladium on carbon in MeOH and hydrogen balloon. Purification on silica gave 191. NMR: 400 MHz CDCl3 8.27 (1H, s): 8.19 (1H, d, J=7.4); 7.52 (2H, m); 7.33 (3H, m); 4.08 (4H, m); 3.91 (4H, m); 3.49 (4H, m); 2.94 (3H, s). MS: MH+=443.02

Example 118

N-((2-(1H-indazol-4-yl)-4-morpholinothieno[3,2-d]pyrimidin-6-yl)methyl)-N-methylacetamide 192

Following the procedure of Example 106 to prepare 193, N-[2-(1H-Indazol-4-yl)-4-morpholin-4-yl-thieno[3,2-d]pyrimidin-6-ylmethyl]-N-methyl-acetamide was reacted with 4-(4,4,5,5-Tetramethyl-[1,3,2]dioxaborolan-2-yl)-1H-indazole in general procedure A. Purification on silica yielded 192. NMR: 400 MHz; CDCl$_3$ 2.20, 2.27 (3H, s, 2 rotamers); 3.07 (3H, s); 3.90 (4H, m); 4.05 (4H, m); 4.82, 4.86 (2H, s, 2 rotamers); 7.40 (1H, s); 7.50 (1H, t, J=7.8 Hz); 7.60 (1H, d, J=8.2 Hz); 8.28 (1H, d, J=7.2 Hz); 9.00 (1H, s); 10.15 (1H, br s). MS: (ESI+): M+H (423)

Example 119

N-((2-(1H-indol-4-yl)-4-morpholinothieno[3,2-d]pyrimidin-6-yl)methyl)-N-methylacetamide 193

To 2-chloro-4-morpholin-4-yl-thieno[3,2-d]pyrimidine-6-carbaldehyde 10 (1.0 g) in methanol under nitrogen was added methylamine solution (11.79 g methylamine in 50 ml methanol) (1.39 ml). The reaction mixture was stirred at room temperature overnight. The solvents were then removed in vacuo to yield [1-(2-Chloro-4-morpholin-4-yl-thieno[3,2-d]pyrimidin-6-yl)-meth-(E)-ylidene]-methyl-amine.

To [1-(2-Chloro-4-morpholin-4-yl-thieno[3,2-d]pyrimidin-6-yl)-meth-(E)-ylidene]-methyl-amine (0.9 g) in methanol (25 ml) and tetrahydrofuran (10 ml) under nitrogen was added sodium borohydride (0.17 g) and molecular sieves. The reaction mixture was stirred at room temperature overnight. The solvents were removed in vacuo, quenched with brine, extracted with dichloromethane, dried (MgSO$_4$) and the solvent removed in vacuo to give a crude product which was purified using flash chromatography to give (2-Chloro-4-morpholin-4-yl-thieno[3,2-d]pyrimidin-6-ylmethyl)-methyl-amine (342 mg).

To a solution of (2-Chloro-4-morpholin-4-yl-thieno[3,2-d]pyrimidin-6-ylmethyl)-methylamine (120 mg) in dichloromethane (2 ml) was added acetyl chloride (31.4 µL) and triethylamine (61.6 µL). The reaction mixture was stirred at room temperature for 3.5 hours, then diluted with dichloromethane, washed with brine, dried (MgSO$_4$) and the solvents removed in vacuo to give a crude residue. This was purified by flash chromatography to yield N-(2-Chloro-4-morpholin-4-yl-thieno[3,2-d]pyrimidin-6-ylmethyl)-N-methyl-acetamide (110 mg).

N-(2-Chloro-4-morpholin-4-yl-thieno[3,2-d]pyrimidin-6-ylmethyl)-N-methyl-acetamide was reacted with indole boronic acid in general procedure A. Purification on silica yielded 193. NMR: 400 MHz; CDCl$_3$ 2.10, 2.18 (3H, s, 2 rotamers); 3.00 (3H, s); 3.84 (4H, m); 4.00 (4H, m); 4.73, 4.77 (2H, s, 2 rotamers); 7.26 (2H, m); 7.33 (1H, s); 7.42 (1H, m); 7.48 (1H, s); 8.13 (1H, m); 8.21 (1H, br s). MS: (ESI+): M+H (422)

Example 120

N-((2-(1H-indol-4-yl)-4-morpholinothieno[3,2-d]pyrimidin-6-yl)methyl)-N-(methyl)methylsulfonamide 194

To a solution of [1-(2-Chloro-4-morpholin-4-yl-thieno[3,2-d]pyrimidin-6-yl)-meth-(E)-ylidene]-methyl-amine (0.76 mmol) in methanol (4 ml) and dichloromethane (4 ml) was added sodium borohydride (114 mg). The reaction mixture was stirred at room temperature overnight. Partitioned between dichloromethane and water. The combined organics were washed with brine, dried (MgSO$_4$) and the solvents removed in vacuo to give a crude residue. This was purified by flash chromatography to yield N-(2-Chloro-4-morpholin-4-yl-thieno[3,2-d]pyrimidin-6-ylmethyl)-N-methyl-methanesulfonamide (85 mg).

N-(2-Chloro-4-morpholin-4-yl-thieno[3,2-d]pyrimidin-6-ylmethyl)-N-methyl-methanesulfonamide was reacted with indole boronic acid in general procedure A. Purification on silica yielded 194. NMR: (400 MHz, DMSO) 2.83 (s, 3H), 3.02 (s, 3H), 3.85 (t, J=4.7, 4H), 3.99 (t, J=4.7, 4H), 4.64 (s, 2H), 7.19 (t, J=7.7, 1H), 7.43 (m, 2H), 7.51 (m, 2H), 8.12 (d, J=7.3, 1H), 11.20 (s br, 1H) MS: (ESI+)[M+H]+ 458.01

Example 121

N-((2-(1H-indazol-4-yl)-4-morpholinothieno[3,2-d]pyrimidin-6-yl)methyl)-N-methylsulfonyl-1-methylpyrrolidin-3-amine 195

To a solution of (+/−)-3-amino-1N—BOC-pyrrolidine (0.5 g) in MeCN (10 mL) was added triethylamine (0.41 mL) then methanesulfonyl chloride (0.22 mL). The mixture was stirred for 2.5 h. An aqueous work-up followed by purification on silica gave 3-methanesulfonylamino-pyrrolidine-1-carboxylic acid tert-butyl ester (0.49 g).

To a solution of 3-Methanesulfonylamino-pyrrolidine-1-carboxylic acid tert-butyl ester (0.47 g) in DMF (5 mL) was added NaH (63 mg). The mixture was stirred for 40 min. then a solution of 6-bromomethyl-2-chloro-4-morpholin-4-yl-thieno[3,2-d]pyrimidine (0.52 g) in DMF (5 mL) was added via cannular. The resulting mixture was stirred at R.T. for 5 h. An aqueous work-up followed by purification on silica gave 3-[(2-chloro-4-morpholin-4-yl-thieno[3,2-d]pyrimidin-6-ylmethyl)-methanesulfonyl-amino]-pyrrolidine-1-carboxylic acid tert-butyl ester (384 mg).

3-[(2-Chloro-4-morpholin-4-yl-thieno[3,2-d]pyrimidin-6-ylmethyl)-methanesulfonyl-amino]-pyrrolidine-1-carboxylic acid tert-butyl ester (380 mg) in CH$_2$Cl$_2$ (10 mL) was treat with 2M HCl in ether (2 mL). After 18 h the mixture was concentrated to give the HCl salt. This was diluted with saturated sodium bicarbonate solution then extracted with CH$_2$Cl$_2$. Combined extracts were dried (MgSO$_4$), filtered and concentrated to gave the freebase (204 mg).

A mixture of N-(2-Chloro-4-morpholin-4-yl-thieno[3,2-d]pyrimidin-6-ylmethyl)-N-pyrrolidin-3-yl-methanesulfonamide (200 mg), formic acid (2.5 mL) and formaldehyde (37% solution, 0.37 mL) was heated at 60° C. overnight. The mixture was diluted with 2M NaOH then extracted with CH$_2$Cl$_2$. Combined extracts were dried (MgSO$_4$), filtered and concentrated. Purification on silica yielded N-(2-chloro-4-morpholin-4-yl-thieno[3,2-d]pyrimidin-6-ylmethyl)-N-(1-methyl-pyrrolidin-3-yl)-methanesulfonamide (38 mg).

N-(2-Chloro-4-morpholin-4-yl-thieno[3,2-d]pyrimidin-6-ylmethyl)-N-(1-methyl-pyrrolidin-3-yl)-methanesulfonamide was reacted with 4-(4,4,5,5-tetramethyl-[1,3,2]dioxaborolan-2-yl)-1H-indazole in General Procedure A to yield 195. NMR: (CDCl₃): 1.96 (1H, m); 2.19 (2H, m); 2.33 (4H, m); 2.48 (1H, m); 2.90 (5H, m); 3.94 (4H, m); 4.10 (4H, m); 4.57 (1H, m); 4.90 (2H, s); 7.50 (1H, s); 7.53 (1H, d, J=7.4 Hz); 7.10 (1H, d, J=8.2 Hz); 8.30 (1H, d, J=7.1 Hz); 9.03 (1H, s); 10.14 (1H, br s). MS: (ESI+): MH+=528

Example 122

2-(1H-indazol-4-yl)-6-(3-((4-methylsulfonylpiperazin-1-yl)methyl)phenyl)-4-morpholinothieno[3,2-d]pyrimidine 196

2-Chloro-6-iodo-4-morpholinothieno[3,2-d]pyrimidine 19 (300 mg), 130 mg of 3-formylbenzeneboronic acid and 55 mg of Bis(triphenylphosphine)palladium(II) dichloride in 0.6 mL of 1M Na₂CO₃ and 0.6 mL of acetonitrile was heated to 100° C. in the microwave reactor for 15 min. The reaction mixture was diluted with ethyl acetate (60 mL), and then washed with H₂O (40 mL). The organic layer was dried over MgSO₄, filtered and evaporated. The residue was purified by ISCO CombiFlash (0-40% ethyl acetate/hexane) to yield 99 mg of 3-(2-chloro-4-morpholinothieno[3,2-d]pyrimidin-6-yl)benzaldehyde.

40 mg of 3-(2-chloro-4-morpholinothieno[3,2-d]pyrimidin-6-yl)benzaldehyde, 25 mg of 1-methanesulfonylpiperazine, 35 mg of sodium triacetoxyborohydride in 1,2-dichloroethane (1 mL) and acetic acid (10 µL) was stirred overnight at room temperature. The reaction mixture was diluted with dichloromethane (20 mL), and then washed with saturated sodium bicarbonate (10 mL) and brine (10 mL). The organic layer was dried over MgSO₄, filtered and evaporated to give 2-chloro-6-(3-((4-methylsulfonylpiperazin-1-yl)methyl)phenyl)-4-morpholinothieno[3,2d]pyrimidine.

50 mg of the crude 2-chloro-6-(3-((4-methylsulfonylpiperazin-1-yl)methyl)phenyl)-4-morpholinothieno[3,2d]pyrimidine was coupled to 4-(4,4,5,5-tetramethyl-1,3,2-dioxaborolan-2-yl)-1H-indazole 7 via General Procedure A. The product was purified by reverse phase HPLC to yield 14.2 mg of 196. MS (Q1) 519 (M)+.

Example 123

2-(1H-indazol-4-yl)-6-(3-((4-methylpiperazin-1-yl)methyl)phenyl)-4-morpholinothieno[3,2-d]pyrimidine 197

40 mg of 3-(2-chloro-4-morpholinothieno[3,2-d]pyrimidin-6-yl)benzaldehyde, 12 mg of 1-methylpiperazine, 28 mg of sodium triacetoxyborohydride in 1,2-dichloroethane (1 mL) and acetic acid (10 µL) was stirred overnight at room temperature. The reaction mixture was diluted with dichloromethane (20 mL), and then washed with saturated sodium bicarbonate (10 mL) and brine (10 mL). The organic layer was dried over MgSO₄, filtered and evaporated to give 2-chloro-6-(3-((4-methylpiperazin-1-yl)methyl)phenyl)-4-morpholinothieno[3,2d]pyrimidine.

50 mg of the crude 2-chloro-6-(3-((4-methylpiperazin-1-yl)methyl)phenyl)-4-morpholinothieno[3,2d]pyrimidine was coupled to 4-(4,4,5,5-tetramethyl-1,3,2-dioxaborolan-2-yl)-1H-indazole 7 via General Procedure A. The product was purified by reverse phase HPLC to yield 8.5 mg of 197. MS (Q1) 526 (M)+.

Example 124

4-(4-morpholinothieno[3,2-d]pyrimidin-2-yl)indolin-2-one 198

To a solution of 2-(1H-Indol-4-yl)-4-morpholin-4-yl-thieno[3,2-d]pyrimidine 199 (90 mg) in acetic acid (2 ml) and water (1 ml) was added pyridinium bromide perbromide (103 mg) as a solution in acetic acid (4 ml) and the reaction mixture was heated to 80° C. for 4 hours. The mixture was then basified and extracted into dichloromethane, organic layer was dried (Mg₂SO₄), filtered and volatiles removed in vacuo. Purification on silica yielded 198 (23 mg). NMR: (CDCl₃): 3.39-3.43 (4H, m), 4.03-4.08 (4H, m), 4.10 (2H, s), 6.95 (1H, d, J=7.4), 7.36 (1H, t, J=7.9), 7.49 (2H, m), 7.79 (1H, d, J=5.6), 8.10 (1H, d, J=7.9) MS: (ESI+): MH+ 353 (100%)

Example 125

2-(1H-indol-4-yl)-4-morpholinothieno[3,2-d]pyrimidine 199

2-Chloro-4-morpholin-4-yl-thieno-[3.2-d]pyrimidine 4 (120 mg), 4-indole-boronic acid (110 mg), sodium hydrogen carbonate (120 mg) and PdCl₂(PPh₃)₂ (30 mg) in DME (3 ml) and water (1 ml) were heated in a microwave for 90 min at 130° C. Dichloromethane/water extraction and purification on silica gave 199 (40 mg). NMR: (400 MHz, CDCl₃): 3.95 (4H, t, J=4.5), 4.13 (4H, t, J=4.5), 7.30-7.38 (2H, m), 7.52 (1H, d, J=8.1), 7.55-7.59 (2H, m), 7.75 (1H, d, J=5.5), 8.22 (1H, d, J=7.4), 8.30 (1H, br) MS: (ESI+): MH+ 337

Example 126

2-(1H-indazol-4-yl)-4-morpholino-6-(pyrimidin-5-yl)thieno[3,2-d]pyrimidine 200

2-Chloro-6-iodo-4-morpholinothieno[3,2-d]pyrimidine 19 (50 mg) was coupled to pyrimidine-5-boronic acid via General Procedure I. The product was purified by reverse phase HPLC to yield 19.2 mg of 200. MS (Q1) 416 (M)+

Example 127

2-(1H-Indazol-4-yl)-4-morpholino-6-phenylfuro[3,2-d]pyrimidine 201

2-Chloro-4-morpholino-6-phenylfuro[3,2-d]pyrimidine 44 (50 mg, 1.0 eq) was dissolved in toluene/ethanol/water (4:2:1, 2.8 ml) and treated with 4-(4,4,5,5-tetramethyl-1,3,2-dioxaborolan-2-yl)-1H-indazole 7 (97 mg, 2.5 eq), PdCl₂(PPh₃)₂ (13.3 mg, 0.12 eq) and sodium carbonate (59 mg, 3.5 eq). The vial was sealed and heated with stirring in the microwave to 150° C. for 25 minutes. The crude reaction mixture was concentrated and purified by reverse phase HPLC to afford 201 MS (Q1) 398 (M)+.

Example 128

N-(cyclopropylmethoxy)-2-(1H-indazol-4-yl)-4-morpholinothieno[3,2-d]pyrimidine-6-carboxamide 202

To 50 mg of 2-chloro-4-morpholinothieno[3,2-d]pyrimidine-6-carboxylic acid was added 1 eq cyclopropyl methoxylamine and 4.5 eq N-methylmorpholine in THF at 0° C. After dropwise addition of 1.2 eq diphenylphosphine at 0° C., the reaction was warmed to room temperature after 10 minutes. The reaction was stirred for several hours until complete. Water was added to the reaction mixture which was then extracted with ethyl acetate. The organic layer was concentrated to dryness and subjected to Procedure A to give 22.4 mg of 202. MS (Q1) 451.2 (M)+.

Example 129

2-(1H-indazol-4-yl)-4-morpholino-6-(1H-pyrazol-4-yl)thieno[3,2-d]pyrimidine 203

2-Chloro-6-iodo-4-morpholinothieno[3,2-d]pyrimidine 19 (50 mg) was coupled to 4,4,5,5-tetramethyl-2-(1H-pyrazol-4-yl)-1,3,2-dioxaborolane via General Procedure I. The product was purified by reverse phase HPLC to yield 18.1 mg of 203. MS (Q1) 404 (M)+.

Example 130

2-(1H-indazol-4-yl)-4-morpholino-6-phenylthieno[3,2-d]pyrimidine 204

2-Chloro-6-iodo-4-morpholinothieno[3,2-d]pyrimidine 19 (50 mg) was coupled to phenylboronic acid via General Procedure I. The product was purified by reverse phase HPLC to yield 17.3 mg of 204. MS (Q1) 414 (M)+

Example 131

(S)-1-((2-(1H-indazol-4-yl)-4-morpholinothieno[3,2-d]pyrimidin-6-yl)methylamino)propan-2-ol 205

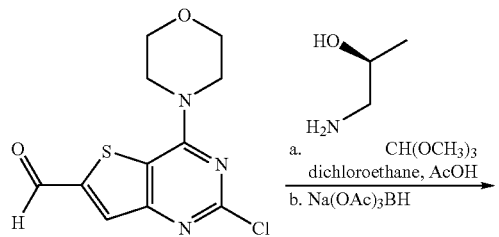

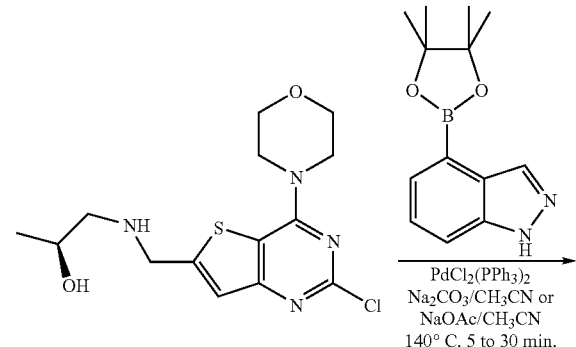

-continued

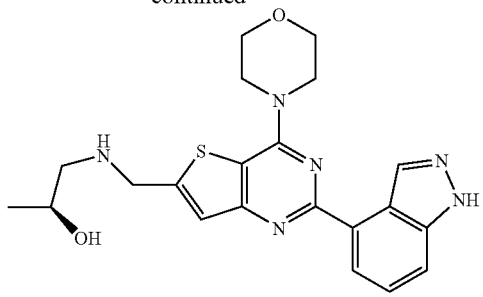

2-Chloro-4-morpholinothieno[3,2-d]pyrimidine-6-carbaldehyde 10 (50 mg) was dissolved in 1 mL of dichloroethane. To this solution was added 2.0 equivalents of (s)-1-amino-2-propanol, 0.2 mL of trimethylorthoformate, and 10 μL of acetic acid. The mixture was allowed to stir for 6 hours prior to adding 1.5 equivalents of sodium triacetoxyborohydride. Following 16 hours of stirring the reaction was poured into saturated sodium bicarbonate and extracted several times with ethylacetate. This intermediate was used crude following the general procedure A to yield 205. MS (Q1) 425 (M)+

Example 132

2-(1H-indazol-4-yl)-N-(methylsulfonyl)-4-morpholinothieno[3,2-d]pyrimidine-6-carboxamide 206

To 50 mg of 2-chloro-4-morpholinothieno[3,2-d]pyrimidine-6-carboxylic acid in 1 mL of DMF was added 2 eq of carbonyldiimidazole. The reaction was stirred for 1 hour at room temperature before addition of a 1 mL solution containing 2.5 eq DBU and 2 eq of methanesulfonamide in DMF. The reaction was stirred overnight at ambient temperature and concentrated to dryness. The crude chloride was subjected to Procedure A to yield 13.8 mg of 206. MS (Q1) 459.1 (M)+.

Example 133

6-(isobutylaminosulfonyl)-2-(1H-indazol-4-yl)-4-morpholinothieno[3,2-d]pyrimidine 207

To 40 mg of 2-chloro-4-morpholinothieno[3,2-d]pyrimidine-6-sulfonyl chloride 17 was added 2-methylpropan-1-amine via General Procedure C. The product was purified via reverse phase HPLC to give 14 mg of 207. MS (Q1) 473.1 (M)+.

Example 134

6-(3-hydroxyphenylaminosulfonyl)-2-(1H-indazol-4-yl)-4-morpholinothieno[3,2-d]pyrimidine 208

To 40 mg of 2-chloro-4-morpholinothieno[3,2-d]pyrimidine-6-sulfonyl chloride 17 was added 3-hydroxyaniline via General Procedure C. The product was purified via reverse phase HPLC to give 10.7 mg of 208. MS (Q1) 509.1 (M)+.

Example 135

6-((4-piperazin-2-one)sulfonyl)-2-(1H-indazol-4-yl)-4-morpholinothieno[3,2-d]pyrimidine 209

To 40 mg of 2-chloro-4-morpholinothieno[3,2-d]pyrimidine-6-sulfonyl chloride 17 was added piperazin-2-one via General Procedure C. The product was purified via reverse phase HPLC to give 4.3 mg of 209. MS (Q1) 500.1 (M)+.

Example 136

6-(4-methylpiperazinesulfonyl)-2-(1H-indazol-4-yl)-4-morpholinothieno[3,2-d]pyrimidine 210

To 40 mg of 2-chloro-4-morpholinothieno[3,2-d]pyrimidine-6-sulfonyl chloride 17 was added 1-methylpiperazine via General Procedure C. The product was purified via reverse phase HPLC to give 6.5 mg of 210. MS (Q1) 500.1 (M)+.

Example 137

6-(2-hydroxymethylpiperidinesulfonyl)-2-(1H-indazol-4-yl)-4-morpholinothieno[3,2-d]pyrimidine 211

To 40 mg of 2-chloro-4-morpholinothieno[3,2-d]pyrimidine-6-sulfonyl chloride 17 was added (piperidin-2-yl)methanol via General Procedure C. The product was purified via reverse phase HPLC to give 4.4 mg of 211. MS (Q1) 515.1 (M)+.

Example 138

6-(3-hydroxymethylpiperidinesulfonyl)-2-(1H-indazol-4-yl)-4-morpholinothieno[3,2-d]pyrimidine 212

To 40 mg of 2-chloro-4-morpholinothieno[3,2-d]pyrimidine-6-sulfonyl chloride 17 was added (piperidin-3-yl)methanol via General Procedure C. The product was purified via reverse phase HPLC to give 12.1 mg of 212. MS (Q1) 515.1 (M)+.

Example 139

6-(4-hydroxymethylpiperidinesulfonyl)-2-(1H-indazol-4-yl)-4-morpholinothieno[3,2-d]pyrimidine 213

To 40 mg of 2-chloro-4-morpholinothieno[3,2-d]pyrimidine-6-sulfonyl chloride 17 was added (piperidin-4-yl)methanol via General Procedure C. The product was purified via reverse phase HPLC to give 7.1 mg of 213. MS (Q1) 515.1 (M)+.

Example 140

6-(4-(2-hydroxyethyl)piperidinesulfonyl)-2-(1H-indazol-4-yl)-4-morpholinothieno[3,2-d]pyrimidine 214

To 40 mg of 2-chloro-4-morpholinothieno[3,2-d]pyrimidine-6-sulfonyl chloride 17 was added 2-(piperazin-1-yl)ethanol via General Procedure C. The product was purified via reverse phase HPLC to give 12.2 mg of 214. MS (Q1) 529.1 (M)+.

Example 141

6-(4-(2-hydroxyethyl)piperazinesulfonyl)-2-(1H-indazol-4-yl)-4-morpholinothieno[3,2-d]pyrimidine 215

To 40 mg of 2-chloro-4-morpholinothieno[3,2-d]pyrimidine-6-sulfonyl chloride 17 was added 2-(piperazin-1-yl)ethanol via General Procedure C. The product was purified via reverse phase HPLC to give 215. MS (Q1) 530.2 (M)+.

Example 142

6-(4-hydroxypiperidinesulfonyl)-2-(1H-indazol-4-yl)-4-morpholinothieno[3,2-d]pyrimidine 216

To 40 mg of 2-chloro-4-morpholinothieno[3,2-d]pyrimidine-6-sulfonyl chloride 17 was added piperidin-4-ol via General Procedure C. The product was purified via reverse phase HPLC to give 6.4 mg of 216. MS (Q1) 501.1 (M)+.

Example 143

6-(3-hydroxypyrrolidinesulfonyl)-2-(1H-indazol-4-yl)-4-morpholinothieno[3,2-d]pyrimidine 217

To 40 mg of 2-chloro-4-morpholinothieno[3,2-d]pyrimidine-6-sulfonyl chloride 17 was added pyrrolidin-3-ol via General Procedure C. The product was purified via reverse phase HPLC to give 3.3 mg of 217. MS (Q1) 487.1 (M)+.

Example 144

6-(2-piperidinylethylaminosulfonyl)-2-(1H-indazol-4-yl)-4-morpholinothieno[3,2-d]pyrimidine 218

To 40 mg of 2-chloro-4-morpholinothieno[3,2-d]pyrimidine-6-sulfonyl chloride 17 was added 2-(piperidin-1-yl)ethanamine via General Procedure C. The product was purified via reverse phase HPLC to give 13.6 mg of 218. MS (Q1) 528.2 (M)+.

Example 145

6-(2-N-morpholinoethylaminosulfonyl)-2-(1H-indazol-4-yl)-4-morpholinothieno[3,2-d]pyrimidine 219

To 40 mg of 2-chloro-4-morpholinothieno[3,2-d]pyrimidine-6-sulfonyl chloride 17 was added 2-morpholinoethanamine via General Procedure C. The product was purified via reverse phase HPLC to give 7.4 mg of 219. MS (Q1) 530.1 (M)+.

Example 146

6-(3-methoxypropylaminosulfonyl)-2-(1H-indazol-4-yl)-4-morpholinothieno[3,2-d]pyrimidine 220

To 40 mg of 2-chloro-4-morpholinothieno[3,2-d]pyrimidine-6-sulfonyl chloride 17 was added 3-methoxypropan-1-amine via General Procedure C. The product was purified via reverse phase HPLC to give 8.5 mg of 220. MS (Q1) 489.1 (M)+.

Example 147

6-(N,N-bis-2-hydroxyethylaminosulfonyl)-2-(1H-indazol-4-yl)-4-morpholinothieno[3,2-d]pyrimidine 221

To 40 mg of 2-chloro-4-morpholinothieno[3,2-d]pyrimidine-6-sulfonyl chloride 17 was added diethanolamine via General Procedure C. The product was purified via reverse phase HPLC to give 6.9 mg of 221. MS (Q1) 505.1 (M)+.

Example 148

6-(2-hydroxyethylaminosulfonyl)-2-(1H-indazol-4-yl)-4-morpholinothieno[3,2-d]pyrimidine 222

To 40 mg of 2-chloro-4-morpholinothieno[3,2-d]pyrimidine-6-sulfonyl chloride 17 was added ethanolamine via General Procedure C. The product was purified via reverse phase HPLC to give 3.6 mg of 222. MS (Q1) 461.1 (M)+.

Example 149

6-(dimethylaminosulfonyl)-2-(1H-indazol-4-yl)-4-morpholinothieno[3,2-d]pyrimidine 223

To 40 mg of 2-chloro-4-morpholinothieno[3,2-d]pyrimidine-6-sulfonyl chloride 17 was added N,N-dimethylamine HCl via General Procedure C. The product was purified via reverse phase HPLC to give 4.9 mg of 223. MS (Q1) 445.1 (M)+.

Example 150

6-(methylaminosulfonyl)-2-(1H-indazol-4-yl)-4-morpholinothieno[3,2-d]pyrimidine 224

To 40 mg of 2-chloro-4-morpholinothieno[3,2-d]pyrimidine-6-sulfonyl chloride 17 was added methylamine HCl via General Procedure C. The product was purified via reverse phase HPLC to give 9.6 mg of 224. MS (Q1) 431.1 (M)+.

Example 151

2-(1H-Indazol-4-yl)-4-morpholinothieno[3,2-d]pyrimidin-6-amine 225

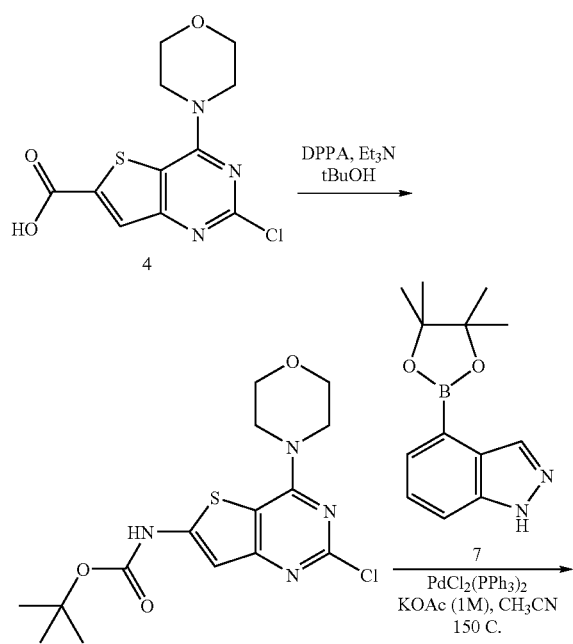

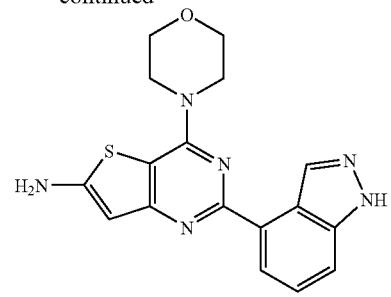

2-Chloro-4-morpholinothieno[3,2-d]pyrimidine-6-carboxylic acid (1 g), 791 µL of diphenylphorylazide, 511 µL of triphenylamine in t-BuOH was refluxed for 4 h. Upon completion, the reaction mixture was evaporated and the residue was dissolved in ethyl acetate (150 mL), and then washed with saturated sodium bicarbonate (50 mL), 5% citric acid (50 mL) and brine (60 mL). The organic layer was dried over $MgSO_4$, filtered and evaporated. The residue was purified by ISCO CombiFlash (0-50% ethyl acetate/hexane) to yield tert-butyl 2-chloro-4-morpholinothieno[3,2-d]pyrimidin-6-ylcarbamate (890 mg, 72%)

Tert-butyl 2-chloro-4-morpholinothieno[3,2-d]pyrimidin-6-ylcarbamate (50 mg) was coupled to 4-(4,4,5,5-tetramethyl-1,3,2-dioxaborolan-2-yl)-1H-indazole 7 via General Procedure A. The product was purified by reverse phase HPLC to yield 8.8 mg of 225. MS (Q1) 353 (M)+

Example 152

2-(2-(1H-indazol-4-yl)-4-morpholinothieno[3,2-d]pyrimidin-6-ylamino)ethanol 226

2-Chloro-6-iodo-4-morpholinothieno[3,2-d]pyrimidine 19 (150 mg), 2-oxazolidinone (103 mg), potassium phosphate tribasic (250 mg), copper iodide (7 mg), 4 µL of N,N-dimethylethylenediamine in 2 mL of 1,4-dioxane was heated to 100° C. for 15 hr. The reaction mixture was evaporated and the residue was diluted with ethyl acetate (50 mL), washed with brine, dried over $MgSO_4$, filtered and evaporated. The crude product was purified on reverse phase HPLC to give 2-(2-chloro-4-morpholinothieno[3,2-d]pyrimidin-6-ylamino)ethanol as a by-product.

2-(2-Chloro-4-morpholinothieno[3,2-d]pyrimidin-6-ylamino)ethanol (28 mg) was coupled to 4-(4,4,5,5-tetramethyl-1,3,2-dioxaborolan-2-yl)-1H-indazole 7 via General Procedure A. The product was purified by reverse phase HPLC to yield 21 mg of 226. MS (Q1) 397 (M)+

Example 153

(2-(1H-indazol-4-yl)-4-morpholinothieno[3,2-d]pyrimidin-6-yl)-N-sulfonylmethyl-N-(2-methoxyethyl)methanamine 227

To a stirring solution of 2-methoxyethylamine (0.58 ml) in dichloromethane (10 ml) was added triethylamine (1.0 ml) and methanesulphonyl chloride (0.51 ml). The mixture was stirred at room temperature overnight. The solvents were removed in vacuo to give a crude product which was purified by flash chromatography to give N-(2-Methoxy-ethyl)-methanesulfonamide (0.74 g).

To a solution of N-(2-Methoxy-ethyl)-methanesulfonamide (61 mg) in tetrahydrofuran (1.5 ml) under nitrogen was added sodium hydride, 60% dispersion in mineral oil, (18 mg). The reaction mixture was stirred at room temperature for 30 minutes. 6-Bromomethyl-2-chloro-4-morpholin-4-yl-thieno[3,2-d]pyrimidine (140 mg) was added. The reaction mixture was stirred at room temperature for 2 hours and then 50° C. for 5 hours. The solvents were removed in vacuo to give a crude product. This was purified by flash chromatography to give N-(2-Chloro-4-morpholin-4-yl-thieno[3,2-d]pyrimidin-6-ylmethyl)-N-(2-methoxy-ethyl)-methanesulfonamide (124 mg).

N-(2-Chloro-4-morpholin-4-yl-thieno[3,2-d]pyrimidin-6-ylmethyl)-N-(2-methoxy-ethyl)-methanesulfonamide was reacted with 4-(4,4,5,5-tetramethyl-[1,3,2]dioxaborolan-2-yl)-1H-indazole in general procedure A. Purification buy flash chromatography on silica yielded 227. NMR: 400 MHz; CDCl3: 3.00 (3H, s); 3.40 (3H, s); 3.56 (2H,m); 3.60 (2H, m); 3.93 (4H, t, J=4.8 Hz); 3.98 (4H, t, J=4.82 Hs); 7.50 (1H, s); 7.54 (1H, d, J=4.2 Hz); 7.51 (1H, d, J=8.2 Hz); 9.3 (1H, s); 10.15 (1H, s) MS: (ESI+): 503

Example 154

1-(4-(4-morpholinothieno[3,2-d]pyrimidin-2-yl)indolin-1-yl)ethanone 228

To a solution of 2-(1H-Indol-4-yl)-4-morpholin-4-yl-thieno[3,2-d]pyrimidine 199 (100 mg) in acetic acid (2 ml) was added sodium cyanoborohydride (76 mg) and the reaction mixture was heated at 60° C. overnight. The mixture was then basified and extracted into dichloromethane, organic layer was dried (Mg$_2$SO$_4$), filtered and volatiles removed in vacuo. Flash chromatography and recrystallization from hot dichloromethane/hexane gave 228 (11 mg). NMR: (DMSOd6): 2.21 (3H, s), 3.70 (2H, t, J=8.6), 3.80-3.86 (4H, m), 3.98-4.04 (4H, m), 4.17 (2H, t, J=8.5), 7.30 (1H, t, J=7.9), 7.55 (1H, d, J=5.6), 8.00 (1H, d, J=8.4), 8.25 (1H, d, J=7.8), 8.30 (1H, d, J=5.6) MS: (ESI+): MH+ 381

Example 155

2-(1H-indazol-6-yl)-4-morpholinothieno[3,2-d]pyrimidine 229

A mixture of 2-chloro-4-morpholin-4-yl-thieno[3,2-d]pyrimidine 4 (772 mg), 3-amino-4-methylbenzeneboronic acid (502 mg), DME (10 mL), water (5 mL), sodium carbonate (640 mg) and PdCl$_2$(PPh$_3$)$_2$ (100 mg) was heated to reflux for 16 hours. The reaction mixture was then cooled, diluted with ethyl acetate, and reduced in vacuo. The residue was purified using flash chromatography to yield 2-methyl-5-(4-morpholin-4-yl-thieno[3,2-d]pyrimidin-2-yl)-phenylamine (930 mg).

To a solution of 2-methyl-5-(4-morpholin-4-yl-thieno[3,2-d]pyrimidin-2-yl)-phenylamine (99 mg) in chloroform (10 mL) and acetic acid (2 mL) was added isoamyl nitrite (44 µL). The reaction mixture was stirred for 2 days at room temperature. The mixture was then quenched with sodium bicarbonate solution and extracted in to chloroform and reduced in vacuo. The residue was purified using flash chromatography to yield 229. MS: ESI MH+ 338

Example 156

4-(2-(1H-indazol-4-yl)-4-morpholinothieno[3,2-d]pyrimidin-6-yl)-1-((thiazol-2-yl)methyl)piperidin-4-ol 230

4-(2-chloro-4-morpholinothieno[3,2-d]pyrimidin-6-yl)piperidin-4-ol dihydrochloride salt (250 mg) and 2-thiazolecarboxaldehyde (0.08 ml) were stirred together in 1,2-dichloroethane (3 ml) and triethylamine (0.18 ml) with sodium triacetoxyborohydride (187 mg) at room temperature overnight. Dichloromethane/brine extraction and purification on silica yielded 4-(2-chloro-4-morpholin-4-yl-thieno[3,2-d]pyrimidin-6-yl)-1-thiazol-2-ylmethyl-piperidin-4-ol (119 mg).

Suzuki coupling with 4-(2-chloro-4-morpholin-4-yl-thieno[3,2-d]pyrimidin-6-yl)-1-thiazol-piperidin-4-ol and indazole boronate ester was carried out using the standard conditions to give 230. NMR: (DMSO): 1.86-1.94 (2H, m), 2.10-2.18 (2H, m), 2.60-2.68 (2H, m), 2.75-2.82 (2H, m), 3.84-3.87 (4H, m), 3.90 (2H, s), 4.03-4.06 (4H, m), 7.44-7.46 (1H, m), 7.62-7.69 (2H, m), 7.73 (1H, d), 8.23 (1H, d), 8.90 (1H, s), 13.15 (1H, br) MS: (ESI+): MH+ 534 (44%)

Example 157

4-(2-(1H-indazol-4-yl)-4-morpholinothieno[3,2-d]pyrimidin-6-yl)-1-(methylsulfonyl)piperidin-4-ol 231

To solution of 2-chloro-4-morpholin-4-yl-thieno[3,2-d]pyrimidine 4 (1.22 g) in anhydrous tetrahydrofuran (20 ml) stirring at −78° C. was added 2.5M n-butyllithium in hexanes (2.3 mL). The reaction mixture was warmed gradually to −40° C. over 1 hour, cooled to −78° C., and 1-BOC-4-Piperidone (950 mg) was added. The reaction mixture was gradually warmed to room temperature and then left to stir for 2 hours, poured into ice/water and extracted into ethyl acetate. After the usual drying and evaporation of the solvent, the residue was purified by flash chromatography to give 4-(2-chloro-4-morpholin-4-yl-thieno[3,2-d]pyrimidin-6-yl)-4-hydroxy-piperidine-1-carboxylic acid tert-butyl ester.

The BOC group was then removed using HCl in ether under standard procedures to yield 4-(2-chloro-4-morpholin-4-yl-thieno[3,2-d]pyrimidine-4-ol dihydrochloride salt. This was reacted with methanesulfonic acid benzotriazol-1-yl ester in DMF and triethylamine to give 4-(2-chloro-4-morpholin-4-yl-thieno[3,2-d]pyrimidin-6-yl)-1-methanesulfonyl-piperidin-4-ol. Methanesulfonic acid benzotriazol-1-yl ester was prepared using conditions described in Tetrahedron Letters, 40(1), pp 117-120, 1999.

Suzuki coupling with 4-(2-chloro-4-morpholin-4-yl-thieno[3,2-d]pyrimidin-6-yl)-1-methanesulfonyl-piperidin-4-ol and indazole boronate ester was carried out using the standard conditions to give 231. NMR: (CDCl3/MeOD): 1.95-2.02 (2H, m), 2.08-2.16 (2H, m), 2.73 (3H, s), 3.08-3.14 (2H, m), 3.55-3.60 (2H, m), 3.75-3.78 (4H, m), 3.98-4.02 (4H, m), 7.28 (1H, s), 7.33-7.38 (1H, m), 7.49-7.52 (1H, d), 7.97-8.02 (1H, d), 8.68 (1H, s) MS: (ESI+): MH+ 515 (100%)

Example 158

4-(2-(1H-indazol-4-yl)-4-morpholinothieno[3,2-d]pyrimidin-6-yl)-1-((pyridin-2-yl)methyl)piperidin-4-ol 232

4-(2-Chloro-4-morpholinothieno[3,2-d]pyrimidin-6-yl)piperidin-4-ol dihydrochloride salt (250 mg) and 2-pyridylcarboxaldehyde (0.084 ml) were stirred together in 1,2-dichloroethane (3 ml) and triethylamine (0.18 ml) with sodium triacetoxyborohydride (187 mg) at room temperature overnight. Dichloromethane/brine extraction and purification on silica yielded 4-(2-chloro-4-morpholin-4-yl-thieno[3,2-d]pyrimidin-6-yl)-1-pyridyl-2-ylmethyl-piperidin-4-ol (204 mg).

Suzuki coupling with 4-(2-chloro-4-morpholin-4-yl-thieno[3,2-d]pyrimidin-6-yl)-1-pyridyl-piperidin-4-ol and indazole boronate ester was carried out using the standard conditions to give 232. NMR: (CDCl3): 2.05-2.11 (2H, m), 2.29-2.38 (2H, m), 2.70-2.78 (2H, m), 2.84-2.89 (2H, m), 3.80 (2H, s), 3.95-4.02 (4H, m), 4.15-4.19 (4H, m), 7.29-7.32 (1H, m), 7.42 (1H, s), 7.53-7.58 (1H, m), 7.60 (1H, d), 7.68 (1h, d), 7.82 (1H, t), 8.20 (1H, d), 8.53 (1H, d), 8.90 (1H, s) MS: (ESI+): MH+ 528 (18%)

Example 159

2-(1H-indazol-4-yl)-4-morpholino-6-phenylfuro[3,2-d]pyrimidine 233

2-Chloro-4-morpholino-6-phenylfuro[3,2-d]pyrimidine (50 mg, 1.0 eq) was dissolved in toluene/ethanol/water (4:2:1, 2.8 ml) and treated with 4-(4,4,5,5-tetramethyl-1,3,2-dioxaborolan-2-yl)-1H-indazole 7 (97 mg, 2.5 eq), PdCl$_2$(PPh$_3$)$_2$ (13.3 mg, 0.12 eq) and sodium carbonate (59 mg, 3.5 eq). The vial was sealed and heated with stirring in the microwave to 150° C. for 25 minutes. The crude reaction mixture was concentrated and purified by reverse phase HPLC to afford 233 MS (Q1) 398 (M)$^+$.

Example 160

2-(1H-indazol-4-yl)-6-(methylsulfonyl)-4-morpholinothieno[3,2-d]pyrimidine 234

2-Chloro-4-morpholinothieno[3,2-d]pyrimidine 4 (2 gm) was cooled to −78° C. in 50 mL of THF before adding 1.3 eq of a 2.5M solution of nBuLi in hexanes. The reaction was stirred at −78° C. for 30 minutes before warming to −40° C. for several minutes to allow for complete formation of the Lithium anion. The reaction was then re-cooled to −78° C. and sulfur dioxide gas was bubbled in via cannula to the reaction solution for 2 minutes. 5 mL of the reaction mixture was removed via syringe and quenched into a saturated ammonium chloride solution. This intermediate was extremely water soluble and had to be purified via reverse phase HPLC to afford 130 mg of pure 2-chloro-4-morpholinothieno[3,2-d]pyrimidine-6-sulfinic acid.

To 40 mg of 2-chloro-4-morpholinothieno[3,2-d]pyrimidine-6-sulfinic acid in 1.5 mL of DMF was added 1.05 eq of NaH (60% oil dispersion). The reaction was stirred at room temperature for 30 minutes prior to addition of 1.05 eq of iodomethane, whereupon the temperature was raised to 70° C. and the reaction was complete in 30 minutes. The reaction was cooled to room temperature and then extracted into ethyl acetate with a saturated bicarbonate solution which was back-extracted one time with ethyl acetate. The organic layers were combined, dried with MgSO$_4$, filtered and concentrated to dryness. The crude chloride was subjected to Procedure A to give 22 mg of 234. MS (Q1) 416.1 (M)+.

Example 161

2-(2-(1H-indazol-4-yl)-4-morpholinothieno[3,2-d]pyrimidin-6-yl)propan-2-ol 235

2-Chloro-4-morpholinothieno[3,2-d]pyrimidine 4 (200 mg) was reacted with acetone following general procedure D to give the corresponding tertiary alcohol. 120 mg of this crude material was used in a palladium catalyzed cross coupling reaction following general procedure A to give 68 mg of 235 after reversed phase HPLC purification. MS (Q1) 396 (M)+

Example 162

2-(1H-indazol-4-yl)-4-morpholinothieno[3,2-d]pyrimidine-6-(N-phenylsulfonyl)carboxamide 236

To 50 mg of 2-chloro-4-morpholinothieno[3,2-d]pyrimidine-6-carboxylic acid in 1 mL of THF was added 1.1 eq of carbonyldiimidazole. The reaction was stirred for 15 minutes at room temperature before addition of a 1 mL solution containing 2 eq DBU and 2 eq of benzenesulfonamide in THF. The reaction was stirred overnight at ambient temperature and extracted into 0.1N HCl and DCM. The organic layer was concentrated and subjected to Procedure A to give 11.6 mg of 236. MS (Q1) 520.7 (M)+.

Example 163

(3-(2-(1H-indazol-4-yl)-4-morpholinothieno[3,2-d]pyrimidin-6-yl)phenyl)methanol 237

2-Chloro-6-iodo-4-morpholinothieno[3,2-d]pyrimidine 19 (50 mg) was coupled to 3-hydroxymethylphenylboronic acid via General Procedure I. The product was purified by reverse phase HPLC to yield 14.3 mg of 237. MS (Q1) 444 (M)$^+$.

Example 164

N-(3-(2-(1H-indazol-4-yl)-4-morpholinothieno[3,2-d]pyrimidin-6-yl)phenyl)acetamide 238

2-Chloro-6-iodo-4-morpholinothieno[3,2-d]pyrimidine 19 (50 mg) was coupled to 3-acetylaminophenylboronic acid via General Procedure I. The product was purified by reverse phase HPLC to yield 24.1 mg of 238. MS (Q1) 471 (M)$^+$

Example 165

2-(1H-indazol-4-yl)-4-morpholino-6-(pyridin-4-yl)thieno[3,2-d]pyrimidine 239

2-Chloro-6-iodo-4-morpholinothieno[3,2-d]pyrimidine 19 (50 mg) was coupled to 4-pyridineboronic acid via General Procedure I. The product was purified by reverse phase HPLC to yield 8.6 mg of 239. MS (Q1) 415 (M)$^+$

Example 166

2-(1H-indazol-4-yl)-4-morpholino-6-(pyridin-3-yl)thieno[3,2-d]pyrimidine 240

2-Chloro-6-iodo-4-morpholinothieno[3,2-d]pyrimidine 19 (50 mg) was coupled to 3-pyridineboronic acid via General Procedure I. The product was purified by reverse phase HPLC to yield 19.7 mg of 240. MS (Q1) 415 (M)+

Example 167

2-(1H-indazol-4-yl)-6-(3,4-dimethoxyphenyl)-4-morpholinothieno[3,2-d]pyrimidine 241

2-Chloro-6-iodo-4-morpholinothieno[3,2-d]pyrimidine 19 (50 mg) was coupled to 3,4-dimethoxyphenylboronic acid via General Procedure I. The product was purified by reverse phase HPLC to yield 35.3 mg of 241. MS (Q1) 474 (M)+

Example 168

2-(1H-indazol-4-yl)-4-morpholino-6-(4-acetyl-piperazinosulfonyl)thieno[3,2-d]pyrimidine 242

To 40 mg of 2-chloro-4-morpholinothieno[3,2-d]pyrimidine-6-sulfonyl chloride 17 was added 1-acetylpiperazine via General Procedure C. The product was purified via reverse phase HPLC to give 32.9 mg of 242. MS (Q1) 527.7 (M)+

Example 169

2-(1H-indazol-4-yl)-4-morpholino-6-(4-methylsulfonyl-piperazinosulfonyl)thieno[3,2-d]pyrimidine 243

2-Chloro-4-morpholinothieno[3,2-d]pyrimidine (2 gm) 4 was cooled to −78° C. in 50 mL of THF before adding 1.3 eq of a 2.5M solution of nBuLi in hexanes. The reaction was stirred at −78° C. for 30 minutes before warming to −40° C. for several minutes to allow for complete formation of the lithium anion. The reaction was then re-cooled to −78° C. and sulfur dioxide gas was bubbled in via cannula to the reaction solution for 2 minutes. The reaction was slowly warmed to 0° C. and 5 eq of n-chlorosuccinmide were added and the reaction was stirred at room temperature until complete. The THF was evaporated by rotovap and then the reaction was quenched with water. The resultant solid that crashed out of the aqueous layer was then collected by Buchner funnel, rinsed with water and dried overnight under vacuum to yield 2.4 g of 2-chloro-4-morpholinothieno[3,2-d]pyrimidine-6-sulfonyl chloride 17 as a brown solid.

To 40 mg of 2-chloro-4-morpholinothieno[3,2-d]pyrimidine-6-sulfonyl chloride 17 was added 1-methansulfonylpiperazine via General Procedure C. The product was purified via reverse phase HPLC to give 10.7 mg of 243. MS (Q1) 563.6 (M)+

Example 170

(2-(1H-indazol-4-yl)-4-morpholinothieno[3,2-d]pyrimidin-6-yl)(4-(2-hydroxyethyl)piperazin-1-yl)methanone 244

2-(1H-Indazol-4-yl)-4-morpholinothieno[3,2-d]pyrimidine-6-carboxylic acid 13 (30 mg) was coupled to 2-(piperazin-1-yl)ethanol via General Procedure B. The product was purified via reverse phase HPLC to give 20.7 mg of 244. MS (Q1) 493.8 (M)+

Example 171

N-benzyl-2-(1H-indazol-4-yl)-4-morpholinothieno[3,2-d]pyrimidine-6-carboxamide 245

2-(1H-Indazol-4-yl)-4-morpholinothieno[3,2-d]pyrimidine-6-carboxylic acid 13 (30 mg) was coupled to benzylamine via General Procedure B. The product was purified via reverse phase HPLC to give 8.9 mg of 245. MS (Q1) 470.8 (M)+

Example 172

N-(3-hydroxyphenyl)-2-(1H-indazol-4-yl)-4-morpholinothieno[3,2-d]pyrimidine-6-carboxamide 246

2-(1H-Indazol-4-yl)-4-morpholinothieno[3,2-d]pyrimidine-6-carboxylic acid 13 (30 mg) was coupled to 3-hydroxyaniline via General Procedure B. The product was purified via reverse phase HPLC to give 7.7 mg of 246. MS (Q1) 472.7 (M)+

Example 173

2-(1H-indazol-4-yl)-4-morpholino-N-phenylthieno[3,2-d]pyrimidine-6-carboxamide 247

2-(1H-Indazol-4-yl)-4-morpholinothieno[3,2-d]pyrimidine-6-carboxylic acid 13 (30 mg) was coupled to aniline via General Procedure B. The product was purified via reverse phase HPLC to give 6.4 mg of 247. MS (Q1) 456.8 (M)+.

Example 174

N-((dimethylcarbamoyl)methyl)-2-(1H-indazol-4-yl)-4-morpholinothieno[3,2-d]pyrimidine-6-carboxamide 248

N-Cbz Glycine (9.6 mmol) was dissolved in DMF (30 mL). Diisopropylethylamine (40 mmol), EDC HCl (10 mmol), HOAt (10 mmol) and dimethylamine hydrochloride (10 mmol) were subsequently added to the solution. The reaction was allowed to stir overnight. Ethyl acetate (100 mL) was added to the solution and the organic was washed with 1 N HCl followed by a wash with an aqueous solution of saturated sodium bicarbonate. The organic layer was dried with magnesium sulfate and concentrated to give 1.02 g of 2-(benzylamino)-N,N-dimethylacetamide. 2-(benzylamino)-N,N-dimethylacetamide (4.3 mmol) was dissolved in methanol (20 mL) and combined with 5% loaded Pd/C (0.21 mmol). The solution was stirred under a hydrogen filled balloon for four hours then filtered through celite and concentrated to give 402 mg of 2-amino-N,N-dimethylacetamide as a yellow oil.

30 mg of 2-(1H-indazol-4-yl)-4-morpholinothieno[3,2-d]pyrimidine-6-carboxylic acid 13 was coupled to 2-amino-N,N-dimethylacetamide via General Procedure B. The product was purified via reverse phase HPLC to give 6.5 mg of 248. MS (Q1) 465.8 (M)+.

Example 175

(2-(1H-indazol-4-yl)-4-morpholinothieno[3,2-d]pyrimidin-6-yl)(4-(pyrrolidin-1-yl)piperidin-1-yl)methanone 249

2-(1H-Indazol-4-yl)-4-morpholinothieno[3,2-d]pyrimidine-6-carboxylic acid 13 (30 mg) was coupled to 4-(pyrrolidin-1-yl)piperidine via General Procedure B. The product was purified via reverse phase HPLC to give 13.2 mg of 249. MS (Q1) 517.8 (M)+.

Example 176

(2-(1H-indazol-4-yl)-4-morpholinothieno[3,2-d]pyrimidin-6-yl)(piperazin-2-one)methanone 250

2-(1H-Indazol-4-yl)-4-morpholinothieno[3,2-d]pyrimidine-6-carboxylic acid 13 (30 mg) was coupled to piperazin-2-one via General Procedure B. The product was purified via reverse phase HPLC to give 16.4 mg of 250. MS (Q1) 463.7 (M)+.

Example 177

(2-(1H-indazol-4-yl)-4-morpholinothieno[3,2-d]pyrimidin-6-yl)(4-hydroxypiperidin-1-yl)methanone 251

2-(1H-Indazol-4-yl)-4-morpholinothieno[3,2-d]pyrimidine-6-carboxylic acid 13 (30 mg) was coupled to piperidin-4-ol via General Procedure B. The product was purified via reverse phase HPLC to give 12.9 mg of 251. MS (Q1) 464.8 (M)+.

Example 178

(2-(1H-indazol-4-yl)-4-morpholinothieno[3,2-d]pyrimidin-6-yl)(morpholino)methanone 252

2-(1H-Indazol-4-yl)-4-morpholinothieno[3,2-d]pyrimidine-6-carboxylic acid 13 (30 mg) was coupled to morpholine via General Procedure B. The product was purified via reverse phase HPLC to give 8.7 mg of 252. MS (Q1) 450.8 (M)+.

Example 179

(2-(1H-indazol-4-yl)-4-morpholinothieno[3,2-d]pyrimidin-6-yl)(3-(methylamino)pyrrolidin-1-yl)methanone 253

2-(1H-Indazol-4-yl)-4-morpholinothieno[3,2-d]pyrimidine-6-carboxylic acid 13 (30 mg) was coupled to N-methylpyrrolidin-3-amine via General Procedure B. The product was purified via reverse phase HPLC to give 16.7 mg of 253. MS (Q1) 463.8 (M)+.

Example 180

N-(2,2,2-trifluoroethyl)-2-(1H-indazol-4-yl)-4-morpholinothieno[3,2-d]pyrimidine-6-carboxamide 254

2-(1H-Indazol-4-yl)-4-morpholinothieno[3,2-d]pyrimidine-6-carboxylic acid 13 (30 mg) was coupled to 2,2,2-trifluoroethanamine via General Procedure B. The product was purified via reverse phase HPLC to give 10.4 mg of 254. MS (Q1) 462.7 (M)+.

Example 181

2-(1H-indazol-4-yl)-4-morpholino-N-(2-morpholinoethyl)thieno[3,2-d]pyrimidine-6-carboxamide 255

2-(1H-Indazol-4-yl)-4-morpholinothieno[3,2-d]pyrimidine-6-carboxylic acid 13 (30 mg) was coupled to 2-morpholinoethanamine via General Procedure B. The product was purified via reverse phase HPLC to give 22 mg of 255. MS (Q1) 493.8 (M)+.

Example 182

2-(1H-indazol-4-yl)-N-isobutyl-4-morpholinothieno[3,2-d]pyrimidine-6-carboxamide 256

2-(1H-Indazol-4-yl)-4-morpholinothieno[3,2-d]pyrimidine-6-carboxylic acid 13 (30 mg) was coupled to 2-methylpropan-1-amine via General Procedure B. The product was purified via reverse phase HPLC to give 13.2 mg of 256. MS (Q1) 436.8 (M)+.

Example 183

2-(1H-indazol-4-yl)-4-morpholino-N-(2-(piperidin-1-yl)ethyl)thieno[3,2-d]pyrimidine-6-carboxamide 257

2-(1H-Indazol-4-yl)-4-morpholinothieno[3,2-d]pyrimidine-6-carboxylic acid 13 (30 mg) was coupled to 2-(piperidin-1-yl)ethanamine via General Procedure B. The product was purified via reverse phase HPLC to give 20.4 mg of 257. MS (Q1) 491.8 (M)+.

Example 184

N,N-bis(2-hydroxyethyl)-2-(1H-indazol-4-yl)-4-morpholinothieno[3,2-d]pyrimidine-6-carboxamide 258

2-(1H-Indazol-4-yl)-4-morpholinothieno[3,2-d]pyrimidine-6-carboxylic acid 13 (30 mg) was coupled to diethanolamine via General Procedure B. The product was purified via reverse phase HPLC to give 15.8 mg of 258. MS (Q1) 468.8 (M)+.

Example 185

2-(2-(1H-indazol-4-yl)-4-morpholinothieno[3,2-d]pyrimidin-6-yl)ethanol 259

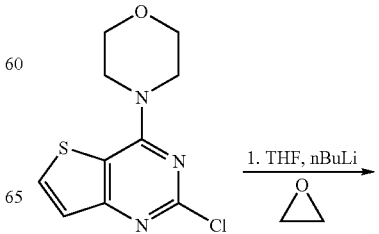

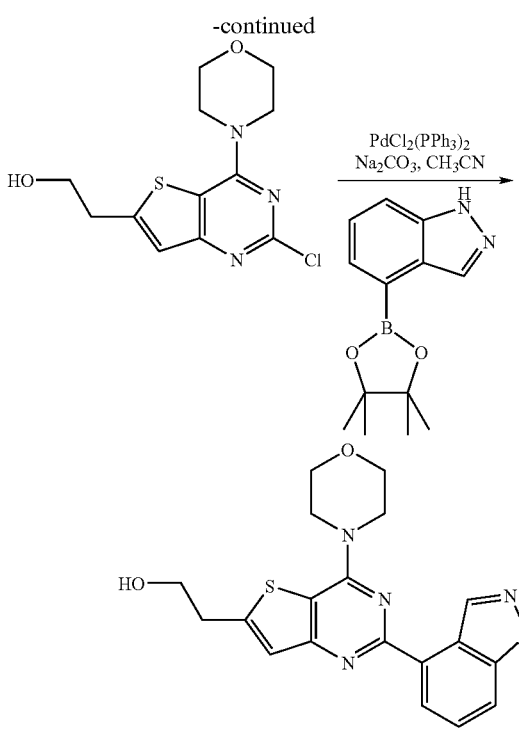

-continued

2-Chloro-4-morpholinothieno[3,2-d]pyrimidine 4 (1 gm) was dissolved in 15 mL of THF and cooled to −78° C. in a dry ice acetone bath before adding 2.0 mL of 2.5 M nBuLi. The reaction was stirred for 30 min and then warmed to −40° C. Ethylene oxide was bubbled in to the solution for approximately 10 min. and the reaction stirred for 2 h at −40° C. It was then pored into saturated ammonium chloride and extracted with ethyl acetate. After evaporation of the organic layer the crude reaction was chromatographed on 40 g of silica using a 0 to 100% ethyl acetate gradient in hexanes to give 333 mg of alcohol. 45 mg of this intermediate was combined with 36 mg of boronic ester, 0.5 mL of acetonitrile, 0.5 mL of 1.0 M sodium carbonate and 5 to 10 mg of $PdCl_2(PPh_3)_2$ and heated to 140° C. for 10 min. in a microwave reactor and then for an additional 20 min at 145° C. The reaction was extracted with ethyl acetate and the product was purified on reversed phase HPLC to yield 18 mg of 259. MS (Q1) 382 (M)+

Example 186

N-(1-hydroxypropan-2-yl)-2-(1H-indazol-4-yl)-4-morpholinothieno[3,2-d]pyrimidine-6-carboxamide 260

2-(1H-Indazol-4-yl)-4-morpholinothieno[3,2-d]pyrimidine-6-carboxylic acid 13 (30 mg) was coupled to 2-aminopropan-1-ol via General Procedure B. The product was purified via reverse phase HPLC to give 22.3 mg of 260. MS (Q1) 438.8 (M)+.

Example 187

(2-(1H-indazol-4-yl)-4-morpholinothieno[3,2-d]pyrimidin-6-yl)(4-methylpiperazin-1-yl)methanone 261

2-(1H-Indazol-4-yl)-4-morpholinothieno[3,2-d]pyrimidine-6-carboxylic acid 13 (30 mg) was coupled to 1-methylpiperazine via General Procedure B. The product was purified via reverse phase HPLC to give 17.6 mg of 261. MS (Q1) 561.8 (M)+.

Example 188

(2-(1H-indazol-4-yl)-4-morpholinothieno[3,2-d]pyrimidin-6-yl)(4-methylsulfonylpiperazin-1-yl)methanone 262

2-(1H-Indazol-4-yl)-4-morpholinothieno[3,2-d]pyrimidine-6-carboxylic acid 13 (30 mg) was coupled to 1-methanesulfonylpiperazine via General Procedure B. The product was purified via reverse phase HPLC to give 19.2 mg of 262. MS (Q1) 527.7 (M)+.

Example 189

2-(1H-indazol-4-yl)-N,N-dimethyl-4-morpholinothieno[3,2-d]pyrimidine-6-carboxamide 263

2-(1H-Indazol-4-yl)-4-morpholinothieno[3,2-d]pyrimidine-6-carboxylic acid 13 (30 mg) was coupled to N,N-dimethylamine HCl via General Procedure B. The product was purified via reverse phase HPLC to give 19.7 mg of 263. MS (Q1) 408.8 (M)+.

Example 190

2-(1H-indazol-4-yl)-6-(4-(methylsulfonyl)phenyl)-4-morpholinothieno[3,2-d]pyrimidine 264

2-Chloro-6-iodo-4-morpholinothieno[3,2-d]pyrimidine 19 (50 mg) was coupled to 4-methylsulfonylphenylboronic acid via General Procedure I. The product was purified by reverse phase HPLC to yield 10.1 mg of 264. MS (Q1) 492 (M)+.

Example 191

2-(1H-indazol-4-yl)-6-(3-(methylsulfonyl)phenyl)-4-morpholinothieno[3,2-d]pyrimidine 265

2-Chloro-6-iodo-4-morpholinothieno[3,2-d]pyrimidine 19 (50 mg) was coupled to 3-methylsulfonylphenylboronic acid via General Procedure I. The product was purified by reverse phase HPLC to yield 26.5 mg of 265. MS (Q1) 492 (M)+.

Example 192

N-(2-hydroxyethyl)-2-(1H-indazol-4-yl)-4-morpholinothieno[3,2-d]pyrimidine-6-carboxamide 266

2-(1H-Indazol-4-yl)-4-morpholinothieno[3,2-d]pyrimidine-6-carboxylic acid 13 (30 mg) was coupled to ethanolamine HCl via General Procedure B. The product was purified via reverse phase HPLC to give 6.3 mg of 266. MS (Q1) 424.8 (M)+.

Example 193

(2-(1H-indazol-4-yl)-4-morpholinothieno[3,2-d]pyrimidin-6-yl)(4-acetylpiperazin-1-yl)methanone 267

2-Chloro-4-morpholinothieno[3,2-d]pyrimidine 4 (2.5 g) was cooled to −78° C. in 50 mL of THF before adding 1.3 eq of a 2.5M solution of nBuLi in hexanes. The reaction was stirred at −78° C. for 30 minutes before warming to −40° C. for several minutes to allow for complete formation of the Lithium anion. The reaction was then re-cooled to −78° C. and carbon dioxide gas evolved from dry ice was bubbled in via cannula to the reaction solution for 1 hour. The reaction was then slowly warmed to 0° C. over 30 minutes and the THF was concentrated by rotovap. The reaction was then quenched with water and extracted with Ethyl Acetate to remove any 2-chloro-4-morpholinothieno[3,2-d]pyrimidine. The aqueous layer was then brought to pH of 2-3 by adding concentrated HCl. The resultant solid that crashed out of the aqueous layer was then collected by Buchner funnel, rinsed with water and dried overnight under vacuum to yield 2.65 g of 2-chloro-4-morpholinothieno[3,2-d]pyrimidine-6-carboxylic acid. 500 mg of this intermediate was then subjected to Procedure A. Upon extraction into Ethyl Acetate, the product remains in the aqueous layer and is treated with 20 eq of Amberlite IR-120 ion-exchange resin for 2 hours or until the solution becomes cloudy. The solution is first filtered thru a coarse Filter Flask to remove the resin and is then filtered thru a Buchner funnel to collect the 637 mg of 2-(1H-indazol-4-yl)-4-morpholinothieno[3,2-d]pyrimidine-6-carboxylic acid 13 as a light brown solid.

30 mg of 2-(1H-indazol-4-yl)-4-morpholinothieno[3,2-d]pyrimidine-6-carboxylic acid 13 was coupled to 1-acetylpiperazine via General Procedure B. The product was purified via reverse phase HPLC to give 16.8 mg of 267. MS (Q1) 491.8 (M)+.

Example 194

(4-(2-(1H-indazol-4-yl)-4-morpholinothieno[3,2-d]pyrimidin-6-yl)phenyl)methanol 268

2-Chloro-6-iodo-4-morpholinothieno[3,2-d]pyrimidine 19 (50 mg) was coupled to 4-hydroxymethylphenylboronic acid via General Procedure I. The product was purified by reverse phase HPLC to yield 20.7 mg of 268. MS (Q1) 444 (M)+.

Example 195

1-(2-(1H-indazol-4-yl)-4-morpholinothieno[3,2-d]pyrimidin-6-yl)-2-methylpropan-2-ol 269

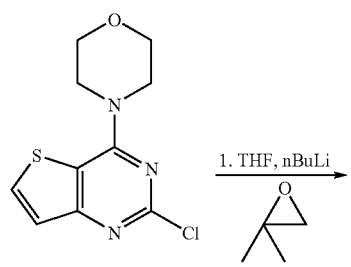

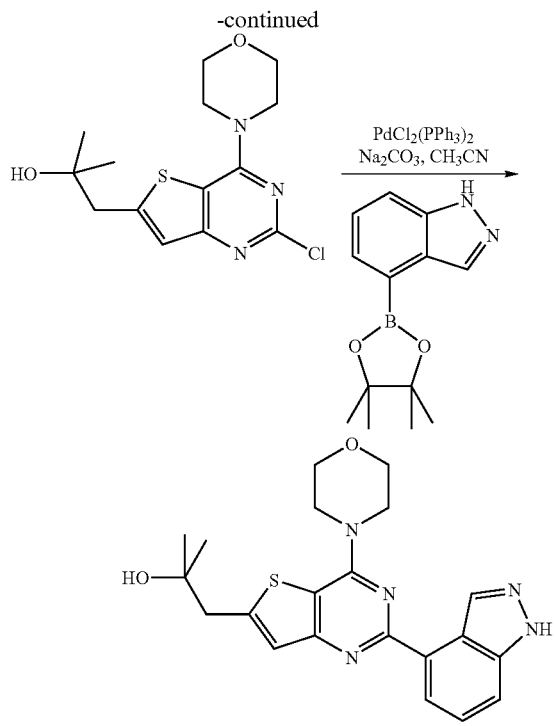

2-Chloro-4-morpholinothieno[3,2-d]pyrimidine 4 (200 mg) was dissolved in 3 mL of THF and cooled to −78° C. in a dry ice acetone bath before adding 0.33 mL of 2.5 M nBuLi. The reaction was stirred for 30 min and then warmed to −40° C. for 20 min and then recooled to −78° C. 0.08 mL of 1,2-epoxy-2-methylpropane was added to the solution and it was slowly warmed to 0° C. over 1 h at which point the reaction turned brownish. It was then pored into saturated ammonium chloride and extracted with ethyl acetate. After evaporation of the organic layer the crude reaction was chromatographed silica using a 0 to 100% ethyl acetate gradient in hexanes to give 35 mg of alcohol. This intermediate was combined with 40 mg of boronic ester, 0.5 mL of acetonitrile, 0.5 mL of 1.0 M sodium carbonate and 5 to 10 mg of PdCl$_2$(PPh$_3$)$_2$ and heated to 140° C. for 10 min. in a microwave reactor. The reaction was extracted with ethyl acetate and purified on reversed phase HPLC to yield 27 mg of 269. MS (Q1) 410 (M)+

Example 196

2-(1H-indazol-4-yl)-4-morpholinothieno[3,2-d]pyrimidine 270

To a solution of 3-bromo-2-methylaniline (1.00 g) in dioxane (15 mL) was added triethylamine (3.0 mL), Pd(OAc)$_2$ (60 mg), 2-dicyclohexylphosphinobiphenyl (377 mg) and pinacol borane (2.34 mL) and the reaction mixture was heated to 80° C. for 1 hour. The reaction mixture was then cooled, diluted with ethyl acetate, and reduced in vacuo. The residue was purified using flash chromatography to yield 2-methyl-3-(4,4,5,5-tetramethyl-[1,3,2]dioxaborolan-2-yl)-phenylamine (1.07 g).

Reaction of 2-methyl-3-(4,4,5,5-tetramethyl-[1,3,2]dioxaborolan-2-yl)-phenylamine with 2-chloro-4-morpholin-4-yl-thieno[3,2-d]pyrimidine under Suzuki conditions yielded 2-methyl-3-(4-morpholin-4-yl-thieno[3,2-d]pyrimidin-2- yl)-phenylamine. To a solution of 2-methyl-3-(4-morpholin-4-yl-thieno[3,2-d]pyrimidin-2-yl)-phenylamine (80 mg) in chloroform (8 mL) and acetic acid (4 mL) was added isoamyl nitrite (36 μL). The reaction mixture was stirred for 1 day at room temperature. The mixture was then quenched with sodium bicarbonate solution and extracted in to chloroform and reduced in vacuo. The residue was purified using flash chromatography to yield 270. MS: ESI MH+ 338

Example 197

2-(1H-indol-5-yl)-4-morpholinothieno[3,2-d]pyrimidine 271

2-Chloro-4-moropholinothieno[3.2-d]pyrimidine 4 was reacted with 5-indole boronic acid in General Procedure A on a 23.5 mmol scale to give 25.7 mg. of 271 after RP-HPLC purification. MS (Q1) 337.1 (M)+.

Example 198

2-(1H-indol-6-yl)-4-morpholinothieno[3,2-d]pyrimidine 272

2-Chloro-4-moropholinothieno[3.2-d]pyrimidine 4 was reacted with 6-indole boronic acid in General Procedure A on a 23.5 mmol scale to give 30 mg. of 272 after RP-HPLC purification. MS (Q1) 337.1 (M)+.

Example 199

N-((2-(1H-indazol-4-yl)-4-morpholinothieno[3,2-d]pyrimidin-6-yl)methyl)-N-(methyl)methylsulfonamide 273

N-(2-Chloro-4-morpholin-4-yl-thieno[3,2-d]pyrimidin-6-ylmethyl)-N-methyl-methanesulfonamide was reacted with 4-(4,4,5,5-Tetramethyl-[1,3,2]dioxaborolan-2-yl)-1H-indazole in general procedure A. Purification on silica yielded 273. NMR: (400 MHz, CDCl$_3$) 10.20 (br s, 1H), 9.02 (br s, 1H), 8.28 (d, J=7.4, 1H), 7.60 (d, J=8.3, 1H), 7.51 (t, J=7.7, 1H), 7.47 (s, 1H), 4.67 (s, 2H), 4.09 (t, J=4.8, 4H), 3.92 (t, J=4.8, 4H), 2.95 (s, 3H), 2.93 (s, 3H). MS: (ESI+)[M+H]+ 459.06

Example 200

N-[2-(1H-Indazol-4-yl)-4-morpholin-4-yl-thieno[3,2-d]pyrimidin-6-ylmethyl]-acetamide 274

Prepared according to the General Procedure K to give 274. MS (Q1) 409 (M)+

Example 201

N-[2-(1H-Indazol-4-yl)-4-morpholin-4-yl-thieno[3,2-d]pyrimidin-6-ylmethyl]-benzamide 275

Prepared according to the General Procedure K to give 275. MS (Q1) 471 (M)+

Example 202

Pyridine-2-carboxylic acid [2-(1H-indazol-4-yl)-4-morpholin-4-yl-thieno[3,2-d]pyrimidin-6-ylmethyl]-amide 276

Prepared according to the General Procedure K to give 276. MS (Q1) 472 (M)+

Example 203

N-[2-(1H-Indazol-4-yl)-4-morpholin-4-yl-thieno[3,2-d]pyrimidin-6-ylmethyl]-nicotinamide 277

Prepared according to the General Procedure K to give 277. MS (Q1) 472 (M)+

Example 204

N-[2-(1H-Indazol-4-yl)-4-morpholin-4-yl-thieno[3,2-d]pyrimidin-6-ylmethyl]-isonicotinamide 278

Prepared according to the General Procedure K to give 278. MS (Q1) 472 (M)+

Example 205

3-(2-(1H-indazol-4-yl)-4-morpholinothieno[3,2-d]pyrimidin-6-yl)-1-(4-methylpiperazin-1-yl)propan-1-one 279

Following the procedures to prepare 148, and using N-methyl piperazine, 279 was prepared. NMR: DMSO: 2.16 (3 H, s, Me), 2.20-2.28 (4 H, m, CH$_2$), 2.80-2.86 (2H, m, CH$_2$), 3.19 (2 H, t, J 7.24, CH$_2$), 3.48-3.50 (4 H, m, CH$_2$), 3.79-3.84 (4 H, m, CH$_2$), 3.98-4.02 (4 H, m, CH$_2$), 7.40 (1 H, s, Ar), 7.44 (1 H, t, J 8.0, Ar), 7.62 (1 H, d, J 8.15, Ar), 8.21 (1 H, d, J 7.35, Ar), 8.85 (1 H, s, Ar) and 13.15 (1 H, s, NH). MS: (ESI+): MH+ 492.21

Example 206

2-(1H-indazol-4-yl)-6-(methoxymethyl)-4-morpholinothieno[3,2-d]pyrimidine 280

To a suspension of 2-chloro-4-morpholin-4-yl-thieno[3,2-d]pyrimidine-6-carbaldehyde (500 mg) in methanol (20 mL) at 0° C. was added sodium borohydride (66 mg). The reaction was stirred for 2 h then quenched with 1:1 saturated aqueous sodium hydrogencarbonate solution—water (20 mL). The mixture was stirred for 10 min and then filtered, washed with water and air dried to give (2-chloro-4-morpholin-4-yl-thieno[3,2-d]pyrimidin-6-yl)-methanol as a white solid (489 mg).

To a solution of (2-chloro-4-morpholin-4-yl-thieno[3,2-d]pyrimidin-6-yl)-methanol (300 mg) in DMF (10 mL) at 0° C. was added sodium hydride (46 mg). The mixture was stirred for 1 h at 0° C. and then methyliodide (0.07 mL) was added. The reaction mixture was stirred at room temperature for 16 h and then quenched with water (20 mL) and extracted into ethyl acetate (2×20 mL). The combined organics were washed with aqueous brine solution (2×20 mL), dried (MgSO$_4$) and concentrated to give 2-chloro-6-methoxymethyl-4-morpholin-4-yl-thieno[3,2-d]pyrimidine as a yellow solid (92 mg).

Suzuki coupling with 2-chloro-6-methoxymethyl-4-morpholin-4-yl-thieno[3,2-d]pyrimidine (85 mg) was carried out using the standard method. Purification using column chromatography gave 280 as a white solid (24 mg). NMR: CDCl$_3$: 3.41 (3 H, s, Me), 3.81-3.89 (4 H, m, CH$_2$), 4.01-4.08 (4 H, m, CH$_2$), 4.70 (2 H, s, CH$_2$), 7.31 (1 H, s, Ar), 7.42 (1 H, t, J 8.25, Ar), 7.50 (1 H, d, J 8.24, Ar), 8.21 (1 H, d, J 7.21, Ar), 8.96 (1 H, s, Ar) and 10.03 (1 H, s, NH). MS: (ESI+): MH+ 382.17

Example 207

6-((benzyloxy)methyl)-2-(1H-indazol-4-yl)-4-morpholinothieno[3,2-d]pyrimidine 281

Following the procedures to prepare 280, and using benzyl bromide, 281 was prepared. NMR: $CDCl_3$: 3.88-3.94 (4 H, m, $CH_2$), 4.09-4.14 (4 H, m, $CH_2$), 4.69 (2 H, s, $CH_2$), 4.86 (2 H, s, $CH_2$), 7.31-7.46 (6 H, m, Ar), 7.53 (1 H, t, J 8.22, Ar), 7.56 (1 H, t, J 8.24, Ar), 8.30 (1 H, d, J 6.94, Ar), 9.03 (1 H, s, Ar) and 10.11 (1 H, s, NH). MS: (ESI+): MH+ 458.16

Example 208

6-(((pyridin-2-yl)methoxy)methyl)-2-(1H-indazol-4-yl)-4-morpholinothieno[3,2-d]pyrimidine 282

Following the procedures to prepare 280, and using 2-picolyl chloride, 282 was prepared. NMR: $CDCl_3$: 3.80-3.90 (4 H, m, $CH_2$), 4.01-4.08 (4 H, m, $CH_2$), 4.72 (2 H, s, $CH_2$), 4.88 (2 H, s, $CH_2$), 7.10-7.14 (1 H, m, Ar), 7.38 (1 H, s, Ar), 7.40-7.48 (2 H, m, Ar), 7.51 (1 H, d, J 8.23, Ar), 7.65 (1 H, t, J 8.22, Ar), 8.18 (1 H, d, J 7.20, Ar), 8.52 (1 H, d, J 4.60, Ar), 8.96 (1 H, s, Ar) and 10.06 (1 H, s, NH). MS: (ESI+): MH+ 459.17

Example 209

6-(((pyridin-3-yl)methoxy)methyl)-2-(1H-indazol-4-yl)-4-morpholinothieno[3,2-d]pyrimidine 283

Following the procedures to prepare 280, and using 3-picolyl chloride, 283 was prepared. NMR: $CDCl_3$: 3.90-3.94 (4 H, m, $CH_2$), 4.08-4.13 (4 H, m, $CH_2$), 4.68 (2 H, s, $CH_2$), 4.88 (2 H, s, $CH_2$), 7.30 (1 H, dd, J 7.79 and 4.87, Ar), 7.44 (1 H, s, Ar), 7.51 (1 H, t, J 8.14, Ar), 7.57 (1 H, d, J 8.20, Ar), 7.71 (1 H, d, J 7.79, Ar), 8.28 (1 H, d, J 7.35, Ar), 8.58 (1H, dd, J 4.80 and 1.47, Ar), 8.63 (1 H, d, J 1.86, Ar) and 9.02 (1 H, s, Ar). MS: (ESI+): MH+ 459.16

Example 210

6-(((pyridin-4-yl)methoxy)methyl)-2-(1H-indazol-4-yl)-4-morpholinothieno[3,2-d]pyrimidine 284

Following the procedures to prepare 280, and using 4-picolyl chloride, 284 was prepared. NMR: $CDCl_3$: 3.90-3.94 (4 H, m, $CH_2$), 4.08-4.13 (4 H, m, $CH_2$), 4.68 (2 H, s, $CH_2$), 4.92 (2 H, s, $CH_2$), 7.30 (2 H, d, J 5.81, Ar), 7.46 (1 H, s, Ar), 7.51 (1 H, t, J 8.14, Ar), 7.60 (1 H, d, J 8.20, Ar), 8.28 (1 H, d, J 7.32, Ar), 8.61 (2 H, d, J 5.27, Ar), 9.01 (1 H, s, Ar) and 10.14 (1 H, s, NH). MS: (ESI+): MH+ 459.17

Example 211

2-(1H-indazol-4-yl)-4-morpholino-6-(phenoxymethyl)thieno[3,2-d]pyrimidine 285

To a solution of phenol (142 mg) in DMF (8 mL) at 0° C. was added sodium hydride (64 mg) portionwise. The reaction mixture was stirred at 0° C. for 1 h and then 6-bromomethyl-2-chloro-4-morpholin-4-yl-thien[3,2-d]pyrimidine (240 mg) was added. The reaction mixture was stirred at room temperature for 16 h and then quenched with water (20 mL) and extracted into ethyl acetate (2×20 mL). The combined organics were washed with 2 M aqueous sodium hydroxide solution (2×20 mL) and aqueous brine solution (2×20 mL), dried ($MgSO_4$) and concentrated to give 2-chloro-4-morpholin-4-yl-6-phenoxymethyl-thieno[3,2-d]pyrimidine as a white solid (123 mg).

Suzuki coupling with 2-chloro-4-morpholin-4-yl-6-phenoxymethyl-thieno[3,2-d]pyrimidine (112 mg) was carried out using the standard method. Purification using column chromatography gave 285 as a white solid (34 mg). NMR: $CDCl_3$: 3.90-3.98 (4 H, m, $CH_2$), 4.08-4.13 (4 H, m, $CH_2$), 5.41 (2 H, s, $CH_2$), 6.98-7.06 (3 H, m, Ar), 7.40-7.46 (2 H, m, Ar), 7.49-7.55 (2 H, m, Ar), 7.60 (1 H, d, J 8.22, Ar), 8.30 (1 H, d, J 7.24, Ar), 9.01 (1 H, s, Ar), 10.14 (1 H, s, NH). MS: (ESI+): MH+ 444.17

Example 212

N-((2-(1H-indazol-4-yl)-4-morpholinothieno[3,2-d]pyrimidin-6-yl)methyl)benzamide 286

(2-Chloro-4-morpholinothieno[3,2-d]pyrimidin-6-yl)methanamine 27 was acylated with benzoyl chloride following General Procedure K and then reacted with 4-(4,4,5,5-tetramethyl-1,3,2-dioxaborolan-2-yl)-1H-indazole 7 (34 mg) following General Procedure A to give 286. MS (Q1) 471 (M)+

Example 213

N-((2-(1H-indazol-4-yl)-4-morpholinothieno[3,2-d]pyrimidin-6-yl)methyl)picolinamide 287

(2-Chloro-4-morpholinothieno[3,2-d]pyrimidin-6-yl)methanamine 27 was acylated with picolinoyl chloride following General Procedure K and then reacted with 4-(4,4,5,5-tetramethyl-1,3,2-dioxaborolan-2-yl)-1H-indazole 7 (34 mg) following General Procedure A to give 287. MS (Q1) 472 (M)+

Example 214

N-((2-(1H-indazol-4-yl)-4-morpholinothieno[3,2-d]pyrimidin-6-yl)methyl)nicotinamide 288

(2-Chloro-4-morpholinothieno[3,2-d]pyrimidin-6-yl)methanamine 27 was acylated with nicotinoyl chloride following General Procedure K and then reacted with 4-(4,4,5,5-tetramethyl-1,3,2-dioxaborolan-2-yl)-1H-indazole 7 (34 mg) following General Procedure A to give 288. MS (Q1) 472 (M)+

Example 215

N-((2-(1H-indazol-4-yl)-4-morpholinothieno[3,2-d]pyrimidin-6-yl)methyl)acetamide 289

(2-Chloro-4-morpholinothieno[3,2-d]pyrimidin-6-yl)methanamine 27 was acylated with acetylchloride following General Procedure K and then reacted with 4-(4,4,5,5-tetramethyl-1,3,2-dioxaborolan-2-yl)-1H-indazole 7 (34 mg) following General Procedure A to give 289. MS (Q1) 409 (M)+

Example 216

N-((2-(1H-indazol-4-yl)-4-morpholinothieno[3,2-d]pyrimidin-6-yl)methyl)isonicotinamide 290

(2-Chloro-4-morpholinothieno[3,2-d]pyrimidin-6-yl)methanamine 27 was acylated with isonicotinoyl chloride following General Procedure K and then reacted with 4-(4,5,5-tetramethyl-1,3,2-dioxaborolan-2-yl)-1H-indazole 7 (34 mg) following General Procedure A to give 290. MS (Q1) 472 (M)+

Example 217

2-(1H-indazol-4-yl)-4-morpholinofuro[3,2-d]pyrimidine-6-carboxamide 291

2-Chloro-4-morpholinofuro[3,2-d]pyrimidine-6-carboxamide was reacted with 4-(4,4,5,5-tetramethyl-1,3,2-dioxaborolan-2-yl)-1H-indazole 7 via General Procedure A to give, after purification by reverse HPLC, 291. MS (Q1) 365 (M$^+$)

Example 218

(2-(1H-indazol-4-yl)-4-morpholinofuro[3,2-d]pyrimidin-6-yl)(4-N-methylsulfonylpiperazin-1-yl)methanone 292

A solution of 2-chloro-4-morpholinofuro[3,2-d]pyrimidine-6-carboxylic acid (1.0 eq), HATU (1.5 eq), hydrochloride salt of 1-methanesulfonylpiperazine (1.5 eq), diisopropylethylamine (3.0 eq) in DMF was stirred for 30 minutes. The solid that precipitated out from the reaction was filtered to give 2-chloro-4-morpholinofuro[3,2-d]pyrimidin-6-yl(4-methylsulfonylpiperazin-1-yl)methanone. MS (Q1) 430 (M)$^+$ 2-Chloro-4-morpholinofuro[3,2-d]pyrimidin-6-yl(4-methylsulfonylpiperazin-1-yl)methanone was reacted with 4-(4,4,5,5-tetramethyl-1,3,2-dioxaborolan-2-yl)-1H-indazole 7 via General Procedure A to give, after purification by reverse HPLC, 292. MS (Q1) 352 (M$^+$)

Example 219

2-(1H-indazol-4-yl)-N-methyl-4-morpholinofuro[3,2-d]pyrimidine-6-carboxamide 293

To a solution of 2-chloro-4-morpholinofuro[3,2-d]pyrimidine 45 from Example 27 (1.0 eq) dissolved in THF at -78° C. was added 1.6M solution of n-butyllithium in hexanes (1.3 eq). Reaction mixture was stirred at -78° C. for 30 minutes. A gentle flow of CO$_2$ gas was then bubbled in the reaction flask for 1 h at -78° C., then at 0° C. for 40 min. Reaction mixture was concentrated, then quenched with water. Mixture was extracted with ethyl acetate to remove any starting material remaining. Then, aqueous layer was acificied with HCl 6M up to pH 3. Resulting solid was filtered to give 2-chloro-4-morpholinofuro[3,2-d]pyrimidine-6-carboxylic acid. MS (Q1) 284 (M)+

A solution of 2-chloro-4-morpholinofuro[3,2-d]pyrimidine-6-carboxylic acid (1.0 eq), HATU (1.5 eq), hydrochloride salt of methylamine (1.5 eq), diisopropylethylamine (3.0 eq) in DMF was stirred for 30 minutes. Reaction mixture was quenched with saturated aq. NaHCO$_3$ and extracted with ethyl acetate. The combined organic layers were dried (Na$_2$SO$_4$) and concentrated. The crude reaction mixture was purified by flash chromatography to give 2-chloro-N-methyl-4-morpholinofuro[3,2-d]pyrimidine-6-carboxamide. MS (Q1) 297 (M)$^+$ 2-Chloro-N-methyl-4-morpholinofuro[3,2-d]pyrimidine-6-carboxamide was reacted with 4-(4,4,5,5-tetramethyl-1,3,2-dioxaborolan-2-yl)-1H-indazole 7 via General Procedure A to give, after purification by reverse HPLC, 293. MS (Q1) 379 (M$^+$)

Example 220

(2-(1H-indazol-4-yl)-4-morpholinofuro[3,2-d]pyrimidin-6-yl)methanol 296

2-Chloro-4-morpholinofuro[3,2-d]pyrimidine-6-carbaldehyde (1.0 eq) was dissolved in 1,2-dichloroethane and treated with hydrochloride salt of 1-methanesulfonylpiperazine (1.4 eq), sodium acetate (1.4 eq) and trimethyl orthoformate (10 eq). Reaction mixture was stirred at r.t. for 12 h. Sodium triacetoxyborohydride (1.2 eq) was added and reaction mixture was stirred at r.t. for 8 h. Reaction mixture was quenched with saturated aq. NaHCO$_3$ and extracted with dichloromethane. The combined organic layers were dried (Na$_2$SO$_4$) and concentrated. The crude reaction mixture was purified by flash chromatography to yield 2-chloro-4-morpholinofuro[3,2-d]pyrimidin-6-yl)methanol: MS (Q1) 270 (M)$^+$ 2-Chloro-4-morpholinofuro[3,2-d]pyrimidin-6-yl)methanol was reacted with 4-(4,4,5,5-tetramethyl-1,3,2-dioxaborolan-2-yl)-1H-indazole 7 via General Procedure A to give, after purification by reverse HPLC, 296. MS (Q1) 352 (M$^+$)

Example 221

2-(1H-indazol-4-yl)-6-(4-methoxypyridin-3-yl)-4-morpholinofuro[3,2-d]pyrimidine 297

2-Chloro-6-iodo-4-morpholinofuro[3,2-d]pyrimidine 45 from Example 27 was reacted with 4-methoxypyridin-3-yl-3-boronic acid via General Procedure A to give the corresponding intermediate, after purification by flash chromatography, which was then reacted with 4-(4,4,5,5-tetramethyl-1,3,2-dioxaborolan-2-yl)-1H-indazole 7 to give, after purification by reverse phase HPLC, 297. MS (Q1) 429 (M$^+$)

Example 222

2-(1H-indazol-4-yl)-4-morpholinothieno[2,3-d]pyrimidine-6-carboxamide 298

2-Chloro-4-morpholinothieno[2,3-d]pyrimidine-6-carboxylic acid from Example 67 (100 mg) was treated with 90 mg of ammonium chloride via General Procedure B to yield 2-chloro-4-morpholinothieno[3,2-d]pyrimidine-6-carboxamide. Crude intermediate 2-chloro-4-morpholinothieno[3,2-d]pyrimidine-6-carboxamide was then reacted with 4-(4,4,5,5-tetramethyl-1,3,2-dioxaborolan-2-yl)1H-indazole 7 via General Procedure A to give 17.4 mg of 298 after reverse phase HPLC purification. MS (Q1) 381.1 (M)+

Example 223

2-(1H-indazol-4-yl)-4-morpholino-6-(3-(morpholinomethyl)phenyl)thieno[3,2-d]pyrimidine 299

2-Chloro-6-iodo-4-morpholinothieno[3,2-d]pyrimidine 19 (50 mg) was coupled to 4-[3-(4,4,5,5-tetramethyl-1,3,2-dioxaborolan-2-yl)]benzylmorpholine, and then reacted with 4-(4,4,5,5-tetramethyl-1,3,2-dioxaborolan-2-yl)-1H-indazole 7 via General Procedure F. The product was purified by reverse phase HPLC to yield 2.6 mg of 299. MS. (Q1) 513.2 (M)$^+$

Example 224 methyl 3-(2-(1H-indazol-4-yl)-4-morpholinothieno[3,2-d]pyrimidin-6-yl)-5-aminobenzoate 300

2-Chloro-6-iodo-4-morpholinothieno[3,2-d]pyrimidine 19 (50 mg) was coupled to 3-amino-5-methoxycarbonylphenyl boronic acid, and then reacted with 4-(4,4,5,5-tetramethyl-1,3,2-dioxaborolan-2-yl)-1H-indazole via General Procedure F. The product was purified by reverse phase HPLC to yield 5.2 mg of 300. MS. (Q1) 487.1 (M)+

Example 225

N-(3-((2-(1H-indazol-4-yl)-4-morpholinothieno[3,2-d]pyrimidin-6-yl)methylamino)phenyl)acetamide 301

To a solution of 6-(bromomethyl)-2-chloro-4-morpholinothieno[3,2-d]pyrimidine 30 from Example 9 (90 mg, 0.3 mmol) in DMF (3 mL) was added 3-aminoacetanilide (39 mg, 0.3 mmol) and $K_2CO_3$ (50 mg, 0.4 mmol). The resulting solution stirred at room temperature overnight then was concentrated in vacuo. The residue was diluted with water and filtered. The crude product was utilized in a Suzuki coupling using General Procedure A with 4-(4,4,5,5-tetramethyl-1,3,2-dioxaborolan-2-yl)-1H-indazole 7 to provide 301 after reverse phase HPLC purification (39 mg). MS (Q1) 500 (M)+

Example 226

N-((2-(1H-indazol-4-yl)-4-morpholinothieno[3,2-d]pyrimidin-6-yl)methyl)benzenamine 302

To a solution of 6-(bromomethyl)-2-chloro-4-morpholinothieno[3,2-d]pyrimidine 30 from Example 9 (90 mg, 0.3 mmol) in DMF (3 mL) was added aniline (24 µL, 0.3 mmol) and $K_2CO_3$ (50 mg, 0.4 mmol). The resulting solution stirred at room temperature overnight then was concentrated in vacuo. The residue was diluted with water and filtered. The crude product was utilized in a Suzuki coupling using General Procedure A with 4-(4,4,5,5-tetramethyl-1,3,2-dioxaborolan-2-yl)-1H-indazole 7 to provide 302 after reverse phase HPLC purification (49 mg). MS (Q1) 443 (M)+

Example 227

3-((2-(1H-indazol-4-yl)-4-morpholinothieno[3,2-d]pyrimidin-6-yl)methylamino)benzamide 303

To a solution of 6-(bromomethyl)-2-chloro-4-morpholinothieno[3,2-d]pyrimidine 30 from Example 9 (90 mg, 0.3 mmol) in DMF (3 mL) was added 3-aminobenzamide (35 mg, 0.3 mmol) and $K_2CO_3$ (50 mg, 0.4 mmol). The resulting solution stirred at room temperature overnight then was concentrated in vacuo. The residue was diluted with water and filtered. The crude product was utilized in a Suzuki coupling using General Procedure A with 4-(4,4,5,5-tetramethyl-1,3,2-dioxaborolan-2-yl)-1H-indazole 7 to provide 303 after reverse phase HPLC purification (28 mg). MS (Q1) 486 (M)+

Example 228

(2-(1H-indazol-4-yl)-4-morpholinothieno[3,2-d]pyrimidin-6-yl)-N,N-dimethylmethanamine 304

To a solution of 6-(bromomethyl)-2-chloro-4-morpholinothieno[3,2-d]pyrimidine 30 from Example 9 (90 mg, 0.3 mmol) in DMF (3 mL) was added dimethylamine hydrochloride (21 mg, 0.3 mmol) and $K_2CO_3$ (90 mg, 0.6 mmol). The resulting solution stirred at room temperature overnight then was concentrated in vacuo. The residue was diluted with water and filtered. The crude product was utilized in a Suzuki coupling using General Procedure A with 4-(4,4,5,5-tetramethyl-1,3,2-dioxaborolan-2-yl)-1H-indazole 7 to provide 304 after reverse phase HPLC purification (34 mg). MS (Q1) 395 (M)+

Example 229

N-((2-(1H-indazol-4-yl)-4-morpholinothieno[3,2-d]pyrimidin-6-yl)methyl)morpholine-4-carboxamide 305

To a solution of (2-chloro-4-morpholinothieno[3,2-d]pyrimidin-6-yl)methanamine 27 from Example 11 (50 mg, 0.2 mmol) in $CH_2Cl_2$ (4 mL) was added $Et_3N$ (84 µL, 0.6 mmol) and 4-Morpholinylcarbonyl chloride (40 µL, 0.3 mmol). The reaction stirred 18 h at room temperature before being quenched with water. The aqueous layer was extracted with EtOAc. The combined organics were dried over $Na_2SO_4$ and concentrated in vacuo. The crude product was utilized in a Suzuki coupling using General Procedure A with 4-(4,4,5,5-tetramethyl-1,3,2-dioxaborolan-2-yl)-1H-indazole 7 to provide 305 after reverse phase HPLC purification (24 mg). MS (Q1) 480 (M)+

Example 230

(2-(1H-indazol-4-yl)-4-morpholinothieno[3,2-d]pyrimidin-6-yl)N-phenylsulfonylmethanamine 306

To a solution of (2-chloro-4-morpholinothieno[3,2-d]pyrimidin-6-yl)methanamine 27 from Example 11 (50 mg, 0.2 mmol) in $CH_2Cl_2$ (4 mL) was added $Et_3N$ (84 µL, 0.6 mmol) and benzenesulfonyl chloride (44 µL, 0.3 mmol). The reaction stirred 18 h at room temperature before being quenched with water. The aqueous layer was extracted with EtOAc. The combined organics were dried over $Na_2SO_4$ and concentrated in vacuo. The crude product was utilized in a Suzuki coupling using General Procedure A with 4-(4,4,5,5-tetramethyl-1,3,2-dioxaborolan-2-yl)-1H-indazole 7 to provide 306 after reverse phase HPLC purification (3 mg). MS (Q1) 507 (M)+

Example 231

3-((2-(1H-indazol-4-yl)-4-morpholinothieno[3,2-d]pyrimidin-6-yl)methyl)-1,1-dimethylurea 307

To a solution of (2-chloro-4-morpholinothieno[3,2-d]pyrimidin-6-yl)methanamine 27 from Example 11 (50 mg, 0.2 mmol) in $CH_2Cl_2$ (4 mL) was added $Et_3N$ (84 µL, 0.6 mmol) and dimethylcarbamyl chloride (0.3 mmol). The reaction stirred 18 h at room temperature before being quenched with water. The aqueous layer was extracted with EtOAc. The combined organics were dried over $Na_2SO_4$ and concentrated in vacuo. The crude product was utilized in a Suzuki coupling using General Procedure A with 4-(4,4,5,5-tetramethyl-1,3,

Example 232

1-(2-(1H-indazol-4-yl)-4-morpholinothieno[2,3-d]pyrimidin-6-yl)ethanol 308

2-chloro-4-morpholinothieno[2,3-d]pyrimidine (300 mg) was reacted with acetaldehyde via General Procedure D to give 1-(2-chloro-4-morpholinothieno[2,3-d]pyrimidin-6-yl)ethanol. This crude intermediate was reacted with 4-(4,4,5,5-tetramethyl-1,3,2-dioxaborolan-2-yl)1H-indazole 7 via General Procedure A to yield 100.2 mg of 308 following reverse phase HPLC purification. MS (Q1) 382.1 (M)+

Example 233

2-(1H-indazol-4-yl)-4-morpholinothieno[3,2-d]pyrimidin-6-yl)sulfonamide 309

2-Chloro-4-morpholinothieno[3,2-d]pyrimidine-6-sulfonyl chloride 17 was reacted with ammonium chloride via General Procedure C. The crude intermediate was then reacted with 4-(4,4,5,5-tetramethyl-1,3,2-dioxaborolan-2-yl)1H-indazole 7 via General Procedure A to give 36.3 mg of 309 following reverse phase HPLC purification. MS (Q1) 417.1 (M)+

Example 234

2-(2-(1H-indazol-4-yl)-4-morpholinothieno[3,2-d]pyrimidin-6-yl)propan-2-amine 310

Zirconium(IV) chloride (320 mg) was added to a mixture of 410 mg of 2-(1H-indazol-4-yl)-4-morpholinothieno[3,2-d]pyrimidine-6-carboxamide in THF at −10° C. The reaction mixture was stirred for 30 min at −10° C. Methylmagnesium bromide (2.7 mL, 3.0 M in diethyl ether) was added. The reaction mixture was allowed to warm to room temperature and stirred overnight. Saturated ammonium chloride aqueous solution was added, and then extracted with ethyl acetate. The organic layer was dried over (MgSO$_4$) and evaporated to yield 2-(2-chloro-6-iodo-4-morpholinothieno[3,2-d]pyrimidine-6-yl)propan-2-amine (380 mg).

2-(2-Chloro-6-iodo-4-morpholinothieno[3,2-d]pyrimidine-6-yl)propan-2-amine (30 mg) was coupled to 4-(4,4,5,5-tetramethyl-1,3,2-dioxaborolan-2-yl)-1H-indazole 7 via General Procedure A to yield 11.5 mg of 310. MS (Q1) 395.0 (M)$^+$

Example 235

3-((2-(1H-indazol-4-yl)-4-morpholinothieno[3,2-d]pyrimidin-6-yl)methyl)oxazolidin-2-one 311

To a solution of 2-oxazolidinone (50 mg, 0.6 mmol) in DMF (2 mL) at 0° C. NaH (60% in mineral oil; 0.7 mmol) was added. After 15 minutes, 6-(bromomethyl)-2-chloro-4-morpholinothieno[3,2-d]pyrimidine 30 from Example 9 (200 mg, 0.6 mmol) in DMF (0.5 mL) was added and the reaction stirred 15 min. The reaction was quenched by the addition of saturated aqueous ammonium chloride. The aqueous layer was extracted with EtOAc. The combined organics were dried over Na$_2$SO$_4$, filtered, and concentrated in vacuo. The crude product was utilized in a Suzuki coupling using General Procedure A with 4-(4,4,5,5-tetramethyl-1,3,2-dioxaborolan-2-yl)-1H-indazole 7 to provide 311 after reverse phase HPLC purification (6 mg). MS (Q1) 437 (M)+

Example 236

6-((1H-imidazol-1-yl)methyl)-2-(1H-indazol-4-yl)-4-morpholinothieno[3,2-d]pyrimidine 312

To a solution of 6-(bromomethyl)-2-chloro-4-morpholinothieno[3,2-d]pyrimidine 30 from Example 9 (90 mg, 0.3 mmol) in DMF (3 mL) was added imidazole (18 mg, 0.3 mmol) and K$_2$CO$_3$ (50 mg, 0.4 mmol). The resulting solution stirred at room temperature overnight then was concentrated in vacuo. The residue was diluted with water and filtered. The crude product was utilized in a Suzuki coupling using General Procedure A with 4-(4,4,5,5-tetramethyl-1,3,2-dioxaborolan-2-yl)-1H-indazole 7 to provide 312 after reverse phase HPLC purification (32 mg). MS (Q1) 418 (M)+

Example 237

6-((1H-1,2,4-triazol-1-yl)methyl)-2-(1H-indazol-4-yl)-4-morpholinothieno[3,2-d]pyrimidine 313

To a solution of 6-(bromomethyl)-2-chloro-4-morpholinothieno[3,2-d]pyrimidine 30 from Example 9 (90 mg, 0.3 mmol) in DMF (3 mL) was added 1,2,4-triazole (18 mg, 0.3 mmol) and K$_2$CO$_3$ (50 mg, 0.4 mmol). The resulting solution stirred at room temperature overnight then was concentrated in vacuo. The residue was diluted with water and filtered. The crude product was utilized in a Suzuki coupling using General Procedure A with 4-(4,4,5,5-tetramethyl-1,3,2-dioxaborolan-2-yl)-1H-indazole 7 to provide 313 after reverse phase HPLC purification (16 mg). MS (Q1) 419 (M)+

Example 238

2-(1H-indazol-4-yl)-6-(methoxymethyl)-4-morpholinothieno[3,2-d]pyrimidine 314

To a suspension of 2-chloro-4-morpholin-4-yl-thieno[3,2-d]pyrimidine-6-carbaldehyde 10 from Example 3 (500 mg) in methanol (20 mL) at 0° C. was added sodium borohydride (66 mg). The reaction was stirred for 2 h then quenched with 1:1 saturated aqueous sodium hydrogencarbonate solution:water (20 mL). The mixture was stirred for 10 min and then filtered, washed with water and air dried to give (2-chloro-4-morpholin-4-yl-thieno[3,2-d]pyrimidin-6-yl)-methanol as a white solid (489 mg).

To a solution of (2-chloro-4-morpholin-4-yl-thieno[3,2-d]pyrimidin-6-yl)-methanol (300 mg) in DMF (10 mL) at 0° C. was added sodium hydride (46 mg). The mixture was stirred for 1 h at 0° C. and then methyliodide (0.07 mL) was added. The reaction mixture was stirred at room temperature for 16 h and then quenched with water (20 mL) and extracted into ethyl acetate (2×20 mL). The combined organics were washed with aqueous brine solution (2×20 mL), dried (MgSO$_4$) and concentrated to give 2-chloro-6-methoxymethyl-4-morpholin-4-yl-thieno[3,2-d]pyrimidine as a yellow solid (92 mg). Suzuki coupling with 2-chloro-6-methoxymethyl-4-morpholin-4-yl-thieno[3,2-d]pyrimidine (85 mg) was carried out via General Procedure A. Purification using column chromatography gave 314 as a white solid (24 mg). NMR: CDCl$_3$: 3.41 (3 H, s, Me), 3.81-3.89 (4 H, m, CH$_2$), 4.01-4.08 (4 H, m, CH$_2$), 4.70 (2 H, s, CH$_2$), 7.31 (1 H, s, Ar), 7.42 (1 H, t, J 8.25, Ar), 7.50 (1 H, d, J 8.24, Ar), 8.21 (1 H, d, J 7.21, Ar), 8.96 (1 H, s, Ar) and 10.03 (1 H, s, NH). MS: (ESI+): MH+ 382.17

Example 239

6-((benzyloxy)methyl)-2-(1H-indazol-4-yl)-4-morpholinothieno[3,2-d]pyrimidine 315

Following the procedures for compound 314, (2-chloro-4-morpholin-4-yl-thieno[3,2-d]pyrimidin-6-yl)-methanol in DMF and sodium hydride was alkylated with benzyl bromide to give 2-chloro-6-benzyloxymethyl-4-morpholin-4-yl-thieno[3,2-d]pyrimidine. Suzuki coupling of 2-chloro-6-benzyloxymethyl-4-morpholin-4-yl-thieno[3,2-d]pyrimidine and 7 was carried out via General Procedure A. Purification using column chromatography gave 315. NMR: CDCl$_3$: 3.88-3.94 (4 H, m, CH$_2$), 4.09-4.14 (4 H, m, CH$_2$), 4.69 (2 H, s, CH$_2$), 4.86 (2 H, s, CH$_2$), 7.31-7.46 (6 H, m, Ar), 7.53 (1 H, t, J 8.22, Ar), 7.56 (1 H, t, J 8.24, Ar), 8.30 (1 H, d, J 6.94, Ar), 9.03 (1 H, s, Ar) and 10.1 (1 H, s, NH). MS: (ESI+): MH+ 458.16

Example 240

2-(1H-indazol-4-yl)-4-morpholino-6-(phenoxymethyl)thieno[3,2-d]pyrimidine 316

To a solution of phenol (142 mg) in DMF (8 mL) at 0° C. was added sodium hydride (64 mg) portionwise. The reaction mixture was stirred at 0° C. for 1 h and then 6-bromomethyl-2-chloro-4-morpholin-4-yl-thien[3,2-d]pyrimidine (240 mg) was added. The reaction mixture was stirred at room temperature for 16 h and then quenched with water (20 mL) and extracted into ethyl acetate (2×20 mL). The combined organics were washed with 2 M aqueous sodium hydroxide solution (2×20 mL) and aqueous brine solution (2×20 mL), dried (MgSO$_4$) and concentrated to give 2-chloro-4-morpholin-4-yl-6-phenoxymethyl-thieno[3,2-d]pyrimidine as a white solid (123 mg).

Suzuki coupling of 2-chloro-4-morpholin-4-yl-6-phenoxymethyl-thieno[3,2-d]pyrimidine (112 mg) and 7 was carried out using the standard method. Purification using column chromatography gave 316 as a white solid (34 mg). NMR: CDCL$_3$: 3.90-3.98 (4 H, m, CH$_2$), 4.08-4.13 (4 H, m, CH$_2$), 5.41 (2 H, s, CH$_2$), 6.98-7.06 (3 H, m, Ar), 7.40-7.46 (2 H, m, Ar), 7.49-7.55 (2 H, m, Ar), 7.60 (1 H, d, J 8.22, Ar), 8.30 (1 H, d, J 7.24, Ar), 9.01 (1 H, s, Ar), 10.14 (1 H, s, NH). MS: (ESI+): MH+ 444.17

Example 241

6-(((pyridin-2-yl)methoxy)methyl)-2-(1H-indazol-4-yl)-4-morpholinothieno[3,2-d]pyrimidine 317

Following the procedures for compound 314, (2-chloro-4-morpholin-4-yl-thieno[3,2-d]pyrimidin-6-yl)-methanol in DMF and sodium hydride was alkylated with 2-picolyl chloride to give 4-(2-chloro-6-((pyridin-2-ylmethoxy)methyl)thieno[3,2-d]pyrimidin-4-yl)morpholine. Suzuki coupling of 4-(2-chloro-6-((pyridin-2-ylmethoxy)methyl)thieno[3,2-d]pyrimidin-4-yl)morpholine and 7 was carried out via General Procedure A. Purification using column chromatography gave 317. NMR: CDCl$_3$: 3.80-3.90 (4 H, m, CH$_2$), 4.01-4.08 (4 H, m, CH$_2$), 4.72 (2 H, s, CH$_2$), 4.88 (2 H, s, —CH$_2$), 7.10-7.14 (1H, m, Ar), 7.38 (1 H, s, Ar), 7.40-7.48 (2 H, m, Ar), 7.51 (1 H, d, J 8.23, Ar), 7.65 (1 H, t, J 8.22, Ar), 8.18 (1 H, d, J 7.20, Ar), 8.52 (1 H, d, J 4.60, Ar), 8.96 (1 H, s, Ar) and 10.06 (1 H, s, NH). MS: (ESI+): MH+ 459.17

Example 242

4-morpholino-2-(1H-pyrrolo[2,3-b]pyridin-5-yl)-7-(thiazol-5-yl)thieno[3,2-d]pyrimidine 318

2-Chloro-4-morpholin-4-yl-7-thiazol-5-yl-thieno[3,2-d]pyrimidine and 5-(4,4,5,5-tetramethyl-[1.3.2]dioxaborolan-2-yl)-1H-pyrrolo[2,3-b]pyridine were reacted according to General Procedure A to give 318. NMR (DMSO, 400 MHz), 3.86 (4 H, t, J=4.4), 4.09 (4 H, t, J=5.2), 6.61-6.63 (1 H, m), 7.54-7.57 (1 H, m), 8.78 (2 H, s), 9.03 (1 H, s), 9.20 (1 H, s), 9.44-9.46 (1 H, m), 11.88 (1 H, s). MS: (ESI+): MH+=421

Example 243

6-(((pyridin-3-yl)methoxy)methyl)-2-(1H-indazol-4-yl)-4-morpholinothieno[3,2-d]pyrimidine 319

Following the procedures for compound 314, (2-chloro-4-morpholin-4-yl-thieno[3,2-d]pyrimidin-6-yl)-methanol in DMF and sodium hydride was alkylated with 3-picolyl chloride to give 4-(2-chloro-6-((pyridin-3-ylmethoxy)methyl)thieno[3,2-d]pyrimidin-4-yl)morpholine. Suzuki coupling of 4-(2-chloro-6-((pyridin-3-ylmethoxy)methyl)thieno[3,2-d]pyrimidin-4-yl)morpholine and 7 was carried out via General Procedure A. Purification using column chromatography gave 319. NMR: CDCl$_3$: 3.90-3.94 (4 H, m, CH$_2$), 4.08-4.13 (4 H, m, CH$_2$), 4.68 (2 H, s, CH$_2$), 4.88 (2 H, s, CH$_2$), 7.30 (1 H, dd, J 7.79 and 4.87, Ar), 7.44 (1 H, s, Ar), 7.51 (1 H, t, J 8.14, Ar), 7.57 (1 H, d, J 8.20, Ar), 7.71 (1 H, d, J 7.79, Ar), 8.28 (1 H, d, J 7.35, Ar), 8.58 (1 H, dd, J 4.80 and 1.47, Ar), 8.63 (1 H, d, J 1.86, Ar) and 9.02 (1 H, s, Ar). MS: (ESI+): MH+ 459.16

Example 244

6-(((pyridin-4-yl)methoxy)methyl)-2-(1H-indazol-4-yl)-4-morpholinothieno[3,2-d]pyrimidine 320

Following the procedures for compound 314, (2-chloro-4-morpholin-4-yl-thieno[3,2-d]pyrimidin-6-yl)-methanol in DMF and sodium hydride was alkylated with 4-picolyl chloride to give 4-(2-chloro-6-((pyridin-4-ylmethoxy)methyl)thieno[3,2-d]pyrimidin-4-yl)morpholine. Suzuki coupling of 4-(2-chloro-6-((pyridin-4-ylmethoxy)methyl)thieno[3,2-d]pyrimidin-4-yl)morpholine and 7 was carried out via General Procedure A. Purification using column chromatography gave 320. NMR: CDCl$_3$: 3.90-3.94 (4 H, m, CH$_2$), 4.08-4.13 (4 H, m, CH$_2$), 4.68 (2 H, s, CH$_2$), 4.92 (2 H, s, CH$_2$), 7.30 (2 H, d, J 5.81, Ar), 7.46 (1 H, s, Ar), 7.51 (1 H, t, J 8.14, Ar), 7.60 (1 H, d, J 8.20, Ar), 8.28 (1 H, d, J 7.32, Ar), 8.61 (2 H, d, J 5.27, Ar), 9.01 (1 H, s, Ar) and 10.14 (1 H, s, NH). MS: (ESI+): MH+ 459.17

Example 245

N-((2-(1H-indazol-4-yl)-4-morpholinothieno[3,2-d]pyrimidin-6-yl)methyl)-2-hydroxy-2-methylpropanamide 321

2-Chloro-4-morpholinothieno[3,2-d]pyrimidine 4 (4 g) was reacted with acetone following General Procedure D to give the corresponding tertiary alcohol. 75 mg of this crude material was used in a palladium catalyzed cross coupling reaction following General Procedure A to give 69 mg of 321 after reversed phase HPLC purification. MS (Q1) 395 (M)+

Example 246

2-(2-(1H-indol-4-yl)-4-morpholinothieno[3,2-d]pyrimidin-6-yl)propan-2-ol 322

To a solution of (2-chloro-4-morpholinothieno[3,2-d]pyrimidin-6-yl)methanamine 27 from Example 11 (50 mg, 0.2 mmol) in DMF (1.5 mL) was added O-(7-azabenzotriazol-1-yl)-(N,N,N',N'-tetramethyluronium hexafluorophosphate (134 mg, 0.4 mmol), N,N-diisopropylethylamine (190 µL, 1.1 mmol), then 2-hydroxyisobutyric acid (53 mg, 0.5 mmol). The resulting solution stirred 30 min at room temperature. Excess hydroxylamine hydrochloride was added then the reaction was quenched with saturated aqueous $NaHCO_3$. The aqueous layer was extracted with EtOAc. The combined organics were dried over $Na_2SO_4$, filtered, and concentrated in vacuo. The crude product was utilized in a Suzuki coupling using General Procedure A with 4-(4,4,5,5-tetramethyl-1,3,2-dioxaborolan-2-yl)-1H-indazole 7 to provide 322 after reverse phase HPLC purification (2 mg). MS (Q1) 453 (M)+

Example 247

N-((2-(1H-indazol-4-yl)-4-morpholinothieno[3,2-d]pyrimidin-6-yl)methyl)-2-hydroxyacetamide 323

To a solution of (2-chloro-4-morpholinothieno[3,2-d]pyrimidin-6-yl)methanamine 27 from Example 11 (50 mg, 0.2 mmol) in DMF (1.5 mL) was added O-(7-azabenzotriazol-1-yl)-(N,N,N',N'-tetramethyluronium hexafluorophosphate (134 mg, 0.4 mmol), N,N-diisopropylethylamine (190 µL, 1.1 mmol), then glycolic acid (38 mg, 0.5 mmol). The resulting solution stirred 30 min at room temperature. Excess hydroxylamine hydrochloride was added then the reaction was quenched with saturated aqueous $NaHCO_3$. The aqueous layer was extracted with EtOAc. The combined organics were dried over $Na_2SO_4$, filtered, and concentrated in vacuo. The crude product was utilized in a Suzuki coupling using General Procedure A with 4-(4,4,5,5-tetramethyl-1,3,2-dioxaborolan-2-yl)1H-indazole 7 to provide 323 after reverse phase HPLC purification (26 mg). MS (Q1) 425 (M)+

Example 248

2-(2-(1H-indol-4-yl)-4-morpholinothieno[3,2-d]pyrimidin-6-yl)propan-2-ol 324

To a solution of (2-chloro-4-morpholinothieno[3,2-d]pyrimidin-6-yl)methanamine 27 from Example 11 (50 mg, 0.2 mmol) in DMF (1.5 mL) was added O-(7-azabenzotriazole-1-yl)-N,N,N',N'-tetramethyluronium hexafluorophosphate (134 mg, 0.4 mmol), N,N-diisopropylethylamine (190 µL, 1.1 mmol), then 3-(methylsulfonyl)benzoic acid (102 mg, 0.5 mmol). The resulting solution stirred 30 min at room temperature. Excess hydroxylamine hydrochloride was added then the reaction was quenched with saturated aqueous $NaHCO_3$. The aqueous layer was extracted with EtOAc. The combined organics were dried over $Na_2SO_4$, filtered, and concentrated in vacuo. The crude product was utilized in a Suzuki coupling using General Procedure A with 4-(4,4,5,5-tetramethyl-1,3,2-dioxaborolan-2-yl)-1H-indazole 7 to provide 324 after reverse phase HPLC purification (28 mg). MS (Q1) 549 (M)+

Example 249

6-((1H-pyrazol-1-yl)methyl)-2-(1H-indazol-4-yl)-4-morpholinothieno[3,2-d]pyrimidine 325

To a solution of 6-(bromomethyl)-2-chloro-4-morpholinothieno[3,2-d]pyrimidine 30 from Example 9 (90 mg, 0.3 mmol) in DMF (3 mL) was added pyrazole (18 mg, 0.3 mmol) and $K_2CO_3$ (50 mg, 0.4 mmol). The resulting solution stirred at room temperature overnight then was concentrated in vacuo. The residue was diluted with water and filtered. The crude product was utilized in a Suzuki coupling using General Procedure A with 4-(4,4,5,5-tetramethyl-1,3,2-dioxaborolan-2-yl)-1H-indazole 7 to provide 325 after reverse phase HPLC purification (13 mg). MS (Q1) 418 (M)+

Example 250

1-((2-(1H-indazol-4-yl)-4-morpholinothieno[3,2-d]pyrimidin-6-yl)methyl)-1H-benzo[d]imidazol-2(3H)-one 326

To a solution of 6-(bromomethyl)-2-chloro-4-morpholinothieno[3,2-d]pyrimidine 30 from Example 9 (90 mg, 0.3 mmol) in DMF (3 mL) was added 2-hydroxybenzimidazole (35 mg, 0.3 mmol) and $K_2CO_3$ (50 mg, 0.4 mmol). The resulting solution stirred at room temperature overnight then was concentrated in vacuo. The residue was diluted with water and filtered. The crude product was utilized in a Suzuki coupling using General Procedure A with 4-(4,4,5,5-tetramethyl-1,3,2-dioxaborolan-2-yl)-1H-indazole 7 to provide 326 after reverse phase HPLC purification (3 mg). MS (Q1) 484 (M)+

Example 251

3-(2-(1H-indazol-4-yl)-4-morpholinofuro[3,2-d]pyrimidin-6-yl)-N-methylsulfonylbenzenamine 327

2-Chloro-6-iodo-4-morpholinofuro[3,2-d]pyrimidine 45 from Example 27 was reacted with 3-(methylsulfonylamino)phenylboronic acid via General Procedure A to give the corresponding intermediate, after purification by flash chromatography, which was then reacted with 4-(4,4,5,5-tetramethyl-1,3,2-dioxaborolan-2-yl)-1H-indazole 7 to give, after purification by reverse phase HPLC, 327. MS (Q1) 491 (M⁺)

Example 252

2-(1H-indazol-4-yl)-6-(isoxazol-4-yl)-4-morpholinothieno[3,2-d]pyrimidine 328

2-Chloro-6-iodo-4-morpholinothieno[3,2-d]pyrimidine 19 (150 mg), 84 mg of 4-isoxazoleboronic acid pinacol ester and 14 mg of bis(triphenylphosphine)palladium(II) dichloride in 0.7 mL of 1M $Na_2CO_3$ aqueous solution and 0.7 mL of acetonitrile was heated to 100° C. in a sealed microwave reactor for 10 min. The reaction mixture was evaporated. The crude product was purified by flash chromatography eluting with 0-20% MeOH/DCM to yield 2-chloro-6-(isoxazol-4-yl)-4-morpholinothieno[3,2-d]pyrimidine (85 mg, 67%).

2-Chloro-6-(isoxazol-4-yl)-4-morpholinothieno[3,2-d]pyrimidine (85 mg) was coupled to 4-(4,4,5,5-tetramethyl-1,3,2-dioxaborolan-2-yl)-1H-indazole 7 via General Procedure A to yield 4.3 mg of 328. MS (Q1) 405.1 (M)+

Example 253

3-(2-(1H-indazol-4-yl)-4-morpholinothieno[3,2-d]pyrimidin-6-yl)-N-ethylbenzamide 329

3-(2-Chloro-4-morpholinothieno[3,2-d]pyrimidin-6-yl)benzoic acid (55 mg) was reacted with ethylamine via General Procedure B to yield 3-(2-chloro-4-morpholinothieno[3,2-d]pyrimidin-6-yl)-N-ethylbenamide. Crude 3-(2-chloro-4-morpholinothieno[3,2-d]pyrimidin-6-yl)-N-ethylbenamide (59 mg) was coupled to 4-(4,4,5,5-tetramethyl-1,3,2-dioxaborolan-2-yl)-1H-indazole 7 via General Procedure A to yield 14.5 mg of 329. MS (Q1) 485.1 (M)+

Example 254

N-((2-(1H-indazol-4-yl)-4-morpholinothieno[3,2-d]pyrimidin-6-yl)methyl)-2-(N-methylsulfonylamino)acetamide 330

To a solution of (2-chloro-4-morpholinothieno[3,2-d]pyrimidin-6-yl)methanamine 27 from Example 11 (150 mg, 0.5 mmol) in DMF (4.5 mL) was added O-(7-azabenzotriazol-1-yl)-(N,N,N',N'-tetramethyluronium hexafluorophosphate (400 mg, 1 mmol), N,N-diisopropylethylamine (550 μL, 3.2 mmol), then N-Boc glycine (270 mg, 1.5 mmol). The resulting solution stirred 30 min at room temperature. Excess hydroxylamine hydrochloride was added then the reaction was quenched with saturated aqueous NaHCO$_3$. The aqueous layer was extracted with EtOAc. The combined organics were dried over Na$_2$SO$_4$, filtered, and concentrated in vacuo. A portion of the crude product (0.5 mmol) was dissolved in CH$_2$Cl$_2$ (15 mL), MeOH (15 mL), Et$_2$O (6 mL), and 4 M HCl in dioxane (6 mL) was added. The resulting mixture stirred at room temperature overnight. The reaction mixture was concentrated in vacuo. A portion of the crude material (0.3 mmol) was dissolved in CH$_2$Cl$_2$ (8 mL) and Et$_3$N (4 mL) and methanesulfonyl chloride (450 μL, 6 mmol) was added. The reaction mixture stirred at room temperature overnight. The reaction was quenched by the addition of water then extracted with EtOAc. The combined organics were dried over Na$_2$SO$_4$, filtered, and concentrated in vacuo. The crude material was utilized in a Suzuki coupling according to General Procedure A using 4-(4,4,5,5-tetramethyl-1,3,2-dioxaborolan-2-yl)-1H-indazole 7 to provide 330 after reverse phase HPLC purification (36 mg). MS (Q1) 502 (M)+

Example 255

N-((2-(1H-indazol-4-yl)-4-morpholinothieno[3,2-d]pyrimidin-6-yl)methyl)-2-aminoacetamide 331

To a solution of (2-chloro-4-morpholinothieno[3,2-d]pyrimidin-6-yl)methanamine 27 from Example 11 (150 mg, 0.5 mmol) in DMF (4.5 mL) was added O-(7-azabenzotriazol-1-yl)-(N,N,N',N'-tetramethyluronium hexafluorophosphate (400 mg, 1 mmol), N,N-diisopropylethylamine (550 μL, 3.2 mmol), then N-Boc glycine (270 mg, 1.5 mmol). The resulting solution stirred 30 min at room temperature. Excess hydroxylamine hydrochloride was added then the reaction was quenched with saturated aqueous NaHCO$_3$. The aqueous layer was extracted with EtOAc. The combined organics were dried over Na$_2$SO$_4$, filtered, and concentrated in vacuo. A portion of the crude product (0.5 mmol) was dissolved in CH$_2$Cl$_2$ (15 mL), MeOH (15 mL), Et$_2$O (6 mL), and 4 M HCl in dioxane (6 mL) was added. The resulting mixture stirred at room temperature overnight. The reaction mixture was concentrated in vacuo. A portion of the crude material (0.2 mmol) was utilized in a Suzuki coupling according to General Procedure A using 4-(4,4,5,5-tetramethyl-1,3,2-dioxaborolan-2-yl)-1H-indazole 7 to provide 331 after reverse phase HPLC purification (2 mg). MS (Q1) 424 (M)+

Example 256

2-(1H-indazol-4-yl)-4-morpholino-6-(1-(4-N-methylsulfonylpiperazin-1-yl)ethyl)thieno[3,2-d]pyrimidine 332

To a solution of 2-chloro-4-morpholin-4-yl-thieno[3,2-d]pyrimidine (500 mg) in THF (20 mL) at −78° C. was added n-butyllithium (0.94 mL of a 2.5 M solution in hexanes) and the reaction stirred at −78° C. for 1 h. Then, acetaldehyde (0.33 mL) was added and the reaction allowed to warm to room temperature over 16 h. The reaction was quenched with water (20 mL) and extracted into dichloromethane (2×20 mL). The combined organics were dried (MgSO$_4$) and reduced in vacuo to give 1-(2-chloro-4-morpholin-4-yl-thieno[3,2-d]pyrimidin-6-yl)-ethanol as a cream solid.

To a solution of 1-(2-chloro-4-morpholin-4-yl-thieno[3,2-d]pyrimidin-6-yl)-ethanol (500 mg) in dichloromethane (20 mL) at 0° C. was added triethylamine (0.28 mL) and then methanesulphonyl chloride (0.14 mL) and the reaction stirred at room temperature for 16 h. The reaction was quenched with water (20 mL) and extracted into dichloromethane (2×20 mL). The combined organic layers were washed with aqueous brine solution (2×20 mL), dried (MgSO$_4$) and reduced in vacuo to give methanesulfonic acid 1-(2-chloro-4-morpholin-4-yl-thieno[3,2-d]pyrimidin-6-yl)-ethyl ester as a yellow solid.

To a solution of methanesulfonic acid 1-(2-chloro-4-morpholin-4-yl-thieno[3,2-d]pyrimidin-6-yl)-ethyl ester (300 mg) in acetonitrile (20 mL) was added N-sulfonylpiperazine amide (239 mg) and potassium carbonate (548 mg) and the reaction heated at reflux for 16 h. After cooling to room temperature, the solvent was reduced in vacuo and the residue redissolved in dichloromethane (20 mL) and washed with saturated aqueous sodium hydrogen carbonate solution (2×20 mL), aqueous brine solution (2×20 mL), dried (MgSO$_4$), reduced in vacuo and purified by column chromatography to give 2-chloro-6-[1-(4-methanesulfonyl-piperazin-1-yl)-ethyl]-4-morpholin-4-yl-thieno[3,2-d]pyrimidine as an off-white solid.

2-Chloro-6-[1-(4-methanesulfonyl-piperazin-1-yl)-ethyl]-4-morpholin-4-yl-thieno[3,2-d]pyrimidine was reacted with 4-(4,4,5,5-tetramethyl-[1,3,2]dioxaborolan-2-yl)-1H-indazole in general procedure A. Purification by column chromatography yielded 332. NMR: CDCl$_3$: 1.56 (3 H, d, J 7.1, Me), 2.62-2.80 (4 H, m, CH$_2$), 2.81 (3 H, s, Me), 3.26-3.31 (4 H, m, CH$_2$), 3.95-3.99 (4 H, m, CH$_2$), 4.02-4.11 (5 H, m), 7.45 (1 H, s, Ar), 7.50 (1 H, apparent triplet, J 8.2, Ar), 7.61 (1 H, d, J 8.2, Ar), 8.28 (1 H, d, J 7.5, Ar) and 9.03 (1 H, s, Ar). MS: (ESI+): MH+ 528.31

Example 257

2-((2-(1H-indazol-4-yl)-4-morpholinothieno[3,2-d]pyrimidin-6-yl)methoxy)-N,N-dimethylacetamide 333

To a suspension of 2-chloro-4-morpholin-4-yl-thieno[3,2-d]pyrimidine-6-carbaldehyde (500 mg) in methanol (20 mL) at 0° C. was added sodium borohydride (66 mg). The reaction was stirred for 2 h then quenched with 1:1 saturated aqueous sodium hydrogencarbonate solution—water (20 mL). The mixture was stirred for 10 min and then filtered, washed with water and air dried to give (2-chloro-4-morpholin-4-yl-thieno [3,2-d]pyrimidin-6-yl)-methanol as a white solid (489 mg).

To a solution of (2-chloro-4-morpholin-4-yl-thieno[3,2-d]pyrimidin-6-yl)-methanol (180 mg) in THF (20 mL) was added sodium hydride (2 eq., 50 mg) and the mixture stirred at room temperature for 1 h. Then 2-chloro-N,Ndimethyl acetamide (2 eq., 0.13 ml) was added and the reaction stirred at reflux for 16 h. After cooling to room temperature the reaction was quenched with water (20 mL) and extracted into ethyl acetate (2×20 mL). The combined organics were washed with aqueous brine solution (2×20 mL), dried (MgSO$_4$), reduced in vacuo and purified by column chromatography to give 2-(2-chloro-4-morpholin-4-yl-thieno[3,2-d]pyrimidin-6-ylmethoxy)-N,N-dimethyl-acetamide as a yellow solid.

2-(2-chloro-4-morpholin-4-yl-thieno[3,2-d]pyrimidin-6-ylmethoxy)-N,N-dimethyl-acetamide was reacted with 4-(4,4,5,5-tetramethyl-[1,3,2]dioxaborolan-2-yl)-1H-indazole in general procedure A. Purification by column chromatography yielded 333. NMR: CDCl$_3$: 3.02 (6 H, s, Me), 3.96-3.99 (4 H, m, CH$_2$), 4.09-4.13 (4 H, m, CH$_2$), 4.31 (2 H, s, CH$_2$), 4.95 (2 H, s, CH$_2$), 7.45 (1 H, s, Ar), 7.50 (1 H, apparent triplet, J 8.2, Ar), 7.61 (1 H, d, J 8.2, Ar), 8.28 (1 H, d, J 7.5, Ar), 9.03 (1 H, s, Ar) and 10.30 (1 H, s, NH). MS: (ESI+): MH+ 453.20

Example 258

2-(1H-indazol-4-yl)-6-((E)-3-methoxyprop-1-enyl)-4-morpholinothieno[3,2-d]pyrimidine 334

2-Chloro-6-iodo-4-morpholinothieno[3,2-d]pyrimidine 19 (150 mg), 85 mg of (E)-2-(3-methoxy-1-propen-1-yl)-4,4,5,5-tetramethyl-1,3,2-dioxaborolane and 14 mg of bis (triphenylphosphine)palladium(II) dichloride in 1 mL of 1M Na$_2$CO$_3$ aqueous solution and 1 mL of acetonitrile was heated to 100° C. in a sealed microwave reactor for 10 min. The reaction mixture was evaporated. The crude product was purified by flash chromatography eluting with 5-50% EtOAc/hexane to yield 2-chloro-6-((E)-3-methoxyprop-1-enyl)-4-morpholinothieno[3,2-d]pyrimidine (87 mg, 68%). 2-Chloro-6-((E)-3-methoxyprop-1-enyl)-4-morpholinothieno[3,2-d]pyrimidine (40 mg) was coupled to 4-(4,4,5,5-tetramethyl-1,3,2-dioxaborolan-2-yl)-1H-indazole 7 via General Procedure A to yield 29.1 mg of 334. MS (Q1) 408.1 (M)$^+$

Example 259

2-(1H-indazol-4-yl)-6-(3-methoxyphenyl)-4-morpholinothieno[3,2-d]pyrimidine 335

2-Chloro-6-iodo-4-morpholinothieno[3,2-d]pyrimidine 19 (150 mg), 66 mg of 3-methoxyphenylboronic acid and 14 mg of bis(triphenylphosphine)palladium(II) dichloride in 1 mL of 1M Na$_2$CO$_3$ aqueous solution and 1 mL of acetonitrile was heated to 100° C. in a sealed microwave reactor for 20 min. The reaction mixture was evaporated. The crude product was purified by flash chromatography eluting with 0-50% EtOAc/hexane to yield 2-chloro-6-(3-methoxyphenyl)-4-morpholinothieno[3,2-d]pyrimidine (94 mg, 66%). 2-Chloro-6-(3-methoxyphenyl)-4-morpholinothieno[3,2-d]pyrimidine (94 mg) was coupled to 4-(4,4,5,5-tetramethyl-1,3,2-dioxaborolan-2-yl)-1H-indazole 7 via General Procedure A to yield 8.1 mg of 335. MS (Q1) 444.2 (M)$^+$

Example 260

3-(2-(1H-indazol-4-yl)-4-morpholinothieno[3,2-d]pyrimidin-6-yl)-N-((S)-2-hydroxypropyl)benzamide 336

3-(2-Chloro-4-morpholinothieno[3,2-d]pyrimidin-6-yl) benzoic acid (49 mg) was reacted with (S)-(+)-1-amino-2-propanol via General Procedure B to yield 3-(2-chloro-4-morpholinothieno[3,2-d]pyrimidin-6-yl)-N-((S)-2-hydroxypropyl)benzamide. 3-(2-Chloro-4-morpholinothieno[3,2-d]pyrimidin-6-yl)-N-((S)-2-hydroxypropyl)benzamide (56 mg) was coupled to 4-(4,4,5,5-tetramethyl-1,3,2-dioxaborolan-2-yl)-1H-indazole 7 via General Procedure A to yield 24.8 mg of 336. MS (Q1) 515.2 (M)$^+$

Example 261

(3-(2-(1H-indazol-4-yl)-4-morpholinothieno[3,2-d]pyrimidin-6-yl)phenyl)(morpholino)methanone 337

3-(2-Chloro-4-morpholinothieno[3,2-d]pyrimidin-6-yl) benzoic acid (49 mg) was reacted with morpholine via General Procedure B to yield 3-(2-chloro-4-morpholinothieno[3,2-d]pyrimidin-6-yl)phenyl(morpholino)methanone. Crude 3-(2-chloro-4-morpholinothieno[3,2-d]pyrimidin-6-yl)phenyl(morpholino)methanone (58 mg) was coupled to 4-(4,4,5,5-tetramethyl-1,3,2-dioxaborolan-2-yl)-1H-indazole 7 via General Procedure A to yield 23.7 mg of 337. MS (Q1) 527.2 (M)$^+$

Example 262

3-(2-(1H-indazol-4-yl)-4-morpholinothieno[3,2-d]pyrimidin-6-yl)benzoic acid 338

3-(2-Chloro-4-morpholinothieno[3,2-d]pyrimidin-6-yl) benzoic acid was coupled to 4-(4,4,5,5-tetramethyl-1,3,2-dioxaborolan-2-yl)-1H-indazole 7 (100 mg) via General Procedure A to yield 7.6 mg of 338. MS (Q1) 458.1 (M)$^+$

Example 263

(3-(2-(1H-indazol-4-yl)-4-morpholinothieno[3,2-d]pyrimidin-6-yl)phenyl)(4-methylpiperazin-1-yl)methanone 339

3-(2-Chloro-4-morpholinothieno[3,2-d]pyrimidin-6-yl) benzoic acid (60 mg) was reacted with 1-methylpiperizine via General Procedure B to yield 3-(2-chloro-4-morpholinothieno[3,2-d]pyrimidin-6-yl)phenyl)(4-methylpiperazin-1-yl)methanone. Crude 3-(2-chloro-4-morpholinothieno[3,2-d]pyrimidin-6-yl)phenyl)(4-methylpiperazin-1-yl) methanone (71 mg) was coupled to 4-(4,4,5,5-tetramethyl-1,3,2-dioxaborolan-2-yl)-1H-indazole 7 via General Procedure A to yield 22.4 mg of 339. MS (Q1) 540.1 (M)$^+$

Example 264

3-(2-(1H-indazol-4-yl)-4-morpholinothieno[3,2-d]pyrimidin-6-yl)-N-(2-(dimethylamino)ethyl)benzamide 340

3-(2-Chloro-4-morpholinothieno[3,2-d]pyrimidin-6-yl)benzoic acid (60 mg) was reacted with N,N-dimethylethlenediamine via General Procedure B to yield 3-(2-chloro-4-morpholinothieno[3,2-d]pyrimidin-6-yl)-N-(2-dimethylamino)ethyl)benzamide. Crude 3-(2-chloro-4-morpholinothieno[3,2-d]pyrimidin-6-yl)-N-(2-dimethylamino)ethyl)benzamide (73 mg) was coupled to 4-(4,4,5,5-tetramethyl-1,3,2-dioxaborolan-2-yl)-1H-indazole 7 via General Procedure A to yield 16 mg of 340. MS (Q1) 528.0 (M)+

Example 265

N-(3-(2-(1H-indazol-4-yl)-4-morpholinofuro[3,2-d]pyrimidin-6-yl)phenyl)acetamide 341

2-Chloro-6-iodo-4-morpholinofuro[3,2-d]pyrimidine 45 from Example 27 was reacted with 3-acetamidophenylboronic acid via General Procedure A to give the corresponding intermediate, after purification by flash chromatography, which was then reacted with 4-(4,4,5,5-tetramethyl-1,3,2-dioxaborolan-2-yl)-1H-indazole 7 to give, after purification by reverse phase HPLC, 341. MS (Q1) 455 (M+)

Example 266

5-(2-(1H-indazol-4-yl)-4-morpholinothieno[3,2-d]pyrimidin-6-yl)-N-((S)-2-hydroxypropyl)pyridine-3-carboxamide 342

5-(2-Chloro-4-morpholinothieno[3,2-d]pyrimidin-6-yl)pyridine-3-carboxylic acid (40 mg) was reacted with (S)-(+)-1-amino-2-propanol via General Procedure B to yield 5-(2-chloro-4-morpholinothieno[3,2-d]pyrimidin-6-yl)-N-((S)-2-hydroxypropyl)pyridine-3-carboxamide. Crude 5-(2-chloro-4-morpholinothieno[3,2-d]pyrimidin-6-yl)-N-((S)-2-hydroxypropyl)pyridine-3-carboxamide (46 mg) was coupled to 4-(4,4,5,5-tetramethyl-1,3,2-dioxaborolan-2-yl)-1H-indazole 7 via General Procedure A to yield 7.6 mg of 342. MS (Q1) 516.5. (M)+.

Example 267

5-(2-(1H-indazol-4-yl)-4-morpholinothieno[3,2-d]pyrimidin-6-yl)-N-(2-(dimethylamino)ethyl)pyridine-3-carboxamide 343

5-(2-Chloro-4-morpholinothieno[3,2-d]pyrimidin-6-yl)pyridine-3-carboxylic acid (40 mg) was reacted with N,N-dimethylethylenediamine via General Procedure B to yield 5-(2-chloro-4-morpholinothieno[3,2-d]pyrimidin-6-yl)-N-(2-dimethylamino)ethyl)pyridine-3-carboxamide. Crude 5-(2-chloro-4-morpholinothieno[3,2-d]pyrimidin-6-yl)-N-(2-dimethylamino)ethyl)pyridine-3-carboxamide (46 mg) was coupled to 4-(4,4,5,5-tetramethyl-1,3,2-dioxaborolan-2-yl)-1H-indazole 7 via General Procedure A to yield 22.3 mg of 343. MS (Q1) 529.0 (M)+

Example 268

5-(2-(1H-indazol-4-yl)-4-morpholinothieno[3,2-d]pyrimidin-6-yl)-N-methylpyridine-3-carboxamide 344

5-(2-Chloro-4-morpholinothieno[3,2-d]pyrimidin-6-yl)pyridine-3-carboxylic acid (40 mg) was reacted with methylamine hydrochloride via General Procedure B to yield 5-(2-chloro-4-morpholinothieno[3,2-d]pyrimidin-6-yl)-N-methylpyridine-3-carboxamide. Crude 5-(2-chloro-4-morpholinothieno[3,2-d]pyrimidin-6-yl)-N-methylpyridine-3-carboxamide (41 mg) was coupled to 4-(4,4,5,5-tetramethyl-1,3,2-dioxaborolan-2-yl)-1H-indazole 7 via General Procedure A to yield 10.6 mg of 344. MS (Q1) 472.0 (M)+

Example 269

2-(2-(1H-indol-6-yl)-4-morpholinothieno[3,2-d]pyrimidin-6-yl)propan-2-ol 345

2-Chloro-4-morpholinothieno[3,2-d]pyrimidine 4 (4 g) was reacted with acetone following General Procedure D to give the corresponding tertiary alcohol. 75 mg of this crude material was used in a palladium catalyzed cross coupling reaction following General Procedure A to give 18 mg of 345 after reversed phase HPLC purification. MS (Q1) 395 (M)+

Example 270

2-(4-morpholino-2-(quinolin-3-yl)thieno[3,2-d]pyrimidin-6-yl)propan-2-ol 346

2-Chloro-4-morpholinothieno[3,2-d]pyrimidine 4 (2 g) was used along with acetone following General Procedure D to give the corresponding tertiary alcohol. 75 mg of this crude material was used in a palladium catalyzed cross coupling reaction following General Procedure A to give 8 mg of 346 after reversed phase HPLC purification. MS (Q1) 407 (M)+

Example 271

(5-(2-(1H-indazol-4-yl)-4-morpholinothieno[3,2-d]pyrimidin-6-yl)pyridin-3-yl)(morpholino)methanone 347

5-(2-Chloro-4-morpholinothieno[3,2-d]pyrimidin-6-yl)pyridine-3-carboxylic acid (40 mg) was reacted with morpholine via General Procedure B to yield 5-(2-chloro-4-morpholinothieno[3,2-d]pyrimidin-6-yl)pyridine-3-yl)(morpholine)methanone. Crude 5-(2-chloro-4-morpholinothieno[3,2-d]pyrimidin-6-yl)pyridine-3-yl)(morpholine)methanone (47 mg) was coupled to 4-(4,4,5,5-tetramethyl-1,3,2-dioxaborolan-2-yl)-1H-indazole 7 via General Procedure A to yield 10.6 mg of 347 MS (Q1) 528.1 (M)+

Example 272

(5-(2-(1H-indazol-4-yl)-4-morpholinothieno[3,2-d]pyrimidin-6-yl)pyridin-3-yl)(4-methylpiperazin-1-yl)methanone 348

5-(2-Chloro-4-morpholinothieno[3,2-d]pyrimidin-6-yl)pyridine-3-carboxylic acid (40, mg) was reacted with 1-methylpiperizine via General Procedure B to yield 5-(2-chloro- 4-morpholinothieno[3,2-d]pyrimidin-6-yl)pyridine-3-yl)(4-methylpiperazin-1-yl)methanone. Crude 5-(2-chloro-4-morpholinothieno[3,2-d]pyrimidin-6-yl)pyridine-3-yl)(4-methylpiperazin-1-yl)methanone (48 mg) was coupled to 4-(4,4,5,5-tetramethyl-1,3,2-dioxaborolan-2-yl)-1H-indazole 7 via General Procedure A to yield 14.6 mg of 348. MS (Q1) 541.1 (M)$^+$ Example 273

5-(2-(1H-indazol-4-yl)-4-morpholinothieno[3,2-d]pyrimidin-6-yl)pyridine-3-carboxylic acid 349

2-Chloro-6-iodo-4-morpholinothieno[3,2-d]pyrimidine 19, 200 mg of 3-ethoxycarbonylpyridine-5-boronic acid pinacol ester (250 mg) and 23 mg of bis(triphenylphosphine)palladium(II) dichloride in 1.5 mL of 1M Na$_2$CO$_3$ aqueous solution and 1.5 mL of acetonitrile was heated to 100° C. in a sealed microwave reactor for 10 min. The reaction mixture was evaporated. The crude product was purified by flash chromatography eluting with 10-100% EtOAc/hexane to yield ethyl 5-(2-chloro-4-morpholinothieno[3,2-d]pyrimidin-6-yl)pyridine-3-carboxylate (240 mg, 75%).

Ethyl 5-(2-chloro-4-morpholinothieno[3,2-d]pyrimidin-6-yl)pyridine-3-carboxylate (240 mg) and 27 mg of lithium hydroxide monohydrate were dissolved in 4 mL of THF and 4 mL of H$_2$O. The reaction was stirred for 2 h at room temperature. The mixture was evaporated, and then added H$_2$O. The mixture was acidified with 1N HCl to pH=2~3. The resulting solid was filtered and washed with H$_2$O to yield 5-(2-chloro-4-morpholinothieno[3,2-d]pyrimidin-6-yl)pyridine-3-carboxylic acid (250 mg).

5-(2-Chloro-4-morpholinothieno[3,2-d]pyrimidin-6-yl)pyridine-3-carboxylic acid (40 mg) was coupled to 4-(4,4,5,5-tetramethyl-1,3,2-dioxaborolan-2-yl)-1H-indazole 7 via General Procedure A to yield 5 mg of 349. MS (Q1) 459.1 (M)$^+$ Example 274

N-((2-(1H-indazol-4-yl)-4-morpholinothieno[3,2-d]pyrimidin-6-yl)methyl)-2-(dimethylamino)acetamide 350

To a solution of (2-chloro-4-morpholinothieno[3,2-d]pyrimidin-6-yl)methanamine 27 from Example 11 (50 mg, 0.2 mmol) in CH$_2$Cl$_2$ (4 mL) was added Et$_3$N (84 μL, 0.6 mmol) and dimethylglycine ethyl ester (0.3 mmol). The reaction stirred 18-48 h at room temperature before being quenched with water. The aqueous layer was extracted with EtOAc. The combined organics were dried over Na$_2$SO$_4$ and concentrated in vacuo to give N-((2-chloro-4-morpholinothieno[3,2-d]pyrimidin-6-yl)methyl)-2-(dimethylamino)acetamide which was utilized in a Suzuki coupling according to General Procedure A. The crude material was purified by reversed phase HPLC to give 350 (10 mg). MS (Q1) 452 (M)+

Example 275

2-(4-morpholino-2-(1H-pyrrolo[2,3-b]pyridin-5-yl)thieno[2,3-d]pyrimidin-6-yl)propan-2-ol 351

2-(2-Chloro-4-morpholinothieno[2,3-d]pyrimidin-6-yl)propan-2-ol (100 mg) was reacted with 5-(4,4,5,5-tetramethyl-1,3,2-dioxaborolan-2-yl)-1H-pyrrolo[2,3-b]pyridine via General Procedure A to give 120 mg of 351 following reverse phase HPLC purification. MS (Q1) 396.2 (M)+

Example 276

N-(3-(2-(1H-indazol-4-yl)-4-morpholinothieno[3,2-d]pyrimidin-6-yl)phenyl)-N-methylacetamide 352

2-Chloro-6-iodo-4-morpholinothieno[3,2-d]pyrimidine 19, 129 mg of 3-acetamidophenylboronic acid (250 mg) and 23 mg of bis(triphenylphosphine)palladium(II) dichloride in 1.5 mL of 1M Na$_2$CO$_3$ aqueous solution and 1.5 mL of acetonitrile was heated to 100° C. in a sealed microwave reactor for 15 min. Upon completion, the reaction mixture was evaporated. The crude product was purified by flash chromatography eluting with 20~100% EtOAc/hexane to yield N-(3-(2-chloro-6-iodo-4-morpholinothieno[3,2-d]pyrimidine-6-yl)phenyl)acetamide (530 mg, 53%).

To a solution of 60 mg of N-(3-(2-chloro-6-iodo-4-morpholinothieno[3,2-d]pyrimidine-6-yl)phenyl)acetamide and 78 mg of cesium carbonate in DMF was added 12 μL of iodomethane. The reaction mixture was stirred for 2 h at room temperature. The mixture was diluted with ethyl acetate, washed with H$_2$O. The organic layer was dried over (MgSO$_4$) and evaporated to yield N-(3-(2-chloro-6-iodo-4-morpholinothieno[3,2-d]pyrimidine-6-yl)phenyl)-N-methylacetamide.

N-(3-(2-Chloro-6-iodo-4-morpholinothieno[3,2-d]pyrimidine-6-yl)phenyl)-N-methylacetamide (62 mg) was coupled to 4-(4,4,5,5-tetramethyl-1,3,2-dioxaborolan-2-yl)-1H-indazole 7 via General Procedure A to yield 352. MS (Q1) 485.2 (M)$^+$ Example 277

(2-(1H-indazol-4-yl)-4-morpholinothieno[3,2-d]pyrimidin-6-yl)(4-N-methylsulfonylpiperidin-4-yl)methanol 353

Tert-butyl 4-(hydroxymethyl)piperidine-1-carboxylate (1 g) in 20 mL of dichloromethane was combined with 2 g of Dess-Martin periodinane and stirred for 2 h, filtered through celite, extracted with saturated sodium bicarbonate, and evaporated. The crude product was placed on a column and 325 mg of the aldehyde, tert-butyl 4-formylpiperidine-1-carboxylate, was isolated. 260 mg 2-chloro-4-morpholinothieno[3,2-d]pyrimidine 4 was reacted with 325 mg of tert-butyl 4-formylpiperidine-1-carboxylate following General Procedure D to give 100 mg of tert-butyl 4-((2-chloro-4-morpholinothieno[3,2-d]pyrimidin-6-yl)(hydroxy)methyl)piperidine-1-carboxylate. The Boc group was removed from 100 mg of the alcohol using 0.125 mL of a 4.0 M HCl solution in dioxane in 10 mL of DCM with 0.5 mL of methanol. After several hours the DCM, methanol, and HCl was evaporated. The crude amine, (2-chloro-4-morpholinothieno[3,2-d]pyrimidin-6-yl)(piperidin-4-yl)methanol, was mesylated in 3 mL of DCM and 0.04 mL of triethylamine with 0.03 mL of methanesulfonyl chloride. The 4-N-methylsulfonylpiperidinyl compound was then coupled to 4-(4,4,5,5-tetramethyl-1,3,2-dioxaborolan-2-yl)1H-indazole 7 following General Procedure A to give 70 mg of 353 after reversed phase HPLC purification. MS (Q1) 530 (M)+

Example 278

1-(2-(1H-indazol-4-yl)-4-morpholinofuro[3,2-d]pyrimidin-6-yl)ethanol 354; and enantiomers: (S)-1-(2-(1H-indazol-4-yl)-4-morpholinofuro[3,2-d]pyrimidin-6-yl)ethanol 294 and (R)-1-(2-(1H-indazol-4-yl)-4-morpholinofuro[3,2-d]pyrimidin-6-yl)ethanol 295

A solution of 2-chloro-4-morpholinofuro[3,2-d]pyrimidine 38 from Example 19 (0.3 mmol) dissolved in THF (3 mL) at −78° C. was added 1.6M solution of n-butyllithium (0.39 mmol). The reaction mixture was stirred for 30 mins at which point acetaldehyde (1.2 mmol) was added. The reaction was stirred for one hour and quenched with ice and allowed to warm to room temperature. The aqueous layer was extracted with methylene chloride and the organic layer was filtered through sodium sulfate. The organic phase was concentrated to yield 1-(2-chloro-4-morpholinofuro[3,2-d]pyrimidine-6-yl)ethanol (72 mg).

1-(2-Chloro-4-morpholinofuro[3,2-d]pyrimidine-6-yl)ethanol (0.25 mmol) was dissolved in acetonitrile (1.5 mL) and treated with 4-(4,4,5,5-tetramethyl-1,3,2-dioxaborolan-2-yl)1H-indazole (0.62 mmol), PdCl2(PPh3)2 (0.025 mmol) and aqueous 1M potassium acetate (0.75 mmol). The vial was sealed and heated with stirring in a microwave to 150 deg C. for 14 mins. The crude reaction mixture was filtered and concentrated. The racemic product was purified by reverse phase chromatography to give racemic 354. Chiral chromatography of racemic 354 separated the two enantiomers 294- and 295.

Example 279

2-(1H-indazol-4-yl)-4-morpholino-6-((pyridin-3-yloxy)methyl)thieno[3,2-d]pyrimidine 355

To a suspension of 2-chloro-4-morpholin-4-yl-thieno[3,2-d]pyrimidine-6-carbaldehyde (900 mg) in toluene (20 mL) at 40° C. was added phosphorus tribromide (0.10 mL) and the reaction mixture was heated at 100° C. for 16 h. After cooling to room temperature, the reaction was diluted with dichloromethane (40 mL) and washed with saturated aqueous sodium hydrogen carbonate solution (2×40 mL). The organic layer was dried (MgSO$_4$) and reduced in vacuo to give 6-bromomethyl-2-chloro-4-morpholin-4-yl-thieno[3,2-d]pyrimidine as a yellow solid.

To a solution of 3-hydroxypyridine (102 mg) in THF (10 mL) was added sodium hydride (43 mg) and the reaction stirred at room temperature for 1 h. Then, 6-bromomethyl-2-chloro-4-morpholin-4-yl-thieno[3,2-d]pyrimidine (150 mg) was added and the reaction stirred at room temperature for 16 h. The reaction was quenched with water (20 mL) and extracted into ethyl acetate (2×20 mL). The combined organics were washed with aqueous brine solution (2×20 mL), dried (MgSO$_4$), reduced in vacuo and purified by column chromatography to give 2-chloro-4-morpholin-4-yl-6-phenoxymethyl-thieno[3,2-d]pyrimidine as a white solid.

2-Chloro-4-morpholin-4-yl-6-phenoxymethyl-thieno[3,2-d]pyrimidine was reacted with 4-(4,4,5,5-tetramethyl-[1,3,2]dioxaborolan-2-yl)-1H-indazole in general procedure A. Purification by column chromatography yielded 355. NMR: CDCl$_3$: 3.81-3.84 (4 H, m, CH$_2$), 4.02-4.05 (4 H, m, CH$_2$), 5.41 (2 H, s, CH$_2$), 7.12-7.15 (1 H, m, Ar), 7.21-7.23 (1 H, m, Ar), 7.42-7.43 (1 H, m, Ar), 7.45 (1 H, s, Ar), 7.50 (1 H, d, J 8.2, Ar), 8.28 (1 H, d, J 7.5, Ar), 8.40-8.42 (1 H, m, Ar) and 9.03 (1 H, s, Ar). MS: (ESI+): MH+ 445.18

Example 280

7-methyl-6-(5-(methylsulfonyl)pyridin-3-yl)-4-morpholino-2-(1H-pyrrolo[2,3-b]pyridin-5-yl)thieno[3,2-d]pyrimidine 356

2-Chloro-6-iodo-7-methyl-4-morpholinothieno[3,2-d]pyrimidine (150 mg) was coupled to 3-methanesulphonylamino methyl benzeneboronic acid, and then reacted with 7-azaindole-5-boronic acid pinacol ester via General Procedure F. The product was purified by reverse phase HPLC to yield 79 mg of 356. MS. (Q1) 507.1 (M)$^+$

Example 281

6-((hexahydro-2-methylsulfonylpyrrolo[3,4-c]pyrrol-5(1H)-yl)methyl)-2-(1H-indazol-4-yl)-4-morpholinothieno[3,2-d]pyrimidine 357

To intermediate 2-chloro-4-morpholinothieno[3,2-d]pyrimidine-6-carbaldehyde 10 from Example 3 (100 mg, 0.35 mmol) in 1,2-dichloroethane (2 mL) was added acetic acid (20 μL, 0.35 mmol), and 2-BOC-Hexahydro-pyrrolo[3,4-c]pyrrole (98 mg, 0.5 mmol) then Na(OAc)$_3$BH (90 mg, 0.42 mmol). The reaction stirred overnight at room temperature. The reaction was quenched with water and extracted with DCM. The combined organics were dried over Na$_2$SO$_4$, filtered, and concentrated in vacuo. The crude product was dissolved in CH$_2$Cl$_2$ (10 mL), MeOH (10 mL), Et$_2$O (2 mL), and 4 M HCl in dioxane (7 mL) was added. The resulting mixture stirred at room temperature overnight. The reaction mixture was concentrated in vacuo. The crude material was dissolved in CH$_2$Cl$_2$ (5 mL) and Et$_3$N (4 mL) and methanesulfonyl chloride (54 μL, 0.7 mmol) were added. The reaction mixture stirred at room temperature overnight. The reaction was quenched by the addition of water then extracted with EtOAc. The combined organics were dried over Na$_2$SO$_4$, filtered, and concentrated in vacuo. The crude material was utilized in a Suzuki coupling according to General Procedure A using 4-(4,4,5,5-tetramethyl-1,3,2-dioxaborolan-2-yl)-1H-indazole 7 to provide 357 after reverse phase HPLC purification (21 mg). MS (Q1) 540 (M)+

Example 282

3-(2-(1H-indazol-4-yl)-7-methyl-4-morpholinothieno[3,2-d]pyrimidin-6-yl)-N-methylbenzamide 358

2-Chloro-6-iodo-7-methyl-4-morpholinothieno[3,2-d]pyrimidine from Example 12 (0.1 g, 0.3 mmol), 3-(N-Methylaminocarbonyl)benzeneboronic acid (50 mg, 0.3 mmol), and bis(triphenylphosphine)palladium(II) dichloride (9 mg, 13 μmol) in 1 M aqueous Na$_2$CO$_3$ (0.5 mL) and acetonitrile (0.5 mL) were heated to 100° C. in a sealed microwave reactor for 10 min. Upon completion, 4-(4,4,5,5-tetramethyl-1,3,2-dioxaborolan-2-yl)-1H-indazole 7 (122 mg, 0.5 mmol), bis(triphenylphosphine)palladium(II) dichloride (9 mg, 13 μmol), 1 M aqueous Na$_2$CO$_3$ (1 mL), and acetonitrile (1 mL) were added into the same pot. The reaction mixture was heated to 150° C. in a sealed microwave reactor for 20 min. The mixture was extracted with EtOAc and CH$_2$Cl$_2$. The combined organics

Example 283

N-(3-(2-(1H-indazol-4-yl)-7-methyl-4-morpholinothieno[3,2-d]pyrimidin-6-yl)phenyl)acetamide 359

2-Chloro-6-iodo-7-methyl-4-morpholinothieno[3,2-d]pyrimidine from Example 12 (0.1 g, 0.3 mmol), 3-Acetamidobenzeneboronic acid (50 mg, 0.3 mmol), and bis(triphenylphosphine)palladium(II) dichloride (9 mg, 13 µmol) in 1 M aqueous $Na_2CO_3$ (0.5 mL) and acetonitrile (0.5 mL) were heated to 100° C. in a sealed microwave reactor for 10 min. Upon completion, 4-(4,4,5,5-tetramethyl-1,3,2-dioxaborolan-2-yl)-1H-indazole 7 (122 mg, 0.5 mmol), bis(triphenylphosphine)palladium(II) dichloride (9 mg, 13 µmol), 1 M aqueous $Na_2CO_3$ (1 mL), and acetonitrile (1 mL) were added into the same pot. The reaction mixture was heated to 150° C. in a sealed microwave reactor for 20 min. The mixture was extracted with EtOAc and $CH_2Cl_2$. The combined organics were concentrated to yield 359 after reverse phase HPLC purification (10 mg). MS (Q1) 485 (M)+

Example 284

2-(1H-indazol-4-yl)-7-methyl-6-(3-(methylsulfonyl)phenyl)-4-morpholinothieno[3,2-d]pyrimidine 360

2-Chloro-6-iodo-7-methyl-4-morpholinothieno[3,2-d]pyrimidine from Example 12 (0.6 g, 1.5 mmol), 3-(methylsulfonyl)phenylboronic acid (0.3 g, 1.5 mmol), and bis(triphenylphosphine)palladium(II) dichloride (53 mg, 80 µmol) in 1 M aqueous $Na_2CO_3$ (3 mL) and acetonitrile (3 mL) were heated to 100° C. in a sealed microwave reactor for 10 min. Upon completion the organic layer was separated and the aqueous layer was extracted with EtOAc. The combined organics were concentrated in vacuo. A portion of the residue (0.38 mmol) was dissolved in 1 M $Na_2CO_3$ (1.5 mL) and $CH_3CN$ (1.5 mL) and 4-(4,4,5,5-tetramethyl-1,3,2-dioxaborolan-2-yl)1H-indazole 7 (0.2 g, 0.8 mmol) and bis(triphenylphosphine)palladium(II) dichloride (13 mg, 20 µmol) were added into the same pot. The reaction mixture was heated to 150° C. in a sealed microwave reactor for 30 min. The mixture was extracted with EtOAc and $CH_2Cl_2$. The combined organics were concentrated to yield 360 after reverse phase HPLC purification (90 mg). MS (Q1) 506 (M)+

Example 285

2-(1H-indazol-4-yl)-6-(4-methoxypyridin-3-yl)-7-methyl-4-morpholinothieno[3,2-d]pyrimidine 361

2-Chloro-6-iodo-7-methyl-4-morpholinothieno[3,2-d]pyrimidine from Example 12 (0.1 g, 0.3 mmol), 4-Methoxy-3-pyridineboronic acid (42 mg, 0.3 mmol), and bis(triphenylphosphine)palladium(II) dichloride (9 mg, 13 µmol) in 1 M aqueous $Na_2CO_3$ (0.5 mL) and acetonitrile (0.5 mL) were heated to 100° C. in a sealed microwave reactor for 10 min. Upon completion, 4-(4,4,5,5-tetramethyl-1,3,2-dioxaborolan-2-yl)-1H-indazole 7 (122 mg, 0.5 mmol), bis(triphenylphosphine)palladium(II) dichloride (9 mg, 13 µmol), 1 M aqueous $Na_2CO_3$ (1 mL), and acetonitrile (1 mL) were added into the same pot. The reaction mixture was heated to 150° C. in a sealed microwave reactor for 20 min. The mixture was extracted with EtOAc and $CH_2Cl_2$. The combined organics were concentrated to yield 361 after reverse phase HPLC purification (28 mg). MS (Q1) 459 (M)+

Example 286

N-((2-(1H-indazol-4-yl)-4-morpholinothieno[3,2-d]pyrimidin-6-yl)methyl)-3-methoxybenzamide 362

(2-Chloro-4-morpholinothieno[3,2-d]pyrimidin-6-yl)methanamine 27 from Example 11 (50.0 mg, 0.17 mM) was dissolved in 1.5 mL DMF. To this was added 77.6 mg (3.0 eq) of p-anisic acid, 129.3 mg (2.0 eq) HATU and 0.18 uL (6.0 eq) DIPEA and the reaction heated at 40° C. for 18 hours. Complete reaction was confirmed by HPLC and 2.0 eq $NH_2OH$—$H_2O$ was added to the cooled reaction and the reaction stirred for ten minutes. The reaction was diluted with Sat. $NaHCO_3$, extracted with EtOAc, washed with brine, dried over $MgSO_4$ and concentrated in vacuo. This intermediate was purified by flash chromatography (EtOAc/Hexanes) followed by Suzuki coupling of 4-(4,4,5,5-tetramethyl-1,3,2-dioxaborolan-2-yl) 1H-indazole 7 as per General Procedure A. Complete reaction was confirmed by LCMS and the reaction was concentrated in vacuo to give 18.9 mg of the final product after RP-HPLC purification (38% yield). MS (Q1) 501.3 (M)+

Example 287

N-((2-(1H-indazol-4-yl)-4-morpholinothieno[3,2-d]pyrimidin-6-yl)methyl)-4-methoxybenzamide 363

(2-Chloro-4-morpholinothieno[3,2-d]pyrimidin-6-yl)methanamine 27 from Example 11 (50.0 mg, 0.17 mM) was dissolved in 1.5 mL DMF. To this was added 77.6 mg (3.0 eq) of p-anisic acid, 129.3 mg (2.0 eq) HATU and 0.18 uL (6.0 eq) DIPEA and the reaction heated at 40° C. for 18 hours. Complete reaction was confirmed by HPLC and 2.0 eq $NH_2OH$—$H_2O$ was added to the cooled reaction and the reaction stirred for ten minutes. The reaction was diluted with sat. $NaHCO_3$, extracted with EtOAc, washed with brine, dried over $MgSO_4$ and concentrated in vacuo. This intermediate was purified by flash chromatography (EtOAc/Hexanes) followed by Suzuki coupling of 4-(4,4,5,5-tetramethyl-1,3,2-dioxaborolan-2-yl) 1H-indazole 7 as per General Procedure A. Complete reaction was confirmed by LCMS and the reaction was concentrated in vacuo to give 18.9 mg of 363 after RP-HPLC purification (38% yield). MS (Q1) 501.3 (M)+

Example 288

N-((2-(1H-indazol-4-yl)-4-morpholinothieno[3,2-d]pyrimidin-6-yl)methyl)-4-methoxybenzenamine 364

To a 20 mL vial containing 6-(bromomethyl)-2-chloro-4-morpholinothieno[3,2-d]pyrimidine 30 from Example 9 (54.8 mg, 0.16 mM) dissolved in 3 mL DMF was added 19.7 mg (1.0 eq) p-Anisidine and 30.4 mg (1.4 eq) $K_2CO_3$. The vial was capped and the reaction was stirred overnight at RT. Complete reaction was confirmed by LCMS and the resulting intermediate was purified by flash chromatography to give 42.6 mg of product (68% yield). This intermediate was reacted with 4-(4,4,5,5-tetramethyl-1,3,2-dioxaborolan-2-yl) 1H-indazole 7 as per General Procedure A. Complete reaction was confirmed by LCMS and the reaction was concentrated in vacuo to give 24.7 mg of 364 after RP-HPLC purification (47% yield). MS (Q1) 473.3 (M)+

Example 289

2-(1H-indazol-4-yl)-6-((2-methyl-1H-imidazol-1-yl)methyl)-4-morpholinothieno[3,2-d]pyrimidine 365

To a 20 mL vial containing 6-(bromomethyl)-2-chloro-4-morpholinothieno[3,2-d]pyrimidine 30 from Example 9 (54.8 mg, 0.16 mM) dissolved in 3 mL DMF was added 13.14 mg (1.0 eq) 2-methylimidazole and 30.4 mg (1.4 eq) $K_2CO_3$. The vial was capped and the reaction was stirred overnight at RT. Complete reaction was confirmed by LCMS and the resulting intermediate was purified by flash chromatography to give 40 mg of product (71% yield). This intermediate was reacted with 4-(4,4,5,5-tetramethyl-1,3,2-dioxaborolan-2-yl)1H-indazole 7 as per General Procedure A. Complete reaction was confirmed by LCMS and the reaction was concentrated in vacuo to give 24.3 mg of 365 after RP-HPLC purification (51% yield). MS (Q1) 432.2 (M)+

Example 290

N-((2-(1H-indazol-4-yl)-4-morpholinothieno[3,2-d]pyrimidin-6-yl)methyl)-2-methoxybenzenamine 366

To a 20 mL vial containing 6-(bromomethyl)-2-chloro-4-morpholinothieno[3,2-d]pyrimidine 30 from Example 9 (54.8 mg, 0.16 mM) dissolved in 3 mL DMF was added 19.7 mg (1.0 eq) o-anisidine and 30.4 mg (1.4 eq) $K_2CO_3$. The vial was capped and the reaction was stirred overnight at RT. Complete reaction was confirmed by LCMS and the resulting intermediate was purified by flash chromatography to give 40 mg of product (64% yield). This intermediate was reacted with 4-(4,4,5,5-tetramethyl-1,3,2-dioxaborolan-2-yl)1H-indazole 7 as per General Procedure A. Complete reaction was confirmed by LCMS and the reaction was concentrated in vacuo to give 23.0 mg of 366 after RP-HPLC purification (49% yield). MS (Q1) 473.3 (M)+

Example 291

3-((2-(1H-indazol-4-yl)-4-morpholinothieno[3,2-d]pyrimidin-6-yl)methylamino)-N-methylbenzamide 367

To a 20 mL vial containing 6-(bromomethyl)-2-chloro-4-morpholinothieno[3,2-d]pyrimidine 30 from Example 9 (54.8 mg, 0.16 mM) dissolved in 3 mL DMF was added 24.0 mg (1.0 eq) 3-Aminobenzoylmethylamide and 30.4 mg (1.4 eq) $K_2CO_3$. The vial was capped and the reaction was stirred overnight at RT. Complete reaction was confirmed by LCMS and the resulting intermediate was purified by flash chromatography to give 50.1 mg of product (75% yield). This intermediate was reacted with 4-(4,4,5,5-tetramethyl-1,3,2-dioxaborolan-2-yl)1H-indazole 7 as per General Procedure A. Complete reaction was confirmed by LCMS and the reaction was concentrated in vacuo to give 33.3 mg of 367 after RP-HPLC purification (56% yield). MS (Q1) 500.3 (M)+

Example 292

N-((2-(1H-indazol-4-yl)-4-morpholinothieno[3,2-d]pyrimidin-6-yl)methyl)-6-methoxypyridin-3-amine 368

To a 20 mL vial containing 6-(bromomethyl)-2-chloro-4-morpholinothieno[3,2-d]pyrimidine 30 from Example 9 (54.8 mg, 0.16 mM) dissolved in 3 mL DMF was added 19.9 mg (1.0 eq) of 5-amino-2-methoxypyridine and 30.4 mg (1.4 eq) $K_2CO_3$. The vial was capped and the reaction was stirred overnight at RT. Complete reaction was confirmed by LCMS and the resulting intermediate was purified by flash chromatography to give 56.0 mg of product (89% yield). This intermediate was reacted with 4-(4,4,5,5-tetramethyl-1,3,2-dioxaborolan-2-yl)1H-indazole 7 as per General Procedure A. Complete reaction was confirmed by LCMS and the reaction was concentrated in vacuo to give 8.8 mg of 368 after RP-HPLC purification (12% yield). MS (Q1) 474.2 (M)+

Example 293

N-((2-(1H-indazol-4-yl)-4-morpholinothieno[3,2-d]pyrimidin-6-yl)methyl)pyridin-3-amine 369

To a 20 mL vial containing 6-(bromomethyl)-2-chloro-4-morpholinothieno[3,2-d]pyrimidine 30 from Example 9 (54.8 mg, 0.16 mM) dissolved in 3 mL DMF was added 15.06 mg (1.0 eq) of 3-aminopyridine and 30.4 mg (1.4 eq) $K_2CO_3$. The vial was capped and the reaction was stirred overnight at RT. Complete reaction was confirmed by LCMS and the resulting intermediate was purified by flash chromatography to give 55.0 mg of product (95% yield). This intermediate was reacted with 4-(4,4,5,5-tetramethyl-1,3,2-dioxaborolan-2-yl)1H-indazole 7 as per General Procedure A. Complete reaction was confirmed by LCMS and the reaction was concentrated in vacuo to give 1.5 mg of 369 after RP-HPLC purification (2% yield). MS (Q1) 444.2 (M)+

Example 294

N-((2-(1H-indazol-4-yl)-4-morpholinothieno[3,2-d]pyrimidin-6-yl)methyl)-4-morpholinobenzenamine 370

To a 20 mL vial containing 6-(bromomethyl)-2-chloro-4-morpholinothieno[3,2-d]pyrimidine 30 from Example 9 (54.8 mg, 0.16 mM) dissolved in 3 mL DMF was added 28.5 mg (1.0 eq) of 4-morpholinoaniline and 30.4 mg (1.4 eq) $K_2CO_3$. The vial was capped and the reaction was stirred overnight at RT. Complete reaction was confirmed by LCMS and the resulting intermediate was purified by flash chromatography to give 60.0 mg of product (84% yield). This intermediate was reacted with 4-(4,4,5,5-tetramethyl-1,3,2-dioxaborolan-2-yl)1H-indazole 7 as per General Procedure A. Complete reaction was confirmed by LCMS and the reaction was concentrated in vacuo to give 11.2 mg of 370 after RP-HPLC purification (16% yield). MS (Q1) 528.3 (M)+

Example 295

N-((2-(1H-indazol-4-yl)-4-morpholinothieno[3,2-d]pyrimidin-6-yl)methyl)-1H-pyrazol-5-amine 371

To a 20 mL vial containing 6-(bromomethyl)-2-chloro-4-morpholinothieno[3,2-d]pyrimidine 30 from Example 9 (54.8 mg, 0.16 mM) dissolved in 3 mL DMF was added 13.3 mg (1.0 eq) of 3-aminopyrazole and 30.4 mg (1.4 eq) $K_2CO_3$. The vial was capped and the reaction was stirred overnight at RT. Complete reaction was confirmed by LCMS and the resulting intermediate was purified by flash chromatography to give 46 mg of product (82% yield). This intermediate was reacted with 4-(4,4,5,5-tetramethyl-1,3,2-dioxaborolan-2-yl)1H-indazole 7 as per General Procedure A. Complete reaction was confirmed by LCMS and the reaction was concentrated in vacuo to give 15.3 mg of 371 after RP-HPLC purification (27% yield). MS (Q1) 433.2 (M)+

Example 296

N-((2-(1H-indazol-4-yl)-4-morpholinothieno[3,2-d]pyrimidin-6-yl)methyl)-1,3-dihydrobenzo[c]thiophen-1,1-dioxide-5-amine 372

To a 20 mL vial containing 6-(bromomethyl)-2-chloro-4-morpholinothieno[3,2-d]pyrimidine 30 from Example 9 (54.8 mg, 0.16 mM) dissolved in 3 mL DMF was added 29.3 mg (1.0 eq) of 5-amino-2,3-dihydro-1H-2 lambda-6-benzo[c]thiophene-2,2-dione and 30.4 mg (1.4 eq) $K_2CO_3$. The vial was capped and the reaction was stirred overnight at RT. Complete reaction was confirmed by LCMS and the resulting intermediate was purified by flash chromatography to give 57.5 mg of product (80% yield). This intermediate was reacted with 4-(4,4,5,5-tetramethyl-1,3,2-dioxaborolan-2-yl)1H-indazole 7 as per General Procedure A. Complete reaction was confirmed by LCMS and the reaction was concentrated in vacuo to give 17.4 mg of 372 after RP-HPLC purification (25% yield). MS (Q1) 533.2 (M)+

Example 297

N-((2-(1H-indazol-4-yl)-4-morpholinothieno[3,2-d]pyrimidin-6-yl)methyl)-6-morpholinopyridin-3-amine 373

To a 20 mL vial containing 6-(bromomethyl)-2-chloro-4-morpholinothieno[3,2-d]pyrimidine 30 from Example 9 (54.8 mg, 0.16 mM) dissolved in 3 mL DMF was added 28.7 mg (1.0 eq) of 3-amino-6-morpholino-pyridine and 30.4 mg (1.4 eq) $K_2CO_3$. The vial was capped and the reaction was stirred overnight at RT. Complete reaction was confirmed by LCMS and the resulting intermediate was purified by flash chromatography to give 58.0 mg of product (81% yield). This intermediate was reacted with 4-(4,4,5,5-tetramethyl-1,3,2-dioxaborolan-2-yl)1H-indazole 7 as per General Procedure A. Complete reaction was confirmed by LCMS and the reaction was concentrated in vacuo to give 34.8 mg of 373 after RP-HPLC purification (51% yield). MS (Q1) 529.3 (M)+

Example 298

N-((2-(1H-indazol-4-yl)-4-morpholinothieno[3,2-d]pyrimidin-6-yl)methyl)-3-methylsulfonylaminobenzene-1-amine 374

To a 20 mL vial containing 6-(bromomethyl)-2-chloro-4-morpholinothieno[3,2-d]pyrimidine 30 from Example 9 (54.8 mg, 0.16 mM) dissolved in 3 mL DMF was added 29.8 mg (1.0 eq) of N-(3-aminophenyl)methane sulfonamide and 30.4 mg (1.4 eq) $K_2CO_3$. The vial was capped and the reaction was stirred overnight at RT. Complete reaction was confirmed by LCMS and the resulting intermediate was purified by flash chromatography to give 20 mg of product (28% yield). This intermediate was reacted with 4-(4,4,5,5-tetramethyl-1,3,2-dioxaborolan-2-yl)1H-indazole 7 as per General Procedure A. Complete reaction was confirmed by LCMS and the reaction was concentrated in vacuo to give 14.3 mg of 374 after RP-HPLC purification (53% yield). MS (Q1) 536.2 (M)+

Example 299

N-((2-(1H-indazol-4-yl)-4-morpholinothieno[3,2-d]pyrimidin-6-yl)methyl)-3-(methylsulfonyl)benzenamine 375

To a 20 mL vial containing 6-(bromomethyl)-2-chloro-4-morpholinothieno[3,2-d]pyrimidine 30 from Example 9 (54.8 mg, 0.16 mM) dissolved in 3 mL DMF was added 24.5 mg (1.0 eq) of 3-(methylsulfonyl)aniline and 30.4 mg (1.4 eq) $K_2CO_3$. The vial was capped and the reaction was stirred overnight at RT. Complete reaction was confirmed by LCMS and the resulting intermediate was purified by flash chromatography to give 25.6 mg of product (36% yield). This intermediate was reacted with 4-(4,4,5,5-tetramethyl-1,3,2-dioxaborolan-2-yl)1H-indazole 7 as per General Procedure A. Complete reaction was confirmed by LCMS and the reaction was concentrated in vacuo to give 11.8 mg of 375 after RP-HPLC purification (38% yield). MS (Q1) 521.2 (M)+

Example 300

(2-(1H-indazol-4-yl)-4-morpholinothieno[3,2-d]pyrimidin-6-yl)-N-cyclopropylsulfonylmethanamine 376

(2-Chloro-4-morpholinothieno[3,2-d]pyrimidin-6-yl)methanamine 27 from Example 11 (53.2 mg, 0.19 mM) was reacted with cyclopropane sulfonylchloride (2.2 eq) followed by Suzuki coupling of 4-(4,4,5,5-tetramethyl-1,3,2-dioxaborolan-2-yl)1H-indazole 7 as per general procedure K. Complete reaction was confirmed by LCMS and the reaction was concentrated in vacuo to give 16.7 mg of 376 after RP-HPLC purification (40% yield). MS (Q1) 471.3 (M)+

Example 301

N-((2-(1H-indazol-4-yl)-4-morpholinothieno[3,2-d]pyrimidin-6-yl)methyl)-2-(3-methoxyphenyl)acetamide 377

(2-Chloro-4-morpholinothieno[3,2-d]pyrimidin-6-yl)methanamine 27 from Example 11 (53.2 mg, 0.19 mM) was reacted with 3-methoxyphenylacetyl chloride (2.2 eq) followed by Suzuki coupling of 4-(4,4,5,5-tetramethyl-1,3,2-dioxaborolan-2-yl)1H-indazole 7 as per General Procedure K. Complete reaction was confirmed by LCMS and the reaction was concentrated in vacuo to give 16.0 mg of 377 after RP-HPLC purification (33% yield). MS (Q1) 515.3 (M)+

Example 302

N-((2-(1H-indazol-4-yl)-4-morpholinothieno[3,2-d]pyrimidin-6-yl)methyl)-2-(4-methoxyphenyl)acetamide 378

(2-Chloro-4-morpholinothieno[3,2-d]pyrimidin-6-yl)methanamine 27 from Example 11 (53.2 mg, 0.19 mM) was reacted with 4-methoxyphenylacetyl chloride (2.2 eq) followed by Suzuki coupling of 4-(4,4,5,5-tetramethyl-1,3,2-dioxaborolan-2-yl)1H-indazole 7 as per General Procedure K. Complete reaction was confirmed by LCMS and the reaction was concentrated in vacuo to give 18.8 mg of 378 after RP-HPLC purification (42% yield). MS (Q1) 515.3 (M)+

Example 303

(2-(1H-indazol-4-yl)-4-morpholinothieno[3,2-d]pyrimidin-6-yl)-N-methylsulfonylmethanamine 379

(2-Chloro-4-morpholinothieno[3,2-d]pyrimidin-6-yl)methanamine 27 from Example 11 (53.2 mg, 0.19 mM) was reacted with isopropylsulfonyl chloride (2.2 eq) followed by Suzuki coupling of 4-(4,4,5,5-tetramethyl-1,3,2-dioxaborolan-2-yl)1H-indazole 7 as per General Procedure K. Complete reaction was confirmed by LCMS and the reaction was concentrated in vacuo to give 2.8 mg of 379 after RP-HPLC purification (17% yield). MS (Q1) 473.2 (M)+

Example 304

2-(N-((2-(1H-indazol-4-yl)-4-morpholinothieno[3,2-d]pyrimidin-6-yl)methyl)-N,N-bis-(N-cyclopropylacetamide)-methanamine 380

To (2-Chloro-4-morpholinothieno[3,2-d]pyrimidin-6-yl)methanamine 27 from Example 11 (110 mg, 0.39 mM) in 5 mL DMF was added 48.2 uL (1.06 eq) 2,6-lutidine and N1-cyclopropyl-2-chloroacetamide (1.2 eq) followed by Suzuki coupling of 4-(4,4,5,5-tetramethyl-1,3,2-dioxaborolan-2-yl)1H-indazole 7 as per General Procedure K. Complete reaction was confirmed by LCMS and the reaction was concentrated in vacuo to give 10.0 mg of 380 after RP-HPLC purification (22% yield). MS (Q1) 561.3 (M)+

Example 305

1-((2-(1H-indazol-4-yl)-4-morpholinothieno[3,2-d]pyrimidin-6-yl)methyl)-N-methylsulfonylazetidin-3-amine 381

To 2-chloro-4-morpholinothieno[3,2-d]pyrimidine-6-carbaldehyde 10 from Example 3 (100 mg, 0.35 mmol) in 1,2-dichloroethane (2 mL) was added acetic acid (20 µL, 0.35 mmol), and 3-N-BOC-aminoazetidine (78 mg, 0.5 mmol) then Na(OAc)$_3$BH (90 mg, 0.42 mmol). The reaction stirred overnight at room temperature then was quenched with water and extracted with DCM. The combined organics were dried over Na$_2$SO$_4$, filtered, and concentrated in vacuo. The crude product was dissolved in CH$_2$Cl$_2$ (10 mL), MeOH (10 mL), and 4 M HCl in dioxane (10 mL) was added. The resulting mixture stirred at room temperature for 1 h then was concentrated in vacuo. The crude material was dissolved in CH$_2$Cl$_2$ (5 mL) and Et$_3$N (4 mL) and methanesulfonyl chloride (110 µL, 1.4 mmol) was added. The reaction mixture stirred at room temperature overnight then was quenched by the addition of water and extracted with EtOAc. The combined organics were dried over Na$_2$SO$_4$, filtered, and concentrated in vacuo to give N-(1-((2-chloro-4-morpholinothieno[3,2-d]pyrimidin-6-yl)methyl)azetidin-3-yl)methanesulfonamide which was utilized in a Suzuki coupling according to General Procedure A using 4-(4,4,5,5-tetramethyl-1,3,2-dioxaborolan-2-yl)-1H-indazole 7 to provide 381 after reverse phase HPLC purification (2 mg). MS (Q1) 500 (M)+

Example 306

2-((2-(1H-indazol-4-yl)-4-morpholinothieno[3,2-d]pyrimidin-6-yl)methylamino)-N-cyclopropylacetamide 382

To (2-Chloro-4-morpholinothieno[3,2-d]pyrimidin-6-yl)methanamine 27 from Example 11 (110 mg, 0.39 mM) in 5 mL DMF was added 48.2 uL (1.06 eq) 2,6-lutidine and N1-cyclopropyl-2-chloroacetamide (1.2 eq) followed by Suzuki coupling of 4-(4,4,5,5-tetramethyl-1,3,2-dioxaborolan-2-yl)1H-indazole 7 as per General Procedure K. Complete reaction was confirmed by LCMS and the reaction was concentrated in vacuo to give 6.5 mg of 382 after RP-HPLC purification (40% yield). MS (Q1) 464.3 (M)+

Example 307

N-((2-(1H-indazol-4-yl)-4-morpholinothieno[3,2-d]pyrimidin-6-yl)methyl)-2-(methylsulfonyl)ethanamine 383

To a mixture of N-(2-bromoethyl)phthalimide (500 mg) in DMSO (8 mL) was added sodium thiomethoxide (152 mg) and the reaction stirred at room temperature for 16 h. Then with water (2 mL) was added and the mixture stirred at room temperature for 10 min. The reaction was diluted with water (20 mL) and extracted into ethyl acetate (2×20 mL). The combined organics were washed with aqueous brine solution (2×20 mL), dried (MgSO$_4$) and reduced in vacuo to give 2-(2-methylsulfanyl-ethyl)-isoindole-1,3-dione as a white solid.

To a solution of 2-(2-methylsulfanyl-ethyl)-isoindole-1,3-dione (400 mg) in methanol (10 mL) was added a solution of oxone (1.67 g) in water (10 mL) and the reaction stirred at room temperature for 16 h. The reaction was then diluted with water (20 mL) and extracted into dichloromethane (2×20 mL). The combined organics were washed with aqueous brine solution (2×20 mL), dried (MgSO$_4$) and reduced in vacuo to give 2-(2-methanesulfonyl-ethyl)-isoindole-1,3-dione as a white solid.

To a solution of 2-(2-methanesulfonyl-ethyl)-isoindole-1,3-dione (387 mg) in ethanol (10 mL) was added hydrazine monohydrate (0.60 mL) and the reaction was heated at reflux for 3 h. After cooling to room temperature, the mixture was filtered and the filtrate reduced in vacuo to give 2-methanesulfonyl-ethylamine as a white solid.

To a solution of 2-chloro-4-morpholin-4-yl-thieno[3,2-d]pyrimidine-6-carbaldehyde (277 mg) in methanol (10 mL) was added 2-methanesulfonyl-ethylamine (234 mg) and the reaction stirred at room temperature for 16 h. The solvent was reduced in vacuo and the residue redissolved in ethanol (50 mL). Palladium on carbon (20 mg) was added and the reaction stirred at room temperature under a hydrogen balloon for 48 h. The reaction was then filtered through Celite and the filtrate reduced in vacuo to give (2-chloro-4-morpholin-4-yl-thieno[3,2-d]pyrimidin-6-ylmethyl)-(2-methanesulfonyl-ethyl)-amine as a white solid.

(2-Chloro-4-morpholin-4-yl-thieno[3,2-d]pyrimidin-6-ylmethyl)-(2-methanesulfonyl-ethyl)-amine was reacted with 4-(4,4,5,5-tetramethyl-[1,3,2]dioxaborolan-2-yl)-1H-indazole in General Procedure A. Purification by column chromatography yielded 383. NMR: CDCl$_3$: 2.95 (3 H, s, Me), 3.18-3.21 (4 H, m, CH$_2$), 3.82-3.85 (4 H, m, CH$_2$), 4.01-4.04 (4 H, m, CH$_2$), 4.12 (2 H, s, CH$_2$), 7.45 (1 H, s, Ar), 7.50 (1 H, apparent triplet, J 8.2, Ar), 7.61 (1 H, d, J 8.2, Ar), 8.28 (1 H, d, J 7.5, Ar) and 9.03 (1 H, s, Ar). MS: (ESI+): MH+ 473.22

Example 308

N-((2-(1H-indazol-4-yl)-4-morpholinothieno[3,2-d]pyrimidin-6-yl)methyl)-3-(methylsulfonyl)propan-1-amine 384

To a mixture of N-(3-bromopropyl)phthalimide (500 mg) in DMSO (8 mL) was added sodium thiomethoxide (144 mg) and the reaction stirred at room temperature for 16 h. Then with water (2 mL) was added and the mixture stirred at room temperature for 10 min. The reaction was diluted with water (20 mL) and extracted into ethyl acetate (2×20 mL). The combined organics were washed with aqueous brine solution (2×20 mL), dried (MgSO$_4$) and reduced in vacuo to give 2-(3-methylsulfanyl-propyl)-isoindole-1,3-dione as a white solid.

To a solution of 2-(3-methylsulfanyl-propyl)-isoindole-1,3-dione (440 mg) in methanol (10 mL) was added a solution of oxone (1.73 g) in water (10 mL) and the reaction stirred at room temperature for 16 h. The reaction was then diluted with water (20 mL) and extracted into dichloromethane (2×20 mL). The combined organics were washed with aqueous brine solution (2×20 mL), dried (MgSO$_4$) and reduced in vacuo to give 2-(3-methanesulfonyl-propyl)-isoindole-1,3-dione as a white solid.

To a solution of 2-(3-methanesulfonyl-propyl)-isoindole-1,3-dione (407 mg) in ethanol (10 mL) was added hydrazine monohydrate (0.80 mL) and the reaction was heated at reflux for 3 h. After cooling to room temperature, the mixture was filtered and the filtrate reduced in vacuo to give 3-methanesulfonyl-propylamine as a white solid.

To a solution of 6-bromomethyl-2-chloro-4-morpholin-4-yl-thieno[3,2-d]pyrimidine (200 mg) in acetonitrile (10 mL) was added 3-methanesulfonyl-propylamine (86 mg) and potassium carbonate (317 mg) and the reaction heated at 80° C. for 16 h. After cooling to room temperature, the solvent was reduced in vacuo and the residue redissolved in dicholoromethane (20 mL). The solution was washed with saturated aqueous sodium hydrogen carbonate solution (20 mL), aqueous brine solution (2×20 mL), dried (MgSO$_4$), reduced in vacuo and purified by column chromatography to give (2-chloro-4-morpholin-4-yl-thieno[3,2-d]pyrimidin-6-ylmethyl)-(3-methanesulfonyl-propyl)-amine as a yellow solid.

(2-Chloro-4-morpholin-4-yl-thieno[3,2-d]pyrimidin-6-ylmethyl)-(3-methanesulfonyl-propyl)-amine was reacted with 4-(4,4,5,5-tetramethyl-[1,3,2]dioxaborolan-2-yl)-1H-indazole in general procedure A. Purification by column chromatography yielded 384. NMR: CDCl$_3$: 1.99-2.05 (2 H, m, CH$_2$), 2.80 (2 H, t, J 7.2, CH$_2$), 2.81 (3 H, s, Me), 3.10-3.13 (2 H, m, CH$_2$), 3.85-3.88 (4 H, m, CH$_2$), 4.01-4.06 (6 H, m), 7.45 (1 H, s, Ar), 7.50 (1 H, apparent triplet, J 8.2, Ar), 7.61 (1 H, d, J 8.2, Ar), 8.28 (1 H, d, J 7.5, Ar) and 9.03 (1H, s, Ar). MS: (ESI+): MH+ 487.20

Example 309

N-((2-(1H-indazol-4-yl)-4-morpholinothieno[3,2-d]pyrimidin-6-yl)methyl)-3-(dimethylaminosulfonyl)propan-1-amine 385

To a suspension of dimethylamine hydrochloride (1.38 g) in dichloromethane (20 mL) was added triethylamine (2.52 mL) and then 3-chloropropanesulfonyl chloride (0.69 mL) and the reaction was stirred at room temperature for 16 h. The reaction was quenched with water (20 mL) and extracted into dichloromethane (2×30 mL). The combined organics were washed with 1 M aqueous hydrochloric acid solution (40 mL) then saturated aqueous sodium hydrogen carbonate solution, dried (MgSO$_4$) and reduced in vacuo to give 3-chloro-propane-1-sulfonic acid dimethylamide as a yellow solid.

A mixture of 3-chloro-propane-1-sulfonic acid dimethylamide (1.06 g) and sodium iodide (2.57 g) in 2-butanone (20 mL) was heated at 80° C. for 16 h. After cooling to room temperature the solvent was reduced in vacuo. The residue was partitioned between ethyl acetate (20 mL) and water (20 mL). The organic layer was dried (MgSO$_4$) and reduced in vacuo to give 3-iodo-propane-1-sulfonic acid dimethylamide as a yellow solid.

To a solution of 3-iodo-propane-1-sulfonic acid dimethylamide (600 mg) in DMF (10 mL) was added potassium phthalimide (590 mg) and the reaction heated at 100° C. for 16 h. After cooling to room temperature, the reaction was partitioned between dichloromethane (30 mL) and water (30 mL). The organic layer was washed with aqueous brine solution (3×30 mL), dried (MgSO$_4$) and reduced in vacuo to give 3-(1,3-dioxo-1,3-dihydro-isoindol-2-yl)-propane-1-sulfonic acid dimethylamide as a white solid.

To a solution of 3-(1,3-dioxo-1,3-dihydro-isoindol-2-yl)-propane-1-sulfonic acid dimethylamide (530 mg) in ethanol (10 mL) was added hydrazine monohydrate (0.80 mL) and the reaction was heated at reflux for 3 h. After cooling to room temperature, the mixture was filtered and the filtrate reduced in vacuo to give 3-amino-propane-1-sulfonic acid dimethylamide as a white solid.

To a solution of 2-chloro-4-morpholin-4-yl-thieno[3,2-d]pyrimidine-6-carbaldehyde (280 mg) in methanol (10 mL) was added 3-amino-propane-1-sulfonic acid dimethylamide (284 mg) and the reaction stirred at room temperature for 16 h. The solvent was reduced in vacuo and the residue redissolved in ethanol (50 mL). Palladium on carbon (20 mg) was added and the reaction stirred at room temperature under a hydrogen balloon for 48 h. The reaction was then filtered through Celite and the filtrate reduced in vacuo to give 3-[(2-chloro-4-morpholin-4-yl-thieno[3,2-d]pyrimidin-6-ylmethyl)-amino]-propane-1-sulfonic acid dimethylamide as a yellow solid.

3-[(2-Chloro-4-morpholin-4-yl-thieno[3,2-d]pyrimidin-6-ylmethyl)-amino]-propane-1-sulfonic acid dimethylamide was reacted with 4-(4,4,5,5-tetramethyl-[1,3,2]dioxaborolan-2-yl)-1H-indazole in general procedure A. Purification by column chromatography yielded 385. NMR: CDCl$_3$: 1.99-2.01 (2 H, m, CH$_2$), 2.78-2.81 (2 H, m, CH$_2$), 2.82 (6 H, s, Me), 2.98-3.01 (2 H, m, CH$_2$), 3.84-3.88 (4 H, m, CH$_2$), 4.02-4.05 (4 H, m, CH$_2$), 4.07 (2 H, s, CH$_2$), 7.45 (1 H, s, Ar), 7.50 (1 H, apparent triplet, J 8.2, Ar), 7.61 (1H, d, J 8.2, Ar), 8.28 (1 H, d, J 7.5, Ar) and 9.03 (1 H, s, Ar). MS: (ESI+): MH+ 516.34

Example 310

N-((2-(1H-indazol-4-yl)-4-morpholinothieno[3,2-d]pyrimidin-6-yl)methyl)-N-methyl(phenyl)methanamine 386

2-Chloro-4-morpholin-4-yl-thieno[3,2-d]pyrimidine-6-carbaldehyde 10 from Example 3 (101 mg) was dissolved in 1,2-DCE and 1 eq AcOH and a small scoop of molecular sieves (4 A) was added. To this 57 mg (1.3 eq) of N-benzyl-methylamine was added. The reaction was stirred for 25 minutes and 0.5 mL MeOH added. This was stirred an additional 5 minutes before adding 91.1 mg Na(OAc)₃BH and allowed to stir at room temperature 48 hours. Complete reaction was confirmed by LCMS. Reaction was filtered and concentrated in vacuo and purified by flash chromatography to give 58.6 mg of the intermediate (42% yield) followed by Suzuki coupling of 4-(4,4,5,5-tetramethyl-1,3,2-dioxaborolan-2-yl)1H-indazole 7 as per General Procedure A. Complete reaction was confirmed by LCMS and the reaction was concentrated in vacuo to give 12.9 mg of 386 after RP-HPLC purification (18% yield). MS (Q1) 471.3 (M)+.

Example 311

N-((2-(1H-indazol-4-yl)-4-morpholinothieno[3,2-d]pyrimidin-6-yl)methyl)(3-methoxyphenyl)-N-methylmethanamine 387

2-Chloro-4-morpholin-4-yl-thieno[3,2-d]pyrimidine-6-carbaldehyde 10 from Example 3 (101 mg) was dissolved in 1,2-DCE and 1 eq AcOH and a small scoop of molecular sieves (4 A) was added. To this 71.1 mg (1.3 eq) of 3-Methoxy-N-methylbenzylamine was added. The reaction was stirred for 25 minutes and 0.5 ml MeOH added. This was stirred an additional 5 minutes before adding 91.1 mg Na(OAc)₃BH and allowed to stir at room temperature 48 hours. Complete reaction was confirmed by LCMS. Reaction was filtered and concentrated in vacuo and purified by flash chromatography to give 54.6 mg of the intermediate (36% yield) followed by suzuki coupling of 4-(4,4,5,5-tetramethyl-1,3,2-dioxaborolan-2-yl)1H-indazole 7 as per General Procedure A. Complete reaction was confirmed by LCMS and the reaction was concentrated in vacuo to give 31.5 mg of 387 after RP-HPLC purification (42% yield). MS (Q1) 501z.3 (M)+

Example 312

N-(2-(2-(1H-indazol-4-yl)-4-morpholinothieno[3,2-d]pyrimidin-6-yl)propan-2-yl)benzamide 388

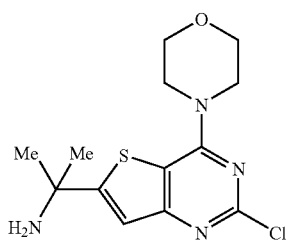

To a mixture of 4-morpholino-2-(pyridine-3-yl)thieno[3,2-d]pyrimidine-6-carboxylic acid (610 mg, 2.04 mmol), 1-hydroxy-7-azabenzotriazole (56 mg, 0.4 mmol), O-(7-azabenzotriazol-1-yl)-(N,N,N',N'-tetramethyluronium hexafluorophosphate (HATU; 1.2 g, 3.1 mmol), and N,N-diisopropylethylamine (1.4 mL, 8.1 mmol) in DMF (3 mL) was added ammonium chloride (330 mg, 6.1 mmol). The reaction mixture was stirred overnight at room temperature. The mixture was diluted with EtOAc, washed with saturated aqueous NaHCO₃ and brine. The aqueous layer was extracted with EtOAc. The combined organics were washed with saturated NaHCO₃ and brine then dried over MgSO₄, filtered and concentrated in vacuo. The residue was purified by silica gel chromatography (0-20% MeOH in CH₂Cl₂) to afford 2-chloro-4-morpholinothieno[3,2-d]pyrimidine-6-carboxamide (490 mg, 81% yield).

Zirconium (IV) chloride (780 mg, 3.3 mmol) was added to a mixture of 2-chloro-4-morpholinothieno[3,2-d]pyrimidine-6-carboxamide (400 mg, 1.3 mmol) in THF (8 mL) at −10° C. The reaction mixture was stirred for 1 h at −10° C. A solution of methylmagnesium bromide (2.7 mL, 3 M in Et₂O) was added dropwise. The resulting mixture was warmed to room temperature and stirred overnight. The reaction was quenched by the addition of water. The organic layer was separated and the aqueous layer was extracted with EtOAc. The aqueous solution was then basified with saturated NaHCO₃ and again extracted with EtOAc. The combined organic layers were dried over MgSO₄, filtered, and concentrated in vacuo. The crude mixture was purified by silica gel chromatography (0-15% MeOH in CH₂Cl₂) to afford 2-(2-chloro-4-morpholinothieno[3,2-d]pyrimidin-6-yl)propan-2-amine (220 mg, 53% yield).

To a solution of 2-(2-chloro-4-morpholinothieno[3,2-d]pyrimidin-6-yl)propan-2-amine (1.1 g, 3.5 mmol) in CH₂Cl₂ (50 mL) was added Et₃N (0.6 mL, 4.9 mmol) and benzoyl chloride (0.6 mL, 4.2 mmol). The resulting mixture stirred at room temperature overnight. The reaction was diluted with 1 M HCl and extracted with DCM, dried over MgSO₄, and concentrated in vacuo. The crude material was purified by silica gel chromatography (0-50% EtOAc in hexane). A portion (0.65 mmol) of the crude material was utilized in a Suzuki coupling using General Procedure A with 4-(4,4,5,5-tetramethyl-1,3,2-dioxaborolan-2-yl)-1H-indazole 7 to provide 388 after reverse phase HPLC purification (133 mg). MS (Q1) 499 (M)+

Example 313

(2-(1H-indazol-4-yl)-4-morpholinothieno[3,2-d]pyrimidin-6-yl)-N-methylmethanamine 389

1-(2-Chloro-4-morpholinothieno[3,2-d]pyrimidin-6-yl)-N-methylmethanamine 55 from Example 11a was reacted with 0.18 g (1.3 eq) of 4-(4,4,5,5-tetramethyl-1,3,2-dioxaborolan-2-yl)1H-indazole 7 as per General Procedure A to give 18 mg of 389 after RP-HPLC purification (28% yield). MS (Q1) 381.2 (M)+

Example 314

N-((2-(1H-indazol-4-yl)-4-morpholinothieno[3,2-d]pyrimidin-6-yl)methyl)-N-methylbenzamide 390

1-(2-Chloro-4-morpholinothieno[3,2-d]pyrimidin-6-yl)-N-methylmethanamine 55 from Example 11a was reacted with benzoyl chloride (1.2 eq) followed by Suzuki coupling of 4-(4,4,5,5-tetramethyl-1,3,2-dioxaborolan-2-yl)1H-indazole 7 as per General Procedure K. Complete reaction was confirmed by LCMS and the reaction was concentrated in vacuo to give 59.5 mg of 390 after RP-HPLC, purification (72% yield). MS (Q1) 485.3 (M)+

Example 315

N-((2-(1H-indazol-4-yl)-7-methyl-4-morpholinothieno[3,2-d]pyrimidin-6-yl)methyl)-N-methylsulfonyl-methanamine 391

1-(2-Chloro-7-methyl-4-morpholinothieno[3,2-d]pyrimidin-6-yl)-N-methylmethanamine 56 from Example 11b was reacted with methanesulfonylchloride (1.2 eq) followed by Suzuki coupling of 4-(4,4,5,5-tetramethyl-1,3,2-dioxaborolan-2-yl)1H-indazole 7 as per General Procedure K. Complete reaction was confirmed by LCMS and the reaction was concentrated in vacuo to give 31.0 mg of 391 after RP-HPLC purification (29% yield). MS (Q1) 473.2 (M)+

Example 316

N-((2-(1H-indol-5-yl)-4-morpholinothieno[3,2-d]pyrimidin-6-yl)methyl)-N-methylacetamide 392

1-(2-Chloro-4-morpholinothieno[3,2-d]pyrimidin-6-yl)-N-methylmethanamine 55 from Example 11a was reacted with acetyl chloride (1.2 eq) followed by Suzuki coupling of indole-5-boronic acid as per General Procedure K. Complete reaction was confirmed by LCMS and the reaction was concentrated in vacuo to give 33.1 mg of 392 after RP-HPLC purification (44% yield). MS (Q1) 422.2 (M)+

Example 317

N-(3-(2-(1H-indazol-4-yl)-4-morpholinothieno[2,3-d]pyrimidin-6-yl)phenyl)acetamide 393

2-Chloro-6-iodo-4-morpholinothieno[3,2-d]pyrimidine 19 was reacted with 3-acetamidophenylboronic acid via General Procedure C to give the corresponding intermediate, after purification by flash chromatography, which was then reacted with 4-(4,4,5,5-tetramethyl-1,3,2-dioxaborolan-2-yl)-1H-indazole 7 via General Procedure A again to give, after purification by reverse HPLC, 393. MS (Q1) 471 (M+)

Example 318

2-(1H-indazol-4-yl)-6-(3-(methylsulfonyl)phenyl)-4-morpholinothieno[2,3-d]pyrimidine 394

2-Chloro-6-iodo-4-morpholinothieno[3,2-d]pyrimidine 19 was reacted with 3-methylsulfonylphenylboronic acid via General Procedure A to give the corresponding intermediate, after purification by flash chromatography, which was then reacted with 4-(4,4,5,5-tetramethyl-1,3,2-dioxaborolan-2-yl)-1H-indazole 7 via General Procedure A again to give, after purification by reverse HPLC, 394. MS (Q1) 507 (M+)

Example 319

7-methyl-6-(3-(methylsulfonyl)phenyl)-4-morpholino-2-(1H-pyrrolo[2,3-b]pyridin-5-yl)thieno[3,2-d]pyrimidine 395

2-Chloro-6-iodo-7-methyl-4-morpholinothieno[3,2-d]pyrimidine from Example 12 (0.3 g, 0.8 mmol), 3-(methylsulfonyl)phenylboronic acid (0.3 g, 1.5 mmol), and bis(triphenylphosphine)palladium(II) dichloride (30 mg, 40 µmol) in 1 M aqueous Na$_2$CO$_3$ (1.5 mL) and acetonitrile (1.5 mL) were heated to 100° C. in a sealed microwave reactor for 10 min. Upon completion, 5-(4,4,5,5-tetramethyl-1,3,2-dioxaborolan-2-yl)-1H-pyrrolo[2,3-b]pyridine (0.4 g, 1.7 mmol), and bis(triphenylphosphine)palladium(II) dichloride (30 mg, 40 µmol) were added into the same pot. The reaction mixture was heated to 150° C. in a sealed microwave reactor for 20 min. The mixture was extracted with EtOAc and CH$_2$Cl$_2$. The combined organics were concentrated to yield 395 after reverse phase HPLC purification (82 mg). MS (Q1) 506 (M+)

Example 320

2-(1H-indazol-4-yl)-6-(4-methoxypyridin-3-yl)-4-morpholinothieno[2,3-d]pyrimidine 396

2-Chloro-6-iodo-4-morpholinothieno[3,2-d]pyrimidine 19 was reacted with 4-methoxypyridin-3-yl-3-boronic acid via General Procedure C to give the corresponding intermediate, after purification by flash chromatography, which was then reacted with 4-(4,4,5,5-tetramethyl-1,3,2-dioxaborolan-2-yl)-1H-indazole 7 via General Procedure A again to give, after purification by reverse HPLC, 396. MS (Q1) 445 (M+)

Example 321

2-(1H-indazol-4-yl)-6-(1H-indol-4-yl)-4-morpholinothieno[3,2-d]pyrimidine 397

2-Chloro-6-iodo-4-morpholinothieno[3,2-d]pyrimidine 19 was reacted with 4-(4,4,5,5-tetramethyl-1,3,2-dioxaborolan-2-yl)-1H-indole via General Procedure A to give the corresponding intermediate, after purification by flash chromatography, which was then reacted with 4-(4,4,5,5-tetramethyl-1,3,2-dioxaborolan-2-yl)-1H-indazole 7 via General Procedure A again to give, after purification by reverse HPLC, 397. MS (Q1) 453 (M+)

Example 322

2-(2-(1H-indazol-4-yl)-4-morpholinothieno[3,2-d]pyrimidin-6-yl)-N-methylsulfonylpropan-2-amine 398

To a solution of 2-(2-chloro-4-morpholinothieno[3,2-d]pyrimidin-6-yl)propan-2-amine (400 mg, 1.3 mmol) in CH$_2$Cl$_2$ (20 mL) was added Et$_3$N (630 µL, 4.5 mmol) and methanesulfonyl chloride (200 µL, 2.6 mmol). The resulting mixture stirred at room temperature overnight. The reaction was quenched by the addition of saturated aqueous NaHCO$_3$. The organic layer was separated and the aqueous layer was extracted with EtOAc. The combined organic layers were dried over Na$_2$SO$_4$, filtered, and concentrated in vacuo. The crude material was purified by silica gel chromatography (0-100% EtOAc in hexane). A portion (0.1 mmol) of the resulting pure product was utilized in a Suzuki coupling using General Procedure A with 4-(4,4,5,5-tetramethyl-1,3,2-dioxaborolan-2-yl)-1H-indazole 7 to provide 398 after reverse phase HPLC purification (8 mg). MS (Q1) 473 (M)+

Example 323

N-(2-(2-(1H-indazol-4-yl)-4-morpholinothieno[3,2-d]pyrimidin-6-yl)propan-2-yl)acetamide 399

To a solution of 2-(2-chloro-4-morpholinothieno[3,2-d]pyrimidin-6-yl)propan-2-amine (400 mg, 1.3 mmol) in CH$_2$Cl$_2$ (20 mL) was added Et$_3$N (630 µL, 4.5 mmol) and acetyl chloride (180 µL, 2.6 mmol). The resulting mixture stirred at room temperature overnight. The reaction was quenched by the addition of saturated aqueous NaHCO$_3$. The organic layer was separated and the aqueous layer was extracted with EtOAc. The combined organic layers were dried over Na$_2$SO$_4$, filtered, and concentrated in vacuo. The crude material was purified by silica gel chromatography (0-100% EtOAc in hexane). A portion (0.2 mmol) of the resulting pure product was utilized in a Suzuki coupling using General Procedure A with 4-(4,4,5,5-tetramethyl-1,3,2-dioxaborolan-2-yl)-1H-indazole 7 to provide 399 after reverse phase HPLC purification (36 mg). MS (Q1) 437 (M)+

Example 324

2-(1H-indazol-4-yl)-4-morpholino-6-(6-morpholinopyridin-3-yl)thieno[3,2-d]pyrimidine 400

2-Chloro-6-iodo-4-morpholinothieno[3,2-d]pyrimidine 19 was reacted with 4-(5-(4,4,5,5-tetramethyl-1,3,2-dioxaborolan-2-yl)pyridin-2-yl)morpholine via General Procedure A to give the corresponding intermediate, after purification by flash chromatography, which was then reacted with 4-(4,4,5,5-tetramethyl-1,3,2-dioxaborolan-2-yl)-1H-indazole 7 via General Procedure A again to give, after purification by reverse HPLC, 400. MS (Q1) 500 (M$^+$)

Example 325

2-(1H-indazol-4-yl)-6-(2-(4-N-methylsulfonylpiperazin-1-yl)propan-2-yl)-4-morpholinothieno[3,2-d]pyrimidine 401

To a solution of 2-chloro-4-morpholin-4-yl-thieno[3,2-d]pyrimidine (6 g mg) in THF (300 mL) at −78° C. was added n-butyllithium (11.3 mL of a 2.5 M solution in hexanes) and the reaction stirred at −78° C. for 1 h. Carbon dioxide gas was then bubbled slowly through the reaction mixture for several minutes. The reaction mixture was warmed slowly to room temperature. THF was reduced in vacuo and the residue was dissolved in sodium bicarbonate solution, washed with ethyl acetate, and the basic phase was then carefully acidified to pH 3, yielding a pale precipitate which was collected by filtration. Air drying yielded 2-chloro-4-morpholin-4-yl-thieno[3,2-d]pyrimidine-6-carboxylic acid (5.5 g).

To a solution of 2-chloro-4-morpholin-4-yl-thieno[3,2-d]pyrimidine-6-carboxylic acid (2.0 g) in DMF (50 mL) was added 1,1-carbonyldiimidazole (2.16 g). After 1 hour, triethylamine (2.8 ml) and 1-methanesulfonyl-piperazine hydrochloride salt (2.7 g) were added. After stirring overnight, water was added and (2-chloro-4-morpholin-4-yl-thieno[3,2-d]pyrimidin-6-yl)-(4-methanesulfonyl-piperazin-1-yl)-methanone was collected as a white solid by filtration.

(2-Chloro-4-morpholin-4-yl-thieno[3,2-d]pyrimidin-6-yl)-(4-methanesulfonyl-piperazin-1-yl)-methanone (1.8 g) was dissolved in THF (40 mL) at −10° C. and zirconium chloride (4.7 g) was added. After stirring for one hour, methyl magnesium bromide (3M solution in ether, 8.1 mL) was added dropwise. After 24 hours, the reaction mixture was quenched with water, extracted with EtOAc, dried (MgSO$_4$) and the solvent was removed in vacuo. The residue was purified using flash chromatography to yield 2-chloro-6-[1-(4-methanesulfonyl-piperazin-1-yl)-1-methyl-ethyl]-4-morpholin-4-yl-thieno[3,2-d]pyrimidine (100 mg).

2-Chloro-6-[1-(4-methanesulfonyl-piperazin-1-yl)-1-methyl-ethyl]-4-morpholin-4-yl-thieno[3,2-d]pyrimidine was reacted with 4-(4,4,5,5-tetramethyl-[1,3,2]dioxaborolan-2-yl)-1H-indazole in General Procedure A. Purification by column chromatography yielded 401. (400 MHz CDCl3): 1.48 (6H, s, CH3), 2.66-2.68 (4H, m, CH2), 2.75 (3H, s, CH3), 3.21 (4H, m, CH2), 3.86-3.88 (4H, m, CH2), 4.01-4.04 (4H, m, CH2), 7.29 (1H, s, ar), 7.42-7.46 (1H, m, ar), 7.53 (1 h, d (J=8.33), ar), 8.21 (1 h, d (J=7.09), ar), 8.95 (1H, s, ar), 10.04 (1H, b, NH). MH+=542.46

Example 326

2-(1H-indazol-4-yl)-4-morpholinothieno[3,2-d]pyrimidine-6-carbonitrile 402

A solution of 2-chloro-6-iodo-4-morpholinothieno[3,2-d]pyrimidine 19 from Example 12 (0.2 g, 0.5 mmol) and CuCN (50 mg, 0.6 mmol) in pyridine (1 mL) was heated at 115° C. for 2 h then cooled to room temperature and stirred 18 h. The reaction was poured into 1 M HCl and ice and the aqueous layer was extracted with CH$_2$Cl$_2$. The product was purified by silica gel chromatography (0-75% EtOAc in hexane) to provide 2-chloro-4-morpholinothieno[3,2-d]pyrimidine-6-carbonitrile (35 mg).

2-Chloro-4-morpholinothieno[3,2-d]pyrimidine-6-carbonitrile (35 mg) was reacted with 4-(4,4,5,5-tetramethyl-1,3,2-dioxaborolan-2-yl)-1H-indazole 7 (6 mg) by Suzuki coupling according to the General Procedure A to give 402. MS (Q1) 363 (M)+

Example 327

N-((2-(1H-indazol-4-yl)-4-morpholinothieno[3,2-d]pyrimidin-6-yl)methyl)-2-methoxy-N-methylacetamide 403

1-(2-Chloro-4-morpholinothieno[3,2-d]pyrimidin-6-yl)-N-methylmethanamine 55 from Example 1a (0.22 g) was reacted with methoxyacetyl chloride (1.2 eq) followed by Suzuki coupling of 4-(4,4,5,5-tetramethyl-1,3,2-dioxaborolan-2-yl)1H-indazole 7 as per General Procedure K. Complete reaction was confirmed by LCMS and the reaction was concentrated in vacuo to give 52.7 mg of 403 after RP-HPLC purification (52% yield). MS (Q1) 453.2 (M)+

Example 328

(2-(1H-indazol-4-yl)-4-morpholinothieno[3,2-d]pyrimidin-6-yl)(4-(methylthio)phenyl)methanol 404

To a solution of 2-chloro-4-morpholin-4-yl-thieno[3,2-d]pyrimidine (2.74 g) in THF (40 mL) at −78° C. was added n-butyllithium (5.15 mL of a 2.5 M solution in hexanes) and the reaction stirred at −78° C. for 1 h. 4-Methylmercaptobenzaldehyde (1.43 mL) was then added and the reaction mixture was lowly warmed to room temperature. Water was added and the resulting precipitate was collected by filtration. Recyrstalisation from EtOAc/hexane yielded (2-chloro-4-morpholin-4-yl-thieno[3,2-d]pyrimidin-6-yl)-(4-methylsulfanyl-phenyl)-methanol (2.53 g).

(2-Chloro-4-morpholin-4-yl-thieno[3,2-d]pyrimidin-6-yl)-(4-methylsulfanyl-phenyl)-methanol was reacted with 4-(4,4,5,5-tetramethyl-[1,3,2]dioxaborolan-2-yl)-1H-indazole in general procedure A. Purification by column chromatography yielded 404. (400 MHz, CDCl3): 2.52 (3H, s, CH3), 2.60 (1H, m, CH), 3.91-3.93 (4H, m, CH2), 4.09-4.11 (4H, m, CH2), 6.15 (1H, b, OH), 7.30 (1H, m, ar), 7.33 (1H, m, ar), 7.35 (1H, m, ar), 7.43 (1H, m, ar), 7.46 (1H, m, ar), 7.51 (1H, m, ar), 7.59 (1H, m, ar), 8.38 (1H, d, ar), 9.02 (1H, s, ar), 10.10 (1H, b, NH). (M+H)+ 490.27

Example 329

(2-(1H-indazol-4-yl)-4-morpholinothieno[2,3-d]
pyrimidin-6-yl)-N-methylsulfonyl,N-methylmetha-
namine 405

(2-Chloro-4-morpholinothieno[2,3-d]pyrimidin-6-yl)-n-
methyl-N-(methylsulfonyl)methaneamine (56% yield; MS
(Q1) 377 (M)+) prepared following General Procedure H,
and 1H-pyrrolo[2,3-b]pyridine boronic pinacol ester were
reacted following General Procedure A to produce 405 in
3.6% yield MS (Q1) 459.1 (M)+

Example 330

N-((2-(1H-indazol-4-yl)-4-morpholinothieno[2,3-d]
pyrimidin-6-yl)methyl)-N-methylacetamide 406

N-((2-chloro-4-morpholinothieno[2,3-d]pyrimidin-6-yl)-
N-methylacetamide (68% yield; MS (Q1) 341.1 (M)+) pre-
pared following General Procedure H, and 1H-pyrrolo[2,3-
b]pyridine boronic pinacol ester were reacted following
General Procedure A to produce 406 in 35.5% yield MS (Q1)
384.5 (M)+

Example 331

N-((2-(1H-indazol-4-yl)-4-morpholinothieno[3,2-d]
pyrimidin-6-yl)methyl)-2-hydroxy-N,2-dimethylpro-
panamide 407

1-(2-Chloro-4-morpholinothieno[3,2-d]pyrimidin-6-yl)-
N-methylmethanamine 55 from Example 11a (0.22 g) was
reacted with 2-acetoxyisobutyryl chloride (1.2 eq) followed
by suzuki coupling of 4-(4,4,5,5-tetramethyl-1,3,2-diox-
aborolan-2-yl)1H-indazole 7 as per general procedure K. The
resulting compound was dissolved in 2 mL THF and 2 mL
MeOH followed by the addition of 2 mL 1M liOH and the
resulting solution stirred for 2.5 hours. Complete reaction
was confirmed by LCMS and the reaction was concentrated in
vacuo to give 80.2 mg of 407 after RP-HPLC purification
(52% yield). MS (Q1) 467.2 (M)+

Example 332

N-((2-(1H-indazol-4-yl)-7-methyl-4-morpholi-
nothieno[3,2-d]pyrimidin-6-yl)methyl)-N-methylac-
etamide 408

1-(2-Chloro-7-methyl-4-morpholinothieno[3,2-d]pyrimi-
din-6-yl)-N-methylmethanamine 56 from Example 11b was
reacted with acetyl chloride (1.2 eq) followed by Suzuki
coupling of 4-(4,4,5,5-tetramethyl-1,3,2-dioxaborolan-2-yl)
1H-indazole 7 as per General Procedure K. Complete reac-
tion was confirmed by LCMS and the reaction was concen-
trated in vacuo to give 101.9 mg of 408 after RP-HPLC
purification (40% yield). MS (Q1) 437.2 (M)+.

Example 333

N-((2-(1H-indazol-4-yl)-4-morpholinothieno[3,2-d]
pyrimidin-6-yl)methyl)-2-hydroxy-N-methylaceta-
mide 409

1-(2-Chloro-4-morpholinothieno[3,2-d]pyrimidin-6-yl)-
N-methylmethanamine 55 from Example 11a (0.22 g) was
reacted with acetoxyacetyl chloride (1.2 eq) followed by
Suzuki coupling of 4-(4,4,5,5-tetramethyl-1,3,2-dioxaboro-
lan-2-yl)1H-indazole 7 as per General Procedure K. The
resulting compound was dissolved in 2 mL THF and 2 mL
MeOH followed by the addition of 2 mL 1M LiOH and the
resulting solution stirred for 2.5 hours. Complete reaction
was confirmed by LCMS and the reaction was concentrated in
vacuo to give 31.1 mg of 409 after RP-HPLC purification
(24% yield). MS (Q1) 439.2 (M)+.

Example 334

N-(2-(2-(1H-indazol-4-yl)-4-morpholinothieno[3,2-
d]pyrimidin-6-yl)propan-2-yl)nicotinamide 410

To a solution of 2-(2-chloro-4-morpholinothieno[3,2-d]
pyrimidin-6-yl)propan-2-amine (150 mg, 0.5 mmol) in
CH$_2$Cl$_2$ (10 mL) was added Et$_3$N (450 µL, 3.2 mmol) and
nicotinoyl chloride hydrochloric acid (160 mg, 0.9 mmol).
The resulting mixture stirred at room temperature overnight.
The reaction was quenched by the addition of saturated aque-
ous NaHCO$_3$. The organic layer was separated and the aque-
ous layer was extracted with EtOAc. The combined organic
layers were dried over Na$_2$SO$_4$, filtered, and concentrated in
vacuo. A portion (0.2 mmol) of the resulting crude product
was utilized in a Suzuki coupling using General Procedure A
with 4-(4,4,5,5-tetramethyl-1,3,2-dioxaborolan-2-yl)1H-in-
dazole 7 to provide 410 after reverse phase HPLC purification
(22 mg). MS (Q1) 500 (M)+

Example 335

N-(2-(2-(1H-indazol-4-yl)-4-morpholinothieno[3,2-
d]pyrimidin-6-yl)propan-2-yl)-3-methoxybenzamide
411

To a solution of 2-(2-chloro-4-morpholinothieno[3,2-d]
pyrimidin-6-yl)propan-2-amine (150 mg, 0.5 mmol) in
CH$_2$Cl$_2$ (10 mL) was added Et$_3$N (230 µL, 1.6 mmol) and
m-anisoyl chloride (160 mg, 0.9 mmol). The resulting mix-
ture stirred at room temperature overnight. The reaction was
quenched by the addition of saturated aqueous NaHCO$_3$. The
organic layer was separated and the aqueous layer was
extracted with EtOAc. The combined organic layers were
dried over Na$_2$SO$_4$, filtered, and concentrated in vacuo. A
portion (0.2 mmol) of the resulting crude product was utilized
in a Suzuki coupling using General Procedure A with 4-(4,4,
5,5-tetramethyl-1,3,2-dioxaborolan-2-yl)-1H-indazole 7 to
provide 411 after reverse phase HPLC purification (13 mg).
MS (Q1) 529 (M)+

Example 336

N-(2-(2-(1H-indazol-4-yl)-4-morpholinothieno[3,2-
d]pyrimidin-6-yl)propan-2-yl)-4-methoxybenzamide
412

To a solution of 2-(2-chloro-4-morpholinothieno[3,2-d]
pyrimidin-6-yl)propan-2-amine (150 mg, 0.5 mmol) in
CH$_2$Cl$_2$ (10 mL) was added Et$_3$N (230 µL, 1.6 mmol) and the
HCl salt of p-anisoyl chloride (160 mg, 0.9 mmol). The result-
ing mixture stirred at room temperature overnight. The reac-
tion was quenched by the addition of saturated aqueous
NaHCO$_3$. The organic layer was separated and the aqueous
layer was extracted with EtOAc. The combined organic lay-
ers were dried over Na$_2$SO$_4$, filtered, and concentrated in
vacuo. A portion (0.2 mmol) of the resulting crude material
was utilized in a Suzuki coupling using General Procedure A with 4-(4,4,5,5-tetramethyl-1,3,2-dioxaborolan-2-yl)-1H-indazole 7 to provide 412 after reverse phase HPLC purification (30 mg). MS (Q1) 529 (M)+

Example 337

(2-(1H-indazol-4-yl)-4-morpholinothieno[3,2-d]pyrimidin-6-yl)(4-(methylsulfonyl)phenyl)methanol 413

To (2-chloro-4-morpholin-4-yl-thieno[3,2-d]pyrimidin-6-yl)-(4-methylsulfanyl-phenyl)-methanol (712 mg) in DCM (50 mL) was added meta-chloroperbenzoic acid (820 mg) at 0° C. After 4 hours, the reaction mixture was quenched with sodium thiosulphate solution, extracted with DCM, dried (MgSO$_4$) and the solvent removed in vacuo. The residue was purified using flash chromatography to yield (2-chloro-4-morpholin-4-yl-thieno[3,2-d]pyrimidin-6-yl)-(4-methanesulfonyl-phenyl)-methanol.

(2-Chloro-4-morpholin-4-yl-thieno[3,2-d]pyrimidin-6-yl)-(4-methanesulfonyl-phenyl)-methanol was reacted with 4-(4,4,5,5-tetramethyl-[1,3,2]dioxaborolan-2-yl)-1H-indazole in General Procedure A. Purification by column chromatography yielded 413. (400 MHz, CDCl3): 3.00 (3H, s, CH3), 3.82-3.84 (4H, m, CH2), 3.99-4.01 (4H, m, CH2), 6.21 (1H, b, NH), 7.29 (1H, d (J=0.80), ar), 7.43 (1H, t (J=7.80), ar), 7.53 (1H, d (J=8.30), ar), 7.66 (2H, d (J=8.26), ar), 7.91 (2H, d (J=8.46), ar), 8.18 (1H, d (J=6.56), ar), 8.91 (1H, s, ar). (M+H)+ 522.21

Example 338

2-(2-(2-methyl-3H-imidazo[4,5-b]pyridin-6-yl)-4-morpholinothieno[2,3-d]pyrimidin-6-yl)propan-2-ol 414

2-(2-Chloro-4-morpholinothieno[2,3-d]pyrimidin-6-yl)propan-2-ol (100 mg) was reacted with 161 mg of 3-((2-(trimethylsilyl)ethoxy)methyl)-2-methyl-6-(4,4,5,5-tetramethyl-1,3,2-dioxaborolan-2-yl)-3H-imidazo[4,5-b]pyridine 54 via Example 6b and General Procedure A. Crude 2-(2-(1-((2-(trimethylsilyl)ethoxy)methyl)-2-methyl-1H-benzo[d]imidazol-6-yl)-4-morpholinothieno[2,3-d]pyrimidin-6-yl)propan-2-ol was then refluxed overnight with 2 equivalents of tetrabutylammoniumfluoride in THF to remove the SEM protecting group. The crude material was then extracted with water and ethyl acetate. The organic layer was concentrated to dryness and then purified via reverse phase HPLC to give 5.1 mg of 414. MS (Q1) 411.2 (M)+

Example 339

(S)-1-(3-(7-methyl-4-morpholino-2-(1H-pyrrolo[2,3-b]pyridin-5-yl)thieno[3,2-d]pyrimidin-6-yl)phenylsulfonyl)propan-2-ol 415

(S)-1-(3-(2-chloro-7-methyl-4-morpholinothieno[3,2-d]pyrimidin-6-yl)phenylsulfonyl)propan-2-ol (10 mg) was coupled to 7-azaindole-5-boronic acid pinacol ester via General Procedure A. The product was purified by reverse phase HPLC to yield 38 mg of 415. MS (Q1) 550.0 (M)+

Example 340

7-methyl-6-(3-(N-morpholino)sulfonyl)phenyl)-4-morpholino-2-(1H-pyrrolo[2,3-b]pyridin-5-yl)thieno[3,2-d]pyrimidine 416

2-Chloro-6-iodo-7-methyl-4-morpholinothieno[3,2-d]pyrimidine (70 mg) was coupled to N-morpholinyl-3-boronobenzene sulfonamide, and then reacted with 7-azaindole-5-boronic acid pinacol ester via General Procedure F. The product was purified by reverse phase HPLC to yield 39 mg of 416. MS (Q1) 577.0 (M)+

Example 341

N-methyl,N-methylsulfonyl(4-morpholino-2-(1H-pyrrolo[2,3-b]pyridin-5-yl)thieno[2,3-d]pyrimidin-6-yl)methanamine 417

(2-Chloro-4-morpholinothieno[2,3-d]pyrimidin-6-yl-n-methyl-N-(methylsulfonyl)methaneamine and 1H-pyrrolo[2,3-b]pyridin-5-yl-5-boronic acid were reacted following General Procedure A to produce 417 in 6.0% yield MS (Q1) 459.2 (M)+

Example 342

6-(3-(methylsulfonyl)phenyl)-4-morpholino-2-(1H-pyrrolo[2,3-b]pyridin-5-yl)thieno[3,2-d]pyrimidine 418

2-Chloro-6-iodo-4-morpholinothieno[3,2-d]pyrimidine 19 from Example 12 (0.2 g, 0.6 mmol), 3-(methylsulfonyl)phenylboronic acid (120 mg, 0.6 mmol), and bis(triphenylphosphine)palladium(II) dichloride (20 mg, 30 µmol) in 1M aqueous Na$_2$CO$_3$ (1 mL) and acetonitrile (1 mL) were heated to 100° C. in a sealed microwave reactor for 10 min. Upon completion, 5-(4,4,5,5-tetramethyl-1,3,2-dioxaborolan-2-yl)-1H-pyrrolo[2,3-b]pyridine (210 mg, 0.87 mmol) and bis(triphenylphosphine)palladium(II) dichloride (20 mg, 30 µmol) were added and the mixture was heated to 150° C. in a sealed microwave reactor for 20 min. The mixture was extracted with EtOAc and CH$_2$Cl$_2$. The combined organics were concentrated to yield 418 after reverse phase HPLC purification (40 mg). MS (Q1) 492 (M)+

Example 343

4-morpholino-6-phenyl-2-(1H-pyrrolo[2,3-b]pyridin-5-yl)thieno[3,2-d]pyrimidine 419

2-Chloro-6-iodo-4-morpholinothieno[3,2-d]pyrimidine 19 from Example 12 (0.2 g, 0.6 mmol), phenylboronic acid (70 mg, 0.6 mmol), and bis(triphenylphosphine)palladium(II) dichloride (20 mg, 30 µmol) in 1 M aqueous Na$_2$CO$_3$ (1 mL) and acetonitrile (1 mL) were heated to 100° C. in a sealed microwave reactor for 10 min. Upon completion, 5-(4,4,5,5-tetramethyl-1,3,2-dioxaborolan-2-yl)-1H-pyrrolo[2,3-b]pyridine (210 mg, 0.87 mmol) and bis(triphenylphosphine)palladium(II) dichloride (20 mg, 30 µmol) were added and the mixture was heated to 150° C. in a sealed microwave reactor for 20 min. The mixture was extracted with EtOAc and CH$_2$Cl$_2$. The combined organics were concentrated to yield 419 after reverse phase HPLC purification (45 mg). MS (Q1) 414 (M)+

Example 344

7-methyl-4-morpholino-6-phenyl-2-(1H-pyrrolo[2,3-b]pyridin-5-yl)thieno[3,2-d]pyrimidine 420

2-Chloro-6-iodo-7-methyl-4-morpholinothieno[3,2-d]pyrimidine from Example 12 (0.2 g, 0.5 mmol), phenylboronic acid (60 mg, 0.5 mmol), and bis(triphenylphosphine)palladium(II) dichloride (18 mg, 25 µmol) in 1 M aqueous Na$_2$CO$_3$ (1 mL) and acetonitrile (1 mL) were heated to 100° C. in a sealed microwave reactor for 10 min. Upon completion, 5-(4,4,5,5-tetramethyl-1,3,2-dioxaborolan-2-yl)-1H-pyrrolo[2,3-b]pyridine (180 mg 0.75 mmol) and bis(triphenylphosphine) palladium(II) dichloride (13 mg, 20 µmol) were added and the mixture was heated to 150° C. in a sealed microwave reactor for 20 min. The mixture was extracted with EtOAc and CH$_2$Cl$_2$. The combined organics were concentrated to yield 420 after reverse phase HPLC purification (57 mg). MS (Q1) 428 (M)+

Example 345

(2S)-2-hydroxy-N-((3-(7-methyl-4-morpholino-2-(1H-pyrrolo[2,3-b]pyridin-5-yl)thieno[3,2-d]pyrimidin-6-yl)phenyl)methyl)propanamide 421

Crude (2S)-N-(3-(2-chloro-7-methyl-4-morpholinothieno[3,2-d]pyrimidin-6-yl)phenyl)methyl-2-hydroxypropanamide (65 mg) was coupled to 7-azaindole-5-boronic acid pinacol ester via General Procedure A. The product was purified by reverse phase HPLC to yield 48.4 mg of 421. MS (Q1) 529.2 (M)$^+$

Example 346

2-(4-morpholino-2-(1H-pyrrolo[2,3-b]pyridin-5-yl)thieno[3,2-d]pyrimidin-6-yl)propan-2-ol 422

To 209 mg of 12 in 2 mL 1M KOAc and 2 mL acetonitrile, was added 195.2 mg (1.2 eq) of 7-azaindole-5-boronic acid pinacol ester and 77.4 mg (0.1 eq) of Pd(PPh$_3$)$_4$ as per General Procedure A to give 99.2 mg of 422 after RP-HPLC purification (75% yield). MS (Q1) 396.2 (M)+

Example 347

7-methyl-6-(3-(2-hydroxyethylaminosulfonyl)phenyl)-4-morpholino-2-(1H-pyrrolo[2,3-b]pyridin-5-yl)thieno[3,2-d]pyrimidine 423

2-Chloro-6-iodo-7-methyl-4-morpholinothieno[3,2-d]pyrimidine (50 mg) was coupled to N-(2-hydroxyethyl)-3-boronobenzene sulfonamide, and then reacted with 7-azaindole-5-boronic acid pinacol ester via General Procedure F. The product was purified by reverse phase HPLC to yield 17.7 mg of 423. MS (Q1) 551.1 (M)$^+$

Example 348

N-methylsulfonyl(3-(7-methyl-4-morpholino-2-(1H-pyrrolo[2,3-b]pyridin-5-yl)thieno[3,2-d]pyrimidin-6-yl)phenyl)methanamine 424

2-Chloro-6-iodo-7-methyl-4-morpholinothieno[3,2-d]pyrimidine (50 mg) was coupled to 3-methanesulphonylaminomethyl benzeneboronic acid, and then reacted with 7-azaindole-5-boronic acid pinacol ester via General Procedure F. The product was purified by reverse phase HPLC to yield 34.5 mg of 424. MS (Q1) 535.2 (M)$^+$

Example 349

(4-hydroxypiperidin-1-yl)(3-(7-methyl-4-morpholino-2-(1H-pyrrolo[2,3-b]pyridin-5-yl)thieno[3,2-d]pyrimidin-6-yl)phenyl)methanone 425

3-(2-Chloro-7-methyl-4-morpholinothieno[3,2-d]pyrimidin-6-yl)benzoic acid (60 mg) was reacted with 4-hydroxypiperidine via General Procedure B to yield 3-(2-chloro-7-methyl-4-morpholinothieno[3,2-d]pyrimidin-6-yl)phenyl(4-hydroxypiperidin-1-yl)methanone. Crude 3-(2-chloro-7-methyl-4-morpholinothieno[3,2-d]pyrimidin-6-yl)phenyl(4-hydroxypiperidin-1-yl)methanone (72 mg) was coupled to 7-azaindole-5-boronic acid pinacol ester via General Procedure A. The product was purified by reverse phase HPLC to yield 29.5 mg of 425. MS (Q1) 555.2 (M)+

Example 350

N-(2-hydroxyethyl)-3-(7-methyl-4-morpholino-2-(1H-pyrrolo[2,3-b]pyridin-5-yl)thieno[3,2-d]pyrimidin-6-yl)benzamide 426

3-(2-Chloro-7-methyl-4-morpholinothieno[3,2-d]pyrimidin-6-yl)benzoic acid (60 mg) was reacted with ethanolamine via General Procedure B to yield 3-(2-chloro-7-methyl-4-morpholinothieno[3,2-d]pyrimidin-6-yl)-N-(2-hydroxyethyl)benzamide. Crude 3-(2-chloro-7-methyl-4-morpholinothieno[3,2-d]pyrimidin-6-yl)-N-(2-hydroxyethyl)benzamide (74 mg) was coupled to 7-azaindole-5-boronic acid pinacol ester via General Procedure A. The product was purified by reverse phase HPLC to yield 2.6 mg of 426. MS (Q1) 515.2 (M)$^+$

Example 351

(3-(7-methyl-4-morpholino-2-(1H-pyrrolo[2,3-b]pyridin-5-yl)thieno[3,2-d]pyrimidin-6-yl)phenyl)(4-methylpiperazin-1-yl)methanone 427

3-(2-Chloro-7-methyl-4-morpholinothieno[3,2-d]pyrimidin-6-yl)benzoic acid (60 mg) was reacted with 1-methylpiperizine via General Procedure B to yield 3-(2-chloro-7-methyl-4-morpholinothieno[3,2-d]pyrimidin-6-yl)phenyl(4-methylpiperazin-1-yl)methanone. Crude 3-(2-chloro-7-methyl-4-morpholinothieno[3,2-d]pyrimidin-6-yl)phenyl(4-methylpiperazin-1-yl)methanone (67 mg) was coupled to 7-azaindole-5-boronic acid pinacol ester via General Procedure A. The product was purified by reverse phase HPLC to yield 19.8 mg of 427. MS (Q1) 554.0 (M)$^+$

Example 352

4-morpholino-6-(6-morpholinopyridin-3-yl)-2-(1H-pyrrolo[2,3-b]pyridin-5-yl)thieno[3,2-d]pyrimidine 428

2-Chloro-6-iodo-4-morpholinothieno[3,2-d]pyrimidine 19 was reacted with 4-(5-(4,4,5,5-tetramethyl-1,3,2-dioxaborolan-2-yl)pyridin-2-yl)morpholine via General Procedure A to give the corresponding intermediate, after purification by flash chromatography, which was then reacted with 5-(4,4,5,5-tetramethyl-1,3,2-dioxaborolan-2-yl)-1H-pyrrolo[2,3-b]pyridine via General Procedure A again to give, after purification by reverse HPLC, 22 mg of 428. MS (Q1) 500 (M+)

Example 353

4-(4-morpholino-2-(1H-pyrrolo[2,3-b]pyridin-5-yl)thieno[3,2-d]pyrimidin-6-yl)thiazol-2-amine 429

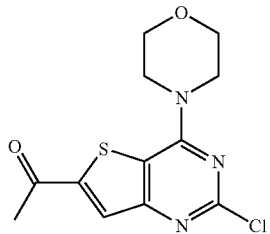

To a solution of 2-chloro-4-morpholinothieno[3,2-d]pyrimidine 4, Example 2) (1.0 eq) dissolved in THF (0.1M) at −78° C. was added a solution of n-butyllithium (1.3 eq, 1.6M in hexanes) following General Procedure D. The reaction mixture was stirred at −40° C. for 30 minutes. N,N-dimethylacetamide (4.0 eq) was added and reaction mixture was allowed to slowly warm up to 0° C. and stirred for 2 hours. Reaction mixture was poured in a cold solution of 0.25M HCl, and extracted with dichloromethane. The combined organic layers were dried (Na$_2$SO$_4$) and concentrated. The crude reaction mixture was purified by flash chromatography to yield 1-(2-chloro-4-morpholinothieno[3,2-d]pyrimidin-6-yl)ethanone.

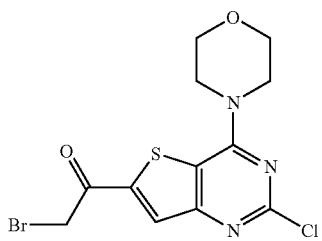

To a solution of 1-(2-chloro-4-morpholinothieno[3,2-d]pyrimidin-6-yl)ethanone (1.0 eq) dissolved in a mixture of CHCl$_3$, 33% wt HBr and acetic acid (1:1:1) at −0° C. was added a solution of Br$_2$ in CHCl$_3$ (1.05 eq). Reaction mixture was stirred at −0° C. until completed, then extracted in dichloromethane with saturated bicarbonate solution one time. The organic layer is dried, filtered and concentrated to yield the crude intermediate. This intermediate is purified by flash chromatography to yield 2-bromo-1-(2-chloro-4-morpholinothieno[3,2-d]pyrimidin-6-yl)ethanone.

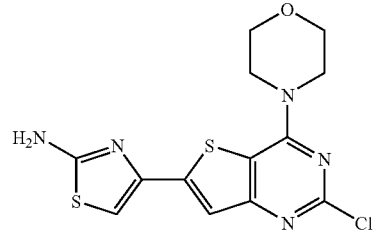

To a solution of 2-bromo-1-(2-chloro-4-morpholinothieno[3,2-d]pyrimidin-6-yl)ethanone (1.0 eq) dissolved in EtOH was added thiourea. Reaction mixture was heated at 70° C. until completed, then extracted in dichloromethane with saturated bicarbonate solution one time. The organic layer is dried, filtered and concentrated to yield the crude intermediate. This intermediate is purified by flash chromatography to yield 4-(2-chloro-4-morpholinothieno[3,2-d]pyrimidin-6-yl)thiazol-2-amine. MS (Q1) 413 (M+)

4-(2-chloro-4-morpholinothieno[3,2-d]pyrimidin-6-yl)thiazol-2-amine was reacted with 5-(4,4,5,5-tetramethyl-1,3,2-dioxaborolan-2-yl)-1H-pyrrolo[2,3-b]pyridine via General Procedure B to give, after purification by reverse HPLC, 41 mg of 429. MS (Q1) 436 (M+)

Example 354

6-(7-methyl-6-(3-(methylsulfonyl)phenyl)-4-morpholinothieno[3,2-d]pyrimidin-2-yl)-3H-imidazo[4,5-b]pyridine 430

To 215 mg of 4-(2-chloro-7-methyl-6-(3-(methylsulfonyl)phenyl)thieno[3,2-d]pyrimidin-4-yl)morpholine in 5 mL DMF in a microwave vial was added 0.41 g (1.5 eq) of 50 and 36 mg (0.1 eq) of Pd(PPh$_3$)$_2$Cl$_2$ and the vial placed in a Biotage microwave reactor for 30 minutes at 150° C. Complete reaction was confirmed by LCMS. The reaction mixture was diluted with EtOAc, partitioned with 1 M HCl, and the EtOAc layer dried over MgSO$_4$ and concentrated in vacuo. The crude solid was purified by flash chromatography (EtOAc/Hexanes) to give 0.22 g (69% yield) of protected product which was dissolved in 20 mL THF and 0.55 g TBAF (6.0 eq) and heated to 80° C. for 72 hours to remove the protecting group. Complete deprotection was confirmed by LCMS and the reaction mixture was diluted with water, extracted with EtOAc, and concentrated in vacuo to give 38.5 mg (22% yield) of 430 after RP-HPLC purification. MS (Q1) 507.1 (M)+

Example 355

2-(2-(1H-imidazo[4,5-b]pyridin-6-yl)-4-morpholinothieno[3,2-d]pyrimidin-6-yl)propan-2-ol 431

To 100 mg of 12 in 5 mL DMF in a microwave vial was added 0.26 g (1.5 eq) of 50 and 22 mg (0.1 eq) of Pd(PPh$_3$)$_2$Cl$_2$ and the vial placed in a biotage microwave reactor for 20 minutes at 150° C. Reaction was not complete and 0.1 eq more Pd(PPh$_3$)$_2$Cl$_2$ was added and the mixture was placed on the microwave again for 30 minutes at 150° C. Complete reaction was confirmed by LCMS. The reaction mixture was diluted with water and brine and the product extracted out with EtOAc and concentrated in vacuo. The crude solid was purified by RP-HPLC to give 431. MS (Q1) 397.2 (M)+

Example 356

2-methyl-6-(7-methyl-6-(3-(methylsulfonyl)phenyl)-4-morpholinothieno[3,2-d]pyrimidin-2-yl)-3H-imidazo[4,5-b]pyridine 432

To 120 mg of 4-(2-chloro-7-methyl-6-(3-(methylsulfonyl)phenyl)thieno[3,2-d]pyrimidin-4-yl)morpholino in 2 mL 1M KOAc and 2 mL acetonitrile was added 0.16 g (1.5 eq) of 54 and 32 mg (0.1 eq) of Pd(PPh$_3$)$_4$ as per General Procedure A to give 180 mg (99% yield) of the of the protected product after flash chromatography (EtOAc/Hexanes). MS (Q1) 652 (M)+. This compound was dissolved in 10 mL THF and 0.45 g TBAF (6.0 eq) was added and the reaction heated to 90° C. overnight to remove the SEM protecting group. Complete deprotection was confirmed by LCMS and the reaction mixture was diluted with water, extracted with EtOAc, dried over MgSO$_4$ and concentrated in vacuo to give 44.8 mg of 432 after RP-HPLC purification (46% yield). MS (Q1) 521 (M)+

Example 357

2-(2-(2-methyl-3H-imidazo[4,5-b]pyridin-6-yl)-4-morpholinothieno[3,2-d]pyrimidin-6-yl)propan-2-ol 433

To 236 mg of compound 12 in 2 mL 1M KOAc and 2 mL acetonitrile was added 0.44 g (1.5 eq) of 54 and 87 mg (0.1 eq) of Pd(PPh$_3$)$_4$ as per General Procedure A to give 330 mg of the SEM adduct after RP-HPLC purification (81% yield). MS (Q1) 396.2 (M)+. This compound was dissolved in 10 mL THF and 0.96 g TBAF was added and the reaction heated to 90° C. overnight to remove the SEM protecting group. Complete deprotection was confirmed by LCMS and the reaction mixture was diluted with water, extracted with EtOAc and a small amount of MeOH, washed with brine and concentrated in vacuo to give 113.8 mg of 433 after RP-HPLC purification (46% yield). MS (Q1) 411.2 (M)+

Example 358

5-(7-methyl-4-morpholino-2-(1H-pyrrolo[2,3-b]pyridin-5-yl)thieno[3,2-d]pyrimidin-6-yl)-N-(2-morpholinoethyl)pyridin-2-amine 434

2-Chloro-6-iodo-7-methyl-4-morpholinothieno[3,2-d]pyrimidine (1 eq), 2-fluoro-5-pyridineboronic acid (1.1 eq) and bis(triphenylphosphine)palladium(II) dichloride (0.1 eq) in 1M Na$_2$CO$_3$ aqueous solution (3 eq) and an equal volume of acetonitrile was heated to 100° C. in a sealed microwave reactor for 30 min. Reaction mixture was concentrated, then crude product was purified by flash chromatography to give 4-(2-chloro-6-(6-fluoropyridin-3-yl)-7-methylthieno[3,2-d]pyrimidin-4-yl)morpholine. MS (Q1) 365 (M$^+$)

4-(2-chloro-6-(6-fluoropyridin-3-yl)-7-methylthieno[3,2-d]pyrimidin-4-yl)morpholine was reacted with 2-morpholinoethylamino via General Procedure L to give, after purification by flash chromatography, the corresponding intermediate, which was then reacted with 5-(4,4,5,5-tetramethyl-1,3,2-dioxaborolan-2-yl)-1H-pyrrolo[2,3-b]pyridine via General Procedure A to give, after purification by reverse HPLC, 40 mg of 434. MS (Q1) 557 (M$^+$)

Example 359

3-(5-(7-methyl-4-morpholino-2-(1H-pyrrolo[2,3-b]pyridin-5-yl)thieno[3,2-d]pyrimidin-6-yl)pyridin-2-ylamino)propane-1,2-diol 435

4-(2-chloro-6-(6-fluoropyridin-3-yl)-7-methylthieno[3,2-d]pyrimidin-4-yl)morpholine was reacted with 3-amino-1,2-propanediol via General Procedure L to give, after purification by flash chromatography, the corresponding intermediate, which was then reacted with 5-(4,4,5,5-tetramethyl-1,3,2-dioxaborolan-2-yl)-1H-pyrrolo[2,3-b]pyridine via General Procedure A to give, after purification by reverse HPLC, 50 mg of 435. MS (Q1) 518 (M$^+$)

Example 360

2-(2-(5-(7-methyl-4-morpholino-2-(1H-pyrrolo[2,3-b]pyridin-5-yl)thieno[3,2-d]pyrimidin-6-yl)pyridin-2-ylamino)ethoxy)ethanol 436

4-(2-chloro-6-(6-fluoropyridin-3-yl)-7-methylthieno[3,2-d]pyrimidin-4-yl)morpholine was reacted with 2-(2-aminoethoxy)ethanol via General Procedure L to give, after purification by flash chromatography, the corresponding intermediate, which was then reacted with 5-(4,4,5,5-tetramethyl-1,3,2-dioxaborolan-2-yl)-1H-pyrrolo[2,3-b]pyridine via General Procedure A to give, after purification by reverse HPLC, 52 mg of 436. MS (Q1) 532 (M$^+$)

Example 361

N-methyl(4-morpholino-2-(1H-pyrrolo[2,3-b]pyridin-5-yl)thieno[3,2-d]pyrimidin-6-yl)methanamine 437

(2-Chloro-4-morpholin-4-yl-thieno[3,2-d]pyrimidin-6-ylmethyl)-methylamine and 5-(4,4,5,5-tetramethyl-[1.3.2]dioxaborolan-2-yl)-1H-pyrrolo[2,3-b]pyridine were reacted according to the General Procedure A to give 437. NMR (DMSO, 400 MHz), 2.35 (3H, s), 3.78-3.82 (4H, m), 3.99-4.06 (6H, m), 6.54 (1H, s) 7.36 (1H, s), 7.48-7.51 (1H, m), 8.97 (1H, s), 9.28 (1H, s). MS: (ESI+): MH+=381

Example 362

1-(2-(1H-indazol-4-yl)-4-morpholinothieno[3,2-d]pyrimidin-6-yl)pyrrolidin-2-one 438

2-Chloro-6-iodo-4-morpholinothieno[3,2-d]pyrimidine (150 mg), 90 μL of 2-pyrrolidinone, potassium phosphate tribasic (250 mg), copper iodide (7 mg), 4 μL of N,N-dimethylethylenediamine in 2 mL of 1,4-dioxane was heated to 100° C. for 16 h. The reaction mixture was evaporated and the residue was diluted with ethyl acetate (60 mL), washed with brine (30 mL), dried over MgSO$_4$, filtered and evaporated. The crude product was purified on reverse phase HPLC to give 53 mg of 1-(2-chloro-4-morpholinothieno[3,2-d]pyrimidin-6-yl)pyrrolidin-2-one.

1-(2-Chloro-4-morpholinothieno[3,2-d]pyrimidin-6-yl)pyrrolidin-2-one (35 mg) was coupled to 4-(4,4,5,5-tetramethyl-1,3,2-dioxaborolan-2-yl)-1H-indazole via Procedure A. The product was purified by reverse phase HPLC to yield 19.5 mg of 438. MS (Q1) 421 (M)+

Example 363

3-(2-(1H-indazol-4-yl)-4-morpholinothieno[3,2-d]pyrimidin-6-yl)oxazolidin-2-one 439

N-Butyllithium (9.4 mL, 22.48 mmol, 2.5 M in hexane solution) was added to a mixture of 2-chloro-4-morpholinothieno[3,2-d]pyrimidine (3.0 g, 11.74 mmol) in 60 mL of THF at −78° C. The reaction mixture was allowed to warm to −40° C. and stirred for 30 min. A solution of iodine (6.0 g, 23.48 mmol) in 10 mL of THF was added dropwise. After the addition was completed. The reaction mixture was brought to room temperature and stirred for 2 h. The mixture was quenched by diluting with dichloromethane (300 mL) and extracting with $H_2O$ (2×100 mL). The organic layer was washed with $Na_2S_2O_3$ (2×100 mL), $H_2O$ (2×100 mL), dried over $MgSO_4$, filtered and evaporated to afford 2-chloro-6-iodo-4-morpholinothieno[3,2-d]pyrimidine (3.4 g, 75%).

2-Chloro-6-iodo-4-morpholinothieno[3,2-d]pyrimidine (150 mg), 2-oxazolidinone (103 mg), potassium phosphate tribasic (250 mg), copper iodide (7 mg), 4 μL of N,N-dimethylethylenediamine in 2 mL of 1,4-dioxane was heated to 100° C. for 15 hr. The reaction mixture was evaporated and the residue was diluted with ethyl acetate (50 mL), washed with brine (30 mL), dried over $MgSO_4$, filtered and evaporated. The crude product was purified on reverse phase HPLC to give 46 mg of 3-(2-chloro-4-morpholinothieno[3,2-d]pyrimidin-6-yl) oxazolidin-2-one.

3-(2-Chloro-4-morpholinothieno[3,2-d]pyrimidin-6-yl) oxazolidin-2-one (46 mg) was coupled to 4-(4,4,5,5-tetramethyl-1,3,2-dioxaborolan-2-yl)-1H-indazole via Procedure A. The product was purified by reverse phase HPLC to yield 8.6 mg of 439. MS (Q1) 423 (M)+

Example 364 p110α (Alpha) PI3K Binding Assay

Binding Assays: Initial polarization experiments were performed on an Analyst HT 96-384 (Molecular Devices Corp, Sunnyvale, Calif.). Samples for fluorescence polarization affinity measurements were prepared by addition of 1:3 serial dilutions of p110alpha PI3K (Upstate Cell Signaling Solutions, Charlottesville, Va.) starting at a final concentration of 20 ug/mL in polarization buffer (10 mM Tris pH 7.5, 50 mM NaCl, 4 mM $MgCl_2$, 0.05% Chaps, and 1 mM DTT) to 10 mM $PIP_2$ (Echelon-Inc., Salt Lake City, Utah) final concentration. After an incubation time of 30 minutes at room temperature, the reactions were stopped by the addition of GRP-1 and PIP3-TAMRA probe (Echelon-Inc., Salt Lake City, Utah) 100 nM and 5 nM final concentrations respectively. Read with standard cut-off filters for the rhodamine fluorophore ($\lambda ex=530$ nm; $\lambda em=590$ nm) in 384-well black low volume Proxiplates (PerkinElmer, Wellesley, Mass.) Fluorescence polarization values were plotted as a function of the protein concentration, and the $EC_{50}$ values were obtained by fitting the data to a 4-parameter equation using KaleidaGraph software (Synergy software, Reading, Pa.). This experiment also establishes the appropriate protein concentration to use in subsequent competition experiments with inhibitors.

Inhibitor $IC_{50}$ values were determined by addition of the 0.04 mg/mL p110alpha PI3K (final concentration) combined with $PIP_2$ (10 mM final concentration) to wells containing 1:3 serial dilutions of the antagonists in a final concentration of 25 mM ATP (Cell Signaling Technology, Inc., Danvers, Mass.) in the polarization buffer. After an incubation time of 30 minutes at room temperature, the reactions were stopped by the addition of GRP-1 and PIP3-TAMRA probe (Echelon-Inc., Salt Lake City, Utah) 100 nM and 5 nM final concentrations respectively. Read with standard cut-off filters for the rhodamine fluorophore ($\lambda ex=530$ nm; $\lambda em=590$ nm) in 384-well black low volume proxi plates (PerkinElmer, Wellesley, Mass.) Fluorescence polarization values were plotted as a function of the antagonist concentration, and the $IC_{50}$ values were obtained by fitting the data to a 4-parameter equation in Assay Explorer software (MDL, San Ramon, Calif.).

Alternatively, inhibition of PI3K was determined in a radiometric assay using purified, recombinant enzyme and ATP at a concentration of 1 uM. The compound was serially diluted in 100% DMSO. The kinase reaction was incubated for 1 h at room temperature, and the reaction was terminated by the addition of PBS. $IC_{50}$ values were subsequently determined using sigmoidal dose-response curve fit (variable slope).

Example 365 p110 Isoform Selectivity Scintillation Proximity Binding Assay

The ability of Formula Ia and Ib compounds from Tables 1a and 1b to inhibit the lipid kinase activity of purified preparations of human PI3K isoforms alpha, beta, delta, and gamma was determined by a radiometric scintillation proximity assay (SPA, GE Healthcare, Amersham Biosciences). Concentration dependent inhibition at 50% ($IC_{50}$ μMol) was determined for all four isoforms (alpha) and fold potency over beta, delta, and gamma relative to alpha was calculated for a selection of compounds in Table 2. Each compound has a p110 alpha $IC_{50} < 1$ μMol.

TABLE 2

| compound | alpha/beta | alpha/delta | alpha/gamma |
|---|---|---|---|
| 101 | >10 | <10 | >10 |
| 133 | <10 | <10 | >10 |
| 137 | >10 | <10 | <10 |
| 170 | <10 | <10 | <10 |
| 202 | <10 | <10 | >10 |
| 203 | <10 | <10 | >10 |
| 205 | <10 | <10 | >10 |
| 208 | >10 | <10 | >10 |
| 218 | >10 | <10 | >10 |
| 226 | <10 | <10 | >10 |
| 233 | >10 | <10 | <10 |
| 235 | >10 | <10 | >10 |
| 237 | >10 | <10 | >10 |
| 238 | >10 | <10 | >10 |
| 257 | <10 | <10 | >10 |
| 263 | <10 | <10 | >10 |
| 265 | >10 | <10 | >10 |
| 304 | 10 | <10 | >10 |
| 305 | <10 | <10 | >10 |
| 312 | <10 | <10 | >10 |
| 321 | >10 | <10 | >10 |
| 324 | >10 | <10 | >10 |
| 334 | >10 | <10 | >10 |
| 336 | >10 | <10 | >10 |
| 338 | >10 | <10 | >10 |
| 353 | <10 | <10 | >10 |
| 360 | >10 | >10 | >10 |
| 368 | <10 | <10 | >10 |
| 388 | >10 | <10 | >10 |
| 390 | <10 | <10 | <10 |
| 395 | >10 | >10 | >10 |

TABLE 2-continued

| compound | alpha/beta | alpha/delta | alpha/gamma |
|---|---|---|---|
| 417 | >10 | >10 | >10 |
| 418 | >10 | 10 | >10 |
| 422 | >10 | <10 | >10 |
| 428 | >10 | >10 | >10 |
| 429 | >10 | >10 | >10 |

Example 366

In vitro Cell Proliferation Assay

Efficacy of Formula Ia and Ib compounds were measured by a cell proliferation assay employing the following protocol (Promega Corp. Technical Bulletin TB288; Mendoza et al (2002) Cancer Res. 62:5485-5488):
1. An aliquot of 100 μl of cell culture containing about $10^4$ cells (PC3, Detroit562, or MDAMB361.1) in medium was deposited in each well of a 384-well, opaque-walled plate.
2. Control wells were prepared containing medium and without cells.
3. The compound was added to the experimental wells and incubated for 3-5 days.
4. The plates were equilibrated to room temperature for approximately 30 minutes.
5. A volume of CellTiter-Glo Reagent equal to the volume of cell culture medium present in each well was added.
6. The contents were mixed for 2 minutes on an orbital shaker to induce cell lysis.
7. The plate was incubated at room temperature for 10 minutes to stabilize the luminescence signal.
8. Luminescence was recorded and reported in graphs as RLU=relative luminescence units.

Alternatively, cells were seeded at optimal density in a 96 well plate and incubated for 4 days in the presence of test compound. Alamar Blue™ was subsequently added to the assay medium, and cells were incubated for 6 h before reading at 544 nm excitation, 590 nm emission. $EC_{50}$ values were calculated using a sigmoidal dose response curve fit.

Example 367

Caco-2 Permeability

Caco-2 cells were seeded onto Millipore Multiscreen plates at $1\times10^5$ cells/cm$^2$, and were cultured for 20 days. Assessment of compound permeability was subsequently conducted. The compounds were applied to the apical surface (A) of cell monolayers and compound permeation into the basolateral (B) compartment was measured. This was performed in the reverse direction (B–A) to investigate active transport. A permeability coefficient value, $P_{app}$, for each compound, a measure of the rate of permeation of the compound across the membrane, was calculated. Compounds were grouped into low ($P_{app}</=1.0\times10^6$ cm/s) or high ($P_{app}>/=1.0\times10^6$ cm/s) absorption potential based on comparison with control compounds with established human absorption.

For assessment of a compound's ability to undergo active efflux, the ratio of basolateral (B) to apical (A) transport compared with A to B was determined. Values of B–A/A–B>/=1.0 indicated the occurrence of active cellular efflux. The had $P_{app}$ values>/=1.0×10$^6$ cm/s.

Example 368

Hepatocyte Clearance

Suspensions of cryopreserved human hepatocytes were used. Incubations were performed at compound concentration of 1 mM or 3 μM at a cell density of 0.5×10$^6$ viable cells/mL. The final DMSO concentration in the incubation was 0.25%. Control incubations were also performed in the absence of cells to reveal any non-enzymatic degradation. Duplicate samples (50 μL) were removed from the incubation mixture at 0, 5, 10, 20, 40 and 60 minutes (control sample at 60 minutes only) and added to methanol-containing internal standard (100 μL)—to terminate the reaction. Tolbutamide, 7-hydroxycoumarin, and testosterone were used as control compounds. Samples were centrifuged and the supernatants at each time point pooled for analysis by LC-MSMS. From a plot of ln peak area ratio (parent compound peak area/internal standard peak area) against time, intrinsic clearance ($CL_{int}$) was calculated as follows: $CL_{int}$ (μl/min/million cells)=V×k, where k is the elimination rate constant, obtained from the gradient of ln concentration plotted against time; V is a volume term derived from the incubation volume and is expressed as uL 10$^6$ cells$^{-1}$.

Compounds from Tables 1a and 1b were characterized on the basis of low (CL</=4.6 μL/min/10$^6$ cells), medium (CL>/=4.6; </=25.2 μl/min/10$^6$ cells) and high (>/=25.2 μl/min/10$^6$ cells) hepatocyte clearance.

Example 369

Cytochrome P450 Inhibition

Certain compound of the invention was screened against five CYP450 targets (1A2, 2C9, 2C19, 2D6, 3A4) at 10 concentrations in duplicate, with a top concentration of 100 uM being used. Standard inhibitors (furafylline, sulfaphenazole, tranylcypromine, quinidine, ketoconazole) were used as controls. Plates were read using a BMG LabTechnologies PolarStar in fluorescence mode.

Example 370

Cytochrome P450 Induction

Freshly isolated human hepatocytes from a single donor were cultured for 48 h prior to addition of test compound at three concentrations and were incubated for 72 h. Probe substrates for CYP3A4 and CYP1A2 were added for 30 minutes and 1 h before the end of the incubation. At 72 h, cells and media were removed and the extent of metabolism of each probe substrate quantified by LC-MS/MS. The experiment was controlled by using inducers of the individual P450s incubated at one concentration in triplicate to determine the extent of induction of cytochrome P450 enzymes.

Example 371

Plasma Protein Binding

Solutions of test compound (5 um, 0.5% final DMSO concentration) were prepared in buffer and 10% plasma (v/v in buffer). A 96 well HT dialysis plate was assembled so that each well was divided in two by a semi-permeable cellulose membrane. The buffer solution was added to one side of the membrane and the plasma solution to the other side; incubations were then conducted at 37° C. over 2 h in triplicate. The cells were subsequently emptied, and the solutions for each batch of compounds were combined into two groups (plasma-free and plasma-containing) then analysed by LC-MSMS using two sets of calibration standards for plasma-free (6 points) and plasma-containing solutions (7 points). The fraction unbound value for the compounds of Tables 1a and 1b was calculated as: highly protein bound compounds (>/=90% bound) had an Fu</=0.1.

Example 372

HERG Channel Blockage

The compounds of Tables 1a and 1b were evaluated for modulation of rubidium efflux from HEK-294 cells stably expressing HERG potassium channels using established flux methodology. Cells were prepared in medium containing RbCl and were plated into 96-well plates and grown overnight to form monolayers. The efflux experiment was initiated by aspirating the media and washing each well with 3×100 μL of pre-incubation buffer (containing low [K+]) at room temperature. Following the final aspiration, 50 μL of working stock (2×) compound was added to each well and incubated at room temperature for 10 minutes. 50 μL of stimulation buffer (containing high [K+]) was then added to each well giving the final test compound concentrations. Cell plates were then incubated at room temperature for a further 10 minutes. 80 μL of supernatant from each well was then transferred to equivalent wells of a 96-well plate and analysed via atomic emission spectroscopy. The compound was screened as 10pt duplicate $IC_{50}$ curves, n=2, from a top concentration of 100 μM.

The foregoing description is considered as illustrative only of the principles of the invention. Further, since numerous modifications and changes will be readily apparent to those skilled in the art, it is not desired to limit the invention to the exact construction and process shown as described above. Accordingly, all suitable modifications and equivalents may be considered to fall within the scope of the invention as defined by the claims that follow.

The words "comprise," "comprising," "include," "including," and "includes" when used in this specification and in the following claims are intended to specify the presence of stated features, integers, components, or steps, but they do not preclude the presence or addition of one or more other features, integers, components, steps, or groups thereof.

What is claimed is:
1. A compound selected from Formula Ia and Formula Ib:

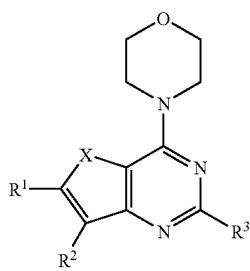

Ia

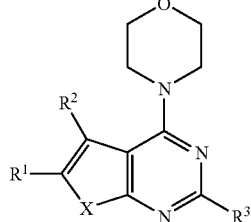

Ib and stereoisomers, geometric isomers, tautomers, and pharmaceutically acceptable salts thereof, wherein:

X is O or S;

$R^1$ is H;

$R^2$ is selected from H, F, Cl, Br, I, CN, $CF_3$, $—NO_2$, $—C(=Y)R^{10}$, $—C(=Y)OR^{10}$, $—C(=Y)NR^{10}R^{11}$, $—(CR^{14}R^{15})_mNR^{10}R^{11}$, $—(CR^{14}R^{15})_nOR^{10}$, $—(CR^{14}R^{15})_r—NR^{12}C(=O)(CR^{14}R^{15})NR^{10}R^{11}$, $—NR^{12}C(=Y)R^{10}$, $—NR^{12}C(=Y)OR^{10}$, $—NR^{12}C(=Y)NR^{10}R^{11}$, $—NR^{12}SO_2R^{10}$, $—OC(=Y)R^{10}$, $—OC(=Y)NR^{10}R^{11}$, $—OS(O)_2(OR^{10})$, $—OP(=Y)(OR^{10})(OR^{11})$, $—OP(OR^{10})(OR^{11})$, $SR^{10}$, $—S(O)R^{10}$, $—S(O)_2R^{10}$, $—S(O)_2NR^{10}R^{11}$, $—S(O)(OR^{10})$, $—S(O)_2(OR^{10})$, $—SC(=Y)R^{10}$, $—SC(=Y)OR^{10}$, $—SC(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

$R^3$ is fused bicyclic $C_4$-$C_{20}$ heterocyclyl or fused bicyclic $C_1$-$C_{20}$ heteroaryl;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, $(CH_2)_mOR^{10}$, $NR^{10}R^{11}$, $CF_3$, F, Cl, Br, I, $SO_2R^{10}$, $C(=O)R^{10}$, $NR^{12}C(=Y)R^{11}$, $NR^{12}S(O)_2R^{11}$, $C(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or $—(CH_2)_n$-aryl, or $R^{14}$ and $R^{15}$ together with the atoms to which they are attached form a saturated or partially unsaturated $C_3$-$C_{12}$ carbocyclic ring, where said alkyl, alkenyl, alkynyl, carbocyclyl, heterocyclyl, aryl, heteroaryl, fused bicyclic $C_4$-$C_{20}$ heterocyclyl, and fused bicyclic $C_1$-$C_{20}$ heteroaryl are optionally substituted with one or more groups independently selected from F, Cl, Br, I, CN, $CF_3$, $—NO_2$, oxo, $R^{10}$, $—C(=Y)R^{10}$, $—C(=Y)OR^{10}$, $—C(=Y)NR^{10}R^{11}$, $—(CR^{14}R^{15})_nNR^{10}R^{11}$, $—(CR^{14}R^{15})_nOR^{10}$, $—NR^{10}R^{11}$, $—NR^{12}C(=Y)R^{10}$, $—NR^{12}C(=Y)OR^{11}$, $—NR^{12}C(=Y)NR^{10}R^{11}$, $—NR^{12}SO_2R^{10}$, $=NR^{12}$, $OR^{10}$, $—OC(=Y)R^{10}$, $—OC(=Y)OR^{10}$, $—OC(=Y)NR^{10}R^{11}$, $—OS(O)_2(OR^{10})$, $—OP(=Y)(OR^{10})(OR^{11})$, $—OP(OR^{10})(OR^{11})$, $SR^{10}$, $—S(O)R^{10}$, $—S(O)_2R^{10}$, $—S(O)_2NR^{10}R^{11}$, $—S(O)(OR^{10})$, $—S(O)_2(OR^{10})$, $—SC(=Y)R^{10}$, $—SC(=Y)OR^{10}$, $—SC(=Y)NR^{10}R^{11}$, $C_1$-$C_{12}$ optionally substituted alkyl, $C_2$-$C_8$ optionally substituted alkenyl, $C_2$-$C_8$ optionally substituted alkynyl, $C_3$-$C_{12}$ optionally substituted carbocyclyl, $C_2$-$C_{20}$ optionally substituted heterocyclyl, $C_6$-$C_{20}$ optionally substituted aryl, $C_1$-$C_{20}$ optionally substituted heteroaryl, —$(CR^{14}R^{15})_t$—$NR^{12}C(=O)$$(CR^{14}R^{15})NR^{10}R^{11}$, and $(CR^4R^5)_t$—$NR^{10}R^{11}$;

Y is O, S, or $NR^{12}$;

m is 0, 1, 2, 3, 4, 5 or 6;

n is 1, 2, 3, 4, 5 or 6; and t is 2, 3, 4, 5 or 6.

2. A compound selected from Formula Ia and Formula Ib:

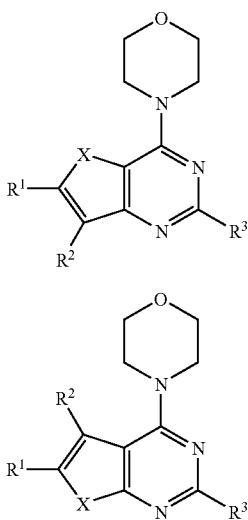

and stereoisomers, geometric isomers, tautomers, and pharmaceutically acceptable salts thereof, wherein:

X is O or S;

$R^1$ is —$(CR^{14}R^{15})_n NR^{12}S(O)_2R^{10}$ where n is 1 or 2; $R^{12}$, $R^{14}$, and $R^{15}$ are independently selected from H and $C_1$-$C_{12}$ alkyl; and $R^{10}$ is $C_1$-$C_{12}$ alkyl or $C_6$-$C_{20}$ aryl; $R^2$ is selected from H, F, Cl, Br, I, CN, $CF_3$, —$NO_2$, —$C(=Y)R^{10}$, —$C(=Y)OR^{10}$, —$C(=Y)NR^{10}R^{11}$, —$(CR^{14}R^{15})_m NR^{10}R^{11}$, —$CR^{14}R^{15})_n OR^{10}$, —$(CR^{14}R^{15})_t$—$NR^{12}C(=O)CR^{14}R^{15})NR^{10}R^{11}$, —$NR^{12}C(=Y)R^{10}$, —$NR^{12}C(=Y)OR^{10}$, —$NR^{12}C(=Y)NR^{10}R^{11}$, —$NR^{12}SO_2R^{10}$, $OR^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})(OR^{11})$, $SR^{10}$, —$S(O)R^{10}$, —$S(O)_2R^{10}$, —$S(O)_2NR^{10}R^{11}$, —$S(O)(OR^{10})$, —$S(O)_2(OR^{10})$, —$SC(=Y)R^{10}$, $SC(=Y)OR^{10}$, —$SC(=Y)NR^{10}R^{11}$, $C_1$-$C_{12}$ alkyl, $C_2$-$C_8$ alkenyl, $C_3$-$C_{12}$ carbocyclyl, $C_2$-$C_{20}$ heterocyclyl, $C_6$-$C_{20}$ aryl, and $C_1$-$C_{20}$ heteroaryl;

$R^3$ is fused bicyclic $C_4$-$C_{20}$ heterocyclyl or fused bicyclic $C_1$-$C_{20}$ heteroaryl;

$R_{10}$, $R^{11}$ and $R^{12}$ are independently H, $C_1$-$C_{12}$ alkyl, $C_2$-$C_8$ alkenyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, $(CH_2)_m OR^{10}$, $NR^{10}R^{11}$, $CF_3$, F, Cl, Br, I, $SO_2R^{10}$, $C(=O)R^{10}$, $NR^{12}C(=Y)R^{11}$, $NR^{12}S(O)_2R^{11}$, $C(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or —$(CH_2)_n$-aryl, or $R^{14}$ and $R^{15}$ together with the atoms to which they are attached form a saturated or partially unsaturated $C_3$-$C_{12}$ carbocyclic ring, where said alkyl, alkenyl, alkynyl, carbocyclyl, heterocyclyl, aryl, heteroaryl, fused bicyclic $C_4$-$C_{20}$ heterocyclyl, and fused bicyclic $C_1$-$C_{20}$ heteroaryl are optionally substituted with one or more groups independently selected from F, Cl, Br, I, CN, $CF_3$, —$NO_2$, oxo, $R^{10}$, —$C(=Y)R^{10}$, —$C(=Y)OR^{10}$, —$C(=Y)NR^{10}R^{11}$, —$(CR^{14}R^{15})_n OR^{10}$, —$NR^{10}R^{11}$, —$NR^{12}C(=Y)R^{10}$, —$NR^{12}C(=Y)OR^{11}$, —$NR^{12}C(=Y)NR^{10}R^{11}$, —$NR^{12}SO_2R^{10}$, =$NR^{12}$, $OR^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})(OR^{11})$, $SR^{10}$, —$S(O)R^{10}$, —$S(O)_2R^{10}$, —$S(O)_2NR^{10}R^{11}$, —$S(O)(OR^{10})$, —$S(O)(OR^{10})$, —$SC(=Y)R^{10}$, —$SC(=Y)OR^{10}$, —$SC(=Y)NR^{10}R^{11}$, $C_1$-$C_{12}$ optionally substituted alkyl, $C_2$-$C_8$ optionally substituted alkenyl, $C_2$-$C_8$ optionally substituted alkynyl, $C_3$-$C_{12}$ optionally substituted carbocyclyl, $C_2$-$C_{20}$ optionally substituted heterocyclyl, $C_6$-$C_{20}$ optionally substituted aryl, $C_1$-$C_{20}$ optionally substituted heteroaryl, —$(CR^{14}R^{15})_t$—$NR^{12}C(=O)(CR^{14}R^{15})NR^{10}R^{11}$, and $(CR^{14}R^{15})_t$—$NR^{10}R^{11}$;

Y is O, S, or $NR^{12}$;

m is 0, 1, 2, 3, 4, 5 or 6;

n is 1, 2, 3, 4, 5 or 6; and t is 2, 3, 4, 5 or 6.

3. A compound selected from Formula Ia and Formula Ib:

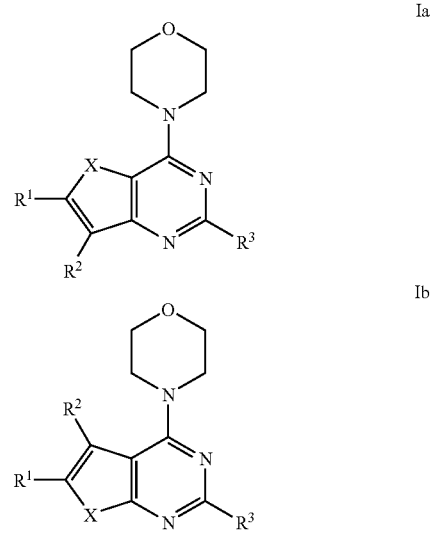

and stereoisomers, geometric isomers, tautomers, and pharmaceutically acceptable salts thereof, wherein:

X is O or S;

$R^1$ is —$(CR^{14}R^{15})_n OR^{10}$ where n is 1 or 2, and $R^{10}$, $R^{14}$, and $R^{15}$ are independently selected from H and $C_1$-$C_{12}$ alkyl;

$R^2$ is selected from H, F, Cl, Br, I, CN, $CF_3$, —$NO_2$, —$C(=Y)R^{10}$, —$C(=Y)OR^{10}$, —$C(=Y)NR^{10}R^{11}$, —$(CR^{14}R^{15})_m NR^{10}R^{11}$, —$(CR^{14}R^{15})_n OR^{10}$, —$CR^{14}R^{15})_t$—$NR^{12}C(=O)(CR^{14}R^{15})NR^{10}R^{11}$, —NR$^{12}$C(=Y)R$^{10}$, —NR$^{12}$C(=Y)OR$^{10}$, —NR$^{12}$C(=Y)NR$^{10}$R$^{11}$, —NR$^{12}$SO$_2$R$^{10}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)OR$^{11}$), SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl;

R$^3$ is fused bicyclic C$_4$-C$_{20}$ heterocyclyl or fused bicyclic C$_1$-C$_{20}$ heteroaryl;

R$^{10}$, R$^{11}$ and R$^{12}$ are independently H, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, or C$_1$-C$_{20}$ heteroaryl, or R$^{10}$ and R$^{11}$ together with the nitrogen to which they are attached optionally form a saturated, partially unsaturated or fully unsaturated C$_3$-C$_{20}$ heterocyclic ring optionally containing one or more additional ring atoms selected from N, O or S, wherein said heterocyclic ring is optionally substituted with one or more groups independently selected from oxo, (C$_2$)$_m$OR$^{10}$, NR$^{10}$R$^{11}$, CF$_3$, F, Cl, Br, I, SO$_2$R$^{10}$, C(=Y)R$^{10}$, NR$^{12}$C(=Y)R$^{11}$, NR$^{12}$S(O)$_{2R}$R$^{11}$, C(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl and C$_1$-C$_{20}$ heteroaryl;

R$^{14}$ and R$^{15}$ are independently selected from H, C$_1$-C$_{12}$ alkyl, or —(CH$_2$)$_n$-aryl, or R$^{14}$ and R$^{15}$ together with the atoms to which they are attached form a saturated or partially unsaturated C$_3$-C$_{12}$ carbocyclic ring, where said alkyl, alkenyl, alkynyl, carbocyclyl, heterocyclyl, aryl, heteroaryl, fused bicyclic C$_4$-C$_{20}$ heterocyclyl, and fused bicyclic C$_1$-C$_{20}$ heteroaryl are optionally substituted with one or more groups independently selected from F, Cl, Br, I, CN, CF$_3$, —NO$_2$, oxo, R$^{10}$, —C(=Y)R$^{10}$, —C(=Y)OR$^{10}$, —C(=Y)NR$^{10}$R$^{11}$, —(CR$^{14}$R$^{15}$)$_n$NR$^{10}$R$^{11}$, —(CR$^{14}$R$^{15}$)$_n$OR$^{10}$, —NR$_{10}$R$^{11}$, —NR$^{12}$C(=Y)R$^{10}$, —NR$^{12}$C(=Y)OR$^{11}$, —NR$^{12}$C(=Y)NR$^{10}$R$^{11}$, —NR$^{12}$SO$_2$R$^{10}$, =NR$^{12}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, C$_1$-C$_{12}$ optionally substituted alkyl, C$_2$-C$_8$ optionally substituted alkenyl, C$_2$-C$_8$ optionally substituted alkynyl, C$_3$-C$_{12}$ optionally substituted carbocyclyl, C$_2$-C$_{20}$ optionally substituted heterocyclyl, C$_6$-C$_0$ optionally substituted aryl, C$_1$-C$_{20}$ optionally substituted heteroaryl, —(CR$^{14}$R$^{15}$)$_t$—NR$^{12}$C(=O)(CR$^{14}$R$^{15}$)$_t$NR$^{12}$C(=O)(CR$^{14}$R$^{15}$)NR$^{10}$R$^{11}$, and (CR$^{14}$R$^{15}$)$_t$NR$^{10}$R$^{11}$;

Y is O, S, or NR$^{12}$;

m is 0, 1, 2, 3, 4, 5 or 6;

n is 1, 2, 3, 4, 5 or 6; and t is 2, 3, 4, 5 or 6.

4. A compound selected from Formula Ia and Formula Ib:

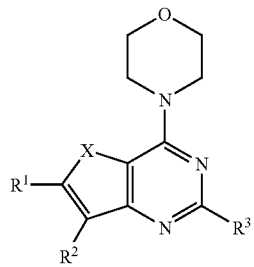

Ia

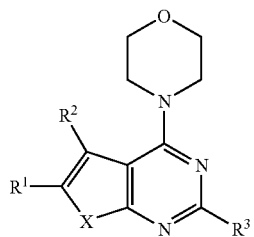

Ib and stereoisomers, geometric isomers, tautomers, and pharmaceutically acceptable salts thereof, wherein:

X is O or S;

R$^1$ is —(CR$^{14}$R$^{15}$)$_n$S(O)$_2$R$^{10}$ where n is 1 or 2, and R$^{14}$ R$^{15}$ are H;

R$^2$ is selected from H, F, Cl, Br, I, CN, CF$_3$, —NO$_2$, —C(=Y)R$^{10}$, —C(=Y)OR$^{10}$, —C(=Y)NR$^{10}$R$^{11}$, —(CR$^{14}$R$^{15}$)$_m$NR$^{10}$R$^{11}$, —(CR$^{14}$R$^{15}$)$_n$OR$^{10}$, —CR$^{14}$R$^{15}$)$_t$—NR$^{12}$C(=O)(CR$^{14}$R$^{15}$)NR$^{10}$R$^{11}$, —NR$^{12}$C(=Y)R$^{10}$, —NR$^{12}$C(=Y)OR$^{10}$, —NR$^{12}$C(=Y)NR$^{10}$R$^{11}$, —NR$^{12}$SO$_2$R$^{10}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)OR$^{11}$), SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl;

R$^3$ is fused bicyclic C$_4$-C$_{20}$ heterocyclyl or fused bicyclic C$_1$-C$_{20}$ heteroaryl;

R$^{10}$, R$^{11}$ and R$^{12}$ are independently H, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, or C$_1$-C$_{20}$ heteroaryl, or R$^{10}$ and R$^{11}$ together with the nitrogen to which they are attached optionally form a saturated, partially unsaturated or fully unsaturated C$_3$-C$_{20}$ heterocyclic ring optionally containing one or more additional ring atoms selected from N, O or S, wherein said heterocyclic ring is optionally substituted with one or more groups independently selected from oxo, (C$_2$)$_m$OR$^{10}$, NR$^{10}$R$^{11}$, CF$_3$, F, Cl, Br, I, SO$_2$R$^{10}$, C(=O)R$^{10}$, NR$^{12}$C(=Y)R$^{11}$, NR$^{12}$S(O)$_2$R$^{11}$, C(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl and C$_1$-C$_{20}$ heteroaryl;

R$^{14}$ and R$^{15}$ are independently selected from H, C$_1$-C$_{12}$ alkyl, or —(CH$_2$)$_n$-aryl, or R$^{14}$ and R$^{15}$ together with the atoms to which they are attached form a saturated or partially unsaturated C$_3$-C$_{12}$ carbocyclic ring, where said alkyl, alkenyl, alkynyl, carbocyclyl, heterocyclyl, aryl, heteroaryl, fused bicyclic C$_4$-C$_{20}$ heterocyclyl, and fused bicyclic $C_1$-$C_{20}$ heteroaryl are optionally substituted with one or more groups independently selected from F, Cl, Br, I, CN, $CF_3$, —$NO_2$, oxo, $R^{10}$, —C(=Y)$R^{10}$, —C(=Y)O$R^{10}$, —C(=Y)N$R^{10}R^{11}$, —(C$R^{14}R^{15}$)$_n$N$R^{10}R^{11}$, —(C$R^{14}R^{15}$)$_n$N$R^{10}R^{11}$, —(C$R^{14}R^{15}$)$_n$O$R^{10}$, —N$R^{10}R^{11}$, —N$R^{12}$C(=Y)$R_{10}$, —N$R^{12}$C(=Y)O$R^{11}$, —N$R^{12}$C(=Y)N$R^{10}R^{11}$, —N$R^{12}$S$O_2R^{10}$, =N$R^{12}$, O$R^{10}$, —OC(=Y)$R^{10}$, —OC(=Y)O$R^{10}$, —OC(=Y)N$R^{10}R^{11}$, —OS(O)$_2$(O$R^{10}$), —OP(=Y)(O$R^{10}$)(O$R^{11}$), —OP(O$R^{10}$)(O$R^{11}$), S$R^{10}$, —S(O)$R^{10}$, —S(O)$_2R^{10}$, —S(O)$_2$N$R^{10}R^{11}$, —S(O)(O$R^{10}$), —S(O)$_2$(O$R^{10}$), —SC(=Y)$R^{10}$, —SC(=Y)O$R^{10}$, —SC(=Y)N$R^{10}R^{11}$, $C_1$-$C_{12}$ optionally substituted alkyl, $C_2$-$C_8$ optionally substituted alkenyl, $C_2$-$C_8$ optionally substituted alkynyl, $C_3$-$C_{12}$ optionally substituted carbocyclyl, $C_2$-$C_{20}$ optionally substituted heterocyclyl, $C_6$-$C_{20}$ optionally substituted aryl, $C_1$-$C_{20}$ optionally substituted heteroaryl, —(C$R^{14}R^{15}$)$_t$—N$R^{12}$C(=O)(C$R^{14}R^{15}$)N$R^{10}R^{11}$, and (C$R^{14}R^{15}$)$_t$—N$R^{10}R^{11}$;

Y is O, S, or N$R^{12}$;

m is 0, 1, 2, 3, 4, 5 or 6;

n is 1, 2, 3, 4, 5 or 6; and t is 2, 3, 4, 5 or 6.

5. The compound of claim 4 wherein $R^{10}$ is $C_1$-$C_{12}$ alkyl or $C_6$-$C_{20}$ aryl.

6. A compound selected from Formula Ia and Formula Ib:

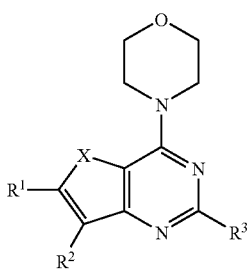

Ia

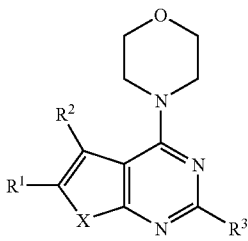

Ib and stereoisomers, geometric isomers, tautomers, and pharmaceutically acceptable salts thereof, wherein:

X is O or S;

$R^1$ is —(C$R^{14}R^{15}$)$_n$S(O)$_2$N$R^{10}R^{11}$ where n is 1 or 2, and $R^{14}$ and $R^{15}$ are H;

$R^2$ is selected from H, F, Cl, Br, I, CN, $CF_3$, —$NO_2$, —C(=Y)$R^{10}$, —C(=Y)O$R^{10}$, —C(=Y)N$R^{10}R^{11}$, —(C$R^{14}R^{15}$)$_m$N$R^{10}R^{11}$, —(C$R^{14}R^{15}$)$_n$O$R^{10}$, —C$R^{14}R^{15}$)$_t$—N$R^{12}$C(=O)(C$R^{14}R^{15}$)N$R^{10}R^{11}$, —N$R^{12}$C(=Y)$R^{10}$, —N$R^{12}$C(=Y)O$R^{10}$, —N$R^{12}$C(=Y)N$R^{10}R^{11}$, —N$R^{12}$S$O_2R^{10}$, O$R^{10}$, —OC(=Y)$R^{10}$, —OC(=Y)O$R^{10}$, —OC(=Y)N$R^{10}R^{11}$, —OS(O)$_2$(O$R^{10}$), —OP(=Y)(O$R^{10}$)(O$R^{11}$), —OP(O$R^{10}$)(O$R^{11}$), S$R^{10}$, —S(O)$R^{10}$, —S(O)$_2R^{10}$, —S(O)$_2$N$R^{10}R^{11}$, —S(O)(O$R^{10}$), —S(O)$_2$(O$R^{10}$), —SC(=Y)$R^{10}$, —SC(=Y)O$R^{10}$, —SC(=Y)N$R^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

$R^3$ is fused bicyclic $C_4$-$C_{20}$ heterocyclyl or fused bicyclic $C_1$-$C_{20}$ heteroaryl;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, (C$H_2$)$_m$O$R^{10}$, N$R^{10}R^{11}$, $CF_3$, F, Cl, Br, I, S$O_2R^{10}$, C(=O)$R^{10}$, N$R^{12}$C(=Y)$R^{11}$, N$R^{12}$S(O)$_2R^{11}$, C(=Y)N$R^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or —(C$H_2$)$_n$-aryl, or $R^{14}$ and $R^{15}$ together with the atoms to which they are attached form a saturated or partially unsaturated $C_3$-$C_{12}$ carbocyclic ring, $R^{16}$ and $R^{17}$ are independently H, $C_1$-$C_{12}$ alkyl, $C_2$-$C_8$ alkynyl, $C_3$-$C_{12}$ carbocyclyl, or $C_6$-$C_{20}$ aryl, $R^{18}$ and $R^{19}$ together with the carbon to which they are attached form a $C_3$-$C_{20}$ heterocyclic ring, where said alkyl, alkenyl, alkynyl, carbocyclyl, heterocyclyl, aryl, heteroaryl, fused bicyclic $C_4$-$C_{20}$ heterocyclyl, and fused bicyclic $C_1$-$C_{20}$ heteroaryl are optionally substituted with one or more groups independently selected from F, Cl, Br, I, CN, $CF_3$, —$NO_2$, oxo, $R^{10}$, —C(=Y)$R^{10}$, —C(=Y)O$R^{10}$, —C(=Y)N$R^{10}R^{11}$, —(C$R^{14}R^{15}$)$_n$N$R^{10}R^{11}$, —(C$R^{14}R^{15}$)$_n$O$R^{10}$, —N$R^{10}R^{11}$, —N$R^{12}$C(=Y)$R_{10}$, —N$R^{12}$C(=Y)O$R^{11}$, —N$R^{12}$C(=Y)N$R^{10}R^{11}$, —N$R^{12}$S$O_2R^{10}$, =N$R^{12}$, O$R^{10}$, —OC(=Y)$R^{10}$, —OC(=Y)O$R^{10}$, —OC(=Y)N$R^{10}R^{11}$, —OS(O)$_2$(O$R^{10}$), —OP(=Y)(O$R^{10}$)(O$R^{11}$), —OP(O$R^{10}$)(O$R^{11}$), S$R^{10}$, —S(O)$R^{10}$, —S(O)$_2R^{10}$, —S(O)$_2$N$R^{10}R^{11}$, —S(O)(O$R^{10}$), —S(O)$_2$(O$R^{10}$), —SC(=Y)$R^{10}$, —SC(=Y)O$R^{10}$, —SC(=Y)N$R^{10}R^{11}$, $C_1$-$C_{12}$ optionally substituted alkyl, $C_2$-$C_8$ optionally substituted alkenyl, $C_2$-$C_8$ optionally substituted alkynyl, $C_3$-$C_{12}$ optionally substituted carbocyclyl, $C_2$-$C_{20}$ optionally substituted heterocyclyl, $C_6$-$C_{20}$ optionally substituted aryl, $C_1$-$C_{20}$ optionally substituted heteroaryl, —(C$R^{14}R^{15}$)$_t$—N$R^{12}$C(=O)(C$R^{14}R^{15}$)N$R^{10}R^{11}$, and (C$R^{14}R^{15}$)$_t$—N$R^{10}R^{11}$;

Y is O, S, or N$R^{12}$;

m is 0, 1, 2, 3, 4, 5 or 6;

n is 1, 2, 3, 4, 5 or 6; and t is 2, 3, 4, 5 or 6.

7. A compound selected from Formula Ia and Formula Ib:

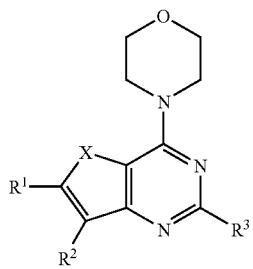

Ia

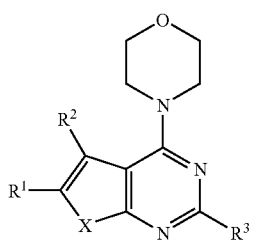

Ib and stereoisomers, geometric isomers, tautomers, and pharmaceutically acceptable salts thereof, wherein:

X is O or S;

$R^1$ is —C(=Y)NR$^{10}$R$^{11}$ where Y is O and R$^{10}$ and R$^{11}$ together with the nitrogen to which they are attached form a $C_2$-$C_{20}$ heterocyclic ring;

$R^2$ is selected from H, F, Cl, Br, I, CN, CF$_3$, —NO$_2$, —C(=Y)R$^{10}$, —C(=Y)OR$^{10}$, —C(=Y)NR$^{10}$R$^{11}$, —(CR$^{14}$R$^{15}$)$_m$NR$^{10}$R$^{11}$, —(CR$^{14}$R$^{15}$)$_n$OR$^{10}$, —CR$^{14}$R$^{15}$)$_t$—NR$^{12}$C(=O)(CR$^{14}$R$^{15}$)NR$^{10}$R$^{11}$, —NR$^{12}$C(=Y)R$^{10}$, —NR$^{12}$C(=Y)OR$^{10}$, —NR$^{12}$C(=Y)NR$^{10}$R$^{11}$, —NR$^{12}$SO$_2$R$^{10}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)OR$^{11}$), SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

$R^3$ is fused bicyclic $C_4$-$C_{20}$ heterocyclyl or fused bicyclic $C_1$-$C_{20}$ heteroaryl;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, (CH$_2$)$_m$OR$^{10}$, NR$^{10}$R$^{11}$, CF$_3$, F, Cl, Br, I, SO$_2$R$^{10}$, C(=O)R$^{10}$, NR$^{12}$C(=Y)R$^{11}$, NR$^{12}$S(O)$_2$R$^{11}$, C(=Y)NR$^{10}$R$^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or —(CH$_2$)$_n$-aryl, or $R^{14}$ and $R^{15}$ together with the atoms to which they are attached form a saturated or partially unsaturated $C_3$-$C_{12}$ carbocyclic ring, where said alkyl, alkenyl, alkynyl, carbocyclyl, heterocyclyl, aryl, heteroaryl, fused bicyclic $C_4$-$C_{20}$ heterocyclyl, and fused bicyclic $C_1$-$C_{20}$ heteroaryl are optionally substituted with one or more groups independently selected from F, Cl, Br, I, CN, CF$_3$, —NO$_2$, oxo, R$^{10}$, —C(=Y)R$^{10}$, —C(=Y)OR$^{10}$, —C(=Y)NR$^{10}$R$^{11}$, —(CR$^{14}$R$^{15}$)$_n$NR$^{10}$R$^{11}$, —(CR$^{14}$R$^{15}$)$_n$OR$^{10}$, —NR$^{10}$R$^{11}$, —NR$^{12}$C(=Y)R$_{10}$, —NR$^{12}$C(=Y)OR$^{11}$, —NR$^{12}$C(=Y)NR$^{10}$R$^{11}$, —NR$^{12}$SO$_2$R$^{10}$, =NR$^{12}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, $C_1$-$C_{12}$ optionally substituted alkyl, $C_2$-$C_8$ optionally substituted alkenyl, $C_2$-$C_8$ optionally substituted alkynyl, $C_3$-$C_{12}$ optionally substituted carbocyclyl, $C_2$-$C_{20}$ optionally substituted heterocyclyl, $C_6$-$C_{20}$ optionally substituted aryl, $C_1$-$C_{20}$ optionally substituted heteroaryl, —(CR$^{14}$R$^{15}$)$_t$—NR$^{12}$C(=O)(CR$^{14}$R$^{15}$)NR$^{10}$R$^{11}$, and (CR$^{14}$R$^{15}$)$_t$—NR$^{10}$R$^{11}$;

Y is O, S, or NR$^{12}$;

m is 0, 1, 2, 3, 4, 5 or 6;

n is 1, 2, 3, 4, 5 or 6; and t is 2, 3, 4, 5 or 6.

8. The compound of claim 7 wherein $R^{10}$ and $R^{11}$ together with the nitrogen to which they are attached form a $C_2$-$C_{20}$ heterocyclic ring selected from morpholinyl, piperidinyl, piperazinyl, and pyrrolidinyl.

9. A compound selected from Formula Ia and Formula Ib:

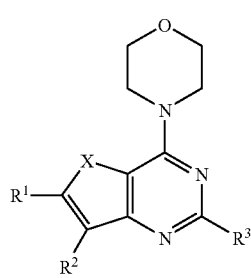

Ia

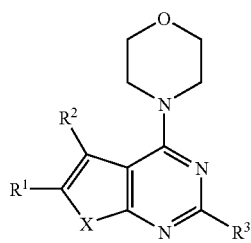

Ib and stereoisomers, geometric isomers, tautomers, and pharmaceutically acceptable salts thereof, wherein:

X is O or S;

$R^1$ is —C(=Y)NR$^{10}$R$^{11}$ where Y is O and R$^{10}$ and R$^{11}$ are independently selected from H and $C_1$-$C_{12}$ alkyl;

$R^2$ is selected from H, F, Cl, Br, I, CN, CF$_3$, —NO$_2$, —C(=Y)R$^{10}$, —C(=Y)OR$^{10}$, —C(=Y)NR$^{10}$R$^{11}$, —(CR$^{14}$R$^{15}$)$_m$NR$^{10}$R$^{11}$, —(CR$^{14}$R$^{15}$)$_n$OR$^{10}$, —CR$^{14}$R$^{15}$)$_t$—NR$^{12}$C(=O)(CR$^{14}$R$^{15}$)NR$^{10}$R$^{11}$, —NR$^{12}$C(=Y)R$^{10}$, —NR$^{12}$C(=Y)OR$^{10}$, —NR$^{12}$C(=Y)NR$^{10}$R$^{11}$, —NR$^{12}$SO$_2$R$^{10}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)

OR$^{11}$), SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl;

R$^3$ is fused bicyclic C$_4$-C$_{20}$ heterocyclyl or fused bicyclic C$_1$-C$_{20}$ heteroaryl;

R$^{10}$, R$^{11}$ and R$^{12}$ are independently H, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, or C$_1$-C$_{20}$ heteroaryl, or R$^{10}$ and R$^{11}$ together with the nitrogen to which they are attached optionally form a saturated, partially unsaturated or fully unsaturated C$_3$-C$_{20}$ heterocyclic ring optionally containing one or more additional ring atoms selected from N, O or S, wherein said heterocyclic ring is optionally substituted with one or more groups independently selected from oxo, (CH$_2$)$_m$OR$^{10}$, NR$^{10}$R$^{11}$, CF$_3$, F, Cl, Br, I, SO$_2$R$^{10}$, C(=O)R$^{10}$, NR$^{12}$C(=Y)R$^{11}$, NR$^{12}$S(O)$_2$R$^{11}$, C(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl and C$_1$-C$_{20}$ heteroaryl;

R$^{14}$ and R$^{15}$ are independently selected from H, C$_1$-C$_{12}$ alkyl, or —(CH$_2$)$_n$-aryl, or R$^{14}$ and R$^{15}$ together with the atoms to which they are attached form a saturated or partially unsaturated C$_3$-C$_{12}$ carbocyclic ring, where said alkyl, alkenyl, alkynyl, carbocyclyl, heterocyclyl, aryl, heteroaryl, fused bicyclic C$_4$-C$_{20}$ heterocyclyl, and fused bicyclic C$_1$-C$_{20}$ heteroaryl are optionally substituted with one or more groups independently selected from F, Cl, Br, I, CN, CF$_3$, —NO$_2$, oxo, R$^{10}$, —C(=Y)R$^{10}$, —C(=Y)OR$^{10}$, —C(=Y)NR$^{10}$R$^{11}$, —(CR$^{14}$R$^{15}$)$_n$NR$^{10}$R$^{11}$, —(CR$^{14}$R$^{15}$)$_n$OR$^{10}$, —NR$^{10}$R$^{11}$, —NR$^{12}$C(=Y)R$_{10}$, —NR$^{12}$C(=Y)OR$^{11}$, —NR$^{12}$C(=Y)NR$^{10}$R$^{11}$, —NR$^{12}$SO$_2$R$^{10}$, =NR$^{12}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, C$_1$-C$_{12}$ optionally substituted alkyl, C$_2$-C$_8$ optionally substituted alkenyl, C$_2$-C$_8$ optionally substituted alkynyl, C$_3$-C$_{12}$ optionally substituted carbocyclyl, C$_2$-C$_{20}$ optionally substituted heterocyclyl, C$_6$-C$_{20}$ optionally substituted aryl, C$_1$-C$_{20}$ optionally substituted heteroaryl, —(CR$^{14}$R$^{15}$)$_t$—NR$^{12}$C(=O)(CR$^{14}$R$^{15}$)NR$^{10}$R$^{11}$, and (CR$^{14}$R$^{15}$)$_t$—NR$^{10}$R$^{11}$;

Y is O, S, or NR$^{12}$;

m is 0, 1, 2, 3, 4, 5 or 6;

n is 1, 2, 3, 4, 5 or 6; and t is 2, 3, 4, 5 or 6.

10. A compound selected from Formula Ia and Formula Ib:

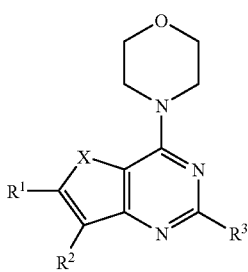

Ia

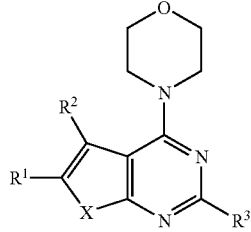

Ib and stereoisomers, geometric isomers, tautomers, and pharmaceutically acceptable salts thereof, wherein:

X is O or S;

R$^1$ is —C(=Y)NR$^{10}$R$^{11}$ where Y is O and R$^{10}$ and R$^{11}$ are independently selected from H, C$_3$-C$_{12}$ carbocyclyl, C$_2$-C$_{20}$ heterocyclyl, C$_6$-C$_{20}$ aryl, and C$_1$-C$_{20}$ heteroaryl;

R$^2$ is selected from H, F, Cl, Br, I, CN, CF$_3$, —NO$_2$, —C(=Y)R$^{10}$, —C(=Y)OR$^{10}$, —C(=Y)NR$^{10}$R$^{11}$, —(CR$^{14}$R$^{15}$)$_m$NR$^{10}$R$^{11}$, —(CR$^{14}$R$^{15}$)$_n$OR$^{10}$, —CR$^{14}$R$^{15}$)$_t$—NR$^{12}$C(=O)(CR$^{14}$R$^{15}$)NR$^{10}$R$^{11}$, —NR$^{12}$C(=Y)R$^{10}$, —NR$^{12}$C(=Y)OR$^{10}$, —NR$^{12}$C(=Y)NR$^{10}$R$^{11}$, —NR$^{12}$SO$_2$R$^{10}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)OR$^{11}$), SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl;

R$^3$ is fused bicyclic C$_4$-C$_{20}$ heterocyclyl or fused bicyclic C$_1$-C$_{20}$ heteroaryl;

R$^{10}$, R$^{11}$ and R$^{12}$ are independently H, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, or C$_1$-C$_{20}$ heteroaryl, or R$^{10}$ and R$^{11}$ together with the nitrogen to which they are attached optionally form a saturated, partially unsaturated or fully unsaturated C$_3$-C$_{20}$ heterocyclic ring optionally containing one or more additional ring atoms selected from N, O or S, wherein said heterocyclic ring is optionally substituted with one or more groups independently selected from oxo, (CH$_2$)$_m$OR$^{10}$, NR$^{10}$R$^{11}$, CF$_3$, F, Cl, Br, I, SO$_2$R$^{10}$, C(=O)R$^{10}$, NR$^{12}$C(=Y)R$^{11}$, NR$^{12}$S(O)$_2$R$^{11}$, C(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl and C$_1$-C$_{20}$ heteroaryl;

R$^{14}$ and R$^{15}$ are independently selected from H, C$_1$-C$_{12}$ alkyl, or —(CH$_2$)$_n$-aryl, or R$^{14}$ and R$^{15}$ together with the atoms to which they are attached form a saturated or partially unsaturated C$_3$-C$_{12}$ carbocyclic ring, where said alkyl, alkenyl, alkynyl, carbocyclyl, heterocyclyl, aryl, heteroaryl, fused bicyclic C$_4$-C$_{20}$ heterocyclyl, and fused bicyclic C$_1$-C$_{20}$ heteroaryl are optionally substituted with one or more groups independently selected from F, Cl, Br, I, CN, CF$_3$, —NO$_2$, oxo, R$^{10}$, —C(=Y)R$^{10}$, —C(=Y)OR$^{10}$, —C(=Y)NR$^{10}$R$^{11}$, —(CR$^{14}$R$^{15}$)$_n$NR$^{10}$R$^{11}$, —(CR$^{14}$R$^{15}$)$_n$OR$^{10}$, —NR$^{10}$R$^{11}$, —NR$^{12}$C(=Y)R$_{10}$, —NR$^{12}$C(=Y)OR$^{11}$, —NR$^{12}$C(=Y)NR$^{10}$R$^{11}$, —NR$^{12}$SO$_2$R$^{10}$, =NR$^{12}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, C$_1$-C$_{12}$ optionally substituted alkyl, C$_2$-C$_8$ optionally substituted alkenyl, C$_2$-C$_8$ optionally substituted alkynyl, C$_3$-C$_{12}$ optionally substituted carbocyclyl, C$_2$-C$_{20}$ optionally substituted heterocyclyl, C$_6$-C$_{20}$ optionally substituted aryl, C$_1$-C$_{20}$ optionally substituted heteroaryl, —(CR$^{14}$R$^{15}$)$_t$—NR$^{12}$C(=O)(CR$^{14}$R$^{15}$)NR$^{10}$R$^{11}$, and (CR$^{14}$R$^{15}$)$_t$—NR$^{10}$R$^{11}$;

Y is O, S, or NR$^{12}$;

m is 0, 1, 2, 3, 4, 5 or 6;

n is 1, 2, 3, 4, 5 or 6; and t is 2, 3, 4, 5 or 6.

11. A compound selected from Formula Ia and Formula Ib:

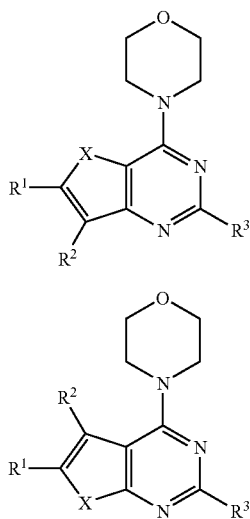

Ia

Ib and stereoisomers, geometric isomers, tautomers, and pharmaceutically acceptable salts thereof, wherein:

X is O or S;

R$^1$ is —NHR$^{12}$ where R$^{12}$ is C$_3$-C$_{12}$ carbocyclyl, C$_2$-C$_{20}$ heterocyclyl, C$_6$-C$_{20}$ aryl, or C$_1$-C$_{20}$ heteroaryl;

R$^2$ is selected from H, F, Cl, Br, I, CN, CF$_3$, —NO$_2$, —C(=Y)R$^{10}$, —C(=Y)OR$^{10}$, —C(=Y)NR$^{10}$R$^{11}$, —(CR$^{14}$R$^{15}$)$_m$NR$^{10}$R$^{11}$, —(CR$^{14}$R$^{15}$)$_n$OR$^{10}$, —CR$^{14}$R$^{15}$)$_t$—NR$^{12}$C(=O)(CR$^{14}$R$^{15}$)NR$^{10}$R$^{11}$, —NR$^{12}$C(=Y)R$^{10}$, —NR$^{12}$C(=Y)OR$^{10}$, —NR$^{12}$C(=Y)NR$^{10}$R$^{11}$, —NR$^{12}$SO$_2$R$^{10}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl;

R$^3$ is fused bicyclic C$_4$-C$_{20}$ heterocyclyl or fused bicyclic C$_1$-C$_{20}$ heteroaryl;

R$^{10}$, R$^{11}$ and R$^{12}$ are independently H, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, or C$_1$-C$_{20}$ heteroaryl, or R$^{10}$ and R$^{11}$ together with the nitrogen to which they are attached optionally form a saturated, partially unsaturated or fully unsaturated C$_3$-C$_{20}$ heterocyclic ring optionally containing one or more additional ring atoms selected from N, O or S, wherein said heterocyclic ring is optionally substituted with one or more groups independently selected from oxo, (CH$_2$)$_m$OR$^{10}$, NR$^{10}$R$^{11}$, CF$_3$, F, Cl, Br, I, SO$_2$R$^{10}$, C(=O)R$^{10}$, NR$^{12}$C(=Y)R$^{11}$, NR$^{12}$S(O)$_2$R$^{11}$, C(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl and C$_1$-C$_{20}$ heteroaryl;

R$^{14}$ and R$^{15}$ are independently selected from H, C$_1$-C$_{12}$ alkyl, or —(CH$_2$)$_n$-aryl, or R$^{14}$ and R$^{15}$ together with the atoms to which they are attached form a saturated or partially unsaturated C$_3$-C$_{12}$ carbocyclic ring, where said alkyl, alkenyl, alkynyl, carbocyclyl, heterocyclyl, aryl, heteroaryl, fused bicyclic C$_4$-C$_{20}$ heterocyclyl, and fused bicyclic C$_1$-C$_{20}$ heteroaryl are optionally substituted with one or more groups independently selected from F, Cl, Br, I, CN, CF$_3$, —NO$_2$, oxo, R$^{10}$, —C(=Y)R$^{10}$, —C(=Y)OR$^{10}$, —C(=Y)NR$^{10}$R$^{11}$, —(CR$^{14}$R$^{15}$)$_n$NR$^{10}$R$^{11}$, —(CR$^{14}$R$^{15}$)$_n$OR$^{10}$, —NR$^{10}$R$^{11}$, —NR$^{12}$C(=Y)R$_{10}$, —NR$^{12}$C(=Y)OR$^{11}$, —NR$^{12}$C(=Y)NR$^{10}$R$^{11}$, —NR$^{12}$SO$_2$R$^{10}$, =NR$^{12}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, C$_1$-C$_{12}$ optionally substituted alkyl, C$_2$-C$_8$ optionally substituted alkenyl, C$_2$-C$_8$ optionally substituted alkynyl, C$_3$-C$_{12}$ optionally substituted carbocyclyl, C$_2$-C$_{20}$ optionally substituted heterocyclyl, C$_6$-C$_{20}$ optionally substituted aryl, C$_1$-C$_{20}$ optionally substituted heteroaryl, —(CR$^{14}$R$^{15}$)$_t$—NR$^{12}$C(=O)(CR$^{14}$R$^{15}$)NR$^{10}$R$^{11}$, and (CR$^{14}$R$^{15}$)$_t$—NR$^{10}$R$^{11}$;

Y is O, S, or NR$^{12}$;

m is 0, 1, 2, 3, 4, 5 or 6;

n is 1, 2, 3, 4, 5 or 6; and t is 2, 3, 4, 5 or 6.

12. The compound of claim 11 wherein R$^{12}$ is phenyl or 4-pyridyl.

13. A compound selected from Formula Ia and Formula Ib:

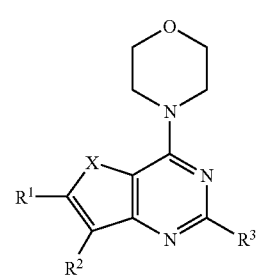

Ia

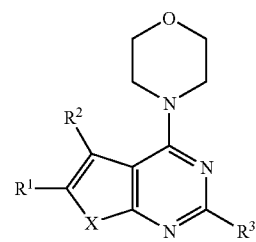

Ib and stereoisomers, geometric isomers, tautomers, and pharmaceutically acceptable salts thereof, wherein:

X is O or S;

$R^1$ is —$NR^{12}C(=Y)R^{11}$ where Y is O, $R^{12}$ is H or $C_1$-$C_{12}$ alkyl, and $R^{11}$ is $C_1$-$C_{12}$ alkyl, $C_3$-$C_{12}$ carbocyclyl, $C_2$-$C_{20}$ heterocyclyl, $C_6$-$C_{20}$ aryl, or $C_1$-$C_{20}$ heteroaryl;

$R^2$ is selected from H, F, Cl, Br, I, CN, $CF_3$, —$NO_2$, —$C(=Y)R^{10}$, —$C(=Y)OR^{10}$, —$C(=Y)NR^{10}R^{11}$, —$(CR^{14}R^{15})_mNR^{10}R^{11}$, —$(CR^{14}R^{15})_nOR^{10}$, —$CR^{14}R^{15})_t$—$NR^{12}C(=O)(CR^{14}R^{15})NR^{10}R^{11}$, —$NR^{12}C(=Y)R^{10}$, —$NR^{12}C(=Y)OR^{10}$, —$NR^{12}C(=Y)NR^{10}R^{11}$, —$NR^{12}SO_2R^{10}$, $OR^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})OR^{11})$, $SR^{10}$, —$S(O)R^{10}$, —$S(O)_2R^{10}$, —$S(O)_2NR^{10}R^{11}$, —$S(O)(OR^{10})$, —$S(O)_2(OR^{10})$, —$SC(=Y)R^{10}$, —$SC(=Y)OR^{10}$, —$SC(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

$R^3$ is fused bicyclic $C_4$-$C_{20}$ heterocyclyl or fused bicyclic $C_1$-$C_{20}$ heteroaryl;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, $(CH_2)_mOR^{10}$, $NR^{10}R^{11}$, $CF_3$, F, Cl, Br, I, $SO_2R^{10}$, $C(=O)R^{10}$, $NR^{12}C(=Y)R^{11}$, $NR^{12}S(O)_2R^{11}$, $C(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or —$(CH_2)_n$-aryl, or $R^{14}$ and $R^{15}$ together with the atoms to which they are attached form a saturated or partially unsaturated $C_3$-$C_{12}$ carbocyclic ring, where said alkyl, alkenyl, alkynyl, carbocyclyl, heterocyclyl, aryl, heteroaryl, fused bicyclic $C_4$-$C_{20}$ heterocyclyl, and fused bicyclic $C_1$-$C_{20}$ heteroaryl are optionally substituted with one or more groups independently selected from F, Cl, Br, I, CN, $CF_3$, —$NO_2$, oxo, $R^{10}$, —$C(=Y)R^{10}$, —$C(=Y)OR^{10}$, —$C(=Y)NR^{10}R^{11}$, —$(CR^{14}R^{15})_nNR^{10}R^{11}$, —$(CR^{14}R^{15})_nOR^{10}$, —$NR^{10}R^{11}$, —$NR^{12}C(=Y)R_{10}$, —$NR^{12}C(=Y)OR^{11}$, —$NR^{12}C(=Y)NR^{10}R^{11}$, —$NR^{12}SO_2R^{10}$, =$NR^{12}$, $OR^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})(OR^{11})$, $SR^{10}$, —$S(O)R^{10}$, —$S(O)_2R^{10}$, —$S(O)_2NR^{10}R^{11}$, —$S(O)(OR^{10})$, —$S(O)_2(OR^{10})$, —$SC(=Y)R^{10}$, —$SC(=Y)OR^{10}$, —$SC(=Y)NR^{10}R^{11}$, $C_1$-$C_{12}$ optionally substituted alkyl, $C_2$-$C_8$ optionally substituted alkenyl, $C_2$,-$C_8$ optionally substituted alkynyl, $C_3$-$C_{12}$ optionally substituted carbocyclyl, $C_2$-$C_{20}$ optionally substituted heterocyclyl, $C_6$-$C_{20}$ optionally substituted aryl, $C_1$-$C_{20}$ optionally substituted heteroaryl, —$(CR^{14}R^{15})_t$—$NR^{12}C(=O)(CR^{14}R^{15})NR^{10}R^{11}$, and $(CR^{14}R^{15})_t$—$NR^{10}R^{11}$;

Y is O, S, or $NR^{12}$;

m is 0, 1, 2, 3, 4, 5 or 6;

n is 1, 2, 3, 4, 5 or 6; and t is 2, 3, 4, 5 or 6.

14. The compound of claim 13 wherein $R^{11}$ is selected from methyl, ethyl, propyl, isopropyl, isobutyl, 2,2-dimethylpropyl, and tert-butyl.

15. The compound of claim 13 wherein $R^{11}$ is selected from cyclopropyl, cyclobutyl, cyclopentyl, and cyclohexyl.

16. A compound selected from Formula Ia and Formula Ib:

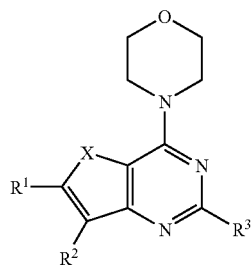

Ia

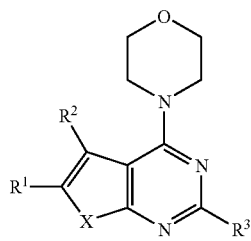

Ib and stereoisomers, geometric isomers, tautomers, and pharmaceutically acceptable salts thereof, wherein:

X is O or S;

$R^1$ is —$NR^{12}S(O)_2R^{10}$ where $R^{12}$ is H or $C_1$-$C_{12}$ alkyl, and $R^{10}$ is $C_1$-$C_{12}$ alkyl, $C_3$-$C_{12}$ carbocyclyl, $C_2$-$C_{20}$ heterocyclyl, $C_6$-$C_{20}$ aryl, or $C_1$-$C_{20}$ heteroaryl;

$R^2$ is selected from H, F, Cl, Br, I, CN, $CF_3$, —$NO_2$, —$C(=Y)R^{10}$, —$C(=Y)OR^{10}$, —$C(=Y)NR^{10}R^{11}$, —$(CR^{14}R^{15})_mNR^{10}R^{11}$, —$(CR^{14}R^{15})_nOR^{10}$, —$CR^{14}R^{15})_t$—$NR^{12}C(=O)(CR^{14}R^{15})NR^{10}R^{11}$, —$NR^{12}C(=Y)R^{10}$, —$NR^{12}C(=Y)OR^{10}$, —$NR^{12}C(=Y)NR^{10}R^{11}$, —$NR^{12}SO_2R^{10}$, $OR^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})OR^{11})$, $SR^{10}$, —$S(O)R^{10}$, —$S(O)_2R^{10}$, —$S(O)_2NR^{10}R^{11}$, —$S(O)(OR^{10})$, —$S(O)_2(OR^{10})$, —$SC(=Y)R^{10}$, —$SC(=Y)OR^{10}$, —$SC(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

$R^3$ is fused bicyclic $C_4$-$C_{20}$ heterocyclyl or fused bicyclic $C_1$-$C_{20}$ heteroaryl;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, $(CH_2)_mOR^{10}$, $NR^{10}R^{11}$, $CF_3$, F, Cl, Br, I, $SO_2R^{10}$, $C(=O)R^{10}$, $NR^{12}C(=Y)R^{11}$, $NR^{12}S(O)_2R^{11}$, $C(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or —$(CH_2)_n$-aryl, or $R^{14}$ and $R^{15}$ together with the atoms to which they are attached form a saturated or partially unsaturated $C_3$-$C_{12}$ carbocyclic ring, where said alkyl, alkenyl, alkynyl, carbocyclyl, heterocyclyl, aryl, heteroaryl, fused bicyclic $C_4$-$C_{20}$ heterocyclyl, and fused bicyclic $C_1$-$C_{20}$ heteroaryl are optionally substituted with one or more groups independently selected from F, Cl, Br, I, CN, $CF_3$, $-NO_2$, oxo, $R^{10}$, $-C(=Y)R^{10}$, $-C(=Y)OR^{10}$, $-C(=Y)NR^{10}R^{11}$, $-(CR^{14}R^{15})_nNR^{10}R^{11}$, $-(CR^{14}R^{15})_nOR^{10}$, $-NR^{10}R^{11}$, $-NR^{12}C(=Y)R_{10}$, $-NR^{12}C(=Y)OR^{11}$, $-NR^{12}C(=Y)NR^{10}R^{11}$, $-NR^{12}SO_2R^{10}$, $=NR^{12}$, $OR^{10}$, $-OC(=Y)R^{10}$, $-OC(=Y)OR^{10}$, $-OC(=Y)NR^{10}R^{11}$, $-OS(O)_2(OR^{10})$, $-OP(=Y)(OR^{10})(OR^{11})$, $-OP(OR^{10})(OR^{11})$, $SR^{10}$, $-S(O)R^{10}$, $-S(O)_2R^{10}$, $-S(O)_2NR^{10}R^{11}$, $-S(O)(OR^{10})$, $-S(O)_2(OR^{10})$, $-SC(=Y)R^{10}$, $-SC(=Y)OR^{10}$, $-SC(=Y)NR^{10}R^{11}$, $C_1$-$C_{12}$ optionally substituted alkyl, $C_2$-$C_8$ optionally substituted alkenyl, $C_2$-$C_8$ optionally substituted alkynyl, $C_3$-$C_{12}$ optionally substituted carbocyclyl, $C_2$-$C_{20}$ optionally substituted heterocyclyl, $C_6$-$C_{20}$ optionally substituted aryl, $C_1$-$C_{20}$ optionally substituted heteroaryl, $-(CR^{14}R^{15})_t-NR^{12}C(=O)(CR^{14}R^{15})NR^{10}R^{11}$, and $(CR^{14}R^{15})_t-NR^{10}R^{11}$;

Y is O, S, or $NR^{12}$;

m is 0, 1, 2, 3, 4, 5 or 6;

n is 1, 2, 3, 4, 5 or 6; and t is 2, 3, 4, 5 or 6.

17. A compound selected from Formula Ia and Formula Ib:

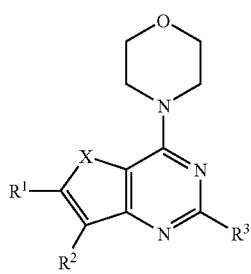

Ia

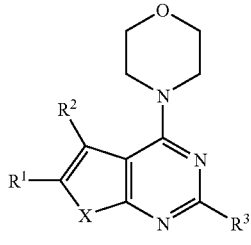

Ib and stereoisomers, geometric isomers, tautomers, and pharmaceutically acceptable salts thereof, wherein:

X is O or S;

$R^1$ is $S(O)_2NR^{10}R^{11}$ where $R^{10}$ and $R^{11}$ together with the nitrogen to which they are attached form a $C_2$-$C_{20}$ heterocyclic ring selected from morpholinyl, piperazinyl, and pyrrolidinyl;

$R^2$ is selected from H, F, Cl, Br, I, CN, $CF_3$, $-NO_2$, $-C(=Y)R^{10}$, $-C(=Y)OR^{10}$, $-C(=Y)NR^{10}R^{11}$, $-(CR^{14}R^{15})_mNR^{10}R^{11}$, $-(CR^{14}R^{15})_nOR^{10}$, $-CR^{14}R^{15})_t-NR^{12}C(=O)(CR^{14}R^{15})NR^{10}R^{11}$, $-NR^{12}C(=Y)R^{10}$, $-NR^{12}C(=Y)OR^{10}$, $-NR^{12}C(=Y)NR^{10}R^{11}$, $-NR^{12}SO_2R^{10}$, $OR^{10}$, $-OC(=Y)R^{10}$, $-OC(=Y)OR^{10}$, $-OC(=Y)NR^{10}R^{11}$, $-OS(O)_2(OR^{10})$, $-OP(=Y)(OR^{10})(OR^{11})$, $-OP(OR^{10})(OR^{11})$, $SR^{10}$, $-S(O)R^{10}$, $-S(O)_2R^{10}$, $-S(O)_2NR^{10}R^{11}$, $-S(O)(OR^{10})$, $-S(O)_2(OR^{10})$, $-SC(=Y)R^{10}$, $-SC(=Y)OR^{10}$, $-SC(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

$R^3$ is fused bicyclic $C_4$-$C_{20}$ heterocyclyl or fused bicyclic $C_1$-$C_{20}$ heteroaryl;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, $(CH_2)_mOR^{10}$, $NR^{10}R^{11}$, $CF_3$, F, Cl, Br, I, $SO_2R^{10}$, $C(=O)R^{10}$, $NR^{12}C(=Y)R^{11}$, $NR^{12}S(O)_2R^{11}$, $C(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or $-(CH_2)_n$-aryl, or $R^{14}$ and $R^{15}$ together with the atoms to which they are attached form a saturated or partially unsaturated $C_3$-$C_{12}$ carbocyclic ring, where said alkyl, alkenyl, alkynyl, carbocyclyl, heterocyclyl, aryl, heteroaryl, fused bicyclic $C_4$-$C_{20}$ heterocyclyl, and fused bicyclic $C_1$-$C_{20}$ heteroaryl are optionally substituted with one or more groups independently selected from F, Cl, Br, I, CN, $CF_3$, $-NO_2$, oxo, $R^{10}$, $-C(=Y)R^{10}$, $-C(=Y)OR^{10}$, $-C(=Y)NR^{10}R^{11}$, $-(CR^{14}R^{15})_nNR^{10}R^{11}$, $-(CR^{14}R^{15})_nOR^{10}$, $-NR^{10}R^{11}$, $-NR^{12}C(=Y)R_{10}$, $-NR^{12}C(=Y)OR^{11}$, $-NR^{12}C(=Y)NR^{10}R^{11}$, $-NR^{12}SO_2R^{10}$, $=NR^{12}$, $OR^{10}$, $-OC(=Y)R^{10}$, $-OC(=Y)OR^{10}$, $-OC(=Y)NR^{10}R^{11}$, $-OS(O)_2(OR^{10})$, $-OP(=Y)(OR^{10})(OR^{11})$, $-OP(OR^{10})(OR^{11})$, $SR^{10}$, $-S(O)R^{10}$, $-S(O)_2R^{10}$, $-S(O)_2NR^{10}R^{11}$, $-S(O)(OR^{10})$, $-S(O)_2(OR^{10})$, $-SC(=Y)R^{10}$, $-SC(=Y)OR^{10}$, $-SC(=Y)NR^{10}R^{11}$, $C_1$-$C_{12}$ optionally substituted alkyl, $C_2$-$C_8$ optionally substituted alkenyl, $C_2$-$C_8$ optionally substituted alkynyl, $C_3$-$C_{12}$ optionally substituted carbocyclyl, $C_2$-$C_{20}$ optionally substituted heterocyclyl, $C_6$-$C_{20}$ optionally substituted aryl, $C_1$-$C_{20}$ optionally substituted heteroaryl, $-(CR^{14}R^{15})_t-NR^{12}C(=O)(CR^{14}R^{15})NR^{10}R^{11}$, and $(CR^{14}R^{15})_t-NR^{10}R^{11}$;

Y is O, S, or $NR^{12}$;

m is 0, 1, 2, 3, 4, 5 or 6;

n is 1, 2, 3, 4, 5 or 6; and t is 2, 3, 4, 5 or 6.

18. A compound selected from Formula Ia and Formula Ib:

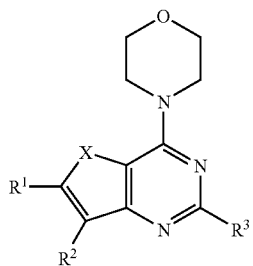

Ia

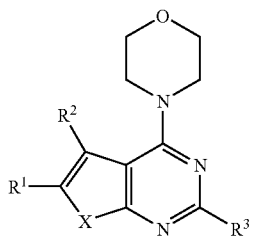

Ib and stereoisomers, geometric isomers, tautomers, and pharmaceutically acceptable salts thereof, wherein:

X is O or S;

$R^1$ is $S(O)_2NR^{10}R^{11}$ where $R^{10}$ and $R^{11}$ are independently selected from H and $C_1$-$C_{12}$ alkyl;

$R^2$ is selected from H, F, Cl, Br, I, CN, $CF_3$, $-NO_2$, $-C(=Y)R^{10}$, $-C(=Y)OR^{10}$, $-C(=Y)NR^{10}R^{11}$, $-(CR^{14}R^{15})_mNR^{10}R^{11}$, $-(CR^{14}R^{15})_nOR^{10}$, $-CR^{14}R^{15})_t-NR^{12}C(=O)(CR^{14}R^{15})NR^{10}R^{11}$, $-NR^{12}C(=Y)R^{10}$, $-NR^{12}C(=Y)OR^{10}$, $-NR^{12}C(=Y)NR^{10}R^{11}$, $-NR^{12}SO_2R^{10}$, $OR^{10}$, $-OC(=Y)R^{10}$, $-OC(=Y)OR^{10}$, $-OC(=Y)NR^{10}R^{11}$, $-OS(O)_2(OR^{10})$, $-OP(=Y)(OR^{10})(OR^{11})$, $-OP(OR^{10})(OR^{11})$, $SR^{10}$, $-S(O)R^{10}$, $-S(O)_2R^{10}$, $-S(O)_2NR^{10}R^{11}$, $-S(O)(OR^{10})$, $-S(O)_2(OR^{10})$, $-SC(=Y)R^{10}$, $-SC(=Y)OR^{10}$, $-SC(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

$R^3$ is fused bicyclic $C_4$-$C_{20}$ heterocyclyl or fused bicyclic $C_1$-$C_{20}$ heteroaryl;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, $(CH_2)_mOR^{10}$, $NR^{10}R^{11}$, $CF_3$, F, Cl, Br, I, $SO_2R^{10}$, $C(=O)R^{10}$, $NR^{12}C(=Y)R^{11}$, $NR^{12}S(O)_2R^{11}$, $C(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or $-(CH_2)_n$-aryl, or $R^{14}$ and $R^{15}$ together with the atoms to which they are attached form a saturated or partially unsaturated $C_3$-$C_{12}$ carbocyclic ring, where said alkyl, alkenyl, alkynyl, carbocyclyl, heterocyclyl, aryl, heteroaryl, fused bicyclic $C_4$-$C_{20}$ heterocyclyl, and fused bicyclic $C_1$-$C_{20}$ heteroaryl are optionally substituted with one or more groups independently selected from F, Cl, Br, I, CN, $CF_3$, $-NO_2$, oxo, $R^{10}$, $-C(=Y)R^{10}$, $-C(=Y)OR^{10}$, $-C(=Y)NR^{10}R^{11}$, $-(CR^{14}R^{15})_nNR^{10}R^{11}$, $-(CR^{14}R^{15})_nOR^{10}$, $-NR^{10}R^{11}$, $-NR^{12}C(=Y)R_{10}$, $-NR^{12}C(=Y)OR^{11}$, $-NR^{12}C(=Y)NR^{10}R^{11}$, $-NR^{12}SO_2R^{10}$, $=NR^{12}$, $OR^{10}$, $-OC(=Y)R^{10}$, $-OC(=Y)OR^{10}$, $-OC(=Y)NR^{10}R^{11}$, $-OS(O)_2(OR^{10})$, $-OP(=Y)(OR^{10})(OR^{11})$, $-OP(OR^{10})(OR^{11})$, $SR^{10}$, $-S(O)R^{10}$, $-S(O)_2R^{10}$, $-S(O)_2NR^{10}R^{11}$, $-S(O)(OR^{10})$, $-S(O)_2(OR^{10})$, $-SC(=Y)R^{10}$, $-SC(=Y)OR^{10}$, $-SC(=Y)NR^{10}R^{11}$, $C_1$-$C_{12}$ optionally substituted alkyl, $C_2$-$C_8$ optionally substituted alkenyl, $C_2$-$C_8$ optionally substituted alkynyl, $C_3$-$C_{12}$ optionally substituted carbocyclyl, $C_2$-$C_{20}$ optionally substituted heterocyclyl, $C_6$-$C_{20}$ optionally substituted aryl, $C_1$-$C_{20}$ optionally substituted heteroaryl, $-(CR^{14}R^{15})_t-NR^{12}C(=O)(CR^{14}R^{15})NR^{10}R^{11}$, and $(CR^{14}R^{15})_t-NR^{10}R^{11}$;

Y is O, S, or $NR^{12}$;

m is 0, 1, 2, 3, 4, 5 or 6;

n is 1, 2, 3, 4, 5 or 6; and t is 2, 3, 4, 5 or 6.

19. The compound of claim 18 wherein $R^{10}$ and $R^{11}$ are independently selected from H, substituted ethyl, and substituted propyl.

20. A compound selected from Formula Ia and Formula Ib:

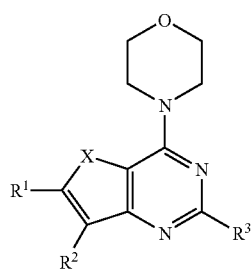

Ia

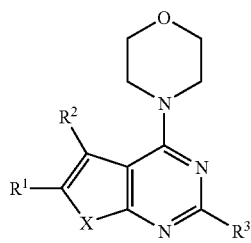

Ib and stereoisomers, geometric isomers, tautomers, and pharmaceutically acceptable salts thereof, wherein:

X is O or S;

$R^1$ is $C_2$-$C_{12}$ alkyl;

$R^2$ is selected from H, F, Cl, Br, I, CN, $CF_3$, $-NO_2$, $-C(=Y)R^{10}$, $-C(=Y)OR^{10}$, $-C(=Y)NR^{10}R^{11}$, $-(CR^{14}R^{15})_mNR^{10}R^{11}$, $-(CR^{14}R^{15})_nOR^{10}$, $-CR^{14}R^{15})_t-NR^{12}C(=O)(CR^{14}R^{15})NR^{10}R^{11}$, $-NR^{12}C(=Y)R^{10}$, $-NR^{12}C(=Y)OR^{10}$, $-NR^{12}C(=Y)NR^{10}R^{11}$, $-NR^{12}SO_2R^{10}$, $OR^{10}$, $-OC(=Y)R^{10}$, $-OC(=Y)OR^{10}$, $-OC(=Y)NR^{10}R^{11}$, $-OS(O)_2(OR^{10})$, $-OP(=Y)(OR^{10})(OR^{11})$, $OR^{11})$, $SR^{10}$, $-S(O)R^{10}$, $-S(O)_2R^{10}$, $-S(O)_2NR^{10}R^{11}$, $-S(O)(OR^{10})$, $-S(O)_2(OR^{10})$, $-SC(=Y)R^{10}$, $-SC(=Y)OR^{10}$, $-SC(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

$R^3$ is fused bicyclic $C_4$-$C_{20}$ heterocyclyl or fused bicyclic $C_1$-$C_{20}$ heteroaryl;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, $(CH_2)_m OR^{10}$, $NR^{10}R^{11}$, $CF_3$, F, Cl, Br, I, $SO_2R^{10}$, $C(=O)R^{10}$, $NR^{12}C(=Y)R^{11}$, $NR^{12}S(O)_2R^{11}$, $C(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or —$(CH_2)_n$-aryl, or $R^{14}$ and $R^{15}$ together with the atoms to which they are attached form a saturated or partially unsaturated $C_3$-$C_{12}$ carbocyclic ring, where said alkyl, alkenyl, alkynyl, carbocyclyl, heterocyclyl, aryl, heteroaryl, fused bicyclic $C_4$-$C_{20}$ heterocyclyl, and fused bicyclic $C_1$-$C_{20}$ heteroaryl are optionally substituted with one or more groups independently selected from F, Cl, Br, I, CN, $CF_3$, —$NO_2$, oxo, $R^{10}$, —$C(=Y)R^{10}$, —$C(=Y)OR^{10}$, —$C(=Y)NR^{10}R^{11}$, —$(CR^{14}R^{15})_n NR^{10}R^{11}$, —$(CR^{14}R^{15})_n OR^{10}$, —$NR^{10}R^{11}$, —$NR^{12}C(=Y)R_{10}$, —$NR^{12}C(=Y)OR^{11}$, —$NR^{12}C(=Y)NR^{10}R^{11}$, —$NR^{12}SO_2R^{10}$, =$NR^{12}$, $OR^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})(OR^{11})$, $SR^{10}$, —$S(O)R^{10}$, —$S(O)_2R^{10}$, —$S(O)_2NR^{10}R^{11}$, —$S(O)(OR^{10})$, —$S(O)_2(OR^{10})$, —$SC(=Y)R^{10}$, —$SC(=Y)OR^{10}$, —$SC(=Y)NR^{10}R^{11}$, $C_1$-$C_{12}$ optionally substituted alkyl, $C_2$-$C_8$ optionally substituted alkenyl, $C_2$-$C_8$ optionally substituted alkynyl, $C_3$-$C_{12}$ optionally substituted carbocyclyl, $C_2$-$C_{20}$ optionally substituted heterocyclyl, $C_6$-$C_{20}$ optionally substituted aryl, $C_1$-$C_{20}$ optionally substituted heteroaryl, —$(CR^{14}R^{15})_t$—$NR^{12}C(=O)(CR^{14}R^{15})NR^{10}R^{11}$, and $(CR^{14}R^{15})_t$—$NR^{10}R^{11}$;

Y is O, S, or $NR^{12}$;

m is 0, 1, 2, 3, 4, 5 or 6;

n is 1, 2, 3, 4, 5 or 6; and t is 2, 3, 4, 5 or 6.

21. A compound selected from Formula Ia and Formula Ib:

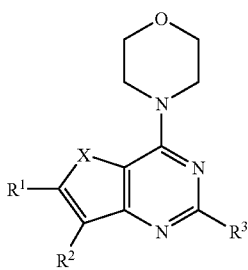

Ia

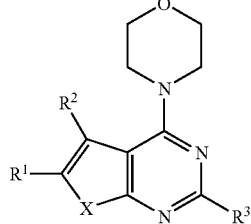

Ib and stereoisomers, geometric isomers, tautomers, and pharmaceutically acceptable salts thereof, wherein:

X is O or S;

$R^1$ is $C_2$-$C_8$ alkenyl;

$R^2$ is selected from H, F, Cl, Br, I, CN, $CF_3$, —$NO_2$, —$C(=Y)R^{10}$, —$C(=Y)OR^{10}$, —$C(=Y)NR^{10}R^{11}$, —$(CR^{14}R^{15})_m NR^{10}R^{11}$, —$(CR^{14}R^{15})_n OR^{10}$, —$CR^{14}R^{15})_t$—$NR^{12}C(=O)(CR^{14}R^{15})NR^{10}R^{11}$, —$NR^{12}C(=Y)R^{10}$, —$NR^{12}C(=Y)OR^{10}$, —$NR^{12}C(=Y)NR^{10}R^{11}$, —$NR^{12}SO_2R^{10}$, $OR^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})(OR^{11})$, $SR^{10}$, —$S(O)R^{10}$, —$S(O)_2R^{10}$, —$S(O)_2NR^{10}R^{11}$, —$S(O)(OR^{10})$, —$S(O)_2(OR^{10})$, —$SC(=Y)R^{10}$, —$SC(=Y)OR^{10}$, —$SC(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

$R^3$ is fused bicyclic $C_4$-$C_{20}$ heterocyclyl or fused bicyclic $C_1$-$C_{20}$ heteroaryl;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, $(CH_2)_m OR^{10}$, $NR^{10}R^{11}$, $CF_3$, F, Cl, Br, I, $SO_2R^{10}$, $C(=O)R^{10}$, $NR^{12}C(=Y)R^{11}$, $NR^{12}S(O)_2R^{11}$, $C(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or —$(CH_2)_n$-aryl, or $R^{14}$ and $R^{15}$ together with the atoms to which they are attached form a saturated or partially unsaturated $C_3$-$C_{12}$ carbocyclic ring, where said alkyl, alkenyl, alkynyl, carbocyclyl, heterocyclyl, aryl, heteroaryl, fused bicyclic $C_4$-$C_{20}$ heterocyclyl, and fused bicyclic $C_1$-$C_{20}$ heteroaryl are optionally substituted with one or more groups independently selected from F, Cl, Br, I, CN, $CF_3$, —$NO_2$, oxo, $R^{10}$, —$C(=Y)R^{10}$, —$C(=Y)OR^{10}$, —$C(=Y)NR^{10}R^{11}$, —$(CR^{14}R^{15})_n NR^{10}R^{11}$, —$(CR^{14}R^{15})_n OR^{10}$, —$NR^{10}R^{11}$, —$NR^{12}C(=Y)R_{10}$, —$NR^{12}C(=Y)OR^{11}$, —$NR^{12}C(=Y)NR^{10}R^{11}$, —$NR^{12}SO_2R^{10}$, =$NR^{12}$, $OR^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})(OR^{11})$, $SR^{10}$, —$S(O)R^{10}$, —$S(O)_2R^{10}$, —$S(O)_2NR^{10}R^{11}$, —$S(O)(OR^{10})$, —$S(O)_2(OR^{10})$, —$SC(=Y)R^{10}$, —$SC(=Y)OR^{10}$, —$SC(=Y)NR^{10}R^{11}$, $C_1$-$C_{12}$ optionally substituted alkyl, $C_2$-$C_8$ optionally substituted alkenyl, $C_2$-$C_8$ optionally substituted alkynyl, $C_3$-$C_{12}$ optionally substituted carbocyclyl, $C_2$-$C_{20}$ optionally substituted heterocyclyl, $C_6$-$C_{20}$ optionally substituted aryl, $C_1$-$C_{20}$ optionally substituted heteroaryl, —$(CR^{14}R^{15})_t$—$NR^{12}C(=O)(CR^{14}R^{15})NR^{10}R^{11}$, and $(CR^{14}R^{15})_t$—$NR^{10}R^{11}$;

Y is O, S, or $NR^{12}$;

m is 0, 1, 2, 3, 4, 5 or 6;

n is 1, 2, 3, 4, 5 or 6; and t is 2, 3, 4, 5 or 6.

22. A compound selected from Formula Ia and Formula Ib:

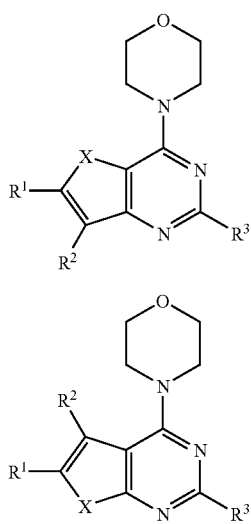

and stereoisomers, geometric isomers, tautomers, and pharmaceutically acceptable salts thereof, wherein:

X is O or S;

$R^1$ is $C_2$-$C_8$ alkenyl;

$R^2$ is selected from H, F, Cl, Br, I, CN, $CF_3$, —$NO_2$, —$C(=Y)R^{10}$, —$C(=Y)OR^{10}$, —$C(=Y)NR^{10}R^{11}$, —$(CR^{14}R^{15})_mNR^{10}R^{11}$, —$(CR^{14}R^{15})_nOR^{10}$, —$CR^{14}R^{15})_t$—$NR^{12}C(=O)(CR^{14}R^{15})NR^{10}R^{11}$, —$NR^{12}C(=Y)R^{10}$, —$NR^{12}C(=Y)OR^{10}$, —$NR^{12}C(=Y)NR^{10}R^{11}$, —$NR^{12}SO_2R^{10}$, $OR^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})OR^{11})$, $SR^{10}$, —$S(O)R^{10}$, —$S(O)_2R^{10}$, —$S(O)_2NR^{10}R^{11}$, —$S(O)(OR^{10})$, —$S(O)_2(OR^{10})$, —$SC(=Y)R^{10}$, —$SC(=Y)OR^{10}$, —$SC(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

$R^3$ is fused bicyclic $C_4$-$C_{20}$ heterocyclyl or fused bicyclic $C_1$-$C_{20}$ heteroaryl;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, $(CH_2)_mOR^{10}$, $NR^{10}R^{11}$, $CF_3$, F, Cl, Br, I, $SO_2R^{10}$, $C(=O)R^{10}$, $NR^{12}C(=Y)R^{11}$, $NR^{12}S(O)_2R^{11}$, $C(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or —$(CH_2)_n$-aryl, or $R^{14}$ and $R^{15}$ together with the atoms to which they are attached form a saturated or partially unsaturated $C_3$-$C_{12}$ carbocyclic ring, where said alkyl, alkenyl, alkynyl, carbocyclyl, heterocyclyl, aryl, heteroaryl, fused bicyclic $C_4$-$C_{20}$ heterocyclyl, and fused bicyclic $C_1$-$C_{20}$ heteroaryl are optionally substituted with one or more groups independently selected from F, Cl, Br, I, CN, $CF_3$, —$NO_2$, oxo, $R^{10}$, —$C(=Y)R^{10}$, —$C(=Y)OR^{10}$, —$C(=Y)NR^{10}R^{11}$, —$(CR^{14}R^{15})_nNR^{10}R^{11}$, —$(CR^{14}R^{15})_nOR^{10}$, —$NR^{10}R^{11}$, —$NR^{12}C(=Y)R_{10}$, —$NR^{12}C(=Y)OR^{11}$, —$NR^{12}C(=Y)NR^{10}R^{11}$, —$NR^{12}SO_2R^{10}$, =$NR^{12}$, $OR^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})(OR^{11})$, $SR^{10}$, —$S(O)R^{10}$, —$S(O)_2R^{10}$, —$S(O)_2NR^{10}R^{11}$, —$S(O)(OR^{10})$, —$S(O)_2(OR^{10})$, —$SC(=Y)R^{10}$, —$SC(=Y)OR^{10}$, —$SC(=Y)NR^{10}R^{11}$, $C_1$-$C_{12}$ optionally substituted alkyl, $C_2$-$C_8$ optionally substituted alkenyl, $C_2$-$C_8$ optionally substituted alkynyl, $C_3$-$C_{12}$ optionally substituted carbocyclyl, $C_2$-$C_{20}$ optionally substituted heterocyclyl, $C_6$-$C_{20}$ optionally substituted aryl, $C_1$-$C_{20}$ optionally substituted heteroaryl, —$(CR^{14}R^{15})_t$—$NR^{12}C(=O)(CR^{14}R^{15})NR^{10}R^{11}$, and $(CR^{14}R^{15})_t$—$NR^{10}R^{11}$;

Y is O, S, or $NR^{12}$;

m is 0, 1, 2, 3, 4, 5 or 6 ;

n is 1, 2, 3, 4, 5 or 6; and t is 2, 3, 4, 5 or 6.

23. The compound of claim 22 wherein $C_2$-$C_8$ alkynyl is substituted with $C_2$-$C_{20}$ heterocyclyl.

24. The compound of claim 23 wherein $C_2$-$C_{20}$ heterocyclyl is selected from morpholinyl, piperidinyl, piperazinyl, and pyrrolidinyl.

25. The compound of claim 22 wherein $R^1$ is selected from the groups:

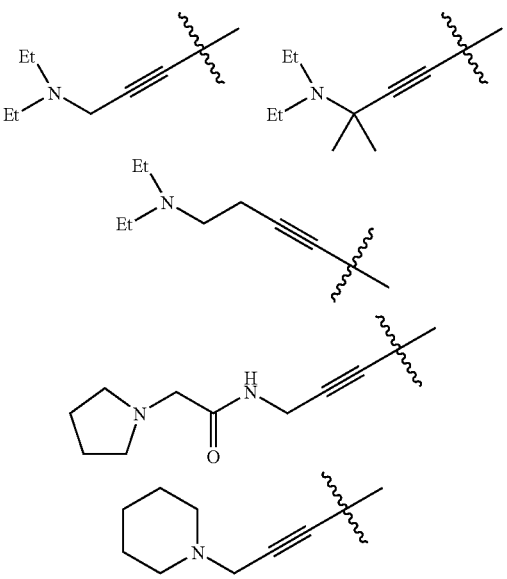

-continued

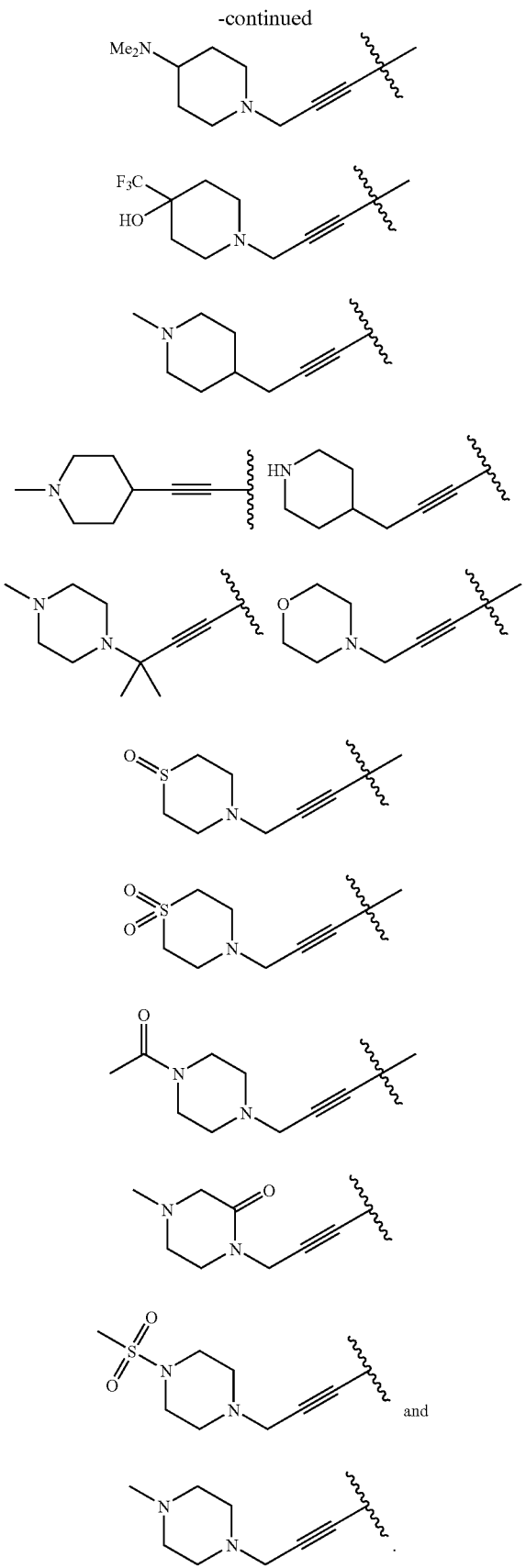

and

26. A compound selected from Formula Ia and Formula Ib:

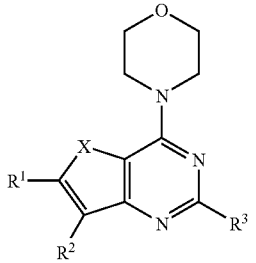

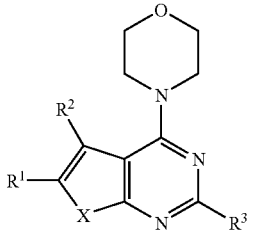

and stereoisomers, geometric isomers, tautomers, and pharmaceutically acceptable salts thereof, wherein:

X is O or S;

$R^1$ is $C_6$-$C_{20}$ aryl;

$R^2$ is selected from H, F, Cl, Br, I, CN, $CF_3$, $-NO_2$, $-C(=Y)R^{10}$, $-C(=Y)OR^{10}$, $-C(=Y)NR^{10}R^{11}$, $-(CR^{14}R^{15})_mNR^{10}R^{11}$, $-(CR^{14}R^{15})_nOR^{10}$, $-CR^{14}R^{15})_t-NR^{12}C(=O)(CR^{14}R^{15})NR^{10}R^{11}$, $-NR^{12}C(=Y)R^{10}$, $-NR^{12}C(=Y)OR^{10}$, $-NR^{12}C(=Y)NR^{10}R^{11}$, $-NR^{12}SO_2R^{10}$, $OR^{10}$, $-OC(=Y)R^{10}$, $-OC(=Y)OR^{10}$, $-OC(=Y)NR^{10}R^{11}$, $-OS(O)_2(OR^{10})$, $-OP(=Y)(OR^{10})(OR^{11})$, $-OP(OR^{10})OR^{11})$, $SR^{10}$, $-S(O)R^{10}$, $-S(O)_2R^{10}$, $-S(O)_2NR^{10}R^{11}$, $-S(O)(OR^{10})$, $-S(O)_2(OR^{10})$, $-SC(=Y)R^{10}$, $-SC(=Y)OR^{10}$, $-SC(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

$R^3$ is fused bicyclic $C_4$-$C_{20}$ heterocyclyl or fused bicyclic $C_1$-$C_{20}$ heteroaryl;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, $(CH_2)_mOR^{10}$, $NR^{10}R^{11}$, $CF_3$, F, Cl, Br, I, $SO_2R^{10}$, $C(=O)R^{10}$, $NR^{12}C(=Y)R^{11}$, $NR^{12}S(O)_2R^{11}$, $C(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or $-(CH_2)_n$-aryl, or $R^{14}$ and $R^{15}$ together with the atoms to which they are attached form a saturated or partially unsaturated $C_3$-$C_{12}$ carbocyclic ring, where said alkyl, alkenyl, alkynyl, carbocyclyl, heterocyclyl, aryl, heteroaryl, fused bicyclic $C_4$-$C_{20}$ heterocyclyl, and fused bicyclic $C_1$-$C_{20}$ heteroaryl are optionally substituted with one or more groups independently selected from F, Cl, Br, I, CN, CF$_3$, —NO$_2$, oxo, R$^{10}$, —C(=Y)R$^{10}$, —C(=Y)OR$^{10}$, —C(=Y)NR$^{10}$R$^{11}$, —(CR$^{14}$R$^{15}$)$_m$NR$^{10}$R$^{11}$, —(CR$^{14}$R$^{15}$)$_n$OR$^{10}$, —NR$^{10}$R$^{11}$, —NR$^{12}$C(=Y)R$_{10}$, —NR$^{12}$C(=Y)OR$^{11}$, —NR$^{12}$C(=Y)NR$^{10}$R$^{11}$, —NR$^{12}$SO$_2$R$^{10}$, =NR$^{12}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, C$_1$-C$_{12}$ optionally substituted alkyl, C$_2$-C$_8$ optionally substituted alkenyl, C$_{2-C8}$ optionally substituted alkynyl, C$_3$-C$_{12}$ optionally substituted carbocyclyl, C$_2$-C$_{20}$ optionally substituted heterocyclyl, C$_6$-C$_{20}$ optionally substituted aryl, C$_1$-C$_{20}$ optionally substituted heteroaryl, —(CR$^{14}$R$^{15}$)$_t$—NR$^{12}$C(=O)(CR$^{14}$R$^{15}$)NR$^{10}$R$^{11}$, and (CR$^{14}$R$^{15}$)$_t$—NR$^{10}$R$^{11}$;

Y is O, S, or NR$^{12}$;

m is 0, 1, 2, 3, 4, 5 or 6 ;

n is 1, 2, 3, 4, 5 or 6; and t is 2, 3, 4, 5 or 6.

27. The compound of claim 26 wherein R$^1$ is optionally substituted phenyl.

28. The compound of claim 27 wherein phenyl is substituted with one or more groups selected from N-methylcarboxamide, isopropylsulfonylamino, methylsulfonyl, 2-hydroxy-2-methylpropanamide, 2-hydroxypropanamide, 2-methoxyacetamide, (propan-2-ol)sulfonyl, 2-amino-2-methylpropanamide, 2-aminoacetamide, 2-hydroxyacetamide, methylsulfonylamino, 2-9dimethylamino)acetamide, amino, acetylamino, carboxamide, (4-methylsulfonylpiperazino)-1-methyl, (4-methylpiperazino)-1-methyl, hydroxymethyl, and methoxy.

29. A compound selected from Formula Ia and Formula Ib:

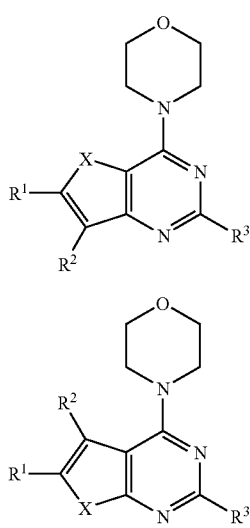

and stereoisomers, geometric isomers, tautomers, and pharmaceutically acceptable salts thereof, wherein:

X is O or S;

R$^1$ is C$_3$-C$_{12}$ carbocyclyl;

R$^2$ is selected from H, F, Cl, Br, I, CN, CF$_3$, —NO$_2$, —C(=Y)R$^{10}$, —C(=Y)OR$^{10}$, —C(=Y)NR$^{10}$R$^{11}$, —(CR$^{14}$R$^{15}$)$_m$NR$^{10}$R$^{11}$, —(CR$^{14}$R$^{15}$)$_n$OR$^{10}$, —CR$^{14}$R$^{15}$)$_t$—NR$^{12}$C(=O)(CR$^{14}$R$^{15}$)NR$^{10}$R$^{11}$, —NR$^{12}$C(=Y)R$^{10}$, —NR$^{12}$C(=Y)OR$^{10}$, —NR$^{12}$C(=Y)NR$^{10}$R$^{11}$, —NR$^{12}$SO$_2$R$^{10}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)OR$^{11}$), SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, and C$_1$-C$_{20}$ heteroaryl;

R$^3$ is fused bicyclic C$_4$-C$_{20}$ heterocyclyl or fused bicyclic C$_1$-C$_{20}$ heteroaryl;

R$^{10}$, R$^{11}$ and R$^{12}$ are independently H, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl, or C$_1$-C$_{20}$ heteroaryl, or R$^{10}$ and R$^{11}$ together with the nitrogen to which they are attached optionally form a saturated, partially unsaturated or fully unsaturated C$_3$-C$_{20}$ heterocyclic ring optionally containing one or more additional ring atoms selected from N, O or S, wherein said heterocyclic ring is optionally substituted with one or more groups independently selected from oxo, (CH$_2$)$_m$OR$^{10}$, NR$^{10}$R$^{11}$, CF$_3$, F, Cl, Br, I, SO$_2$R$^{10}$, C(=O)R$^{10}$, NR$^{12}$C(=Y)R$^{11}$, NR$^{12}$S(O)$_2$R$^{11}$, C(=Y)NR$^{10}$R$^{11}$, C$_1$-C$_{12}$ alkyl, C$_2$-C$_8$ alkenyl, C$_2$-C$_8$ alkynyl, C$_3$-C$_{12}$ carbocyclyl, C$_2$-C$_{20}$ heterocyclyl, C$_6$-C$_{20}$ aryl and C$_1$-C$_{20}$ heteroaryl;

R$^{14}$ and R$^{15}$ are independently selected from H, C$_1$-C$_{12}$ alkyl, or —(CH$_2$)$_n$-aryl, or R$^{14}$ and R$^{15}$ together with the atoms to which they are attached form a saturated or partially unsaturated C$_3$-C$_{12}$ carbocyclic ring, where said alkyl, alkenyl, alkynyl, carbocyclyl, heterocyclyl, aryl, heteroaryl, fused bicyclic C$_4$-C$_{20}$ heterocyclyl, and fused bicyclic C$_1$-C$_{20}$ heteroaryl are optionally substituted with one or more groups independently selected from F, Cl, Br, I, CN, CF$_3$, —NO$_2$, oxo, R$^{10}$, —C(=Y)R$^{10}$, —C(=Y)OR$^{10}$, —C(=Y)NR$^{10}$R$^{11}$, —(CR$^{14}$R$^{15}$)$_m$NR$^{10}$R$^{11}$, —(CR$^{14}$R$^{15}$)$_n$OR$^{10}$, —NR$^{10}$R$^{11}$, —NR$^{12}$C(=Y)R$_{10}$, —NR$^{12}$C(=Y)OR$^{11}$, —NR$^{12}$C(=Y)NR$^{10}$R$^{11}$, —NR$^{12}$SO$_2$R$^{10}$, =NR$^{12}$, OR$^{10}$, —OC(=Y)R$^{10}$, —OC(=Y)OR$^{10}$, —OC(=Y)NR$^{10}$R$^{11}$, —OS(O)$_2$(OR$^{10}$), —OP(=Y)(OR$^{10}$)(OR$^{11}$), —OP(OR$^{10}$)(OR$^{11}$), SR$^{10}$, —S(O)R$^{10}$, —S(O)$_2$R$^{10}$, —S(O)$_2$NR$^{10}$R$^{11}$, —S(O)(OR$^{10}$), —S(O)$_2$(OR$^{10}$), —SC(=Y)R$^{10}$, —SC(=Y)OR$^{10}$, —SC(=Y)NR$^{10}$R$^{11}$, C$_1$-C$_{12}$ optionally substituted alkyl, C$_2$-C$_8$ optionally substituted alkenyl, C$_{20-C8}$ optionally substituted alkynyl, C$_3$-C$_{12}$ optionally substituted carbocyclyl, C$_2$-C$_{20}$ optionally substituted heterocyclyl, C$_6$-C$_{20}$ optionally substituted aryl, C$_1$-C$_{20}$ optionally substituted heteroaryl, —(CR$^{14}$R$^{15}$)$_t$—NR$^{12}$C(=O)(CR$^{14}$R$^{15}$)NR$^{10}$R$^{11}$, and (CR$^{14}$R$^{15}$)$_t$—NR$^{10}$R$^{11}$;

Y is O, S, or NR$^{12}$;

m is 0, 1, 2, 3, 4, 5 or 6 ;

n is 1, 2, 3, 4, 5 or 6; and t is 2, 3, 4, 5 or 6.

30. A compound selected from Formula Ia and Formula Ib:

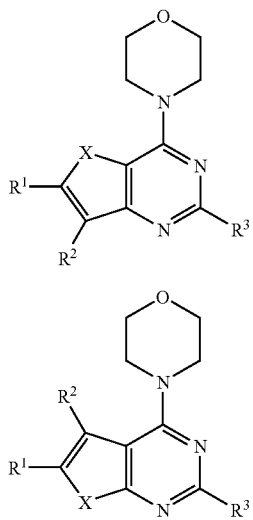

and stereoisomers, geometric isomers, tautomers, and pharmaceutically acceptable salts thereof, wherein:

X is O or S;

$R^1$ is $C_2$-$C_{20}$ heterocyclyl;

$R^2$ is selected from H, F, Cl, Br, I, CN, $CF_3$, $-NO_2$, $-C(=Y)R^{10}$, $-C(=Y)OR^{10}$, $-C(=Y)NR^{10}R^{11}$, $-(CR^{14}R^{15})_mNR^{10}R^{11}$, $-(CR^{14}R^{15})_nOR^{10}$, $-CR^{14}R^{15})_t-NR^{12}C(=O)(CR^{14}R^{15})NR^{10}R^{11}$, $-NR^{12}C(=Y)R^{10}$, $-NR^{12}C(=Y)OR^{10}$, $-NR^{12}C(=Y)NR^{10}R^{11}$, $-NR^{12}SO_2R^{10}$, $OR^{10}$, $-OC(=Y)R^{10}$, $-OC(=Y)OR^{10}$, $-OC(=Y)NR^{10}R^{11}$, $-OS(O)_2(OR^{10})$, $-OP(=Y)(OR^{10})(OR^{11})$, $-OP(OR^{10})(OR^{11})$, $SR^{10}$, $-S(O)R^{10}$, $-S(O)_2R^{10}$, $-S(O)_2NR^{10}R^{11}$, $-S(O)(OR^{10})$, $-S(O)_2(OR^{10})$, $-SC(=Y)R^{10}$, $-SC(=Y)OR^{10}$, $-SC(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

$R^3$ is fused bicyclic $C_4$-$C_{20}$ heterocyclyl or fused bicyclic $C_1$-$C_{20}$ heteroaryl;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, $(CH_2)_mOR^{10}$, $NR^{10}R^{11}$, $CF_3$, F, Cl, Br, I, $SO_2R^{10}$, $C(=O)R^{10}$, $NR^{12}C(=Y)R^{11}$, $NR^{12}S(O)_2R^{11}$, $C(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or $-(CH_2)_n$-aryl, or $R^{14}$ and $R^{15}$ together with the atoms to which they are attached form a saturated or partially unsaturated $C_3$-$C_{12}$ carbocyclic ring, where said alkyl, alkenyl, alkynyl, carbocyclyl, heterocyclyl, aryl, heteroaryl, fused bicyclic $C_4$-$C_{20}$ heterocyclyl, and fused bicyclic $C_1$-$C_{20}$ heteroaryl are optionally substituted with one or more groups independently selected from F, Cl, Br, I, CN, $CF_3$, $-NO_2$, oxo, $R^{10}$, $-C(=Y)R^{10}$, $-C(=Y)OR^{10}$, $-C(=Y)NR^{10}R^{11}$, $-(CR^{14}R^{15})_mNR^{10}R^{11}$, $-(CR^{14}R^{15})_nOR^{10}$, $-NR^{10}R^{11}$, $-NR^{12}C(=Y)R_{10}$, $-NR^{12}C(=Y)OR^{11}$, $-NR^{12}C(=Y)NR^{10}R^{11}$, $-NR^{12}SO_2R^{10}$, $=NR^{12}$, $OR^{10}$, $-OC(=Y)R^{10}$, $-OC(=Y)OR^{10}$, $-OC(=Y)NR^{10}R^{11}$, $-OS(O)_2(OR^{10})$, $-OP(=Y)(OR^{10})(OR^{11})$, $-OP(OR^{10})(OR^{11})$, $SR^{10}$, $-S(O)R^{10}$, $-S(O)_2R^{10}$, $-S(O)_2NR^{10}R^{11}$, $-S(O)(OR^{10})$, $-S(O)_2(OR^{10})$, $-SC(=Y)R^{10}$, $-SC(=Y)OR^{10}$, $-SC(=Y)NR^{10}R^{11}$, $C_1$-$C_{12}$ optionally substituted alkyl, $C_2$-$C_8$ optionally substituted alkenyl, $C_2$-$C_8$ optionally substituted alkynyl, $C_3$-$C_{12}$ optionally substituted carbocyclyl, $C_2$-$C_{20}$ optionally substituted heterocyclyl, $C_6$-$C_{20}$ optionally substituted aryl, $C_1$-$C_{20}$ optionally substituted heteroaryl, $-(CR^{14}R^{15})_t-NR^{12}C(=O)(CR^{14}R^{15})NR^{10}R^{11}$, and $(CR^{14}R^{15})_t-NR^{10}R^{11}$;

Y is O, S, or $NR^{12}$;

m is 0, 1, 2, 3, 4, 5 or 6;

n is 1, 2, 3, 4, 5 or 6; and t is 2, 3, 4, 5 or 6.

31. A compound selected from Formula Ia and Formula Ib:

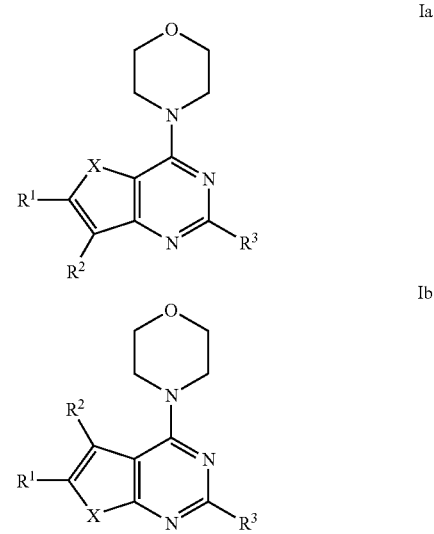

and stereoisomers, geometric isomers, tautomers, and pharmaceutically acceptable salts thereof, wherein:

X is O or S;

$R^1$ is $C_1$-$C_{20}$ heterocyclyl;

$R^2$ is selected from H, F, Cl, Br, I, CN, $CF_3$, $-NO_2$, $-C(=Y)R^{10}$, $-C(=Y)OR^{10}$, $-C(=Y)NR^{10}R^{11}$, $-(CR^{14}R^{15})_mNR^{10}R^{11}$, $-(CR^{14}R^{15})_nOR^{10}$, $-CR^{14}R^{15})_t-NR^{12}C(=O)(CR^{14}R^{15})NR^{10}R^{11}$, $-NR^{12}C(=Y)R^{10}$, $-NR^{12}C(=Y)OR^{10}$, $-NR^{12}C(=Y)NR^{10}R^{11}$, $-NR^{12}SO_2R^{10}$, $OR^{10}$, $-OC(=Y)R^{10}$, $-OC(=Y)OR^{10}$, $-OC(=Y)NR^{10}R^{11}$, $-OS(O)_2(OR^{10})$, $-OP(=Y)(OR^{10})(OR^{11})$, $-OP(OR^{10})(OR^{11})$, $SR^{10}$, $-S(O)R^{10}$, $-S(O)_2R^{10}$, $-S(O)_2NR^{10}R^{11}$, $-S(O)(OR^{10})$, $-S(O)_2(OR^{10})$, $-SC(=Y)R^{10}$, $-SC(=Y)OR^{10}$, $-SC(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

$R^3$ is fused bicyclic $C_4$-$C_{20}$ heterocyclyl or fused bicyclic $C_1$-$C_{20}$ heteroaryl;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, $(CH_2)_m OR^{10}$, $NR^{10}R^{11}$, $CF_3$, F, Cl, Br, I, $SO_2R^{10}$, $C(=O)R^{10}$, $NR^{12}C(=Y)R^{11}$, $NR^{12}S(O)_2R^{11}$, $C(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or —$(CH_2)_n$-aryl, or $R^{14}$ and $R^{15}$ together with the atoms to which they are attached form a saturated or partially unsaturated $C_3$-$C_{12}$ carbocyclic ring, where said alkyl, alkenyl, alkynyl, carbocyclyl, heterocyclyl, aryl, heteroaryl, fused bicyclic $C_4$-$C_{20}$ heterocyclyl, and fused bicyclic $C_1$-$C_{20}$ heteroaryl are optionally substituted with one or more groups independently selected from F, Cl, Br, I, CN, $CF_3$, —$NO_2$, oxo, $R^{10}$, —$C(=Y)R^{10}$, —$C(=Y)OR^{10}$, —$C(=Y)NR^{10}R^{11}$, —$(CR^{14}R^{15})_n NR^{10}R^{11}$, —$(CR^{14}R^{15})_n OR^{10}$, —$NR^{10}R^{11}$, —$NR^{12}C(=Y)R_{10}$, —$NR^{12}C(=Y)OR^{11}$, —$NR^{12}C(=Y)NR^{10}R^{11}$, —$NR^{12}SO_2R^{10}$, =$NR^{12}$, $OR^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})(OR^{11})$, $SR^{10}$, —$S(O)R^{10}$, —$S(O)_2R^{10}$, —$S(O)_2NR^{10}R^{11}$, —$S(O)(OR^{10})$, —$S(O)_2(OR^{10})$, —$SC(=Y)R^{10}$, —$SC(=Y)OR^{10}$, —$SC(=Y)NR^{10}R^{11}$, $C_1$-$C_{12}$ optionally substituted alkyl, $C_2$-$C_8$ optionally substituted alkenyl, $C_2$-$C_8$ optionally substituted alkynyl, $C_3$-$C_{12}$ optionally substituted carbocyclyl, $C_2$-$C_{20}$ optionally substituted heterocyclyl, $C_6$-$C_{20}$ optionally substituted aryl, $C_1$-$C_{20}$ optionally substituted heteroaryl, —$(CR^{14}R^{15})_t$—$NR^{12}C(=O)(CR^{14}R^{15})NR^{10}R^{11}$, and $(CR^{14}R^{15})_t$—$NR^{10}R^{11}$;

Y is O, S, or $NR^{12}$;

m is 0, 1, 2, 3, 4, 5 or 6;

n is 1, 2, 3, 4, 5 or 6; and t is 2, 3, 4, 5 or 6.

32. The compound of claim 31 wherein $R^1$ is 2-pyridyl, 3-pyridyl, 4-pyridyl, or 5-pyrimidinyl.

33. A compound selected from Formula Ia and Formula Ib:

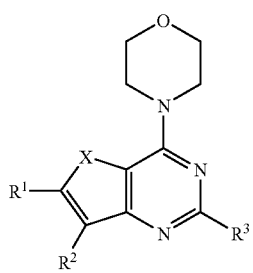

Ia

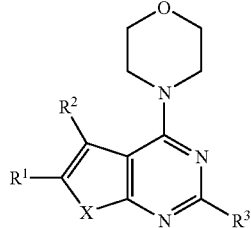

Ib and stereoisomers, geometric isomers, tautomers, and pharmaceutically acceptable salts thereof, wherein:

X is O or S;

$R^1$ is selected from H, F, Cl, Br, I, CN, —$CR^{14}R^{15}$—$NR^{16}R^{17}$, —$CR^{14}R^{15}$—$NHR^{10}$, —$(CR^{14}R^{15})_t NR^{10}R^{11}$, —$C(R^{14}R^{15})_n NR^{12}C(=Y)R^{10}$, —$(CR^{14}R^{15})_n NR^{12}S(O)_2R^{10}$, —$(CR^{14}R^{15})_m OR^{10}$, —$(CR_{14}R^{15})_n S(O)^2R^{10}$, —$(CR^{14}R^{15})_n S(O)_2NR^{10}R^{11}$, —$C(OR^{10},)R^{11}R^{14}$, —$C(R^{14})$=$CR^{18}R^{19}$, —$(=Y)R^{10}$, —$C(=Y)OR^{10}$, —$C(=Y)NR^{10}R^{11}$, —$C(=Y)NR^{10}OR^{10}$, —$C(=O)NR^{12}S(O)_2R^{10}$, —$C(=O)NR^{12}(CR^{14}R^{15})_m NR^{10}R^{11}$, —$NO_2$, —$NHR^{12}$, —$NR^{12}C(=Y)R^{11}$, —$NR^{12}C(=Y)OR^{11}$, —$NR^{12}C(=Y)NR^{10}R^{11}$, —$NR^{12}S(O)_2R^{10}$, —$NR^{12}SO_2NR^{10}R^{11}$, —$S(O)_2R^{10}$, —$S(O)_2NR^{10}R^{11}$, —$SC(=Y)R^{10}$, —$SC(=Y)OR^{10}$, $C_2$-$C_{12}$ alkyl, $C_2$-$C_8$ alkenyl, $C_2$-$C_8$ alkynyl, $C_3$-$C_{12}$ carbocycyclyl, $C_2$-$C_{20}$ heterocyclyl, $C_6$-$C_{20}$ aryl, or $C_1$-$C_{20}$ heteroaryl;

$R^2$ is selected from H, F, Cl, Br, I, CN, $CF_3$, —$NO_2$, —$C(=Y)R^{10}$, —$C(=Y)OR^{10}$, —$C(=Y)NR^{10}R^{11}$, —$(CR^{14}R^{15})_m NR^{10}R^{11}$, —$(CR^{14}R^{15})_n OR^{10}$, —$CR^{14}R^{15})_t$—$NR^{12}C(=O)(CR^{14}R^{15})NR^{10}R^{11}$, —$NR^{12}C(=Y)R^{10}$, —$NR^{12}C(=Y)OR^{10}$, —$NR^{12}C(=Y)NR^{10}R^{11}$, —$NR^{12}SO_2R^{10}$, $OR^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})OR^{11})$, $SR^{10}$, —$S(O)R^{10}$, —$S(O)_2R^{10}$, —$S(O)_2NR^{10}R^{11}$, —$S(O)(OR^{10})$, —$S(O)_2(OR^{10})$, —$SC(=Y)R^{10}$, —$SC(=Y)OR^{10}$, —$SC(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, and $C_1$-$C_{20}$ heteroaryl;

$R^3$ is selected from:

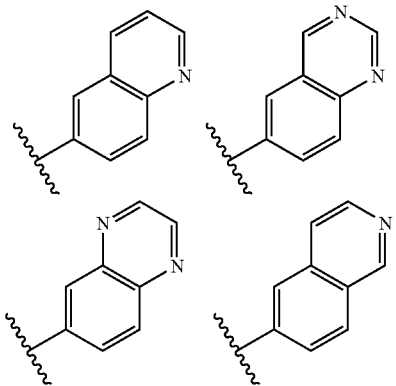

-continued

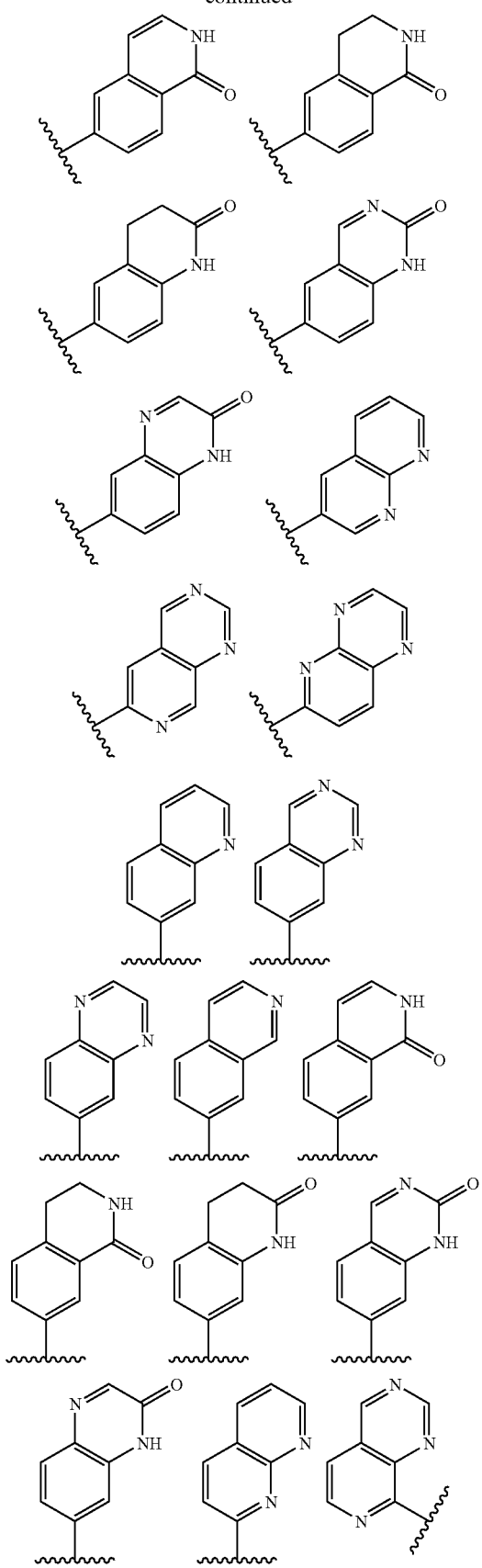

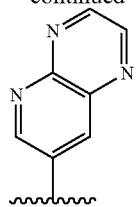

where the wavy line indicates the site of attachment;

$R^{10}$, $R^{11}$ and $R^{12}$ are independently H, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl, or $C_1$-$C_{20}$ heteroaryl, or $R^{10}$ and $R^{11}$ together with the nitrogen to which they are attached optionally form a saturated, partially unsaturated or fully unsaturated $C_3$-$C_{20}$ heterocyclic ring optionally containing one or more additional ring atoms selected from N, O or S, wherein said heterocyclic ring is optionally substituted with one or more groups independently selected from oxo, $(CH_2)_m OR^{10}$, $NR^{10}R^{11}$, $CF_3$, F, Cl, Br, I, $SO_2R^{10}$, $C(=O)R^{10}$, $NR^{12}C(=Y)R^{11}$, $NR^{12}S(O)_2R^{11}$, $C(=Y)NR^{10}R^{11}$, $C_1$-$C_{12}$ alkyl, $C_2$-$C_8$ alkenyl, $C_2$-$C_8$ alkynyl, $C_3$-$C_{12}$ carbocyclyl, $C_2$-$C_{20}$ heterocyclyl, $C_6$-$C_{20}$ aryl and $C_1$-$C_{20}$ heteroaryl;

$R^{14}$ and $R^{15}$ are independently selected from H, $C_1$-$C_{12}$ alkyl, or —$(CH_2)_n$-aryl, or $R^{14}$ and $R^{15}$ together with the atoms to which they are attached form a saturated or partially unsaturated $C_3$-$C_{12}$ carbocyclic ring, $R^{16}$ and $R^{17}$ are independently H, $C_1$-$C_{12}$ alkyl, $C_2$-$C_8$ alkynyl, $C_3$-$C_{12}$ carbocyclyl, or $C_6$-$C_{20}$ aryl, $R^{18}$ and $R^{19}$ together with the carbon to which they are attached form a $C_3$-$C_{20}$ heterocyclic ring, where said alkyl, alkenyl, alkynyl, carbocyclyl, heterocyclyl, aryl, heteroaryl, fused bicyclic $C_4$-$C_{20}$ heterocyclyl, and fused bicyclic $C_1$-$C_{20}$ heteroaryl are optionally substituted with one or more groups independently selected from F, Cl, Br, I, CN, $CF_3$, —$NO_2$, oxo, $R^{10}$, —$C(=Y)R^{10}$, —$C(=Y)OR^{10}$, —$C(=Y)NR^{10}R^{11}$, —$(CR^{14}R^{15})_n NR^{10}R^{11}$, —$(CR^{14}R^{15})_n OR^{10}$, —$NR^{10}R^{11}$, —$NR^{12}C(=Y)R_{10}$, —$NR^{12}C(=Y)OR^{11}$, —$NR^{12}C(=Y)NR^{10}R^{11}$, —$NR^{12}SO_2R^{10}$, =$NR^{12}$, $OR^{10}$, —$OC(=Y)R^{10}$, —$OC(=Y)OR^{10}$, —$OC(=Y)NR^{10}R^{11}$, —$OS(O)_2(OR^{10})$, —$OP(=Y)(OR^{10})(OR^{11})$, —$OP(OR^{10})(OR^{11})$, $SR^{10}$, —$S(O)R^{10}$, —$S(O)_2R^{10}$, —$S(O)_2NR^{10}R^{11}$, —$S(O)(OR^{10})$, —$S(O)_2(OR^{10})$, —$SC(=Y)R^{10}$, —$SC(=Y)OR^{10}$, —$SC(=Y)NR^{10}R^{11}$, $C_1$-$C_{12}$ optionally substituted alkyl, $C_2$-$C_8$ optionally substituted alkenyl, $C_2$-$C_8$ optionally substituted alkynyl, $C_3$-$C_{12}$ optionally substituted carbocyclyl, $C_2$-$C_{20}$ optionally substituted heterocyclyl, $C_6$-$C_{20}$ optionally substituted aryl, $C_1$-$C_{20}$ optionally substituted heteroaryl, —$(CR^{14}R^{15})_t$—$NR^{12}C(=O)(CR^{14}R^{15})NR^{10}R^{11}$, and $(CR^{14}R^{15})_t$—$NR^{10}R^{11}$;

Y is O, S, or $NR^{12}$;

m is 0, 1, 2, 3, 4, 5 or 6;

n is 1, 2, 3, 4, 5 or 6; and t is 2, 3, 4, 5 or 6.

34. A pharmaceutical composition comprised of a compound of claim 2 and a pharmaceutically acceptable carrier.

35. The composition according to claim 34, further comprising a therapeutic agent selected from a chemotherapeutic agent, an anti-inflammatory agent, an immunomodulatory agent, a neurotropic factor, an agent for treating cardiovascular disease, an agent for treating liver disease, an anti-viral agent, an agent for treating blood disorders, an agent for treating diabetes, or an agent for treating immunodeficiency disorders.

36. A composition comprising a compound of claim 2 in an amount to detectably inhibit PI3 kinase activity and a pharmaceutically acceptable carrier, adjuvant, or vehicle.

37. A kit comprising:
(a) a first pharmaceutical composition comprising a compound as defined in claim 2;
(b) a second pharmaceutical composition that comprises a compound having anti-hyperproliferative activity; and
(c) instructions for the simultaneous, sequential or separate administration of said first and second pharmaceutical compositions to a patient in need thereof;
wherein said first and second pharmaceutical compositions are contained in separate containers.

38. A pharmaceutical composition comprised of a compound of claim 1 and a pharmaceutically acceptable carrier.

39. A pharmaceutical composition comprised of a compound of claim 3 and a pharmaceutically acceptable carrier.

40. A pharmaceutical composition comprised of a compound of claim 4 and a pharmaceutically acceptable carrier.

41. A pharmaceutical composition comprised of a compound of claim 6 and a pharmaceutically acceptable carrier.

42. A pharmaceutical composition comprised of a compound of claim 7 and a pharmaceutically acceptable carrier.

43. A pharmaceutical composition comprised of a compound of claim 9 and a pharmaceutically acceptable carrier.

44. A pharmaceutical composition comprised of a compound of claim 10 and a pharmaceutically acceptable carrier.

45. A pharmaceutical composition comprised of a compound of claim 11 and a pharmaceutically acceptable carrier.

46. A pharmaceutical composition comprised of a compound of claim 13 and a pharmaceutically acceptable carrier.

47. A pharmaceutical composition comprised of a compound of claim 16 and a pharmaceutically acceptable carrier.

48. A pharmaceutical composition comprised of a compound of claim 17 and a pharmaceutically acceptable carrier.

49. A pharmaceutical composition comprised of a compound of claim 18 and a pharmaceutically acceptable carrier.

50. A pharmaceutical composition comprised of a compound of claim 20 and a pharmaceutically acceptable carrier.

51. A pharmaceutical composition comprised of a compound of claim 21 and a pharmaceutically acceptable carrier.

52. A pharmaceutical composition comprised of a compound of claim 22 and a pharmaceutically acceptable carrier.

53. A pharmaceutical composition comprised of a compound of claim 26 and a pharmaceutically acceptable carrier.

54. A pharmaceutical composition comprised of a compound of claim 29 and a pharmaceutically acceptable carrier.

55. A pharmaceutical composition comprised of a compound of claim 30 and a pharmaceutically acceptable carrier.

56. A pharmaceutical composition comprised of a compound of claim 31 and a pharmaceutically acceptable carrier.

57. A pharmaceutical composition comprised of a compound of claim 33 and a pharmaceutically acceptable carrier.

* * * * *

UNITED STATES PATENT AND TRADEMARK OFFICE
CERTIFICATE OF CORRECTION

PATENT NO. : 7,846,929 B2
APPLICATION NO. : 11/789427
DATED : December 7, 2010
INVENTOR(S) : Adrian Folkes et al.

Page 1 of 9

It is certified that error appears in the above-identified patent and that said Letters Patent is hereby corrected as shown below:

In the Claims:

In Claim 1

*Col. 336, line 23*
After     $-NR^{12}SO_2R^{10}$,
Insert    $OR^{10}$,

After     $-OC(=Y)R^{10}$,
Insert    $-OC(=Y)OR^{10}$

*Col. 337, line 5*
Replace   $(CR^4R^5)_t-NR^{10}R^{11}$
With      $(CR^{14}R^{15})_t-NR10R11$

In Claim 2

*Col. 337, line 38*
Replace   $-(CR^{14}R^{15})^nNR^{12}S(O)_2R^{10}$
With      $-(CR^{14}R^{15})_nNR^{12}S(O)_2R^{10}$

*Col. 337, line 43*
Replace   $-CR^{14}R^{15})_nOR^{10}$
With      $-(CR^{14}R^{15})_nOR^{10}$

*Col. 337, line 44*
Replace   $-(CR^{14}R^{15})_t-NR^{12}C(=O)CR^{14}R-)NR^{10}R^{11}$
With      $-(CR^{14}R^{15})_t-NR^{12}C(=O)(CR^{14}R-)NR^{10}R^{11}$ Signed and Sealed this
Sixteenth Day of July, 2013

Teresa Stanek Rea
*Acting Director of the United States Patent and Trademark Office*

*Col 337, line 51*
Replace  SC(=Y)OR$^{10}$
With  –SC(=Y)OR$^{10}$

*Col 337, line 52*
After  alkenyl,
insert  $C_2 - C_8$ alkynyl,

*Col 337, line 57*
After  alkenyl,
insert  $C_2 - C_8$ alkynyl,

*Col 338, line 13*
After  NR$^{10}$R$^{11}$
Insert  –(CR$^{14}$R$^{15}$)$_n$NR$^{10}$R$^{11}$,

*Col 338, line 15*
Replace  –NR$^{12}$C(=Y)R$_{10}$
With  –NR$^{12}$C(=Y)R$^{10}$

*Col 338, line 20*
Replace  –S(O)(OR$^{10}$),
With  –S(O)$_2$(OR$^{10}$),

In Claim 3

*Col 338, line 67*
Replace  –CR$^{14}$R$^{15}$)$_t$
With  –(CR$^{14}$R$^{15}$)$_t$

*Col. 339, line 4*
Replace  -OP(OR$^{10}$)OR$^{11}$)
with  -OP(OR$^{10}$)(OR$^{11}$)

*Col. 339, line 25*
Replace  (C$_2$)$_m$OR$^{10}$
With  (CH$_2$)$_m$OR$^{10}$

*Col. 339, line 26*
Replace  C(=Y)R$^{10}$
With  C(=O)R$^{10}$

*Col. 339, line 27*
Replace    $-NR^{12}SO_{2R}R^{11}$
With       $-NR^{12}SO_2R^{11}$

*Col. 339, line 45*
Replace    $-NR_{10}R^{11}$
With       $-NR^{10}R^{11}$

*Col. 339, line 57*
Replace    $C_6 - C_0$
With       $C_6 - C_{20}$

*Col. 339, lines 59-60*
Replace    $-(CR^{14}R^{15})_t-NR^{12}C(=O)(CR^{14}R^{15})tNR^{12}C(=O)(CR^{14}R^{15})NR^{10}R^{11}$
With       $-(CR^{14}R^{15})_tNR^{12}C(=O)(CR^{14}R^{15})NR^{10}R^{11}$

*Col. 339, line 62*
Replace    $NR^{10}R^{11}$
With       $-NR^{10}R^{11}$

*Col. 340, line 29*
Insert     and
Between   $R^{14}$ and $R^{15}$

*Col. 340, line 34*
Replace    $-CRR^{14}R^{15})_t-NR^{12}C(=O)(CR^{14}R^{15})RN^{10}R^{11}$
With       $-(CRR^{14}R^{15})_t-NR^{12}C(=O)(CR^{14}R^{15})RN^{10}R^{11}$

*Col. 340, line 39*
Replace    $OR^{11})$
With       $(OR^{11})$

*Col. 340, line 56*
Replace    $(C_2)_mOR^{10}$
With       $(CH_2)_mOR^{10}$

*Col. 341, line 6*
Replace    $NR^{12}C(=Y)R_{10}$
With       $NR^{12}C(=Y)R^{10}$

*Col. 341, line 61*
Replace    $-CR^{14}R^{15})_t-NR^{12}C(=O)(CR^{14}R^{15})NR^{10}R^{11}$
With       $-(CR^{14}R^{15})_t-NR^{12}C(=O)(CR^{14}R^{15})NR^{10}R^{11}$

*Col. 341, line 67*
Replace    $OR^{11}),$
With       $(OR^{11}),$

*Col. 342, line 47*
Replace     $-NR^{12}C(=Y)R_{10}$,
With        $-NR^{12}C(=Y)R^{10}$,

In Claim 7

*Col. 343, line 35*
Replace     $-CR^{14}R^{15})_t-NR^{12}C(=O)(CR^{14}R^{15})NR^{10}R^{11}$
With        $-(CR^{14}R^{15})_t-NR^{12}C(=O)(CR^{14}R^{15})NR^{10}R^{11}$

*Col. 343, line 40*
Replace     $OR^{11})$
With        $(OR^{11})$

*Col. 344, line 8*
Replace     $-NR^{12}C(=Y)R_{10}$,
With        $-NR^{12}C(=Y)R^{10}$,

In Claim 9

*Col. 344, line 63*
Replace     $-CR^{14}R^{15})_t-NR^{12}C(=O)(CR^{14}R^{15})NR^{10}R^{11}$
With        $-(CR^{14}R^{15})_t-NR^{12}C(=O)(CR^{14}R^{15})NR^{10}R^{11}$

*Col. 345, line 1*
Replace     $OR^{11})$
With        $(OR^{11})$

*Col. 345, line 35*
Replace     $-NR^{12}C(=Y)R_{10}$,
With        $-NR^{12}C(=Y)R^{10}$,

In Claim 10

*Col. 346, line 24*
Replace     $-CR^{14}R^{15})_t-NR^{12}C(=O)(CR^{14}R^{15})NR^{10}R^{11}$
With        $-(CR^{14}R^{15})_t-NR^{12}C(=O)(CR^{14}R^{15})NR^{10}R^{11}$

*Col. 346, line 29*
Replace     $OR^{11})$
With        $(OR^{11})$

*Col. 346, line 63*
Replace     $-NR^{12}C(=Y)R_{10}$,
With        $-NR^{12}C(=Y)R^{10}$,

In Claim 11

*Col. 347, line 47*
Replace  $- CR^{14}R^{15})_t\text{-}NR^{12}C(=O)(CR^{14}R^{15})NR^{10}R^{11}$
With  $- (CR^{14}R^{15})_t\text{-}NR^{12}C(=O)(CR^{14}R^{15})NR^{10}R^{11}$

*Col. 347, line 52*
Replace  $OR^{11})$
With  $(OR^{11})$

*Col. 348, line 19*
Replace  $-NR^{12}C(=Y)R_{10'}$
With  $-NR^{12}C(=Y)R^{10,}$

In Claim 13

*Col. 349, line 7*
Replace  $- CR^{14}R^{15})_t\text{-}NR^{12}C(=O)(CR^{14}R^{15})NR^{10}R^{11}$
With  $- (CR^{14}R^{15})_t\text{-}NR^{12}C(=O)(CR^{14}R^{15})NR^{10}R^{11}$

*Col. 349, line 12*
Replace  $OR^{11})$
With  $(OR^{11})$

*Col. 349, line 47*
Replace  $-NR^{12}C(=Y)R_{10'}$
With  $-NR^{12}C(=Y)R^{10,}$

In Claim 16

*Col. 350, line 37*
Replace  $- CR^{14}R^{15})_t\text{-}NR^{12}C(=O)(CR^{14}R^{15})NR^{10}R^{11}$
With  $- (CR^{14}R^{15})_t\text{-}NR^{12}C(=O)(CR^{14}R^{15})NR^{10}R^{11}$

*Col. 350, line 43*
Replace  $OR^{11})$
With  $(OR^{11})$

*Col. 351, line 12*
Replace  $-NR^{12}C(=Y)R_{10'}$
With  $-NR^{12}C(=Y)R^{10,}$

In Claim 17

*Col. 352, line 1*
Replace  — CR$^{14}$R$^{15}$)$_t$-NR$^{12}$C(=O)(CR$^{14}$R$^{15}$)NR$^{10}$R$^{11}$
With      — (CR$^{14}$R$^{15}$)$_t$-NR$^{12}$C(=O)(CR$^{14}$R$^{15}$)NR$^{10}$R$^{11}$

*Col. 350, line 6*
Replace   OR$^{11}$)
With      (OR$^{11}$)

*Col. 352, line 47*
Replace   –NR$^{12}$C(=Y)R$_{10}$'
With      –NR$^{12}$C(=Y)R$^{10,}$

In Claim 18

*Col. 353, line 34*
Replace  — CR$^{14}$R$^{15}$)$_t$-NR$^{12}$C(=O)(CR$^{14}$R$^{15}$)NR$^{10}$R$^{11}$
With      — (CR$^{14}$R$^{15}$)$_t$-NR$^{12}$C(=O)(CR$^{14}$R$^{15}$)NR$^{10}$R$^{11}$

*Col. 353, line 39*
Replace   OR$^{11}$)
With      (OR$^{11}$)

*Col. 354, line 6*
Replace   –NR$^{12}$C(=Y)R$_{10}$'
With      –NR$^{12}$C(=Y)R$^{10,}$

In Claim 20

*Col. 354, line 60*
Replace  — CR$^{14}$R$^{15}$)$_t$-NR$^{12}$C(=O)(CR$^{14}$R$^{15}$)NR$^{10}$R$^{11}$
With      — (CR$^{14}$R$^{15}$)$_t$-NR$^{12}$C(=O)(CR$^{14}$R$^{15}$)NR$^{10}$R$^{11}$

*Col. 354, line 65*
Replace   OR$^{11}$)
With      (OR$^{11}$)

*Col. 355, line 34*
Replace   –NR$^{12}$C(=Y)R$_{10}$'
With      –NR$^{12}$C(=Y)R$^{10,}$

In Claim 21

*Col. 356, line 21*
Replace $-CR^{14}R^{15})_t-NR^{12}C(=O)(CR^{14}R^{15})NR^{10}R^{11}$
With $-(CR^{14}R^{15})_t-NR^{12}C(=O)(CR^{14}R^{15})NR^{10}R^{11}$

*Col. 356, line 26*
Replace $OR^{11})$
With $(OR^{11})$

*Col. 356, line 60*
Replace $-NR^{12}C(=Y)R_{10'}$
With $-NR^{12}C(=Y)R^{10'}$

In Claim 22

*Col. 357, line 38*
Replace alkenyl
With alkynyl

*Col. 357, line 42*
Replace $-CR^{14}R^{15})_t-NR^{12}C(=O)(CR^{14}R^{15})NR^{10}R^{11}$
With $-(CR^{14}R^{15})_t-NR^{12}C(=O)(CR^{14}R^{15})NR^{10}R^{11}$

*Col. 357, line 48*
Replace $OR^{11})$
With $(OR^{11})$

*Col. 358, line 16*
Replace $-NR^{12}C(=Y)R_{10'}$
With $-NR^{12}C(=Y)R^{10'}$

In Claim 26

*Col. 360, line 33*
Replace $-CR^{14}R^{15})_t-NR^{12}C(=O)(CR^{14}R^{15})NR^{10}R^{11}$
With $-(CR^{14}R^{15})_t-NR^{12}C(=O)(CR^{14}R^{15})NR^{10}R^{11}$

*Col. 360, line 39*
Replace $OR^{11})$
With $(OR^{11})$

*Col. 361, line 5*
Replace $-NR^{12}C(=Y)R_{10'}$
With $-NR^{12}C(=Y)R^{10'}$

In Claim 28

*Col. 361, line 32*
Replace  2-9dimethylamino)acetamide
With  2-(dimethylamino)acetamide

In Claim 29

*Col. 362, line 1*
Replace  $- CR^{14}R^{15})_t\text{-}NR^{12}C(=O)(CR^{14}R^{15})NR^{10}R^{11}$
With  $- (CR^{14}R^{15})_t\text{-}NR^{12}C(=O)(CR^{14}R^{15})NR^{10}R^{11}$

*Col. 362, line 6*
Replace  $OR^{11})$
With  $(OR^{11})$

*Col. 362, line 47*
Replace  $-NR^{12}C(=Y)R_{10'}$
With  $-NR^{12}C(=Y)R^{10'}$

*Col. 362, line 56*
Replace  $C_{20\text{-}C8}$
With  $C_2\text{-}C_8$

In Claim 30

*Col. 363, line 33*
Replace  $- CR^{14}R^{15})_t\text{-}NR^{12}C(=O)(CR^{14}R^{15})NR^{10}R^{11}$
With  $- (CR^{14}R^{15})_t\text{-}NR^{12}C(=O)(CR^{14}R^{15})NR^{10}R^{11}$

*Col. 363, line 38*
Replace  $OR^{11})$
With  $(OR^{11})$

*Col. 364, line 5*
Replace  $-NR^{12}C(=Y)R_{10'}$
With  $-NR^{12}C(=Y)R^{10'}$

In Claim 31

*Col. 364, line 51*
Replace heterocyclyl
With heteroaryl

*Col. 364, line 55*
Replace $- CR^{14}R^{15})_t\text{-}NR^{12}C(=O)(CR^{14}R^{15})NR^{10}R^{11}$
With $- (CR^{14}R^{15})_t\text{-}NR^{12}C(=O)(CR^{14}R^{15})NR^{10}R^{11}$

*Col. 364, line 60*
Replace $OR^{11})$
With $(OR^{11})$

*Col. 365, line 30*
Replace $-NR^{12}C(=Y)R_{10'}$
With $-NR^{12}C(=Y)R^{10,}$

In Claim 33

*Col. 366, line 23*
Replace $-(CR_{14}R^{15})_nS(O)^2R^{10}$
With $-(CR^{14}R^{15})_nS(O)^2R^{10}$

*Col. 366, line 24*
Replace $-(=Y)R^{10}$
With $-C(=Y)R^{10}$

*Col. 366, line 26*
Replace $NR^{10}OR^{10}$
With $NR^{12}OR^{10}$

*Col. 366, line 37*
Replace $- CR^{14}R^{15})_t\text{-}NR^{12}C(=O)(CR^{14}R^{15})NR^{10}R^{11}$
With $- (CR^{14}R^{15})_t\text{-}NR^{12}C(=O)(CR^{14}R^{15})NR^{10}R^{11}$

*Col. 366, line 43*
Replace $OR^{11})$
With $(OR^{11})$

*Col. 368, line 43*
Replace $-NR^{12}C(=Y)R_{10'}$
With $-NR^{12}C(=Y)R^{10,}$